(12) United States Patent
Hanotin et al.

(10) Patent No.: US 9,682,013 B2
(45) Date of Patent: *Jun. 20, 2017

(54) PHARMACEUTICAL COMPOSITIONS COMPRISING HUMAN ANTIBODIES TO PCSK9

(75) Inventors: Corinne Hanotin, Paris (FR); Laurence Bessac, Paris (FR); Umesh Chaudhari, Bridgewater, NJ (US)

(73) Assignee: SANOFI BIOTECHNOLOGY, Paris (FR)

( * ) Notice: Subject to any disclaimer, the term of this patent is extended or adjusted under 35 U.S.C. 154(b) by 338 days.

This patent is subject to a terminal disclaimer.

(21) Appl. No.: 13/982,381

(22) PCT Filed: Jan. 27, 2012

(86) PCT No.: PCT/EP2012/051321
§ 371 (c)(1),
(2), (4) Date: Jul. 29, 2013

(87) PCT Pub. No.: WO2012/101253
PCT Pub. Date: Aug. 2, 2012

(65) Prior Publication Data
US 2014/0178402 A1      Jun. 26, 2014

(30) Foreign Application Priority Data

| Jan. 28, 2011 | (EP) | 11305088 |
| Jan. 28, 2011 | (EP) | 11305089 |
| Apr. 29, 2011 | (EP) | 11305513 |
| Apr. 29, 2011 | (EP) | 11305514 |
| Aug. 12, 2011 | (EP) | 11306039 |
| Aug. 12, 2011 | (EP) | 11306040 |
| Sep. 22, 2011 | (EP) | 11306201 |
| Sep. 22, 2011 | (EP) | 11306202 |
| Nov. 8, 2011 | (EP) | 11306449 |
| Nov. 8, 2011 | (EP) | 11306450 |

(51) Int. Cl.
| *A61K 39/395* | (2006.01) |
| *A61P 3/06* | (2006.01) |
| *C07K 16/40* | (2006.01) |
| *A61J 1/05* | (2006.01) |
| *A61K 31/215* | (2006.01) |
| *A61K 31/366* | (2006.01) |
| *A61K 31/404* | (2006.01) |
| *A61K 31/435* | (2006.01) |

(Continued)

(52) U.S. Cl.
CPC ............... *A61J 1/05* (2013.01); *A61K 31/215* (2013.01); *A61K 31/366* (2013.01); *A61K 31/404* (2013.01); *A61K 31/435* (2013.01); *A61K 31/47* (2013.01); *A61K 31/505* (2013.01); *A61K 39/395* (2013.01); *A61K 39/3955* (2013.01); *A61K 45/06* (2013.01); *C07K 16/40* (2013.01); *A61K 2039/505* (2013.01); *C07K 14/4703* (2013.01); *C07K 2317/21* (2013.01); *C07K 2317/76* (2013.01)

(58) Field of Classification Search
None
See application file for complete search history.

(56) References Cited

U.S. PATENT DOCUMENTS

| 5,260,440 A | 11/1993 | Hirai et al. |
| 5,273,995 A | 12/1993 | Roth |

(Continued)

FOREIGN PATENT DOCUMENTS

| CN | 101489565 A | 7/2009 |
| EP | 0521471 B1 | 10/2000 |

(Continued)

OTHER PUBLICATIONS

Miettinen et al (Circulation, 1971: 44: 842-850).*

(Continued)

*Primary Examiner* — Zachary Howard
(74) *Attorney, Agent, or Firm* — Lathrop & Gage LLP; James H. Velema, Esq.

(57) ABSTRACT

The present invention relates to Pharmaceutical compositions comprising an antibody specifically binding to human proprotein convertase subtilisin/kexin type 9 (PCSK9), to methods for treating diseases or conditions in which proprotein convertase subtilisin/kexin type 9 (PCSK9) expression or activity causes an impact by administration of PCSK9-specific antibodies or antigen-binding fragments thereof and preferably by additional administration of an inhibitor of 3-hydroxy-3-methyl-glutaryl-CoA reductase (HMG-CoA reductase). The present invention further relates to PCSK9-specific antibodies or antigen-binding fragments thereof for use in the treatment of diseases or conditions in which PCSK9 expression or activity causes an impact.

The present invention also relates to articles of manufacture comprising packaging material, PCSK9-specific antibodies or antigen-binding fragments thereof, and a label or packaging insert indicating which groups of patients can be treated with said antibodies or fragments, which groups of patients must not be treated with said antibodies or fragments, and which dosage regimen should be used.

The present invention further relates to methods of testing the efficacy of PCSK9-specific antibodies or antigen-binding fragments thereof for the treatment of certain diseases or conditions and for the treatment of specific sub-groups of patients.

15 Claims, 6 Drawing Sheets

(51) Int. Cl.
*A61K 31/47* (2006.01)
*A61K 31/505* (2006.01)
*A61K 45/06* (2006.01)
*C07K 14/47* (2006.01)
*A61K 39/00* (2006.01)

(56) References Cited

U.S. PATENT DOCUMENTS

| | | | |
|---|---|---|---|
| 5,399,670 A | 3/1995 | Bhattacharya et al. | |
| 5,851,999 A | 12/1998 | Ulrich et al. | |
| 5,939,598 A | 8/1999 | Kucherlapati et al. | |
| 6,011,003 A | 1/2000 | Charnock-Jones et al. | |
| 6,171,586 B1 | 1/2001 | Lam et al. | |
| 6,267,958 B1 | 7/2001 | Andya et al. | |
| 6,270,993 B1 | 8/2001 | Shibuya et al. | |
| 6,596,541 B2 | 7/2003 | Murphy et al. | |
| 6,629,949 B1 | 10/2003 | Douglas | |
| 6,659,982 B2 | 12/2003 | Douglas et al. | |
| 6,875,432 B2 | 4/2005 | Liu et al. | |
| 7,001,892 B1 | 2/2006 | Chmielewski et al. | |
| 7,029,895 B2 | 4/2006 | Glucksmann et al. | |
| 7,060,268 B2 | 6/2006 | Andya et al. | |
| 7,129,338 B1 | 10/2006 | Ota et al. | |
| 7,300,754 B2 | 11/2007 | Fadel et al. | |
| 7,482,147 B2 | 1/2009 | Glucksmann et al. | |
| 7,572,618 B2 | 8/2009 | Mintier et al. | |
| 7,608,693 B2 | 10/2009 | Martin et al. | |
| 7,754,208 B2 | 7/2010 | Ledbetter et al. | |
| 8,030,457 B2 | 10/2011 | Jackson et al. | |
| 8,062,640 B2 | 11/2011 | Sleeman et al. | |
| 8,080,243 B2 | 12/2011 | Liang et al. | |
| 8,092,803 B2 | 1/2012 | Furfine et al. | |
| 8,168,762 B2 | 5/2012 | Jackson et al. | |
| 8,188,233 B2 | 5/2012 | Condra et al. | |
| 8,188,234 B2 | 5/2012 | Condra et al. | |
| 8,357,371 B2 | 1/2013 | Sleeman et al. | |
| 8,501,184 B2 | 8/2013 | Sleeman et al. | |
| 2003/0092606 A1 | 5/2003 | L'Italien et al. | |
| 2003/0113316 A1 | 6/2003 | Kaisheva et al. | |
| 2003/0118592 A1 | 6/2003 | Ledbetter et al. | |
| 2003/0133939 A1 | 7/2003 | Ledbetter et al. | |
| 2004/0101920 A1 | 5/2004 | Radziejewski et al. | |
| 2004/0197324 A1 | 10/2004 | Liu et al. | |
| 2005/0281831 A1 | 12/2005 | Davis-Smyth et al. | |
| 2006/0147945 A1 | 7/2006 | Edmonds et al. | |
| 2007/0082345 A1 | 4/2007 | Ota et al. | |
| 2007/0224663 A1 | 9/2007 | Rosen et al. | |
| 2008/0008697 A1 | 1/2008 | Mintier et al. | |
| 2009/0142352 A1 | 6/2009 | Jackson et al. | |
| 2009/0232795 A1 | 9/2009 | Condra et al. | |
| 2009/0246192 A1 | 10/2009 | Condra et al. | |
| 2009/0269350 A1 | 10/2009 | Glucksmann et al. | |
| 2009/0318536 A1 | 12/2009 | Freier et al. | |
| 2009/0326202 A1 | 12/2009 | Jackson et al. | |
| 2010/0040610 A1 | 2/2010 | Sitlani et al. | |
| 2010/0040611 A1 | 2/2010 | Sparrow et al. | |
| 2010/0041102 A1 | 2/2010 | Sitlani et al. | |
| 2010/0068199 A1 | 3/2010 | Liang et al. | |
| 2010/0136028 A1 | 6/2010 | Sparrow et al. | |
| 2010/0150937 A1 | 6/2010 | Sparrow et al. | |
| 2010/0166768 A1 | 7/2010 | Sleeman et al. | |
| 2010/0233177 A1 | 9/2010 | Yowe et al. | |
| 2011/0027287 A1 | 2/2011 | Jackson et al. | |
| 2011/0033465 A1 | 2/2011 | Hedrick et al. | |
| 2011/0065902 A1 | 3/2011 | Sleeman et al. | |
| 2011/0098450 A1 | 4/2011 | Igawa et al. | |
| 2011/0111406 A1 | 5/2011 | Igawa et al. | |
| 2011/0142849 A1 | 6/2011 | Rue et al. | |
| 2011/0171241 A1 | 7/2011 | Dix et al. | |
| 2011/0229489 A1 | 9/2011 | Pons et al. | |
| 2011/0256148 A1 | 10/2011 | Sleeman et al. | |
| 2012/0014951 A1 | 1/2012 | Liang et al. | |
| 2012/0015435 A1 | 1/2012 | Liang et al. | |
| 2012/0020975 A1 | 1/2012 | Jackson et al. | |
| 2012/0027765 A1 | 2/2012 | Jackson et al. | |
| 2012/0076799 A1 | 3/2012 | Sparrow et al. | |
| 2012/0077964 A1 | 3/2012 | Sparrow et al. | |
| 2012/0082679 A1 | 4/2012 | Sparrow et al. | |
| 2012/0082680 A1 | 4/2012 | Sitlani et al. | |
| 2012/0093818 A1 | 4/2012 | Jackson et al. | |
| 2012/0097565 A1 | 4/2012 | Dix et al. | |
| 2012/0195910 A1 | 8/2012 | Wu et al. | |
| 2012/0213794 A1 | 8/2012 | Luo et al. | |
| 2012/0213797 A1 | 8/2012 | Jackson et al. | |
| 2012/0219558 A1 | 8/2012 | Ni et al. | |
| 2012/0231005 A1 | 9/2012 | Luo et al. | |
| 2012/0251544 A1 | 10/2012 | Jackson et al. | |
| 2013/0011866 A1 | 1/2013 | Igawa et al. | |
| 2013/0064825 A1 | 3/2013 | Chan et al. | |
| 2013/0064834 A1 | 3/2013 | Sleeman et al. | |
| 2013/0085266 A1 | 4/2013 | Sleeman et al. | |
| 2013/0245235 A1 | 9/2013 | Jackson et al. | |
| 2014/0004122 A1 | 1/2014 | Chan et al. | |
| 2014/0030270 A1 | 1/2014 | Clogston et al. | |
| 2014/0065649 A1 | 3/2014 | Schafer et al. | |
| 2014/0099312 A1 | 4/2014 | Sleeman et al. | |
| 2014/0154262 A1 | 6/2014 | Hanotin et al. | |
| 2014/0161821 A1 | 6/2014 | Udata | |
| 2014/0178402 A1 | 6/2014 | Hanotin et al. | |
| 2015/0152191 A1 | 6/2015 | Baccara-Dinet et al. | |
| 2015/0283236 A1 | 10/2015 | Baccara-Dinet et al. | |
| 2015/0284473 A1 | 10/2015 | Bessac et al. | |
| 2015/0284474 A1 | 10/2015 | Sleeman et al. | |
| 2016/0152734 A1 | 6/2016 | Udata | |

FOREIGN PATENT DOCUMENTS

| | | |
|---|---|---|
| EP | 1067182 A2 | 1/2001 |
| EP | 0409281 B1 | 10/2001 |
| EP | 1514933 A1 | 3/2005 |
| EP | 1317537 B1 | 12/2006 |
| EP | 1618212 B1 | 11/2007 |
| EP | 2 703 009 A1 | 3/2014 |
| EP | 2 706 070 A1 | 3/2014 |
| WO | 93/00807 A1 | 1/1993 |
| WO | 97/35620 A1 | 10/1997 |
| WO | 98/22136 A2 | 5/1998 |
| WO | 99/38495 A2 | 8/1999 |
| WO | 0157081 A2 | 8/2001 |
| WO | 2004/055164 A2 | 7/2004 |
| WO | 2005103081 A2 | 11/2005 |
| WO | WO 2005/103081 A2 | 11/2005 |
| WO | 2007/143315 A2 | 12/2007 |
| WO | 2007/149334 A2 | 12/2007 |
| WO | 2008057457 A2 | 5/2008 |
| WO | 2008057458 A2 | 5/2008 |
| WO | 2008057459 A2 | 5/2008 |
| WO | 2008063382 A2 | 5/2008 |
| WO | WO 2008/057457 A2 | 5/2008 |
| WO | WO 2008/057458 A2 | 5/2008 |
| WO | WO 2008/057459 A2 | 5/2008 |
| WO | WO 2008/063382 A2 | 5/2008 |
| WO | 2008125623 A2 | 10/2008 |
| WO | WO 2008/125623 A2 | 10/2008 |
| WO | 2008133647 A1 | 11/2008 |
| WO | 2009026558 A1 | 2/2009 |
| WO | 2009055783 A2 | 4/2009 |
| WO | 2009100297 A1 | 8/2009 |
| WO | 2009100318 A1 | 8/2009 |
| WO | 2010/032220 A1 | 3/2010 |
| WO | 2010029513 A2 | 3/2010 |
| WO | 2010077854 A1 | 7/2010 |
| WO | 2010/102241 A1 | 9/2010 |
| WO | 2011028938 A1 | 3/2011 |
| WO | 2011039578 A1 | 4/2011 |
| WO | 2011/053759 A1 | 5/2011 |
| WO | 2011/061712 A1 | 5/2011 |
| WO | 2011/072263 A1 | 6/2011 |
| WO | 2011/111007 A2 | 9/2011 |
| WO | 2011/117401 A1 | 9/2011 |
| WO | 2012054438 A1 | 4/2012 |
| WO | 2012064792 A2 | 5/2012 |
| WO | 2012101251 A1 | 8/2012 |
| WO | 2012101252 A1 | 8/2012 |

(56) References Cited

FOREIGN PATENT DOCUMENTS

| WO | 2012101253 A1 | 8/2012 |
|---|---|---|
| WO | 2012109530 A1 | 8/2012 |
| WO | 2012146776 A1 | 11/2012 |
| WO | 2012154999 A1 | 11/2012 |
| WO | 2013039969 A1 | 3/2013 |
| WO | WO 2013/158984 A1 | 10/2013 |
| WO | 2013/166448 A1 | 11/2013 |
| WO | 2014/197752 A1 | 12/2014 |
| WO | 2014194111 A1 | 12/2014 |
| WO | 2015/054619 A2 | 4/2015 |
| WO | 2015/073494 A1 | 5/2015 |
| WO | 2015/123423 A2 | 8/2015 |
| WO | 2015/140079 A1 | 9/2015 |
| WO | 2015/142668 A1 | 9/2015 |
| WO | 2016/011256 A1 | 1/2016 |
| WO | 2016/011260 A1 | 1/2016 |

OTHER PUBLICATIONS

Holliger et al., 'Diabodies: small bivalent and bispecific antibody fragments.' Proceedings of the National Academy of Sciences. 1993, vol. 90,No. 14, pp. 6444-6448.

Hopkins et al., 'Familial Hypercholesterolemias: Prevalence, genetics, diagnosis and screening recommendations from the National Lipid Association Expert Panel on Familial Hypercholesterolemia.' Journal of Clinical Lipidology. 2011, 5(3):S9-S17.

Horton et al., 'Molecular biology of PCSK9: its role in LDL metabolism.' Trends Biochem Sci., 2007, 32(2): 71-77.

Huston et al. 'Protein engineering of antibody binding sites: recovery of specific activity in an anti-digoxin single-chain Fv analogue produced in *Escherichia coli*.' Proceedings of the National Academy of Sciences. 1988, vol. 85, No. 16, pp. 5879.

Igawa et al., 'Antibody recycling by engineered pH-dependent antigen binding improves the duration of antigen neutralization.' Nature Biotechnology. 2010, 28(11):1203-1208.

International Search Report for International Application No. PCT/EP2012/051320, Sep. 21, 2012 (9 pages).

Ito et al., 'The His-probe method: effects of histidine residues introduced into the complementarity-determining regions of antibodies on antigen-antibody interactions at different pH values.' Federation of European Biochemical Societies. 1992, 309(1):85-88.

Jorgensen et al., 'Genetically elevated non-fasting triglycerides and calculated remnant cholesterol as casual risk factors for myocardial infarction.' European Heart Journal. 2013, 34:1826-1833.

Kawashiri et al., 'Statin Therapy Improves Fractional Catabolic Rate of LDL without Affecting Impaired VLDL and VLDL Remnant Catabolism in Homozygous FH Patient Due to PCSK9 Gene Mutation: Evidence from Kinetic Study with Stable Isotope.' Circulation. 2012, 126(21):13869.

Lagace et al., 'Secreted PCSK9 decreases the number of LDL receptors in hepatocytes and in liver of parabiotic mice.' J Clin Invest Am Soc Clin Invest., 2006, 116(11):2995-3005.

Langer et al., 'New methods of drug delivery.' Science. 1990, vol. 249, No. 4976, pp. 1527-1533.

Langer et al., 'Medical Applications of Controlled Release.' CRC Press, Boca Raton, Florida. 1974, pp. 115-138.

Leuenberger et al., 'A Multilingual Glossary of Biotechnological Terms.' Recueil des Travaux Chimiques des Pays Bas. 1996, vol. 115, No. 7, pp. 382.

Lippi et al., 'Lipoprotein(a): from ancestral benefit to modern pathogen?' QJ Med., 2000, 93:75-84.

Lopez, Dayami, 'Inhibition of PCSK9 as a Novel Strategy for the Treatment of Hypercholesterolemia.' Drug News & Perspectives Abstract. 2008, 21(6): 323.

Lose et al., 'Evaluation of Proprotein Convertase Subtilisin/Kexin Type 9: Focus on Potential Clinical and Therapeutic Implications for Low-Density Lipoprotein Cholesterol Lowering.' Journal of Human Pharmacology and Drug Therapy. 2013, 33(4):447-460.

Maeda et al., 'pH-dependent receptor/ligand dissociation as a determining factor for intracellular sorting of ligands for epidermal growth factor receptors in rat hepatocytes.' J. Controlled Release. 2002, 82:71-82.

Marcovina et al., 'Lipoprotein(a) as a Risk Factor for Coronary Artery Disease.' The American Journal of Cardiology. 1998, 82(12A):57U-66U.

Maxwell et al., 'Adenoviral-mediated expression of Pcsk9 in mice results in a low-density lipoprotein receptor knockout phenotype.' PNAS. 2004, 101(18):7100-7105.

Mckenney et al., 'Safety and Efficacy of a Monoclonal Antibody to Proprotein Convertase Subtilisin/Kexin Type 9 Serine Protease, SAR236553/REGN727, in Patients With Primary Hyperchoesterolemia Receiving Ongoing Stable Atorvastatin Therapy.' Journal of American College of Cardiology. 2012, 59(25):2335-2353.

Nakasako et al., 'The pH-dependent structural variation of complementarity-determining region H3 in the crystal structures of the Fv fragment from an anti-dansyl monoclonal antibody.' Journal of Molecular Biology. 1999, 291:117-134.

Naureckiene et al., 'Functional characterization of Narc 1, a novel proteinase related to proteinase K.' Archives of Biochemistry and Biophysics. 2003, 420:55-67.

Noguchi et al., 'The E32K variant of PCSK9 exacerbates the phenotype of familial hypercholesterolemia by increasing PCSK9 function and concentration in the circulation.' Atherosclerosis. 2010, 210(1):166-172.

Nordestgaard et al., 'Lipoprotein(s) as cardiovascular risk factor: current status.' European Heart Journal. 2010, 31:2844-2853.

Padlan et al., 'Identification of specificity-determining residues in antibodies.' The FASEB Journal. 1995, vol. 9, No. 1, pp. 133-139.

Parhofer, 'Lipoprotein(a): Medical Treatment Options for an Elusive Molecule.' Current Pharmaceutical Design. 2011, 17:871-876.

Duff et al: Antibody-mediated disruption of the interaction between PCSK9 and the low-density lipoprotein receptor; Biochem J; 2009, vol. 419, No. 3, pp. 577-584.

International Search Report, PCT/EP12/051321, dated Feb. 28, 2012, 2 pages.

International Preliminary Report on Patentability, PCT/EP12/051321, dated Jul. 30, 2013, 7 pages.

Almagro et al: Humanization of Antibodies; Frontiers in Bioscience; 2008, vol. 13, pp. 1619-1633.

Altschul et al: Basic Local Alignment Search Tool; J. Mol. Biol., 1990, vol. 215, pp. 403-410.

Altschul et al: Gapped BLAST and PSI-BLAST: a new generation of protein database search programs; Nucleic Acids Research; 1997, vol. 25, No. 17, pp. 3389-3402.

Angal et al: A Single Amino Acid Substitution Abolishes the Heterogeneity of Chimeric Mouse/Human (IgG4) Antibody; Molecular Immunology; 1993, vol. 30, No. 1, pp. 105-108.

Bird et al: Single-Chain Antigen-Binding Proteins; 1988, Science; vol. 242, pp. 423-426.

Gonnet et al: Exhaustive Matching of the Entire Protein Sequence Database; Science; 1992, vol. 256, pp. 1443-1445.

Heap et al: Analysis of a 17-amino acid residue, virus-netutralizing microantibody; J Gen Virol; 2005, vol. 86, No. 6, pp. 1791-1800.

Hochleitner et al: Characterization of a discontinuous epitope of the human immunodeficiency virus (HIV) core protein P24 by epitope excision and differential chemical modification followed by mass spectrometric peptide mapping analysis; Protein Science; 2000, vol. 9, pp. 487-496.

Holliger et al: "Diabodies": Small bivalent and bispecific antibody fragments; Proc. Natl. Acad. Sci USA, Jul. 1993, vol. 90, pp. 6444-6448.

Huston et al: Protein engineering of antibody binding sites: Recovery of specific activity in an anti-digoxin single-chain Fv analogue produced in *Escherichia coli*; Proc. Natl. Acad. Sci. USA; 1988, vol. 85, pp. 5879-5883.

Junghans et al: Anti-Tac-H, a Humanized Antibody to the Interleukin 2 Receptor with New Features for Immunotherapy in Malignant and Immune Disorders; Cancer Research; 1990, vol. 50, pp. 1495-1502.

(56) References Cited

OTHER PUBLICATIONS

Langer: New Methods of Drug Delivery; Science; 1990, vol. 249, pp. 1527-1533.
Padlan et al: Identification of specificity-determining residues in antibodies; FASEB J., 1995, vol. 9, pp. 133-139.
Qiu et al: Small antibody mimetics comprising two complementarity-determining regions and a framework region for tumor targeting; Nature Biotechnology; 2007, vol. 25, No. 8, pp. 921-929.
Reddy et al: Elimination of Fc Receptor Dependent Effector Functions of a Modified IgG4 Monoclonal Antibody to Human CD4; J Immunol; 2000, vol. 164, pp. 1925-1933.
Reineke: Antibody Epitope Mapping Using Arrays of Synthetic Peptides; Methods in Molecular Biology; 2004, vol. 248, pp. 443-463.
Tiwari et al: Statins therapy: a review on conventional and novel formulation approaches; Journal of Pharmacy and Pharmacology; 2011, vol. 63, pp. 983-998.
Vajdos et al: Comprehensive Functional Maps of the Antigen-binding Site of an Anti-ErbB2 Antibody Obtained with Shotgun Scanning Mutagenesis; JMB; 2002, vol. 320, pp. 415-428.
Ward et al: Binding activities of a repertoire of single immunoglobulin variable domains secreted from *Escherichia coli*; Nature; 1989, vol. 341, pp. 544-546.
Wu et al: Receptor-mediated in Vitro Gene Transformation by a Soluble DNA Carrier System; J Bol Chem; 1987, vol. 262, pp. 4429-4432.
Park et al., 'Lipids and Lipoproteins: Post-transcriptional Regulation of Low Density Lipoprotein Receptor Protein by Proprotein Convertase Subtilisin/Kexin Type 9a in Mouse Liver.' J. Biol. Chem. 2004, 279: 50630-50638.
Partial International Search Report mailed Nov. 6, 2014 for International Application No. PCT/US2014/040163.
Pfizer: 'Safety and Tolerability of Multiple Doses of PF-04950615 (RN316) in Subjects With Hypercholesterolemia.' Nov. 3, 2012, XP002682100. Retrieved from the Internet: URL:http://clinicaltrials.gov/ct2/show?term=m316&rank=2.
Pearson, William R., 'Using the FASTA program to search protein and DNA sequence databases.' Computer Analysis of Sequence Data. 1994, pp. 307-331.
Powell et al., 'Compendium of Excipients for Parenteral Formulations PDA.' Journal of Pharmaceutical Science and Technology. 1998, vol. 52, No. 5, pp. 238-311.
Qiu et al., 'Small antibody mimetics comprising two complementarity-determining regions and a framework region for tumor targeting.' Nature Biotechnology. 2007, vol. 25, No. 8, pp. 921-929.
Reddy et al., 'Elimination of Fc receptor-dependent effector functions of a modified IgG4 monoclonal antibody to human CD4.' The Journal of Immunology. 2000, vol. 164, No. 4, pp. 1925-1933.
Reineke, Ulrich, 'Antibody epitope mapping using arrays of synthetic peptides.' Antibody Engineering. Humana Press. 2004, pp. 443-463.
Rhainds et al., 'PCSK9 inhibition and LDL cholesterol lowering: The biology of an attractive therapeutic target and critical review of the latest clinical trials.' Clinical Lipidology. 2012, 7(6):621-640.
Rashid et al., 'Decreased plasma cholesterol and hypersensitivity to statins in mice lacking Pcsk9.' PNAS. 2005, 102(15):5374-5379.
Sarkar et al., 'Rational cytokine design for increased lifetime and enhanced potency using pH-activated "histidine switching".' Nature Biotechnology. 2002, 20:908-913.
Sefton, Michael V., 'Implantable Pumps.' Critical Reviews in Biomedical Engineering. 1986, vol. 14, No. 3, pp. 201-240.
Seidah et al., 'The secretory proprotein convertase neural apoptosis-regulated convertase 1 (NARC-1): liver regeneration and neuronal differentiation.' 2003,100(3):928-933.
Shields et al., 'Lack of fucose on human IgG1 N-linked oligosaccharide improves binding to human FcγRIII and antibody-dependent cellular toxicity.' Journal of Biological Chemistry. 2002, vol. 277, No. 30, pp. 26733-26740.
Soutar, Anne, 'Unexpected Roles for PCSK9 in Lipid Metabolism.' Current Opinion in Lipodology. 2011, vol. 22, pp. 192-196.

Stein et al., 'Potential of proprotein Convertase Subtilisin/Kexin Type 9 Based Therapeutics.' Current Atherosclerosis Reports. 2013, 15(310):1-14.
Stein et al., 'Effect of a monoclonal antibody to PCSK9 on LDL cholesterol.' Obstetrical and Gynecological Survey. 2012, 67(7):413-414.
Stein et al., 'Effect of a Monoclonal Antibody to PCSK9 on D Cholesterol.' New England Journal of Medicine. 2012, 366:1108-1118.
Stein et al., 'Effect of a monoclonal antibody to PCSK9, REGN727/SAR236553, to reduce low-density lipoprotein cholesterol in patients with heterozygofamilial hypercholesterolemia on stable statin dose with or without ezetimibe therapy: a phase 2 randomized controlled trial.' The Lancet. 2012, 380:29-36.
Timms et al., 'A mutation in PCSK9 causing autosomal-dominant hypercholesterolemia in a Utah pedigree.' Human Genetics. 2004, 114(4):349-353.
Tiwari et al., 'Statins therapy: a review on conventional and novel formulation approaches.' Journal of Pharmacy and Pharmacology. 2011, vol. 63, No. 8, pp. 983-998.
Toth et al., 'Alirocumab, a Proprotein Convertase Substilisin/Kexin Type 9 Monoclonal Antibody, Reduces Cholesterol Concentrations of Serum Remnant Lipoprotein Fractions, Very Low-Density Lipoproteins and Triglycerides.' Circulation. 2013, 128(22):17492.
Tutt et al., 'Trispecific F (ab') 3 derivatives that use cooperative signaling via the TCR/CD3 complex and CD2 to activate and redirect resting cytotoxic T cells.' The Journal of Immunology. 1991, vol. 147, No. 1, pp. 60-69.
Vajdos et al., 'Comprehensive functional maps of the antigen-binding site of an anti-ErbB2 antibody obtained with shotgun scanning mutagenesis.' Journal of Molecular Biology. 2002, vol. 320, No. 2, pp. 415-428.
Varbo et al., 'Remnant Cholesterol as a Casual Risk Factor for Ischemic Heart Disease.' Journal of the American College of Cardiology. 2013, 61(4):427-436.
Ward et al., 'Binding activities of a repertoire of single immunoglobulin variable domains secreted from *Escherichia coli*.' Nature. 1989, vol. 341, No. 6242, pp. 544-546.
Watanabe et al., 'Optimizing pH response of affinity between protein G and IgG Fc.' J. Biological Chemistry. 2009, 284(18):12373-12383.
Winter et al., 'Humanized Antibodies.' Immunology Today. 1993, 14(6):243-246.
Written Opinion of the International Searching Authority for International Application No. PCT/EP2012/051320, Jul. 30, 2013 (16 pages).
Wu et al., 'Receptor-mediated in vitro gene transformation by a soluble DNA carrier system.' Journal of Biological Chemistry. 1987, vol. 262, No. 10, pp. 4429-4432.
Abifadel et al., 'Identification and characterization of new gain-of-function mutations in the PCSK9 gene responsible for autosomal dominant hypercholesterolemia.' Atherosclerosis. 2012, 223(2):394-400.
Abifadel et al., 'Mutations and polymorphisms in the proprotein convertase subtilisin kexin 9 (PCSK9) gene in cholesterol metabolism and disease.' Human Mutation. 2009, 30(4):520-529.
Abifadel et al., 'Mutations in PCSK9 cause autosomal dominant hypercholesterolemia.' Nature Genetics. 2003, 34(2):154-156.
Alborn et al., 'Serum proprotein convertase subtilisin Kexin type 9 is correlated directly with serum LDL cholesterol.' Clinical Chemistry. 2007, 53(10):1814-1819.
Almagro et al., 'Humanization of antibodies.' Frontiers in Bioscience. 2008, vol. 13, pp. 1619-1633.
Al-Mashhadi et al., 'Atherosclerosis: Familial hypercholesterolemia and atherosclerosis in clones minipigs created by DNA transposition of a human PCSK9 gain-of-function mutant.' Science Translation Medicine, American Association for the Advancement of Science. 2013, 5(166):44-53.
Altschul et al., 'Basic local alignment search tool.' Journal of Molecular Biology. 1990, vol. 215, No. 3, pp. 403-410.
Altschul et al., 'Gapped BLAST and PSI-BLAST: a new generation of protein database search programs.' Nucleic Acids Research. 1997, vol. 25, No. 17, pp. 3389-3402.

(56) References Cited

OTHER PUBLICATIONS

Amgen: 'Ascending Multiple Dose Study to Evaluate the Safety, Tolerability, Pharmacokinetics and Pharmacodynamics of AMG 145 in Subjects With Hyperlipidemia on Stable Doses of a Statin'. May 27, 2010, XP002682099. Retrieved from the Internet: URL:http://clinicaltrials.gov/ct2/show/nct01133522?term=amg+145&rank=2 Accessed on Aug. 6, 2014.

Angal et al., 'A single amino acid substitution abolishes the heterogeneity of chimeric mouse/human (IgG4) antibody.' Molecular Immunology. 1993, vol. 30, No. 1, pp. 105-108.

Attie et al., 'Dual regulation of the LDL receptor—Some clarity and new questions.' Cell Metabolism. 2005, 5:290-292.

Annex to Form PCT/ISA/206—Communication Relating to the Results of the Partial International Search for PCT/US2009/068013, mailed Mar. 10, 2010.

Benjannet et al., 'The Proprotein Convertase (PC) PCSK9 Is Inactivated by Furin and/or PC5/6A.' J. Biological Chemistry. 2006, 281(41): 30561-30572.

Bird et al., 'Single-chain antigen-binding proteins.' Science. 1988, vol. 242, No. 4877, pp. 423-426.

Chan et al., 'A Proprotein Convertase subtilisin/kexin type 9 Neutralizing Antibody Reduces Serum Cholesterol in Mice and Non-human primates.' PNAS. 2009, vol. 106, No. 24, pp. 9820-9825.

Chaparro-Riggers et al., 'Increasing serum half-life and extending cholesterol lowering in vivo by engineering antibody with pH-sensitive binding to PCSK9.' J. Biological Chemistry. 2012, 287(14):11090-11097.

Fallon et al., 'Increased endosomal sorting of ligand to recycling enhances potency of an intereukin-2 analog.' J. Biological Chemistry. 2000, 275(10):6790-6797.

Farnier, Michel, 'The role of proprotein convertase subtilisin/kexin type 9 in hyperlipidemia: Focus on therapeutic implications.' American Journal of Cardiovascular Drugs. 2011, 11(3):145-152.

Fasano et al., 'Activity of Gain-of-Function PCSK9 Mutants on LDLR Correlates with Total-Cholesterol Values in ADH patients.' NMCD Nutrition Metabolism and Cardiovascular Diseases. 2008, 18(1):S46.

Foote et al., 'Antibody Framework Residues Affecting the Conformation of the Hypervariable Loops.' J. Mol. Biol. 1992, 224:487-499.

Gonnet et al. 'Exhaustive matching of the entire protein sequence database.' Science. 1992, vol. 256, No. 5062, pp. 1443-1445.

Grozdanov et al., 'Expression and localization of PCSK9 in rat hepatic cells.' Biochem. Cell. Biol., 2006, 84:80-92.

Heap et al., 'Analysis of a 17-amino acid residue, virus-neutralizing microantibody.' Journal of General Virology. 2005, vol. 86, No. 6, pp. 1791-1800.

Hochleitner et al. 'Characterization of a discontinuous epitope of the human immunodeficiency virus (HIV) core protein p24 by epitope excision and differential chemical modification followed by mass spectrometric peptide mapping analysis.' Protein Science. 2000, vol. 9, No. 3, pp. 487-496.

Bays H., et al. Efficacy and safety of combining alirocumab with atorvastatin or rosuvastatin versus statin intensification or adding ezetimibe in high cardiovascular risk patients: Odyssey Options I and II. 2014;130:2105-2126.

Bays H., et al. PCSK9 Inhibitor Alirocumab as Add-on to Atorvastatin versus Other Lipid Treatment Strategies in Patients at High CVD Risk: Odyssey Options I. Circulation. 2014;130:A16194.

Cannon CP, et al. Efficacy and safety of alirocumab in high cardiovascular risk patients with inadequately controlled hypercholesterolaemia on maximally tolerated daily statin: results from the Odyssey Combo II study; presented at ESC Congress; Aug. 31, 2014, abstract not published.

Cannon CP, et al. Efficacy and safety of alirocumab in high cardiovascular risk patients with inadequately controlled hypercholesterolaemia on maximally tolerated doses of statins: the Odyssey Combo II randomized controlled trial Eur Heart J.; May 14, 2015;36(19):1186-94.

Catapano AL, et al. The safety of therapeutic monoclonal antibodies: implications for cardiovascular disease and targeting the PCSK9 pathway. Atherosclerosis 2013;228(1):18-28.

Colhoun HM, et al. Efficacy and safety of alirocumab, a fully human PCSK9 monoclonal antibody, in high cardiovascular risk patients with poorly controlled hypercholesterolemia on maximally tolerated doses of statins: rationale and design of the Odyssey Combo I and II trials. BMC Cardiovasc Disord. 2014;14(1):121.

Duff et al. Biochem Journal, the Biochemical Society, vol. 419, No. 3, May 1, 2009; pp. 577-584.

Dufour R, et al. Effect of REGN727/SAR236553 PCSK9 fully human monoclonal antibody in patients with elevated triglycerides/low high-density lipoprotein cholesterol: data from three phase 2 studies. Circulation 2012; 126:Abstract A16127.

Farnier M, et al. Relationship between alirocumab, PCSK9 and LDL-C levels: results from the Odyssey Mono Phase 3 trial of alirocumab 75 mg every 2 weeks, Atherosclerosis. 2014;235(2):e34-e35; Abstract MP02E.

Foody J, et al. Attainment of low-density lipoprotein cholesterol goals in patients at high cardiovascular risk: results from a manages care population study. Circulation. 2013;128: A17254.

Gaudet D, et al. Alirocumab, a fully human monoclonal antibody to PCSK9, reduces high plasma Lp(a) concentration: pooled analysis of 352 patients from phase 2. J Clin Lipidol 2013:7(2): 283-284.

Gaudet D, et al. Effect of Alirocumab, a Monoclonal Proprotein Convertase Subtilisin/Kexin 9 Antibody, on Lipoprotein(a) Concentrations (a Pooled Analysis of 150 mg Every 2 Weeks Dosing from Phase 2 Trials). Am J Cardiol. 2014;114(5):711-715.

Gaudet D, et al. Effect of SAR236553/REGN727 fully human monoclonal anti-proprotein convertase subtilisin/kexin type 9 antibody on plasma lipoprotein(a) concentration: pooled analysis from three phase 2 studies (NCT:01266876; 01288469; 01288443). Circulation 2012;126:Abstract A16125.

Ginsberg HN, et al. Odyssey High FH: efficacy and safety of alirocumab in patients with severe heterozygous familial hypercholesterolemia. Circulation. 2014;130:2119.

Gusarova V, et al. Reduction of LDL cholesterol by a monoclonal antibody to PCSK9 in rodents and nonhuman primates. Clin Lipidol 2012;7(6):737-743.

Hopkins PN, et al. A randomized placebo-phase clinical trial with the monoclonal antibody alirocumab demonstrates reductions in low-density lipoprotein cholesterol in patients with proprotein convertase subtilisin/kexin type 9 gain-of-function mutations. Circulation. 2013;128:A17156.

Hovingh GK, et al. Diagnosis and treatment of familial hypercholesterolaemia. Eur Heart J 2013;34(13):962-971.

Jones P, et al. Pooled safety and adverse events in nine randomized, placebo-controlled, phase 2 and 3 clinical trials of alirocumab. J Am Coll Cardiol 2015;65(10_S):A1363.

Kastelein JJ, et al. Efficacy and Safety of Alirocumab in Patients with Heterozygous Familial Hypercholesterolemia not Adequately Controlled with Current Lipid-Lowering Therapy: Design and Rationale of the Odyssey FH Studies. Cardiovasc Drugs Ther 2014; 28(3):281-289.

Kastelein JJP, et al. Efficacy and safety of alirocumab in patients with heterozygous familial hypercholesterolaemia not adequately controlled with current lipid-lowering therapy: results of Odyssey FH I and FH II studies; presented at ESC Congress; Aug. 31, 2014, abstract not published.

Kereiakes DJ, et al. Efficacy and safety of alirocumab in high cardiovascular risk patients with suboptimally controlled hypercholesterolemia on maximally tolerated doses of statins: the Odyssey Combo I study. Circulation. 2014;130:2119.

Kereiakes DJ, et al. Efficacy and safety of the PCSK9 inhibitor alirocumab among high cardiovascular risk patients on maximally tolerated statin therapy: the Odyssey Combo I study. Am Heart J. 2015. 169(6), 906-915.

Koren M, et al. Efficacy, safety and tolerability of 150 mg Q2W dose of the anti-PCSK9 mAb, REGN727/SAR236553: data from 3 phase 2 studies. Eur Heart J 2012;33(Abstract Supplement);37. Abstract 429.

Koren MJ, Kereiakes D, Pourfarzib R, Winegar D, Banerjee P, Hamon S, Hanotin C, McKenney JM. Effects of alirocumab, a fully

(56) References Cited

OTHER PUBLICATIONS human monoclonal antibody to proprotein convertase subtilisin/kexin type 9, on lipoprotein particle concentrations determined by nuclear magnetic resonance: substudy of a randomized double-blind phase II clinical trial. J Am Coll Cardiol 2014;63(12 Suppl 1): A1373.
Koren MJ, et al. Safety and efficacy of alirocumab 150 mg every 2 weeks, a fully human proprotein convertase subtilisin/kexin type 9 monoclonal antibody: a Phase II pooled analysis. Postgrad Med 2015;22:1-8.
Koren MJ, et al. Efficacy, safety and tolerability of alirocumab 150 mg Q2W, a fully human PCSK9 monoclonal antibody: a pooled analysis of 352 patients from phase 2. J Clin Lipidol 2013:7(3); 279-280.
Krauss RM, Banerjee P, Hamon S, Hanotin C, Sasiela B, Koren MJ, McKenney JM. Alirocumab, a fully human monoclonal antibody to proprotein convertase subtilisin/kexin type 9, and its effects on lipoprotein subfractions determined by ion mobility. Circulation. 2014;130:A15525.
Kühnast S, et al. PCSK-9 monoclonal antibody alirocumab dose-dependently decreases atherosclerosis development and enhances the effects of atorvastatin in APOE*3Leiden.CETP mice. Circulation. 2013;128:A15823.
Kühnast S, et al. Alirocumab inhibits atherosclerosis, improves the plaque morphology, and enhances the effects of a statin. J Lipid Res. 2014;55(10):2103-2112.
Lambert G, et al. Normalization of Low-Density Lipoprotein Receptor Expression in Receptor Defective Homozygous Familial Hypercholesterolemia by Inhibition of PCSK9 With Alirocumab. J Am Coll Cardiol. 2014;64(21):2299-2300.
Lambert G, et al. The PCSK9 decade. J Lipid Res 2012; 53(12):2515-2524.
Lunven C, et al. A randomized study of the relative bioavailability, pharmacodynamics, and safety of alirocumab, a fully human monoclonal antibody to proprotein convertase subtilison/ kexin type 9, after single subcutaneous administration at three different injection sites in healthy subjects. J Am Coll Cardiol 2014;63(12 Suppl 1): A1377.
Lunven C, et al. A randomized study of the relative pharmacokinetics, pharmacodynamics and safety of alirocumab, a fully human monoclonal antibody to PCSK9, after single subcutaneous administration at three different injection sites in healthy subjects. Cardiovasc Ther. Dec. 2014;32(6):297-301.
Mckenney J, et al. A randomized, double-blind, placebo-controlled trial of the safety and efficacy of a monoclonal antibody to proprotein convertase subtilisin/kexin type 9 serine protease, REGN727/SAR236553, in patients with primary hypercholesterolemia (NCT:0128443). Presented as a late-breaking oral presentation at the American College of Cardiology (ACC) Annual Scientific Session, Mar. 24-27, 2012, Chicago, Illinois, USA.
Moriarty PM, et al. Efficacy and safety of alirocumab, a monoclonal antibody to PCSK9, in statin-intolerant patients: Design and Rationale of Odyssey Alternative, a randomized Phase 3 trial. J Clin Lipidol. 2014; 8(6):554-561.
Moriarty PM, et al. Homogeneity of treatment effect of REGN727/SAR236553, a fully human monoclonal antibody against PCSK9, in lowering LDL-C: data from three phase 2 studies. Eur Heart J. 2013;34(Suppl 1):doi:10.1093/eurheartj/eht307.142.
Moriarty PM, Thompson PD, Cannon CP, Guyton JR, Bergeron J, Zieve FJ, Bruckert E, Jacobson TA, Baccara-Dinet MT, Zhao J, Pordy R, Gipe R. Odyssey Alternative: Efficacy and safety of the proprotein convertase subtilisin/kexin type 9 monoclonal antibody, alirocumab, versus ezetimibe, in patients with statin intolerance as defined by a placebo run-in and statin rechallenge arm. Circulation. 2014;130:2108.
Pordy R, et al. Alirocumab, a fully human monclonal antibody to proprotein convertase subtilisin/kexin type 9: therapeutic dosing in phase 3 studies. J Clin Lipidol 2013;7(3): 279.
Ramanathan A, et al. Role of alirocumab (proprotein convertase subtilisin/kexin type 9 antibody) on CD81 levels and hepatitis C virus entry into hepatocytes. Circulation. 2013;128: A12052.
Ray KK, et al. Attainment of low-density lipoprotein cholesterol goals in patients at very high cardiovascular risk in the United Kingdom: results from a general practice population study. Value Health 2013;16(7): A513.
Rey J, et al. Randomized, partial blind study of the pharmacodynamics, pharmacokinetics and safety of multiple subcutaneous doses of alirocumab, a fully human monoclonal antibody to proprotein convertase subtilisin/kexin type 9, administered every 4 weeks alone or in combination with ezetimibe or fenofibrate in healthy subjects. J Am Coll Cardiol 2014;63(12 Suppl 1):A1375.
Robinson JG, et al. Adverse events in patients with low-density lipoprotein cholesterol levels <25 or <15 mg/dL on at least two consecutive visits in fourteen randomized, controlled, clinical trials of alirocumab. J Am Coll Cardiol 2015;65(10_S): A1350.
Robinson JG, et al. Efficacy and safety of alirocumab as add-on therapy in high-cardiovascular-risk patients with hypercholesterolemia not adequately controlled with atorvastin (20 or 40 mg) or rosuvastatin (10 or 20mg): design and rationale of the Odyssey Options studies. Clin Cardiol. 2014; 37(10): 597-604.
Robinson JG, et al. Long-term safety, tolerability and efficacy of alirocumab versus placebo in high cardiovascular risk patients: first results from the Odyssey Long tem study in 2,341 patients; presented at ESC Congress Aug. 31, 2014, abstract not published.
Robinson JG, et al. Long-term safety, tolerability and efficacy of alirocumab versus placebo in high cardiovascular risk patients: first results from the Odyssey Long Term study in 2,341 patients. Circulation. 2014;130:2120.
Robinson JG, et al. Efficacy and Safety of Alirocumab in Reducing Lipids and Cardiovascular Events. N Eng J Med. 2015.
Roth EM, et al. A 24-week study of alirocumab monotherapy versus ezetimibe: The first phase 3 data of a proprotein convertase subtilisin/kexin type 9 inhibitor. J Am Coll Cardiol 2014;63(12 Suppl 1).
Roth EM, et al. The effects of co-administering a monoclonal antibody to proprotein convertase subtilisin/kexin type 9 serine protease, REGN727/SAR236553, with 10 and 80 mg atorvastatin compared to 80 mg atorvastatin alone in patients with primary hypercholesterolemia (NCT: 01288469). J Am Coll Cardiol 2012;59:E1620.
Roth EM, et al. Atorvastatin with or without an antibody to PCSK9 in primary hypercholesterolemia. N Engl J Med. 2012;367(20):1891-1900.
Roth EM, et al. Odyssey Mono: effect of alirocumab 75 mg subcutaneously every 2 weeks as monotherapy versus ezetimibe over 24 weeks. Future Cardiol 2015;11(1):27-37.
Roth EM, et al. Monotherapy with the PCSK9 inhibitor alirocumad versus ezetimibe in patients with hypercholesterolemia: Results of a 24 week, double-blind, randomized Phase 3 trial. Int J Cardiol. 2014;176(1):55-61.
Schwartz GG, et al. Effect of alirocumab, a monoclonal antibody to pcsk9, on long-term cardiovascular outcomes following acute coronary syndromes: Rationale and design of the odyssey outcomes trial. Am Heart J. 2014;168(5):682-689.
Steen D, et al. Attainment of Lipid Levels in Patients at High Cardiovascular Risk: Results from a U.S. Managed Care Population Study. Circulation. 2014;130:A19949.
Steen D, et al. Carsiovascular Event Rates in a High-Risk Managed Care Population in the United States. J Am Coll Cardiol 2015;65(10_S):A1647.
Stein E, et al. Safety and efficacy of a monoclonal antibody to PCSK9, REGN727/SAR236553, in statin-treated heterozygous familial hypercholesterolemia patients. Presented as an oral presentation at the 80th European Atherosclerosis Society (EAS) Congress, May 25-28, 2012, Milan, Italy. Abstract 1398.
Stein EA, et al. One year open-label treatment with alirocumab 150 mg every two weeks in heterozygous familial hypercholesterolemic patients. J Am Coll Cardiol 2014;63(12 Suppl 1): A1371.
Stroes E, et al. Efficacy and safety of different dosing regimens of alirocumab (starting doses of 75 mg every two weeks and 150 mg every four weeks) versus placebo in patients with

(56) References Cited

OTHER PUBLICATIONS hypercholesterolemia not treated using statins: the Odyssey Choice II study. J Am Coll Cardiol 2015;65(10_S):A1370.

Swergold G, et al. REGN727/SAR236553, a fully-human monoclonal antibody to proprotein convertase subtilisin kexin 9 (PCSK9), decreases ApoB and non-HDL-C when administered intravenously to healthy volunteers. J Clin Lipidol 2011;5(3):219.

Swergold G, et al. REGN727/SAR236553, a fully human proprotein convertase subtilisin kexin 9 (PCSK9) monoclonal antibody: effects on safety and lipid and lipoprotein profiles when administered subcutaneously. J. Am Coll Cardiol 2011;57(14s1):E2023.

Swergold G, et al. Safety, lipid, and lipoprotein effects of REGN727/SAR236553, a fully human proprotein convertase subtilisin kexin 9 (PCSK9) neutralizing monoclonal antibody administered intravenously to healthy volunteers. Circulation 2010;122:Abstract A23251.

Swergold G, et al. Inhibition of proprotein convertase subtilisin/kexin type 9 with a monoclonal antibody REGN727/SAR236553, effectively reduces low-density-lipoprotein cholesterol, as mono or add-on therapy in heterozygous familial and non-familial hypercholesterolemia. Circulation 2011;124:Abstract A16265.

Teramoto T, et al. Efficacy and safety of alirocumab in Japanese patients with hypercholesterolemia on stable statin therapy: first data with the 75 mg every two weeks dose. Circulation. 2014;130:A13651.

Toth PP, et al. Alirocumab, a proprotein convertase subtilisin/kexin type 9 monoclonal antibody, reduces cholesterol concentrations of all serum low-density lipoprotein cholesterol fractions. Circulation. 2013;128:A17313.

Toth PP, et al. Alirocumab, a proprotein convertase subtilisin/kexin type 9 monoclonal antibody, reduces cholesterol concentrations of serum remant lipoprotein fraction, very low-density lipoproteins and triglycerides. Circulation 2013;128: A17492.

Toth PP, et al. Proprotein convertase subtilisin/kexin 9 monoclonal antibody therapy significantly reduces apoprotein CII and CIII levels in serum. Atherosclerosis. 2014;235(2):e107-e108; Abstract 593.

Van Der Hoorn JWA, et al. Alirocumab, a monoclonal antibody to PCSK-9, dose-dependently decreases atherosclerosis, improves plaque stability and shows additive effects with atorvastatin in APOE*3 Leiden.CETP mice. Atherosclerosis. 2014;235(2):e19; Abstract WS16.

Wong ND, et al. Residual Dyslipidemia According to LDL-C, non-HDL-C and Apolipoprotein B by Cardiovascular Risk Category in Statin Treated US Adults. J Clin Lipidol. 2014;8:323-324. Presented as a poster presentation at the National Lipid Association Scientific Sessions, May 1-4, 2014, Orlando, Florida, USA.

Chinese Patent Application No. 201280015571.1, Office Action dated Sep. 3, 2014 with English summary, 12 pages.

European Patent Application No. 12701015.5, Communcation pursuant to Article 94(3) EPC dated May 30, 2014, 8 pages.

Gusarova V, et al. Fully human antibody that blocks PCSK9 demonstrates reduction in LDL-C preclinically and in early clinical trials.Abstract of oral presentation at the Keystone Symposia on Molecular and Cellular Biology, Mar. 25-30, 2012, Montana, USA.

European Patent Application No. 12701015.5, Communication pursuant to Article 94(3) EPC dated Apr. 24, 2015, 9 pages.

European Patent Application No. 12701742.4, Communication pursuant to Article 94(3) EPC dated May 28, 2014, 8 pages.

Chinese Patent Application No. 201280015477.6, Office Action dated Dec. 2, 2014 with English summary, 12 pages.

Shao W. New Therapies for Lowering LDL-C: Targeting PCSK9. Abstract of oral presentation at the Sino-American Pharmaceutical Professionals Association—2014 Scientific Symposium, Apr. 26, 2014, New Jersey, USA.

Swergold GD, et al. Identification and characterization of patients with autosomal dominant hypercholesterolemia caused by gain-of-function mutations in proprotein convertase subtilisin/kexin type 9 and comparison with patients with Familial Hypercholesterolemia (FH) and Familial Defective apolipoprotein B (FDB). Abstract of a poster presentaion at the American Society of Human Genetics (ASHG), Oct. 22-26, 2013, Boston, USA.

Missouri DU Report, Drug Use Review Newsletter, vol. 8, No. 6, Oct./Nov. 2003 "Statin Therapy" pp. 1-9.

Sullivan, et al. Effect of a Monoclonal Antibody to PCSK9 on Low-Density Lipoprotein Cholesterol Levels in Statin Intolerant Patients. JAMA. Dec. 19, 2012. vol. 308, No. 23. pp. 2497-2506.

Costet. PCSK9 inhibitors as LDL cholesterol-lowering agents: Rationale, concerns and preliminary outcomes. Drugs of the Future. May 1, 2012. vol. 37, No. 5, pp. 331-341.

Roth et al. Alirocumab for hyperlipidemia: physiology of PCSK9 inhibition, pharmacodynamics and Phase I and II clinical trial results of a PCSK9 monoclonal antibody. Future Cardiology. Mar. 2014; vol. 10, No. 2. pp. 183-199.

Haddley et al. Alirocumab Anti-Proprotein Convertase 9 (PCSK9) Mab Treatment of Hypercholesterolemia. Drugs of the Future; Apr. 1, 2013. vol. 38, No. 4. pp. 214-219.

International Search Report and Written Opinion mailed Feb. 3, 2015 for International Application No. PCT/US2014/065149 (17 pages).

International Search Report and Written Opinion mailed Apr. 16, 2015 for International Application No. PCT/US2014/060109 (19 pages).

International Search Report and Written Opinion mailed Jun. 12, 2015 for International Application No. PCT/US2015/020564 (20 pages).

Anonymous: Long-term Safety and Tolerability of Alirocumab SAR236553 (REGN727) in High Cardiovascular Risk Patients With Hypercholesterolemia Not Adequately Controlled With Their Lipid Modifying Therapy: A Randomized, Double-Blind, Placebo-Controlled Study. Archive from ClinicalTrials.gov for NCT01507831 on Jun. 27, 2013 (3 pages).

Anonymous: A Randomized, Double-Blind, Placebo-Controlled, Parallel Group Study to Evaluate the Effect of Alirocumab (SAR236553/REGN727) on the Occurrence of Cardiovascular Events in Patients Who Have Recently Experienced an Acute Coronary Syndrome. Archive from ClinicalTrials.gov for NCT01663402 on Mar. 11, 2014 (3 pages).

Anthem (Sep. 21, 2015) "Proprotein Convertase Subtilisin Kexin 9 (PCSK9) Inhibitors," Policy No. DRUG.00078. American Medical Association. Accessible on the Internet at URL:https://www.anthem.com/ca/medicalpolicies/policies/mp_pw_c182635.htm. [Last Accessed Apr. 27, 2016].

Barbie et al. (1998) "The Human Immunoglobulin Kappa Variable (IGKV) Genes and Joining (IGKJ) Segments," Exp. Clin. Immunogenet. 15:171-183.

Bays et al. (May 2015) "Alirocumab treatment effect on non-HDL-C: pooled analyses of ten Phase 3 trials in the Odyssey program," J Clin Lipidol. 9(3):471-472. Abstract 183.

Blom et al. (May 8, 2014) "A 52-Week Placebo-Controlled Trial of Evolocumab in Hyperlipidemia," The New England Journal of Medicine. 370(19)1809-1819.

Breen et al. (2001) "Effect of moisture on the stability of a lyophilized humanized monoclonal antibody formulation," Pharmaceutical Research. 18(9)1345-1353.

Cariou et al. (May 23-26, 2015) "Patient and physician perspectives on administration of the PCSK9 monoclonal antibody alirocumab, an injectable medication to lower LDL-C levels," International Symposium on Atherosclerosis. Abstract No. 1039.

Carpenter (1997) "Rational Design of Stable Lyophilized Protein Formulations: Some Practical Advice," Pharm. Res. 14(8):969-975.

clinicaltrials.gov (Feb. 1, 2011) "View of NCT01288443," US National Institutes of Health. [accessible on the internet at: https://clinicaltrials.gov/archive/NCT01288443/2011_02_01].

clinicaltrials.gov (Jan. 12, 2012) "View of NCT01288443," US National Institutes of Health. [accessible on the internet at: https://clinicaltrials.gov/archive/NCT01288443/2012_01_12].

clinicaltrials.gov (Feb. 1, 2011) "View of NCT01288469," US National Institutes of Health. [accessible on the internet at: https://clinicaltrials.gov/archive/NCT01288469/2011_02_01].

clinicaltrials.gov (Nov. 16, 2011) "View of NCT01288469," US National Institutes of Health. [accessible on the internet at: https://clinicaltrials.gov/archive/NCT01288469/2011_11_16].

(56) References Cited

OTHER PUBLICATIONS clinicaltrials.gov (Jul. 12, 2010) "View of NCT01161082," US National Institutes of Health. [accessible on the internet at: https://clinicaltrials.gov/archive/NCT01161082/2010_07_12].

clinicaltrials.gov (Jan. 10, 2012) "View of NCT01507831," US National Institutes of Health. [accessible on the internet at: https://clinicaltrials.gov/archive/NCT01507831/2012_01_10].

clinicaltrials.gov (Dec. 23, 2010) "View of NCT01266876," US National Institutes of Health. [accessible on the internet at: https://clinicaltrials.gov/archive/NCT01266876/2010_12_23].

clinicaltrials.gov (Nov. 18, 2011) "View of NCT01266876," US National Institutes of Health. [accessible on the internet at: https://clinicaltrials.gov/archive/NCT01266876/2011_11_18].

Daugherty et al. (2006) "Formulation and delivery issues for monoclonal antibody therapeutics," Advanced Drug Delivery Reviews 58:686-706.

Davidson et al. (2011) "Clinical utility of inflammatory markers and advanced lipoprotein testing: Advice from an expert panel of lipid specialists," Journal of Clinical Lipidology. 5:338-367.

Dube et al. (Apr. 2012) "Lipoprotein(a): more interesting than ever after 50 years," Curr. Opin. Lipidol. 23:133-140.

Dufour et al. (Sep. 30, 2014) "One year open-label treatment with alirocumab 150 mg every two weeks in heterozygous familial hypercholesterolemic patients," Can J Cardiol. 30(10 suppl):S338. Abstract 546.

Gorcyca et al. (May 2015) "Prevalence of atherosclerotic cardiovascular disease and diabetes in the United States," J Clin Lipidol. 9(3):424. Abstract 118.

Hiriyama et al. (Jan. 1, 2014) "Effects of evolocumab (AMG 145), a monoclonal antibody to PCSK9, in hypercholesterolemic, statin-treated Japanese patients at high cardiovascular risk—primary results from the phase 2 Yukawa study," Circulation Journal. 78(5):1073-1082.

Hopkins et al. (Dec. 2015) "Characterization of Autosomal Dominant Hypercholesterolemia Caused by PCSK9 Gain of Function Mutations and its Specific Treatment with Alirocumab, a PCSK9 Monoclonal Antibody," Circ Cardiovasc Genet. 8(6):823-831.

Huang et al. (May 2015) "Clinical characteristics and unmet need among real-world atherosclerotic cardiovascular disease (ASCVD) patients stratified by statin use," J Clin Lipidol. 9(3):437-438. Abstract 134.

Kastelein et al. (Sep. 1, 2015) "Odyssey FH I and FH II: 78-week results with alirocumab treatment in 735 patients with heterozygous familial hypercholesterolemia," Eur Heart J. 36(43):2996-3003.

Katayama et al. (2004) "Retrospective statistical analysis of lyophilized Protein Formulations of Progenipoietin Using PLS: Determination of the Critical Parameters for Long-Term Storage Stability," J. Pharm. Sci. 93(10):2609-2623.

Konrad et al. (2011) "Effects of currently prescribed LDL-C-lowering drugs on PCSK9 and implications for the next generation of LDL-C-lowering agents," Lipids in Health and Disease. 10(1):38.

Koschinsky et al. (Dec. 2014) "Lipoprotein(a): an important cardiovascular risk factor and a clinical conundrum," Endocrinol. Metab. Clin. North Am. 43:949-962.

Kostner et al. (Jun. 4, 2013) "When should we measure lipoprotein (a)?" European Heart Journal. 34:3268-3276.

Kuiper et al. (May 2015) "Statin use and low density lipoprotein cholesterol goal attainment among a high cardiovascular risk population in the Netherlands," Pharmo ISA Poster.

Lamon-Fava et al. (Apr. 7, 2011) "Lipoprotein(a) levels, apo(a) isoform size, and coronary heart disease risk in the Framingham Offspring Study," J. Lipid Res. 52:1181-1187.

Lefranc et al. (2009) "IMGT®, the international ImMunoGeneTics information system®," Nucl. Acids Res. 37:D1006-D1012.

Li et al. (2009) "Recent Patents on PCSK9: A New Target for Treating Hypercholesterolemia," Recent Patents on DNA and Gene Sequences. 3(3)201-212.

Majumdar et al. (2011) "Evaluation of the effect of syringe surfaces on protein formulations," Journal of Pharmaceutical Sciences. 100(7):2563-2573.

Moriarty et al. (Aug. 29, 2015) "Efficacy and safety of alirocumab versus ezetimibe in statin-intolerant patients, with a statin-re-challenge arm: The Odyssey Alternative randomized trial," J Clin Lipidol. 9(6):758-769.

Rader et al. (1995) "The Low Density Lipoprotein Receptor is Not Required for Normal Catabolism of Lp(a) Humans," The Journal of Clinical Investigation. 95:1403-1408.

Ray (Jan. 2015) "Alirocumab: an investigational treatment for hypercholesterolemia," Clin Lipidol. 10(1):9-12.

Reyes-Soffer et al. (2015) "Abstract 129: Effects of a proprotein convertase subtilisin/kexin type 9 inhibitor, alirocumab, on lipid and lipoprotein metabolism in normal subjects," Arterioscler, Thromb Vasc Biol. 35:A129.

Robinson (2002) "Protein Deamidation," Proc. Natl. Acad. Sci. USA. 99(8):5283-5288.

Romagnuolo et al. (Mar. 16, 2015) "Lipoprotein(a) Catabolism is Regulated by Proprotein Convertase Subtilisin/Kexin Type 9 through the Low Density Lipoprotein Receptor," The Journal of Biological Chemistry. 290 (18):11649-11662.

Roth et al. (May 2015) "Patient and physician perspectives on administration of the PCSK9 monoclonal antibody alirocumab, an injectable medication to lower LDL-C levels," J. Clin. Lipidol. 37(9):1945-1954.

Roth et al. (May 23-26, 2015) "Phase 3 Randomized Trial Evaluating Alirocumab Every Four Weeks Dosing as Add-on to Statin or as Monotherapy: Odyssey Choice I," International Symposium on Atherosclerosis, Abstract No. 254.

Scaviner et al. (1999) "Protein Displays of the Human Immunoglobulin Heavy, Kappa and Lambda Variable and Joining Regions," Exp. Clin. Immunogenet. 16:234-240.

Stahl (Jul. 15, 2010) "Early Clinical Development #1 REGN727: anti-PCSK9," Regeneron Pharmaceuticals. Accessible on the Internet at URL: http://files.shareholder.com/downloads/REGN/0x0x387214/534aaeb6-5e66-4e8f-86a9-0f9cac20d72f/REGN%20Investor%20Day%20Early%20Clinical%20Development1.pdf.

Steinberg et al. (2009) "Inhibition of PCSK9: A powerful weapon for achieving ideal LDL cholesterol levels," Proceedings of theNational Academy of Sciences USA. 106(24):9546-9547.

Stroes et al. (Jun. 17, 2014) "Anti-PCSK9 Antibody Effectively Lowers Cholesterol in Patients With Statin Intolerance," J. Am. Coll. Cardiol. 63(23):2541-2548.

Tsimikas et al. (Jul. 22, 2015) "Antisense therapy targeting apolipoprotein(a): A randomised double-blind, placebo-controlled phase 1 study," Lancet. 386:1472-1483.

Varrett et al. (1999) "A third major locus for autosomal dominant hypercholesterolemia Maps to 1p. 34.1-p. 32," Am. J. Hum. Genet. 64:1378-1387.

Wang (1999) "Instability, stabilization, and formulation of liquid protein pharmaceuticals," International J. Pharmaceutics 185(2):129-188.

Webb et al. (2002) "A new mechanism for decreasing aggregation of Recombinant Human Interferon-Y by a Surfactant: Slowed Dissolution of Lyophilized Formulations in a Solution Containing 0.03% Polysorbate 20," J. Pharm. Sci. 91(2):543-558.

Westerterp et al. (2006) "Cholesteryl Ester Transfer Protein Decreases High-Density Lipoprotein and Severely Aggravates Atherosclerosis in APOE*3-Leiden Mice," Arterioscler Thromb. Vasc. Biol. Nov. 2006; 26(11):2552-2559.

International Preliminary Report on Patentability corresponding to International Patent Application No. PCT/EP2012/051320, dated Jul. 30, 2013, 17 pages.

International Search Report with Written Opinion corresponding to International Patent Application No. PCT/EP2012/057890, mailed Aug. 28, 2012, 14 pages.

International Search Report with Written Opinion corresponding to International Patent Application No. PCT/EP2015/055369, mailed May 21, 2015, 11 pages.

(56) References Cited

OTHER PUBLICATIONS

International Search Report with Written Opinion corresponding to International Patent Application No. PCT/US2014/041204, mailed Oct. 17, 2014, 14 pages.
International Search Report with Written Opinion corresponding to International Patent Application No. PCT/US2015/015633, mailed Aug. 19, 2015, 23 pages.
International Search Report with Written Opinion corresponding to International Patent Application No. PCT/US2015/040754, mailed Oct. 14, 2015, 15 pages.
International Search Report with Written Opinion corresponding to International Patent Application No. PCT/US2015/040765, mailed Nov. 26, 2015, 15 pages.
Office Action corresponding to European Patent Application No. 12701742.4, dated Jun. 1, 2015, 10 pages.
Third Party Observations corresponding to European Patent Application No. 12761864.3, dated Feb. 24, 2016, 9 pages.
Wang (2009) "Fixed dosing versus body size-based dosing of monoclonal antibodies in adult clinical trials," J Clin Pharmacol. 49(9):1012-1024.

* cited by examiner

PHARMACEUTICAL COMPOSITIONS COMPRISING HUMAN ANTIBODIES TO PCSK9

SEQUENCE LISTING

The instant application contains a Sequence Listing, which has been submitted electronically in ASCII format and is hereby incorporated by reference in its entirety. Said ASCII copy, created on Dec. 17, 2013, is named 13-982,381 SL.txt and is 397,905 bytes in size.

This application is a 371 National Phase Entry application of co-pending International Application No. PCT/EP2012/051321, filed Jan. 27, 2012, which claims the benefit under 35 U.S.C. §119 of European Application No. 11305088.4, filed Jan. 28, 2011, European Application No. 11305089.2, filed Jan. 28, 2011, European Application No. 11305513.1, filed Apr. 29, 2011, European Application No. 11305514.9, filed Apr. 29, 2011, European Application No. 11306039.6, filed Aug. 12, 2011, European Application No. 11306040.4, filed Aug. 12, 2011, European Application No. 11306201.2 filed Sep. 22, 2011, European Application No. 11306202.0, filed Sep. 22, 2011, European Application No. 11306449.7, filed Nov. 8, 2011, and European Application No. 11306450.5, filed Nov. 8, 2011, all of which are hereby incorporated by reference.

The present invention relates to pharmaceutical compositions comprising proprotein convertase subtilisin/kexin type 9 (PCSK9)-specific antibodies or antigen-binding fragments thereof, preferably comprising an inhibitor of 3-hydroxy-3-methyl-glutaryl-CoA reductase (HMG-CoA reductase). The present invention further relates to injection solutions, dry formulations and unit dosage forms comprising PCSK9-specific antibodies or antigen-binding fragments thereof as well as their use (preferably in combination with HMG-CoA reductase inhibitors) for use in the treatment of diseases or conditions in which PCSK9 expression or activity causes an impact.

The present invention also relates to articles of manufacture comprising packaging material, PCSK9-specific antibodies or antigen-binding fragments thereof, and a label or packaging insert indicating e.g. which groups of patients can be treated with said antibodies or fragments, which groups of patients must not be treated with said antibodies or fragments, and which dosage regimen should be used.

BACKGROUND OF THE INVENTION

Proprotein convertase subtilisin/kexin type 9 (PCSK9) is a proprotein convertase belonging to the proteinase K subfamily of the secretory subtilase family. The encoded protein is synthesized as a soluble zymogen that undergoes autocatalytic intramolecular processing in the endoplasmic reticulum. Evidence suggest that PCSK9 increases plasma LDL cholesterol by promoting degradation of the LDL receptor, which mediates LDL endocytosis in the liver, the major route of LDL clearance from circulation. The structure of PCSK9 protein shows that it has a signal sequence, followed by a prodomain, a catalytic domain that contains a conserved triad of residues (D186, H226 and S386), and a C-terminal domain. It is synthesized as a soluble 74-kDa precursor that undergoes autocatalytic cleavage in the ER, generating a 14-kDa prodomain and 60-kDa catalytic fragment. The autocatalytic activity has been shown to be required for secretion. After cleavage the prodomain remains tightly associated with the catalytic domain.

Antibodies to PCSK9 are described in, for example, WO 2008/057457, WO 2008/057458, WO 2008/057459, WO 2008/063382, WO 2008/125623, and US 2008/0008697. Anti-PCSK9 antibodies that are particularly well-suited for practicing the present invention are disclosed in US 2010/0166768 A1, the content of which is hereby incorporated by reference in its entirety.

Technical Problems Underlying the Present Invention

Statins are among the most widely used drugs in the world. Although statins generally exhibit an excellent safety profile, it is desirable to further optimize the safety profile by reducing the already low rate of unwanted side-effects (such as myopathies).

Despite the widespread availability of lipid-lowering agents such as statins, approximately 30% of all adult patients treated for hypercholesterolemia in the United States between 1999 and 2006 failed to achieve their recommended LDL-C targets. Reasons for this include poor adherence to therapy, drug-resistance/intolerance and the positive relationship between adverse event rates and increasing dosage. Moreover, since the most effective lipid-lowering agents can only reduce LDL-C levels by up to 55%, target attainment rates in patients that require substantial reductions in LDL-C, such as those with familial hypercholesterolemia, are often significantly lower than might be expected. More effective lipid-lowering agents and treatment regimes are therefore required to improve target attainment rates in these patients.

Quite surprisingly, the inventors of the present invention found that the administration of anti-PCSK9 antibodies or fragments thereof increases the LDL-cholesterol lowering activity of statins, when administered in particular dosage regimens and/or to particular groups of patient.

Thus, the co-administration of anti-PCSK9 antibodies or fragments thereof enhances the efficacy of a statin therapy and allows a reduction in the dosage of statins, thereby reducing unwanted side-effects.

Furthermore, the inventors of the present invention found out that particular dosage regimens of anti-PCSK9 antibodies and/or statins are better suited for reducing LDL-cholesterol levels than others. The inventors also found out that some sub-groups of patients benefit more than others from a treatment with anti-PCSK9 antibodies or fragments thereof and/or statins. The inventors further found out that treatment with anti-PCSK9 antibodies or fragments thereof and/or statins is contraindicated for some sub-groups of patients.

The above overview does not necessarily describe all problems solved by the present invention.

SUMMARY OF THE INVENTION

In a first aspect the present invention is directed to a pharmaceutical composition comprising the antibody or antigen-binding fragment thereof binding specifically to proprotein convertase subtilisin/kexin type 9 (PCSK9) together with a pharmaceutically acceptable excipient or carrier.

In a second aspect, the present invention concerns an injection solution as herein described comprising the antibody or antigen-binding fragment thereof of present invention, and preferably comprising about 40 mg to about 200 mg or about 50 to about 200 mg, e.g. about 40 mg, about 50 mg, about 75 mg, at about 100 mg, about 150 mg or about 200 mg of the antibody or antigen-binding fragment thereof per 1 ml volume.

In a third aspect the present invention concerns a dry formulation as herein described comprising the antibody or antigen-binding fragment thereof of present invention, and preferably comprising about 40 mg to about 500 mg, 50 to about 500 mg, about 50 to about 400, about 50 to about 300 e.g. about 40 mg, about 50 mg, about 75 mg, at about 100 mg, about 150 mg, about 200 mg, about 250 mg, about 300 mg, about 350 mg, about 400 mg, about 450 mg or about 500 mg and more preferably about 50 mg, about 100 mg, about 150 mg, about 200 mg, about 250 mg, about 300 mg and even more preferably about 150 mg, about 200 mg or about 300 mg of the antibody or antigen-binding fragment thereof per dose.

In a a fourth aspect, present invention concerns an antibody or antigen binding fragment thereof as comprised in one of the pharmaceutical compositions according to the nineteenth aspect.

In a fifth aspect the present invention is directed to a unit dosage form comprising the antibody, antigen-binding fragment thereof or pharmaceutical composition of present invention.

In a sixth aspect, present invention concerns an article of manufacture comprising, the pharmaceutical composition of present invention, the liquid formulation of present invention or the dry formulation of present invention, the antibody or antigen-binding fragment thereof of present invention or one or more unit dosage forms of present invention and a container or package.

In a seventh aspect, present invention concerns a pharmaceutical composition or antibody or antigen-binding fragment thereof of present invention, for use in the treatment of a disease or condition in which PCSK9 expression or activity causes an impact. If in the following embodiments of the seventh aspect, it is referred e.g. to the "antibody for use in." or the "antibody or antigen-binding fragment thereof for use in . . . " a certain medical regime, this reference also applies for the respective use of the pharmaceutical composition of the invention.

In an eighth aspect, present invention concerns a method for preparing a pharmaceutical composition of present invention, e.g. according to the nineteenth aspect, comprising mixing the antibody or antigen-binding fragment thereof and optionally the HMG-CoA reductase inhibitor with one or more pharmaceutical excipients or carriers.

In a ninth aspect, present invention concerns a method for preparing a unit dosage form of present comprising admeasuring an amount of the pharmaceutical composition, of the antibody or antigen-binding fragment thereof, of the liquid formulation or of the dry formulation according to present invention comprising one or more doses of the antibody or antigen fragment thereof and optionally of the HMG-CoA reductase inhibitor and tailoring them as physically discrete units suitable as unitary dosages for human and/or animal administration.

In a tenth aspect, present invention concerns a method for preparing or assembling an article of manufacture of present invention comprising packaging the pharmaceutical composition, of the antibody according, of the liquid formulation, of the dry formulation according or of or more of the unit dosage forms of present invention in a container, optionally together with one or more of the following: a label, instructions for use, an application device.

In an eleventh aspect the present invention relates to a method for treating a disease or condition in which PCSK9 expression or activity causes an impact, comprising:
administering a therapeutic amount of an antibody or an antigen-binding fragment thereof which specifically binds hPCSK9 (human proprotein convertase subtilisin/kexin type 9) to a subject in need thereof, wherein the antibody or antigen-binding fragment thereof is administered in a dosage amount ranging from 5 mg to 500 mg, and
administering a therapeutic amount of an HMG-CoA reductase inhibitor to said subject, wherein the HMG-CoA reductase inhibitor is administered in a dosage amount ranging from 0.05 mg to 100 mg.

In a twelfth aspect the present invention relates to a method of testing the efficacy of an antibody or an antigen-binding fragment thereof which specifically binds hPCSK9 for the treatment of a disease or condition selected from the group consisting of hypercholesterolemia, hyperlipidemia, dyslipidemia, atherosclerosis and cardiovascular diseases, said method comprising:
treating a selected patient population with said antibody or antigen-binding fragment thereof, wherein each patient in said population has an LDL cholesterol (LDL-C) level of more than 100 mg/dL; and
determining the efficacy of said antibody or antigen-binding fragment thereof by determining the LDL-C level in the patient population before and after administration of said antibody or antigen-binding fragment thereof, wherein a reduction of the LDL-C level by at least 25% relative to a predose level in at least 75% of the patient population indicates that said antibody or antigen-binding fragment thereof is efficacious for the treatment of said disease or condition in said patient population.

In a thirteenth aspect the present invention relates to a method of testing the efficacy of an antibody or an antigen-binding fragment thereof which specifically binds hPCSK9 for the treatment of a disease or condition selected from the group consisting of hypercholesterolemia, hyperlipidemia, dyslipidemia, atherosclerosis and cardiovascular diseases, said method comprising:
determining the efficacy of an antibody or antigen-binding fragment thereof that has been used for the treatment of a selected patient population with said antibody or antigen-binding fragment thereof, wherein each patient in said population has an LDL cholesterol (LDL-C) level of more than 100 mg/dL by determining the LDL-C level in the patient population before and after administration of said antibody or antigen-binding fragment thereof, wherein a reduction of the LDL-C level by at least 25% relative to a predose level in at least 75% of the patient population indicates that said antibody or antigen-binding fragment thereof is efficacious for the treatment of said disease or condition in said patient population.

In a fourteenth aspect the present invention relates to a package comprising an antibody or antigen-binding fragment thereof which specifically binds hPCSK9 (see section "Preferred Antibodies for Practicing the Present Invention") and a label.

In a fifteenth aspect the present invention relates to a method of regulating the LDL level in the blood comprising:
administering a therapeutic amount of an antibody or an antigen-binding fragment thereof which specifically binds hPCSK9 (human proprotein convertase subtilisin/kexin type 9) to a subject in need thereof, wherein the antibody or antigen-binding fragment thereof is administered in a dosage amount ranging from 5 mg to 500 mg, and administering a therapeutic amount of an HMG-CoA reductase inhibitor to said subject, wherein the HMG-CoA reductase inhibitor is administered in a dosage amount ranging from 0.05 mg to 100 mg.

In a sixteenth aspect the present invention relates to a method of preventing effects of a (persistently) increased LDL level in the blood comprising:

administering a therapeutic amount of an antibody or an antigen-binding fragment thereof which specifically binds hPCSK9 (human proprotein convertase subtilisin/kexin type 9) to a subject in need thereof, wherein the antibody or antigen-binding fragment thereof is administered in a dosage amount ranging from 5 mg to 500 mg, and administering a therapeutic amount of an HMG-CoA reductase inhibitor to said subject, wherein the HMG-CoA reductase inhibitor is administered in a dosage amount ranging from 0.05 mg to 100 mg.

In a seventeenth aspect the present invention relates to a method of determining whether a pharmaceutical compound is utilizable for ameliorating, improving, inhibiting or preventing a disease or condition in which PCSK9 activity or expression has an impact comprising: (a) administering to a subject a compound that specifically binds to PCSK9, preferably an antibody or antigen-binding fragment thereof specifically binding to PCSK9, and (b) determining what fraction of PCSK9 in the blood is attached to the compound from (a).

In an eighteenth aspect the present invention relates to a method for treating a disease or condition in which PCSK9 expression or activity causes an impact comprising administering a therapeutic amount of an antibody or an antigen-binding fragment thereof which specifically binds hPCSK9 (human proprotein convertase subtilisin/kexin type 9) to a subject in need thereof, wherein the subject in need thereof falls into one or more of the following groups of subjects: (i) subjects having a serum LDL cholesterol (LDL-C) level of at least 100 mg/dL; (ii) subjects having a serum HDL-C level of less than 40 mg/dL; (iii) subjects having a serum cholesterol level of at least 200 mg/dL; (iv) subjects having a serum triacylglycerol level of at least 150 mg/dL, wherein said triacylglycerol level is determined after fasting for at least 8 hours; (v) subjects being at least 35 years old; (vi) subjects younger than 75 years; (vii) subjects having a BMI of 25 or more; (viii) male subjects; (ix) female subjects; (x) subjects in which the administration of said antibody or antigen-binding fragment thereof leads to a reduction in the serum LDL-C level by at least 30 mg/dL relative to predose level; or (xi) subjects in which the administration of said antibody or antigen-binding fragment thereof leads to a reduction in the serum LDL-C level by at least 20% relative to predose level.

In a nineteenth aspect the present invention relates to a method for treating a disease or condition in which PCSK9 expression or activity causes an impact comprising administering a therapeutic amount of an antibody or an antigen-binding fragment thereof which specifically binds hPCSK9 (human proprotein convertase subtilisin/kexin type 9) to a subject in need thereof, wherein the subject in need thereof does not fall into one or more of the following groups of subjects: (i) smokers; (ii) persons being 70 years old or older; (iii) persons suffering from hypertension; (iv) women who are pregnant; (v) women who are trying to become pregnant; (vi) women who are breast-feeding; (vii) persons who have or ever had a disease affecting the liver; (viii) persons who had any unexplained abnormal blood tests for liver function; (ix) persons who drink excessive amounts of alcohol; (x) persons having kidney problems; (xi) persons suffering from hypothyroidism; (xii) persons suffering from muscle disorders; (xiii) persons having encountered previous muscular problems during treatment with lipid-lowering medicine; (xiv) persons having serious problems with their breathing; (xv) persons taking one or more of the following medicines: medicines altering the way the immune systems works (e.g. ciclosporin or antihistamines), antibiotics or antifungal medicines (e.g. erythromycin, clarithromycin, ketoconazole, itraconazole, rifampicin, fusidic acid), medicines regulating lipid levels (e.g. gemfibrozil, colestipol), calcium channel blockers (e.g. verapamil, diltiazem), medicines regulating the heart rhythm (digoxin, amiodarone), protease inhibitors used in the treatment of HIV (e.g. nelfinavir), warfarin, oral contraceptives, antacids or St. John's Wort; or (xvi) persons drinking more than 0.1 L of grapefruit juice per day; (xvii) persons having a body mass index (BMI) of more than 40; (xviii) persons having a body mass index (BMI) of less than 18; (xix) persons suffering from type 1 diabetes or type 2 diabetes; (xx) persons positive for hepatitis B or hepatitis C; or (xxi) persons having a known sensitivity to monoclonal antibody therapeutics.

In a twentieth aspect the present invention relates to a method of testing the efficacy of an antibody or an antigen-binding fragment thereof which specifically binds hPCSK9 for the treatment of a disease or condition selected from the group consisting of hypercholesterolemia, hyperlipidemia, dyslipidemia, atherosclerosis and cardiovascular diseases, said method comprising:

treating a selected patient population with said antibody or antigen-binding fragment thereof, wherein each patient in said population has an LDL cholesterol (LDL-C) level of more than 100 mg/dL; and determining the efficacy of said antibody or antigen-binding fragment thereof by determining the LDL-C level in the patient population before and after administration of said antibody or antigen-binding fragment thereof, wherein a reduction of the LDL-C level by at least 25% relative to a predose level in at least 75% of the patient population indicates that said antibody or antigen-binding fragment thereof is efficacious for the treatment of said disease or condition in said patient population;

wherein each patient falls into one or more groups of subjects as recited in the thirteenth aspect.

In a twentyfirst aspect the present invention relates to a method of testing the efficacy of an antibody or an antigen-binding fragment thereof which specifically binds hPCSK9 for the treatment of a disease or condition selected from the group consisting of hypercholesterolemia, hyperlipidemia, dyslipidemia, atherosclerosis and cardiovascular diseases, said method comprising:

determining the efficacy of an antibody or antigen-binding fragment thereof that has been used for the treatment of a selected patient population with said antibody or antigen-binding fragment thereof, wherein each patient in said population has an LDL cholesterol (LDL-C) level of more than 100 mg/dL by determining the LDL-C level in the patient population before and after administration of said antibody or antigen-binding fragment thereof, wherein a reduction of the LDL-C level by at least 25% relative to a predose level in at least 75% of the patient population indicates that said antibody or antigen-binding fragment thereof is efficacious for the treatment of said disease or condition in said patient population;

wherein each patient falls into one or more groups of subjects as recited in the thirteenth aspect.

In a twentysecond aspect the present invention relates to a method for testing the efficacy of a compound in lowering cholesterol levels in a subject, comprising the steps: (a) providing a rodent; (b) administering an antibody or an antigen-binding fragment thereof which specifically binds CSK9 to the rodent; (c) administering a test compound to said rodent; (d) determining the effect of the test compound in the rodent, wherein a lowering of the cholesterol level in the rodent as compared to the cholesterol level of a control animal indicates that the test compound is efficacious in lowering cholesterol levels in a subject, wherein the control animal is from the same species as said rodent, and wherein the control animal has not been challenged with the test compound.

In a twentythird aspect, present invention concerns a method of enhancing the LDL-C lowering activity in a subject undergoing statin therapy, the method comprising administering to the subject an antibody, or antigen-binding fragment thereof, which specifically binds to human proprotein convertase subtilisin/kexin type 9 (hPCSK9), wherein the antibody or antigen-binding fragment thereof is administered at a dosage amount within the range of about 5 mg to about 500 mg, thereby enhancing LCL-C lowering activity of the statin therapy in the subject.

In a twentyfourth aspect, present invention concerns a kit for treating elevated low-density lipoprotein cholesterol (LDL-C) levels in a subject, the kit comprising (a) pharmaceutical unit dosage form comprising an antibody, or antigen-binding fragment thereof, which specifically binds to hPCSK9; and pharmaceutically acceptable carrier, wherein the antibody or antigen-binding fragment is present in a dosage amount within the range of about 5 mg to about 500 mg; and (b) a label or packaging insert with instructions for use.

In a twentyfifth aspect, present invention concerns a method of treating a subject suffering from a disease or disorder characterized by elevated low-density lipoprotein cholesterol (LDL-C) levels, the method comprising:
 (a) selecting a subject with a blood LDL-C level greater than 100 mg/dL; and
 (b) administering to said subject a composition comprising an antibody or antigen binding fragment thereof that specifically binds to human proprotein convertase subtilisin/kexin type 9 (hPCSK9); thereby lowering cholesterol levels in the subject in need thereof.

In a twentysixth aspect, present invention concerns a method of lowering cholesterol levels in a subject in need thereof, comprising:
 (a) selecting a subject with a blood low density lipoprotein cholesterol (LDL-C) level greater than 100 mg/dL; and
 (b) administering to said subject a composition comprising an antibody or antigen binding fragment thereof that specifically binds to human proprotein convertase subtilisin/kexin type 9 (hPCSK9); thereby lowering cholesterol levels in the subject in need thereof.

This summary of the invention does not necessarily describe all features of the present invention. Other embodiments will become apparent from a review of the ensuing detailed description.

DETAILED DESCRIPTION OF THE INVENTION

Definitions

Figure 1:
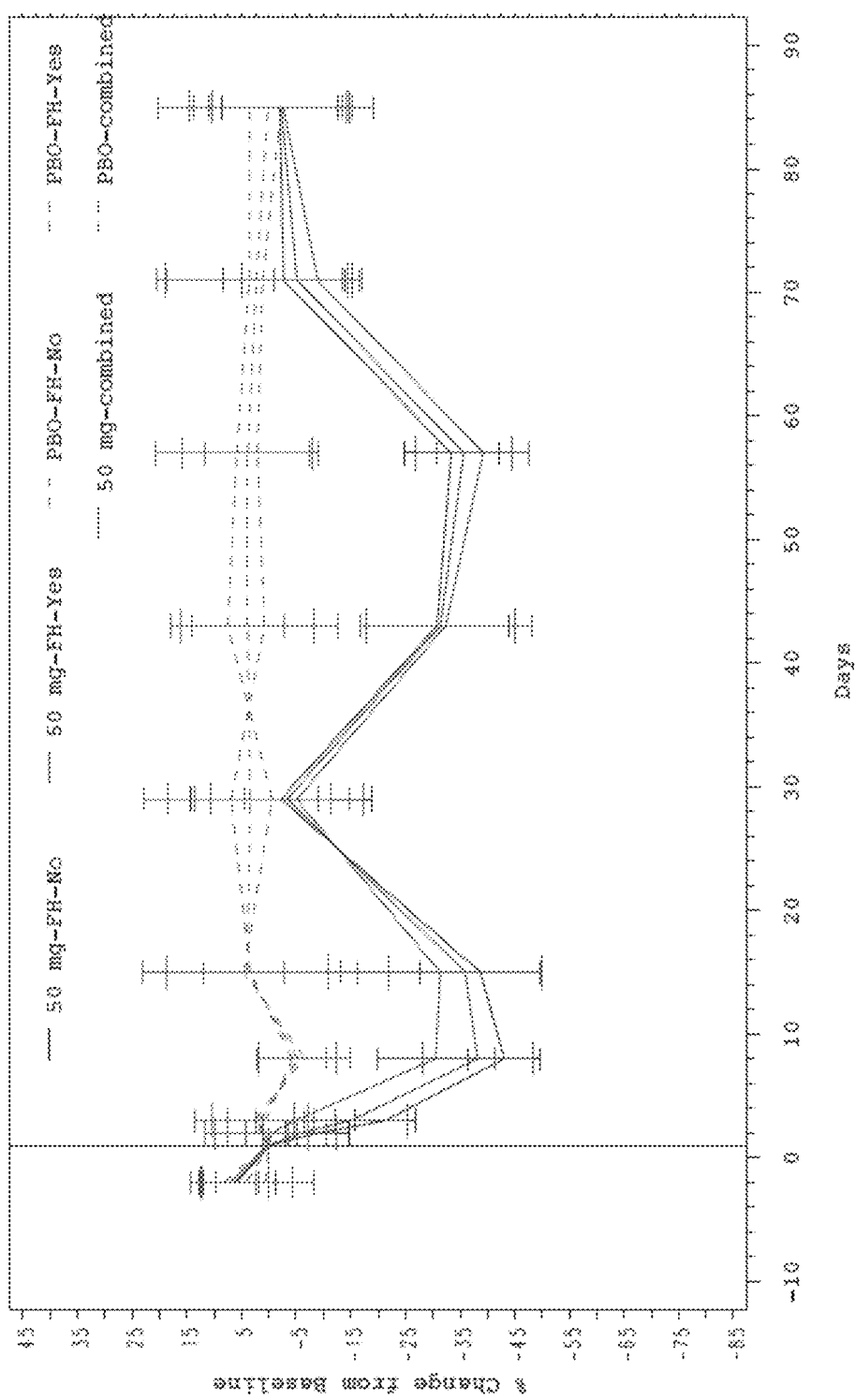
FIG. 1 shows the percentage reduction in LDL-cholesterol (LDL-C) levels relative to the baseline for three groups of patients upon treatment with anti-PCSK9 antibody 316P. These patient groups are: (1) patients with familial hypercholesterolemia (HeFH); (2) patients with other forms of primary hypercholesterolemia (non-FH) on diet and on stable atorvastatin therapy; and (3) patients with other forms of primary hypercholesterolemia (non-FH) on diet alone. A dose of 50 mg of the anti-PCSK9 antibody was administered subcutaneously on days 1, 29 and 43. Results from patient groups receiving the antibody (50-mg-FH-no; 50-mg-FH-Yes; 50-mg-combined) are shown in solid lines, while results from patients receiving a placebo (PBO-FH-no; PBO-FH-Yes; PBO-combined) are shown in dashed lines.

Before the present invention is described in detail below, it is to be understood that this invention is not limited to the particular methodology, protocols and reagents described herein as these may vary. It is also to be understood that the terminology used herein is for the purpose of describing particular embodiments only, and is not intended to limit the scope of the present invention which will be limited only by the appended claims. Unless defined otherwise, all technical and scientific terms used herein have the same meanings as commonly understood by one of ordinary skill in the art to which this invention belongs.

Preferably, the terms used herein are defined as described in "A multilingual glossary of biotechnological terms: (IUPAC Recommendations)", Leuenberger, H. G. W, Nagel, B. and Kölbl, H. eds. (1995), Helvetica Chimica Acta, CH-4010 Basel, Switzerland).

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integer or step.

Several documents (for example: patents, patent applications, scientific publications, manufacturer's specifications, instructions, GenBank Accession Number sequence submissions etc.) are cited throughout the text of this specification. Nothing herein is to be construed as an admission that the invention is not entitled to antedate such disclosure by virtue of prior invention. Some of the documents cited herein are characterized as being "incorporated by reference". In the event of a conflict between the definitions or teachings of such incorporated references and definitions or teachings recited in the present specification, the text of the present specification takes precedence.

Sequences: All sequences referred to herein are disclosed in the attached sequence listing that, with its whole content and disclosure, is a part of this specification.

The term "about" when used in connection with a numerical value is meant to encompass numerical values within a range having a lower limit that is 5% smaller than the indicated numerical value and having an upper limit that is 5% larger than the indicated numerical value.

The term "human proprotein convertase subtilisin/kexin type 9" or "hPCSK9", as used herein, refers to hPCSK9 having the nucleic acid sequence shown in SEQ ID NO: 754 and the amino acid sequence of SEQ ID NO: 755, or a biologically active fragment thereof.

The terms "specifically binds", "specific binding" or the like, mean that an antibody or antigen-binding fragment thereof forms a complex with an antigen that is relatively stable under physiologic conditions. Specific binding can be characterized by an equilibrium dissociation constant of at least about $1\times10^{-6}$ M or less (e.g., a smaller $K_D$ denotes a tighter binding). Methods for determining whether two molecules specifically bind are well known in the art and include, for example, equilibrium dialysis, surface plasmon resonance, and the like. An isolated antibody that specifically binds hPCSK9 may, however, exhibit cross-reactivity to other antigens such as PCSK9 molecules from other species. Moreover, multi-specific antibodies (e.g., bispecifics) that bind to hPCSK9 and one or more additional antigens are nonetheless considered antibodies that "specifically bind" hPCSK9, as used herein.

The term "$K_D$", as used herein, is intended to refer to the equilibrium dissociation constant of a particular antibody-antigen interaction. The equilibrium dissociation constant is typically measured in "mol/L" (abbreviated as "M").

By the term "slow off rate", "Koff" or "kd" is meant an antibody that dissociates from hPCSK9 with a rate constant of $1\times10^{-3}$ $s^{-1}$ or less, preferably $1\times10^{-4}$ $s^{-1}$ or less, as determined by surface plasmon resonance, e.g., BIACORE™.

The term "high affinity" antibody refers to those mAbs having a binding affinity to hPCSK9 of at least $10^{-10}$ M; preferably $10^{-11}$ M; even more preferably $10^{-12}$ M, as measured by surface plasmon resonance, e.g., BIACORE™ or solution-affinity ELISA.

The term "surface plasmon resonance", as used herein, refers to an optical phenomenon that allows for the analysis of real-time biospecific interactions by detection of alterations in protein concentrations within a biosensor matrix, for example using the BIACORE™ system (Pharmacia Biosensor AB, Uppsala, Sweden and Piscataway, N.J.).

An "epitope", also known as antigenic determinant, is the region of an antigen that is recognized by the immune system, specifically by antibodies, B cells, or T cells. As used herein, an "epitope" is the part of an antigen capable of binding to an antibody or antigen-binding fragment thereof as described herein. In this context, the term "binding" preferably relates to a "specific binding", as defined herein. Epitopes usually consist of chemically active surface groupings of molecules such as amino acids, sugar side chains, phosphoryl groups, or sulfonyl groups and may have specific three-dimensional structural characteristics and/or specific charge characteristics.

Conformational and non-conformational epitopes can be distinguished in that the binding to the former but not the latter is lost in the presence of denaturing solvents.

A "paratope" is the part of an antibody that specifically binds to the epitope.

The term "antibody", as used herein, is intended to refer to immunoglobulin molecules comprised of four polypeptide chains, two heavy (H) chains and two light (L) chains inter-connected by disulfide bonds. The term "antibody" also includes all recombinant forms of antibodies, in particular of the antibodies described herein, e.g. antibodies expressed in prokaryotes, unglycosylated antibodies, and any antigen-binding antibody fragments and derivatives as described below. Each heavy chain is comprised of a heavy chain variable region ("HCVR" or "VH") and a heavy chain constant region (comprised of domains CH1, CH2 and CH3). Each light chain is comprised of a light chain variable region ("LCVR" or "VL") and a light chain constant region (CL). The VH and VL regions can be further subdivided into regions of hypervariability, termed complementarity determining regions (CDR), interspersed with regions that are more conserved, termed framework regions (FR). Each VH and VL is composed of three CDRs and four FRs, arranged from amino-terminus to carboxy-terminus in the following order: FR1, CDR1, FR2, CDR2, FR3, CDR3, FR4. The variable regions of the heavy and light chains contain a binding domain that interacts with an antigen. The constant regions of the antibodies may mediate the binding of the immunoglobulin to host tissues or factors, including various cells of the immune system (e.g., effector cells) and the first component (Clq) of the classical complement system.

Substitution of one or more CDR residues or omission of one or more CDRs is also possible. Antibodies have been described in the scientific literature in which one or two CDRs can be dispensed with for binding. Padlan et al. (1995 FASEB J. 9:133-139) analyzed the contact regions between antibodies and their antigens, based on published crystal structures, and concluded that only about one fifth to one third of CDR residues actually contact the antigen. Padlan also found many antibodies in which one or two CDRs had no amino acids in contact with an antigen (see also, Vajdos et al. 2002 J Mol Biol 320:415-428).

CDR residues not contacting antigen can be identified based on previous studies (for example residues H60-H65 in CDRH2 are often not required), from regions of Kabat CDRs lying outside Chothia CDRs, by molecular modeling and/or empirically. If a CDR or residue(s) thereof is omitted, it is usually substituted with an amino acid occupying the corresponding position in another human antibody sequence or a consensus of such sequences. Positions for substitution within CDRs and amino acids to substitute can also be selected empirically. Empirical substitutions can be conservative or non-conservative substitutions.

The term "antigen-binding fragment" of an antibody (or simply "binding portion"), as used herein, refers to one or more fragments of an antibody that retain the ability to specifically bind to hPCSK9. It has been shown that the antigen-binding function of an antibody can be performed by fragments of a full-length antibody. Examples of binding fragments encompassed within the term "antigen-binding fragment" of an antibody include (i) Fab fragments, monovalent fragments consisting of the VL, VH, CL and CH domains; (ii) F(ab')₂ fragments, bivalent fragments comprising two Fab fragments linked by a disulfide bridge at the hinge region; (iii) Fd fragments consisting of the VH and CH domains; (iv) Fv fragments consisting of the VL and VH domains of a single arm of an antibody, (v) dAb fragments (Ward et al., (1989) Nature 341: 544-546), which consist of a VH domain; (vi) isolated complementarity determining regions (CDR), and (vii) combinations of two or more isolated CDRs which may optionally be joined by a synthetic linker. Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules (known as single chain Fv (scFv); see e.g., Bird et al. (1988) Science 242: 423-426; and Huston et al. (1988) Proc. Natl. Acad. Sci. USA 85: 5879-5883). Such single chain antibodies are also intended to be encompassed within the term "antigen-binding fragment" of an antibody. A further example is a binding-domain immunoglobulin fusion protein comprising (i) a binding domain polypeptide that is fused to an immunoglobulin hinge region polypeptide, (ii) an immunoglobulin heavy chain CH2 constant region fused to the hinge region, and (iii) an immunoglobulin heavy chain CH3 constant region fused to the CH2 constant region. The binding domain polypeptide can be a heavy chain variable region or a light chain variable region. The binding-domain immunoglobulin fusion proteins are further disclosed in US 2003/0118592 and US 2003/0133939. These antibody fragments are obtained using conventional techniques known to those with skill in the art, and the fragments are screened for utility in the same manner as are intact antibodies. Further examples of "antigen-binding fragments" are so-called microantibodies, which are derived from single CDRs. For example, Heap et al. describe a 17 amino acid residue microantibody derived from the heavy chain CDR3 of an antibody directed against the gp120 envelope glycoprotein of HIV-1 (Heap C J et al. (2005) J. Gen. Virol. 86:1791-1800). Other examples include small antibody mimetics comprising two or more CDR regions that are fused to each other, preferably by cognate framework regions. Such a small antibody mimetic comprising VH CDR1 and VL CDR3 linked by the cognate VH FR2 has been described by Qiu et al. (Qiu X-Q, et al. (2007) Nature biotechnology 25(8):921-929).

Thus, the term "antibody or antigen-binding fragment thereof", as used herein, refers to immunoglobulin molecules and immunologically active portions of immunoglobulin molecules, i.e. molecules that contain an antigen-binding site that immunospecifically binds an antigen.

Antibodies and antigen-binding fragments thereof usable in the invention may be from any animal origin including birds and mammals. Preferably, the antibodies or fragments are from human, chimpanzee, rodent (e.g. mouse, rat, guinea pig, or rabbit), chicken, turkey, pig, sheep, goat, camel, cow, horse, donkey, cat, or dog origin. It is particularly preferred that the antibodies are of human or murine origin. Antibodies of the invention also include chimeric molecules in which an antibody constant region derived from one species, preferably human, is combined with the antigen binding site derived from another species, e.g. mouse. Moreover antibodies of the invention include humanized molecules in which the antigen binding sites of an antibody derived from a non-human species (e.g. from mouse) are combined with constant and framework regions of human origin.

As exemplified herein, antibodies of the invention can be obtained directly from hybridomas which express the antibody, or can be cloned and recombinantly expressed in a host cell (e.g., a CHO cell, or a lymphocytic cell). Further examples of host cells are microorganisms, such as E. coli, and fungi, such as yeast. Alternatively, they can be produced recombinantly in a transgenic non-human animal or plant.

The term "chimeric antibody" refers to those antibodies wherein one portion of each of the amino acid sequences of heavy and light chains is homologous to corresponding sequences in antibodies derived from a particular species or belonging to a particular class, while the remaining segment of the chain is homologous to corresponding sequences in another species or class. Typically the variable region of both light and heavy chains mimics the variable regions of antibodies derived from one species of mammals, while the constant portions are homologous to sequences of antibodies derived from another. One clear advantage to such chimeric forms is that the variable region can conveniently be derived from presently known sources using readily available B-cells or hybridomas from non-human host organisms in combination with constant regions derived from, for example, human cell preparations. While the variable region has the advantage of ease of preparation and the specificity is not affected by the source, the constant region being human is less likely to elicit an immune response from a human subject when the antibodies are injected than would the constant region from a non-human source. However, the definition is not limited to this particular example.

The term "humanized antibody" refers to a molecule having an antigen binding site that is substantially derived from an immunoglobulin from a non-human species, wherein the remaining immunoglobulin structure of the molecule is based upon the structure and/or sequence of a human immunoglobulin. The antigen binding site may either comprise complete variable domains fused onto constant domains or only the complementarity determining regions (CDR) grafted onto appropriate framework regions in the variable domains. Antigen-binding sites may be wild-type or modified by one or more amino acid substitutions, e.g. modified to resemble human immunoglobulins more closely. Some forms of humanized antibodies preserve all CDR sequences (for example a humanized mouse antibody which contains all six CDRs from the mouse antibody). Other forms have one or more CDRs which are altered with respect to the original antibody.

Different methods for humanizing antibodies are known to the skilled person, as reviewed by Almagro & Fransson, the content of which is herein incorporated by reference in its entirety (Almagro J C and Fransson J (2008) Frontiers in Bioscience 13:1619-1633). Almagro & Fransson distinguish between rational approaches and empirical approaches. Rational approaches are characterized by generating few variants of the engineered antibody and assessing their binding or any other property of interest. If the designed variants do not produce the expected results, a new cycle of design and binding assessment is initiated. Rational approaches include CDR grafting, Resurfacing, Superhumanization, and Human String Content Optimization. In contrast, empirical approaches are based on the generation of large libraries of humanized variants and selection of the best clones using enrichment technologies or high-throughput screening. Accordingly, empirical approaches are dependent on a reliable selection and/or screening system that is able to search through a vast space of antibody variants. In vitro display technologies, such as phage display and ribosome display fulfill these requirements and are well-known to the skilled person. Empirical approaches include FR libraries, Guided selection, Framework-shuffling, and Humaneering.

The term "human antibody", as used herein, is intended to include antibodies having variable and constant regions derived from human germline immunoglobulin sequences. The human mAbs of the invention may include amino acid residues not encoded by human germline immunoglobulin sequences (e.g., mutations introduced by random or site-specific mutagenesis in vitro or by somatic mutation in vivo), for example in the CDRs and in particular CDR3. However, the term "human antibody", as used herein, is not intended to include mAbs in which CDR sequences derived from the germline of another mammalian species (e.g., mouse), have been grafted onto human FR sequences. Human antibodies of the invention include antibodies isolated from human immunoglobulin libraries or from animals transgenic for one or more human immunoglobulin and that do not express endogenous immunoglobulins, as described for example in U.S. Pat. No. 5,939,598 by Kucherlapati & Jakobovits.

The term "monoclonal antibody" as used herein refers to a preparation of antibody molecules of single molecular composition. A monoclonal antibody displays a single binding specificity and affinity for a particular epitope. In one embodiment, the monoclonal antibodies are produced by a hybridoma which includes a B cell obtained from a non-human animal, e.g. mouse, fused to an immortalized cell.

The term "recombinant antibody", as used herein, includes all antibodies that are prepared, expressed, created or isolated by recombinant means, such as (a) antibodies isolated from an animal (e.g., a mouse) that is transgenic or transchromosomal with respect to the immunoglobulin genes or a hybridoma prepared therefrom, (b) antibodies isolated from a host cell transformed to express the antibody, e.g. from a transfectoma, (c) antibodies isolated from a recombinant, combinatorial antibody library, and (d) antibodies prepared, expressed, created or isolated by any other means that involve splicing of immunoglobulin gene sequences to other DNA sequences.

The term "transfectoma", as used herein, includes recombinant eukaryotic host cells expressing an antibody, such as CHO cells, NS/0 cells, HEK293 cells, HEK293T cells, plant cells, or fungi, including yeast cells.

As used herein, a "heterologous antibody" is defined in relation to a transgenic organism producing such an antibody. This term refers to an antibody having an amino acid sequence or an encoding nucleic acid sequence corresponding to that found in an organism not consisting of the transgenic organism, and being generally derived from a species other than the transgenic organism.

As used herein, a "heterohybrid antibody" refers to an antibody having light and heavy chains of different organismal origins. For example, an antibody having a human heavy chain associated with a murine light chain is a heterohybrid antibody.

Thus, "antibodies and antigen-binding fragments thereof" suitable for use in the present invention include, but are not limited to, polyclonal, monoclonal, monovalent, bispecific, heteroconjugate, multispecific, recombinant, heterologous, heterohybrid, chimeric, humanized (in particular CDR-grafted), deimmunized, or human antibodies, Fab fragments, Fab' fragments, F(ab')$_2$ fragments, fragments produced by a Fab expression library, Fd, Fv, disulfide-linked Fvs (dsFv), single chain antibodies (e.g. scFv), diabodies or tetrabodies (Holliger P. et al. (1993) Proc. Natl. Acad. Sci. U.S.A. 90(14), 6444-6448), nanobodies (also known as single domain antibodies), anti-idiotypic (anti-Id) antibodies (including, e.g., anti-Id antibodies to antibodies of the invention), and epitope-binding fragments of any of the above.

The antibodies described herein are preferably isolated. An "isolated antibody", as used herein, is intended to refer to an antibody that is substantially free of other mAbs having different antigenic specificities (e.g., an isolated antibody that specifically binds hPCSK9 is substantially free of mAbs that specifically bind antigens other than hPCSK9). An isolated antibody that specifically binds hPCSK9 may, however, have cross-reactivity to other antigens, such as PCSK9 molecules from other species.

As used herein, a "PCSK9 antagonist" denotes a compound that inhibits at least one biological activity of PCSK9, preferably the proteinase activity of PCSK9. Preferred PCSK9 antagonists are characterized in that they bind from 10% to 100% (preferably from 50% to 100%) of the PCSK9 present in the blood when used in stoichiometric amounts. Preferred PCSK9 antagonists of the present invention are neutralizing antibodies.

A "neutralizing antibody", as used herein (or an "antibody that neutralizes PCSK9 activity"), is intended to refer to an antibody whose binding to hPCSK9 results in inhibition of at least one biological activity of PCSK9, preferably inhibition of the proteinase activity of PCSK9. This inhibition of the biological activity of PCSK9 can be assessed by measuring one or more indicators of PCSK9 biological activity by one or more of several standard in vitro or in vivo assays known in the art. Such assays are described for example in US 2010/0166768 A1, the content of which is hereby incorporated by reference in its entirety.

Since PCSK9 increases plasma LDL cholesterol by promoting degradation of the LDL receptor, the activity of PCSK9 has an effect on several diseases associated with increased plasma LDL cholesterol levels. Accordingly, PCSK9 antagonists, such as neutralizing anti-hPCSK9 antibodies or antigen-binding fragments thereof, are useful to reduce elevated total cholesterol, non-HDL cholesterol, LDL cholesterol, and/or apolipoprotein B100 (ApoB100). Consequently, PCSK9 antagonists are useful for ameliorating, improving, inhibiting or preventing several such diseases, including without limitation hypercholesterolemia, hyperlipidemia, dyslipidemia, atherosclerosis and cardiovascular diseases.

In specific embodiments, the anti-PCSK9 antibodies or antigen-binding fragments thereof described herein may be conjugated to a therapeutic moiety ("immunoconjugate"), such as a cytotoxin, a chemotherapeutic drug, an immunosuppressant or a radioisotope.

A "conservative amino acid substitution" is one in which an amino acid residue is substituted by another amino acid residue having a side chain (R group) with similar chemical properties (e.g., charge or hydrophobicity). In general, a conservative amino acid substitution will not substantially change the functional properties of a protein. In cases where two or more amino acid sequences differ from each other by conservative substitutions, the percent or degree of similarity may be adjusted upwards to correct for the conservative nature of the substitution. Means for making this adjustment are well known to those of skill in the art. See, e.g., Pearson (1994) Methods Mol. Biol. 24: 307-331. Examples of groups of amino acids that have side chains with similar chemical properties include 1) aliphatic side chains: glycine, alanine, valine, leucine and isoleucine;
2) aliphatic-hydroxyl side chains: serine and threonine;
3) amide-containing side chains: asparagine and glutamine;
4) aromatic side chains: phenylalanine, tyrosine, and tryptophan;
5) basic side chains: lysine, arginine, and histidine;
6) acidic side chains: aspartate and glutamate, and
7) sulfur-containing side chains: cysteine and methionine.

Preferred conservative amino acids substitution groups are: valine-leucine-isoleucine, phenylalanine-tyrosine, lysine-arginine, alanine-valine, glutamate-aspartate, and asparagine-glutamine. Alternatively, a conservative replacement is any change having a positive value in the PAM250 log-likelihood matrix disclosed in Gonnet et al. (1992) Science 256: 1443-45. A "moderately conservative" replacement is any change having a nonnegative value in the PAM250 log-likelihood matrix. Given the known genetic code, and recombinant and synthetic DNA techniques, the skilled scientist can readily construct DNAs encoding conservative amino acid variants.

As used herein, "non-conservative substitutions" or "non-conservative amino acid exchanges" are defined as exchanges of an amino acid by another amino acid listed in a different group of the seven standard amino acid groups 1) to 7) shown above.

The term "substantial identity" or "substantially identical," when referring to a nucleic acid or fragment thereof, indicates that, when optimally aligned with appropriate nucleotide insertions or deletions with another nucleic acid (or its complementary strand), there is nucleotide sequence identity in at least about 90%, and more preferably at least about 95%, 96%, 97%, 98% or 99% of the nucleotide bases, as measured by any well-known algorithm of sequence identity, such as FASTA, BLAST or GAP, as discussed below.

As applied to polypeptides, the term "substantial similarity" or "substantially similar" means that two peptide sequences, when optimally aligned, such as by the programs GAP or BESTFIT using default gap weights, share at least 90% sequence identity, even more preferably at least 95%, 98% or 99% sequence identity. Preferably, residue positions which are not identical differ by conservative amino acid substitutions.

Sequence similarity for polypeptides is typically measured using sequence analysis software. Protein analysis software matches similar sequences using measures of similarity assigned to various substitutions, deletions and other modifications, including conservative amino acid substitutions. For instance, GCG software contains programs such as GAP and BESTFIT which can be used with default parameters to determine sequence homology or sequence identity between closely related polypeptides, such as homologous polypeptides from different species of organisms or between a wild type protein and a mutein thereof. See, e.g., GCG Version 6.1. Polypeptide sequences also can be compared using FASTA with default or recommended parameters; a program in GCG Version 6.1. FASTA (e.g., FASTA2 and FASTA3) provides alignments and percent sequence identity of the regions of the best overlap between the query and search sequences (Pearson (2000) supra). Another preferred algorithm when comparing a sequence of the invention to a database containing a large number of sequences from different organisms is the computer program BLAST, especially BLASTP or TBLASTN, using default parameters. See, e.g., Altschul et al. (1990) J. Mol. Biol. 215: 403 410 and (1997) Nucleic Acids Res. 25:3389 402, each of which is herein incorporated by reference.

When percentages of sequence identity are referred to in the present application, these percentages are calculated in relation to the full length of the longer sequence, if not specifically indicated otherwise. This calculation in relation to the full length of the longer sequence applies both to nucleic acid sequences and to polypeptide sequences.

As used herein, "treat", "treating" or "treatment" of a disease or disorder means accomplishing one or more of the following: (a) reducing the severity and/or duration of the disorder; (b) limiting or preventing development of symptoms characteristic of the disorder(s) being treated; (c) inhibiting worsening of symptoms characteristic of the disorder(s) being treated; (d) limiting or preventing recurrence of the disorder(s) in patients that have previously had the disorder(s); and (e) limiting or preventing recurrence of symptoms in patients that were previously symptomatic for the disorder(s).

As used herein, "prevent", "preventing", "prevention", or "prophylaxis" of a disease or disorder means preventing that a disorder occurs in subject.

As used herein, the expressions "is for administration" and "is to be administered" have the same meaning as "is prepared to be administered". In other words, the statement that an active compound "is for administration" has to be understood in that said active compound has been formulated and made up into doses so that said active compound is in a state capable of exerting its therapeutic activity.

The terms "therapeutically effective amount" or "therapeutic amount" are intended to mean that amount of a drug or pharmaceutical agent that will elicit the biological or medical response of a tissue, a system, animal or human that is being sought by a researcher, veterinarian, medical doctor or other clinician. The term "prophylactically effective amount" is intended to mean that amount of a pharmaceutical drug that will prevent or reduce the risk of occurrence of the biological or medical event that is sought to be prevented in a tissue, a system, animal or human by a researcher, veterinarian, medical doctor or other clinician. Particularly, the dosage a patient receives can be selected so as to achieve the amount of LDL (low density lipoprotein) cholesterol lowering desired; the dosage a patient receives may also be titrated over time in order to reach a target LDL level. The dosage regimen utilizing an antibody or an antigen-binding fragment thereof as described herein is selected in accordance with a variety of factors including type, species, age, weight, body mass index, sex and medical condition of the patient; the severity of the condition to be treated; the potency of the compound chosen to be administered; the route of administration; the purpose of the administration; and the renal and hepatic function of the patient.

As used herein, a "patient" means any human or non-human animal, such as mammal, reptile or bird who may benefit from a treatment with the antibodies and antigen-biding fragments thereof described herein. Preferably, a "patient" is selected from the group consisting of laboratory animals (e.g. mouse or rat), domestic animals (including e.g. guinea pig, rabbit, chicken, turkey, pig, sheep, goat, camel, cow, horse, donkey, cat, or dog), rodent or primates including chimpanzee, gorilla, bonobo and human beings. It is particularly preferred that the "patient" is a human being. The terms "subject" or "individual" are used interchangeably herein. As used herein, a "subject" refers to a human or a non-human animal (e.g. a mammal, avian, reptile, fish, amphibian or invertebrate; preferably an individual that can either benefit from one of the different aspects of present invention (e.g. a method of treatment or a drug identified by present methods) or that can be used as laboratory animal for the identification or characterisation of a drug or a method of treatment. The individual can e.g. be a human, a wild-animal, domestic animal or laboratory animal; examples comprise: mammal, e.g. human, non-human primate (chimpanzee, bonobo, gorilla), dog, cat, rodent (e.g. mouse, guinea pig, rat, hamster or rabbit, horse, donkey, cow, sheep, goat, pig, camel; avian, such as duck, dove, turkey, goose or chick; reptile such as: turtle, tortoise, snake, lizard, amphibian such as frog (e.g. *Xenopus laevis*); fish such as koy or zebrafish; invertebrate such as a worm (e.g. *C. elegans*) or an insect (such as a fly, e.g. *drosophila melanogaster*). The term individual also comprises the different morphological developmental stages of avian, fish, reptile or insects, such as egg, pupa, larva or imago. It is further preferred if the subject is a "patient".

As used herein, "unit dosage form" refers to physically discrete units suitable as unitary dosages for human and/or animal subjects, each unit containing a predetermined quantity of active material (e.g., about 50 to about 500 mg of PCSK5 antibody and/or of e.g. 0.05 mg to 100 mg HMG-CoA reductase inhibitor) calculated to produce the desired therapeutic effect in association with the required pharmaceutical diluent, carrier or vehicle. The specifications for the novel unit dosage forms of this invention are dictated by and are directly dependent on (a) the unique characteristics of the active material and the particular therapeutic effect to be achieved, and (b) the limitation inherent in the art of compounding such an active material for therapeutic use in animals or humans, as disclosed in this specification, these being features of the present invention. Examples of suitable unit dosage forms in accord with this invention are vials, tablets, capsules, troches, suppositories, powder packets, wafers, cachets, ampules, segregated multiples of any of the foregoing, and other forms as herein described or generally known in the art. One or more such unit dosage forms of the antibody can be comprised in an article of manufacture of present invention, optionally further comprising one or more unit dosage forms of an HMG-CoA reductase inhibitor (e.g. a blister of tablets comprising as active ingredient the HMG-CoA reductase inhibitor).

The term "active material" refers to any material with therapeutic activity, such as one or more active ingredients. The active ingredients to be employed as therapeutic agents can be easily prepared in such unit dosage form with the employment of pharmaceutical materials which themselves are available in the art and can be prepared by established procedures.

The following preparations are illustrative of the preparation of the unit dosage forms of the present invention, and not as a limitation thereof. Several dosage forms may be prepared embodying the present invention. For example, a unit dosage per vial may contain 0.5 ml, 1 ml, 2 ml, 3 ml, 4 ml, 5 ml, 6 ml, 7 ml, 8 ml, 9 ml, 10 ml, 15 ml, or 20 ml of PCSK5 antibody or a fragment thereof ranging from about 40 to about 500 mg of PCSK5 antibody. If necessary, these preparations can be adjusted to a desired concentration by adding a sterile diluent to each vial. In one embodiment, the ingredients of formulation of the invention are supplied either separately or mixed together in unit dosage form, for example, as a dry lyophilized powder or water free concentrate in a hermetically sealed container such as a vial, an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

The formulations of the invention include bulk drug compositions useful in the manufacture of pharmaceutical compositions (e.g., compositions that are suitable for administration to a subject or patient) which can be used in the preparation of unit dosage forms. In a preferred embodiment, a composition of the invention is a pharmaceutical composition. Such compositions comprise a prophylactically or therapeutically effective amount of one or more prophylactic or therapeutic agents (e.g., an antibody of the invention or other prophylactic or therapeutic agent), and a pharmaceutically acceptable carrier. Preferably, the pharmaceutical compositions are formulated to be suitable for the route of administration to a subject.

The active materials or ingredients (e.g. antibodies or fragments thereof and HMG-CoA reductase inhibitors) can be formulated as various dosage forms including solid dosage forms for oral administration such as capsules, tablets, pills, powders and granules, liquid dosage forms for oral administration such as pharmaceutically acceptable emulsions, microemulsions, solutions, suspensions, syrups and elixirs, injectable preparations, for example, sterile injectable aqueous or oleaginous suspensions, compositions for rectal or vaginal administration, preferably suppositories, and dosage forms for topical or transdermal administration such as ointments, pastes, creams, lotions, gels, powders, solutions, sprays, inhalants or patches.

In a specific embodiment, the term "pharmaceutically acceptable" means approved by a regulatory agency of the U.S. Federal or a state government or the EMA (European Medicines Agency) or listed in the U.S. Pharmacopeia Pharmacopeia (United States Pharmacopeia-33/National Formulary-28 Reissue, published by the United States Pharmacopeial Convention, Inc., Rockville Md., publication date: April 2010) or other generally recognized pharmacopeia for use in animals, and more particularly in humans.

The term "carrier" refers to a diluent, adjuvant {e.g., Freund's adjuvant (complete and incomplete)), excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. For the use of (further) excipients and their use see also "Handbook of Pharmaceutical Excipients", fifth edition, R. C. Rowe, P. J. Seskey and S. C. Owen, Pharmaceutical Press, London, Chicago. The composition, if desired, can also contain minor amounts of wetting or emulsifying agents, or pH buffering agents. These compositions can take the form of solutions, suspensions, emulsion, tablets, pills, capsules, powders, sustained-release formulations and the like. Oral formulation can include standard carriers such as pharmaceutical grades of mannitol, lactose, starch, magnesium stearate, sodium saccharine, cellulose, magnesium carbonate, etc. Examples of suitable pharmaceutical carriers are described in "Remington's Pharmaceutical Sciences" by E. W. Martin. Such compositions will contain a prophylactically or therapeutically effective amount of the antibody, preferably in purified form, together with a suitable amount of carrier so as to provide the form for proper administration to the patient. The formulation should suit the mode of administration.

Generally, the ingredients of compositions of the invention are supplied either separately or mixed together in unit dosage form, for example, as a dry formulation for dissolution such as a lyophilized powder, freeze-dried powder or water free concentrate in a hermetically sealed container such as an ampoule or sachette indicating the quantity of active agent. The ingredients of compositions of the invention can also be supplied as admixed liquid formulation (i.e. injection or infusion solution) in a hermetically sealed container such as an ampoule, sachette, a pre-filled syringe or autoinjector, or a cartridge for a reusable syringe or applicator (e.g. pen or autoinjector). Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

The invention also provides that the formulation is packaged in a hermetically sealed container such as an ampoule or sachette indicating the quantity of antibody. In one embodiment, the formulation of the invention comprising an antibody is supplied as a dry formulation, such as a sterilized lyophilized powder, freeze-dried powder, spray-dried powder or water free concentrate in a hermetically sealed container and can be reconstituted, e.g., with water or saline to the appropriate concentration for administration to a subject. In another embodiment the antibody or antigen binding fragment thereof is supplied as a liquid formulation such as an injection or infusion solution. In one embodiment, the formulation of the invention comprising an antibody is supplied as a dry formulation or as a liquid formulation in a hermetically sealed container at a unit dosage of at least 40 mg, at least 50 mg, more preferably at least 75 mg, at least 100 mg, at least 150 mg, at least 200 mg, at least 250 mg, at least 300 mg, at least 350 mg, at least 400 mg, at least 450 mg, or at least 500 mg, of antibody or antigen-binding fragment thereof. The lyophilized formulation of the invention comprising an antibody should be stored at between 2 and 8° C. in its original container and the antibody should be administered within 12 hours, preferably within 6 hours, within 5 hours, within 3 hours, or within 1 hour after being reconstituted. The formulation of the invention comprising antibodies can be formulated as neutral or salt forms. Pharmaceutically acceptable salts include those formed with anions such as those derived from hydrochloric, phosphoric, acetic, oxalic, tartaric acids, etc., and those formed with cations such as those derived from sodium, potassium, ammonium, calcium, ferric hydroxides, isopropylamine, triethylamine, 2-ethylamino ethanol, histidine, procaine, etc.

Adult subjects are characterized as having "hypertension" or a high blood pressure when they have a systolic blood pressure of more than 140 mmHg and/or a diastolic blood pressure of more than 90 mmHg.

Specific populations treatable by the therapeutic methods of the invention include subjects with one or more of the following conditions: subjects indicated for LDL apheresis, subjects with PCSK9-activating mutations (gain of function mutations, "GOF"), subjects with elevated total cholesterol levels, subjects with elevated low-density lipoprotein cholesterol (LDL-C) levels, subjects with primary hypercholesterolemia, such as subjects primary with Familial or Non-Familial Hypercholesterolemia, subjects with heterozygous Familial Hypercholesterolemia (heFH); subjects with hypercholesterolemia, especially primary hypercholesterolemia, who are statin intolerant or statin uncontrolled; and subjects at risk for developing hypercholesterolemia who may be preventably treated. Other indications include hyperlipidemia and dyslipidemia, especially if associated with secondary causes such as Type 2 diabetes mellitus, cholestatic liver diseases (primary biliary cirrhosis), nephrotic syndrome, hypothyroidism, obesity; and the prevention and treatment of atherosclerosis and cardiovascular diseases, such as coronary heart disease (CHD). The conditions or disorders as listed for the above populations or subjects are conditions or disorders, for which treatment with the antibody of the invention is especially suitable.

However, depending on the severity of the afore-mentioned diseases and conditions, the treatment of subjects with the antibodies and antigen-binding fragments of the invention may be contraindicated for certain diseases and conditions.

The term "adverse effect" (or side-effect) refers to a harmful and undesired effect resulting from a medication. An adverse effect may be termed a "side effect", when judged to be secondary to a main or therapeutic effect. Some adverse effects occur only when starting, increasing or discontinuing a treatment. Adverse effects may cause medical complications of a disease and negatively affect its prognosis. Examples of side effects are allergic reactions, vomiting, headache, or dizziness or any other effect herein described.

As used herein, "treat", "treating" or "treatment" of a disease or disorder means accomplishing one or more of the following: (a) reducing the severity and/or duration of the disorder; (b) limiting or preventing development of symptoms characteristic of the disorder(s) being treated; (c) inhibiting worsening of symptoms characteristic of the disorder(s) being treated; (d) limiting or preventing recurrence of the disorder(s) in patients that have previously had the disorder(s); and (e) limiting or preventing recurrence of symptoms in patients that were previously symptomatic for the disorder(s).

As used herein, "prevent", "preventing", "prevention", or "prophylaxis" of a disease, condition or disorder means preventing that a disorder, disease or condition occurs in subject.

Elevated total cholesterol levels are understood in the context of present invention to be total cholesterol levels of 200 mg/dL or more, especially 240 mg/dL or more. International treatment guidelines recommend lowering LDL-C to <2.0-2.6 mmol/L (<77-100 mg/dL) in patients with established cardiovascular diseases (CVDs) and to <1.8-2.0 mmol/L (<70-77 mg/dL) in high-risk groups such as those with CVDs plus diabetes, smoking, poorly controlled hypertension, metabolic syndrome, or previous myocardial infarction. Elevated LDL-C levels are thus understood in the context of present invention to be LDL-C levels of 77 mg/dL or more (especially for patients with one or more of the following characteristics: established CVDs and diabetes, with smoking, poorly controlled hypertension, metabolic syndrome or previous myocardial infarction) and 100 mg/dL or more (especially for patients with established CVDs), 130 mg/dL or more, or 160 mg/dL or 190 mg/dL or more. Low High-density lipoprotein levels (HDL-levels) in the context of present invention are understood to be preferably less than about 40 mg/dL.

Elevated total cholesterol levels are understood in the context of present invention to preferably be total cholesterol levels of 200 mg/dL or more, especially 240 mg/dL or more. International treatment guidelines recommend lowering LDL-C to <2.0-2.6 mmol/L (<77-100 mg/dL) in patients with established cardiovascular diseases (CVDs) and to <1.8-2.0 mmol/L (<70-77 mg/dL) in high-risk groups such as those with CVDs plus diabetes, smoking, poorly controlled hypertension, metabolic syndrome, or previous myocardial infarction. Elevated LDL-C levels are thus understood in the context of present invention to be LDL-C levels of 77 mg/dL or more (especially for patients with one or more of the following characteristics: established CVDs and one or more of [diabetes, with smoking, poorly controlled hypertension, metabolic syndrome or previous myocardial infarction]) and 100 mg/dL or more (especially for patients with established CVDs), 130 mg/dL or more, or 160 mg/dL or 190 mg/dL or more. Low High-density lipoprotein levels (HDL-levels) in the context of present invention are understood to be preferably less than about 40 mg/dL.

The terms "uncontrolled by statins" or "statin-resistant", especially in the context of hyperlipidemia, hypercholesterolemia etc., are used synonymously herein and refer to conditions such as hyperlipidemia, wherein treatment with a statin (i.e. regular administration of a statin such as atorvastatin to a patient) does not significantly lower total cholesterol or LDL-C or does not suffice to establish normolipidemic levels for the patient or to establish a lipidemic (e.g. total cholesterol or LDL-C) level that is not a significant risk factor for developing cardiovascular diseases. This means for example that statin-treatment does not suffice to establish levels of less than 130 mg/dL in general, or of less than 100 mg/dL (e.g. about ≥77 mg/dL to about 100 mg/dL), especially in patients with established cardiovascular diseases, or to establish levels of about less than 77 mg/dL (e.g. about ≥70-77 mg/dL), especially in high-risk groups such as those with CVDs plus diabetes, smoking, poorly controlled hypertension, metabolic syndrome, or previous myocardial infarction. In the context of present invention, statin resistance preferably relates to atorvastatin resistance.

EMBODIMENTS OF THE INVENTION

The present invention will now be further described. In the following passages different aspects of the invention are defined in more detail. Each aspect so defined may be combined with any other aspect or aspects unless clearly indicated to the contrary. In particular, any feature indicated as being preferred or advantageous may be combined with any other feature or features indicated as being preferred or advantageous, unless clearly indicated to the contrary.

In a first aspect the present invention is directed to a pharmaceutical composition comprising about 40 to about 500 mg of an antibody binding specifically to proprotein convertase subtilisin/kexin type 9 (PCSK9) together with a pharmaceutically acceptable excipient or carrier.

Suitable antibodies or fragments thereof for practicing the first aspect are described in the section, "Preferred Antibodies for Practicing the Present Invention". Preferred embodiments of the antibodies or fragments thereof are e.g. described in the fourth, seventh and eleventh aspect of present invention.

According to a preferred embodiment, the pharmaceutical composition comprises about 40 to about 500 mg or about 50 to about 500 mg of the antibody or antigen-binding fragment per dose.

According to another preferred embodiment, the pharmaceutical composition comprises about 50 mg to about 500 mg, about 50 mg to about 300 mg, about 50 mg, about 100 mg, about 150 mg, about 200 mg, about 250 mg, about 300 mg, about 350 mg, of about 400 mg, about 450 mg or about 500 mg of the antibody or antigen-binding fragment thereof.

According to another preferred embodiment, the pharmaceutical composition comprises about 150, 200 or 300 mg of the antibody or antigen-binding fragment thereof.

According to another preferred embodiment, the pharmaceutical composition comprises an effective dose of an antibody or an antigen-binding fragment thereof which specifically binds hPCSK9 (human proprotein convertase subtilisin/kexin type 9), wherein the dose is sufficient for sustained reduction of low-density lipoprotein (LDL-C) levels over a period of at least 14, at least 15, at least 16, at least 17, at least 18, at least 19, at least 20, at least 21, at least 22, at least 23 or at least 28 days after administration, together with a pharmaceutically acceptable excipient or carrier. According to another preferred embodiment, the dose is sufficient for sustained reduction of LDL-C levels over a period of at least 14 days, 28 days or 1 month.

According to another preferred embodiment, the pharmaceutical composition comprises an effective amount of an HMG-CoA reductase inhibitor.

According to another preferred embodiment the pharmaceutical composition is arranged together with an effective amount of an HMG-CoA reductase inhibitor.

According to another preferred embodiment, the HMG-CoA reductase inhibitor is a statin, preferably selected from the list consisting or: cerivastatin, atorvastatin, simvastatin, pitavastatin, rosuvastatin, fluvastatin, lovastatin or pravastatin and is preferably atorvastatin.

According to another preferred embodiment, the pharmaceutical composition comprises about 0.05 mg to about 100 mg, about 0.5 mg to about 100 mg, about 5 mg to about 90 mg, about 10 mg, about 20 mg, about 40 mg or about 80 mg of HMG-CoA reductase inhibitor and preferably about 10, about 20, about 40 or about 80 mg.

In more preferred embodiments of the first and the other aspects of present invention, the statin is cerivastatin in an amount of between 0.05 mg and 2 mg, preferably of 0.2 mg, 0.4 mg, or 0.8 mg;
atorvastatin in an amount of between 2 mg and 100 mg, preferably of 10 mg, 20 mg, 40 mg, or 80 mg;
simvastatin in an amount of between 2 mg and 100 mg, of 5 mg, 10 mg, 20 mg, 40 mg, or 80 mg;
pitavastatin in an amount of between 0.2 mg and 100 mg, preferably in a daily dosage of 1 mg, 2 mg, 5 mg, 10 mg, or 20 mg;
rosuvastatin in an amount of between 2 mg and 100 mg, preferably in a daily dosage of 5 mg, 10 mg, 20 mg, or 40 mg;
fluvastatin in an amount of between 2 mg and 100 mg, preferably in a daily dosage of 20 mg, 40 mg, or 80 mg;
lovastatin in an amount of between 2 mg and 100 mg, preferably in a daily dosage of 10 mg, 20 mg, 40 mg, or 80 mg; or
pravastatin in an amount of between 2 mg and 100 mg, preferably in a daily dosage of 10 mg, 20 mg, 40 mg, or 80 mg.

According to another preferred embodiment, the pharmaceutical composition comprises an effective dose of HMG-CoA reductase inhibitor for lowering LDL-D levels by administration once per day.

In more preferred embodiments of the first aspect of present invention, the statin is
cerivastatin in a daily dosage of between 0.05 mg and 2 mg, preferably in a daily dosage of 0.2 mg, 0.4 mg, or 0.8 mg;
atorvastatin in a daily dosage of between 2 mg and 100 mg, preferably in a daily dosage of 10 mg, 20 mg, 40 mg, or 80 mg;
simvastatin in a daily dosage of between 2 mg and 100 mg, preferably in a daily dosage of 5 mg, 10 mg, 20 mg, 40 mg, or 80 mg;
pitavastatin in a daily dosage of between 0.2 mg and 100 mg, preferably in a daily dosage of 1 mg, 2 mg, 5 mg, 10 mg, or 20 mg;
rosuvastatin in a daily dosage of between 2 mg and 100 mg, preferably in a daily dosage of 5 mg, 10 mg, 20 mg, or 40 mg;
fluvastatin in a daily dosage of between 2 mg and 100 mg, preferably in a daily dosage of 20 mg, 40 mg, or 80 mg;
lovastatin in a daily dosage of between 2 mg and 100 mg, preferably in a daily dosage of 10 mg, 20 mg, 40 mg, or 80 mg; or
pravastatin in a daily dosage of between 2 mg and 100 mg, preferably in a daily dosage of 10 mg, 20 mg, 40 mg, or 80 mg.

According to a preferred embodiment, the antibody or antigen-binding fragment thereof has one or more of the following features when administered to a subject, such as a human or non-human mammal:
a. reduction of low-density lipoprotein (LDL-C) levels of at least about −25% to about −40% relative to a predose level with a sustained reduction over at least a 14 day-period upon administration to a subject, wherein the sustained reduction is preferably at least −25% and more preferably at least −30% relative to a predose level, particularly if administered in a dose of about 40 to about 60 mg, preferably about 45 to about 55 mg and more preferably about 50 mg in a biweekly administration regime (every other week, E2W);
b. reduction of low-density lipoprotein (LDL-C) of at least about −50% to about −65% relative to a predose level with a sustained reduction over at least a 14 day-period upon administration to a subject, wherein the sustained reduction is preferably at least −40% and more preferably at least −45% relative to a predose level, particularly if administered in a dose of about 100 mg E2W.
c. reduction of low-density lipoprotein (LDL-C) of at least about −60% to at least about −75% [e.g. at least about −60%, at least about −65%, at least about −70 or at least about −75%] relative to a predose level with a sustained reduction over at least a 14 day-period upon administration to a subject, wherein the sustained reduction is preferably at least −55% and more preferably at least −60% relative to a predose level, particularly when administered in a dose of about 150 mg E2W,
d. reduction of low-density lipoprotein (LDL-C) of at least about 40% to about 75% relative to a predose level with a sustained reduction over at least a 28 day period, wherein the sustained reduction is preferably at least −35% and more preferably at least −40% relative to a predose level, particularly when administered in a dose of about 200 mg E4W
e. reduction of low-density lipoprotein (LDL-C) of at least about −50% to about −75% relative to a predose level with a sustained reduction over at least a 28 day-period upon administration to a subject, wherein the sustained reduction is preferably at least −40% and more preferably at least −45% relative to a predose level, particularly when administered in a dose of about 300 mg E4W,
f. increase of serum HDL cholesterol levels of at least 2%, at least 2.5%, at least, 3%, at least 3.5%, at least 4%, at least 4.5%, at least 5% or at least 5.5% relative to a predose level upon administration to a subject, particularly when administered in a dose of about 150 mg E2W,
g. little or no measurable effect on troponin levels upon administration to a subject,
h. increase of one or more of: Total-Cholesterol levels, ApoB levels, non HDL-C levels, Apo-B/ApoA-1 ratio, upon administration to a subject.

According to another preferred embodiment, the antibody or antigen-binding fragment thereof is capable of overcoming statin resistance when administered to a subject with statin-resistant hypercholesterolemia.

According to another preferred embodiment, the antibody or antigen-binding fragment thereof comprises the heavy and light chain CDRs of a HCVR/LCVR amino acid sequence pair as shown in SEQ ID NOs: 90/92 substantially identical sequences having at least 98% or 99% identity therewith.

According to another preferred embodiment, the antibody or antigen-binding fragment thereof comprises a HCVR/LCVR amino acid sequence pair as shown in SEQ ID NOs: 90/92 or a pair of substantially identical sequences having at least 98% or 99% identity therewith.

According to another preferred embodiment, the antibody or antigen-binding fragment thereof competes for binding to hPCSK9 with an antibody or antigen-binding fragment comprising a HCVR/LCVR amino acid sequence pair as shown in SEQ ID NOs: 90/92.

According to another preferred embodiment, the antibody or antigen-binding fragment thereof binds an epitope comprising amino acid residue 238 of hPCSK9 (SEQ ID NO:755).

According to another preferred embodiment, the antibody or antigen-binding fragment thereof binds an epitope comprising one or more of amino acid residues at positions 238, 153, 159 and 343 of hPCSK9 (SEQ ID NO:755).

According to another preferred embodiment, the antibody or antigen-binding fragment thereof binds an epitope which does not comprise an amino acid residue at positions 192, 194, 197 and/or 237 of hPCSK9 (SEQ ID NO:755).

The pharmaceutical composition can be formulated according to any pharmaceutically applicable formulation as known in the art, and specifically as herein described, such as dry formulation for dissolution or liquid formulation. Suitable formulations of antibodies are known in the art and comprise dry formulations (e.g. freeze-dried, spray-dried or lyophilized, water-free concentrate) as well as liquid formulations (e.g. solutions). Suitable formulations of statins are as well known in the art and comprise dry formulations as well as liquid formulations, e.g suspensions, dispersions and solutions (for a reference, see e.g. "Statins therapy: a review on conventional and novel formulation approaches" R. Tiwari and K. Pathak, Journal of Pharmacy and Pharmacology, 2011, that is hereby incorporated in entirety).

According to a preferred embodiment, the pharmaceutical composition comprises the antibody or antigen-binding fragment thereof as dry formulation for dissolution such as a lyophilized powder, freeze-dried or spray-dried powder or water free concentrate.

According to another preferred embodiment, the pharmaceutical composition comprises the antibody or antigen-binding fragment thereof as liquid formulation, e.g. injection or infusion solution.

According to another preferred embodiment, the pharmaceutical composition comprises the HMG-CoA reductase inhibitor as oral or peroral formulation, e.g. capsule or tabled, or as liquid formulation, e.g. suspension, dispersion or solution, e.g. for peroral administration, injection or infusion.

According to another preferred embodiment the pharmaceutical composition is for use in the treatment of a disease or condition in which PCSK9 expression or activity causes an impact or for lowering elevated total cholesterol or elevated LDL-C levels. Further preferred uses, dosage regimens, administration regimens of the antibody or fragment thereof or of the HMG-CoA reductase inhibitor, or populations to be treated with the pharmaceutical composition described in present application, for example in the seventh, eleventh to thirteenth or eighteenth to nineteenth aspect.

In a second aspect, the present invention concerns an injection solution as herein described comprising the antibody or antigen-binding fragment thereof of present invention, and preferably comprising about 40 mg to about 200 mg or about 50 to about 200 mg, e.g. about 40 mg, about 50 mg, about 75 mg, at about 100 mg, about 150 mg or about 200 mg of the antibody or antigen-binding fragment thereof per 1 ml volume.

The injectable preparations may include dosage forms for intravenous, subcutaneous, intracutaneous and intramuscular injections, drip infusions, etc. These injectable preparations may be prepared by methods publicly known. For example, the injectable preparations may be prepared, e.g., by dissolving, suspending or emulsifying the antibody or its salt described above in a sterile aqueous medium or an oily medium conventionally used for injections. As the aqueous medium for injections, there are, for example, physiological saline, an isotonic solution containing glucose and other auxiliary agents, etc., which may be used in combination with an appropriate solubilizing agent such as an alcohol (e.g., ethanol), a polyalcohol (e.g., propylene glycol, polyethylene glycol), a nonionic surfactant [e.g., polysorbate 80, HCO-50 (polyoxyethylene (50 mol) adduct of hydrogenated castor oil)], etc. As the oily medium, there are employed, e.g., sesame oil, soybean oil, etc., which may be used in combination with a solubilizing agent such as benzyl benzoate, benzyl alcohol, etc. The injection thus prepared is preferably filled in an appropriate ampoule. A pharmaceutical composition of the present invention can be delivered subcutaneously or intravenously with a standard needle and syringe. In addition, with respect to subcutaneous delivery, a pen delivery device readily has applications in delivering a pharmaceutical composition of the present invention. Such a pen delivery device can be reusable or disposable. A reusable pen delivery device generally utilizes a replaceable cartridge that contains a pharmaceutical composition. Once all of the pharmaceutical composition within the cartridge has been administered and the cartridge is empty, the empty cartridge can readily be discarded and replaced with a new cartridge that contains the pharmaceutical composition. The pen delivery device can then be reused. In a disposable pen delivery device, there is no replaceable cartridge. Rather, the disposable pen delivery device comes prefilled with the pharmaceutical composition held in a reservoir within the device. Once the reservoir is emptied of the pharmaceutical composition, the entire device is discarded.

In a third aspect the present invention concerns a dry formulation as herein described comprising the antibody or antigen-binding fragment thereof of present invention, and preferably comprising about 40 mg to about 500 mg, 50 to about 500 mg, about 50 to about 400, about 50 to about 300 e.g. about 40 mg, about 50 mg, about 75 mg, at about 100 mg, about 150 mg, about 200 mg, about 250 mg, about 300 mg, about 350 mg, about 400 mg, about 450 mg or about 500 mg and more preferably about 50 mg, about 100 mg, about 150 mg, about 200 mg, about 250 mg, about 300 mg and even more preferably about 150 mg, about 200 mg or about 300 mg of the antibody or antigen-binding fragment thereof per dose.

Suitable formulations of antibodies in general are known in the art and comprise dry formulations (e.g. freeze-dried, spray-dried or lyophilized, water-free concentrate) as well as liquid formulations (e.g. solutions). Suitable formulations of statins are as well known in the art and comprise dry formulations as well as liquid formulations, e.g suspensions, dispersions and solutions (for a reference, see e.g. "Statins therapy: a review on conventional and novel formulation approaches" R. Tiwari and K. Pathak, Journal of Pharmacy and Pharmacology, 2011, that is hereby incorporated in entirety).

The formulations of present invention can comprise further active ingredients such as an HMG-CoA reductase inhibitor as herein described. Preferred embodiments of the formulations according to present invention are described in other sections of present application, e.g. in the other aspects of present invention such as the first or fourth aspect.

According to a fourth aspect, present invention concerns an antibody or antigen binding fragment thereof specifically binding hPCSK9 (human proprotein convertase subtilisin/kexin type 9), as comprised in one of the pharmaceutical compositions of the invention.

According to a preferred embodiment, the antibody is characterized by one or more of the following features upon administration to a subject, preferably a human or non-human mammal:
  1. reduction of low-density lipoprotein (LDL-C) levels of at least about −25% to about −40% relative to a predose level with a sustained reduction over at least a 14 day-period, wherein the sustained reduction is preferably at least −25% and more preferably at least −30% relative to a predose level, particularly if administered in a dose of about 40 to about 60 mg, preferably about 45 to about 55 mg and more preferably about 50 mg in a biweekly administration regime (every other week, E2W), 2. reduction of low-density lipoprotein (LDL-C) of at least about −50% to about −65% relative to a predose level with a sustained reduction over at least a 14 day-period, wherein the sustained reduction is preferably at least −40% and more preferably at least −45% relative to a predose level, particularly if administered in a dose of about 100 mg E2W, 2. reduction of low-density lipoprotein (LDL-C) of at least about −60% to at least about −75% [e.g. at least about −60%, at least about −65%, at least about −70 or at least about −75%] relative to a predose level with a sustained reduction over at least a 14 day-period, wherein the sustained reduction is preferably at least −55% and more preferably at least −60% relative to a predose level, particularly when administered in a dose of about 150 mg E2W, 3. reduction of low-density lipoprotein (LDL-C) of at least about 40% to about 75% relative to a predose level with a sustained reduction over at least a 28 day period, wherein the sustained reduction is preferably at least −35% and more preferably at least −40% relative to a predose level, particularly when administered in a dose of about 200 mg E4W, 4. reduction of low-density lipoprotein (LDL-C) of at least about −50% to about −75% relative to a predose level with a sustained reduction over at least a 28 day-period, wherein the sustained reduction is preferably at least −40% and more preferably at least −45% relative to a predose level, particularly when administered in a dose of about 300 mg E4W, 5. increase of serum HDL cholesterol levels of at least 2%, at least 2.5%, at least, 3%, at least 3.5%, at least 4%, at least 4.5%, at least 5% or at least 5.5% relative to a predose level, particularly when admimistered in a dose of about 150 mg E2W, 6. reduction of serum total cholesterol at least about 25% to about 35% relative to a predose level with a sustained reduction over at least a 24 day period, 7. reduction of serum total cholesterol at least about 65% to about 80% relative to a predose level with a sustained reduction over at least a 24 day period, 8. reduction of serum triglyeride levels at least about 25% to about 40% relative to a predose level, 9. little or no measurable effect on liver function, as determined by ALT and AST measurements, 10. little or no measurable effect on troponin levels, 11. Increase of one or more of: Total-Cholesterol levels, ApoB levels, non HDL-C levels, Apo-B/ApoA-1 ratio, The antibody according to present invention exhibits the above properties preferably if administered in combination with an HMG-CoA reductase inhibitor treatment. Preferred embodiments of HMG-CoA reductase inhibitors to be used in conjunction with the antibody of the invention and dosage and administration regimes thereof can be found throughout the specification, particularly as described in the aspects related to medical uses and methods of treatment.

According to a preferred embodiment of the antibodies and antigen-binding fragments thereof of present invention, particularly of the antibody or antigen-binding fragment according to the fourth aspect, the antibody or antigen binding fragment thereof has one or more of the following characteristics:
(i) The antibody or the antigen-binding fragment comprises the heavy and light chain CDRs of a HCVR/LCVR amino acid sequence pair as shown in SEQ ID NOs: 90/92.
(ii) The antibody or antigen-binding fragment thereof comprises a HCVR/LCVR amino acid sequence pair as shown in SEQ ID NOs: 90/92.
(iii) The antibody or antigen-binding fragment thereof competes for binding to hPCSK9 with an antibody or antigen-binding fragment comprising a HCVR/LCVR amino acid sequence pair as shown in SEQ ID NOs: 90/92.

According to another preferred embodiment of the antibodies and antigen-binding fragments thereof of present invention, particularly of the antibody or antigen-binding fragment according to the fourth aspect, the antibody or antigen binding fragment thereof has one or more of the following characteristics:
(i) overcomes statin resistance in mammals, especially in rodents such as hamster
(ii) increase in LDLR expression in mammals, particularly in rodents such as hamster
(iii) decrease of serum LDL-C in rodents such as hamster
(iv) synergistic decrease of LDL-C in conjunction with HMG-CoA reductase inhibitor administration, particularly in rodents such as hamster, wherein the HMG-CoA reductase inhibitor is preferably Atorvastatin.

Further suitable characteristics and structural features of the antibody of present invention and particularly of the antibody of the fourth aspect, as well as antibodies and antigen-binding fragments thereof that can be used for practicing the fifteenth aspect and the other aspects of the present invention are described in the section "Preferred Antibodies for Practicing the Present Invention".

The antibody of present invention, such as the antibody according to the fourth aspect, is preferably formulated as a pharmaceutically applicable formulation as known in the art, and specifically as herein described, such as dry formulation for dissolution or liquid formulation, e.g. as described at the second or third aspect.

In a fifth aspect the present invention is directed to a unit dosage form comprising the antibody, antigen-binding fragment thereof or pharmaceutical composition of present invention. Suitable embodiments of the antibody, pharmaceutical composition or formulation to be used for practicing the fifth aspect of present invention can be gained from the respective sections of present application, such as the first to fourth aspects or from the section "Preferred Antibodies for Practicing the Present Invention".

According to a preferred embodiment, the unit dosage form comprises about 40 mg, about 50 mg, about 75 mg, at about 100 mg, about 150 mg, about 200 mg, about 250 mg, about 300 mg, about 350 mg, about 400 mg, about 450 mg, or about 500 mg of the antibody or antigen-binding fragment thereof.

According to another preferred embodiment, the unit dosage form comprises the antibody or fragment thereof as dry formulation for dissolution in a hermetically sealed container such as a vial, an ampoule or sachette.

According to another preferred embodiment, the unit dosage form comprises the antibody or fragment thereof as liquid formulation in a hermetically sealed container such as a vial, a sachette, a pre-filled syringe, a pre-filled autoinjector or a cartridge for a reusable syringe or applicator.

According to another preferred embodiment, the quantity of active ingredient is indicated on the hermetically-sealed container.

As used in the different aspects and embodiments of present invention and in particularly of the fifth aspect, the term "unit dosage form" refers to physically discrete units suitable as unitary dosages for human and animal subjects, each unit containing a predetermined quantity of active material (e.g., about 40 mg or about 50 mg to about 500 mg of PCSK5 antibody and/or of e.g. 0.05 mg to 100 mg HMG-CoA reductase inhibitor) calculated to produce the desired therapeutic effect in association with the required pharmaceutical diluent, carrier or vehicle. The specifications for the novel unit dosage forms of this invention are dictated by and are directly dependent on (a) the unique characteristics of the active material and the particular therapeutic effect to be achieved, and (b) the limitation inherent in the art of compounding such an active material for therapeutic use in animals or humans, as disclosed in this specification, these being features of the present invention. Examples of suitable unit dosage forms in accord with this invention are vials, tablets, capsules, troches, suppositories, powder packets, wafers, cachets, ampules, segregated multiples of any of the foregoing, and other forms as herein described or generally known in the art.

One or more such unit dosage forms of the antibody can be comprised in an article of manufacture of present invention, optionally further comprising one or more unit dosage forms of an HMG-CoA reductase inhibitor (e.g. a blister of tablets comprising as active ingredient the HMG-CoA reductase inhibitor).

The term "active material" refers to any material with therapeutic activity, such as one or more active ingredients. The active ingredients to be employed as therapeutic agents can be easily prepared in such unit dosage form with the employment of pharmaceutical materials which themselves are available in the art and can be prepared by established procedures. Preferred active ingredients of present invention are the antibody or fragment thereof or an HMG-CoA reductase inhibitor such as a statin.

In a preferred embodiment, the unit dosage form comprises 40-about 500 mg of the antibody or an antigen-binding fragment of present invention. According to another preferred embodiment, the unit dosage form comprises about 40 mg, about 50 mg, about 75 mg, at about 100 mg, about 150 mg, about 200 mg, about 250 mg, about 300 mg, about 350 mg, about 400 mg, about 450 mg, or about 500 mg and more preferably about 150 mg, about 200 mg or about 300 mg of the antibody or antigen-binding fragment thereof. Further preferred dosages, and dosage regimens are as described elsewhere in the application, such as at the first, second or fifteenth to nineteenth aspect.

According to another preferred aspect, the unit dosage form comprises the antibody, antigen-binding fragment thereof or pharmaceutical composition as dry formulation for dissolution such as a lyophilized powder, freeze-dried powder or water free concentrate. According to another preferred embodiment the dry formulation is comprised in a hermetically sealed container such as a vial, an ampoule or sachette.

According to another preferred embodiment, the unit dosage form comprises the antibody, antigen-binding fragment thereof or pharmaceutical composition as liquid formulation, e.g. injection or infusion solution. According to another preferred embodiment the liquid formulation is comprised in a hermetically sealed container such as a vial, a sachette, a pre-filled syringe, a pre-filled autoinjector or a cartridge for a reusable syringe or applicator.

It is further preferred, if the quantity of active ingredient (e.g. antibody) is indicated on the hermetically-sealed container of the unit dosage form.

The following preparations are illustrative of the preparation of the unit dosage forms of the present invention, and not as a limitation thereof. Several dosage forms may be prepared embodying the present invention. For example, a unit dosage per vial may contain 0.5 ml, 1 ml, 2 ml, 3 ml, 4 ml, 5 ml, 6 ml, 7 ml, 8 ml, 9 ml, 10 ml, 15 ml, or 20 ml of PCSK5 antibody or a fragment thereof ranging from about 40 to about 500 mg or from about 50 mg to about 500 mg of PCSK5 antibody. If necessary, these preparations can be adjusted to a desired concentration by adding a sterile diluent to each vial.

In one embodiment, the ingredients of the compositions of the invention are supplied either separately or mixed together in a unit dosage form, for example, as a dry formulation for dissolution or a liquid formulation. The preparation of pharmaceutically acceptable formulations of proteinaceous biomolecules such as antibodies or antigen-binding fragments thereof or of small molecule compounds such as statins is generally known in the art. In addition, see section "Preferred antibodies for practicing the invention" or the second or third aspect of present invention for some suitable formulations of antibodies and for small molecule HMG-CoA reductase inhibitors such as statins, see e.g. "Statins therapy: a review on conventional and novel formulation approaches", r. Tiwari and K. Pathak, Journal of Pharmacy and Pharmacology 2011, p. 983-998. According to a preferred embodiment, the active ingredients, active material or pharmaceutical composition according to present invention is a dry formulation for liquid dissolution, such as a lyophilized powder, freeze-dried powder or water free concentrate, preferably comprised in a hermetically sealed container such as a vial, an ampoule or sachette, and preferably indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

The formulations of the invention include bulk drug compositions useful in the manufacture of pharmaceutical compositions (e.g., compositions that are suitable for administration to a subject or patient) which can be used in the preparation of unit dosage forms. In a preferred embodiment, a composition of the invention is a pharmaceutical composition. Such compositions comprise a prophylactically or therapeutically effective amount of one or more prophylactic or therapeutic agents (e.g., an antibody of the invention or other prophylactic or therapeutic agent), and a pharmaceutically acceptable carrier. Preferably, the pharmaceutical compositions are formulated to be suitable for the route of administration to a subject.

In a specific embodiment, the term "pharmaceutically acceptable" means approved by a regulatory agency of the U.S. Federal or a state government or the EMA (European Medicines Agency) or listed in the U.S. Pharmacopeia Pharmacopeia (United States Pharmacopeia-33/National Formulary-28 Reissue, published by the United States Pharmacopeial Convention, Inc., Rockville Md., publication date: April 2010) or other generally recognized pharmacopeia for use in animals, and more particularly in humans.

The term "carrier" refers to a diluent, adjuvant {e.g., Freund's adjuvant (complete and incomplete)), excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents. These compositions can take the form of solutions, suspensions, emulsion, tablets, pills, capsules, powders, sustained-release formulations and the like. Oral formulation can include standard carriers such as pharmaceutical grades of mannitol, lactose, starch, magnesium stearate, sodium saccharine, cellulose, magnesium carbonate, etc. Examples of suitable pharmaceutical carriers are described in "Remington's Pharmaceutical Sciences" by E. W. Martin. Such compositions will contain a prophylactically or therapeutically effective amount of the antibody, preferably in purified form, together with a suitable amount of carrier so as to provide the form for proper administration to the patient. The composition may further contain one or more other active ingredients such as an HMG-CoA reductase inhibitor. The formulation should suit the mode of administration.

Generally, the ingredients of compositions of the invention are supplied either separately or mixed together in unit dosage form, for example, as a dry formulation for dissolution such as a lyophilized powder, freeze-dried powder or water free concentrate in a hermetically sealed container such as an ampoule or sachette indicating the quantity of active agent. The ingredients of compositions of the invention can also be supplied as admixed liquid formulation (i.e. injection or infusion solution) in a hermetically sealed container such as an ampoule, sachette, a pre-filled syringe or autoinjector, or a cartridge for a reusable syringe or applicator (e.g. pen or autoinjector). Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration. The composition can also comprise two or more active ingredients that are each formulated in a different or the same manner, e.g. a combination of an antibody of present invention together with an HMG-CoA reductase inhibitor or present invention.

The invention also provides that the formulation is packaged in a hermetically sealed container such as an ampoule or sachette indicating the quantity of antibody. In one embodiment, the formulation of the invention comprising an antibody is supplied as a dry sterilized lyophilized powder, freeze-dried powder or water free concentrate in a hermetically sealed container and can be reconstituted, e.g., with water or saline to the appropriate concentration for administration to a subject. In one embodiment, the formulation of the invention comprising an antibody is supplied as a dry sterile lyophilized powder in a hermetically sealed container at a unit dosage of at least 40 mg, at least 50 mg, more preferably at least 75 mg, at least 100 mg, at least 150 mg, at least 200 mg, at least 250 mg, at least 300 mg, at least 350 mg, at least 400 mg, at least 450 mg, or at least 500 mg, of antibody or antigen-binding fragment thereof. The lyophilized formulation of the invention comprising an antibody should be stored at between 2 and 8° C. in its original container and the antibody should be administered within 12 hours, preferably within 6 hours, within 5 hours, within 3 hours, or within 1 hour after being reconstituted. The formulation of the invention comprising antibodies can be formulated as neutral or salt forms. Pharmaceutically acceptable salts include those formed with anions such as those derived from hydrochloric, phosphoric, acetic, oxalic, tartaric acids, etc., and those formed with cations such as those derived from sodium, potassium, ammonium, calcium, ferric hydroxides, isopropylamine, triethylamine, 2-ethylamino ethanol, histidine, procaine, etc.

In a sixth aspect, present invention concerns an article of manufacture comprising the pharmaceutical composition of present invention, the liquid formulation of present invention or the dry formulation of present invention, the antibody or antigen-binding fragment thereof of present invention or one or more unit dosage forms of present invention and a container or package.

According to a preferred embodiment, the article of manufacture comprises sufficient unit dosage forms of antibody for a two-week (14 day), four-week (28 day) or one month period, with either E2W, E4W or once-a-month administration regime.

The article of manufacture can comprise one or more unit dosage form that contain(s) both, the antibody and the HMG CoA-inhibitor, e.g. a unit dosage form comprising a liquid formulation for injection or infusion comprising both active ingredients. The article of manufacture can also comprise the antibody (or antigen-binding fragment thereof) and the HMG-CoA reductase inhibitor in two or more separate unit dosage forms.

According one embodiment, the article of manufacture comprises one or more separate unit dosage forms of the and the HMG-CoA reductase inhibitor according to present invention.

According to a preferred embodiment, each unit dosage form of HMG-CoA reductase inhibitor comprises about 0.05 mg to about 100 mg HMG-CoA reductase inhibitor.

According to another preferred embodiment the HMG-CoA reductase inhibitor is a statin, preferably selected from the list containing: cerivastatin, atorvastatin, simvastatin, pitavastatin, rosuvastatin, fluvastatin, lovastatin or pravastatin and preferably atorvastatin.

According to another preferred embodiment the HMG-CoA reductase inhibitor, e.g. the statin, is in an effective dose for administration once per day.

According to another preferred embodiment, the unit dosage form of HMG-CoA reductase inhibitor comprises about 0.5 to about 100 mg, about 5 to about 90 mg, of about 10, 20, 40 or 80 mg HMG-CoA reductase inhibitor.

According to another preferred embodiment, the article of manufacture comprises sufficient unit dosage forms of HMG-CoA reductase inhibitor for a daily administration regime.

According to another preferred embodiment, the unit dosage form comprising the antibody is a sachette, a pre-filled syringe, a pre-filled autoinjector or a cartridge for a reusable syringe or applicator, especially comprising 1 ml or 2 ml of injection solution.

According to another embodiment, the article of manufacture comprises one or more of the following components:

a. One or more unit dosage forms comprising the antibody of present invention
b. One or more unit dosage forms comprising the HMG-CoA reductase inhibitor of present invention;
c. Instructions for use;
d. A device for application of the antibody such as a syringe.

According to another preferred embodiment, the article of manufacture comprises sufficient unit dosage forms of the antibody and preferably also of the HMG-CoA reductase inhibitor . . .

(a) for one single administration of antibody and HMG-CoA reductase inhibitor, e.g. comprising an ampoule, sachette, vial, cartridge or pre-filled syringe comprising about 50 mg, about 100 mg, about 150 mg, about 200 mg, about 250 mg, about 300 mg, about 350 mg, about 400 mg, about 450 mg or about 500 mg antibody and preferably about 150 mg antibody, about 200 mg antibody or about 300 mg antibody, together with tablet or capsule, e.g. for oral or peroral administration comprising the HMG, CoA-inhibitor, e.g. comprising about 10 mg, about 20 mg, about 40 mg or about 80 mg of the HMG CoA-inhibitor such as atorvastatin.

(b) for a two-week (i.e. 14-day) treatment with antibody and HMG-CoA reductase inhibitor, e.g. comprising an ampoule, sachette, vial, cartridge or pre-filled syringe comprising about 50 mg, about 100 mg, about 150 mg, about 200 mg, about 250 mg, about 300 mg, about 350 mg, about 400 mg, about 450 mg or about 500 mg antibody and preferably about 150 mg antibody, about 200 mg antibody or about 300 mg antibody; together with sufficient units comprising of HMG-CoA reductase inhibitor (e.g. tablets or capsules, e.g. for oral or peroral administration) for a 14-day treatment, e.g. 14 units for a once-a day administration regime of HMG-CoA reductase inhibitor or 28 units for a twice-a day administration regime etc, wherein the units per day of HMG CoA-inhibitor preferably comprise about 10 mg, about 20 mg, about 40 mg or about 80 mg of the HMG CoA-inhibitor such as atorvastatin. In the case the antibody is to be administered in a dosage of more than 200 mg, two unit dosage forms of antibody together comprising the total dose may be preferable (e.g. two pre-filled syringes comprising about 150 mg of antibody in 1 ml of liquid formulation each for a total administration (e.g. subcutaneous injection) of about 300 mg antibody in two shots) may be preferable (or two units with about 100 mg each for a total administration of about 200 mg antibody, two units with about 175 mg for a total administration of about 350 antibody, etc. . . . ).

(c) for a four week (i.e, 28-day) treatment with antibody and HMG-CoA reductase inhibitor, e.g.
 1. for a E2W administration regimen of the antibody with about 50 to about 200 mg antibody per two weeks: comprising two unit dosage forms (e.g. as exemplified above) with each about 50 mg, about 100 mg, about 150 mg or about 200 mg antibody or antigen-binding fragment thereof together with 28 unit dosage forms of HMG-CoA reductase inhibitor (as exemplified above) for a daily once a day administration regime or together with 56 unit dosage forms of HMG-CoA reductase inhibitor for a daily twice-a day administration regime, preferably 28 unit dosage forms (e.g. capsules or tablets) of about 10 mg, about 20 mg, about 40 mg or about 80 mg atorvastatin 2. for an E4W administration regime of the antibody or fragment thereof with an administration of about 200 mg per four weeks (28 days): e.g. comprising one unit dosage form of the antibody with about 200 mg antibody (e.g. as exemplified above) together with 28 or 56, and preferably 28 unit dosage forms of HMG-CoA reductase inhibitor (e.g. as exemplified above)
 3. for an E4W administration regime of the antibody with more than 200 mg per four weeks (28 days): comprising two unit dosage forms that together comprise the total dose of antibody (e.g. two pre-filled syringes each comprising 1 ml of liquid antibody formulation with 150 mg antibody each) or comprising one unit dosage form that comprises the total amount of antibody to be administered (e.g. a vial comprising about 300 mg antibody for dissolution or a vial, cartridge or pre-filled syringe comprising about 300 mg of the antibody in liquid formulation (i.e. about 2 ml of liquid formulation, wherein 1 ml of liquid formulation comprises about 150 mg of the antibody); together with 28 or 56, and preferably 28 unit dosage forms of HMG-CoA reductase inhibitor (e.g. as exemplified above)

(d) for a one-month treatment with antibody and HMG-CoA reductase inhibitor: comprising the same numbers of unit dosage forms of antibody as exemplified under (c) for an administration once or twice per month, e.g. every first day of the month or every first Monday etc. of the month for a once a month administration, or e.g. every first and $14^{th}$ or $15^{th}$ day of the month for a twice-a-month administration regime; in addition the article of manufacture comprises 31 unit dosage forms of HMG-CoA reductase inhibitor, preferably tablets or capsules arranged in a blister containing a consecutive numbering from 1-31 for the days of the month (wherein the superfluous tablets or capsules for excess days are to be discarded).

According to another preferred embodiment the article of manufacture comprises: (a) a packaging material; (b) an antibody or an antigen-binding fragment thereof which specifically binds hPCSK9; and (c) a label or packaging insert contained within the packaging material indicating that patients receiving treatment with said antibody or antigen-binding fragment can be treated for a disease or condition selected from the group consisting of hypercholesterolemia, hyperlipidemia, dyslipidemia, atherosclerosis and cardiovascular diseases.

According to another preferred embodiment the article of manufacture comprises: (a) a packaging material; (b) an antibody or an antigen-binding fragment thereof which specifically binds hPCSK9; and (c) a label or packaging insert contained within the packaging material indicating the treatment of patients with said antibody or antigen-binding fragment thereof together with the application of an HMG Co A inhibitor such as a statin.

According to another preferred embodiment the article of manufacture comprises: (a) a packaging material; (b) an antibody or an antigen-binding fragment thereof which specifically binds hPCSK9; and (c) a label or packaging insert indicating that the treatment of patients with said antibody or antigen-binding fragment thereof together with an HMG-Co A inhibitor such as a statin is contraindicated for patients belonging to one or more of the following groups: (i) smokers; (ii) persons being 70 years old or older; (iii) persons suffering from hypertension; (iv) women who are pregnant; (v) women who are trying to become pregnant;

(vi) women who are breast-feeding; (vii) persons who have or ever had a disease affecting the liver; (viii) persons who had any unexplained abnormal blood tests for liver function; (ix) persons who drink excessive amounts of alcohol; (x) persons having kidney problems; (xi) persons suffering from hypothyroidism; (xii) persons suffering from muscle disorders; (xiii) persons having encountered previous muscular problems during treatment with lipid-lowering medicine; (xiv) persons having serious problems with their breathing; (xv) persons taking one or more of the following medicines: medicines altering the way the immune systems works (e.g. cyclosporin or antihistamines), antibiotics or antifungal medicines (e.g. erythromycin, clarithromycin, ketoconazole, itraconazole, rifampicin, fusidic acid), medicines regulating lipid levels (e.g. gemfibrozil, colestipol), calcium channel blockers (e.g. verapamil, diltiazem), medicines regulating the heart rhythm (digoxin, amiodarone), protease inhibitors used in the treatment of HIV (e.g. nelfinavir), warfarin, oral contraceptives, antacids or St. John's Wort; or (xvi) persons drinking more than 0.1 L of grapefruit juice per day or eating more than half a grapefruit per day; (xvii) persons having a body mass index (BMI) of more than 40; (xviii) persons having a body mass index (BMI) of less than 18; (xix) persons suffering from type 1 diabetes or type 2 diabetes; (xx) persons positive for hepatitis B or hepatitis C; (xxi) persons having a known sensitivity to monoclonal antibody therapeutics; (xxii) persons having a neutrophil concentration of less than $1500/mm^3$; (xxiii) persons having a platelet concentration of less than $100000/mm^3$; (xxiv) men having a serum creatinine level larger than 1.5×ULN (upper limit of normal); (xxv) women having a serum creatinine level larger than 1.4×ULN (upper limit of normal); (xxvi) persons having an alanine transaminase (ALT) level or aspartate transaminase (AST) level larger than 2×ULN; or (xxvii) persons having a CPK level larger than 3×ULN.

In preferred embodiments of the sixth aspect, the antibody or antigen-binding fragment is an antibody or antigen-binding fragment as specified below in the section "Preferred Antibodies for Practicing the Present Invention".

The label or packaging insert according to the different aspects and embodiments of the invention, particularly in respect to the different articles of manufacture of the invention, can be any kind of data carrier suitable to be arranged within (either loose or attached to another component of the article of manufacture, e.g. to a blister or a vial containing unit dosage forms of the antibody and/or the HMG-CoA reductase inhibitor) the package or container or on the outside of the package or container. Preferably, the data carrier (i.e. label or, chip, bar code or leaflet or label comprising a bar code etc.) comprises information such as (i) composition, formulation, concentration and total amount, identity of active ingredient (s) contained in the article of manufacture, i.e. of the antibody or antigen-fragments, HMG-CoA reductase inhibitor, pharmaceutical compositon, unit dosage form or formulation of present invention (ii) number and composition of unit dosage form contained in the article of manufacture (iii) indications, contra-indications of the antibody or antigen-fragments, pharmaceutical compositon, unit dosage form or formulation of present invention (iv) (ii) subjects/patients or subject/patient populations indicated or contra-indicated for treatment with the antibody or antigen-fragments, pharmaceutical compositon, unit dosage form or formulation of present invention (v) instructions for use, dosage regimens and/or administration regimes (vi) quality information such as information about the lot/batch number of the of the antibody or antigen-fragments, pharmaceutical compositon, unit dosage form or formulation of present invention, the manufacturing or assembly site or the expiry or sell-by date, (vii) information concerning the correct storage or handling of the article of manufacture, of the device for application, or of the antibody or antigen-fragments, pharmaceutical compositon, unit dosage form or formulation of present invention, (iv) information concerning the composition of the buffer(s), diluent(s), reagent(s), excipients, carriers, formulations of the antibody or antigen-fragments, pharmaceutical compositon, unit dosage form or formulation of present invention, (vi) a warning concerning possible consequences when applying unsuitable dosage or administration regimens and/or use in contraindicated indications of patient populations.

In preferred embodiments of the sixth aspect, the label or packaging insert contains reference to a method of treatment or medical use according to the seventh, eleventh to thirteenth, eighteenth or nineteenth aspect and the embodiments of the first or second aspect as described herein.

According to another preferred embodiment, the article of manufacture comprises (a) a packaging material; (b) an antibody or an antigen-binding fragment thereof which specifically binds hPCSK9; and (c) a label or packaging insert contained within the packaging material indicating that patients receiving treatment with said antibody or antigen-binding fragment can be treated for a disease or condition selected from the group consisting of hypercholesterolemia, hyperlipidemia, dyslipidemia, atherosclerosis and cardiovascular diseases and further indicating that subjects falling into one or more groups of subjects as recited in the eighteenth aspect can be treated.

According to another preferred embodiment the article of manufacture comprises: (a) a packaging material; (b) an antibody or an antigen-binding fragment thereof which specifically binds hPCSK9; and (c) a label or packaging insert contained within the packaging material indicating that patients receiving treatment with said antibody or antigen-binding fragment can be treated for a disease or condition selected from the group consisting of hypercholesterolemia, hyperlipidemia, dyslipidemia, atherosclerosis and cardiovascular diseases and further indicating that the treatment of patients with said antibody or antigen-binding fragment thereof is contraindicated for patients belonging to one or more groups of subjects as recited in the nineteenth aspect.

In preferred embodiments of sixth aspect, the label or packaging insert contains a reference to a method of treatment according to the medical uses and methods of treatment as herein described, e.g. according to the seventh, eleventh to thirteenth, eighteenth or nineteenth aspect and the embodiments thereof as described herein.

According to a seventh aspect, present invention concerns the pharmaceutical composition, antibody or antigen-binding fragment thereof of present invention, for use in the treatment of a disease or condition in which PCSK9 expression or activity causes an impact.

According to a preferred embodiment of the seventh aspect, the disease or condition is selected from the group consisting of: elevated total cholesterol levels, elevated low-density lipoprotein (LDL-C) levels, hypercholesterolemia, hyperlipidemia, dyslipidemia, and atherosclerosis, particularly primary hypercholesterolemia, familial hypercholesterolemia, or hypercholesteremia which is uncontrolled by statins.

According to another preferred embodiment, the composition, the antibody or antigen-binding fragment thereof is administered to the subject every other week (E2W), every fourth week (E4W) or once a month.

According to another preferred embodiment an HMG-CoA reductase inhibitor is co-administered with the pharmaceutical composition, the antibody or antigen-binding fragment thereof, preferably an HMG-CoA reductase inhibitor according to one of the different aspects of present invention, such as according to the first or second aspect.

According to another preferred embodiment the HMG-CoA reductase inhibitor is administered once a day and preferably every day.

In a second aspect the present invention is directed to an antibody or an antigen-binding fragment thereof which specifically binds hPCSK9 (human proprotein convertase subtilisin/kexin type 9) for use in the treatment of a disease or condition in which PCSK9 expression or activity causes an impact,
wherein the antibody or antigen-binding fragment thereof is for administration in a dosage amount ranging from 5 mg to 500 mg,
wherein the antibody or antigen-binding fragment thereof is further for administration in combination with an HMG-CoA reductase inhibitor at a dosage amount ranging from 0.05 mg to 100 mg.

In preferred embodiments of seventh the other aspects of present invention, the disease or condition in which PCSK9 expression or activity causes an impact is ameliorated, improved, inhibited or prevented with a PCSK9 antagonist.

In further preferred embodiments of the seventh and the other aspects of present invention, the disease or condition is selected from the group consisting of: elevated low-density lipoprotein cholesterol (LDL-C) levels, hypercholesterolemia, particularly hypercholesterolemia uncontrolled by statins, hyperlipidemia, dyslipidemia, atherosclerosis and cardiovascular diseases, particularly primary hypercholesterolemia such as primary familial hypercholesterolemia or primary non-familial hypercholesterolemia.

In preferred embodiments of the seventh and the other aspects of present invention, the antibody or antigen-binding fragment thereof is for administration to a subject indicated for LDL apheresis, a subject with PCSK9-activating mutations, a subject with heterozygous Familial Hypercholesterolemia, a subject with primary hypercholesterolemia, a subject with primary hypercholesterolemia who is statin uncontrolled, a subject at risk for developing hypercholesterolemia, a subject with hypercholesterolemia, a subject with hyperlipidemia, a subject with dyslipidemia, a subject with atherosclerosis or a subject with cardiovascular diseases. Most preferably, the subject is a human subject.

In some embodiments of the seventh and the other aspects of present invention, the antibody or antigen-binding fragment thereof is for administration in combination with an HMG-CoA reductase inhibitor, which is to be administered three times per day, twice per day, or once per day. In some embodiments of the second and the other aspects of present invention, the HMG-CoA reductase inhibitor is to be administered every day, every other day, every third day, every fourth day, every fifth day, or every sixth day. In some embodiments of the second and the other aspects of present invention, the HMG-CoA reductase inhibitor is to be administered every week, every other week, every third week, or every fourth week. In some embodiments of the second and the other aspects of present invention, the HMG-CoA reductase inhibitor is to be administered in the morning, at noon or in the evening. In preferred embodiments, the HMG-CoA reductase inhibitor is to be administered once per day, preferably orally, preferably in the evening.

In preferred embodiments of the seventh and the other aspects of present invention, the HMG-CoA reductase inhibitor is a statin. More preferably, the statin is selected from the group consisting of cerivastatin, atorvastatin, simvastatin, pitavastatin, rosuvastatin, fluvastatin, lovastatin, and pravastatin.

In more preferred embodiments of the seventh and the other aspects of present invention, the statin is
cerivastatin which is to be administered in a daily dosage of between 0.05 mg and 2 mg, preferably in a daily dosage of 0.2 mg, 0.4 mg, or 0.8 mg;
atorvastatin which is to be administered in a daily dosage of between 2 mg and 100 mg, preferably in a daily dosage of 10 mg, 20 mg, 40 mg, or 80 mg;
simvastatin which is to be administered in a daily dosage of between 2 mg and 100 mg, preferably in a daily dosage of 5 mg, 10 mg, 20 mg, 40 mg, or 80 mg;
pitavastatin which is to be administered in a daily dosage of between 0.2 mg and 100 mg, preferably in a daily dosage of 1 mg, 2 mg, 5 mg, 10 mg, or 20 mg;
rosuvastatin which is to be administered in a daily dosage of between 2 mg and 100 mg, preferably in a daily dosage of 5 mg, 10 mg, 20 mg, or 40 mg;
fluvastatin which is to be administered in a daily dosage of between 2 mg and 100 mg, preferably in a daily dosage of 20 mg, 40 mg, or 80 mg;
lovastatin which is to be administered in a daily dosage of between 2 mg and 100 mg, preferably in a daily dosage of 10 mg, 20 mg, 40 mg, or 80 mg; or
pravastatin which is to be administered in a daily dosage of between 2 mg and 100 mg, preferably in a daily dosage of 10 mg, 20 mg, 40 mg, or 80 mg.

In further preferred embodiments of the seventh and the other aspects of present invention, the antibody or antigen-binding fragment thereof is for administration to the subject every other week, every fourth week or once a month. Administration every fourth week or administration once a month is preferred in view of patient compliance. Administration every other week is preferred in viw of a very low variation of blood cholesterol levels. Other suitable time schedules for administration of the antibody or antigen-binding fragment thereof include without limitation an administration once per day, every other day, every third day, every fourth day, every fifth day, every sixth day, every week, every third week, every fifth week, every sixth week, every eighth week, every tenth week, and every twelfth week.

In a further preferred embodiment of the seventh and the other aspects of present invention, the antibody or antigen-binding fragment thereof is for administration in a dosage amount ranging from about 40 mg to about 500 mg or from about 50 mg to about 500 mg or from about 50 mg to about 400 mg or from about 50 mg to about 300 mg, or from about 100 mg to about 300 mg or from about 100 mg to about 200 mg. In more preferred embodiments, the antibody or antigen-binding fragment thereof is for administration in a dosage amount of about 50 mg, of about 100 mg, of about 150 mg, of about 200 mg, of about 250 mg, of about 300 mg, of about 350 or of about 400 mg.

According to another preferred embodiment of the seventh aspect, the antibody or antigen-binding fragment thereof is administered to the subject every other week (E2W), every fourth week (E4W) or once a month.

In preferred embodiments of the seventh and the other aspects of present invention the antibody or antigen-binding fragment thereof is for administration in a dosage amount (i.e. a dosage regimen) ranging from about 50 mg to about 200 mg every other week (E2W), preferably about 50 mg E2W, about 100 mg E2W, about 150 mg E2W, about 200 mg E2W, about 250 mg E2W or about 300 mg E2W, with about 50 mg E2W, about 100 mg E2W, about 150 mg E2W, about 200 mg E2W, being even more preferred. According to an especially advantageous embodiment of the second and the other aspects of present invention of present invention the antibody or antigen-binding fragment thereof is for administration in a dosage amount (i.e. a dosage regimen) E2W from about 50 mg to about 200 mg from about 100 mg to about 180 mg, from about 130 mg to about 170 mg, from about 140 to about 160 mg or about 90, about 100, about 110, about 120, about 130, about 140, about 145, about 150, about 155, about 160, about 170, about 180, about 190 or about 200 mg E2W, with dosage regimens of about 145 mg to about 155 mg E2W and particularly about 150 mg E2W belonging to the particularly preferred embodiments.

In other preferred embodiments of the seventh and the other aspects of present invention, the antibody or antigen-binding fragment thereof is for administration in a dosage amount ranging from about 100 mg to about 400 mg every fourth week (E4W), preferably about 100 mg E4W, about 150 mg E4W, about 200 mg E4W, about 250 mg E4W, about 300 mg E4W, about 350 mg E4W or about 400 mg E4W, with dosage amounts of about 190 to about 310 E4W, of about 200 to about 300 mg E4W, about 190 to about 210 E4W, about 195 to about 205 E4W, about 290 to about 310 E4W, about 295 to about 305 E4W, about 200 mg E4W or about 300 mg E4W belonging to the particularly preferred embodiments. These dosage amounts indicated for administration E4W are also suitable for administration once a month.

The seventh aspect is further directed to an antibody or an antigen-binding fragment thereof which specifically binds hPCSK9 (human proprotein convertase subtilisin/kexin type 9) for use in the treatment of a disease or condition in which PCSK9 expression or activity causes an impact, wherein the antibody or antigen-binding fragment thereof is for administration in a dose of about 50 to 500 mg.

Antibodies and antigen-binding fragments thereof that can be used for practicing the sixteenth aspect of the present invention are described in the section "Preferred Antibodies for Practicing the Present Invention". Preferred embodiments of the seventh aspect of present invention are described in the fourth aspect.

According to another preferred embodiment of the seventh aspect, the antibody or antigen-binding fragment thereof is for administration in a dose of about 50, 100, 150, 200, 250, 300, 350, 400, 450 or 500 mg and preferably of about 150, 200 or 300 mg.

According to another preferred embodiment of the seventh aspect, the disease or condition is selected from the group consisting of: elevated total cholesterol levels, elevated low-density lipoprotein (LDL-C) levels, hypercholesterolemia, hyperlipidemia, dyslipidemia, and atherosclerosis, particularly primary hypercholesterolemia, familial hypercholesterolemia. or hypercholesteremia which is uncontrolled by statins.

According to another preferred embodiment of the seventh aspect, the antibody or antigen-binding fragment thereof has one or more of the following characteristics:
(i) is for use in the reduction of low-density lipoprotein (LDL-C) levels of at least about −25% to about −40% relative to a predose level with a sustained reduction over at least a 14 day-period, wherein the sustained reduction is preferably at least −25% and more preferably at least −30% relative to a predose level, wherein the antibody or antigen-binding fragment thereof is preferably administered in a dose of about 40 to about 60 mg, about 45 to about 55 mg or about 50 mg E2W.
(ii) is for use in the reduction of low-density lipoprotein (LDL-C) of at least about −50% to about −65% relative to a predose level with a sustained reduction over at least a 14 day-period, wherein the sustained reduction is preferably at least −40% and more preferably at least −45% relative to a predose level, wherein the antibody or fragment thererof is preferably administered in a dose of about 100 mg E2W.
(iii) is for use in the reduction of low-density lipoprotein (LDL-C) of at least about −60% to at least about −75% [e.g. at least about −60%, at least about −65%, at least about −70 or at least about −75%] relative to a predose level with a sustained reduction over at least a 14 day-period, wherein the sustained reduction is preferably at least −55% and more preferably at least −60% relative to a predose level. wherein the antibody or fragment thereof is preferably administered in a dose of about 150 mg E2W.
(iv) is for use in the reduction of low-density lipoprotein (LDL-C) of at least about 40% to about 75% relative to a predose level with a sustained reduction over at least a 28 day period, wherein the sustained reduction is preferably at least −35% and more preferably at least −40% relative to a predose level, wherein the antibody or fragment thereof is preferably administered in a dose of about 200 mg E4W.
(v) is for use in the reduction of low-density lipoprotein (LDL-C) of at least about −50% to about −75% relative to a predose level with a sustained reduction over at least a 28 day-period, wherein the sustained reduction is preferably at least −40% and more preferably at least −45% relative to a predose level, wherein the antibody or fragment thereof is preferably administered in a dose of about 300 mg E4W.
(vi) is for use in the increase of serum HDL cholesterol levels of at least 2%, at least 2.5%, at least, 3%, at least 3.5%, at least 4%, at least 4.5%, at least 5% or at least 5.5% relative to a predose level.
(vii) Is for use in the reduction of serum total cholesterol at least about 25% to about 35% relative to a predose level with sustained reduction over at least a 24 day period.
(viii) Is for use in the reduction of serum total cholesterol at least about 65% to about 80% relative to a predose level with sustained reduction over at least a 24 day period.
12. Is for use in the reduction of serum triglyeride levels at least about 25% to about 40% relative to a predose level.
13. has little or no measurable effect on liver function, as determined by ALT and AST measurements, or on troponin levels.
14. Is for use in the increase of one or more of: Total-Cholesterol levels, ApoB levels, non HDL-C levels, Apo-B/ApoA-1 ratio.

According to another preferred embodiment of the seventh aspect, the antibody or antigen-binding fragment thereof is for use together with an HMG-CoA reductase inhibitor, wherein the HMG-CoA reductase inhibitor is preferably administered in a dosage amount in the range of about 0.05 mg to about 100 mg and is preferably a statin, wherein the statin is preferably selected from the group consisting of: cerivastatin, atorvastatin, simvastatin, pitavastatin, rosuvastatin, fluvastatin, lovastatin or pravastatin.

According to another preferred embodiment of the seventh aspect the statin is administered according to one or more of the following dosage or admimistration regimes:
(i) the statin is administered once per day,
(ii) the statin administered at a dosage of about 0.5 to about 100 mg, about 5 to about 90 mg, of about 10, 20, 40 or 80 mg and is preferably atorvastatin.
Further dosage and administration regimes of the antibody, antigen fragment thereof or the HMG-CoA reductase inhibitor are described at the other aspects of present invention and preferably at the eleventh aspect.

In a further preferred embodiment of the seventh aspect the present invention is directed to an antibody or an antigen-binding fragment thereof which specifically binds hPCSK9 (human proprotein convertase subtilisin/kexin type 9) for use in the treatment of a disease or condition in which PCSK9 expression or activity causes an impact, wherein the antibody or antigen-binding fragment thereof is for administration to a subject falling at least into one of the following groups of subjects: (i) subjects having a serum LDL cholesterol (LDL-C) level of at least 100 mg/dL, preferably at least 130 mg/dL, more preferably at least 160 mg/dL, even more preferably at least 200 mg/dL; (ii) subjects having a serum HDL-C level of less than 40 mg/dL; (iii) subjects having a serum cholesterol level of at least 200 mg/dL, preferably at least 240 mg/dL; (iv) subjects having a serum triacylglycerol level of at least 150 mg/dL, e.g. at least 200 mg/dL or at least 500 mg/dL, wherein said triacylglycerol level is determined after fasting for at least 8 hours; (v) subjects being at least 35 years old, e.g. at least 40 years old, at least 45 years old, at least 50 years old, at least 55 years old, at least 60 years old, at least 65 years old, or at least 75 years old; (vi) subjects younger than 75 years, e.g. younger than 70 years, younger than 65 years, younger than 60 years, younger than 55 years, younger than 50 years, younger than 45 years, or younger than 40 years; (vii) subjects having a BMI of 25 or more (e.g. 26 or more, 27 or more, 28 or more, 29 or more, 30 or more, 31 or more, 32 or more, 33 or more, 34 or more, 35 or more, 36 or more, 37 or more, 38 or more, or 39 or more); (viii) male subjects; (ix) female subjects; (x) subjects in which the administration of said antibody or antigen-binding fragment thereof leads to a reduction in the serum LDL-C level by at least 30 mg/dL, preferably by at least 40 mg/dL, more preferably by at least 50 mg/dL, more preferably by at least 60 mg/dL, more preferably by at least 70 mg/dL, relative to predose level; or (xi) subjects in which the administration of said antibody or antigen-binding fragment thereof leads to a reduction in the serum LDL-C level by at least 20%, preferably by at least 30%, more preferably by at least 40%, more preferably by at least 50%, more preferably by at least 60%, relative to predose level.

In a further preferred embodiment of the seventh aspect the present invention is directed to an antibody or an antigen-binding fragment thereof which specifically binds hPCSK9 (human proprotein convertase subtilisin/kexin type 9) for use in the treatment of a disease or condition in which PCSK9 expression or activity causes an impact, wherein the antibody or antigen-binding fragment thereof is for administration to a subject who does not fall into one or more of the following groups of subjects: (i) smokers; (ii) persons being 70 years old or older; (iii) persons suffering from hypertension; (iv) women who are pregnant; (v) women who are trying to become pregnant; (vi) women who are breast-feeding; (vii) persons who have or ever had a disease affecting the liver; (viii) persons who had any unexplained abnormal blood tests for liver function; (ix) persons who drink excessive amounts of alcohol; (x) persons having kidney problems; (xi) persons suffering from hypothyroidism; (xii) persons suffering from muscle disorders; (xiii) persons having encountered previous muscular problems during treatment with lipid-lowering medicine; (xiv) persons having serious problems with their breathing; (xv) persons taking one or more of the following medicines: medicines altering the way the immune systems works (e.g. ciclosporin or antihistamines), antibiotics or antifungal medicines (e.g. erythromycin, clarithromycin, ketoconazole, itraconazole, rifampicin, fusidic acid), medicines regulating lipid levels (e.g. gemfibrozil, colestipol), calcium channel blockers (e.g. verapamil, diltiazem), medicines regulating the heart rhythm (digoxin, amiodarone), protease inhibitors used in the treatment of HIV (e.g. nelfinavir), warfarin, oral contraceptives, antacids or St. John's Wort; or (xvi) persons drinking more than 0.1 L of grapefruit juice per day or eating more than half a grapefruit per day; (xvii) persons having a body mass index (BMI) of more than 40; (xviii) persons having a body mass index (BMI) of less than 18; (xix) persons suffering from type 1 diabetes or type 2 diabetes; (xx) persons positive for hepatitis B or hepatitis C; (xxi) persons having a known sensitivity to monoclonal antibody therapeutics; (xxii) persons having a neutrophil concentration of less than $1500/mm^3$; (xxiii) persons having a platelet concentration of less than $100000/mm^3$; (xxiv) men having a serum creatinine level larger than 1.5×ULN (upper limit of normal); (xxv) women having a serum creatinine level larger than 1.4×ULN (upper limit of normal); (xxvi) persons having an alanine transaminase (ALT) level or aspartate transaminase (AST) level larger than 2×ULN; or (xxvii) persons having a CPK level larger than 3×ULN.

In preferred embodiments of the seventh aspect, the disease or condition in which PCSK9 expression or activity causes an impact is ameliorated, improved, inhibited or prevented with a PCSK9 antagonist.

In preferred embodiments of the seventh aspect, the disease or condition in which PCSK9 expression or activity causes an impact is selected from the group consisting of: elevated LDL-C levels, hypercholesterolemia, hyperlipidemia, dyslipidemia, atherosclerosis and cardiovascular diseases, or any other of the diseases and conditions described in the first or second aspect.

In preferred seventh aspect, the antibody or antigen-binding fragment thereof is for administration to a subject indicated for LDL apheresis, a subject with PCSK9-activating mutations, a subject with heterozygous Familial Hypercholesterolemia, a subject with primary hypercholesterolemia, e.g. a subject with primary Familial or primary non-Familial Hypercholesterolemia, a subject with hypercholesterolemia such as primary hypercholesterolemia who is statin uncontrolled, a subject at risk for developing hypercholesterolemia, a subject with hypercholesterolemia, a subject with hyperlipidemia, a subject with dyslipidemia, a subject with atherosclerosis or a subject with cardiovascular diseases or any other of the subjects as described in the first or second aspect. Most preferably, the subject is a human subject.

In preferred embodiments of the seventh aspect, the antibody or antigen-binding fragment thereof is for administration in combination with a dosage of between 0.05 mg to 100 mg of an HMG-CoA reductase inhibitor. In some embodiments, the HMG-CoA reductase inhibitor is to be administered three times per day, twice per day, or once per day. In some embodiments, the HMG-CoA reductase inhibitor is to be administered every day, every other day, every third day, every fourth day, every fifth day, or every sixth day. In some embodiments, the HMG-CoA reductase inhibitor is to be administered every week, every other week, every third week, or every fourth week. In some embodiments, the HMG-CoA reductase inhibitor is to be administered in the morning, at noon or in the evening. In preferred embodiments, the HMG-CoA reductase inhibitor is to be administered once per day, preferably orally, preferably in the evening. Preferably, the HMG-CoA reductase inhibitor is a statin. More preferably, the statin is selected from the group consisting of cerivastatin, atorvastatin, simvastatin, pitavastatin, rosuvastatin, fluvastatin, lovastatin, and pravastatin. In further preferred embodiment of the sixteenth to eighteenth aspect, the antibody or antigen-binding fragment thereof is for administration in combination with a statin, wherein the statin is
- cerivastatin which is to be administered in a daily dosage of between 0.05 mg and 2 mg, preferably in a daily dosage of 0.2 mg, 0.4 mg, or 0.8 mg;
- atorvastatin which is to be administered in a daily dosage of between 2 mg and 100 mg, preferably in a daily dosage of 10 mg, 20 mg, 40 mg, or 80 mg;
- simvastatin which is to be administered in a daily dosage of between 2 mg and 100 mg, preferably in a daily dosage of 5 mg, 10 mg, 20 mg, 40 mg, or 80 mg;
- pitavastatin which is to be administered in a daily dosage of between 0.2 mg and 100 mg, preferably in a daily dosage of 1 mg, 2 mg, 5 mg, 10 mg, or 20 mg;
- rosuvastatin which is to be administered in a daily dosage of between 2 mg and 100 mg, preferably in a daily dosage of 5 mg, 10 mg, 20 mg, or 40 mg;
- fluvastatin which is to be administered in a daily dosage of between 2 mg and 100 mg, preferably in a daily dosage of 20 mg, 40 mg, or 80 mg;
- lovastatin which is to be administered in a daily dosage of between 2 mg and 100 mg, preferably in a daily dosage of 10 mg, 20 mg, 40 mg, or 80 mg; or
- pravastatin which is to be administered in a daily dosage of between 2 mg and 100 mg, preferably in a daily dosage of 10 mg, 20 mg, 40 mg, or 80 mg.

In an eight aspect, present invention concerns a method for preparing a pharmaceutical composition of present invention, e.g. a pharmaceutical composition according to the first aspect, comprising mixing the antibody or antigen-binding fragment thereof and optionally the HMG-CoA reductase inhibitor with one or more pharmaceutical excipients or carriers.

The skilled person knows how to prepare the compositions of the invention. Moreover, reference is given elsewhere in this specification.

In a ninth aspect, present invention concerns a method for preparing a unit dosage form of present invention (e.g. the fifth aspect) comprising admeasuring an amount of the pharmaceutical composition, of the antibody or antigen-binding fragment thereof, of the liquid formulation or of the dry formulation according to present invention comprising one or more doses of the antibody or antigen fragment thereof and optionally of the HMG-CoA reductase inhibitor and tailoring them as physically discrete units suitable as unitary dosages for human and/or animal administration.

In a tenth aspect, present invention concerns a method for preparing or assembling an article of manufacture of present invention comprising packaging the pharmaceutical composition, of the antibody according, of the liquid formulation, of the dry formulation according or of or more of the unit dosage forms of present invention in a container, optionally together with one or more of the following: a label, instructions for use, an application device (e.g. a syringe).

In an eleventh aspect the present invention is directed to a method for treating a disease or condition in which PCSK9 expression or activity causes an, comprising:
- administering a therapeutic amount of an antibody or an antigen-binding fragment thereof which specifically binds hPCSK9 (human proprotein convertase subtilisin/kexin type 9) to a subject in need thereof, wherein the antibody or antigen-binding fragment thereof is administered in a dosage amount ranging from 5 mg to 500 mg, and
- administering a therapeutic amount of an HMG-CoA reductase inhibitor to said subject, wherein the HMG-CoA reductase inhibitor is preferably administered in a dosage amount ranging from 0.05 mg to 100 mg.

In the context of present application, the term "a disease or condition in which PCSK9 expression or activity causes an impact" is understood to comprise any disease or condition in which the application of a PCSK-9 antibody causes an impact.

In preferred embodiments of the eleventh and the other aspects of present invention, the disease or condition in which PCSK9 expression or activity causes an impact is ameliorated, improved, inhibited or prevented with a PCSK9 antagonist.

In further preferred embodiments of the eleventh and the other aspects of present invention, the disease or condition is selected from the group consisting of: elevated total cholesterol levels, elevated low-density lipoprotein cholesterol (LDL-C) levels, hypercholesterolemia, particularly hypercholesteremia uncontrolled by statins, hyperlipidemia, dyslipidemia, atherosclerosis, cardiovascular diseases, primary hypercholesterolemia, such as primary familial hypercholesterolemia or primary non-familial hypercholesterolemia, hypercholesterolemia (especially primary hypercholesterolemia) uncontrolled by statins (particularly uncontrolled by atorvastatin).

In preferred embodiments of the eleventh and the other aspects of present invention, the subject in need thereof is a subject indicated for LDL apheresis, a subject with PCSK9-activating mutations, a subject with heterozygous Familial Hypercholesterolemia, a subject with primary hypercholesterolemia, a subject with primary hypercholesterolemia who is statin uncontrolled, a subject at risk for developing hypercholesterolemia, a subject with hypercholesterolemia, a subject with hyperlipidemia, a subject with dyslipidemia, a subject with atherosclerosis or a subject with cardiovascular diseases. Most preferably, the subject in need thereof is a human subject.

In some embodiments of the eleventh and other aspects of the invention, the HMG-CoA reductase inhibitor is administered three times per day, twice per day, or once per day. In some embodiments of the first and the other aspects of present invention, the HMG-CoA reductase inhibitor is administered every day, every other day, every third day, every fourth day, every fifth day, or every sixth day. In some embodiments of the first and the other aspects of present invention, the HMG-CoA reductase inhibitor is administered every week, every other week, every third week, or every fourth week. In some embodiments of the first and the other aspects of present invention, the HMG-CoA reductase inhibitor is administered in the morning, at noon or in the evening. In preferred embodiments, the HMG-CoA reductase inhibitor is administered once per day, preferably orally, preferably in the evening.

Preferably, the HMG-CoA reductase inhibitor is a statin. More preferably, the statin is selected from the group consisting of cerivastatin, atorvastatin, simvastatin, pitavastatin, rosuvastatin, fluvastatin, lovastatin, and pravastatin.

In more preferred embodiments of the first and the other aspects of present invention, the statin is
  cerivastatin administered in a daily dosage of between 0.05 mg and 2 mg, preferably in a daily dosage of 0.2 mg, 0.4 mg, or 0.8 mg;
  atorvastatin administered in a daily dosage of between 2 mg and 100 mg, preferably in a daily dosage of 10 mg, 20 mg, 40 mg, or 80 mg;
  simvastatin administered in a daily dosage of between 2 mg and 100 mg, preferably in a daily dosage of 5 mg, 10 mg, 20 mg, 40 mg, or 80 mg;
  pitavastatin administered in a daily dosage of between 0.2 mg and 100 mg, preferably in a daily dosage of 1 mg, 2 mg, 5 mg, 10 mg, or 20 mg;
  rosuvastatin administered in a daily dosage of between 2 mg and 100 mg, preferably in a daily dosage of 5 mg, 10 mg, 20 mg, or 40 mg;
  fluvastatin administered in a daily dosage of between 2 mg and 100 mg, preferably in a daily dosage of 20 mg, 40 mg, or 80 mg;
  lovastatin administered in a daily dosage of between 2 mg and 100 mg, preferably in a daily dosage of 10 mg, 20 mg, 40 mg, or 80 mg; or
  pravastatin administered in a daily dosage of between 2 mg and 100 mg, preferably in a daily dosage of 10 mg, 20 mg, 40 mg, or 80 mg.

In preferred embodiments of the eleventh and the other aspects of present invention, the antibody or antigen-binding fragment thereof is administered to the subject every other week, every fourth week or once a month. Administration every fourth week or administration once a month (i.e. once per calendar month, e.g. every first, second etc. day of the month or every first, second third Monday, Tuesday etc. each month, in contrast to administration every fourth week) is preferred in view of patient compliance. Administration every other week is preferred in view of a very low variation of blood cholesterol levels. Other suitable time schedules for administration of the antibody or antigen-binding fragment thereof include without limitation an administration once per day, every other day, every third day, every fourth day, every fifth day, every sixth day, every week, every third week, every fifth week, every sixth week, every eighth week, every tenth week, and every twelfth week.

In preferred embodiments of the eleventh and the other aspects of present invention, the antibody or antigen-binding fragment thereof is administered in a dosage amount ranging e.g. from about 40 mg to about 500 mg, from about 50 mg to about 500 mg, from about 50 mg to 300 mg or from about 100 mg to 200 mg. In more preferred embodiments, the antibody or antigen-binding fragment thereof is administered in a dosage amount of about 50 mg, of about 100 mg, of about 150 mg, of about 200 mg, of about 250 mg, of about 300 mg, of about 350 mg, of about 400 mg, of about 450 mg or of about 500 mg. Doses of about 50 to about 200 mg, e.g. of about 50 mg, about 100 mg, about 150 mg or about 200 mg are especially suitable for a biweekly dosage regimen (i.e. the application every other week), doses of about 150 mg to about 400 mg, e.g. about 150 mg, about 200 mg, about 250 mg, about 300 mg about 350 mg or about 400 mg are especially suitable for an administration regime with longer intervals, e.g. an administration every third or every fourth week or once a month.

Antibodies and antigen-binding fragments thereof that can be used for practicing the first and the other aspects of the present invention are described in the section "Preferred Antibodies for Practicing the Present Invention" or in the fourth aspect and its embodiments.

In a twelfth aspect the present invention is directed to a method of testing the efficacy of an antibody or an antigen-binding fragment thereof which specifically binds hPCSK9 for the treatment of a disease or condition selected from the group consisting of hypercholesterolemia, hyperlipidemia, dyslipidemia, atherosclerosis and cardiovascular diseases or any of the other conditions or diseases according to the first or second aspect of present invention, said method comprising:
  treating a selected patient population with said antibody or antigen-binding fragment thereof, wherein each patient in said population has an LDL cholesterol (LDL-C) level of more than 100 mg/dL; and
  determining the efficacy of said antibody or antigen-binding fragment thereof by determining the LDL-C level in the patient population before and after administration of said antibody or antigen-binding fragment thereof, wherein a reduction of the LDL-C level by at least 25% relative to a predose level in at least 75% of the patient population indicates that said antibody or antigen-binding fragment thereof is efficacious for the treatment of said disease or condition in said patient population.

In a thirteenth aspect the present invention is directed to a method of testing the efficacy of an antibody or an antigen-binding fragment thereof which specifically binds hPCSK9 for the treatment of a disease or condition selected from the group consisting of hypercholesterolemia, hyperlipidemia, dyslipidemia, atherosclerosis and cardiovascular diseases or any of the other conditions or diseases according to the first or second aspect of present invention, said method comprising:
  determining the efficacy of an antibody or antigen-binding fragment thereof that has been used for the treatment of a selected patient population with said antibody or antigen-binding fragment thereof, wherein each patient in said population has an LDL cholesterol (LDL-C) level of more than 100 mg/dL by determining the LDL-C level in the patient population before and after administration of said antibody or antigen-binding fragment thereof, wherein a reduction of the LDL-C level by at least 25% relative to a predose level in at least 75% of the patient population indicates that said antibody or antigen-binding fragment thereof is efficacious for the treatment of said disease or condition in said patient population.

In preferred embodiments of the twelfth and thirteenth aspect, each patient in said population has received a lipid lowering treatment by administration of an HMG CoA-Inhibitor, such as a statin for at least 6 weeks prior to treatment with said antibody or antigen-binding fragment thereof.

In preferred embodiments of the twelfth and thirteenth aspect, the antibody or antigen-binding fragment is an antibody or antigen-binding fragment as specified below in the section "Preferred Antibodies for Practicing the Present Invention".

In preferred embodiments of the twelfth and thirteenth aspect, the selected patient population is treated with a method of treatment according to the first aspect and the embodiments of the first or second aspect as described herein.

In a fourteenth aspect the present invention is directed to a package comprising an antibody or antigen-binding fragment thereof which specifically binds hPCSK9 of the invention and a label.

According to one embodiment the label is a data carrier containing one or more of the following: a printed statement, a chip or a bar code.

According to a preferred embodiment of the fourteenth aspect, the label comprises or is a data carrier (e.g. a printed statement, chip or bar code) which informs the patient that the treatment of the antibody together with an HMG-CoA reductase inhibitor such as a statin is indicated in one or more of the indications selected from the group consisting of hypercholesterolemia, hyperlipidemia, dyslipidemia, atherosclerosis and cardiovascular diseases or any of the other conditions or diseases according to the first or second aspect of present invention. Antibodies and antigen-binding fragments thereof that can be used for practicing the eighth aspect of the present invention are described in the section "Preferred Antibodies for Practicing the Present Invention".

According to another preferred embodiment, said the label comprises or is a data carrier (e.g. a printed statement, chip or bar code) which informs the patient that the treatment of the antibody together with a statin is contraindicated for patients belonging to one or more of the following groups: (i) smokers; (ii) persons being 70 years old or older; (iii) persons suffering from hypertension; (iv) women who are pregnant; (v) women who are trying to become pregnant; (vi) women who are breast-feeding; (vii) persons who have or ever had a disease affecting the liver; (viii) persons who had any unexplained abnormal blood tests for liver function; (ix) persons who drink excessive amounts of alcohol; (x) persons having kidney problems; (xi) persons suffering from hypothyroidism; (xii) persons suffering from muscle disorders; (xiii) persons having encountered previous muscular problems during treatment with lipid-lowering medicine; (xiv) persons having serious problems with their breathing; (xv) persons taking one or more of the following medicines: medicines altering the way the immune systems works (e.g. ciclosporin or antihistamines), antibiotics or antifungal medicines (e.g. erythromycin, clarithromycin, ketoconazole, itraconazole, rifampicin, fusidic acid), medicines regulating lipid levels (e.g. gemfibrozil, colestipol), calcium channel blockers (e.g. verapamil, diltiazem), medicines regulating the heart rhythm (digoxin, amiodarone), protease inhibitors used in the treatment of HIV (e.g. nelfinavir), warfarin, oral contraceptives, antacids or St. John's Wort; or (xvi) persons drinking more than 0.1 L of grapefruit juice per day or eating more than half a grapefruit per day; (xvii) persons having a body mass index (BMI) of more than 40; (xviii) persons having a body mass index (BMI) of less than 18; (xix) persons suffering from type 1 diabetes or type 2 diabetes; (xx) persons positive for hepatitis B or hepatitis C; (xxi) persons having a known sensitivity to monoclonal antibody therapeutics; (xxii) persons having a neutrophil concentration of less than 1500/mm$^3$; (xxiii) persons having a platelet concentration of less than 100000/mm$^3$; (xxiv) men having a serum creatinine level larger than 1.5×ULN (upper limit of normal); (xxv) women having a serum creatinine level larger than 1.4×ULN (upper limit of normal); (xxvi) persons having an alanine transaminase (ALT) level or aspartate transaminase (AST) level larger than 2×ULN; or (xxvii) persons having a CPK level larger than 3×ULN. Antibodies and antigen-binding fragments thereof that can be used for practicing the fourteenth aspect of the present invention are described in the section "Preferred Antibodies for Practicing the Present Invention".

In a fifteenth aspect the present invention is directed to a method of regulating the LDL level in the blood comprising:

administering a therapeutic amount of an antibody or an antigen-binding fragment thereof which specifically binds hPCSK9 (human proprotein convertase subtilisin/kexin type 9) to a subject in need thereof, wherein the antibody or antigen-binding fragment thereof is administered in a dosage amount ranging from 5 mg to 500 mg, and administering a therapeutic amount of an HMG-CoA reductase inhibitor to said subject, wherein the HMG-CoA reductase inhibitor is administered in a dosage amount ranging from 0.05 mg to 100 mg.

In a sixteenth aspect the present invention is directed to a method of preventing effects of a (persistently) increased LDL level in the blood comprising:

administering a therapeutic amount of an antibody or an antigen-binding fragment thereof which specifically binds hPCSK9 (human proprotein convertase subtilisin/kexin type 9) to a subject in need thereof, wherein the antibody or antigen-binding fragment thereof is administered in a dosage amount ranging from 5 mg to 500 mg, and administering a therapeutic amount of an HMG-CoA reductase inhibitor to said subject, wherein the HMG-CoA reductase inhibitor is administered in a dosage amount ranging from 0.05 mg to 100 mg.

In preferred embodiments of the fifteenth and sixteenth aspect, the disease or condition in which PCSK9 expression or activity causes an impact is ameliorated, improved, inhibited or prevented with a PCSK9 antagonist. In further preferred embodiments of the tenth and eleventh aspect, the disease or condition in which PCSK9 expression or activity causes an impact is selected from the group consisting of: elevated LDL-C levels, hypercholesterolemia, hyperlipidemia, dyslipidemia, atherosclerosis and cardiovascular diseases or any of the other conditions or diseases according to the eleventh, eighteenth or nineteenth aspect of present invention.

In preferred embodiments of the fifteenth and sixteenth aspect, the subject in need thereof is a subject indicated for LDL apheresis, a subject with PCSK9-activating mutations, a subject with heterozygous Familial Hypercholesterolemia, a subject with primary hypercholesterolemia who is statin uncontrolled, a subject at risk for developing hypercholesterolemia, a subject with hypercholesterolemia, a subject with hyperlipidemia, a subject with dyslipidemia, a subject with atherosclerosis or a subject with cardiovascular diseases or any of the subjects as described in the eleventh, eighteenth or nineteenth aspect of present invention. Most preferably, the subject in need thereof is a human subject.

In some embodiments of the fifteenth and sixteenth aspect, the HMG-CoA reductase inhibitor is administered three times per day, twice per day, or once per day. In some embodiments, the HMG-CoA reductase inhibitor is administered every day, every other day, every third day, every fourth day, every fifth day, or every sixth day. In some embodiments, the HMG-CoA reductase inhibitor is administered every week, every other week, every third week, every fourth week, or every month. In some embodiments, the HMG-CoA reductase inhibitor is administered in the morning, at noon or in the evening. In preferred embodiments, the HMG-CoA reductase inhibitor is administered once per day, preferably orally, preferably in the evening. Further suitable administration regimes are described in the first or second aspect.

In further preferred embodiments of the fifteenth and sixteenth aspect, the HMG-CoA reductase inhibitor is a statin. More preferably, the statin is selected from the group consisting of cerivastatin, atorvastatin, simvastatin, pitavastatin, rosuvastatin, fluvastatin, lovastatin, and pravastatin.

In more preferred embodiments of the tenth and eleventh aspect, the statin is cerivastatin administered in a daily dosage of between 0.05 mg and 2 mg, preferably in a daily dosage of 0.2 mg, 0.4 mg, or 0.8 mg;

atorvastatin administered in a daily dosage of between 2 mg and 100 mg, preferably in a daily dosage of 10 mg, 20 mg, 40 mg, or 80 mg;

simvastatin administered in a daily dosage of between 2 mg and 100 mg, preferably in a daily dosage of 5 mg, 10 mg, 20 mg, 40 mg, or 80 mg;

pitavastatin administered in a daily dosage of between 0.2 mg and 100 mg, preferably in a daily dosage of 1 mg, 2 mg, 5 mg, 10 mg, or 20 mg;

rosuvastatin administered in a daily dosage of between 2 mg and 100 mg, preferably in a daily dosage of 5 mg, 10 mg, 20 mg, or 40 mg;

fluvastatin administered in a daily dosage of between 2 mg and 100 mg, preferably in a daily dosage of 20 mg, 40 mg, or 80 mg;

lovastatin administered in a daily dosage of between 2 mg and 100 mg, preferably in a daily dosage of 10 mg, 20 mg, 40 mg, or 80 mg; or pravastatin administered in a daily dosage of between 2 mg and 100 mg, preferably in a daily dosage of 10 mg, 20 mg, 40 mg, or 80 mg.

In further preferred embodiments of the fifteenth and sixteenth aspect, the antibody or antigen-binding fragment thereof is administered to the subject every other week, every fourth week or once a month. Administration every fourth week or every month is preferred in view of patient compliance. Administration every other week is preferred in view of a very low variation of blood cholesterol levels. Other suitable time schedules for administration of the antibody or antigen-binding fragment thereof include without limitation an administration once per day, every other day, every third day, every fourth day, every fifth day, every sixth day, every week, every third week, every fifth week, every sixth week, every eighth week, every tenth week, and every twelfth week.

In preferred embodiments of the fifteenth and sixteenth aspect, the antibody or antigen-binding fragment thereof is administered in a dosage amount ranging from 50 mg to 300 mg, e.g. from 100 mg to 200 mg. In more preferred embodiments, the antibody or antigen-binding fragment thereof is administered in a dosage amount of about 50 mg, of about 100 mg, of about 150 mg, of about 200 mg, or of about 300 mg. Further suitable and preferred dosage regimens are described elsewhere in this specification, e.g. in the eleventh aspect.

Antibodies and antigen-binding fragments thereof that can be used for practicing the tenth and eleventh aspect of the present invention are described in the section "Preferred Antibodies for Practicing the Present Invention".

In a seventeenth aspect the present invention is directed to a method of determining whether a pharmaceutical compound is utilizable for ameliorating, improving, inhibiting or preventing a disease or condition in which PCSK9 activity or expression has an impact comprising: (a) administering to a subject a compound that specifically binds to PCSK9, preferably an antibody or antigen-binding fragment thereof specifically binding to PCSK9, and (b) determining what fraction of PCSK9 in the blood is attached to the compound from (a).

Typically, compounds that specifically bind from 10% to 100% (preferably from 20% to 100%, more preferably from 30% to 100%, more preferably from 40% to 100%, more preferably from 50% to 100%) of the PCSK9 present in the blood when used in stoichiometric amounts, will be utilizable for ameliorating, improving, inhibiting or preventing a disease or condition in which PCSK9 activity or expression has an impact.

Preferably, the disease or condition in which PCSK9 expression or activity has an impact is selected from the group consisting of: elevated LDL-C levels, hypercholesterolemia, hyperlipidemia, dyslipidemia, atherosclerosis and cardiovascular diseases or any of the other diseases described herein, such as in the eleventh aspect.

Antibodies and antigen-binding fragments thereof that can be used for practicing the twelfth aspect of the present invention are described in the section "Preferred Antibodies for Practicing the Present Invention".

In an eighteenth aspect the present invention is directed to a method for treating a disease or condition in which PCSK9 expression or activity causes an impact comprising administering a therapeutic amount of an antibody or an antigen-binding fragment thereof which specifically binds hPCSK9 (human proprotein convertase subtilisin/kexin type 9) to a subject in need thereof, wherein the subject in need thereof falls into one or more of the following groups of subjects: (i) subjects having a serum LDL cholesterol (LDL-C) level of at least 100 mg/dL, preferably at least 130 mg/dL, more preferably at least 160 mg/dL, even more preferably at least 200 mg/dL; (ii) subjects having a serum HDL-C level of less than 40 mg/dL; (iii) subjects having a serum cholesterol level of at least 200 mg/dL, preferably at least 240 mg/dL; (iv) subjects having a serum triacylglycerol level of at least 150 mg/dL, e.g. at least 200 mg/dL or at least 500 mg/dL, wherein said triacylglycerol level is determined after fasting for at least 8 hours; (v) subjects being at least 35 years old, e.g. at least 40 years old, at least 45 years old, at least 50 years old, at least 55 years old, at least 60 years old, at least 65 years old, or at least 75 years old; (vi) subjects younger than 75 years, e.g. younger than 70 years, younger than 65 years, younger than 60 years, younger than 55 years, younger than 50 years, younger than 45 years, or younger than 40 years; (vii) subjects having a BMI of 25 or more (e.g. 26 or more, 27 or more, 28 or more, 29 or more, 30 or more, 31 or more, 32 or more, 33 or more, 34 or more, 35 or more, 36 or more, 37 or more, 38 or more, or 39 or more); (viii) male subjects; (ix) female subjects; (x) subjects in which the administration of said antibody or antigen-binding fragment thereof leads to a reduction in the serum LDL-C level by at least 30 mg/dL, preferably by at least 40 mg/dL, more preferably by at least 50 mg/dL, more preferably by at least 60 mg/dL, more preferably by at least 70 mg/dL, relative to predose level; or (xi) subjects in which the administration of said antibody or antigen-binding fragment thereof leads to a reduction in the serum LDL-C level by at least 20%, preferably by at least 30%, more preferably by at least 40%, more preferably by at least 50%, more preferably by at least 60%, relative to predose level.

In a nineteenth aspect the present invention is directed to a method for treating a disease or condition in which PCSK9 expression or activity causes an impact comprising administering a therapeutic amount of an antibody or an antigen-binding fragment thereof which specifically binds hPCSK9 (human proprotein convertase subtilisin/kexin type 9) to a subject in need thereof, wherein the subject in need thereof does not fall into one or more of the following groups of subjects: (i) smokers; (ii) persons being 70 years old or older; (iii) persons suffering from hypertension; (iv) women who are pregnant; (v) women who are trying to become pregnant; (vi) women who are breast-feeding; (vii) persons who have or ever had a disease affecting the liver; (viii) persons who had any unexplained abnormal blood tests for liver function; (ix) persons who drink excessive amounts of alcohol; (x) persons having kidney problems; (xi) persons suffering from hypothyroidism; (xii) persons suffering from muscle disorders; (xiii) persons having encountered previous muscular problems during treatment with lipid-lowering medicine; (xiv) persons having serious problems with their breathing; (xv) persons taking one or more of the following medicines: medicines altering the way the immune systems works (e.g. ciclosporin or antihistamines), antibiotics or antifungal medicines (e.g. erythromycin, clarithromycin, ketoconazole, itraconazole, rifampicin, fusidic acid), medicines regulating lipid levels (e.g. gemfibrozil, colestipol), calcium channel blockers (e.g. verapamil, diltiazem), medicines regulating the heart rhythm (digoxin, amiodarone), protease inhibitors used in the treatment of HIV (e.g. nelfinavir), warfarin, oral contraceptives, antacids or St. John's Wort; or (xvi) persons drinking more than 0.1 L of grapefruit juice per day or eating more than half a grapefruit per day; (xvii) persons having a body mass index (BMI) of more than 40; (xviii) persons having a body mass index (BMI) of less than 18; (xix) persons suffering from type 1 diabetes or type 2 diabetes; (xx) persons positive for hepatitis B or hepatitis C; (xxi) persons having a known sensitivity to monoclonal antibody therapeutics; (xxii) persons having a neutrophil concentration of less than $1500/mm^3$; (xxiii) persons having a platelet concentration of less than $100000/mm^3$; (xxiv) men having a serum creatinine level larger than 1.5×ULN (upper limit of normal); (xxv) women having a serum creatinine level larger than 1.4×ULN (upper limit of normal); (xxvi) persons having an alanine transaminase (ALT) level or aspartate transaminase (AST) level larger than 2×ULN; or (xxvii) persons having a CPK level larger than 3×ULN.

In preferred embodiments of the eighteenth and nineteenth aspect, the disease or condition in which PCSK9 expression or activity causes an impact is ameliorated, improved, inhibited or prevented with a PCSK9 antagonist.

In preferred embodiments of the thirteenth and the fourteenth aspect, the disease or condition in which PCSK9 expression or activity causes an impact is selected from the group consisting of: elevated LDL-C levels, hypercholesterolemia, hyperlipidemia, dyslipidemia, atherosclerosis and cardiovascular diseases or any of the other diseases or conditions described in the other aspects of present invention, such as the eleventh aspect.

In preferred embodiments of the thirteenth and the fourteenth aspect, the subject in need thereof is a subject indicated for LDL apheresis, a subject with PCSK9-activating mutations, a subject with heterozygous Familial Hypercholesterolemia, a subject with primary hypercholesterolemia, e.g. a subject with primary Familial or primary non-Familial Hypercholesterolemia, a subject with hypercholesterolemia such as primary hypercholesterolemia who is statin uncontrolled, a subject at risk for developing hypercholesterolemia, a subject with hypercholesterolemia, a subject with hyperlipidemia, a subject with dyslipidemia, a subject with atherosclerosis or a subject with cardiovascular diseases, or any of the other subjects described in the first or second aspects. Most preferably, the subject in need thereof is a human subject. Further preferred or suitable subjects are described at the other aspects of present invention such as the eighteenth or nineteenth aspect.

Antibodies and antigen-binding fragments thereof that can be used for practicing the thirteenth and fourteenth aspect and the other aspects of the present invention are described in the section "Preferred Antibodies for Practicing the Present Invention".

In preferred embodiments of the eighteenth and nineteenth aspect, the method further comprises: administering a therapeutic amount of an HMG-CoA reductase inhibitor to the subject in a dosage of between 0.05 mg to 100 mg. In some embodiments, the HMG-CoA reductase inhibitor is administered three times per day, twice per day, or once per day. In some embodiments, the HMG-CoA reductase inhibitor is administered every day, every other day, every third day, every fourth day, every fifth day, or every sixth day. In some embodiments, the HMG-CoA reductase inhibitor is administered every week, every other week, every third week, or every fourth week. In some embodiments, the HMG-CoA reductase inhibitor is administered in the morning, at noon or in the evening. In preferred embodiments, the HMG-CoA reductase inhibitor is administered once per day, preferably orally, preferably in the evening. Preferably, the HMG-CoA reductase inhibitor is a statin. More preferably, the statin is selected from the group consisting of cerivastatin, atorvastatin, simvastatin, pitavastatin, rosuvastatin, fluvastatin, lovastatin, and pravastatin. In further preferred embodiment of the thirteenth and the fourteenth aspect, the method comprises administering a therapeutic amount of a statin to the subject, wherein the statin is:

cerivastatin administered in a daily dosage of between 0.05 mg and 2 mg, preferably in a daily dosage of 0.2 mg, 0.4 mg, or 0.8 mg;

atorvastatin administered in a daily dosage of between 2 mg and 100 mg, preferably in a daily dosage of 10 mg, 20 mg, 40 mg, or 80 mg;

simvastatin administered in a daily dosage of between 2 mg and 100 mg, preferably in a daily dosage of 5 mg, 10 mg, 20 mg, 40 mg, or 80 mg;

pitavastatin administered in a daily dosage of between 0.2 mg and 100 mg, preferably in a daily dosage of 1 mg, 2 mg, 5 mg, 10 mg, or 20 mg;

rosuvastatin administered in a daily dosage of between 2 mg and 100 mg, preferably in a daily dosage of 5 mg, 10 mg, 20 mg, or 40 mg;

fluvastatin administered in a daily dosage of between 2 mg and 100 mg, preferably in a daily dosage of 20 mg, 40 mg, or 80 mg;

lovastatin administered in a daily dosage of between 2 mg and 100 mg, preferably in a daily dosage of 10 mg, 20 mg, 40 mg, or 80 mg; or pravastatin administered in a daily dosage of between 2 mg and 100 mg, preferably in a daily dosage of 10 mg, 20 mg, 40 mg, or 80 mg.

A further preferred embodiment of the present invention combines the features of the eighteenth and nineteenth aspect as described herein.

In a twentieth aspect the present invention is directed to a method of testing the efficacy of an antibody or an antigen-binding fragment thereof which specifically binds hPCSK9 for the treatment of a disease or condition selected from the group consisting of elevated LDL-C levels, hypercholesterolemia, hyperlipidemia, dyslipidemia, atherosclerosis and cardiovascular diseases, or any other disease or condition described in the first or second aspect, said method comprising:

treating a selected patient population with said antibody or antigen-binding fragment thereof, wherein each patient in said population has an LDL cholesterol (LDL-C) level of more than 100 mg/dL; and determining the efficacy of said antibody or antigen-binding fragment thereof by determining the LDL-C level in the patient population before and after administration of said antibody or antigen-binding fragment thereof, wherein a reduction of the LDL-C level by at least 25% relative to a predose level in at least 75% of the patient population indicates that said antibody or antigen-binding fragment thereof is efficacious for the treatment of said disease or condition in said patient population;

wherein each patient falls into one or more groups of subjects as recited in the thirteenth aspect.

In a twentyfirst aspect the present invention is directed to a method of testing the efficacy of an antibody or an antigen-binding fragment thereof which specifically binds hPCSK9 for the treatment of a disease or condition selected from the group consisting of elevated LDL-C levels, hypercholesterolemia, hyperlipidemia, dyslipidemia, atherosclerosis and cardiovascular diseases (or any other method as described in the first or second aspect), said method comprising:

determining the efficacy of an antibody or antigen-binding fragment thereof that has been used for the treatment of a selected patient population with said antibody or antigen-binding fragment thereof, wherein each patient in said population has an LDL cholesterol (LDL-C) level of more than 100 mg/dL by determining the LDL-C level in the patient population before and after administration of said antibody or antigen-binding fragment thereof, wherein a reduction of the LDL-C level by at least 25% relative to a predose level in at least 75% of the patient population indicates that said antibody or antigen-binding fragment thereof is efficacious for the treatment of said disease or condition in said patient population;

wherein each patient falls into one or more groups of subjects as recited in the thirteenth aspect.

In preferred embodiments of the $20^{th}$ and $21^{st}$ aspect, each patient in said population has received a lipid lowering treatment by administration of an HMG-CoA reductase inhibitor such as a statin for at least 6 weeks prior to treatment with said antibody or antigen-binding fragment thereof.

Antibodies and antigen-binding fragments thereof that can be used for practicing the nineteenth and twentieth aspect of the present invention are described in the section "Preferred Antibodies for Practicing the Present Invention" or the other section of present application describing antibodies of present invention, such as e.g. the fourth aspect.

In preferred embodiments of the $20^{th}$ and $21^{st}$ aspect, the selected patient population is or has been treated with a method of treatment according to the eleventh, eighteenth or nineteenth aspect and the embodiments thereof as described herein.

In further preferred embodiments of the $20^{th}$ and $21^{st}$ aspect, the efficacy of said antibody or said antigen-binding fragment thereof is determined for sub-groups of said selected patient population, wherein said sub-groups have been stratified by at least one stratification factor selected from the group consisting of: population with heterozygous familial hypercholesterolemia (heFH); prior history of myocardial infarction (MI); prior history of stroke; receiving high-intensity statin therapy; and geographical region of the patient (e.g. North America, Western Europe, Eastern Europe, and rest of the world).

In hamsters and other rodents statins are not effective on LDL clearance from blood. More specifically, the administration of statins alone (e.g. atorvastatin) has no effect on the expression of the LDL receptor (LDLR) in hamsters or other rodents, presumably due to the activity of the endogenous PCSK9. The experiments contained in the present application (see study 4) show that inhibition of PCSK9 by administration of an anti-PCSK9 antibody renders rodents (e.g. hamsters) sensitive to statin treatment. Accordingly, the present application provides a new animal model for testing the efficacy of statins or other drugs that lower cholesterol levels.

Thus, in a twentysecond aspect the present invention is directed to a method for testing the efficacy of a compound in lowering cholesterol levels in a subject, comprising the steps:

(a) providing a rodent;
(b) administering an antibody or an antigen-binding fragment thereof which specifically binds PCSK9 to the rodent;
(c) administering a test compound to said rodent;
(d) determining the effect of the test compound in the rodent, wherein a lowering of the cholesterol level in the rodent as compared to the cholesterol level of a control animal indicates that the test compound is efficacious in lowering cholesterol levels in a subject, wherein the control animal is from the same species as said rodent, and wherein the control animal has not been challenged with the test compound.

In preferred embodiments of the $22^{nd}$ aspect, the rodent is selected from the group consisting of hamster, mouse, rat, guinea pig, and rabbit.

Antibodies and antigen-binding fragments thereof that can be used for practicing the $22^{nd}$ aspect of the present invention are described the other sections of present application such as the fourth aspect of in the section "Preferred Antibodies for Practicing the Present Invention". Preferably, the antibody or antigen-binding fragment thereof is administered to the rodent in a concentration of 1 mg/kg body weight, 3 mg/kg body weight, or 10 mg/kg body weight.

In preferred embodiments of the $22^{nd}$ aspect, the lowering of the cholesterol level is determined by measuring the level of total cholesterol in the serum. In more preferred embodiments, the lowering of the cholesterol level is determined by measuring the level of LDL cholesterol (LDL-C) in the serum.

In preferred embodiments of the $22^{nd}$ aspect, the control animal is from the same strain as the rodent. Preferably, the same antibody or antigen-binding fragment thereof is administered to the rodent and to the control animal. Preferably, the same concentration (measured in mg/kg body weight) of the antibody or antigen-binding fragment thereof is administered to the rodent and to the control animal.

In one embodiment of the $22^{nd}$ aspect, the control animal is a different animal, i.e. a different individual, than the rodent. It is also possible to determine the cholesterol level in two or more control animals and to calculate the mean value of the cholesterol level in these two or more control animals. Likewise, it is possible to challenge two or more rodents with the antibody or antigen-binding fragment thereof, to determine the cholesterol level in these two or more rodents and to calculate the mean value of the cholesterol level in these two or more rodents.

In an alternative embodiment of the 22$^{nd}$ aspect, the control animal is the very same animal as the rodent but it is examined at a different time-point. More specifically, the cholesterol level in the rodent after administration of the test compound can be compared to a pre-dose cholesterol level in the same animal. Preferably, said pre-dose cholesterol level is determined between steps (b) and (c) recited above.

According to a twentythird aspect, present invention concerns a method of enhancing the LDL-C lowering activity in a subject undergoing statin therapy, the method comprising administering to the subject an antibody, or antigen-binding fragment thereof, which specifically binds to human proprotein convertase subtilisin/kexin type 9 (hPCSK9), wherein the antibody or antigen-binding fragment thereof is administered at a dosage amount within the range of about 5 mg to about 500 mg, thereby enhancing LCL-C lowering activity of the statin therapy in the subject.

According to a preferred embodiment of the 23$^{th}$ aspect, the subject is resistant to the statin therapy prior to administration of the antibody.

According to another preferred embodiment, the subject suffers from a disease or condition selected from the group consisting of hypercholesterolemia, hyperlipidemia, dyslipidemia, and atherosclerosis.

According to another preferred embodiment, the disease condition is primary hypercholesterolemia or familial hypercholesterolemia.

According to another preferred embodiment, the antibody or antigen-binding fragment is administered in a dosage amount within the range of about 50 mg to about 300 mg.

According to another preferred embodiment, the antibody or antigen-binding fragment is administered in a dosage amount of about 150 mg.

According to another preferred embodiment, the antibody or antigen-binding fragment thereof is administered to the subject every other week (E2W).

According to another preferred embodiment, the antibody or antigen-binding fragment thereof is administered to the subject every fourth week (E4W).

According to another preferred embodiment, the treatment reduces serum total cholesterol at least about 25% to about 35% relative to a predose level and sustains the reduction over at least a 24 day period.

According to another preferred embodiment, the treatment reduces serum total cholesterol at least about 65% to about 80% relative to a predose level and sustains the reduction over at least a 24 day period.

According to another preferred embodiment, the treatment reduces serum triglyeride levels at least about 25% to about 40% relative to a predose level.

According to another preferred embodiment, the treatment reduced serum HDL cholesterol no more than 5% relative to a predose level.

According to another preferred embodiment, the treatment has little or no measurable effect on liver function, as determined by ALT and AST measurements.

According to another preferred embodiment, the antibody or the antigen-binding fragment comprises 1 the heavy and light chain CDRs of a HCVR/LCVR amino acid sequence pair as shown in SEQ ID NOs: 90/92.

According to another preferred embodiment, the antibody or antigen-binding fragment comprises a HCVR/LCVR amino acid sequence pair as shown in SEQ ID NOs: 90/92.

According to another preferred embodiment, the antibody or antigen-binding fragment thereof competes for binding to hPCSK9 with an antibody or antigen-binding fragment comprising a HCVR/LCVR amino acid sequence pair as shown in SEQ ID NOs: 90/92.

According to another preferred embodiment, the statin is selected from the group consisting of cerivastatin, atorvastatin, simvastatin, pitavastatin, rosuvastatin, fluvastatin, lovastatin, and pravastatin.

According to another preferred embodiment, the statin is atorvastatin administered at a dosage of 10 mg, 20 mg, 40 mg or 80 mg.

In a twentyfourth aspect, present invention concerns a kit for treating elevated low-density lipoprotein cholesterol (LDL-C) levels in a subject, the kit comprising (a) pharmaceutical unit dosage form comprising an antibody, or antigen-binding fragment thereof, which specifically binds to hPCSK9; and pharmaceutically acceptable carrier, wherein the antibody or antigen-binding fragment is present in a dosage amount within the range of about 5 mg to about 500 mg; and (b) a label or packaging insert with instructions for use.

According to a preferred embodiment of the 24$^{th}$ aspect, the label indicates that patients receiving treatment with said antibody or antigen-binding fragment can be treated for a disease or condition selected from the group consisting of hypercholesterolemia, hyperlipidemia, dyslipidemia, and atherosclerosis and cardiovascular diseases.

According to another preferred embodiment, the disease or condition is primary hypercholesterolemia or familial hypercholesterolemia. According to another preferred embodiment, the disease or condition is hypercholesterolemia which is uncontrolled by statins.

According to another preferred embodiment, the antibody or antigen-binding fragment is present in dosage amount within the range of about 50 mg to about 300 mg. According to another preferred embodiment, the antibody or antigen-binding fragment is present in a dosage amount of about 150 mg.

According to another preferred embodiment, the label or packaging insert indicates that the antibody or antigen-binding fragment thereof is administered to the subject every other week (E2W).

According to another preferred embodiment, the label or packaging insert indicates that the antibody or antigen-binding fragment thereof is administered to the subject every fourth week (E4W).

According to another preferred embodiment, the antibody or the antigen-binding fragment comprises the heavy and light chain CDRs of a HCVR/LCVR amino acid sequence pair as shown in SEQ ID NOs: 90/92

According to another preferred embodiment, the antibody or antigen-binding fragment comprises a HCVR/LCVR amino acid sequence pair as shown in SEQ ID NOs: 90/92.

According to another preferred embodiment, the antibody or antigen-binding fragment thereof competes for binding to hPCSK9 with an antibody or antigen-binding fragment comprising a HCVR/LCVR amino acid sequence pair as shown in SEQ ID NOs: 90/92.

According to another preferred embodiment, the kit further comprises an HMG-CoA reductase inhibitor. According to another preferred embodiment, the inhibitor is in a dosage amount in the range of about 0.05 mg to 100 mg. According to another preferred embodiment, the HMG-CoA reductase inhibitor is a statin. According to another preferred embodiment, the statin is selected from the group consisting of cerivastatin, atorvastatin, simvastatin, pitavastatin, rosuvastatin, fluvastatin, lovastatin, and pravastatin.

According to another preferred embodiment, the instructions indicate that the statin is atorvastatin administered at a dosage of 10 mg, 20 mg, 40 mg or 80 mg.

According to another preferred embodiment, the instructions indicate that treatment with the antibody or an is contraindicated for patients belonging to one or more of the following groups:
(i) smokers;
(ii) persons being 70 years old or older;
(iii) persons suffering from hypertension;
(iv) women who are pregnant;
(v) women who are trying to become pregnant;
(vi) women who are breast-feeding;
(vii) persons who have or ever had a disease affecting the liver;
(viii) persons who had any unexplained abnormal blood tests for liver function;
(ix) persons who drink excessive amounts of alcohol;
(x) persons having kidney problems;
(xi) persons suffering from hypothyroidism;
(xii) persons suffering from muscle disorders;
(xiii) persons having encountered previous muscular problems during treatment with lipid-lowering medicine;
(xiv) persons having serious problems with their breathing;
(xv) persons taking one or more of the following medicines: medicines altering the way the immune systems works (e.g. ciclosporin or antihistamines), antibiotics or antifungal medicines (e.g. erythromycin, clarithromycin, ketoconazole, itraconazole, rifampicin, fusidic acid), medicines regulating lipid levels (e.g. gemfibrozil, colestipol), calcium channel blockers (e.g. verapamil, diltiazem), medicines regulating the heart rhythm (digoxin, amiodarone), protease inhibitors used in the treatment of HIV (e.g. nelfinavir), warfarin, oral contraceptives, antacids or St. John's Wort; or
(xvi) persons drinking more than 0.1 L of grapefruit juice per day;
(xvii) persons having a body mass index (BMI) of more than 40;
(xviii) persons having a body mass index (BMI) of less than 18;
(xix) persons suffering from type 1 diabetes or type 2 diabetes;
(xx) persons positive for hepatitis B or hepatitis C; or
(xxi) persons having a known sensitivity to monoclonal antibody therapeutics.

In a twentyfifth aspect, present invention concerns a method of treating a subject suffering from a disease or disorder characterized by elevated low-density lipoprotein cholesterol (LDL-C) levels, the method comprising:
(a) selecting a subject with a blood LDL-C level greater than 100 mg/dL; and
(b) administering to said subject a composition comprising an antibody or antigen binding fragment thereof that specifically binds to human proprotein convertase subtilisin/kexin type 9 (hPCSK9); thereby lowering cholesterol levels in the subject in need thereof.

According to a preferred embodiment, the disease or condition is selected from the group consisting of: hypercholesterolemia, hyperlipidemia, dyslipidemia, and atherosclerosis.

According to another preferred embodiment, the disease condition is primary hypercholesterolemia or familial hypercholesterolemia.

According to another preferred embodiment, the disease or condition is hypercholesterolemia which is uncontrolled by statins.

According to another preferred embodiment, the subject has a body mass index (BMI) of less than 18 kg/m² or greater than 40 kg/m².

According to another preferred embodiment, subject was not previously instructed to partake in a cholesterol-lowering diet.

According to another preferred embodiment, the subject has not previously taken a cholesterol-lowering drug except for atorvastatin.

According to another preferred embodiment, the atorvastatin was administered at about 10 mg per day.

According to another preferred embodiment, cholesterol-lowering drug is selected from the group consisting of fibrates, bile acid resins, niacin, intestinal cholesterol absorption (ICA) blockers, and omega-3 fatty acids. According to another preferred embodiment, the niacin is administered at greater than 500 mg per day. According to another preferred embodiment, the omega-3 fatty acids are administered at greater than 1000 mg per day.

According to another preferred embodiment, the subject does not suffer from diabetes. According to another preferred embodiment, the diabetes is type 1 diabetes. According to another preferred embodiment, the diabetes is type 2 diabetes. According to another preferred embodiment, the type 2 diabetes is treated with insulin.

According to another preferred embodiment, the subject has a blood glycated hemoglobin concentration greater than or equal to 8.5%.

According to another preferred embodiment, the subject is negative for hepatitis B and C surface antigen.

According to another preferred embodiment, the subject has a blood triglycerides concentration of greater than 350 mg/dL.

According to another preferred embodiment, the subject has fewer than 1500 neutrophils per cubic mm of blood.

According to another preferred embodiment, the subject has fewer than 100,000 platelets per cubic mm of blood.

According to another preferred embodiment, the subject is female.

According to another preferred embodiment, the subject is not pregnant.

According to another preferred embodiment, the subject has a blood thyroid stimulating hormone concentration that is above the lower limit of normal and below the upper limit of normal.

According to another preferred embodiment, the subject has serum creatine of less than 1.4 of the upper limit of normal.

According to another preferred embodiment, the subject is a male.

According to another preferred embodiment, the subject has serum creatine of less than 1.5 of the upper limit of normal.

According to another preferred embodiment, the subject has an amount of aspartate transaminase that is less than two times the upper limit of normal.

According to another preferred embodiment, the subject has an amount of alanine transaminase that is less than two times the upper limit of normal.

According to another preferred embodiment, the antibody or antigen-binding fragment is administered in a dosage amount within the range of about 5 mg to about 500 mg.

According to another preferred embodiment, the antibody or antigen-binding fragment is administered in a dosage amount within the range of about 50 mg to about 300 mg.

According to another preferred embodiment, the antibody is administered at between 200 and 300 mg every four weeks.

According to another preferred embodiment, the antibody or antigen-binding fragment is administered in a dosage amount of about 150 mg.

According to another preferred embodiment, the antibody or antigen-binding fragment thereof is administered to the subject every other week (E2W).

According to another preferred embodiment, the antibody or antigen-binding fragment thereof is administered to the subject every fourth week (E4W).

According to another preferred embodiment, the antibody or the antigen-binding fragment comprises the heavy and light chain CDRs of a HCVR/LCVR amino acid sequence pair as shown in SEQ ID NOs: 90/92.

According to another preferred embodiment, the antibody or antigen-binding fragment comprises a HCVR/LCVR amino acid sequence pair as shown in SEQ ID NOs: 90/92.

According to another preferred embodiment, the antibody or antigen-binding fragment thereof competes for binding to hPCSK9 with an antibody or antigen-binding fragment comprising a HCVR/LCVR amino acid sequence pair as shown in SEQ ID NOs: 90/92.

According to another preferred embodiment, the antibody is administered subcutaneously.

According to another preferred embodiment, the antibody is administered in the abdomen.

According to another preferred embodiment, an HMG-CoA reductase inhibitor is administered to the subject.

According to another preferred embodiment, the HMG-CoA reductase inhibitor is administered in a dosage amount in the range of about 0.05 mg to 100 mg.

According to another preferred embodiment, the HMG-CoA reductase inhibitor is a statin.

According to another preferred embodiment, the statin is selected from the group consisting of cerivastatin, atorvastatin, simvastatin, pitavastatin, rosuvastatin, fluvastatin, lovastatin, and pravastatin.

According to another preferred embodiment, the statin is atorvastatin administered at a dosage of 10 mg or 80 mg.

According to another preferred embodiment, the atorvastatin is administered at about 10 mg per day and at 80 mg one day in an 8 week period.

In a twentysixth aspect, present invention concerns a method of lowering cholesterol levels in a subject in need thereof, comprising:
  (a) selecting a subject with a blood low density lipoprotein cholesterol (LDL-C) level greater than 100 mg/dL; and
  (b) administering to said subject a composition comprising an antibody or antigen binding fragment thereof that specifically binds to human proprotein convertase subtilisin/kexin type 9 (hPCSK9); thereby lowering cholesterol levels in the subject in need thereof.

According to a preferred embodiment of the 26$^{th}$ aspect, the disease or condition is selected from the group consisting of: hypercholesterolemia, hyperlipidemia, dyslipidemia, and atherosclerosis.

According to another preferred embodiment, the disease condition is primary hypercholesterolemia or familial hypercholesterolemia.

According to another preferred embodiment, the disease or condition is hypercholesterolemia which is uncontrolled by statins.

According to another preferred embodiment, the subject has a body mass index (BMI) of less than 18 kg/m$^2$ or greater than 40 kg/m$^2$.

According to another preferred embodiment, the subject was not previously instructed to partake in a cholesterol-lowering diet.

According to another preferred embodiment, the subject has not previously taken a cholesterol-lowering drug except for atorvastatin.

According to another preferred embodiment, the atorvastatin was administered at about 10 mg per day.

According to another preferred embodiment, the cholesterol-lowering drug is selected from the group consisting of fibrates, bile acid resins, niacin, intestinal cholesterol absorption (ICA) blockers, and omega-3 fatty acids.

According to another preferred embodiment, the niacin is administered at greater than 500 mg per day.

According to another preferred embodiment, the omega-3 fatty acids are administered at greater than 1000 mg per day.

According to another preferred embodiment, the subject does not suffer from diabetes.

According to another preferred embodiment, the diabetes is type 1 diabetes.

According to another preferred embodiment, the diabetes is type 2 diabetes.

According to another preferred embodiment, the type 2 diabetes is treated with insulin.

According to another preferred embodiment, the subject has a blood glycated hemoglobin concentration greater than or equal to 8.5%.

According to another preferred embodiment, the subject is negative for hepatitis B and C surface antigen.

According to another preferred embodiment, the subject has a blood triglycerides concentration of greater than 350 mg/dL.

According to another preferred embodiment, the subject has fewer than 1500 neutrophils per cubic mm of blood.

According to another preferred embodiment, the subject has fewer than 100,000 platelets per cubic mm of blood.

According to another preferred embodiment, the subject is female.

According to another preferred embodiment, the subject is not pregnant.

According to another preferred embodiment, the subject has a blood thyroid stimulating hormone concentration that is above the lower limit of normal and below the upper limit of normal.

According to another preferred embodiment, the subject has serum creatine of less than 1.4 of the upper limit of normal.

According to another preferred embodiment, the subject is a male.

According to another preferred embodiment, the subject has serum creatine of less than 1.5 of the upper limit of normal.

According to another preferred embodiment, the subject has an amount of aspartate transaminase that is less than two times the upper limit of normal.

According to another preferred embodiment, the subject has an amount of alanine transaminase that is less than two times the upper limit of normal.

According to another preferred embodiment, the antibody or antigen-binding fragment is administered in a dosage amount within the range of about 5 mg to about 500 mg.

According to another preferred embodiment, the antibody or antigen-binding fragment is administered in a dosage amount within the range of about 50 mg to about 300 mg.

According to another preferred embodiment, the antibody is administered at between 200 and 300 mg every four weeks.

According to another preferred embodiment, the antibody or antigen-binding fragment is administered in a dosage amount of about 150 mg.

According to another preferred embodiment, the antibody or antigen-binding fragment thereof is administered to the subject every other week (E2W).

According to another preferred embodiment, the antibody or antigen-binding fragment thereof is administered to the subject every fourth week (E4W).

According to another preferred embodiment, the antibody or the antigen-binding fragment comprises the heavy and light chain CDRs of a HCVR/LCVR amino acid sequence pair as shown in SEQ ID NOs: 90/92. According to another preferred embodiment, the antibody or antigen-binding fragment comprises a HCVR/LCVR amino acid sequence pair as shown in SEQ ID NOs: 90/92. According to another preferred embodiment, the antibody or antigen-binding fragment thereof competes for binding to hPCSK9 with an antibody or antigen-binding fragment comprising a HCVR/LCVR amino acid sequence pair as shown in SEQ ID NOs: 90/92. According to another preferred embodiment, the antibody is administered subcutaneously. According to another preferred embodiment, the antibody is administered in the abdomen.

According to another preferred embodiment, the methog further comprises administering a HMG-CoA reductase inhibitor to the subject. According to another preferred embodiment, the HMG-CoA reductase inhibitor is administered in a dosage amount in the range of about 0.05 mg to 100 mg. According to another preferred embodiment, the HMG-CoA reductase inhibitor is a statin. According to another preferred embodiment, the statin is selected from the group consisting of cerivastatin, atorvastatin, simvastatin, pitavastatin, rosuvastatin, fluvastatin, lovastatin, and pravastatin. According to another preferred embodiment, the statin is atorvastatin administered at a dosage of 10 mg, 20 mg, 40 mg or 80 mg. According to another preferred embodiment, the atorvastatin is administered at about 10 mg per day and at 80 mg one day in an 8 week period.

Several aspects of the invention can be combined with each other. For example, the method for treating a disease or condition according to the eleventh aspect and the method for treating a disease or condition according to the eighteenth aspect can be combined. As a result of this combination the present invention relates to a method for treating a disease or condition which features the treatment of certain groups of subjects by certain dosage regimens. In an analogous manner, different embodiments of the aspects described herein can be combined with eachother, e.g. the antibody or antigen-binding fragment for use in the treatment of a disease or condition related to certain dosage regimens according to the seventh aspect can be combined with the antibody or antigen-binding fragment for use in the treatment of a disease or condition related to certain patient populations according to the seventh aspect. As a result of this combination the present invention relates to an antibody or antigen-binding fragment thereof for use in the treatment of certain groups of subjects by certain dosage regimens.

According to another example, the method for treating a disease or condition according to the eleventh aspect and the method for treating a disease or condition according to the nineteenth aspect can be combined. As a result of this combination the present invention relates to a method for treating a disease or condition which excludes certain groups of subjects from a treatment by a certain dosage regimen. In an analogous manner, different embodiments of the aspects described herein can be combined with eachother, e.g. the antibody or antigen-binding fragment for use in the treatment of a disease or condition according to an embodiment of the seventh aspect related to certain dosage regimens can be combined with the antibody or antigen-binding fragment for use in the treatment of a disease or condition according to an embodiment of the seventh aspect related to the exclusion of certain groups of subjects from the treatment. As a result of this combination the present invention relates to an antibody or antigen-binding fragment thereof for use in the treatment by a certain dosage regimen, wherein certain groups of subjects are excluded from the treatment.

The skilled artisan will recognize other preferred embodiments resulting of suitable combinations of different aspects and embodiments of present invention.

The pharmaceutical uses of present invention as herein described also relate to uses of the given antibody or antigen-binding fragment thereof, of the given pharmaceutical composition, etc for the manufacture of a medicament for the treatment of one or more of the diseases or conditions as herein described.

Preferred Antibodies for Practicing the Present Invention

The following section describes functional and structural features of antibodies and antigen-binding fragments thereof that can be used for practicing all twenty-one aspects of the present invention. Thus, expressions such as "in preferred embodiments", "in some embodiments", "in another preferred embodiment" and similar expressions should be understood as referring to embodiments of the first aspect of the present invention, the second aspect of the present invention, the third aspect of the present invention, the fourth aspect of the present invention, the fifth aspect of the present invention, the sixth aspect of the present invention, the seventh aspect of the present invention, the eighth aspect of the present invention, the ninth aspect of the present invention, the tenth aspect of the present invention, the eleventh aspect of the present invention, the twelfth aspect of the present invention, the thirteenth aspect of the present invention, the fourteenth aspect of the present invention, the fifteenth aspect of the present invention, the sixteenth aspect of the present invention, the seventeenth aspect of the present invention, the eighteenth aspect of the present invention, the nineteenth aspect of the present invention, the twentieth aspect, and the twenty-first aspect of the present invention, the twentysecond aspect of present invention, the twentythird aspect of present invention, the twentyfourth aspect of present invention, the twentyfifth, the twentysixth aspect of present invention.

All antibodies or antigen-binding fragments thereof suitable for practicing the present invention specifically bind hPCSK9. In preferred embodiments of any aspect of the present invention, the antibody or antigen-binding fragment thereof is a recombinant human antibody or fragment thereof. In more specific embodiments, the antibody or antigen-binding fragment thereof is a fully human monoclonal antibody or antigen-binding fragment thereof that specifically binds hPCSK9 and neutralizes PCSK9 activity.

The mAbs usable in the present invention can be full-length (e.g., an IgG1 or IgG4 antibody) or may comprise only an antigen-binding portion (e.g., a Fab, F(ab')$_2$ or scFv fragment), and may be modified to affect functionality, e.g., to eliminate residual effector functions (Reddy et al. (2000) J. Immunol. 164:1925-1933).

In preferred embodiments, the antibodies of present invention are characterized by one or more of the following features upon administration to a subject, preferably a human or non-human mammal and more preferably a human:

reduction of low density lipoprotein-C (LDL-C) levels of at least about –25% to about –40% relative to a predose level with a sustained reduction over at least a 14 day-period, wherein the sustained reduction is preferably at least –25% and more preferably at least –30% relative to a predose level, particularly if administered in a dose of about 40 to about 60 mg, preferably about 45 to about 55 mg and more preferably about 50 mg in a biweekly administration regime (every other week, E2W), reduction of low density lipoprotein-C (LDL-C) of at least about –50% to about –65% relative to a predose level with a sustained reduction over at least a 14 day-period, wherein the sustained reduction is preferably at least –40% and more preferably at least –45% relative to a predose level, particularly if administered in a dose of about 100 mg E2W, reduction of low-density lipoprotein-C (LDL-C) of at least about –60% to at least about –75% [e.g. at least about –60%, at least about –65%, at least about –70 or at least about –75%] relative to a predose level with a sustained reduction over at least a 14 day-period, wherein the sustained reduction is preferably at least –55% and more preferably at least –60% relative to a predose level, particularly when administered in a dose of about 150 mg E2W, reduction of low density lipoprotein-C (LDL-C) of at least about 40% to about 75% relative to a predose level with a sustained reduction over at least a 28 day period, wherein the sustained reduction is preferably at least –35% and more preferably at least –40% relative to a predose level, particularly when administered in a dose of about 200 mg E4W, reduction of low density lipoprotein-C (LDL-C) of at least about –50% to about –75% relative to a predose level with a sustained reduction over at least a 28 day-period, wherein the sustained reduction is preferably at least –40% and more preferably at least –45% relative to a predose level, particularly when administered in a dose of about 300 mg E4W, increase of serum HDL cholesterol levels of at least 2%, at least 2.5%, at least, 3%, at least 3.5%, at least 4%, at least 4.5%, at least 5% or at least 5.5% relative to a predose level, particularly when admimistered in a dose of about 150 mg E2W, little or no detectable effect on troponin levels, Increase of one or more of: Total-Cholesterol levels, ApoB levels, non HDL-C levels, Apo-B/ApoA-1 ratio, The antibodies according to present invention exhibit the above properties preferably if administered in combination with an HMG-CoA reductase inhibitor treatment. Preferred embodiments of HMG-CoA reductase inhibitors to be used in conjunction with the antibody of the invention and dosage and administration regimes thereof can be found throughout the specification, particularly as described in the aspects related to medical uses and methods of treatment.

According to another preferred embodiment of the antibodies and antigen-binding fragments thereof of present invention, the antibody or antigen binding fragment thereof has one or more of the following characteristics:

The antibody or the antigen-binding fragment comprises the heavy and light chain CDRs of a HCVR/LCVR amino acid sequence pair as shown in SEQ ID NOs: 90/92.

The antibody or antigen-binding fragment thereof comprises a HCVR/LCVR amino acid sequence pair as shown in SEQ ID NOs: 90/92.

The antibody or antigen-binding fragment thereof competes for binding to hPCSK9 with an antibody or antigen-binding fragment comprising a HCVR/LCVR amino acid sequence pair as shown in SEQ ID NOs: 90/92.

According to another preferred embodiment of the antibodies and antigen-binding fragments thereof of present invention, the antibody or antigen binding fragment thereof has one or more of the following characteristics:

overcomes statin resistance in mammals, especially in rodents such as hamster increase in LDLR expression in mammals, particularly in rodents such as hamster decreases serum LDL-C in rodents such as hamster synergistic decrease of LDL-C in conjunction with HMG-CoA reductase inhibitor administration, particularly in rodents such as hamster, wherein the HMG-CoA reductase inhibitor is preferably Atorvastatin.

In preferred embodiments, the antibody or the antigen-binding fragment thereof is characterized by one or more of the following:

(i) capable of reducing serum total cholesterol at least about 25 to about 35% and sustaining the reduction over at least a 24 day period relative to a predose level, preferably the reduction in serum total cholesterol is at least about 30-40%;

(ii) capable of reducing serum LDL cholesterol at least about 65-80% and sustaining the reduction over at least a 24 day period relative to a predose level;

(iii) capable of reducing serum triglyceride at least about 25-40% relative to predose level;

(iv) achieves one or more of (i)-(iii) without reducing serum HDL cholesterol or reducing serum HDL cholesterol no more than 5% relative to predose level;

(v) achieves one or more of (i)-(iii) with little or no measurable effect on liver function, as determined by ALT and AST measurements.

In preferred embodiments, the antibody or the antigen-binding fragment thereof is characterized by one or more of the following:

(i) capable of reducing serum LDL cholesterol at least about 40-70% and sustaining the reduction over at least a 60 or 90 day period relative to a predose level;

(ii) capable of reducing serum triglyceride at least about 25-40% relative to predose level;

(iii) does not reduce serum HDL cholesterol or reduces serum HDL cholesterol no more than 5% relative to predose level.

In one embodiment, the antibody or the antigen-binding fragment thereof is characterized as binding an epitope comprising amino acid residue 238 of hPCSK9 (SEQ ID NO:755). In a more specific embodiment, the antibody or antigen-binding fragment binds an epitope comprising one or more of amino acid residues at positions 238, 153, 159 and 343 of hPCSK9 (SEQ ID NO:755). In a more specific embodiment, the antibody or fragment thereof is characterized as binding an epitope which does not comprise an amino acid residue at positions 192, 194, 197 and/or 237 of SEQ ID NO:755.

In one embodiment, the antibody or the antigen-binding fragment thereof is characterized as binding an epitope comprising amino acid residue 366 of hPCSK9 (SEQ ID NO:755). In a more specific embodiment, the antibody or antigen-binding fragment binds an epitope comprising one or more of amino acid residues at positions 147, 366 and 380 of hPCSK9 (SEQ ID NO:755). In a more specific embodiment, the antibody or antigen-binding fragment of an antibody is characterized as binding an epitope which does not comprise an amino acid residue at position 215 or 238 of SEQ ID NO:755.

In one embodiment, the antibody or the antigen-binding fragment thereof comprises a heavy chain variable region (HCVR) selected from the group consisting of SEQ ID NO:2, 18, 22, 26, 42, 46, 50, 66, 70, 74, 90, 94, 98, 114, 118, 122, 138, 142, 146, 162, 166, 170, 186, 190, 194, 210, 214, 218, 234, 238, 242, 258, 262, 266, 282, 286, 290, 306, 310, 314, 330, 334, 338, 354, 358, 362, 378, 382, 386, 402, 406, 410, 426, 430, 434, 450, 454, 458, 474, 478, 482, 498, 502, 506, 522, 526, 530, 546, 550, 554, 570, 574, 578, 594, 598, 602, 618, 622, 626, 642, 646, 650, 666, 670, 674, 690, 694, 698, 714, 718, 722, 738 and 742, or a substantially similar sequence thereof having at least 90%, at least 95%, at least 98% or at least 99% sequence identity. In one embodiment, the HCVR comprises an amino acid sequence selected from the group consisting of SEQ ID NO:50, 66, 70, 74, 90, 94, 122, 138, 142, 218, 234, 238, 242, 258, 262, 314, 330 and 334. In a more specific embodiment, the HCVR comprises SEQ ID NO:90 or 218.

In one embodiment, the antibody or the antigen-binding fragment thereof further comprises a light chain variable region (LCVR) selected from the group consisting of SEQ ID NO:10, 20, 24, 34, 44, 48, 58, 68, 72, 82, 92, 96, 106, 116, 120, 130, 140, 144, 154, 164, 168, 178, 188, 192, 202, 212, 216, 226, 236, 240, 250, 260, 264, 274, 284, 288, 298, 308, 312, 322, 332, 336, 346, 356, 360, 370, 380, 384, 394, 404, 408, 418, 428, 432, 442, 452, 456, 466, 476, 480, 490, 500, 504, 514, 524, 528, 538, 548, 552, 562, 572, 576, 586, 596, 600, 610, 620, 624, 634, 644, 648, 658, 668, 672, 682, 692, 696, 706, 716, 720, 730, 740 and 744, or a substantially similar sequence thereof having at least 90%, at least 95%, at least 98% or at least 99% sequence identity. In one embodiment, the LCVR comprises an amino acid sequence selected from the group consisting of SEQ ID NO: 58, 68, 72, 82, 92, 96, 130, 140, 144, 226, 236, 240, 250, 260, 264, 322, 332 and 336. In a more specific embodiment, the LCVR comprises SEQ ID NO:92 or 226.

In specific embodiments, the antibody or the antigen-binding fragment thereof comprises a HCVR and LCVR (HCVR/LCVR) sequence pair selected from the group consisting of SEQ ID NO: 2/10, 18/20, 22/24, 26/34, 42/44, 46/48, 50/58, 66/68, 70/72, 74/82, 90/92, 94/96, 98/106, 114/116, 118/120, 122/130, 138/140, 142/144, 146/154, 162/164, 166/168, 170/178, 186/188, 190/192, 194/202, 210/212, 214/216, 218/226, 234/236, 238/240, 242/250, 258/260, 262/264, 266/274, 282/284, 286/288, 290/298, 306/308, 310/312, 314/322, 330/332, 334/336, 338/346, 354/356, 358/360, 362/370, 378/380, 382/384, 386/394, 402/404, 406/408, 410/418, 426/428, 430/432, 434/442, 450/452, 454/456, 458/466, 474/476, 478/480, 482/490, 498/500, 502/504, 506/514, 522/524, 526/528, 530/538, 546/548, 550/552, 554/562, 570/572, 574/576, 578/586, 594/596, 598/600, 602/610, 618/620, 622/624, 626/634, 642/644, 646/648, 650/658, 666/668, 670/672, 674/682, 690/692, 694/696, 698/706, 714/716, 718/720, 722/730, 738/740 and 742/744. In one embodiment, the HCVR and LCVR sequence pair comprises one of SEQ ID NO: 50/58, 66/68, 70/72, 74/82, 90/92, 94/96, 122/130, 138/140, 142/144, 218/226, 234/236, 238/240, 242/250, 258/260, 262/264, 314/322, 330/332 and 334/336. In preferred embodiments, the antibody or antigen-binding fragment thereof comprises an HCVR amino acid sequence as shown in SEQ ID NO: 90 and an LCVR amino acid sequence as shown in SEQ ID NO: 92. In another preferred embodiment, the antibody or antigen-binding fragment thereof comprises an HCVR amino acid sequence as shown in SEQ ID NO: 218 and an LCVR amino acid sequence as shown in SEQ ID NO: 226.

In preferred embodiments, the antibody or the antigen-binding fragment thereof comprises a heavy chain CDR3 (HCDR3) domain selected from the group consisting of SEQ ID NO:8, 32, 56, 80, 104, 128, 152, 176, 200, 224, 248, 272, 296, 320, 344, 368, 392, 416, 440, 464, 488, 512, 536, 560, 584, 608, 632, 656, 680, 704 and 728, or a substantially similar sequence thereof having at least 90%, at least 95%, at least 98% or at least 99% sequence identity; and a light chain CDR3 (LCDR3) domain selected from the group consisting of SEQ ID NO:16, 40, 64, 88, 112, 136, 160, 184, 208, 232, 256, 280, 304, 328, 352, 376, 400, 424, 448, 472, 496, 520, 544, 568, 592, 616, 640, 664, 688, 712 and 736, or substantially similar sequences thereof having at least 90%, at least 95%, at least 98% or at least 99% sequence identity. In one embodiment, the HCDR3/LCDR3 sequence pair is selected from the group consisting of SEQ ID NO:56/64, 80/88, 128/136, 224/232, 248/256 and 320/328. In more preferred embodiments, the antibody or the antigen-binding fragment thereof comprises a HCDR3 domain as shown in SEQ ID NO: 80 and a LCDR3 domain as shown in SEQ ID NO: 88. In another preferred embodiment, the antibody or the antigen-binding fragment thereof comprises a HCDR3 domain as shown in SEQ ID NO: 224 and a LCDR3 domain as shown in SEQ ID NO: 232.

In a further embodiment, the antibody or the antigen-binding fragment thereof further comprises a heavy chain CDR1 (HCDR1) domain selected from the group consisting of SEQ ID NO:4, 28, 52, 76, 100, 124, 148, 172, 196, 220, 244, 268, 292, 316, 340, 364, 388, 412, 436, 460, 484, 508, 532, 556, 580, 604, 628, 652, 676, 700 and 724, or a substantially similar sequence thereof having at least 90%, at least 95%, at least 98% or at least 99% sequence identity; a heavy chain CDR2 (HCDR2) domain selected from the group consisting of SEQ ID NO:6, 30, 54, 78, 102, 126, 150, 174, 198, 222, 246, 270, 294, 318, 342, 366, 390, 414, 438, 462, 486, 510, 534, 558, 582, 606, 630, 654, 678, 702 and 726, or a substantially similar sequence thereof having at least 90%, at least 95%, at least 98% or at least 99% sequence identity; a light chain CDR1 (LCDR1) domain selected from the group consisting of SEQ ID NO:12, 36, 60, 84, 108, 132, 156, 180, 204, 228, 252, 276, 300, 324, 348, 372, 396, 420, 444, 468, 492, 516, 540, 564, 588, 612, 636, 660, 684, 708 and 732, or a substantially similar sequence thereof having at least 90%, at least 95%, at least 98% or at least 99% sequence identity; and a light chain CDR2 (LCDR2) domain selected from the group consisting of SEQ ID NO:14, 38, 62, 86, 110, 134, 158, 182, 206, 230, 254, 278, 302, 326, 350, 374, 398, 422, 446, 470, 494, 518, 542, 566, 590, 614, 638, 662, 686, 710 and 734, or a substantially similar sequence thereof having at least 90%, at least 95%, at least 98% or at least 99% sequence identity. In one embodiment, the heavy and light chain CDR sequences comprise a sequence selected from the group consisting of SEQ ID NO:52, 54, 56, 60, 62, 64; 76, 78, 80, 84, 86, 88; 124, 126, 128, 132, 134, 136; 220, 222, 224, 228, 230, 232; 244, 246, 248, 252, 254, 256; and 316, 318, 320, 324, 326, 328. In more specific embodiments, the CDR sequences comprise SEQ ID NO: 76, 78, 80, 84, 86, 88; or 220, 222, 224, 228, 230, 232. In preferred embodiments, the antibody or antigen-binding fragment thereof comprises heavy and light chain CDR amino acid sequences as shown in SEQ ID NOs: 76, 78, 80, 84, 86 and 88. In another preferred embodiment, the antibody or antigen-binding fragment thereof comprises heavy and light chain CDR amino acid sequences as shown in SEQ ID NOs: 220, 222, 224, 228, 230 and 232.

In a related embodiment, the antibody or antigen-binding fragment thereof comprises heavy and light chain CDR domains contained within heavy and light chain sequence pairs selected from the group consisting of SEQ ID NO: 2/10, 18/20, 22/24, 26/34, 42/44, 46/48, 50/58, 66/68, 70/72, 74/82, 90/92, 94/96, 98/106, 114/116, 118/120, 122/130, 138/140, 142/144, 146/154, 162/164, 166/168, 170/178, 186/188, 190/192, 194/202, 210/212, 214/216, 218/226, 234/236, 238/240, 242/250, 258/260, 262/264, 266/274, 282/284, 286/288, 290/298, 306/308, 310/312, 314/322, 330/332, 334/336, 338/346, 354/356, 358/360, 362/370, 378/380, 382/384, 386/394, 402/404, 406/408, 410/418, 426/428, 430/432, 434/442, 450/452, 454/456, 458/466, 474/476, 478/480, 482/490, 498/500, 502/504, 506/514, 522/524, 526/528, 530/538, 546/548, 550/552, 554/562, 570/572, 574/576, 578/586, 594/596, 598/600, 602/610, 618/620, 622/624, 626/634, 642/644, 646/648, 650/658, 666/668, 670/672, 674/682, 690/692, 694/696, 698/706, 714/716, 718/720, 722/730, 738/740 and 742/744. In one embodiment, the CDR sequences are contained within HCVR and LCVR selected from the amino acid sequence pairs of SEQ ID NO: 50/58, 66/68, 70/72, 74/82, 90/92, 94/96, 122/130, 138/140, 142/144, 218/226, 234/236, 238/240, 242/250, 258/260, 262/264, 314/322, 330/332 and 334/336. In more specific embodiments, the CDR sequences are comprised within HCVR/LCVR sequences selected from SEQ ID NO: 90/92 or 218/226. In preferred embodiments, the antibody or the antigen-binding fragment thereof comprises the heavy and light chain CDRs of an HCVR/LCVR amino acid sequence pair as shown in SEQ ID NOs: 90/92. In another preferred embodiment, the antibody or the antigen-binding fragment thereof comprises the heavy and light chain CDRs of an HCVR/LCVR amino acid sequence pair as shown in SEQ ID NOs: 218/226.

In one specific embodiment, the antibody or the antigen-binding fragment thereof comprises the heavy chain variable region (HCVR), of SEQ ID NO:90 or a substantially similar sequence thereof having at least 90%, at least 95%, at least 98% or at least 99% sequence identity.

In one specific embodiment, the antibody or the antigen-binding fragment thereof further comprises the light chain variable region (LCVR) of SEQ Id NO 92 or a substantially similar sequence thereof having at least 90%, at least 95%, at least 98% or at least 99% sequence identity.

In specific embodiments, the antibody or the antigen-binding fragment thereof comprises HCVR amino acid sequence as shown in SEQ ID NO: 90 and an LCVR amino acid sequence as shown in SEQ ID NO: 92.

In specific embodiments, the antibody or the antigen-binding fragment thereof comprises a heavy chain CDR3 (HCDR3) domain of SEQ ID NO: 80 or a substantially similar sequence thereof having at least 90%, at least 95%, at least 98% or at least 99% sequence identity; and/or a light chain CDR3 (LCDR3) domain of SEQ ID NO: 88, or substantially similar sequences thereof having at least 90%, at least 95%, at least 98% or at least 99% sequence identity. In one embodiment, the HCDR3/LCDR3 sequence pair is SEQ ID NO:80/88. In more preferred embodiments, the antibody or the antigen-binding fragment thereof comprises a HCDR3 domain as shown in SEQ ID NO: 80 and a LCDR3 domain as shown in SEQ ID NO: 88.

In a further specific embodiment, the antibody or the antigen-binding fragment thereof further comprises the heavy chain CDR1 (HCDR1) domain of SEQ ID NO: 76, or a substantially similar sequence thereof having at least 90%, at least 95%, at least 98% or at least 99% sequence identity; and/or the heavy chain CDR2 (HCDR2) domain of SEQ ID NO: 78 or a substantially similar sequence thereof having at least 90%, at least 95%, at least 98% or at least 99% sequence identity; and/or a light chain CDR1 (LCDR1) domain of SEQ ID NO: 84 or a substantially similar sequence thereof having at least 90%, at least 95%, at least 98% or at least 99% sequence identity; and/or a light chain CDR2 (LCDR2) domain of SEQ ID NO: 86, or a substantially similar sequence thereof having at least 90%, at least 95%, at least 98% or at least 99% sequence identity. In one embodiment, the heavy and light chain CDR sequences comprise a sequence selected from the group consisting of SEQ ID NO: 76, 78, 80, 84, 86, 88. In preferred embodiments, the antibody or antigen-binding fragment thereof comprises heavy and light chain CDR amino acid sequences as shown in SEQ ID NOs: 76, 78, 80, 84, 86 and 88.

In another specific embodiment, the antibody or antigen-binding fragment thereof comprises heavy and light chain CDR domains contained within the heavy and light chain sequence pair of SEQ ID NO: 90/92.

A particularly preferred embodiment concerns an antibody comprising HCVR/LCVR sequences SEQ ID Nos: 90/92 and/or CDR sequences SEQ ID Nos: 76, 78, 80 and/or CDR sequences SEQ ID NO:s 84, 86, 88. Another particularly preferred embodiment concerns an antibody comprising the HCVR/LCVR sequences SEQ ID Nos: 90/92 and the CDR sequences SEQ ID Nos: 76, 78, 80 and the CDR sequences SEQ ID NO:s 84, 86, 88 ("316P").

In one embodiment, the antibody or antigen-binding fragment thereof comprises an HCVR encoded by a nucleic acid sequence selected from the group consisting of SEQ ID NO: 1, 17, 21, 25, 41, 45, 49, 65, 69, 73, 89, 93, 97, 113, 117, 121, 137, 141, 145, 161, 165, 169, 185, 189, 193, 209, 213, 217, 233, 237, 241, 257, 261, 265, 281, 285, 289, 305, 309, 313, 329, 333, 337, 353, 357, 361, 377, 381, 385, 401, 405, 409, 425, 429, 433, 449, 453, 457, 473, 477, 481, 497, 501, 505, 521, 525, 529, 545, 549, 553, 569, 573, 577, 593, 597, 601, 617, 621, 625, 641, 645, 649, 665, 669, 673, 689, 693, 697, 713, 717, 721, 737 and 741, or a substantially identical sequence having at least 90%, at least 95%, at least 98%, or at least 99% sequence identity thereof. In one embodiment, the HCVR is encoded by a nucleic acid sequence selected from the group consisting of SEQ ID NO: 49, 65, 69, 73, 89, 93, 121, 137, 141, 217, 233, 237, 241, 257, 261, 313, 329 and 333. In more specific embodiments, the HCVR is encoded by a nucleic acid sequence selected from the group consisting of SEQ ID NO: 89 and 217.

In one embodiment, the antibody or fragment thereof further comprises an LCVR encoded by a nucleic acid sequence selected from the group consisting of SEQ ID NO: 9, 19, 23, 33, 43, 47, 57, 67, 71, 81, 91, 95, 105, 115, 119, 129, 139, 143, 153, 163, 167, 177, 187, 191, 201, 211, 215, 225, 235, 239, 249, 259, 263, 273, 283, 287, 297, 307, 311, 321, 331, 335, 345, 355, 359, 369, 379, 383, 393, 403, 407, 417, 427, 431, 441, 451, 455, 465, 475, 479, 489, 499, 503, 513, 523, 527, 537, 547, 551, 561, 571, 575, 585, 595, 599, 609, 619, 623, 633, 643, 647, 657, 667, 671, 681, 691, 695, 705, 715, 719, 729, 739 and 743, or a substantially identical sequence having at least 90%, at least 95%, at least 98%, or at least 99% sequence identity thereof. In one embodiment, the LCVR is encoded by a nucleic acid sequence selected from the group consisting of SEQ ID NO: 57, 67, 71, 81, 91, 95, 129, 139, 143, 225, 235, 239, 249, 259, 263, 321, 331 and 335. In more specific embodiments, the LCVR is encoded by a nucleic acid sequence selected from the group consisting of SEQ ID NO: 91 and 225.

In one embodiment, the antibody or antigen-binding fragment thereof comprises an HCDR3 domain encoded by a nucleotide sequence selected from the group consisting of SEQ ID NO:7, 31, 55, 79, 103, 127, 151, 175, 199, 223, 247, 271, 295, 319, 343, 367, 391, 415, 439, 463, 487, 511, 535, 559, 583, 607, 631, 655, 679, 703 and 727, or a substantially identical sequence having at least 90%, at least 95%, at least 98%, or at least 99% sequence identity thereof; and a LCDR3 domain encoded by a nucleotide sequence selected from the group consisting of SEQ ID NO: 15, 39, 63, 87, 111, 135, 159, 183, 207, 231, 255, 279, 303, 327, 351, 375, 399, 423, 447, 471, 495, 519, 543, 567, 591, 615, 639, 663, 687, 711 and 735, or a substantially identical sequence having at least 90%, at least 95%, at least 98%, or at least 99% sequence identity thereof. In one embodiment, the HCDR3 and LCDR3 comprise a sequence pair encoded by the nucleic acid sequence of SEQ ID NO: 55/63, 79/87, 127/135, 223/231, 247/255 and 319/327, respectively. In more specific embodiments, the HCDR3 and LCDR3 comprise a sequence pair encoded by the nucleic acid sequence of SEQ ID NO: 79/87 and 223/231.

In a further embodiment, the antibody or antigen-binding fragment thereof further comprises: an HCDR1 domain encoded by a nucleotide sequence selected from the group consisting of SEQ ID NO: 3, 27, 51, 75, 99, 123, 147, 171, 195, 219, 243, 267, 291, 315, 339, 363, 387, 411, 435, 459, 483, 507, 531, 555, 579, 603, 627, 651, 675, 699 and 723, or a substantially identical sequence having at least 90%, at least 95%, at least 98%, or at least 99% sequence identity thereof; an HCDR2 domain encoded by a nucleotide sequence selected from the group consisting of SEQ ID NO:5, 29, 53, 77, 101, 125, 149, 173, 197, 221, 245, 269, 293, 317, 341, 365, 389, 413, 437, 461, 485, 509, 533, 557, 581, 605, 629, 653, 677, 701 and 725, or a substantially identical sequence having at least 90%, at least 95%, at least 98%, or at least 99% sequence identity thereof; an LCDR1 domain encoded by a nucleotide sequence selected from the group consisting of SEQ ID NO: 11, 35, 59, 83, 107, 131, 155, 179, 203, 227, 251, 275, 299, 323, 347, 371, 395, 419, 443, 467, 491, 515, 539, 563, 587, 611, 635, 659, 683, 707 and 731, or a substantially identical sequence having at least 90%, at least 95%, at least 98%, or at least 99% sequence identity thereof; and an LCDR2 domain encoded by a nucleotide sequence selected from the group consisting of SEQ ID NO: 13, 37, 61, 85, 109, 133, 157, 181, 205, 229, 253, 277, 301, 325, 349, 373, 397, 421, 445, 469, 493, 517, 541, 565, 589, 613, 637, 661, 685, 709 and 733, or a substantially identical sequence having at least 90%, at least 95%, at least 98%, or at least 99% sequence identity thereof. In one embodiment, the heavy and light chain CDR sequences are encoded by the nucleic acid sequences of SEQ ID NO: 51, 53, 55, 59, 61, 63; 75, 77, 79, 83, 85, 87; 123, 125, 127, 131, 133, 135; 219, 221, 223, 227, 229, 231; 243, 245, 247, 251, 253, 255; and 315, 317, 319, 323, 325, 327. In more specific embodiments, the heavy and light chain CDR sequences are encoded by the nucleic acid sequences of SEQ ID NO: 75, 77, 79, 83, 85, 87; and 219, 221, 223, 227, 229, 231.

In a further embodiment, the antibody or antigen-binding fragment thereof comprises an HCDR3 and an LCDR3, wherein HCDR3 comprises an amino acid sequence of the formula $X^1$-$X^2$-$X^3$-$X^4$-$X^5$-$X^6$-$X^7$-$X^8$-$X^9$-$X^{10}$-$X^{11}$-$X^{12}$-$X^{13}$-$X^{14}$-$X^{15}$-$X^{16}$-$X^{17}$-$X^{18}$-$X^{19}$-$X^{20}$ (SEQ ID NO:747), wherein $X^1$ is Ala, $X^2$ is Arg or Lys, $X^3$ is Asp, $X^4$ is Ser or Ile, $X^5$ is Asn or Val, $X^6$ is Leu or Trp, $X^7$ is Gly or Met, $X^8$ is Asn or Val, $X^9$ is Phe or Tyr, $X^{10}$ is Asp, $X^{11}$ is Leu or Met, $X^{12}$ is Asp or absent, $X^{13}$ is Tyr or absent, $X^{14}$ is Tyr or absent, $X^{15}$ is Tyr or absent, $X^{16}$ is Tyr or absent, $X^{17}$ is Gly or absent, $X^{18}$ is Met or absent, $X^{19}$ is Asp or absent, and $X^{20}$ is Val or absent; and LCDR3 comprises an amino acid sequence of the formula $X^1$-$X^2$-$X^3$-$X^4$-$X^5$-$X^6$-$X^7$-$X^8$-$X^9$ (SEQ ID NO:750), wherein $X^1$ is Gln or Met, $X^2$ is Gln, $X^3$ is Tyr or Thr, $X^4$ is Tyr or Leu, $X^5$ is Thr or Gln, $X^6$ is Thr, $X^7$ is Pro, $X^8$ is Tyr or Leu, and $X^9$ is Thr.

In a further embodiment, the antibody or antigen-binding fragment thereof further comprises an HCDR1 sequence of the formula $X^1$-$X^2$-$X^3$-$X^4$-$X^5$-$X^6$-$X^7$-$X^8$ (SEQ ID NO:745), wherein $X^1$ is Gly, $X^2$ is Phe, $X^3$ is Thr, $X^4$ is Phe, $X^5$ is Ser or Asn, $X^6$ is Ser or Asn, $X^7$ is Tyr or His, and $X^8$ is Ala or Trp; a HCDR2 sequence of the formula $X^1$-$X^2$-$X^3$-$X^4$-$X^5$-$X^6$-$X^7$-$X^8$ (SEQ ID NO:746), wherein $X^1$ is Ile, $X^2$ is Ser or Asn, $X^3$ is Gly or Gln, $X^4$ is Asp or Ser, $X^5$ is Gly, $X^6$ is Ser or Gly, $X^7$ is Thr or Glu, and $X^8$ is Thr or Lys; a LCDR1 sequence of the formula $X^1$-$X^2$-$X^3$-$X^4$-$X^5$-$X^6$-$X^7$-$X^8$-$X^9$-$X^{10}$-$X^{11}$-$X^{12}$ (SEQ ID NO:748) wherein $X^1$ is Gln, $X^2$ is Ser, $X^3$ is Val or Leu, $X^4$ is Leu, $X^5$ is His or Tyr, $X^6$ is Arg or Ser, $X^7$ is Ser or Asn, $X^8$ is Asn or Gly, $X^9$ is Asn, $X^{10}$ is Arg or Asn, $X^{11}$ is Asn or Tyr, and $X^{12}$ is Phe or absent; an LCDR2 sequence of the formula $X^1$-$X^2$-$X^3$ (SEQ ID NO:749) wherein $X^1$ is Trp or Leu, $X^2$ is Ala or Gly, and $X^3$ is Ser.

In a further embodiment, the antibody or antigen-binding fragment thereof is a human anti-PCSK9 antibody or antigen-binding fragment thereof comprising a heavy chain variable region (HCVR) encoded by nucleotide sequence segments derived from $V_H$, $D_H$ and $J_H$ germline sequences, and a light chain variable region (LCVR) encoded by nucleotide sequence segments derived from $V_K$ and $J_K$ germline sequences, wherein the germline sequences are (a) $V_H$ gene segment 3-23, $D_H$ gene segment 7-27, $J_H$ gene segment 2, $V_K$ gene segment 4-1 and $J_K$ gene segment 2; or (b) $V_H$ gene segment 3-7, $D_H$ gene segment 2-8, $J_H$ gene segment 6, $V_K$ gene segment 2-28 and $J_K$ gene segment 4.

In preferred embodiments, the antibody or antigen-binding fragment thereof binds to the same epitope on hPCSK9 as an antibody comprising heavy and light chain CDR amino acid sequences as shown in SEQ ID NOs: 76, 78, 80, 84, 86, and 88 or as shown in SEQ ID NOs: 220, 222, 224, 228, 230 and 232.

In preferred embodiments, the antibody or antigen-binding fragment thereof competes for binding to hPCSK9 with an antibody comprising heavy and light chain CDR amino acid sequences as shown in SEQ ID NOs: 76, 78, 80, 84, 86, and 88 or as shown in SEQ ID NOs: 220, 222, 224, 228, 230 and 232.

The invention encompasses anti-PCSK9 antibodies having a modified glycosylation pattern. In some applications, modification to remove undesirable glycosylation sites may be useful, or e.g., removal of a fucose moiety to increase antibody dependent cellular cytotoxicity (ADCC) function (see Shield et al. (2002) JBC 277:26733). In other applications, modification of galactosylation can be made in order to modify complement dependent cytotoxicity (CDC).

Some preferred sequences related to preferred antibodies for practicing present invention:

SEQ ID NO: 76:
Gly Phe Thr Phe Asn Asn Tyr Ala

SEQ ID NO: 78:
Ile Ser Gly Ser Gly Gly Thr Thr

SEQ ID NO: 80:
Ala Lys Asp Ser Asn Trp Gly Asn Phe Asp Leu

SEQ ID NO: 84:
Gln Ser Val Leu Tyr Arg Ser Asn Asn Arg Asn Phe

SEQ ID NO: 86:
Trp Ala Ser

SEQ ID NO: 88:
Gln Gln Tyr Tyr Thr Thr Pro Tyr Thr

SEQ ID NO: 90:
Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Asn Asn Tyr
             20                  25                  30

Ala Met Asn Trp Val Arg Gln Ala Pro Gly Lys Gly Leu Asp Trp Val
                 35                  40                  45

Ser Thr Ile Ser Gly Ser Gly Gly Thr Thr Asn Tyr Ala Asp Ser Val
 50                  55                  60

Lys Gly Arg Phe Ile Ile Ser Arg Asp Ser Ser Lys His Thr Leu Tyr
65                  70                  75                  80

Leu Gln Met Asn Ser Leu Arg Ala Glu Asp Thr Ala Val Tyr Tyr Cys
                 85                  90                  95

Ala Lys Asp Ser Asn Trp Gly Asn Phe Asp Leu Trp Gly Arg Gly Thr
            100                 105                 110

Leu Val Thr Val Ser Ser
        115

SEQ ID NO: 92:
Asp Ile Val Met Thr Gln Ser Pro Asp Ser Leu Ala Val Ser Leu Gly
 1               5                  10                  15

Glu Arg Ala Thr Ile Asn Cys Lys Ser Ser Gln Ser Val Leu Tyr Arg
             20                  25                  30

Ser Asn Asn Arg Asn Phe Leu Gly Trp Tyr Gln Gln Lys Pro Gly Gln
             35                  40                  45

Pro Pro Asn Leu Leu Ile Tyr Trp Ala Ser Thr Arg Glu Ser Gly Val
 50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                 85                  90                  95

Tyr Tyr Thr Thr Pro Tyr Thr Phe Gly Gln Gly Thr Lys Leu Glu Ile
            100                 105                 110

Lys

SEQ ID NO: 755 (hPCSK9):
Met Gly Thr Val Ser Ser Arg Arg Ser Trp Trp Pro Leu Pro Leu Leu
 1               5                  10                  15

Leu Leu Leu Leu Leu Leu Leu Gly Pro Ala Gly Ala Arg Ala Gln Glu
             20                  25                  30

Asp Glu Asp Gly Asp Tyr Glu Glu Leu Val Leu Ala Leu Arg Ser Glu
             35                  40                  45

Glu Asp Gly Leu Ala Glu Ala Pro Glu His Gly Thr Thr Ala Thr Phe
 50                  55                  60

His Arg Cys Ala Lys Asp Pro Trp Arg Leu Pro Gly Thr Tyr Val Val

```
                65                  70                  75                  80
Val Leu Lys Glu Glu Thr His Leu Ser Gln Ser Glu Arg Thr Ala Arg
                85                  90                  95

Arg Leu Gln Ala Gln Ala Arg Arg Gly Tyr Leu Thr Lys Ile Leu
            100                 105                 110

His Val Phe His Gly Leu Leu Pro Gly Phe Leu Val Lys Met Ser Gly
            115                 120                 125

Asp Leu Leu Glu Leu Ala Leu Lys Leu Pro His Val Asp Tyr Ile Glu
        130                 135                 140

Glu Asp Ser Ser Val Phe Ala Gln Ser Ile Pro Trp Asn Leu Glu Arg
145                 150                 155                 160

Ile Thr Pro Pro Arg Tyr Arg Ala Asp Glu Tyr Gln Pro Pro Asp Gly
                165                 170                 175

Gly Ser Leu Val Glu Val Tyr Leu Leu Asp Thr Ser Ile Gln Ser Asp
            180                 185                 190

His Arg Glu Ile Glu Gly Arg Val Met Val Thr Asp Phe Glu Asn Val
        195                 200                 205

Pro Glu Glu Asp Gly Thr Arg Phe His Arg Gln Ala Ser Lys Cys Asp
    210                 215                 220

Ser His Gly Thr His Leu Ala Gly Val Val Ser Gly Arg Asp Ala Gly
225                 230                 235                 240

Val Ala Lys Gly Ala Ser Met Arg Ser Leu Arg Val Leu Asn Cys Gln
                245                 250                 255

Gly Lys Gly Thr Val Ser Gly Thr Leu Ile Gly Leu Glu Phe Ile Arg
            260                 265                 270

Lys Ser Gln Leu Val Gln Pro Val Gly Pro Leu Val Val Leu Leu Pro
        275                 280                 285

Leu Ala Gly Gly Tyr Ser Arg Val Leu Asn Ala Ala Cys Gln Arg Leu
    290                 295                 300

Ala Arg Ala Gly Val Val Leu Val Thr Ala Ala Gly Asn Phe Arg Asp
305                 310                 315                 320

Asp Ala Cys Leu Tyr Ser Pro Ala Ser Ala Pro Glu Val Ile Thr Val
                325                 330                 335

Gly Ala Thr Asn Ala Gln Asp Gln Pro Val Thr Leu Gly Thr Leu Gly
            340                 345                 350

Thr Asn Phe Gly Arg Cys Val Asp Leu Phe Ala Pro Gly Glu Asp Ile
        355                 360                 365

Ile Gly Ala Ser Ser Asp Cys Ser Thr Cys Phe Val Ser Gln Ser Gly
    370                 375                 380

Thr Ser Gln Ala Ala Ala His Val Ala Gly Ile Ala Ala Met Met Leu
385                 390                 395                 400

Ser Ala Glu Pro Glu Leu Thr Leu Ala Glu Leu Arg Gln Arg Leu Ile
                405                 410                 415

His Phe Ser Ala Lys Asp Val Ile Asn Glu Ala Trp Phe Pro Glu Asp
            420                 425                 430

Gln Arg Val Leu Thr Pro Asn Leu Val Ala Ala Leu Pro Pro Ser Thr
        435                 440                 445

His Gly Ala Gly Trp Gln Leu Phe Cys Arg Thr Val Trp Ser Ala His
    450                 455                 460

Ser Gly Pro Thr Arg Met Ala Thr Ala Val Ala Arg Cys Ala Pro Asp
465                 470                 475                 480

Glu Glu Leu Leu Ser Cys Ser Ser Phe Ser Arg Ser Gly Lys Arg Arg
                485                 490                 495

Gly Glu Arg Met Glu Ala Gln Gly Gly Lys Leu Val Cys Arg Ala His
```

```
                                  -continued
                500                   505                   510

Asn Ala Phe Gly Gly Glu Gly Val Tyr Ala Ile Ala Arg Cys Cys Leu
            515                 520                 525

Leu Pro Gln Ala Asn Cys Ser Val His Thr Ala Pro Pro Ala Glu Ala
        530                 535                 540

Ser Met Gly Thr Arg Val His Cys His Gln Gln Gly His Val Leu Thr
545                     550                 555                 560

Gly Cys Ser Ser His Trp Glu Val Glu Asp Leu Gly Thr His Lys Pro
                565                 570                 575

Pro Val Leu Arg Pro Arg Gly Gln Pro Asn Gln Cys Val Gly His Arg
            580                 585                 590

Glu Ala Ser Ile His Ala Ser Cys Cys His Ala Pro Gly Leu Glu Cys
            595                 600                 605

Lys Val Lys Glu His Gly Ile Pro Ala Pro Gln Glu Gln Val Thr Val
        610                 615                 620

Ala Cys Glu Glu Gly Trp Thr Leu Thr Gly Cys Ser Ala Leu Pro Gly
625                 630                 635                 640

Thr Ser His Val Leu Gly Ala Tyr Ala Val Asp Asn Thr Cys Val Val
                645                 650                 655

Arg Ser Arg Asp Val Ser Thr Thr Gly Ser Thr Ser Glu Gly Ala Val
            660                 665                 670

Thr Ala Val Ala Ile Cys Cys Arg Ser Arg His Leu Ala Gln Ala Ser
            675                 680                 685

Gln Glu Leu Gln
        690
```

Preparation of Human Antibodies

Methods for generating human antibodies in transgenic mice are known (see for example, U.S. Pat. No. 6,596,541, Regeneron Pharmaceuticals, VELOCIMMUNE™). The VELOCIMMUNE™ technology involves generation of a transgenic mouse having a genome comprising human heavy and light chain variable regions operably linked to endogenous mouse constant region loci such that the mouse produces an antibody comprising a human variable region and a mouse constant region in response to antigenic stimulation. The DNA encoding the variable regions of the heavy and light chains of the antibody are isolated and operably linked to DNA encoding the human heavy and light chain constant regions. The DNA is then expressed in a cell capable of expressing the fully human antibody. In specific embodiment, the cell is a CHO cell.

Antibodies may be therapeutically useful in blocking a ligand-receptor interaction or inhibiting receptor component interaction, rather than by killing cells through fixation of complement and participation in complement-dependent cytotoxicity (CDC), or killing cells through antibody-dependent cell-mediated cytotoxicity (ADCC). The constant region of an antibody is thus important in the ability of an antibody to fix complement and mediate cell-dependent cytotoxicity. Thus, the isotype of an antibody may be selected on the basis of whether it is desirable for the antibody to mediate cytotoxicity.

Human antibodies can exist in two forms that are associated with hinge heterogeneity. In one form, an antibody molecule comprises a stable four-chain construct of approximately 150-160 kDa in which the dimers are held together by an interchain heavy chain disulfide bond. In a second form, the dimers are not linked via inter-chain disulfide bonds and a molecule of about 75-80 kDa is formed composed of a covalently coupled light and heavy chain (half-antibody). These forms have been extremely difficult to separate, even after affinity purification.

The frequency of appearance of the second form in various intact IgG isotypes is due to, but not limited to, structural differences associated with the hinge region isotype of the antibody. A single amino acid substitution in the hinge region of the human IgG4 hinge can significantly reduce the appearance of the second form (Angal et al. (1993) Molecular Immunology 30:105) to levels typically observed using a human IgG1 hinge. The instant invention encompasses antibodies having one or more mutations in the hinge, CH2 or CH3 region which may be desirable, for example, in production, to improve the yield of the desired antibody form.

Generally, a VELOCIMMUNE™ mouse is challenged with the antigen of interest, and lymphatic cells (such as B-cells) are recovered from the mice that express antibodies. The lymphatic cells may be fused with a myeloma cell line to prepare immortal hybridoma cell lines, and such hybridoma cell lines are screened and selected to identify hybridoma cell lines that produce antibodies specific to the antigen of interest. DNA encoding the variable regions of the heavy chain and light chain may be isolated and linked to desirable isotypic constant regions of the heavy chain and light chain. Such an antibody protein may be produced in a cell, such as a CHO cell. Alternatively, DNA encoding the antigen-specific chimeric antibodies or the variable domains of the light and heavy chains may be isolated directly from antigen-specific lymphocytes.

Initially, high affinity chimeric antibodies are isolated having a human variable region and a mouse constant region. As described below, the antibodies are characterized and selected for desirable characteristics, including affinity, selectivity, epitope, etc. The mouse constant regions are replaced with a desired human constant region to generate the fully human antibody of the invention, for example wild-type or modified IgG1 or IgG4 (for example, SEQ ID NO:751, 752, 753). While the constant region selected may vary according to specific use, high affinity antigen-binding and target specificity characteristics reside in the variable region.

Epitope Mapping and Related Technologies

To screen for antibodies that bind to a particular epitope (e.g., those which block binding of IgE to its high affinity receptor), a routine cross-blocking assay such as that described Antibodies, Harlow and Lane (Cold Spring Harbor Press, Cold Spring Harb., N.Y.) can be performed. Other methods include alanine scanning mutants, peptide blots (Reineke (2004) Methods Mol Biol 248:443-63) (herein specifically incorporated by reference in its entirety), or peptide cleavage analysis. In addition, methods such as epitope excision, epitope extraction and chemical modification of antigens can be employed (Tomer (2000) Protein Science 9: 487-496) (herein specifically incorporated by reference in its entirety).

The term "epitope" refers to a site on an antigen to which B and/or T cells respond. B-cell epitopes can be formed both from contiguous amino acids or noncontiguous amino acids juxtaposed by tertiary folding of a protein. Epitopes formed from contiguous amino acids are typically retained on exposure to denaturing solvents, whereas epitopes formed by tertiary folding are typically lost on treatment with denaturing solvents. An epitope typically includes at least 3, and more usually, at least 5 or 8-10 amino acids in a unique spatial conformation.

Modification-Assisted Profiling (MAP), also known as Antigen Structure-based Antibody Profiling (ASAP) is a method that categorizes large numbers of monoclonal antibodies (mAbs) directed against the same antigen according to the similarities of the binding profile of each antibody to chemically or enzymatically modified antigen surfaces (US 2004/0101920, herein specifically incorporated by reference in its entirety). Each category may reflect a unique epitope either distinctly different from or partially overlapping with epitope represented by another category. This technology allows rapid filtering of genetically identical mAbs, such that characterization can be focused on genetically distinct mAbs. When applied to hybridoma screening, MAP may facilitate identification of rare hybridoma clones that produce mAbs having the desired characteristics. MAP may be used to sort the anti-PCSK9 mAbs of the invention into groups of mAbs binding different epitopes.

In various embodiments, the anti-hPCSK9 antibody or antigen-binding fragment of an antibody binds an epitope within the catalytic domain, which is about 153 to 425 of SEQ ID NO:755); more specifically, an epitope from about 153 to about 250 or from about 250 to about 425; more specifically, the antibody or antibody fragment of the invention binds an epitope within the fragment from about 153 to about 208, from about 200 to about 260, from about 250 to about 300, from about 275 to about 325, from about 300 to about 360, from about 350 to about 400, and/or from about 375 to about 425.

In various embodiments, the anti-hPCSK9 antibody or antigen-binding fragment of an antibody binds an epitope within the propeptide domain (residues 31 to 152 of SEQ ID NO:755); more specifically, an epitope from about residue 31 to about residue 90 or from about residue 90 to about residue 152; more specifically, the antibody or antibody fragment of the invention binds an epitope within the fragment from about residue 31 to about residue 60, from about residue 60 to about residue 90, from about residue 85 to about residue 110, from about residue 100 to about residue 130, from about residue 125 to about residue 150, from about residue 135 to about residue 152, and/or from about residue 140 to about residue 152.

In some embodiments, the anti-hPCSK9 antibody or antigen-binding fragment of an antibody binds an epitope within the C-terminal domain, (residues 426 to 692 of SEQ ID NO:755); more specifically, an epitope from about residue 426 to about residue 570 or from about residue 570 to about residue 692; more specifically, the antibody or antibody fragment of the invention binds an epitope within the fragment from about residue 450 to about residue 500, from about residue 500 to about residue 550, from about residue 550 to about residue 600, and/or from about residue 600 to about residue 692.

In some embodiments, the antibody or antibody fragment binds an epitope which includes more than one of the enumerated epitopes within the catalytic, propeptide or C-terminal domain, and/or within two or three different domains (for example, epitopes within the catalytic and C-terminal domains, or within the propeptide and catalytic domains, or within the propeptide, catalytic and C-terminal domains.

In some embodiments, the antibody or antigen-binding fragment binds an epitope on hPCSK9 comprising amino acid residue 238 of hPCSK9 (SEQ ID NO:755). Experimental results (see US 2010/0166768) showed that when D238 was mutated, the $K_D$ of mAb 316P exhibited >400-fold reduction in binding affinity (~1×10$^{-9}$ M to ~410×10$^{-9}$M) and $T_{1/2}$ decreased >30-fold (from ~37 to ~1 min). In a specific embodiment, the mutation was D238R. In specific embodiments, the antibody or antigen-binding fragment of the invention binds an epitope of hPCSK9 comprising two or more of amino acid residues at positions 153, 159, 238 and 343.

As shown before (see US 2010/0166768), a mutation in amino acid residue 153, 159 or 343 resulted in about a 5- to 10-fold decrease in affinity or similar shortening in $T_{1/2}$. In specific embodiments, the mutation was S153R, E159R and/or D343R.

In some embodiments, the antibody or antigen-binding fragment binds an epitope on hPCSK9 comprising amino acid residue 366 of hPCSK9 (SEQ ID NO:755). Experimental results (see US 2010/0166768) showed that when E366 was mutated, the affinity of mAb 300N exhibited about 50-fold decrease (~0.7×10$^{-9}$M to ~36×10$^{-9}$M) and a similar shortening in $T_{1/2}$ (from ~120 to ~2 min). In a specific embodiment, the mutation is E366K.

The present invention includes anti-PCSK9 antibodies that bind to the same epitope as any of the specific exemplary antibodies described herein. Likewise, the present invention also includes anti-PCSK9 antibodies that compete for binding to PCSK9 or a PCSK9 fragment with any of the specific exemplary antibodies described herein.

One can easily determine whether an antibody binds to the same epitope as, or competes for binding with, a reference anti-PCSK9 antibody by using routine methods known in the art. For example, to determine if a test antibody binds to the same epitope as a reference anti-PCSK9 antibody of the invention, the reference antibody is allowed to bind to a PCSK9 protein or peptide under saturating conditions. Next, the ability of a test antibody to bind to the PCSK9 molecule is assessed. If the test antibody is able to bind to PCSK9 following saturation binding with the reference anti-PCSK9 antibody, it can be concluded that the test antibody binds to a different epitope than the reference anti-PCSK9 antibody. On the other hand, if the test antibody is not able to bind to the PCSK9 molecule following saturation binding with the reference anti-PCSK9 antibody, then the test antibody may bind to the same epitope as the epitope bound by the reference anti-PCSK9 antibody of the invention.

To determine if an antibody competes for binding with a reference anti-PCSK9 antibody, the above-described binding methodology is performed in two orientations: In a first orientation, the reference antibody is allowed to bind to a PCSK9 molecule under saturating conditions followed by assessment of binding of the test antibody to the PCSK9 molecule. In a second orientation, the test antibody is allowed to bind to a PCSK9 molecule under saturating conditions followed by assessment of binding of the reference antibody to the PCSK9 molecule. If, in both orientations, only the first (saturating) antibody is capable of binding to the PCSK9 molecule, then it is concluded that the test antibody and the reference antibody compete for binding to PCSK9. As will be appreciated by a person of ordinary skill in the art, an antibody that competes for binding with a reference antibody may not necessarily bind to the identical epitope as the reference antibody, but may sterically block binding of the reference antibody by binding an overlapping or adjacent epitope.

Two antibodies bind to the same or overlapping epitope if each competitively inhibits (blocks) binding of the other to the antigen. That is, a 1-, 5-, 10-, 20- or 100-fold excess of one antibody inhibits binding of the other by at least 50% but preferably 75%, 90% or even 99% as measured in a competitive binding assay (see, e.g., Junghans et al., Cancer Res. 1990 50:1495-1502). Alternatively, two antibodies have the same epitope if essentially all amino acid mutations in the antigen that reduce or eliminate binding of one antibody reduce or eliminate binding of the other. Two antibodies have overlapping epitopes if some amino acid mutations that reduce or eliminate binding of one antibody reduce or eliminate binding of the other.

Additional routine experimentation (e.g., peptide mutation and binding analyses) can then be carried out to confirm whether the observed lack of binding of the test antibody is in fact due to binding to the same epitope as the reference antibody or if steric blocking (or another phenomenon) is responsible for the lack of observed binding. Experiments of this sort can be performed using ELISA, RIA, surface plasmon resonance, flow cytometry or any other quantitative or qualitative antibody-binding assay available in the art.

In a specific embodiment, the invention comprises an anti-PCSK9 antibody or antigen binding fragment of an antibody that binds an PCSK9 protein of SEQ ID NO:755, wherein the binding between the antibody or fragment thereof to PCSK9 and a variant PCSK9 protein is less than 50% of the binding between the antibody or fragment and the PCSK9 protein of SEQ ID NO:755. In one specific embodiment, the variant PCSK9 protein comprises at least one mutation of a residue at a position selected from the group consisting of 153, 159, 238 and 343. In a more specific embodiment, the at least one mutation is S153R, E159R, D238R, and/or D343R. In another specific embodiment, the variant PCSK9 protein comprises at least one mutation of a residue at a position selected from the group consisting of 366. In one specific embodiment, the variant PCSK9 protein comprises at least one mutation of a residue at a position selected from the group consisting of 147, 366 and 380. In a more specific embodiment, the mutation is S147F, E366K and V380M.

Immunoconjugates

The invention encompasses a human anti-PCSK9 monoclonal antibody conjugated to a therapeutic moiety ("immunoconjugate"), such as a cytotoxin, a chemotherapeutic drug, an immunosuppressant or a radioisotope. Cytotoxin agents include any agent that is detrimental to cells. Examples of suitable cytotoxin agents and chemotherapeutic agents for forming immunoconjugates are known in the art, see for example, WO 05/103081.

Bispecifics

The antibodies of the present invention may be monospecific, bispecific, or multispecific. Multispecific mAbs may be specific for different epitopes of one target polypeptide or may contain antigen-binding domains specific for more than one target polypeptide. See, e.g., Tutt et al. (1991) J. Immunol. 147:60-69. The human anti-PCSK9 mAbs can be linked to or co-expressed with another functional molecule, e.g., another peptide or protein. For example, an antibody or fragment thereof can be functionally linked (e.g., by chemical coupling, genetic fusion, noncovalent association or otherwise) to one or more other molecular entities, such as another antibody or antibody fragment, to produce a bispecific or a multispecific antibody with a second binding specificity.

An exemplary bi-specific antibody format that can be used in the context of the present invention involves the use of a first immunoglobulin (Ig) CH3 domain and a second Ig CH3 domain, wherein the first and second Ig CH3 domains differ from one another by at least one amino acid, and wherein at least one amino acid difference reduces binding of the bispecific antibody to Protein A as compared to a bi-specific antibody lacking the amino acid difference. In one embodiment, the first Ig CH3 domain binds Protein A and the second Ig CH3 domain contains a mutation that reduces or abolishes Protein A binding such as an H95R modification (by IMGT exon numbering; H435R by EU numbering). The second CH3 may further comprise a Y96F modification (by IMGT; Y436F by EU). Further modifications that may be found within the second CH3 include: D16E, L18M, N44S, K52N, V57M, and V82I (by IMGT; D356E, L358M, N384S, K392N, V397M, and V422I by EU) in the case of IgG1 antibodies; N44S, K52N, and V82I (IMGT; N384S, K392N, and V422I by EU) in the case of IgG2 antibodies; and Q15R, N44S, K52N, V57M, R69K, E79Q, and V82I (by IMGT; Q355R, N384S, K392N, V397M, R409K, E419Q, and V422I by EU) in the case of IgG4 antibodies. Variations on the bi-specific antibody format described above are contemplated within the scope of the present invention.

Bioequivalents

The anti-PCSK9 antibodies and antibody fragments of the present invention encompass proteins having amino acid sequences that vary from those of the described mAbs, but that retain the ability to bind human PCSK9. Such variant mAbs and antibody fragments comprise one or more additions, deletions, or substitutions of amino acids when compared to parent sequence, but exhibit biological activity that is essentially equivalent to that of the described mAbs. Likewise, the anti-PCSK9 antibody-encoding DNA sequences of the present invention encompass sequences that comprise one or more additions, deletions, or substitutions of nucleotides when compared to the disclosed sequence, but that encode an anti-PCSK9 antibody or antibody fragment that is essentially bioequivalent to an anti-PCSK9 antibody or antibody fragment of the invention. Examples of such variant amino acid and DNA sequences are discussed above.

Two antigen-binding proteins, or antibodies, are considered bioequivalent if, for example, they are pharmaceutical equivalents or pharmaceutical alternatives whose rate and extent of absorption do not show a significant difference when administered at the same molar dose under similar experimental conditions, either single does or multiple dose. Some antibodies will be considered equivalents or pharmaceutical alternatives if they are equivalent in the extent of their absorption but not in their rate of absorption and yet may be considered bioequivalent because such differences in the rate of absorption are intentional and are reflected in the labeling, are not essential to the attainment of effective body drug concentrations on, e.g., chronic use, and are considered medically insignificant for the particular drug product studied. In one embodiment, two antigen-binding proteins are bioequivalent if there are no clinically meaningful differences in their safety, purity, and potency.

In one embodiment, two antigen-binding proteins are bioequivalent if a patient can be switched one or more times between the reference product and the biological product without an expected increase in the risk of adverse effects, including a clinically significant change in immunogenicity, or diminished effectiveness, as compared to continued therapy without such switching.

In one embodiment, two antigen-binding proteins are bioequivalent if they both act by a common mechanism or mechanisms of action for the condition or conditions of use, to the extent that such mechanisms are known.

Bioequivalence may be demonstrated by in vivo and in vitro methods. Bioequivalence measures include, e.g., (a) an in vivo test in humans or other mammals, in which the concentration of the antibody or its metabolites is measured in blood, plasma, serum, or other biological fluid as a function of time; (b) an in vitro test that has been correlated with and is reasonably predictive of human in vivo bioavailability data; (c) an in vivo test in humans or other mammals in which the appropriate acute pharmacological effect of the antibody (or its target) is measured as a function of time; and (d) in a well-controlled clinical trial that establishes safety, efficacy, or bioavailability or bioequivalence of an antibody.

Bioequivalent variants of anti-PCSK9 antibodies of the invention may be constructed by, for example, making various substitutions of residues or sequences or deleting terminal or internal residues or sequences not needed for biological activity. For example, cysteine residues not essential for biological activity can be deleted or replaced with other amino acids to prevent formation of unnecessary or incorrect intramolecular disulfide bridges upon renaturation.

Treatment Population

The invention provides therapeutic methods for treating a human patient in need of a composition of the invention. While modifications in lifestyle and conventional drug treatment are often successful in reducing cholesterol levels, not all patients are able to achieve the recommended target cholesterol levels with such approaches. Various conditions, such as familial hypercholesterolemia (FH), appear to be resistant to lowering of LDL-C levels in spite of aggressive use of conventional therapy. Homozygous and heterozygous familial hypercholesterolemia (hoFH, heFH) is a condition associated with premature atherosclerotic vascular disease. However, patients diagnosed with hoFH are largely unresponsive to conventional drug therapy and have limited treatment options. Specifically, treatment with statins, which reduce LDL-C by inhibiting cholesterol synthesis and upregulating the hepatic LDL receptor, may have little effect in patients whose LDL receptors are non-existent or defective. A mean LDL-C reduction of only less than about 20% has been recently reported in patients with genotype-confirmed hoFH treated with the maximal dose of statins. The addition of ezetimibe 10 mg/day to this regimen resulted in a total reduction of LDL-C levels of 27%, which is still far from optimal. Likewise, many patients are statin non-responsive, poorly controlled with statin therapy, or cannot tolerate statin therapy; in general, these patients are unable to achieve cholesterol control with alternative treatments. There is a large unmet medical need for new treatments that can address the short-comings of current treatment options.

Specific populations treatable by the therapeutic methods of the invention include subjects indicated for LDL apheresis, subjects with PCSK9-activating mutations (gain of function mutations, "GOF"), subjects with heterozygous Familial Hypercholesterolemia (heFH); subjects with primary hypercholesterolemia who are statin intolerant or statin uncontrolled; and subjects at risk for developing hypercholesterolemia who may be preventably treated. Other indications include hyperlipidemia and dyslipidemia associated with secondary causes such as Type 2 diabetes mellitus, cholestatic liver diseases (primary biliary cirrhosis), nephrotic syndrome, hypothyroidism, obesity; and the prevention and treatment of atherosclerosis and cardiovascular diseases. However, depending on the severity of the afore-mentioned diseases and conditions, the treatment of subjects with the antibodies and antigen-binding fragments of the invention may be contraindicated for certain diseases and conditions.

Therapeutic Administration and Formulations

The invention provides therapeutic compositions comprising the anti-PCSK9 antibodies or antigen-binding fragments thereof of the present invention. The administration of therapeutic compositions in accordance with the invention will be administered with suitable carriers, excipients, and other agents that are incorporated into formulations to provide improved transfer, delivery, tolerance, and the like. A multitude of appropriate formulations can be found in the formulary known to all pharmaceutical chemists: Remington's Pharmaceutical Sciences, Mack Publishing Company, Easton, Pa. These formulations include, for example, powders, pastes, ointments, jellies, waxes, oils, lipids, lipid (cationic or anionic) containing vesicles (such as LIPOFECTIN™), DNA conjugates, anhydrous absorption pastes, oil-in-water and water-in-oil emulsions, emulsions carbowax (polyethylene glycols of various molecular weights), semi-solid gels, and semi-solid mixtures containing carbowax. See also Powell et al. "Compendium of excipients for parenteral formulations" PDA (1998) J Pharm Sci Technol 52:238-311.

The dose may vary depending upon the age and the size of a subject to be administered, target disease, conditions, route of administration, and the like. When the antibody of the present invention is used for treating various conditions and diseases associated with PCSK9, including hypercholesterolemia, disorders associated with LDL and apolipoprotein B, and lipid metabolism disorders, and the like, in an adult patient, it is advantageous to intravenously administer the antibody of the present invention normally at a single dose of about 0.01 to about 20 mg/kg body weight, more preferably about 0.02 to about 7, about 0.03 to about 5, or about 0.05 to about 3 mg/kg body weight. Depending on the severity of the condition, the frequency and the duration of the treatment can be adjusted.

Various delivery systems are known and can be used to administer the pharmaceutical composition of the invention, e.g., encapsulation in liposomes, microparticles, microcapsules, recombinant cells capable of expressing the mutant viruses, receptor mediated endocytosis (see, e.g., Wu et al.

(1987) J. Biol. Chem. 262:4429-4432). Methods of introduction include, but are not limited to, intradermal, intramuscular, intraperitoneal, intravenous, subcutaneous, intranasal, epidural, and oral or peroral routes. If the antibody of present invention is administered per injection, subcutaneous injection is preferred. Oral or peroral administration is preferred for the HMG-CoA inhibitor, e.g. the statin. The composition may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local.

The pharmaceutical composition can be also delivered in a vesicle, in particular a liposome (see Langer (1990) Science 249:1527-1533; Treat et al. (1989) in Liposomes in the Therapy of Infectious Disease and Cancer, Lopez Berestein and Fidler (eds.), Liss, New York, pp. 353-365; Lopez-Berestein, ibid., pp. 317-327; see generally ibid.).

In certain situations, the pharmaceutical composition can be delivered in a controlled release system. In one embodiment, a pump may be used (see Langer, supra; Sefton (1987) CRC Crit. Ref. Biomed. Eng. 14:201). In another embodiment, polymeric materials can be used; see, Medical Applications of Controlled Release, Langer and Wise (eds.), CRC Pres., Boca Raton, Fla. (1974). In yet another embodiment, a controlled release system can be placed in proximity of the composition's target, thus requiring only a fraction of the systemic dose (see, e.g., Goodson, in Medical Applications of Controlled Release, supra, vol. 2, pp. 115-138, 1984).

The injectable preparations may include dosage forms for intravenous, subcutaneous, intracutaneous and intramuscular injections, drip infusions, etc. These injectable preparations may be prepared by methods publicly known. For example, the injectable preparations may be prepared, e.g., by dissolving, suspending or emulsifying the antibody or its salt described above in a sterile aqueous medium or an oily medium conventionally used for injections. As the aqueous medium for injections, there are, for example, physiological saline, an isotonic solution containing glucose and other auxiliary agents, etc., which may be used in combination with an appropriate solubilizing agent such as an alcohol (e.g., ethanol), a polyalcohol (e.g., propylene glycol, polyethylene glycol), a nonionic surfactant [e.g., polysorbate 80, HCO-50 (polyoxyethylene (50 mol) adduct of hydrogenated castor oil)], etc. As the oily medium, there are employed, e.g., sesame oil, soybean oil, etc., which may be used in combination with a solubilizing agent such as benzyl benzoate, benzyl alcohol, etc. The injection thus prepared is preferably filled in an appropriate ampoule. A pharmaceutical composition of the present invention can be delivered subcutaneously or intravenously with a standard needle and syringe. In addition, with respect to subcutaneous delivery, a pen delivery device readily has applications in delivering a pharmaceutical composition of the present invention. Such a pen delivery device can be reusable or disposable. A reusable pen delivery device generally utilizes a replaceable cartridge that contains a pharmaceutical composition. Once all of the pharmaceutical composition within the cartridge has been administered and the cartridge is empty, the empty cartridge can readily be discarded and replaced with a new cartridge that contains the pharmaceutical composition. The pen delivery device can then be reused. In a disposable pen delivery device, there is no replaceable cartridge. Rather, the disposable pen delivery device comes prefilled with the pharmaceutical composition held in a reservoir within the device. Once the reservoir is emptied of the pharmaceutical composition, the entire device is discarded.

Numerous reusable pen and autoinjector delivery devices have applications in the subcutaneous delivery of a pharmaceutical composition of the present invention. Examples include, but certainly are not limited to AUTOPEN™ (Owen Mumford, Inc., Woodstock, UK), DISETRONIC™ pen (Disetronic Medical Systems, Burghdorf, Switzerland), HUMALOG MIX 75/25™ pen, HUMALOG™ pen, HUMALIN 70/30™ pen (Eli Lilly and Co., Indianapolis, Ind.), NOVOPEN™ I, II and III (Novo Nordisk, Copenhagen, Denmark), NOVOPEN JUNIOR™ (Novo Nordisk, Copenhagen, Denmark), BD™ pen (Becton Dickinson, Franklin Lakes, N.J.), OPTIPEN™, OPTIPEN PRO™, OPTIPEN STARLET™, and OPTICLIK™ (sanofi-aventis, Frankfurt, Germany), to name only a few. Examples of disposable pen delivery devices having applications in subcutaneous delivery of a pharmaceutical composition of the present invention include, but certainly are not limited to the SOLOSTAR™ pen (sanofi-aventis), the FLEXPEN™ (Novo Nordisk), and the KWIKPEN™ (Eli Lilly).

Advantageously, the pharmaceutical compositions for oral or parenteral use described above are prepared into dosage forms in a unit dose suited to fit a dose of the active ingredients. Such dosage forms in a unit dose include, for example, tablets, pills, capsules, injections (ampoules), suppositories, etc. The amount of the aforesaid antibody contained is generally about 4 to about 500 mg or from about 5 to about 500 mg per dosage form in a unit dose; especially in the form of injection, it is preferred that the aforesaid antibody is contained in about 5 to about 100 mg or about 5 to 400 mg (such as from about 50 to about 200 mg per 1 ml injection solution) and in about 10 to about 250 mg or to about 500 mg for the other dosage forms.

The invention provides therapeutic methods in which the antibody or antibody fragment of the invention is useful to treat hypercholesterolemia associated with a variety of conditions involving hPCSK9. The anti-PCSK9 antibodies or antibody fragments of the invention are particularly useful for the treatment of hypercholesterolemia and the like. Combination therapies may include the anti-PCSK9 antibody of the invention with, for example, one or more of any agent that (1) induces a cellular depletion of cholesterol synthesis by inhibiting 3-hydroxy-3-methylglutaryl (HMG)-coenzyme A (CoA) reductase, such as cerivastatin, atorvastatin, simvastatin, pitavastatin, rosuvastatin, fluvastatin, lovastatin, pravastatin; (2) inhibits cholesterol uptake and or bile acid re-absorption; (3) increase lipoprotein catabolism (such as niacin); and activators of the LXR transcription factor that plays a role in cholesterol elimination such as 22-hydroxycholesterol or fixed combinations such as ezetimibe plus simvastatin; a statin with a bile resin (e.g., cholestyramine, colestipol, colesevelam), a fixed combination of niacin plus a statin (e.g., niacin with lovastatin); or with other lipid lowering agents such as omega-3-fatty acid ethyl esters (for example, omacor).

Preferred Aspects of Present Invention

In the following, some preferred aspects and embodiments of present invention will be listed:
Aspects Related to Patient Populations—A)
1. A method for treating a disease or condition in which PCSK9 expression or activity causes an impact comprising
administering a therapeutic amount of an antibody or an antigen-binding fragment thereof which specifically binds hPCSK9 (human proprotein convertase subtilisin/kexin type 9) to a subject in need thereof,
wherein the subject in need thereof falls into one or more of the following groups of subjects:
(i) subjects having a serum LDL cholesterol (LDL-C) level of at least 100 mg/dL, [at least 130 mg/dL, at least 160 mg/dL/at least 200 mg/dL];
(ii) subjects having a serum HDL-C level of less than 40 mg/dL;
(iii) subjects having a serum cholesterol level of at least 200 mg/dL [240 mg/dL];
(iv) subjects having a serum triacylglycerol level of at least 150 mg/dL [at least 200 mg/dL; at least 500 mg/dL], wherein said triacylglycerol level is determined after fasting for at least 8 hours;
(v) subjects being at least 35 years old [at least 40/50/55/60/65/70 years old];
(vi) subjects younger than 75 years [65/60/55/50/45/40 years];
(vii) subjects having a BMI of 25 [26/27/28/29/30/31/32/33/34/35/36/37/38/39] or more;
(viii) male subjects;
(ix) female subjects;
(x) subjects in which the administration of said antibody or antigen-binding fragment thereof leads to a reduction in the serum LDL-C level by at least 30 mg/dL [40 mg/dL; 50 mg/dL; 60 mg/dL; 70 mg/dL] relative to predose level; or
(xi) subjects in which the administration of said antibody or antigen-binding fragment thereof leads to a reduction in the serum LDL-C level by at least 20% [30%; 40%; 50%; 60%] relative to predose level.

2. A method for treating a disease or condition in which PCSK9 expression or activity causes an impact comprising
administering a therapeutic amount of an antibody or an antigen-binding fragment thereof which specifically binds hPCSK9 (human proprotein convertase subtilisin/kexin type 9) to a subject in need thereof,
wherein the subject in need thereof does not fall into one or more of the following groups of subjects:
(i) smokers;
(ii) persons being 70 years old or older;
(iii) persons suffering from hypertension;
(iv) women who are pregnant;
(v) women who are trying to become pregnant;
(vi) women who are breast-feeding;
(vii) persons who have or ever had a disease affecting the liver;
(viii) persons who had any unexplained abnormal blood tests for liver function;
(ix) persons who drink excessive amounts of alcohol;
(x) persons having kidney problems;
(xi) persons suffering from hypothyroidism;
(xii) persons suffering from muscle disorders;
(xiii) persons having encountered previous muscular problems during treatment with lipid-lowering medicine;
(xiv) persons having serious problems with their breathing;
(xv) persons taking one or more of the following medicines: medicines altering the way the immune systems works (e.g. ciclosporin or antihistamines), antibiotics or antifungal medicines (e.g. erythromycin, clarithromycin, ketoconazole, itraconazole, rifampicin, fusidic acid), medicines regulating lipid levels (e.g. gemfibrozil, colestipol), calcium channel blockers (e.g. verapamil, diltiazem), medicines regulating the heart rhythm (digoxin, amiodarone), protease inhibitors used in the treatment of HIV (e.g. nelfinavir), warfarin, oral contraceptives, antacids or St. John's Wort; or
(xvi) persons drinking more than 0.1 L of grapefruit juice per day;
(xvii) persons having a body mass index (BMI) of more than 40;
(xviii) persons having a body mass index (BMI) of less than 18;
(xix) persons suffering from type 1 diabetes or type 2 diabetes;
(xx) persons positive for hepatitis B or hepatitis C; or
(xxi) persons having a known sensitivity to monoclonal antibody therapeutics.

3. An antibody or an antigen-binding fragment thereof which specifically binds hPCSK9 (human proprotein convertase subtilisin/kexin type 9) for use in the treatment of a disease or condition in which PCSK9 expression or activity causes an impact,
wherein the antibody or antigen-binding fragment thereof is for administration to a subject falling at least into one of the following groups of subjects:
(i) subjects having a serum LDL-C level of at least 100 mg/dL [at least 130 mg/dL/at least 160 mg/dL/at least 200 mg/dL];
(ii) subjects having a serum HDL-C level of less than 40 mg/dL;
(iii) subjects having a serum cholesterol level of at least 200 mg/dL [240 mg/dL];
(iv) subjects having a serum triacylglycerol level of at least 150 mg/dL [at least 200 mg/dL; at least 500 mg/dL], wherein said triacylglycerol level is determined after fasting for at least 8 hours;
(v) subjects being at least 35 years old [at least 40/50/55/60/65/70 years old];
(vi) subjects younger than 75 years [65/60/55/50/45/40 years];
(vii) subjects having a BMI of 25 [26/27/28/29/30/31/32/33/34/35/36/37/38/39] or more;
(viii) male subjects;
(ix) female subjects;
(x) subjects in which the administration of said antibody or antigen-binding fragment thereof leads to a reduction in the serum LDL-C level by at least 20 mg/dL [30 mg/dL; 40 mg/dL; 50 mg/dL; 60 mg/dL; 70 mg/dL]; or
(xi) subjects in which the administration of said antibody or antigen-binding fragment thereof leads to a reduction in the serum LDL-C level by at least 10% [20%; 30%; 40%; 50%; 60%].

4. An antibody or an antigen-binding fragment thereof which specifically binds hPCSK9 (human proprotein convertase subtilisin/kexin type 9) for use in the treatment of a disease or condition in which PCSK9 expression or activity causes an impact,
wherein the antibody or antigen-binding fragment thereof is for administration to a subject who does not fall into one or more of the following groups of subjects:
(i) smokers;
(ii) persons being 70 years old or older;
(iii) persons suffering from hypertension;
(iv) women who are pregnant;
(v) women who are trying to become pregnant;
(vi) women who are breast-feeding;
(vii) persons who have or ever had a disease affecting the liver;

(viii) persons who had any unexplained abnormal blood tests for liver function;
(ix) persons who drink excessive amounts of alcohol;
(x) persons having kidney problems;
(xi) persons suffering from hypothyroidism;
(xii) persons suffering from muscle disorders;
(xiii) persons having encountered previous muscular problems during treatment with lipid-lowering medicine;
(xiv) persons having serious problems with their breathing;
(xv) persons taking one or more of the following medicines: medicines altering the way the immune systems works (e.g. ciclosporin or antihistamines), antibiotics or antifungal medicines (e.g. erythromycin, clarithromycin, ketoconazole, itraconazole, rifampicin, fusidic acid), medicines regulating lipid levels (e.g. gemfibrozil, colestipol), calcium channel blockers (e.g. verapamil, diltiazem), medicines regulating the heart rhythm (digoxin, amiodarone), protease inhibitors used in the treatment of HIV (e.g. nelfinavir), warfarin, oral contraceptives, antacids or St. John's Wort;
(xvi) persons drinking more than 0.1 L of grapefruit juice per day;
(xvii) persons having a body mass index (BMI) of more than 40;
(xviii) persons having a body mass index (BMI) of less than 18;
(xix) persons suffering from type 1 diabetes or type 2 diabetes;
(xx) persons positive for hepatitis B or hepatitis C; or
(xxi) persons having a known sensitivity to monoclonal antibody therapeutics.

5. The method of aspect 1 or 2 or the antibody of aspect 2 or 3, wherein the disease or condition in which PCSK9 expression or activity causes an impact is ameliorated, improved, inhibited or prevented with a PCSK9 antagonist.

6. The method or the antibody of any one of aspects 1 to 5, wherein the disease or condition in which PCSK9 expression or activity causes an impact is selected from the group consisting of:
hypercholesterolemia, hyperlipidemia, dyslipidemia, atherosclerosis and cardiovascular diseases.

7. The method or the antibody of any one of aspects 1 to 6, wherein the subject in need thereof is a subject indicated for LDL apheresis, a subject with PCSK9-activating mutations, a subject with heterozygous Familial Hypercholesterolemia, a subject with primary hypercholesterolemia who is statin uncontrolled, a subject at risk for developing hypercholesterolemia, a subject with hypercholesterolemia, hyperlipidemia, dyslipidemia, atherosclerosis or cardiovascular diseases.

8. The method or the antibody of any one of aspects 1 to 7, wherein the antibody or antigen-binding fragment thereof is a recombinant human antibody or fragment thereof 9. The method or the antibody of any one of aspects 1 to 8, wherein the antibody or the antigen-binding fragment thereof is characterized by one or more of the following:
(i) capable of reducing serum total cholesterol at least about 25 to about 35% and sustaining the reduction over at least a 24 day period relative to a predose level;
(ii) capable of reducing serum LDL cholesterol at least about 65-80% and sustaining the reduction over at least a 24 day period relative to a predose level;
(iii) capable of reducing serum triglyceride at least about 25-40% relative to predose level;
(iv) achieves one or more of (i)-(iii) without reducing serum HDL cholesterol or reducing serum HDL cholesterol no more than 5% relative to predose level;
(v) achieves one or more of (i)-(iii) with little or no measurable effect on liver function, as determined by ALT and AST measurements.

10. The method or the antibody of any one of aspects 1 to 9, wherein the antibody or the antigen-binding fragment thereof comprises
a heavy chain CDR3 (HCDR3) domain selected from the group consisting of SEQ ID NO:8, 32, 56, 80, 104, 128, 152, 176, 200, 224, 248, 272, 296, 320, 344, 368, 392, 416, 440, 464, 488, 512, 536, 560, 584, 608, 632, 656, 680, 704 and 728; and
a light chain CDR3 (LCDR3) domain selected from the group consisting of SEQ ID NO:16, 40, 64, 88, 112, 136, 160, 184, 208, 232, 256, 280, 304, 328, 352, 376, 400, 424, 448, 472, 496, 520, 544, 568, 592, 616, 639, 664, 688, 712 and 736.

11. The method or the antibody of any one of aspects 1 to 9, wherein the antibody or the antigen-binding fragment thereof comprises the heavy and light chain CDRs of a HCVR/LCVR amino acid sequence pair as shown in SEQ ID NOs: 90/92.

12. The method or the antibody of aspect 11, wherein the antibody or antigen-binding fragment thereof comprises heavy and light chain CDR amino acid sequences as shown in SEQ ID NOs: 76, 78, 80, 84, 86, and 88.

13. The method or the antibody of aspect 12, wherein the antibody or antigen-binding fragment thereof comprises an HCVR amino acid sequence as shown in SEQ ID NO: 90 and an LCVR amino acid sequence as shown in SEQ ID NO: 92.

14. The method or the antibody of any one of aspects 1 to 9, wherein the antibody or antigen-binding fragment thereof binds to the same epitope on hPCSK9 as an antibody comprising heavy and light chain CDR amino acid sequences as shown in SEQ ID NOs: 76, 78, 80, 84, 86, and 88.

15. The method or the antibody of any one of aspects 1 to 9, wherein the antibody or antigen-binding fragment thereof competes for binding to hPCSK9 with an antibody comprising heavy and light chain CDR amino acid sequences as shown in SEQ ID NOs: 76, 78, 80, 84, 86, and 88.

16. The method or the antibody of any one of aspects 1 to 15, further comprising:
administering a therapeutic amount of an HMG-CoA reductase inhibitor to the subject in a dosage of between 0.05 mg to 100 mg.

17. The method or the antibody of aspect 16, wherein the HMG-CoA reductase inhibitor is a statin.

18. The method or the antibody of aspect 17, wherein the statin is selected from the group consisting of cerivastatin, atorvastatin, simvastatin, pitavastatin, rosuvastatin, fluvastatin, lovastatin, and pravastatin.

19. The method or the antibody of aspect 18, wherein the statin is
cerivastatin administered in a daily dosage of between 0.05 mg and 2 mg;
atorvastatin administered in a daily dosage of between 2 mg and 100 mg;
simvastatin administered in a daily dosage of between 2 mg and 100 mg;
pitavastatin administered in a daily dosage of between 0.2 mg and 100 mg;

rosuvastatin administered in a daily dosage of between 2 mg and 100 mg;

fluvastatin administered in a daily dosage of between 2 mg and 100 mg;

lovastatin administered in a daily dosage of between 2 mg and 100 mg; or pravastatin administered in a daily dosage of between 2 mg and 100 mg.

20. An article of manufacture comprising
    (a) a packaging material;
    (b) an antibody or an antigen-binding fragment thereof which specifically binds hPCSK9; and
    (c) a label or packaging insert contained within the packaging material indicating that patients receiving treatment with said antibody or antigen-binding fragment can be treated for a disease or condition selected from the group consisting of hypercholesterolemia, hyperlipidemia, dyslipidemia, atherosclerosis and cardiovascular diseases and further indicating that subjects falling into one or more groups of subjects as recited in aspect 1 can be treated.

21. An article of manufacture comprising
    (a) a packaging material;
    (b) an antibody or an antigen-binding fragment thereof which specifically binds hPCSK9; and
    (c) a label or packaging insert contained within the packaging material indicating that patients receiving treatment with said antibody or antigen-binding fragment can be treated for a disease or condition selected from the group consisting of hypercholesterolemia, hyperlipidemia, dyslipidemia, atherosclerosis and cardiovascular diseases and further indicating that the treatment of patients with said antibody or antigen-binding fragment thereof is contraindicated for patients belonging to one or more groups of subjects as recited in aspect 2.

22. The article of manufacture according to aspect 20 or 21, wherein the antibody or antigen-binding fragment is an antibody or antigen-binding fragment as specified in any of aspects 3 to 19.

23. The article of manufacture according to any of aspects 20 to 22, wherein the label or packaging insert contains reference to a method of treatment according to any of aspects 1, 2 or 5-19.

24. A method of testing the efficacy of an antibody or an antigen-binding fragment thereof which specifically binds hPCSK9 for the treatment of a disease or condition selected from the group consisting of hypercholesterolemia, hyperlipidemia, dyslipidemia, atherosclerosis and cardiovascular diseases, said method comprising:
    treating a selected patient population with said antibody or antigen-binding fragment thereof, wherein each patient in said population has an LDL cholesterol (LDL-C) level of more than 100 mg/dL; and
    determining the efficacy of said antibody or antigen-binding fragment thereof by determining the LDL-C level in the patient population before and after administration of said antibody or antigen-binding fragment thereof, wherein a reduction of the LDL-C level by at least 25% relative to a predose level in at least 75% of the patient population indicates that said antibody or antigen-binding fragment thereof is efficacious for the treatment of said disease or condition in said patient population;
    wherein each patient falls into one or more groups of subjects as recited in aspect 1.

25. A method of testing the efficacy of an antibody or an antigen-binding fragment thereof which specifically binds hPCSK9 for the treatment of a disease or condition selected from the group consisting of hypercholesterolemia, hyperlipidemia, dyslipidemia, atherosclerosis and cardiovascular diseases, said method comprising:
    determining the efficacy of an antibody or antigen-binding fragment thereof that has been used for the treatment of a selected patient population with said antibody or antigen-binding fragment thereof, wherein each patient in said population has an LDL cholesterol (LDL-C) level of more than 100 mg/dL by determining the LDL-C level in the patient population before and after administration of said antibody or antigen-binding fragment thereof, wherein a reduction of the LDL-C level by at least 25% relative to a predose level in at least 75% of the patient population indicates that said antibody or antigen-binding fragment thereof is efficacious for the treatment of said disease or condition in said patient population;
    wherein each patient falls into one or more groups of subjects as recited in aspect 1.

26. The method of aspect 25, wherein each patient in said population has received a lipid lowering treatment by administration of a statin for at least 6 weeks prior to treatment with said antibody or antigen-binding fragment thereof 27. The method of any of aspects 24 to 26, wherein the antibody or antigen-binding fragment is an antibody or antigen-binding fragment as specified in any of aspects 3 to 19.

28. The method of any of aspects 24 to 27, wherein the selected patient population is or has been treated with a method of treatment according to any of aspects 1, 2 or 5-19.

29. A method for testing the efficacy of a compound in lowering cholesterol levels in a subject, comprising the steps:
    (a) providing a rodent;
    (b) administering an antibody or an antigen-binding fragment thereof which specifically binds PCSK9 to the rodent;
    (c) administering a test compound to said rodent;
    (d) determining the effect of the test compound in the rodent, wherein a lowering of the cholesterol level in the rodent as compared to the cholesterol level of a control animal indicates that the test compound is efficacious in lowering cholesterol levels in a subject, wherein the control animal is from the same species as said rodent, and wherein the control animal has not been challenged with the test compound.

Aspects Related to Patient Populations—B)

1. A method of treating a subject suffering from a disease or disorder characterized by elevated low-density lipoprotein cholesterol (LDL-C) levels, the method comprising:
    (a) selecting a subject with a blood LDL-C level greater than 100 mg/dL; and
    (b) administering to said subject a composition comprising an antibody or antigen binding fragment thereof that specifically binds to human proprotein convertase subtilisin/kexin type 9 (hPCSK9); thereby lowering cholesterol levels in the subject in need thereof.

2. The method of aspect 1, wherein the disease or condition is selected from the group consisting of: hypercholesterolemia, hyperlipidemia, dyslipidemia, and atherosclerosis.

3. The method of aspect 1, wherein the disease condition is primary hypercholesterolemia or familial hypercholesterolemia.

4. The method of aspect 1, wherein the disease or condition is hypercholesterolemia which is uncontrolled by statins.

5. The method of aspect 1, wherein the subject has a body mass index (BMI) of less than 18 kg/m² or greater than 40 kg/m².

6. The method of aspect 1, wherein the subject was not previously instructed to partake in a cholesterol-lowering diet.

7. The method of aspect 1, wherein the subject has not previously taken a cholesterol-lowering drug except for atorvastatin.

8. The method of aspect 7, wherein the atorvastatin was administered at about 10 mg per day.

9 The method of aspect 7, wherein the cholesterol-lowering drug is selected from the group consisting of fibrates, bile acid resins, niacin, intestinal cholesterol absorption (ICA) blockers, and omega-3 fatty acids.

10. The method of aspect 9, wherein the niacin is administered at greater than 500 mg per day.

11. The method of aspect 9, wherein the omega-3 fatty acids are administered at greater than 1000 mg per day.

12. The method of aspect 1, wherein the subject does not suffer from diabetes.

13. The method of aspect 12, wherein the diabetes is type 1 diabetes.

14. The method of aspect 12, wherein the diabetes is type 2 diabetes.

15. The method of aspect 12, wherein the type 2 diabetes is treated with insulin.

16. The method of aspect 12, wherein the subject has a blood glycated hemoglobin concentration greater than or equal to 8.5%.

17. The method of aspect 1, wherein the subject is negative for hepatitis B and C surface antigen.

18. The method of aspect 1, wherein the subject has a blood triglycerides concentration of greater than 350 mg/dL.

19. The method of aspect 1, wherein the subject has fewer than 1500 neutrophils per cubic mm of blood.

20. The method of aspect 1, wherein the subject has fewer than 100,000 platelets per cubic mm of blood.

21. The method of aspect 1, wherein the subject is female.

22. The method of aspect 21, wherein the subject is not pregnant.

23. The method of aspect 1, wherein the subject has a blood thyroid stimulating hormone concentration that is above the lower limit of normal and below the upper limit of normal.

24. The method of aspect 23, wherein the subject has serum creatine of less than 1.4 of the upper limit of normal.

25. The method of aspect 1, wherein the subject is a male.

26. The method of aspect 25, wherein the subject has serum creatine of less than 1.5 of the upper limit of normal.

27. The method of aspect 1, wherein the subject has an amount of aspartate transaminase that is less than two times the upper limit of normal.

28. The method of aspect 1, wherein the subject has an amount of alanine transaminase that is less than two times the upper limit of normal.

29. The method of aspect 1, wherein the antibody or antigen-binding fragment is administered in a dosage amount within the range of about 5 mg to about 500 mg.

30. The method of aspect 29, wherein the antibody or antigen-binding fragment is administered in a dosage amount within the range of about 50 mg to about 300 mg.

31. The method of aspect 29, wherein the antibody is administered at between 200 and 300 mg every four weeks.

32. The method of aspect 29, wherein the antibody or antigen-binding fragment is administered in a dosage amount of about 150 mg.

33. The method of aspect 1, wherein the antibody or antigen-binding fragment thereof is administered to the subject every other week (E2W).

34. The method of aspect 1, wherein the antibody or antigen-binding fragment thereof is administered to the subject every fourth week (E4W).

35. The method of aspect 1, wherein the antibody or the antigen-binding fragment comprises the heavy and light chain CDRs of a HCVR/LCVR amino acid sequence pair as shown in SEQ ID NOs: 90/92.

36. The method of aspect 1, wherein the antibody or antigen-binding fragment comprises a HCVR/LCVR amino acid sequence pair as shown in SEQ ID NOs: 90/92.

37. The method of aspect 1, wherein the antibody or antigen-binding fragment thereof competes for binding to hPCSK9 with an antibody or antigen-binding fragment comprising a HCVR/LCVR amino acid sequence pair as shown in SEQ ID NOs: 90/92.

38. The method of aspect 1, wherein the antibody is administered subcutaneously.

39. The method of aspect 38, wherein the antibody is administered in the abdomen.

40. The method of aspect 1, further comprising administering a HMG-CoA reductase inhibitor to the subject.

41. The method of aspect 40, wherein the HMG-CoA reductase inhibitor is administered in a dosage amount in the range of about 0.05 mg to 100 mg.

42. The method of aspect 41, wherein the HMG-CoA reductase inhibitor is a statin.

43. The method of aspect 42, wherein the statin is selected from the group consisting of cerivastatin, atorvastatin, simvastatin, pitavastatin, rosuvastatin, fluvastatin, lovastatin, and pravastatin.

44. The method of aspect 42, wherein the statin is atorvastatin administered at a dosage of 10 mg or 80 mg.

45. The method of aspect 44, wherein the atorvastatin is administered at about 10 mg per day and at 80 mg one day in an 8 week period.

46. A method of lowering cholesterol levels in a subject in need thereof, comprising:
  (a) selecting a subject with a blood low density lipoprotein cholesterol (LDL-C) level greater than 100 mg/dL; and
  (b) administering to said subject a composition comprising an antibody or antigen binding fragment thereof that specifically binds to human proprotein convertase subtilisin/kexin type 9 (hPCSK9); thereby lowering cholesterol levels in the subject in need thereof.

47. The method of aspect 46, wherein the disease or condition is selected from the group consisting of: hypercholesterolemia, hyperlipidemia, dyslipidemia, and atherosclerosis.

48. The method of aspect 46, wherein the disease condition is primary hypercholesterolemia or familial hypercholesterolemia.

49. The method of aspect 46, wherein the disease or condition is hypercholesterolemia which is uncontrolled by statins.

50. The method of aspect 46, wherein the subject has a body mass index (BMI) of less than 18 kg/m² or greater than 40 kg/m².
51. The method of aspect 46, wherein the subject was not previously instructed to partake in a cholesterol-lowering diet.
52. The method of aspect 46, wherein the subject has not previously taken a cholesterol-lowering drug except for atorvastatin.
53. The method of aspect 52, wherein the atorvastatin was administered at about 10 mg per day.
54. The method of aspect 52, wherein the cholesterol-lowering drug is selected from the group consisting of fibrates, bile acid resins, niacin, intestinal cholesterol absorption (ICA) blockers, and omega-3 fatty acids.
55. The method of aspect 54, wherein the niacin is administered at greater than 500 mg per day.
56. The method of aspect 54, wherein the omega-3 fatty acids are administered at greater than 1000 mg per day.
57. The method of aspect 46, wherein the subject does not suffer from diabetes.
58. The method of aspect 57, wherein the diabetes is type 1 diabetes.
59. The method of aspect 57, wherein the diabetes is type 2 diabetes.
60. The method of aspect 57, wherein the type 2 diabetes is treated with insulin.
61. The method of aspect 57, wherein the subject has a blood glycated hemoglobin concentration greater than or equal to 8.5%.
62. The method of aspect 46, wherein the subject is negative for hepatitis B and C surface antigen.
63. The method of aspect 46, wherein the subject has a blood triglycerides concentration of greater than 350 mg/dL.
64. The method of aspect 46, wherein the subject has fewer than 1500 neutrophils per cubic mm of blood.
65. The method of aspect 46, wherein the subject has fewer than 100,000 platelets per cubic mm of blood.
66. The method of aspect 46, wherein the subject is female.
67. The method of aspect 66, wherein the subject is not pregnant.
68. The method of aspect 46, wherein the subject has a blood thyroid stimulating hormone concentration that is above the lower limit of normal and below the upper limit of normal.
69. The method of aspect 68, wherein the subject has serum creatine of less than 1.4 of the upper limit of normal.
70. The method of aspect 46, wherein the subject is a male.
71. The method of aspect 70, wherein the subject has serum creatine of less than 1.5 of the upper limit of normal.
72. The method of aspect 46, wherein the subject has an amount of aspartate transaminase that is less than two times the upper limit of normal.
73. The method of aspect 46, wherein the subject has an amount of alanine transaminase that is less than two times the upper limit of normal.
74. The method of aspect 46, wherein the antibody or antigen-binding fragment is administered in a dosage amount within the range of about 5 mg to about 500 mg.
75. The method of aspect 74, wherein the antibody or antigen-binding fragment is administered in a dosage amount within the range of about 50 mg to about 300 mg.
76. The method of aspect 74, wherein the antibody is administered at between 200 and 300 mg every four weeks.
77. The method of aspect 74, wherein the antibody or antigen-binding fragment is administered in a dosage amount of about 150 mg.
78. The method of aspect 46 wherein the antibody or antigen-binding fragment thereof is administered to the subject every other week (E2W).
79. The method of aspect 46, wherein the antibody or antigen-binding fragment thereof is administered to the subject every fourth week (E4W).
80. The method of aspect 46 wherein the antibody or the antigen-binding fragment comprises the heavy and light chain CDRs of a HCVR/LCVR amino acid sequence pair as shown in SEQ ID NOs: 90/92.
81. The method of aspect 46, wherein the antibody or antigen-binding fragment comprises a HCVR/LCVR amino acid sequence pair as shown in SEQ ID NOs: 90/92.
82. The method of aspect 46, wherein the antibody or antigen-binding fragment thereof competes for binding to hPCSK9 with an antibody or antigen-binding fragment comprising a HCVR/LCVR amino acid sequence pair as shown in SEQ ID NOs: 90/92.
83. The method of aspect 46, wherein the antibody is administered subcutaneously.
84. The method of aspect 38, wherein the antibody is administered in the abdomen.
85. The method of aspect 46, further comprising administering a HMG-CoA reductase inhibitor to the subject.
86. The method of aspect 85, wherein the HMG-CoA reductase inhibitor is administered in a dosage amount in the range of about 0.05 mg to 100 mg.
87. The method of aspect 86, wherein the HMG-CoA reductase inhibitor is a statin.
88. The method of aspect 87, wherein the statin is selected from the group consisting of cerivastatin, atorvastatin, simvastatin, pitavastatin, rosuvastatin, fluvastatin, lovastatin, and pravastatin.
89. The method of aspect 88, wherein the statin is atorvastatin administered at a dosage of 10 mg or 80 mg.
90. The method of aspect 89, wherein the atorvastatin is administered at about 10 mg per day and at 80 mg one day in an 8 week period.

Aspects Related to Dosage Regimens—A)

1. A method for treating a disease or condition in which PCSK9 expression or activity causes an impact, comprising:
    administering a therapeutic amount of an antibody or an antigen-binding fragment thereof which specifically binds hPCSK9 (human proprotein convertase subtilisin/kexin type 9) to a subject in need thereof, wherein the antibody or antigen-binding fragment thereof is administered in a dosage amount ranging from 5 mg to 500 mg, and
    administering a therapeutic amount of an HMG-CoA reductase inhibitor to said subject, wherein the HMG-CoA reductase inhibitor is administered in a dosage amount ranging from 0.05 mg to 100 mg.
2. An antibody or an antigen-binding fragment thereof which specifically binds hPCSK9 (human proprotein convertase subtilisin/kexin type 9) for use in the treatment of a disease or condition in which PCSK9 expression or activity causes an impact,
    wherein the antibody or antigen-binding fragment thereof is for administration in a dosage amount ranging from 5 mg to 500 mg,
    wherein the antibody or antigen-binding fragment thereof is further for administration in combination with an HMG-CoA reductase inhibitor at a dosage amount ranging from 0.05 mg to 100 mg.
3. The method of aspect 1 or the antibody of aspect 2, wherein the disease or condition in which PCSK9 expression or activity causes an impact is ameliorated, improved, inhibited or prevented with a PCSK9 antagonist.
4. The method or the antibody of any one of aspects 1-3, wherein the disease or condition in which PCSK9 expression or activity causes an impact is selected from the group consisting of:
hypercholesterolemia, hyperlipidemia, dyslipidemia, atherosclerosis and cardiovascular diseases.
5. The method or the antibody of anyone of aspects 1 to 4, wherein the subject in need thereof is a subject indicated for LDL apheresis, a subject with PCSK9-activating mutations, a subject with heterozygous Familial Hypercholesterolemia, a subject with primary hypercholesterolemia who is statin uncontrolled, a subject at risk for developing hypercholesterolemia, a subject with hypercholesterolemia, hyperlipidemia, dyslipidemia, atherosclerosis or cardiovascular diseases.
6. The method or the antibody of any one of aspects 1 to 5, wherein the HMG-CoA reductase inhibitor is administered three times per day, twice per day, or once per day.
7. The method or the antibody of any one of aspects 1 to 6, wherein the HMG-CoA reductase inhibitor is administered every day, every other day, every third day, every fourth day, every fifth day, or every sixth day.
8. The method or the antibody of any one of aspects 1 to 6, wherein the HMG-CoA reductase inhibitor is administered every week, every other week, every third week, or every fourth week.
9. The method or the antibody of any one of aspects 1 to 8 wherein the HMG-CoA reductase inhibitor is administered in the morning, at noon or in the evening.
10. The method or the antibody of any one of aspects 1 to 9, wherein the HMG-CoA reductase inhibitor is a statin.
11. The method or the antibody of aspect 10, wherein the statin is selected from the group consisting of cerivastatin, atorvastatin, simvastatin, pitavastatin, rosuvastatin, fluvastatin, lovastatin, and pravastatin.
12. The method or the antibody of aspect 11, wherein the statin is
cerivastatin administered in a daily dosage of between 0.05 mg and 2 mg;
atorvastatin administered in a daily dosage of between 2 mg and 100 mg;
simvastatin administered in a daily dosage of between 2 mg and 100 mg;
pitavastatin administered in a daily dosage of between 0.2 mg and 100 mg;
rosuvastatin administered in a daily dosage of between 2 mg and 100 mg;
fluvastatin administered in a daily dosage of between 2 mg and 100 mg;
lovastatin administered in a daily dosage of between 2 mg and 100 mg; or
pravastatin administered in a daily dosage of between 2 mg and 100 mg;
13. The method or the antibody of any one of aspects 1 to 12, wherein the antibody or antigen-binding fragment thereof is administered to the subject every other week.
14. The method or the antibody of any one of aspects 1 to 13, wherein the antibody or antigen-binding fragment thereof is administered in a dosage amount ranging from 50 mg to 300 mg.
15. The method or the antibody of any one of aspects 1 to 14, wherein the antibody or antigen-binding fragment thereof is a recombinant human antibody or fragment thereof
16. The method or the antibody of any one of aspects 1 to 15, wherein the antibody or the antigen-binding fragment thereof is characterized by one or more of the following:
(i) capable of reducing serum total cholesterol at least about 25 to about 35% and sustaining the reduction over at least a 24 day period relative to a predose level;
(ii) capable of reducing serum LDL cholesterol at least about 65-80% and sustaining the reduction over at least a 24 day period relative to a predose level;
(iii) capable of reducing serum triglyceride at least about 25-40% relative to predose level;
(iv) achieves one or more of (i)-(iii) without reducing serum HDL cholesterol or reducing serum HDL cholesterol no more than 5% relative to predose level;
(v) achieves one or more of (i)-(iii) with little or no measurable effect on liver function, as determined by ALT and AST measurements.
17. The method or the antibody of any one of aspects 1 to 16, wherein the antibody or the antigen-binding fragment thereof comprises
a heavy chain CDR3 (HCDR3) domain selected from the group consisting of SEQ ID NO:8, 32, 56, 80, 104, 128, 152, 176, 200, 224, 248, 272, 296, 320, 344, 368, 392, 416, 440, 464, 488, 512, 536, 560, 584, 608, 632, 656, 680, 704 and 728; and
a light chain CDR3 (LCDR3) domain selected from the group consisting of SEQ ID NO:16, 40, 64, 88, 112, 136, 160, 184, 208, 232, 256, 280, 304, 328, 352, 376, 400, 424, 448, 472, 496, 520, 544, 568, 592, 616, 639, 664, 688, 712 and 736.
18. The method or the antibody of any one of aspects 1 to 16, wherein the antibody or the antigen-binding fragment thereof comprises the heavy and light chain CDRs of a HCVR/LCVR amino acid sequence pair as shown in SEQ ID NOs: 90/92.
19. The method or the antibody of aspect 18, wherein the antibody or antigen-binding fragment thereof comprises heavy and light chain CDR amino acid sequences as shown in SEQ ID NOs: 76, 78, 80, 84, 86 and 88.
20. The method or the antibody of aspect 19, wherein the antibody or antigen-binding fragment thereof comprises an HCVR amino acid sequence as shown in SEQ ID NO: 90 and an LCVR amino acid sequence as shown in SEQ ID NO: 92.
21. The method or the antibody of any one of aspects 1 to 16, wherein the antibody or antigen-binding fragment thereof binds to the same epitope on hPCSK9 as an antibody comprising heavy and light chain CDR amino acid sequences as shown in SEQ ID NOs: 76, 78, 80, 84, 86, and 88.
22. The method or the antibody of any one of aspects 1 to 16, wherein the antibody or antigen-binding fragment thereof competes for binding to hPCSK9 with an antibody comprising heavy and light chain CDR amino acid sequences as shown in SEQ ID NOs: 76, 78, 80, 84, 86, and 88.
23. An article of manufacture comprising
(a) a packaging material;
(b) an antibody or an antigen-binding fragment thereof which specifically binds hPCSK9; and
(c) a label or packaging insert contained within the packaging material indicating that patients receiving treatment with said antibody or antigen-binding fragment can be treated for a disease or condition selected from the group consisting of hypercholesterolemia, hyperlipidemia, dyslipidemia, atherosclerosis and cardiovascular diseases.

24. An article of manufacture comprising
   (a) a packaging material;
   (b) an antibody or an antigen-binding fragment thereof which specifically binds hPCSK9; and
   (c) a label or packaging insert contained within the packaging material indicating the treatment of patients with said antibody or antigen-binding fragment thereof together with the application of a statin.

25. An article of manufacture comprising
   (a) a packaging material;
   (b) an antibody or an antigen-binding fragment thereof which specifically binds hPCSK9; and
   (c) a label or packaging insert indicating that the treatment of patients with said antibody or antigen-binding fragment thereof together with a statin is contraindicated for patients belonging to one or more of the following groups:
   (i) smokers;
   (ii) persons being 70 years old or older;
   (iii) persons suffering from hypertension;
   (iv) women who are pregnant;
   (v) women who are trying to become pregnant;
   (vi) women who are breast-feeding;
   (vii) persons who have or ever had a disease affecting the liver;
   (viii) persons who had any unexplained abnormal blood tests for liver function;
   (ix) persons who drink excessive amounts of alcohol;
   (x) persons having kidney problems;
   (xi) persons suffering from hypothyroidism;
   (xii) persons suffering from muscle disorders;
   (xiii) persons having encountered previous muscular problems during treatment with lipid-lowering medicine;
   (xiv) persons having serious problems with their breathing;
   (xv) persons taking one or more of the following medicines: medicines altering the way the immune systems works (e.g. ciclosporin or antihistamines), antibiotics or antifungal medicines (e.g. erythromycin, clarithromycin, ketoconazole, itraconazole, rifampicin, fusidic acid), medicines regulating lipid levels (e.g. gemfibrozil, colestipol), calcium channel blockers (e.g. verapamil, diltiazem), medicines regulating the heart rhythm (digoxin, amiodarone), protease inhibitors used in the treatment of HIV (e.g. nelfinavir), warfarin, oral contraceptives, antacids or St. John's Wort; or
   (xvi) persons drinking more than 0.1 L of grapefruit juice per day;
   (xvii) persons having a body mass index (BMI) of more than 40;
   (xviii) persons having a body mass index (BMI) of less than 18;
   (xix) persons suffering from type 1 diabetes or type 2 diabetes;
   (xx) persons positive for hepatitis B or hepatitis C; or
   (xxi) persons having a known sensitivity to monoclonal antibody therapeutics.

26. The article of manufacture according to one of aspects 23 to 25, wherein the antibody or antigen-binding fragment is an antibody or antigen-binding fragment as specified in any of aspects 2 to 22.

27. The article of manufacture according to one of aspects 23 to 26, wherein the label or packaging insert contains reference to a method of treatment according to any of aspects 1, or 3-22.

28. A method of testing the efficacy of an antibody or an antigen-binding fragment thereof which specifically binds hPCSK9 for the treatment of a disease or condition selected from the group consisting of hypercholesterolemia, hyperlipidemia, dyslipidemia, atherosclerosis and cardiovascular diseases, said method comprising:
   treating a selected patient population with said antibody or antigen-binding fragment thereof, wherein each patient in said population has an LDL cholesterol (LDL-C) level of more than 100 mg/dL; and
   determining the efficacy of said antibody or antigen-binding fragment thereof by determining the LDL-C level in the patient population before and after administration of said antibody or antigen-binding fragment thereof, wherein a reduction of the LDL-C level by at least 25% relative to a predose level in at least 75% of the patient population indicates that said antibody or antigen-binding fragment thereof is efficacious for the treatment of said disease or condition in said patient population.

29. A method of testing the efficacy of an antibody or an antigen-binding fragment thereof which specifically binds hPCSK9 for the treatment of a disease or condition selected from the group consisting of hypercholesterolemia, hyperlipidemia, dyslipidemia, atherosclerosis and cardiovascular diseases, said method comprising:
   determining the efficacy of an antibody or antigen-binding fragment thereof that has been used for the treatment of a selected patient population with said antibody or antigen-binding fragment thereof, wherein each patient in said population has an LDL cholesterol (LDL-C) level of more than 100 mg/dL by determining the LDL-C level in the patient population before and after administration of said antibody or antigen-binding fragment thereof, wherein a reduction of the LDL-C level by at least 25% relative to a predose level in at least 75% of the patient population indicates that said antibody or antigen-binding fragment thereof is efficacious for the treatment of said disease or condition in said patient population.

30. The method of aspect 28 or 29, wherein each patient in said population has received a lipid lowering treatment by administration of a statin for at least 6 weeks prior to treatment with said antibody or antigen-binding fragment thereof 31. The method of any of aspects 28 to 30, wherein the antibody or antigen-binding fragment is an antibody or antigen-binding fragment as specified in any of aspects 2 to 22.

32. The method of any of aspects 28 to 31, wherein the selected patient population is treated with a method of treatment according to any of aspects 1, or 3-22.

33. A package comprising an antibody or antigen-binding fragment thereof of one or more of aspects 2 to 22 and a label, said label comprising a printed statement which informs the patient that the treatment of the antibody together with a statin is indicated in one or more of the indications of aspect 4.

34. A package comprising an antibody or antigen-binding fragment thereof of one or more of aspects 2 to 22 and a label, said label comprising a printed statement which informs the patient that the treatment of the antibody together with a statin is contraindicated for patients belonging to one or more of the following groups:
(i) smokers;
(ii) persons being 70 years old or older;
(iii) persons suffering from hypertension;
(iv) women who are pregnant;
(v) women who are trying to become pregnant;
(vi) women who are breast-feeding;
(vii) persons who have or ever had a disease affecting the liver;
(viii) persons who had any unexplained abnormal blood tests for liver function;
(ix) persons who drink excessive amounts of alcohol;
(x) persons having kidney problems;
(xi) persons suffering from hypothyroidism;
(xii) persons suffering from muscle disorders;
(xiii) persons having encountered previous muscular problems during treatment with lipid-lowering medicine;
(xiv) persons having serious problems with their breathing;
(xv) persons taking one or more of the following medicines: medicines altering the way the immune systems works (e.g. ciclosporin or antihistamines), antibiotics or antifungal medicines (e.g. erythromycin, clarithromycin, ketoconazole, itraconazole, rifampicin, fusidic acid), medicines regulating lipid levels (e.g. gemfibrozil, colestipol), calcium channel blockers (e.g. verapamil, diltiazem), medicines regulating the heart rhythm (digoxin, amiodarone), protease inhibitors used in the treatment of HIV (e.g. nelfinavir), warfarin, oral contraceptives, antacids or St. John's Wort; or
(xvi) persons drinking more than 0.1 L of grapefruit juice per day;
(xvii) persons having a body mass index (BMI) of more than 40;
(xviii) persons having a body mass index (BMI) of less than 18;
(xix) persons suffering from type 1 diabetes or type 2 diabetes;
(xx) persons positive for hepatitis B or hepatitis C; or
(xxi) persons having a known sensitivity to monoclonal antibody therapeutics.

35. A method of regulating the LDL level in the blood comprising:
administering a therapeutic amount of an antibody or an antigen-binding fragment thereof which specifically binds hPCSK9 (human proprotein convertase subtilisin/kexin type 9) to a subject in need thereof, wherein the antibody or antigen-binding fragment thereof is administered in a dosage amount ranging from 5 mg to 500 mg, and
administering a therapeutic amount of an HMG-CoA reductase inhibitor to said subject, wherein the HMG-CoA reductase inhibitor is administered in a dosage amount ranging from 0.05 mg to 100 mg.

36. A method of preventing effects of a (persistently) increased LDL level in the blood comprising:
administering a therapeutic amount of an antibody or an antigen-binding fragment thereof which specifically binds hPCSK9 (human proprotein convertase subtilisin/kexin type 9) to a subject in need thereof, wherein the antibody or antigen-binding fragment thereof is administered in a dosage amount ranging from 5 mg to 500 mg, and
administering a therapeutic amount of an HMG-CoA reductase inhibitor to said subject, wherein the HMG-CoA reductase inhibitor is administered in a dosage amount ranging from 0.05 mg to 100 mg.

37. A method of determining whether a pharmaceutical compound is utilizable for ameliorating, improving, inhibiting or preventing a disease or condition in which PCSK9 activity or expression has an impact comprising
(a) administering to a subject a compound that specifically binds to PCSK9, preferably an antibody or antigen-binding fragment thereof specifically binding to PCSK9, and
(b) determining what fraction of PCSK9 in the blood is attached to the compound from (a).

Aspects Related to Dosage Regimens—B)

1. A method of treating a subject suffering from a disease or disorder characterized by elevated low-density lipoprotein cholesterol (LDL-C) levels, the method comprising administering to the subject: (1) an antibody, or antigen-binding fragment thereof, which specifically binds to human proprotein convertase subtilisin/kexin type 9 (hPCSK9); and (2) an HMG-CoA reductase inhibitor, wherein the antibody or antigen-binding fragment thereof is administered at a dosage amount within the range of about 5 mg to about 500 mg, thereby treating the subject.

2. The method of aspect 1, wherein the disease or condition is selected from the group consisting of: hypercholesterolemia, hyperlipidemia, dyslipidemia, and atherosclerosis.

3. The method of aspect 1, wherein the disease condition is primary hypercholesterolemia or familial hypercholesterolemia.

4. The method of aspect 1, wherein the disease or condition is hypercholesterolemia which is uncontrolled by statins.

5. The method of aspect 1, wherein the antibody or antigen-binding fragment is administered in a dosage amount within the range of about 50 mg to about 300 mg.

6. The method of aspect 1, wherein the antibody or antigen-binding fragment is administered in a dosage amount of about 150 mg.

7. The method of aspect 1, wherein the antibody or antigen-binding fragment thereof is administered to the subject every other week (E2W).

8. The method of aspect 1, wherein the antibody or antigen-binding fragment thereof is administered to the subject every fourth week (E4W).

9. The method of aspect 1, wherein the treatment reduces serum total cholesterol at least about 25% to about 35% relative to a predose level and sustains the reduction over at least a 24 day period.

10. The method of aspect 1, wherein the treatment reduces serum total cholesterol at least about 65% to about 80% relative to a predose level and sustains the reduction over at least a 24 day period.

11. The method of aspect 1, wherein the treatment reduces serum triglyeride levels at least about 25% to about 40% relative to a predose level.

12. The method of aspect 1, wherein the treatment reduced serum HDL cholesterol no more than 5% relative to a predose level.

13. The method of aspect 1, wherein the treatment has little or no measurable effect on liver function, as determined by ALT and AST measurements.

14. The method of aspect 1, wherein the antibody or the antigen-binding fragment comprises the heavy and light chain CDRs of a HCVR/LCVR amino acid sequence pair as shown in SEQ ID NOs: 90/92.

15. The method of aspect 1, wherein the antibody or antigen-binding fragment comprises a HCVR/LCVR amino acid sequence pair as shown in SEQ ID NOs: 90/92.
16. The method of aspect 1, wherein the antibody or antigen-binding fragment thereof competes for binding to hPCSK9 with an antibody or antigen-binding fragment comprising a HCVR/LCVR amino acid sequence pair as shown in SEQ ID NOs: 90/92.
17. The method of aspect 1, wherein the HMG-CoA reductase inhibitor is administered in a dosage amount in the range of about 0.05 mg to 100 mg.
18. The method of aspect 1, wherein the HMG-CoA reductase inhibitor is a statin.
19. The method of aspect 1, wherein the statin is selected from the group consisting of cerivastatin, atorvastatin, simvastatin, pitavastatin, rosuvastatin, fluvastatin, lovastatin, and pravastatin.
20. The method of aspect 1, wherein the statin is atorvastatin administered at a dosage of 10 mg or 80 mg.
21. A method of enhancing the LDL-C lowering activity in a subject undergoing statin therapy, the method comprising administering to the subject an antibody, or antigen-binding fragment thereof, which specifically binds to human proprotein convertase subtilisin/kexin type 9 (hPCSK9), wherein the antibody or antigen-binding fragment thereof is administered at a dosage amount within the range of about 5 mg to about 500 mg, thereby enhancing LCL-C lowering activity of the statin therapy in the subject.
22. The method of aspect 21, wherein the subject is resistant to the statin therapy prior to administration of the antibody.
23. The method of aspect 21, wherein the subject suffers from a disease or condition selected from the group consisting of hypercholesterolemia, hyperlipidemia, dyslipidemia, and atherosclerosis.
24. The method of aspect 21, wherein the disease condition is primary hypercholesterolemia or familial hypercholesterolemia.
25. The method of aspect 21, wherein the antibody or antigen-binding fragment is administered in a dosage amount within the range of about 50 mg to about 300 mg.
26. The method of aspect 21, wherein the antibody or antigen-binding fragment is administered in a dosage amount of about 150 mg.
27. The method of aspect 21, wherein the antibody or antigen-binding fragment thereof is administered to the subject every other week (E2W).
28. The method of aspect 21, wherein the antibody or antigen-binding fragment thereof is administered to the subject every fourth week (E4W).
29. The method of aspect 21, wherein the treatment reduces serum total cholesterol at least about 25% to about 35% relative to a predose level and sustains the reduction over at least a 24 day period.
30. The method of aspect 21, wherein the treatment reduces serum total cholesterol at least about 65% to about 80% relative to a predose level and sustains the reduction over at least a 24 day period.
31. The method of aspect 21, wherein the treatment reduces serum triglyeride levels at least about 25% to about 40% relative to a predose level.
32. The method of aspect 21, wherein the treatment reduced serum HDL cholesterol no more than 5% relative to a predose level.
33. The method of aspect 21, wherein the treatment has little or no measurable effect on liver function, as determined by ALT and AST measurements.
34. The method of aspect 21, wherein the antibody or the antigen-binding fragment comprises 1 the heavy and light chain CDRs of a HCVR/LCVR amino acid sequence pair as shown in SEQ ID NOs: 90/92.
35. The method of aspect 21, wherein the antibody or antigen-binding fragment comprises a HCVR/LCVR amino acid sequence pair as shown in SEQ ID NOs: 90/92.
36. The method of aspect 21, wherein the antibody or antigen-binding fragment thereof competes for binding to hPCSK9 with an antibody or antigen-binding fragment comprising a HCVR/LCVR amino acid sequence pair as shown in SEQ ID NOs: 90/92.
37. The method of aspect 21, wherein the statin is selected from the group consisting of cerivastatin, atorvastatin, simvastatin, pitavastatin, rosuvastatin, fluvastatin, lovastatin, and pravastatin.
38. The method of aspect 21, wherein the statin is atorvastatin administered at a dosage of 10 mg or 80 mg.
39. A pharmaceutical unit dosage form comprising an antibody, or antigen-binding fragment thereof, which specifically binds to hPCSK9; and pharmaceutically acceptable carrier, wherein the antibody or antigen-binding fragment is present in a dosage amount within the range of about 5 mg to about 500 mg.
40. The dosage form of aspect 39, wherein the antibody or antigen binding fragment is present in a dosage amount within the range of about 50 mg to about 300 mg.
41. The dosage form of aspect 39, wherein the antibody or antigen binding fragment is present in a dosage amount of about 150 mg.
42. The dosage form of aspect 39, wherein the antibody or the antigen-binding fragment comprises the heavy and light chain CDRs of a HCVR/LCVR amino acid sequence pair as shown in SEQ ID NOs: 90/92.
43. The dosage form of aspect 39, wherein the antibody or antigen-binding fragment comprises a HCVR/LCVR amino acid sequence pair as shown in SEQ ID NOs: 90/92.
44. The dosage form of aspect 39, wherein the antibody or antigen-binding fragment thereof competes for binding to hPCSK9 with an antibody or antigen-binding fragment comprising a HCVR/LCVR amino acid sequence pair as shown in SEQ ID NOs: 90/92.
45. The dosage form of aspect 39, further comprising a HMG-CoA reductase inhibitor.
46. The dosage form of aspect 39, wherein the HMG-CoA reductase inhibitor is present in a dosage amount in the range of about 0.05 mg to 100 mg.
47. The dosage form of aspect 39, wherein the HMG-CoA reductase inhibitor is a statin.
48. The dosage form of aspect 39, wherein the statin is selected from the group consisting of cerivastatin, atorvastatin, simvastatin, pitavastatin, rosuvastatin, fluvastatin, lovastatin, and pravastatin.
49. The dosage form of aspect 39, wherein the statin is atorvastatin present at dosage amount of 10 mg or 80 mg.
50. A kit for treating elevated low-density lipoprotein cholesterol (LDL-C) levels in a subject, the kit comprising (a) pharmaceutical unit dosage form comprising an antibody, or antigen-binding fragment thereof, which specifically binds to hPCSK9; and pharmaceutically acceptable carrier, wherein the antibody or antigen-binding fragment is present in a dosage amount within the range of about 5 mg to about 500 mg; and (b) a label or packaging insert with instructions for use.
51. The kit of aspect 50, wherein the label indicates that patients receiving treatment with said antibody or antigen-binding fragment can be treated for a disease or condition selected from the group consisting of hypercholesterolemia, hyperlipidemia, dyslipidemia, and atherosclerosis and cardiovascular diseases.
52. The kit of aspect 51, wherein the disease or condition is primary hypercholesterolemia or familial hypercholesterolemia.
53. The kit of aspect 51, wherein the disease or condition is hypercholesterolemia which is uncontrolled by statins.
54. The kit of aspect 50, wherein the antibody or antigen-binding fragment is present in dosage amount within the range of about 50 mg to about 300 mg.
55. The kit of aspect 50, wherein the antibody or antigen-binding fragment is present in a dosage amount of about 150 mg.
56. The kit of aspect 50, wherein the label or packaging insert indicates that the antibody or antigen-binding fragment thereof is administered to the subject every other week (E2W).
57. The kit of aspect 50, wherein the label or packaging insert indicates that the antibody or antigen-binding fragment thereof is administered to the subject every fourth week (E4W).
58. The kit of aspect 50, wherein the antibody or the antigen-binding fragment comprises the heavy and light chain CDRs of a HCVR/LCVR amino acid sequence pair as shown in SEQ ID NOs: 90/92.
59. The kit of aspect 50, wherein the antibody or antigen-binding fragment comprises a HCVR/LCVR amino acid sequence pair as shown in SEQ ID NOs: 90/92.
60. The kit of aspect 50, wherein the antibody or antigen-binding fragment thereof competes for binding to hPCSK9 with an antibody or antigen-binding fragment comprising a HCVR/LCVR amino acid sequence pair as shown in SEQ ID NOs: 90/92.
61. The kit of aspect 50, further comprising an HMG-CoA reductase inhibitor.
62. The kit of aspect 61, wherein the inhibitor in a dosage amount in the range of about 0.05 mg to 100 mg.
63. The kit of aspect 50, wherein the HMG-CoA reductase inhibitor is a statin.
64. The kit of aspect 50, wherein the statin is selected from the group consisting of cerivastatin, atorvastatin, simvastatin, pitavastatin, rosuvastatin, fluvastatin, lovastatin, and pravastatin.
65. The kit of aspect 50, wherein the instructions indicate that the statin is atorvastatin administered at a dosage of 10 mg or 80 mg.
66. The kit of aspect 50, wherein the instructions indicate that treatment with the antibody or an is contraindicated for patients belonging to one or more of the following groups:
(xxii) smokers;
(xxiii) persons being 70 years old or older;
(xxiv) persons suffering from hypertension;
(xxv) women who are pregnant;
(xxvi) women who are trying to become pregnant;
(xxvii) women who are breast-feeding;
(xxviii) persons who have or ever had a disease affecting the liver;
(xxix) persons who had any unexplained abnormal blood tests for liver function;
(xxx) persons who drink excessive amounts of alcohol;
(xxxi) persons having kidney problems;
(xxxii) persons suffering from hypothyroidism;
(xxxiii) persons suffering from muscle disorders;
(xxxiv) persons having encountered previous muscular problems during treatment with lipid-lowering medicine;
(xxxv) persons having serious problems with their breathing;
(xxxvi) persons taking one or more of the following medicines: medicines altering the way the immune systems works (e.g. ciclosporin or antihistamines), antibiotics or antifungal medicines (e.g. erythromycin, clarithromycin, ketoconazole, itraconazole, rifampicin, fusidic acid), medicines regulating lipid levels (e.g. gemfibrozil, colestipol), calcium channel blockers (e.g. verapamil, diltiazem), medicines regulating the heart rhythm (digoxin, amiodarone), protease inhibitors used in the treatment of HIV (e.g. nelfinavir), warfarin, oral contraceptives, antacids or St. John's Wort; or
(xxxvii) persons drinking more than 0.1 L of grapefruit juice per day;
(xxxviii) persons having a body mass index (BMI) of more than 40;
(xxxix) persons having a body mass index (BMI) of less than 18;
(xl) persons suffering from type 1 diabetes or type 2 diabetes;
(xli) persons positive for hepatitis B or hepatitis C; or
(xlii) persons having a known sensitivity to monoclonal antibody therapeutics.

Aspects Related to Compositions

1. Pharmaceutical composition comprising about 40 to about 500 mg per dose of an antibody or an antigen-binding fragment thereof which specifically binds hPCSK9 (human proprotein convertase subtilisin/kexin type 9) together with a pharmaceutically acceptable excipient or carrier.
2. Pharmaceutical composition according to aspect 1, comprising about 50 mg to about 500 mg, about 50 mg to about 300 mg, about 50 mg, about 100 mg, about 150 mg, about 200 mg, about 250 mg, about 300 mg, about 350 mg, of about 400 mg, about 450 mg or about 500 mg of the antibody or antigen-binding fragment thereof
3. Pharmaceutical composition according to one of the aspects 1 or 2 comprising about 150, 200 or 300 mg of the antibody or antigen-binding fragment thereof.
4. Pharmaceutical composition according to one of the aspects 1-3 comprising an effective dose of an antibody or an antigen-binding fragment thereof which specifically binds hPCSK9 (human proprotein convertase subtilisin/kexin type 9), wherein the dose is sufficient for sustained reduction of low-density lipoprotein (LDL-C) levels over a period of at least 14, at least 15, at least 16, at least 17, at least 18, at least 19, at least 20, at least 21, at least 22, at least 23 or at least 28 days after administration, together with a pharmaceutically acceptable excipient or carrier.
5. Pharmaceutical composition according to one of the aspects 1-4, wherein the dose is sufficient for sustained reduction of LDL-C levels over a period of at least 14 days, 28 days or 1 month.
6. Pharmaceutical composition according to one of the aspects 1-5 further comprising an effective amount of an HMG-CoA reductase inhibitor.
7. Pharmaceutical composition according to aspect 6, wherein the HMG-CoA reductase inhibitor is a statin, preferably selected from the list consisting or: cerivastatin, atorvastatin, simvastatin, pitavastatin, rosuvastatin, fluvastatin, lovastatin or pravastatin and is preferably atorvastatin.

8. Pharmaceutical composition according to aspect 6 or 7, comprising about 0.05 mg to about 100 mg, about 0.5 mg to about 100 mg, about 5 mg to about 90 mg, about 10 mg, about 20 mg, about 40 mg or about 80 mg of HMG-CoA reductase inhibitor and preferably about 10, about 20, about 40 or about 80 mg.

9. Pharmaceutical composition according to one of the aspects 6 to 8, comprising an effective dose of HMG-CoA reductase inhibitor for lowering LDL-D levels by administration once per day.

10. Pharmaceutical composition according to one of the aspects 1 to 9, wherein the antibody or antigen-binding fragment thereof has one or more of the following features:
   a. reduction of low-density lipoprotein (LDL-C) levels of at least about −25% to about −40% relative to a predose level with a sustained reduction over at least a 14 day-period upon administration to a subject, wherein the sustained reduction is preferably at least −25% and more preferably at least −30% relative to a predose level, particularly if administered in a dose of about 40 to about 60 mg, preferably about 45 to about 55 mg and more preferably about 50 mg in a biweekly administration regime (every other week, E2W);
   b. reduction of low-density lipoprotein (LDL-C) of at least about −50% to about −65% relative to a predose level with a sustained reduction over at least a 14 day-period upon administration to a subject, wherein the sustained reduction is preferably at least −40% and more preferably at least −45% relative to a predose level, particularly if administered in a dose of about 100 mg E2W.
   c. reduction of low-density lipoprotein (LDL-C) of at least about −60% to at least about −75% [e.g. at least about −60%, at least about −65%, at least about −70 or at least about −75%] relative to a predose level with a sustained reduction over at least a 14 day-period upon administration to a subject, wherein the sustained reduction is preferably at least −55% and more preferably at least −60% relative to a predose level, particularly when administered in a dose of about 150 mg E2W,
   d. reduction of low-density lipoprotein (LDL-C) of at least about 40% to about 75% relative to a predose level with a sustained reduction over at least a 28 day period, wherein the sustained reduction is preferably at least −35% and more preferably at least −40% relative to a predose level, particularly when administered in a dose of about 200 mg E4W
   e. reduction of low-density lipoprotein (LDL-C) of at least about −50% to about −75% relative to a predose level with a sustained reduction over at least a 28 day-period upon administration to a subject, wherein the sustained reduction is preferably at least −40% and more preferably at least −45% relative to a predose level, particularly when administered in a dose of about 300 mg E4W,
   f. increase of serum HDL cholesterol levels of at least 2%, at least 2.5%, at least, 3%, at least 3.5%, at least 4%, at least 4.5%, at least 5% or at least 5.5% relative to a predose level upon administration to a subject, particularly when administered in a dose of about 150 mg E2W,
   g. little or no measurable effect on troponin levels upon administration to a subject,
   h. increase of one or more of: Total-Cholesterol levels, ApoB levels, non HDL-C levels, Apo-B/ApoA-1 ratio, upon administration to a subject.

11. Pharmaceutical composition according to one of the aspects 1-9, wherein the antibody or antigen-binding fragment thereof is capable of overcoming statin resistance when administered to a subject with statin-resistant hypercholesterolemia.

12. Pharmaceutical composition according to one of the aspects 1-10, wherein the antibody or antigen-binding fragment thereof comprises the heavy and light chain CDRs of a HCVR/LCVR amino acid sequence pair as shown in SEQ ID NOs: 90/92 substantially identical sequences having at least 98% or 99% identity therewith.

13. Pharmaceutical composition according to one of the aspects 1-11, wherein the antibody or antigen-binding fragment thereof comprises a HCVR/LCVR amino acid sequence pair as shown in SEQ ID NOs: 90/92 or a pair of substantially identical sequences having at least 98% or 99% identity therewith.

14. Pharmaceutical composition according to one of the aspects 1-10, wherein the antibody or antigen-binding fragment thereof competes for binding to hPCSK9 with an antibody or antigen-binding fragment comprising a HCVR/LCVR amino acid sequence pair as shown in SEQ ID NOs: 90/92.

15. Pharmaceutical composition according to one of the aspects 1-13, wherein the antibody or antigen-binding fragment thereof binds an epitope comprising amino acid residue 238 of hPCSK9 (SEQ ID NO:755).

16. Pharmaceutical composition according to one of the aspects 1-14, wherein the antibody or antigen-binding fragment thereof binds an epitope comprising one or more of amino acid residues at positions 238, 153, 159 and 343 of hPCSK9 (SEQ ID NO:755).

17. Pharmaceutical composition according to one of the aspects 1-15, wherein the antibody or antigen-binding fragment thereof binds an epitope which does not comprise an amino acid residue at positions 192, 194, 197 and/or 237 of hPCSK9 (SEQ ID NO:755).

18. Pharmaceutical composition according to one of the aspects 1-16 comprising the antibody or antigen-binding fragment thereof as dry formulation for dissolution such as a lyophilized powder, freeze-dried powder or water free concentrate.

19. Pharmaceutical composition according to one of the aspects 1-17 comprising the antibody or fragment thereof as liquid formulation, e.g. injection or infusion solution.

20. Pharmaceutical composition according to one of the aspects 4-18 comprising the HMG-CoA reductase inhibitor as peroral formulation, e.g. capsule or tabled, or as liquid formulation, e.g. suspension, dispersion or solution, e.g. for peroral administration, injection or infusion.

21. Injection solution according to aspect 19, preferably comprising about 40 mg to about 200 mg or about 40 to about 200 mg, e.g. about 40 mg, about 50 mg, about 75 mg, at about 100 mg, about 150 mg or about 200 mg of the antibody or antigen-binding fragment thereof per 1 ml volume.

22. Dry formulation according to aspect 17, preferably comprising about 40 mg to about 500 mg, 50 to about 500 mg, about 50 to about 400, about 50 to about 300 e.g. about 40 mg, about 50 mg, about 75 mg, at about 100 mg, about 150 mg, about 200 mg, about 250 mg, about 300 mg, about 350 mg, about 400 mg, about 450 mg or about 500 mg and preferably about 50 mg, about 100 mg, about 150 mg, about 200 mg, about 250 mg, about 300 mg and even more preferably about 150 mg, about 200 mg or about 300 mg of the antibody or antigen-binding fragment thereof per dose.

23. Antibody or antigen binding fragment thereof as comprised in one of the pharmaceutical compositions according to one of the aspects 1-17.

24. Unit dosage form comprising the pharmaceutical composition according to one of the aspects 1-20, the injection solution according to aspect 21, the dry formulation according to aspect 22, or the antibody according to aspect 23.

25. Unit dosage form according to aspect 24, comprising about 40 mg, about 50 mg, about 75 mg, at about 100 mg, about 150 mg, about 200 mg, about 250 mg, about 300 mg, about 350 mg, about 400 mg, about 450 mg, or about 500 mg of the antibody or antigen-binding fragment thereof 26. Unit dosage form according to one of the aspects 24 or 25 comprising the antibody or fragment thereof as dry formulation for dissolution in a hermetically sealed container such as a vial, an ampoule or sachette.

27. Unit dosage form according to one of the aspects 24 or 25 comprising the antibody or fragment thereof as liquid formulation in a hermetically sealed container such as a vial, a sachette, a pre-filled syringe, a pre-filled autoinjector or a cartridge for a reusable syringe or applicator.

28. Unit dosage form according to aspect 26 or 27, wherein the quantity of active ingredient is indicated on the hermetically-sealed container.

29. Article of manufacture comprising, the pharmaceutical composition according to one of the aspects 1-20, the liquid formulation according to aspect 21 or the dry formulation according to aspect 22, the antibody or antigen-binding fragment thereof according to aspect 23 or one or more unit dosage forms according to one of the aspects 24-28, and a container.

30. Article of manufacture according to aspect 29 comprising separate unit dosage forms the antibody according to aspect 23 and the HMG-CoA reductase inhibitor according to one of the aspects 5-9 or 20.

31. Article of manufacture according to aspect 30 comprising one or more of the following components:
 a. One or more unit dosage forms comprising the antibody according to aspect 23;
 b. One or more unit dosage forms comprising the HMG-CoA reductase inhibitor according to one of the aspects 6-9 or 20;
 c. Instructions for use;
 d. A device for application of the antibody such as a syringe.

32. Article of manufacture according to aspect 31, comprising sufficient unit dosage forms of the antibody and preferably also of the HMG-CoA reductase inhibitor, for one single administration of antibody and HMG-CoA reductase inhibitor, for a two-week (i.e. 14-day) treatment with antibody and HMG-CoA reductase inhibitor, for a four week (i.e, 28-day) treatment with antibody and HMG-CoA reductase inhibitor or for a one-month treatment with antibody and HMG-CoA reductase inhibitor.

33. Article of manufacture according to aspect 32, comprising sufficient unit dosage forms of antibody for a bi-weekly administration regime or a four-weekly administration regime or a monthly administration regime.

34. Article of manufacture according to aspect 32 or 33 comprising sufficient unit dosage forms of HMG-CoA reductase inhibitor for a daily administration regime.

35. Pharmaceutical composition according to one of the aspects 1 to 20 or antibody or antigen-binding fragment thereof according to aspect 21 for use in the treatment of a disease or condition in which PCSK9 expression or activity causes an impact, preferably for use in the lowering of elevated LDL-C (low density lipoprotein C) levels 36. Pharmaceutical composition or antibody or antigen-binding fragment thereof according to aspect 35, wherein the disease or condition is selected from the group consisting of: elevated total cholesterol levels, elevated low-density lipoprotein (LDL-C) levels, hypercholesterolemia, hyperlipidemia, dyslipidemia, and atherosclerosis, particularly primary hypercholesterolemia, familial hypercholesterolemia, or hypercholesteremia which is uncontrolled by statins 37. Pharmaceutical composition or antibody or antigen-binding fragment thereof according to aspect 35 or 36, wherein the composition, the antibody or antigen-binding fragment thereof is administered to the subject every other week (E2W), every fourth week (E4W) or once a month.

38. Pharmaceutical composition or antibody or antigen-binding fragment thereof according to one of the aspects 35-37, comprising co-administration of an HMG-CoA reductase inhibitor, preferably an HMG-CoA reductase inhibitor according to one of the aspects 7-9 or 20.

39. Pharmaceutical composition or antibody according to aspect 38, wherein the HMG-CoA reductase inhibitor is administered once a day and preferably every day.

40. Method for preparing a pharmaceutical composition according to one of the aspects 1-20 comprising mixing the antibody or antigen-binding fragment thereof and optionally the HMG-CoA reductase inhibitor with one or more pharmaceutical excipients or carriers.

41. Method for preparing a unit dosage form according to one of the aspects 24 to 28 comprising admeasuring an amount of the pharmaceutical composition according to one of the aspects 1-20, the antibody according to aspect 21, the liquid formulation according to aspect 22 or the dry formulation according to aspect 23 comprising one or more doses of the antibody and optionally of the HMG-CoA reductase inhibitor and tailor them as physically discrete units suitable as unitary dosages for human and/or animal subjects.

42. Method for preparing an article of manufacture according to one of the aspects 29-34 comprising packaging the pharmaceutical composition according to one of the aspects 1-20, the antibody according to aspect 21, the liquid formulation according to aspect 22, the dry formulation according to aspect 23 or one or more of the unit dosage forms of one of aspects 24 to 28 in a container.

EXAMPLES

The following examples are put forth so as to provide those of ordinary skill in the art with a complete disclosure and description of how to make and use the methods and compositions of the invention, and are not intended to limit the scope of what the inventors regard as their invention. Efforts have been made to ensure accuracy with respect to numbers used but some experimental errors and deviations should be accounted for. Unless indicated otherwise, molecular weight is average molecular weight, temperature is in degrees Centigrade, and pressure is at or near atmospheric.

Study 1

This was a multicenter, randomized, double-blind, parallel-group, placebo-controlled, 12-week study to assess the efficacy and safety of antibody 316P in patients with an elevated low-density lipoprotein cholesterol (LDL-C) (≥100 mg/dL or 2.59 mmol/L), when treated with atorvastatin (10 mg, 20 mg, or 40 mg) at a stable dose for at least 6 weeks. The randomization was stratified by the dose of atorvastatin received prior to randomization. After the double-blind period patients were followed during an 8-week follow-up period. The primary objective of the study was to evaluate the effect of antibody 316P on LDL-C levels after 12 weeks of treatment in comparison with placebo in patients with LDL-C (≥100 mg/dL or 2.59 mmol/L) on ongoing stable atorvastatin therapy.

The following doses/dose regimens were evaluated: 50 mg, 100 mg and 150 mg every 2 weeks (E2W), 200 mg and 300 mg every 4 weeks (E4W) in comparison with placebo.

Present study comprised a total of 122 patients (20 in placebo, 19 in 50 mg E2W group, 20 in 100 mg E2W group, 20 in 150 mg E2W group, 22 in 200 mg E4W group, and 21 in 300 mg E4W group).

Forty six (37.7%) of these patients were randomized in the stratum atorvastatin 10 mg, 43 (35.2%) in the stratum atorvastatin 20 mg and 33 (27.0%) in the stratum atorvastatin 40 mg.

Patient Selection

Inclusion criteria:
Patients (patients receiving a lipid lowering treatment other than atorvastatin/or not at stable dose of atorvastatin 10 mg, 20 mg or 40 mg for at least 6 weeks prior to screening period or drug naïve patients) with primary hypercholesterolemia likely to have low-density lipoprotein cholesterol (LDL-C)≥100 mg/dL (≥2.59 mmol/L) at the end of the run-in period on atorvastatin therapy (Week-1).

OR

Patients with primary hypercholesterolemia treated with atorvastatin at stable dose of 10 mg, 20 mg, or 40 mg for at least 6 weeks prior to screening period and likely to have LDL-C≥100 mg/dL (≥2.59 mmol/L) at the screening visit Week-1.

Exclusion criteria:
LDL-C<100 mg/dL (<2.59 mmol/L) at Week-1 (V1):
After the run-in period on atorvastatin (10 mg, 20 mg, or 40 mg) for patients receiving a lipid lowering treatment other than atorvastatin/or not at stable dose of atorvastatin 10 mg, 20 mg or 40 mg for at least 6 weeks prior to the screening period, or drug naive patients.

OR

At the first visit for patients who are being treated with stable dose of atorvastatin (10 mg, 20 mg, or 40 mg) for at least 6 weeks prior to screening visit Week-1.

Use of a statin other than atorvastatin 10 mg, 20 mg, or 40 mg, or use of other lipid lowering drugs including but not limited to fibrates, bile acid resins, niacin >500 mg, intestinal cholesterol absorption (ICA) blockers, or omega-3 fatty acids at doses >1000 mg during the screening period.

Body mass index (BMI)<18 or >40 kg/m² at Week-7 or Week-1.

Patients not previously instructed on a cholesterol-lowering diet.

Patients with type 1 diabetes.

Patients with type 2 diabetes treated with insulin.

Patients with type 2 diabetes and with an HbA1c≥8.5% at Week-7 or Week-1 (considered poorly controlled).

Laboratory findings measured before randomization:
Positive test for hepatitis B surface antigen and/or hepatitis C antibody.
Triglycerides (TG)>350 mg/dL (>3.95 mmol/L) at Week-7 or Week-1.
Neutrophils <1,500/mm3 and/or platelets <100,000/mm3.
Positive serum or urine pregnancy test in females of childbearing potential.
Abnormal sensitive TSH level (>ULN or <LLN) according to the normal values of the Central Laboratory
Evidence of renal impairment as determined by:
Men: serum creatinine >1.5×ULN.
Women: serum creatinine >1.4×ULN.
ALT or AST>2×ULN.
CPK>3×ULN (1 repeat lab is allowed).

All contraindications to the protocol mandated background therapy (i.e. atorvastatin) or warning/precaution of use (when appropriate) as displayed in the respective National Product Labeling that was used for defining these exclusion criteria.

Known sensitivity to monoclonal antibody therapeutics.
Pregnant or breast-feeding women.
Women of childbearing potential with no effective contraceptive method.

Patient population:
Demographics and baseline characteristics were generally similar across treatment groups. The median age of patients was 58.0 years (28.7% of patients were ≥65 years of age) with patients aged 24-75 years. The mean range for baseline LDL-C and Total-C among treatment groups was similar and ranged between 3.214 mmol/L and 3.500 mmol/L for LDL-C and between 5.284 mmol/L and 5.521 mmol/L for Total-C. The BMI (kg/m²) was between 19.7 to 40.5 with a mean value of 29.04 and a median value of 28.4 (with 63.6% of the patients having a BMI of <30 and 36.4% of the patients having a BMI of >30). 80 (65.6%) of the 122 patients had hyperlipoproteinemia Type IIa (familiar hypercholesterinemia) according to Fredrickson classification, 41 (33.6%) type IIb (combined hyperlipidemia) and 1 (0.8%) type IV (endogenous hyperlipidemia). Overall 82% of the patients had received previous treatment with a lipid lowering agent, whereas 22% had not.

Duration of Study Period Per Subject:
The duration of study participation depended on the status of the patient at screening:
For patients receiving atorvastatin 10 mg, 20 mg or 40 mg at a stable dose for at least 6 weeks prior to screening, the study participation was approximately 21 weeks including a screening period of 1 week, a double-blind treatment period of 12 weeks and a follow-up period of 8 weeks.
For patients receiving a lipid lowering treatment other than atorvastatin/or not at stable dose of atorvastatin 10 mg, 20 mg or 40 mg for at least 6 weeks prior to screening, or drug naive patients, the study participation was approximately 27 weeks including a screening period of 7 weeks (including a run-in period of 6 weeks), a double-blind treatment period of 12 weeks, and a follow-up period of 8 weeks.

Active Compounds:
Antibody 316P:
Antibody 316P is a fully human antibody comprising a HCVR as shown in SEQ ID NO: 90 and LCVR as shown in SEQ ID NO: 92 of the sequence listing. The CDR sequences are shown in SEQ ID NOs: 76, 78, and 80 (CDR1, CDR2, CDR3 of the heavy chain) as well as in SEQ ID NOs: 84, 86, and 88 (CDR1, CDR2, CDR3 of the light chain).
Antibody 300N:
Antibody 300N is a fully human antibody comprising a HCVR as shown in SEQ ID NO: 218 and LCVR as shown in SEQ ID NO: 226 of the sequence listing. The CDR sequences are shown in SEQ ID NOs: 220, 222, and 224 (CDR1, CDR2, CDR3 of the heavy chain) as well as in SEQ ID NOs: 228, 230, and 232 (CDR1, CDR2, CDR3 of the light chain).
Study Arms:
Arm 1: The first group of patients received two injections of 1 mL each of antibody 316P, administered subcutaneously in the abdomen, with a dose regimen at 50 mg, every two weeks, for a treatment period of 12 weeks;
  Atorvastatin was administered once per day at a stable dose of 10 mg, 20 mg, or 40 mg as background therapy.
Arm 2: The second group of patients received two injections of 1 mL each of antibody 316P, administered subcutaneously in the abdomen, with a dose regimen at 100 mg, every two weeks, for a treatment period of 12 weeks;
  Atorvastatin was administered once per day at a stable dose of 10 mg, 20 mg, or 40 mg as background therapy.
Arm 3: The third group of patients received two injections of 1 mL each of antibody 316P, administered subcutaneously in the abdomen, with a dose regimen at 150 mg, every two weeks, for a treatment period of 12 weeks;
  Atorvastatin was administered once per day at a stable dose of 10 mg, 20 mg, or 40 mg as background therapy.
Arm 4: The fourth group of patients received two injections of 1 mL each of a placebo solution, administered subcutaneously in the abdomen, every two weeks, for a treatment period of 12 weeks;
  Atorvastatin was administered once per day at stable dose of 10 mg, 20 mg, or 40 mg as background therapy.
Arm 5: The fifth group of patients received two injections of 1 mL each of antibody 316P, administered subcutaneously in the abdomen, with a dose regimen at 200 mg, every four weeks, for a treatment period of 12 weeks;
  a placebo solution was administered alternating with the administration of antibody 316P so that the patient has the same injection scheme as the patients in arms 1 to 4, i.e. the patient received two injections of 1 mL each of a placebo solution in weeks 2, 6, and 10 and two injections of 1 mL each of antibody 316P in weeks 0, 4, 8, and 12;
  Atorvastatin was administered once per day at a stable dose of 10 mg, 20 mg, or 40 mg as background therapy.
Arm 6: The sixth group of patients received two injections of 1 mL each of antibody 316P, administered subcutaneously in the abdomen, with a dose regimen at 300 mg, every four weeks, for a treatment period of 12 weeks;
  a placebo solution was administered alternating with the administration of antibody 316P so that the patient has the same injection scheme as the patients in arms 1 to 4, i.e. the patient received two injections of 1 mL each of a placebo solution in weeks 2, 6, and 10 and two injections of 1 mL each of antibody 316P in weeks 0, 4, 8, and 12;
  Atorvastatin wais administered once per day at a stable dose of 10 mg, 20 mg, or 40 mg as background therapy.

Primary and Key Secondary Endpoints:
The primary efficacy variable is the percent change in calculated LDL-C from baseline to Week 12, which is defined as: 100×(calculated LDL-C value at Week 12−calculated LDL-C value at baseline)/calculated LDL-C value at beseline.
In case of unavailable calculated LDL-C value at Week 12 as defined above, then the last calculated LDL-C value measured during the efficacy period and before the Week 12 time window will be used to impute the missing Week 12 calculated LDL-C value (Last Observation Carried Forward [LOCF] procedure).
Secondary Efficacy Endpoints are:
The absolute change (mmol/L and mg/dL) from baseline in calculated LDL-C to Week 12, defined as: (calculated LDL-C value at Week 12−calculated LDL-C value at beseline), using same definitions and imputation rules as for the primary endpoint.
The percentage of patients with calculated LDL-C<70 mg/dL (1.81 mmol/L) and <100 mg/dL (2.59 mmol/L) at Week 12.
Percent change in ApoB from baseline to Week 12: same definitions and rules as for LDL-C, except for baseline value that will be the ApoB value measured at ransomization visit (Visit2) and before first IP injection, or, if missing, the last unscheduled value obtained from Visit 1 (Week-1) up to before the first IP injection.
Percent and absolute (mmol/L and mg/dL) change in non HDL-C from baseline to Week12: same definitions and rules as for LDL-C.
Percent and absolute (mmol/L and mg/dL) change in fasting Triglycerides from baseline to Week 12: same definitions and rules as for LDL-C, excluding measurements in not fasting patients or measurements with missing fasting status.
Percent change in ApoA-1 from baseline to week 12: same definitions and rules as for AboB.
Absolute change in the ration AboB/ApoA-1 from baseline to Week12: same definitions and rules as for AboB.
Percent change in Lp(a) from baseline to Week12: same definitions and rules as for ApoB. In case of Lp(a) value below the detection limit, a value halfway between zero and the detection limit will be used for calculation
Results:
The Efficacy of 316P Treatment on LDL-C Level-Lowering

TABLE 1

LDL-C in mmol/L (mg/dL) at Week 12

| | Placebo | 50 mg E2W | 200 mg E4W | 100 mg E2W | 300 mg E4W | 150 mg E2W |
|---|---|---|---|---|---|---|
| | \multicolumn{6}{c}{LDL Cholesterol mmol/L (mg/dL)} | | | | | |
| | \multicolumn{6}{c}{Number of patients} | | | | | |
| | N = 20 | N = 19 | N = 20 | N = 20 | N = 21 | N = 18 |
| Baseline | | | | | | |
| Mean | 3.489 (134.7) | 3.214 (124.1) | 3.318 (128.1) | 3.422 (132.1) | 3.500 (135.1) | 3.238 (125.0) |
| Median | 3.134 (121) | 3.121 (120.5) | 3.225 (124.5) | 3.225 (124.5) | 3.250 (125.5) | 3.121 (120.5) |
| Week 12 | | | | | | |
| Mean | 3.173 (122.5) | 1.859 (71.8) | 1.722 (66.5) | 1.251 (48.3) | 1.766 (68.2) | 0.860 (33.2) |

TABLE 1-continued

LDL-C in mmol/L (mg/dL) at Week 12

| | | LDL Cholesterol mmol/L (mg/dL) | | | | |
|---|---|---|---|---|---|---|
| | Placebo | 50 mg E2W | 200 mg E4W | 100 mg E2W | 300 mg E4W | 150 mg E2W |
| | | | Number of patients | | | |
| | N = 20 | N = 19 | N = 20 | N = 20 | N = 21 | N = 18 |
| Median | 3.121 (120.5) | 1.813 (70.0) | 1.567 (60.5) | 1.101 (42.5) | 1.632 (63.0) | 0.984 (38.0) |
| Week 12—change from baseline | | | | | | |
| Mean | −0.317 (−12.2) | −1.355 (−52.3) | −1.595 (−61.6) | −2.171 (−83.8) | −1.733 (−66.9) | −2.378 (−91.8) |
| Median | −0.265 (−10.3) | −1.295 (−50.0) | −1.593 (−61.5) | −2.117 (−81.8) | −1.904 (−73.5) | −2.363 (−91.3) |
| Week 12—% change from baseline | | | | | | |
| Mean | −6.08 | −41.06 | −47.23 | −63.90 | −48.29 | −72.68 |
| Median | −6.92 | −37.04 | −49.46 | −64.28 | −51.98 | −74.83 |

Statistically significant decreases in percent change from baseline in LDL-C at 12 weeks were observed in all groups compared to the placebo group. The greatest decrease was seen in the 100 mg E2W (−63.90%) and 150 mg E2W (−72.68%) groups compared with a slight decrease in the placebo group (−6.08%) (LS mean difference vs. placebo of −58.36% and −68.78%, respectively); these decreases observed after the first injection were maintained throughout the study and more particularly throughout the interval period between the injections. Large decreases from baseline in LDL-C at 12 weeks were also observed in the 200 mg and 300 mg E4W groups (−47.23% and 48.29%, respectively with a LS mean difference vs. placebo of −42.53% and −42.26%) with also significant decreases of at least about −40% during the interval periods. Among 18 patients in the 150 mg E2W group, 17 had a LDL-C reduction from baseline >50% at week 12.

Effects of 316P Treatment on Other Key Efficacy Endpoints

| | Placebo | 50 mg E2W | 200 mg E4W | 100 mg E2W | 300 mg E4W | 150 mg E2W |
|---|---|---|---|---|---|---|
| | | | Number of patients | | | |
| | N = 20 | N = 19 | N = 20 | N = 20 | N = 21 | N = 18 |
| Cholesterol mmol/L Baseline | | | | | | |
| Mean | 5.521 | 5.286 | 5.305 | 5.386 | 5.416 | 5.388 |
| Median | 5.458 | 5.232 | 5.394 | 5.199 | 5.180 | 5.361 |
| Week 12 | | | | | | |
| Mean | 5.378 | 3.974 | 3.709 | 3.288 | 3.778 | 2.922 |
| Median | 5.258 | 3.937 | 3.587 | 3.238 | 3.393 | 2.823 |
| Week 12 change from baseline | | | | | | |
| Mean | −0.143 | −1.313 | −1.596 | −2.098 | −1.638 | −2.466 |
| Median | −0.188 | −1.399 | −1.716 | −2.163 | −2.020 | −2.331 |
| Week 12 % change from baseline | | | | | | |
| Mean | −1.47 | −24.21 | −29.54 | −38.97 | −29.61 | −45.21 |
| Median | −3.73 | −23.34 | −29.51 | −40.21 | −33.48 | −45.03 |

| | Placebo | 50 mg E2W | 200 mg E4W | 100 mg E2W | 300 mg E4W | 150 mg E2W |
|---|---|---|---|---|---|---|
| | | | Number of patients | | | |
| | N = 20 | N = 19 | N = 20 | N = 20 | N = 21 | N = 18 |
| Non-HDL Cholesterol (mmol/L) Week 12 % change from baseline | | | | | | |
| Mean | −2-29 | −35.23 | −40.07 | −54.78 | −41.17 | −63.71 |
| Median | −4.71 | −36.62 | −39.91 | −55.91 | −45.55 | −65.94 |

Consistent results (decrease) were seen for Total-C, ApoB, non HDL-C. For HDL-C there was a trend of increase in all groups, similar pattern was seen for ApoA-1. Antibody 316P was well tolerated during the 12 weeks of treatment at all tested doses/dose regimens. Significantly, no change in troponin levels was noted in all treatment groups.

Conclusion:

The results of this study showed that dosage regimens with E2W or E4W application schemes and different dosages of anti-PCSK 9 antibody 316P as used in this study are efficient and safe therapies for lowering LDL-C levels in patients with hyperlipoproteinemia and or hyperlipidemia and thus for the treatment of hyperlipoproteinemia and/or hyperlipidemia. Best overall results were achieved using the 150 mg E2W dosage regimen. However, taking into consideration the patient comfort in only obtaining antibody treatments once a month, also both E4W dosage regimens tested in present study provided very good results.

Study 2

This was a randomized, double-blind, 3-parallel-groups, placebo-controlled, fixed dose/dose regimen, multicenter, 8-week study in subjects with primary hypercholesterolemia, aged 18-75 years. One aim of this study was to assess the efficacy and safety of 316P in patients with an elevated LDL-C (≥100 mg/dL or 2.59 mmol/L) treated with a stable dose of atorvastatin 10 mg.

During the screening period, patients had to be stabilized to atorvastatin 10 mg for at least 6 weeks, if they are not already. Then, after 1 additional screening week, patients were centrally randomized via IVRS/IWRS in a 1:1:1 ratio to one of the 3 treatment groups (placebo for 316P+atorvastatin 80 mg, 316P 150 mg E2W+atorvastatin 80 mg, 316P 150 mg E2W+atorvastatin 10 mg) and treated in a double-blind manner for approximately 8 weeks. 316P was administered every 2 weeks on site trough subcutaneous injection and atorvastatin was administered orally once daily in the evening at home. The double-blind treatment period was then followed by an 8-week follow-up period.

Approximately 90 patients (30 patients per treatment group) were recruited and randomized from approximately 20 sites.

Objectives

Primary Objective

To evaluate the effect of 316P on low-density lipoprotein cholesterol (LDL-C) levels compared with placebo when co-administered with 80 mg of atorvastatin after 8 weeks of treatment in patients with LDL-C≥100 mg/dL (≥2.59 mmol/L) on atorvastatin 10 mg.

Secondary Objective

The Key Secondary Objectives Presented in this KRM are:

To evaluate the effects of 316P on other lipid levels in comparison with placebo, when co-administered with 80 mg of atorvastatin after 8 weeks of treatment To evaluate the efficacy of 316P when co-administered with a high dose of atorvastatin (80 mg) versus atorvastatin 10 mg To evaluate the safety and tolerability of 316P when co-administered with 2 different doses of atorvastatin To evaluate the effects of 316P on other exploratory endpoints: fasting plasma glucose, glycated hemoglobin A1c (HbA1c), high-sensitivity C-reactive protein (hs-CRP).

Patient Selection:

Inclusion criteria:

Patients (patients receiving a lipid lowering treatment other than atorvastatin/or not at stable dose of atorvastatin 10 mg for at least 6 weeks prior to screening period, or drug naive patients) with primary hypercholesterolemia likely to have low-density lipoprotein cholesterol (LDL-C)≥100 mg/dL (≥2.59 mmol/L) at the end of the run-in period on atorvastatin therapy (Week-1).

OR

Patients with primary hypercholesterolemia treated with stable dose of atorvastatin 10 mg for at least 6 weeks prior to screening period and likely to have low-density lipoprotein cholesterol (LDL-C)≥100 mg/dL (≥2.59 mmol/L) at the screening visit (Week-1).

Exclusion criteria:

LDL-C<100 mg/dL (<2.59 mmol/L) at Week-1 (V1):

After the run-in period on atorvastatin 10 mg for patients receiving a lipid lowering treatment other than atorvastatin/or not at stable dose of atorvastatin 10 mg for at least 6 weeks prior to the screening period, or drug naive patients.

OR

At the first visit for patients who are being treated with atorvastatin 10 mg at stable dose for at least 6 weeks prior to screening visit Week-1.

Body mass index (BMI)<18 or >40 kg/m$^2$ at Week-7 or Week-1.

Patients not previously instructed on a cholesterol-lowering diet.

Use of a statin other than atorvastatin 10 mg, or use of other lipid lowering drugs including but not limited to fibrates, bile acid resins, niacin >500 mg, intestinal cholesterol absorption (ICA) blockers, or omega-3 fatty acids at doses >1000 mg during the screening period.

Patients with type 1 diabetes.

Patients with type 2 diabetes treated with insulin.

Patients with type 2 diabetes and with an HbA1c≥8.5% at Week-7 or Week-1 (considered poorly controlled).

Laboratory findings measured before randomization:

Positive test for hepatitis B surface antigen and/or hepatitis C antibody.

Triglycerides (TG)>350 mg/dL (>3.95 mmol/L) at Week-7 or Week-1.

Neutrophils <1,500/mm$^3$ and/or platelets <100,000/mm$^3$.

Positive serum or urine pregnancy test in females of childbearing potential.

Abnormal sensitive TSH level (>ULN or <LLN) according to the normal values of the Central Laboratory.

Evidence of renal impairment as determined by:
Men: serum creatinine >1.5×ULN.
Women: serum creatinine >1.4×ULN.

ALT or AST>2×ULN (1 repeat lab is allowed).

CPK>3×ULN (1 repeat lab is allowed).

All contraindications to the protocol mandated background therapy (i.e., atorvastatin) or warning/precaution of use (when appropriate) as displayed in the respective National Product Labeling that was used for defining these exclusion criteria.

Known sensitivity to monoclonal antibody therapeutics.

Pregnant or breast-feeding women.

Women of childbearing potential with no effective contraceptive method.

Figure 5:
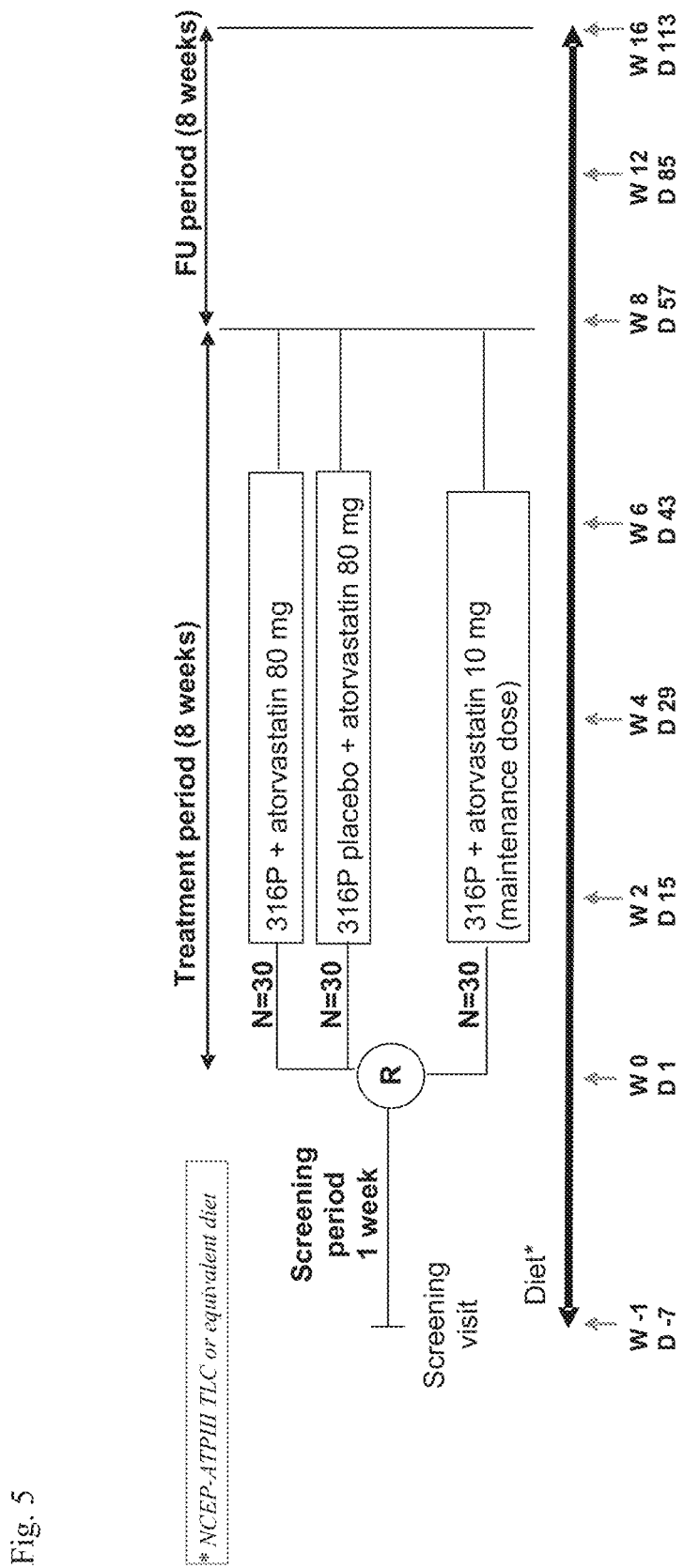
FIG. 5 shows the study design of study 2 for the group of patients receiving atorvastatin 10 mg at stable dose for at least 6 weeks prior to screening.
Figure 6:
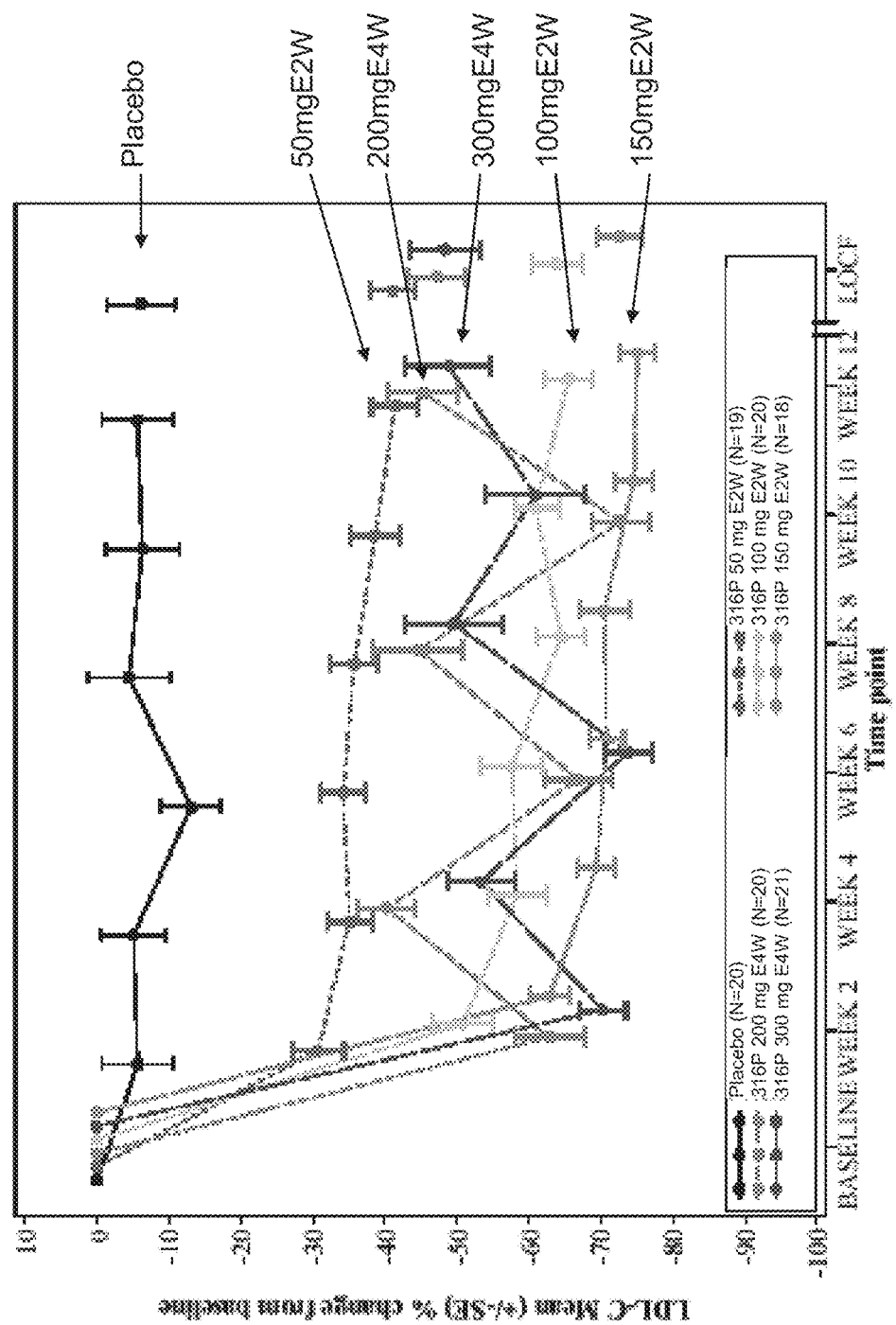
FIG. 6 shows the distribution of the LDL-C mean values of patients of study 1 receiving antibody 316 P at stable atorvastatin treatment over 12 weeks and LOCF (last observation carried forward). The study was designed to assess the efficacy and safety of antibody 316P in hypercholesteremia patients with an elevated LDL-C (≥100 mg/dL or 2.59 mmol/L) treated with stable dose of atorvastatin (10 mg, 20 mg, or 40 mg). During the run-in period, patients were stabilized to atorvastatin treatment (10 mg, 20 mg, or 40 mg) if the were not already. After one additional week, patients were centrally randomized via IVRS/IWRS in a 1:1:1:1:1:1 ratio to one of the 6 treatment groups (placebo, 316P 50 mg E2W, 316P 100 mg E2W, 316P 150 mg E2W, 316P 200 mg E4W, 316P 300 mg E4W) and treated in a double-bind manner for approximately 12 weeks. Thr randomization is stratified by the dose of atorvastatin received prior to randomization. During the double-bind treatment period patients returned to the site every 2 weeks to receive the study treatment (316 P or placebo). The double-bind treatment period was then followed ba an 8-week follow up period. As can be gained from FIG. 6, all treatment groups except for the group of patients receiving placebo had a significant and persistent reduction of LDL-C levels over the whole study period.

Duration of Study Period Per Subject:

The duration of study participation will depend on the status of the patient at screening:

For patients receiving atorvastatin 10 mg at stable dose for at least 6 weeks prior to screening, the study participation will be approximately 17 weeks including a screening period of 1 week, a double-blind treatment period of 8 weeks and a follow-up period of 8 weeks (see FIG. 5).

Figure 4:
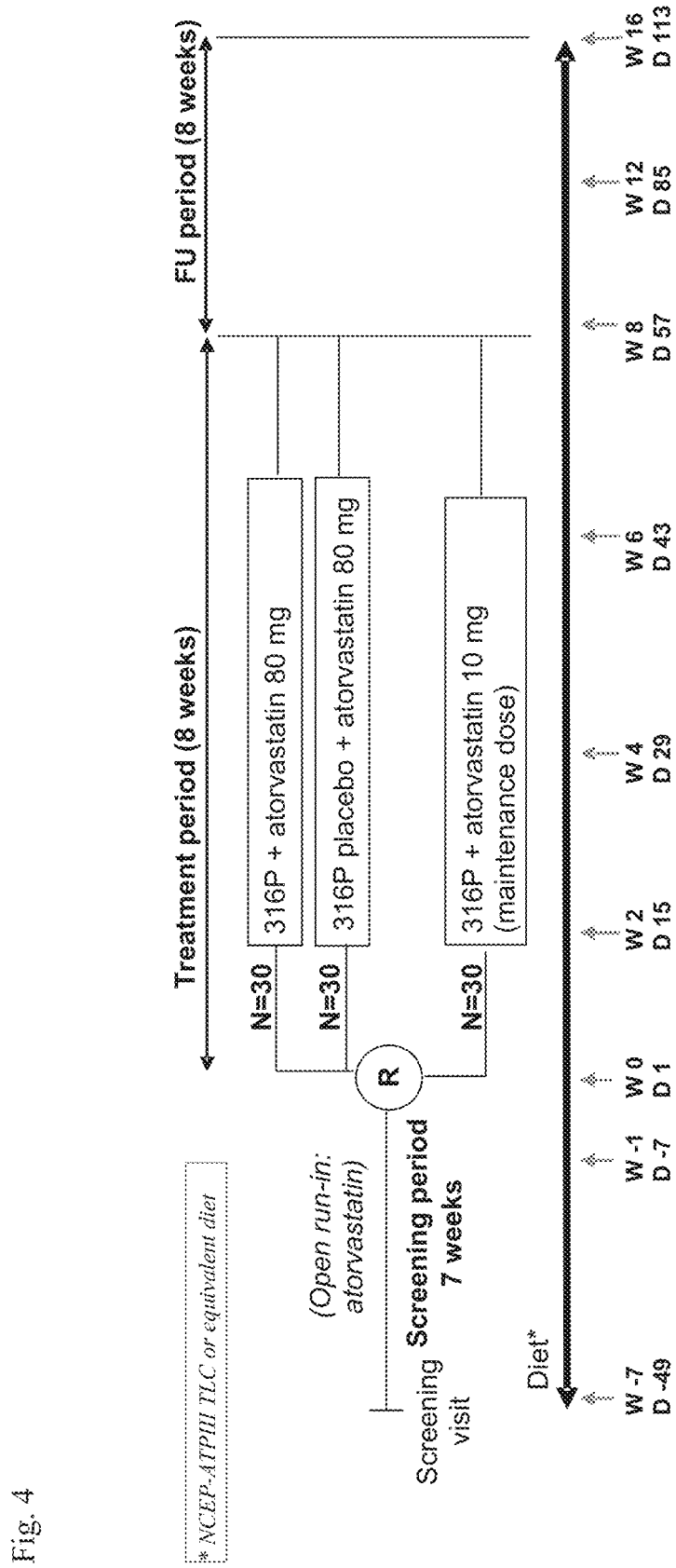
FIG. 4 shows the study design of study 2 for the group of patients receiving a lipid lowering treatment other than atorvastatin or not at stable dose of atorvastatin 10 mg for at least 6 weeks prior to screening, or drug naive patients.

For patients receiving a lipid lowering treatment other than atorvastatin/or not at stable dose of atorvastatin 10 mg for at least 6 weeks prior to screening, or drug naive patients the study participation will be approximately 23 weeks with a screening period of 7 weeks (including a run-in period of 6 weeks), a double-blind treatment period of 8 weeks and a follow-up period of 8 weeks (see FIG. 4).

Active Compounds:

Antibody 316P

Antibody 316P is a fully human antibody comprising a HCVR as shown in SEQ ID NO: 90 and LCVR as shown in SEQ ID NO: 92 of the sequence listing. The CDR sequences are shown in SEQ ID NOs: 76, 78, and 80 (CDR1, CDR2, CDR3 of the heavy chain) as well as in SEQ ID NOs: 84, 86, and 88 (CDR1, CDR2, CDR3 of the light chain).

Antibody 300N

Antibody 300N is a fully human antibody comprising a HCVR as shown in SEQ ID NO: 218 and LCVR as shown in SEQ ID NO: 226 of the sequence listing. The CDR sequences are shown in SEQ ID NOs: 220, 222, and 224 (CDR1, CDR2, CDR3 of the heavy chain) as well as in SEQ ID NOs: 228, 230, and 232 (CDR1, CDR2, CDR3 of the light chain).

Study Arms:

Arm 1: The first group of patients receives one subcutaneous injection of 1 mL of antibody 316P, administered in the abdomen every two weeks, with a dose regimen at 150 mg, for a double-blind treatment period of 8 weeks;

Atorvastatin is administered once per day at a stable dose of 10 mg as background therapy.

Atorvastatin is administered at a dose of 80 mg once during the double-blind treatment period of 8 weeks.

Arm 2: The second group of patients receives one subcutaneous injection of 1 mL of a placebo solution, administered in the abdomen every two weeks, with a dose regimen at 150 mg, for a double-blind treatment period of 8 weeks;

Atorvastatin is administered once per day at a stable dose of 10 mg as background therapy.

Atorvastatin is administered at a dose of 80 mg (2 over-encapsulated atorvastatin 40 mg tablets) once during the double-blind treatment period of 8 weeks.

Arm 3: The third group of patients receives one subcutaneous injection of 1 mL of antibody 316P, administered in the abdomen every two weeks, with a dose regimen at 150 mg, for a double-blind treatment period of 8 weeks;

Atorvastatin is administered once per day at a stable dose of 10 mg as background therapy.

Atorvastatin is administered at a dose of 10 mg (1 over-encapsulated atorvastatin 10 mg tablet+1 matching placebo tablet) once during the double-blind treatment period of 8 weeks.

Primary and Key Secondary Endpoints

Primary Endpoints

The primary efficacy variable is the percent change in calculated LDL-C from baseline to Week 8, which is defined as: 100×(calculated LDL-C value at Week 8-calculated LDL-C value at baseline)/calculated LDL-C value at baseline.

In case of unavailable calculated LDL-C value at Week 8 as defined above, then the last calculated LDL-C value measured during the efficacy period and before the Week 8 time window was used to impute the missing Week 8 calculated LDL-C value (Last Observation Carried Forward [LOCF] procedure).

Key Secondary Endpoints

The secondary efficacy variables are:

The absolute change (mmol/L and mg/dL) from baseline in calculated LDL-C to Week 8, defined as: (calculated LDL-C value at Week 8-calculated LDL-C value at baseline)

The percentage of patients with calculated LDL-C<70 mg/dL (1.81 mmol/L) and <100 mg/dL (2.59 mmol/L) at Week 8

Percent change in ApoB from baseline to Week 8

Percent and absolute (mmol/L and mg/dL) change in non HDL-C from baseline to Week8

Percent and absolute (mmol/L and mg/dL) change in total cholesterol from baseline to Week 8

Percent and absolute (mmol/L and mg/dL) change in HDL-C from baseline to Week 8

Percent and absolute (mmol/L and mg/dL) change in fasting Triglycerides from baseline to Week 8

Percent change in ApoA-1 from baseline to Week 8

Absolute change in the ratio ApoB/ApoA-1 from baseline to Week 8

Percent change in Lp(a) from baseline to Week 8.

Sample Size Calculation Assumptions

The study was expected to enroll approximately 90 patients.

To detect a difference of 20% in LDL-C percent change from baseline to Week 8 between 316P 150 mg+atorvastatin 80 mg group and Placebo for 316P+atorvastatin 80 mg group, assuming a 5% rate of unevaluable primary endpoint, 30 patients by arm were estimated to result in 95% power, with a standard deviation of 20%, and using a two-sided t-test at the 0.05 significance level.

Calculations were made using nQuery Advisor 6.01.

Statistical Methods

Analysis Populations

Efficacy Populations

The primary efficacy analysis population is the modified intent-to-treat (mITT) population.

Modified Intent-to-Treat Population

Modified ITT (mITT) population: randomized population with an evaluable primary endpoint.

The primary endpoint was evaluable when both of the following conditions are met:

Availability of at least one calculated LDL-C value from the Visit 1 (Week-1) and up to before first IP injection.

Availability of at least one calculated LDL-C value during the efficacy period and, within or before the Week 8 time window.

Patients in the mITT population were analyzed according to the treatment group allocated by randomization.

Per-Protocol Population

Per-protocol (PP) population is a subset of the mITT population, excluding patients:

with important protocol deviations impacting LDL-C baseline or LDL-C assessment at Week 8, receiving prohibited therapy potentially impacting lipids levels during the pre-treatment period or during the efficacy period before the primary endpoint assessment with a poor compliance to 316P IP administrations.

with a poor compliance to atorvastatin non IP during the pre-treatment period or with non compliance to atorvastatin IP during the 3 days preceding primary endpoint assessment.

Safety Population

Safety population is defined as the randomized population who did actually receive at least one dose or partial dose of 316P IP analyzed according to the treatment actually received. Patients treated without being randomized would not be considered as randomized and would not be included in any populations. The safety experience of patients treated and not randomized would be reported separately.

Primary Efficacy Analysis

The percent change from baseline in calculated LDL-C at Week 8-LOCF as defined above was analyzed in the mITT population using an analysis of covariance (ANCOVA) model with treatment group as fixed effect and the baseline LDL-C as covariate. The treatment group factor had three levels: placebo+atorvastatin 80 mg, 316P 150 mg E2W+atorvastatin 10 mg and 316P 150 mg E2W+atorvastatin 80 mg.

Throughout the ANCOVA model, the 316P 150 mg E2W+atorvastatin 80 mg group was compared to the placebo+atorvastatin 80 mg group using appropriate contrast and the 95% confidence interval (CI) of the difference was provided.

No formal comparison with the 316P 150 mg E2W+atorvastatin 10 mg group was performed: only 95% CIs for difference versus the other arms was provided.

Key Secondary Efficacy Analysis

Continuous secondary efficacy variables were analyzed in the mITT population using the same ANCOVA model as for the primary endpoint. For triglycerides and LP(a) known to have non Gaussian distribution, the rank-based ANCOVA method was used.

Binary secondary efficacy variables were analyzed in the mITT population using an exact conditional logistic regression model with treatment group and baseline LDL-C level as effects.

Safety Analysis

The safety analysis was based on reported adverse events (AEs) (if any) and other safety information, such as clinical laboratory data, vital signs, and ECG.

The TEAE period was defined as the time from first IP injection to last IP injection +70 days (10 weeks).

AEs of interest included the following terms:

Possible injection site reaction (HLT "Injection site reactions")

Possible allergic events (HLGT "Allergic conditions")

Patients with LDL-C<25 mg/dL (if any) or LDL-C<15 mg/dL (if any).

Other Assessments Analysis

Other assessment endpoints defined below are exploratory variables. They include metabolic and inflammatory parameters:

Absolute change in HbA1c (%) from baseline to Week 8
Absolute change from baseline in fasting plasma glucose (mmol/L) to Week 8
Percent change from baseline in hs-CRP to Week 8.

Those endpoints were summarized in the m-ITT population by time points using descriptive statistics. The time profile (including LOCF value) of each parameter was also plotted by treatment group with the corresponding standard errors.

PCSA criterion for hs-CRP was also summarized by treatment group using descriptive statistics.

Results

Study 2 was a multicenter, randomized, double-blind, parallel-group, placebo-controlled, 8-week study conducted in the United States to assess the efficacy and safety of 316P in patients with an elevated low-density lipoprotein cholesterol (LDL-C) (≥100 mg/dL or 2.59 mmol/L), treated with a stable dose of atorvastatin 10 mg for at least 6 weeks. After the 8-week double-blind period patients were followed during an 8-week follow-up period.

The primary objective of the study was to evaluate the effect of 316P on LDL-C levels compared with placebo when co-administered with 80 mg of atorvastatin after 8 weeks of treatment in patients with LDL-C≥100 mg/dL (≥2.59 mmol/L) previously on atorvastatin 10 mg. Evaluation of the efficacy of the co-administration of 316P with this high dose of atorvastatin (80 mg) compared with that of the co-administration of 316P with atorvastatin 10 mg was one of the secondary objectives. The dose regimen of 150 mg every 2 weeks (E2W) in comparison with placebo was evaluated.

Efficacy analyses were performed on 88 patients (29 in the placebo+atorvastatin 80 mg group, 29 in the 316P 150 mg+atorvastatin 10 mg group, and 30 in the 316P 150 mg+atorvastatin 80 mg group).

Demographics and baseline characteristics were similar across the treatment groups. The median age of patients was 58.0 years (25.0% of patients were >65 years of age). The mean baseline LDL-C and Total-C ranged between 3.101 mmol/L and 3.288 mmol/L, and between 5.447 mmol/L and 5.200 mmol/L, respectively.

Efficacy:

A statistically significant decrease in percent change from baseline in LDL-C at 8 weeks was observed in the 316P 150 mg+atorvastatin 80 mg group compared with the placebo+atorvastatin 80 mg group (LS mean difference of −55.8%; p<0.0001). Because of the non-gaussian distribution and non homogeneity of variance of the primary efficacy endpoint, a sensitivity analysis was also performed using rank-based analysis of covariance which showed similar results: effect size estimate of 316P 150 mg+atorvastatin 80 mg vs placebo+atorvastatin 80 mg of −54.5%, p<0.0001. Large decreases from baseline were seen in both treatments groups where 316P 150 mg was co-administered with atorvastatin, with a median reduction of −70.4% for the 316P 150 mg+atorvastatin 10 mg group, and of −70.6% for the 316P 150 mg+atorvastatin 80 mg group compared with a median reduction of −26.9% in the placebo+atorvastatin 80 mg group.

Consistent results were seen for Total-C, ApoB, non HDL-C and Apo-B/ApoA-1 ratio. For HDL-C, an increase in the percent change from baseline was observed in both treatment groups where 316P 150 mg was co-administered with atorvastatin 10 mg or 80 mg (LS mean+2.6%, and +5.8%, respectively) compared with a decrease in the placebo+atorvastatin 80 mg group (LS mean−3.6%).

Safety:

316P was well tolerated during the 8 weeks of treatment in all treatment groups. Significantly, no change in troponin levels was noted in all treatment groups.

Conclusion:

There was a statistically significant decrease in percent change from baseline in LDL-C at 8 weeks in the 316P 150 mg+atorvastatin 80 mg group as compared with the placebo+atorvastatin 80 mg group (LS mean difference of −55.8%; p<0.0001). A similar magnitude of effect observed with 316P was noted regardless of the dose of atorvastatin (10 mg or 80 mg) with a substantial decrease in LDL-C when co-administered to these 2 atorvastatin doses.

Consistent results were seen for Total-C, ApoB, non HDL-C and Apo-B/ApoA-1 ratio. For HDLC, there was a trend of increase in both treatment groups where 316P 150 mg was co-administered with atorvastatin 10 mg or 80 mg.

316P 150 mg E2W was well tolerated during the 8 weeks of treatment in all treatment groups. No particular safety signal was noted.

Efficacy of 316P 150 mg E2W as well its good safety profile were confirmed in this study regardless of the dose of atorvastatin administered (10 mg or 80 mg).

Study 3

This is a randomized, double-blind, placebo-controlled, multiple ascending dose, multicenter clinical trial in subjects with primary hypercholesterolemia.

Figure 2:
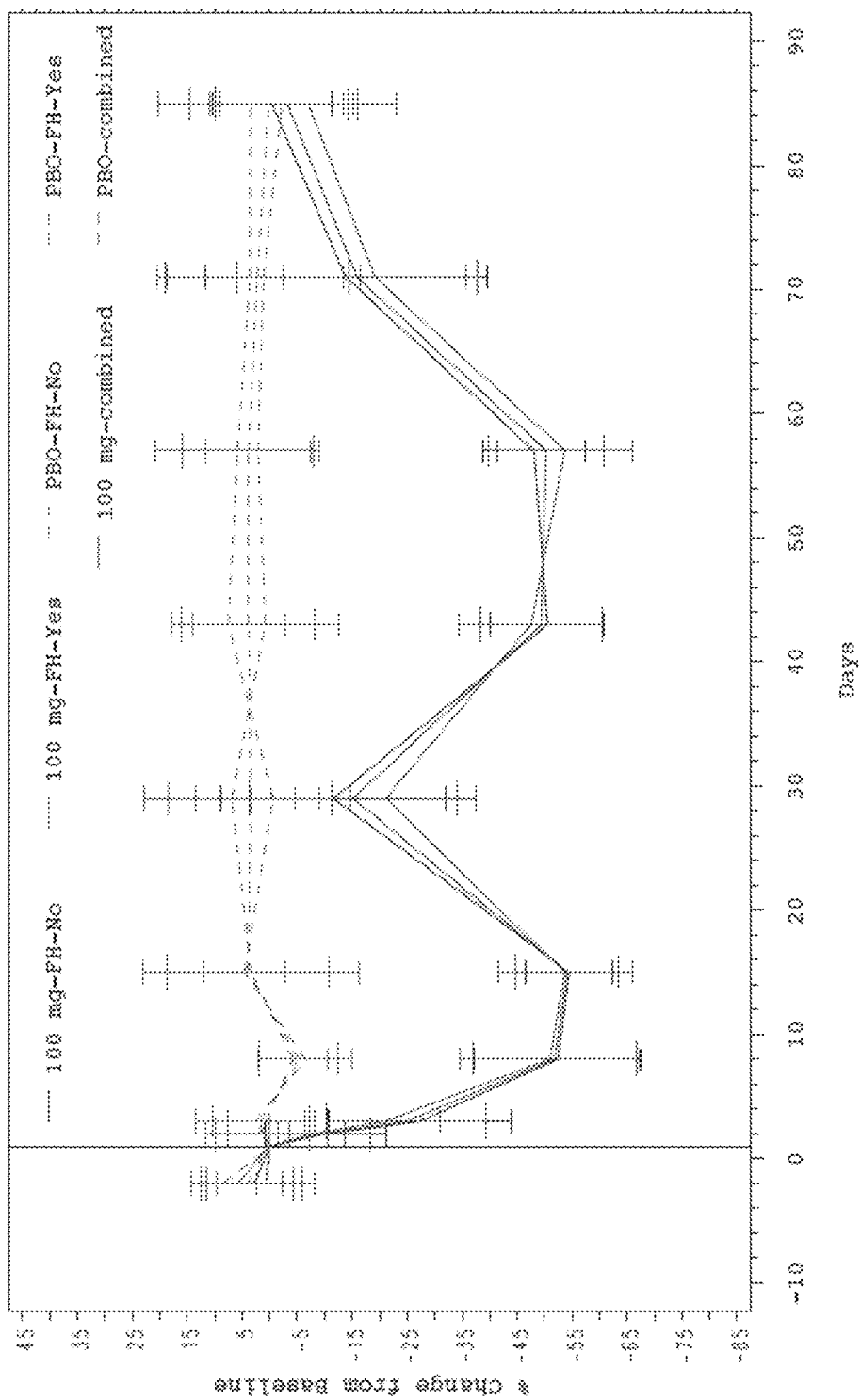
FIG. 2 shows the percentage reduction in LDL-cholesterol (LDL-C) levels relative to the baseline for three groups of patients upon treatment with anti-PCSK9 antibody 316P. These patient groups are: (1) patients with familial hypercholesterolemia (HeFH); (2) patients with other forms of primary hypercholesterolemia (non-FH) on diet and on stable atorvastatin therapy; and (3) patients with other forms of primary hypercholesterolemia (non-FH) on diet alone. A dose of 100 mg of the anti-PCSK9 antibody was administered subcutaneously on days 1, 29 and 43. Results from patient groups receiving the antibody (100-mg-FH-no; 100-mg-FH-Yes; 100-mg-combined) are shown in solid lines, while results from patients receiving a placebo (PBO-FH-no; PBO-FH-Yes; PBO-combined) are shown in dashed lines.
Figure 3:
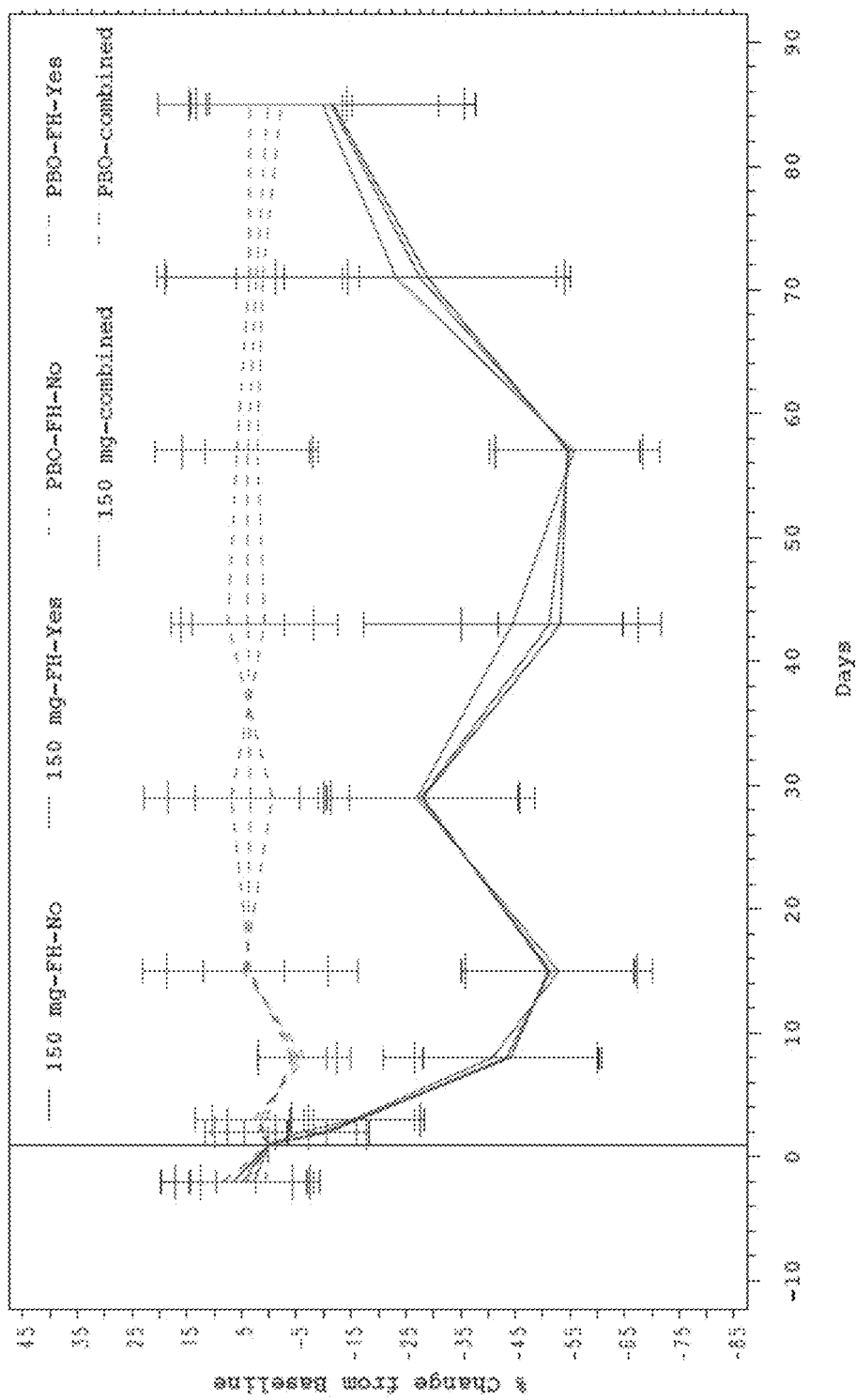
FIG. 3 shows the percentage reduction in LDL-cholesterol (LDL-C) levels relative to the baseline for three groups of patients upon treatment with anti-PCSK9 antibody 316P. These patient groups are: (1) patients with familial hypercholesterolemia (HeFH); (2) patients with other forms of primary hypercholesterolemia (non-FH) on diet and on stable atorvastatin therapy; and (3) patients with other forms of primary hypercholesterolemia (non-FH) on diet alone. A dose of 150 mg of the anti-PCSK9 antibody was administered subcutaneously on days 1, 29 and 43. Results from patient groups receiving the antibody (150-mg-FH-no; 150-mg-FH-Yes; 150-mg-combined) are shown in solid lines, while results from patients receiving a placebo (PBO-FH-no; PBO-FH-Yes; PBO-combined) are shown in dashed lines.

The objective of this study was to determine whether a fully human monoclonal antibody to PCSK9 (316P) is effective and safe as either a primary or adjunctive agent to lower LDL-C in patients with Heterozygous Familial Hypercholesterolemia (HeFH) or other forms of primary hypercholesteremia (nonFH). 61 adults with either documented HeFH (n=21) or nonFH (n=30), on diet plus stable atorvastatin therapy (atorvaRx) or nonFH (n=10) on diet alone enrolled in this clinical trial. Subjects on stable atorvastatin therapy had LDL-C≥2.6 mmol/L and those on diet alone had LDL-C≥3.4 mmol/L. 316P at doses of 50, 100 and 150 mg was administered subcutaneously (sc) at 1, 29 and 43 days. The primary endpoint was the incidence and severity of treatment emergent adverse events (TEAE). The primary efficacy endpoint was percent and absolute change in serum LDL-C from baseline to each visit. Additional endpoints included apolipoprotein (apo) B, total cholesterol, HDL-C, VLDL-C, and the ratio of apoB to apoA1. 109 patients were screened, and 61 patients were randomized (14 placebo, 47 316P) with 100% completing 148+/−7 days of treatment and follow up. Compared to the nonFH cohort, the FH group was younger (mean 40 vs. 52 yrs), had more males (81% vs. 57%) and was on higher doses of atorvastatin (52% on 40 mg vs. 3%). Baseline LDL-C was 3.45, 2.88 and 4.46 mmol/L in the FH, nonFH atorvaRx and nonFH diet only groups, respectively. Treatment with 316P resulted in mean % reductions in LDL-C on top of statins on day 57 of 35.6%, 50.2% and 57.5% at the 50, 100 and 150 mg doses, respectively, in the combined FH and nonFH populations. Although no statistical analysis was performed, there did not appear to be differences in response between FH and nonFH or those on or not on statin therapy. Response to 316P is shown in FIGS. 1, 2 and 3. Favourable changes were observed in HDL-C and apoA1. No serious adverse events were seen and treatment was generally well-tolerated. No drug-related adverse effects were seen on liver function testing or other laboratory parameters.

This first multiple-dose, proof-of-concept trial of a PCSK9 inhibitor, in FH and nonFH on stable statin therapy, shows that treatment with an anti-PCSK9 antibody, such as 316P, is a promising therapeutic option for patients with or without HeFH with elevated cholesterol on statin therapy.

Study 4

This is an animal study on the cholesterol lowering effect of 316P, a fully human PCSK9 blocking monoclonal antibody in male Syrian hamster Introduction The hepatic LDL receptor (LDLR) is the key component for cholesterol homeostasis. PCSK9 regulates hepatic LDLR levels by enhancing its degradation. The transcription of both the LDLR and PCSK9 is up-regulated by statins through SREBP-2, thereby limiting the extent that statins can lower LDL-cholesterol (LDL-C) in humans and even more in rodents where statins are not effective in reducing LDL-C.

Objective

The aim of this study was to investigate the effect of 316P, a human monoclonal antibody to human PCSK9, alone and in combination with statins on expression of the hepatic LDLR and the resulting effects on serum LDL-C.

Results

In hamster, a single s.c. injection of 316P (1/3/10 mg/kg) resulted in a dose-dependent decrease in LDL-C lasting more than 2 weeks. The maximal effect on LDL-C (−17/−27/−60%) was seen within 7 days. PK data of 316P are in line with the dose-dependent effect on LDL-C. Atorvastatin treatment up to the maximal tolerated dose has no effect on hepatic LDLR expression and did not decrease LDL-C. 316P on top of Atorvastatin could overcome the statin resistance increased LDLR expression and decreased serum LDL-C. The combination treatment was more effective than single treatment with 316P alone, although Atorvastatin alone has no effect.

Conclusion

PCSK9 inhibition resulted in dose-related LDL-C-lowering in hamsters. However, when administered in combination with a normally ineffective dose of Atorvastatin, a potentiated reduction in LDL-C was observed. These data suggest that neutralizing PCSK9 is effective in overcoming the statin-resistance observed in the hamster model. This data are in accordance with results in a human phase I study, where LDL-C reduction exceeded 60% and lasted for 30 days following a single i.v. administration. This confirmed that the hamster is a suitable model to investigate drugs targeting PCSK9.

Study 5

This is a randomized, double-blind, placebo-controlled, unbalanced (2:1, 316P:placebo), parallel-group study with an open-label extension.

Objective(s)

The primary objective of this study is to evaluate the long-term safety and tolerability of 316P over the main treatment period in hypercholesterolemic patients at risk of cardiovascular disease not adequately controlled with their lipid lowering treatment.

Secondary objectives are

To evaluate the long-term safety and tolerability of 316P over the whole study duration.

To evaluate the effect of 316P on low-density lipoprotein cholesterol (LDL-C) levels after 12 weeks of treatment in comparison with placebo.

To evaluate the long-term efficacy of 316P on low density lipoprotein cholesterol (LDL-C) levels.

To evaluate the effect of 316P on Total-Cholesterol (TC), non-high density lipoprotein cholesterol (non-HDL-C), Apolipoprotein B (ApoB), HDL-C, Triglycerides (TG), Apolipoprotein A-1 (ApoA-1), ratio ApoB/ApoA-1, and Lipoprotein a (Lp (a)) after 12 weeks of treatment in comparison with placebo and after long term treatment To evaluate the development of anti-316P antibodies.

To evaluate the pharmacokinetics (PK) of 316P.

To explore the effect of 316P on adjudicated cardiovascular events over the main treatment period in comparison with placebo and over the whole study duration.

Study Design

Patients will be stratified according to heterozygous familial hypercholesterolemia (heFH) population, prior history of myocardial infarction (MI) or stroke, high-intensity statin therapy (ie, atorvastatin 40 to 80 mg daily or rosuvastatin 20 to 40 mg daily) and geographic region. Patients randomized to 316P will receive 150 mg subcutaneous (sc) every 2 weeks. This dose/dose regimen, assessed in the Phase 1 program, is also one of the doses/dose regimens being evaluated in the Phase 2 program. For the present study, the administration of 150 mg subcutaneous every 2 weeks has been selected as the dose/dose regimen providing the highest systemic exposure to 316P in the range of doses/regimens likely to be effective. This dose and regimen may be adjusted, if needed, to a different dose/dosing frequency during the course of the study, through a protocol amendment, when the full data set of dose/regimen finding data become available.

The study consists of:

A screening period of up to 2 weeks, including an intermediate visit during which the patient or another designated person (such as spouse, relative, etc. . . . ) will be trained to selfinject/inject with placebo.

A double-blind period of 18 months study treatment with 316P or placebo for all patients.

The main treatment period is defined for the purpose of the primary analysis and this period ends 12 months after the last patient in (LPI) is randomized, and includes patients with variable duration of double blind treatment between 12 months and 18 months.

An open-label period (OLP) which consists of study treatment with 316P in patients who have completed the 18-month double-blind period. The OLP will be of variable duration and ends for all patients at 24 months after the LPI or at 39 months after the FPI, whichever comes first.

A follow-up period (off-treatment) of 8 weeks after the end of the open-label period.

Patients will be instructed to be on a stable diet (NCEP-ATPIII TLC diet or equivalent) throughout the entire study duration from screening. Statin dose as well as dose of other lipid-lowering treatment(s) (if applicable) should be stable throughout the whole study duration. During the double-blind period, modification is allowed under certain conditions. During the open-label period, modification is based upon investigator's judgment. Fibrates other than fenofibrate are not allowed during the study. The lipid parameters will be blinded during the double-blind period.

Study Population:

Inclusion Criteria

Either A or B below AND not adequately controlled with a maximally tolerated stable dose of statin for at least 6 weeks prior to the screening visit (Week-2) with or without other lipid lowering therapy (LLT).

A) Patients with heterozygous familial hypercholesterolemia (heFH)
OR
B) Patients with non-familial hypercholesterolemia (non-FH) with established coronary heart disease (CHD) or CHD risk equivalents Note:
All background LLT, including therapy other than statins, should be at a stable dose for at least 6 weeks prior to the screening visit (week-2).
The only statins which are permissible at study inclusion are simvastatin, atorvastatin, and rosuvastatin taken daily.
Patients are eligible for the study if they are on maximally tolerated statin even if this is not high-intensity statin. Maximally tolerated statin is defined as any daily dose of simvastatin, atorvastatin, and rosuvastatin that is maximally tolerated. High-intensity statin is defined as atorvastatin 40 to 80 mg daily or rosuvastatin 20 to 40 mg daily.
If patient is not on high-intensity statin during screening, then the reason needs to be documented (ie, myalgias, liver enzyme abnormalities, etc.).
If Screening (Week-2 visit) LDL-C is ≥160 mg/dL (4.14 mmol/L), patients should have been offered another LLT in the past in addition to their maximally tolerated statin. In addition, if patients are on maximally tolerated statin therapy only, then reason needs to be documented; such patients are still eligible for the study and are not excluded.
Daily doses above simvastatin 80 mg, atorvastatin 80 mg or rosuvastatin 40 mg are not allowed for study inclusion.
Simvastatin 80 mg should be used only in patients who have been taking this dose for 12 months or more without evidence of muscle injury (myopathy) and should not be started in new patients, including patients already taking lower doses of the drug.
Prescriptions of other LLT should be in accordance with the national product label.

Key Exclusion Criteria
LDL-C<70 mg/dL (<1.8 mmol/L) at the screening visit (Week-2).
TG>350 mg/dL (>3.95 mmol/L) at the screening visit (Week-2)
Use of fibrates other than fenofibrate within 6 weeks prior to screening visit (Week-2) or plan to receive it.

Total Expected Number of Patients:
Approximately 2100 randomized (1400:700, 316P:placebo)

Study Treatment(s)
Investigational Medicinal Product(s): Antibody 316P and Placebo for 316P Antibody 316P is a fully human antibody comprising a HCVR as shown in SEQ ID NO: 90 and LCVR as shown in SEQ ID NO: 92 of the sequence listing. The CDR sequences are shown in SEQ ID NOs: 76, 78, and 80 (CDR1, CDR2, CDR3 of the heavy chain) as well as in SEQ ID NOs: 84, 86, and 88 (CDR1, CDR2, CDR3 of the light chain).

Alternatively, the study can be carried out with antibody 300N (=back-up compound) instead of antibody 316P. Antibody 300N is a fully human antibody comprising a HCVR as shown in SEQ ID NO: 218 and LCVR as shown in SEQ ID NO: 226 of the sequence listing. The CDR sequences are shown in SEQ ID NOs: 220, 222, and 224 (CDR1, CDR2, CDR3 of the heavy chain) as well as in SEQ ID NOs: 228, 230, and 232 (CDR1, CDR2, CDR3 of the light chain).

Formulation
Prefilled syringes: 316P 150 mg/mL, or placebo for 316P.
Route(s) of Administration:
Subcutaneous (SC)
Injection volume: 1 mL in total for the dose of 150 mg
One injection of 1 mL subcutaneous over the abdomen, thigh, or outer area of upper arm (ie, deltoid region).
Dose regimen: Dose of 150 Mg every 2 weeks Primary and Secondary Endpoint(s)
Primary Endpoint:
Safety parameters (adverse events [including adjudicated cardiovascular events], laboratory data, vital signs, and ECG) assessed throughout the main treatment period.
Main Secondary Endpoints:
Safety parameters (adverse events [including adjudicated cardiovascular events], laboratory data, vital signs, and ECG) assessed throughout the whole study duration
The percent change in LDL-C from baseline to Week 12 (as main time point).
Anti-316P antibodies
Serum 316P concentrations Assessment Schedule
Patient's assessments in the screening period:
On-site visits: Week-2 (screening visit), Week-1 (Injection training visit).
Patient's assessments in the double-blind period:
On-site visits: Week 0 (randomization visit=baseline), Week 4, Week 8, Week 12, Week 16, Week 24, Week 36, Week 52/Month 12, Week 64/Month 15, Week 78/Month 18 (end of double blind period).
Phone calls: Week 2*, Week 20, Week 28, Week 32, Week 40, Week 44, Week 48, Week 56, Week 60, Week 68, Week 72 and Week 76.
*Note: Week 2 could become an on-site visit for further injection training with the patient's scheduled injection from the double-blind study treatment kit allocated by IVRS, as needed.
Patient's assessments in the open-label period:
On-site visits: Every 12 weeks after the end of the double-blind period visit and until the end of open label period visit.
Phone calls: Every 4 weeks between on-site visits.
Note: During the course of the study, through the ongoing safety reviews, the Data Monitoring Committee (DMC) will assess the adequacy of the visit frequency and corresponding procedures for the open-label period and make appropriate recommendations.
Patient's assessments in the follow-up period:
On-site visit: 8 weeks after the end of open label period visit.

Statistical Considerations
For safety assessment, a sample size of 2100 patients (randomization ratio 2:1, ie, 316P: 1400 and placebo: 700) will allow to have long term safety data in a broad database. With this sample size, 1050 and 364 patients are expected to be exposed to 316P for a minimum of 12 months and 18 months, respectively, at the time of the primary analysis (12 months after the last patient in). Moreover, with 1400 patients treated with 316P, adverse events with a rate ≥0.002 will be detected with 95% confidence.

The stratification factors include heFH population, prior history of MI or stroke, high-intensity statin and region (North America, Western Europe, Eastern Europe, Rest of World).

Summary of safety variables will be performed based on the safety population. The safety population consists of the randomized population who did actually receive at least one dose or partial dose of Investigational Medicinal Product (IMP) analyzed according to the treatment actually received.

Descriptive statistics will be used for the summary of safety variables from this study. For adverse events, in addition to summary tables presented with crude rates, the table of all TEAEs will be provided using patient-year adjusted incidence rates. If any clinically significant signal is detected and need further characterization or for adverse event or Potentially Clinically Significant Abnormality (PCSA) of interest, a time-to-event analysis will be performed using Kaplan-Meier methodology. Moreover, the frequency of adverse event or PCSA of interest over time will be provided. The primary safety analysis will be done on the safety events that can be attributed to the administration of double blind treatment during the main treatment period. Secondary safety analyses will be conducted on the safety events observed during the double-blind period and the open-label period.

The efficacy analysis population will be the modified intent to-treat (mITT) population, defined as the ITT population (i.e., randomized population) with an evaluable LDL-C endpoint. This endpoint will be considered as evaluable when both of the following conditions are met:

The baseline LDL-C value is available.

At least one LDL-C value collected in the main efficacy period is available.

The main efficacy period will be defined as:

The time from the first IMP injection (excluding training injection) up to 21 days after the last IMP injection for patients who permanently discontinue the IMP before Week 12.

The time from the first IMP injection (excluding training injection) up to Week 12 for patients who were treated at least 12 weeks.

Patients in the mITT population will be analyzed according to the treatment group allocated by randomization.

The percent change in LDL-C from baseline to Week 12 (main secondary endpoint) and at other time points throughout the study (other secondary endpoints) will be analyzed using an analysis of covariance (ANCOVA) model with treatment group and each stratification factor (heFH population, prior history of MI or stroke, high-intensity statin, region) as fixed effect and the baseline LDL C as covariate. The treatment group factor will have 2 levels: placebo and 316P. Throughout the ANCOVA model, the 316P group will be compared to placebo using appropriate contrast, and the 95% CI of the difference will be provided.

In case of missing Week 12 LDL-C on treatment value, the last-observation-carried-forward (LOCF) principle will be used.

Duration of Study Period (Per Patient)

The study duration for each patient is variable. The maximum study duration includes up to 2 weeks of screening period, 18 months study treatment during double blind period, up to 21 months of 316P treatment in the open label period (depending on when patient randomized into study and duration of recruitment) and 8 weeks of follow up period. Thus, the maximum study duration is up to ~42 months for the first patient randomized into the study and up to ~27 months for the last patient randomized into the study.

Study 6

A randomized, double-blind, multi-dose, placebo controlled, 75-patient trial in patients with heterozygous familial hypercholesterolemia (heFH). In this trial, patients must meet the World Health Organization criteria for heFH, be on a stable daly statin regimen for at least 6-weeks before entering the trial, and have serum LDL-C levels ≥100 mg/dL. Patients were permitted to be taking ezetimibe in addition to a daily statin. The primary endpoint of the study is the change in LDL cholesterol from baseline compared to placebo over the 12-week study period.

An interim analysis of study 6 in heterozygous familial hypercholesterolemia patients with elevated cholesterol (LDL-C≥100 mg/dL) on stable doses of statins with or without ezetimibe demonstrated that patients treated with 316P every two or four weeks achieved significantly greater mean LDL-C reductions at 12-weeks compared to patients treated with placebo. Patients treated with different doses of 316P achieved mean LDL-C reductions of approximately 30% to greater than 60% from baseline at 12-weeks compared to a 10% reduction with placebo (p<0.01), which was the primary endpoint of the study. The interim analysis was conducted when all patients completed the primary endpoint at 12-weeks.

The invention claimed is:

1. A unit dosage form of a pharmaceutical composition for single administration comprising a fixed dose of, 75 mg, 150 mg, or 300 mg of an antibody or an antigen-binding fragment thereof which specifically binds human proprotein convertase subtilisin/kexin type 9 (hPCSK9) together with a pharmaceutically acceptable excipient or carrier in a hermetically sealed container, wherein the antibody or antigen-binding fragment thereof comprises the three heavy chain CDRs set forth in SEQ ID NOs: 76, 78, and 80 and the three light chain CDRs set forth in SEQ ID NOs: 84, 86, and 88.

2. The unit dosage form of claim 1, wherein the antibody or antigen-binding fragment thereof comprises the heavy chain variable region (HCVR) amino acid sequence and the light chain variable region (LCVR) amino acid sequence set forth in SEQ ID NOs: 90 and 92, respectively.

3. The unit dosage form of claim 1, comprising fixed dose of 75 mg of the antibody or antigen-binding fragment thereof.

4. The unit dosage form of claim 1, comprising a fixed dose of 150 mg of the antibody or antigen-binding fragment thereof.

5. The unit dosage form of claim 1, comprising a fixed dose of 300 mg of the antibody or antigen-binding fragment thereof.

6. The unit dosage form of claim 1 comprising a fixed dose of 75 mg, 150 mg, or 300 mg of the antibody or antigen-binding fragment thereof in a 1 ml injection solution.

7. The unit dosage form of claim 6, wherein the injection solution comprises a fixed dose of 75 mg of the antibody or antigen-binding fragment thereof.

8. The unit dosage form of claim 6, wherein the injection solution comprises a fixed dose of 150 mg of the antibody or antigen-binding fragment thereof.

9. The unit dosage form of claim 6, wherein the injection solution comprises a fixed dose of 300 mg of the antibody or antigen-binding fragment thereof.

10. The unit dosage form of claim 1, wherein the pharmaceutical composition is in a hermetically sealed container selected from the group consisting of a vial, a sachette, a pre-filled syringe, a pre-filled autoinjector, a cartridge for a reusable syringe, and an applicator.

11. The unit dosage form of claim 1, wherein the antibody or antigen-binding fragment thereof binds an epitope comprising one or more of amino acid residues at positions 153, 159, 238, and 343 of hPCSK9 (SEQ ID NO: 755).

12. The unit dosage form of claim 1, wherein the antibody or antigen-binding fragment thereof achieves one or more of the following when administered to a subject:
    (a) reduction of LDL-C of at least −60% to at least −75% relative to a predose level with a sustained reduction over at least a 14 day-period upon administering to a subject a dose of 150 mg every two weeks;
    (b) reduction of LDL-C of at least −50% to −75% relative to a predose level with a sustained reduction over at least a 28 day-period upon administering to a subject a dose of 300 mg every four weeks;
    (c) increase of serum HDL cholesterol levels of at least 2%, at least 2.5%, at least 3%, at least 3.5%, at least 4%, at least 4.5%, at least 5% or at least 5.5% relative to a predose level upon administering to a subject a dose of 150 mg every two weeks; and
    (d) reduction of one or more of: total-cholesterol levels, ApoB levels, non HDL-C levels, and ApoB/ApoA-1 ratio.

13. A unit dosage form of a pharmaceutical composition for single administration comprising a fixed dose of 75 mg of an antibody or an antigen-binding fragment thereof which specifically binds hPCSK9 together with a pharmaceutically acceptable excipient or carrier in a hermetically sealed container, wherein the antibody or antigen-binding fragment thereof comprises the heavy chain variable region (HCVR) amino acid sequence and the light chain variable region (LCVR) amino acid sequence set forth in SEQ ID NOs: 90 and 92, respectively, and wherein the antibody or antigen-binding fragment thereof is in a 1 ml injection solution.

14. A unit dosage form of a pharmaceutical composition for single administration comprising a fixed dose of 150 mg of an antibody or an antigen-binding fragment thereof which specifically binds hPCSK9 together with a pharmaceutically acceptable excipient or carrier in a hermetically sealed container, wherein the antibody or antigen-binding fragment thereof comprises the heavy chain variable region (HCVR) amino acid sequence and the light chain variable region (LCVR) amino acid sequence set forth in SEQ ID NOs: 90 and 92, respectively, and wherein the antibody or antigen-binding fragment thereof is in a 1 ml injection solution.

15. A unit dosage form of a pharmaceutical composition for a single administration comprising a fixed dose of 300 mg of an antibody or an antigen-binding fragment thereof which specifically binds hPCSK9 together with a pharmaceutically acceptable excipient or carrier in a hermetically sealed container, wherein the antibody or antigen-binding fragment thereof comprises the heavy chain variable region (HCVR) amino acid sequence and the light chain variable region (LCVR) amino acid sequence set forth in SEQ ID NOs: 90 and 92, respectively, and wherein the antibody or antigen-binding fragment thereof is in a 1 ml injection solution.

* * * * *

SEQUENCE LISTING

<160> NUMBER OF SEQ ID NOS: 758

<210> SEQ ID NO 1
<211> LENGTH: 351
<212> TYPE: DNA
<213> ORGANISM: Artificial Sequence
<220> FEATURE:
<223> OTHER INFORMATION: Synthetic

<400> SEQUENCE: 1

```
caggtccagc tggtgcagtc tggggggaggc ttggtacagc ctgggggtc cctgagactc      60 tcctgtgcag cctctggatt tactctaagt agttacgaca tgcactgggt ccgccaatct     120
acaggaaaag gtctggagtg ggtctcagct attggttcta ccggtgacac atactatcca     180
ggctccgtga agggccgatt caccatcacc agagaaaaag ccaagaactc cgtgtatctt     240
caaatgaaca gcctgagagc cggggacacg gctgtgtatt actgtgtaag agaggggtgg     300
gaggtaccct ttgactactg gggccaggga accctggtca ctgtctcctc a              351
```

<210> SEQ ID NO 2

<211> LENGTH: 117
<212> TYPE: PRT
<213> ORGANISM: Artificial Sequence
<220> FEATURE:
<223> OTHER INFORMATION: Synthetic

<400> SEQUENCE: 2

Gln Val Gln Leu Val Gln Ser Gly Gly Gly Leu Val Gln Pro Gly Gly
1               5                   10                  15

Ser Leu Arg Leu Ser Cys Ala Ala Ser Gly Phe Thr Leu Ser Ser Tyr
            20                  25                  30

Asp Met His Trp Val Arg Gln Ser Thr Gly Lys Gly Leu Glu Trp Val
        35                  40                  45

Ser Ala Ile Gly Ser Thr Gly Asp Thr Tyr Tyr Pro Gly Ser Val Lys
    50                  55                  60

Gly Arg Phe Thr Ile Thr Arg Glu Lys Ala Lys Asn Ser Val Tyr Leu
65                  70                  75                  80

Gln Met Asn Ser Leu Arg Ala Gly Asp Thr Ala Val Tyr Tyr Cys Val
                85                  90                  95

Arg Glu Gly Trp Glu Val Pro Phe Asp Tyr Trp Gly Gln Gly Thr Leu
            100                 105                 110

Val Thr Val Ser Ser
        115

<210> SEQ ID NO 3
<211> LENGTH: 24
<212> TYPE: DNA
<213> ORGANISM: Artificial Sequence
<220> FEATURE:
<223> OTHER INFORMATION: Synthetic

<400> SEQUENCE: 3
ggatttactc taagtagtta cgac                                          24

<210> SEQ ID NO 4
<211> LENGTH: 8
<212> TYPE: PRT
<213> ORGANISM: Artificial Sequence
<220> FEATURE:
<223> OTHER INFORMATION: Synthetic

<400> SEQUENCE: 4

Gly Phe Thr Leu Ser Ser Tyr Asp
1               5

<210> SEQ ID NO 5
<211> LENGTH: 21
<212> TYPE: DNA
<213> ORGANISM: Artificial Sequence
<220> FEATURE:
<223> OTHER INFORMATION: Synthetic

<400> SEQUENCE: 5
attggttcta ccggtgacac a                                             21

<210> SEQ ID NO 6
<211> LENGTH: 7
<212> TYPE: PRT
<213> ORGANISM: Artificial Sequence
<220> FEATURE:
<223> OTHER INFORMATION: Synthetic

<400> SEQUENCE: 6

```
Ile Gly Ser Thr Gly Asp Thr
 1               5
```

<210> SEQ ID NO 7
<211> LENGTH: 33
<212> TYPE: DNA
<213> ORGANISM: Artificial Sequence
<220> FEATURE:
<223> OTHER INFORMATION: Synthetic

<400> SEQUENCE: 7

```
gtaagagagg ggtgggaggt acccttgac tac                                    33
```

<210> SEQ ID NO 8
<211> LENGTH: 11
<212> TYPE: PRT
<213> ORGANISM: Artificial Sequence
<220> FEATURE:
<223> OTHER INFORMATION: Synthetic

<400> SEQUENCE: 8

```
Val Arg Glu Gly Trp Glu Val Pro Phe Asp Tyr
 1               5                  10
```

<210> SEQ ID NO 9
<211> LENGTH: 327
<212> TYPE: DNA
<213> ORGANISM: Artificial Sequence
<220> FEATURE:
<223> OTHER INFORMATION: Synthetic

<400> SEQUENCE: 9

```
gacatccaga tgacccagtc tccagccacc ctgtctgtgt ctccagggga aagagccgcc      60
ctctcctgca gggccagtca gagtgttagc agcaacttag cctggtacca ccagaaacct     120
ggccaggctc ccaggctcct catctatggt gcatccacca gggccactgg tatcccagcc     180
aggttcagtg gcattgggtc tgggacagag ttcactctca ttatcagcag cctgcagtct     240
gaagattttg catttattt ctgtcagcag tataataact ggcctccatt cactttcggc      300
cctgggacca aggtggagat caaacga                                         327
```

<210> SEQ ID NO 10
<211> LENGTH: 109
<212> TYPE: PRT
<213> ORGANISM: Artificial Sequence
<220> FEATURE:
<223> OTHER INFORMATION: Synthetic

<400> SEQUENCE: 10

```
Asp Ile Gln Met Thr Gln Ser Pro Ala Thr Leu Ser Val Ser Pro Gly
 1               5                  10                  15

Glu Arg Ala Ala Leu Ser Cys Arg Ala Ser Gln Ser Val Ser Ser Asn
                20                  25                  30

Leu Ala Trp Tyr His Gln Lys Pro Gly Gln Ala Pro Arg Leu Leu Ile
            35                  40                  45

Tyr Gly Ala Ser Thr Arg Ala Thr Gly Ile Pro Ala Arg Phe Ser Gly
        50                  55                  60

Ile Gly Ser Gly Thr Glu Phe Thr Leu Ile Ile Ser Ser Leu Gln Ser
65                  70                  75                  80

Glu Asp Phe Ala Phe Tyr Phe Cys Gln Gln Tyr Asn Asn Trp Pro Pro
                85                  90                  95

Phe Thr Phe Gly Pro Gly Thr Lys Val Glu Ile Lys Arg
```

<210> SEQ ID NO 11
<211> LENGTH: 18
<212> TYPE: DNA
<213> ORGANISM: Artificial Sequence
<220> FEATURE:
<223> OTHER INFORMATION: Synthetic

<400> SEQUENCE: 11
cagagtgtta gcagcaac                                                      18

<210> SEQ ID NO 12
<211> LENGTH: 6
<212> TYPE: PRT
<213> ORGANISM: Artificial Sequence
<220> FEATURE:
<223> OTHER INFORMATION: Synthetic

<400> SEQUENCE: 12

Gln Ser Val Ser Ser Asn
 1               5

<210> SEQ ID NO 13
<211> LENGTH: 9
<212> TYPE: DNA
<213> ORGANISM: Artificial Sequence
<220> FEATURE:
<223> OTHER INFORMATION: Synthetic

<400> SEQUENCE: 13 ggtgcatcc                                                                 9

<210> SEQ ID NO 14
<211> LENGTH: 3
<212> TYPE: PRT
<213> ORGANISM: Artificial Sequence
<220> FEATURE:
<223> OTHER INFORMATION: Synthetic

<400> SEQUENCE: 14

Gly Ala Ser
 1

<210> SEQ ID NO 15
<211> LENGTH: 30
<212> TYPE: DNA
<213> ORGANISM: Artificial Sequence
<220> FEATURE:
<223> OTHER INFORMATION: Synthetic

<400> SEQUENCE: 15
cagcagtata ataactggcc tccattcact                                          30

<210> SEQ ID NO 16
<211> LENGTH: 10
<212> TYPE: PRT
<213> ORGANISM: Artificial Sequence
<220> FEATURE:
<223> OTHER INFORMATION: Synthetic

<400> SEQUENCE: 16

Gln Gln Tyr Asn Asn Trp Pro Pro Phe Thr
 1               5                  10

<210> SEQ ID NO 17

<211> LENGTH: 351
<212> TYPE: DNA
<213> ORGANISM: Artificial Sequence
<220> FEATURE:
<223> OTHER INFORMATION: Synthetic

<400> SEQUENCE: 17

```
gaggtgcagc tggtggagtc tgggggaggc ttggtacagc ctggggggtc cctgagactc    60
tcctgtgcag cctctggatt tactctaagt agttacgaca tgcactgggt ccgccaatct   120
acaggaaaag gtctggagtg gtctcagct attggttcta ccggtgacac atactatcca   180
ggctccgtga agggccgatt caccatcacc agagaaaaag ccaagaactc cgtgtatctt   240
caaatgaaca gcctgagagc cggggacacg gctgtgtatt actgtgtaag agaggggtgg   300
gaggtaccct ttgactactg gggccaggga accctggtca ccgtctcctc a            351
```

<210> SEQ ID NO 18
<211> LENGTH: 117
<212> TYPE: PRT
<213> ORGANISM: Artificial Sequence
<220> FEATURE:
<223> OTHER INFORMATION: Synthetic

<400> SEQUENCE: 18

```
Glu Val Gln Leu Val Glu Ser Gly Gly Gly Leu Val Gln Pro Gly Gly
  1               5                  10                  15
Ser Leu Arg Leu Ser Cys Ala Ala Ser Gly Phe Thr Leu Ser Ser Tyr
             20                  25                  30
Asp Met His Trp Val Arg Gln Ser Thr Gly Lys Gly Leu Glu Trp Val
         35                  40                  45
Ser Ala Ile Gly Ser Thr Gly Asp Thr Tyr Tyr Pro Gly Ser Val Lys
     50                  55                  60
Gly Arg Phe Thr Ile Thr Arg Glu Lys Ala Lys Asn Ser Val Tyr Leu
 65                  70                  75                  80
Gln Met Asn Ser Leu Arg Ala Gly Asp Thr Ala Val Tyr Tyr Cys Val
                 85                  90                  95
Arg Glu Gly Trp Glu Val Pro Phe Asp Tyr Trp Gly Gln Gly Thr Leu
            100                 105                 110
Val Thr Val Ser Ser
        115
```

<210> SEQ ID NO 19
<211> LENGTH: 324
<212> TYPE: DNA
<213> ORGANISM: Artificial Sequence
<220> FEATURE:
<223> OTHER INFORMATION: Synthetic

<400> SEQUENCE: 19

```
gaaatagtga tgacgcagtc tccagccacc ctgtctgtgt ctccagggga aagagccgcc    60
ctctcctgca gggccagtca gagtgttagc agcaacttag cctggtacca ccagaaacct   120
ggccaggctc ccaggctcct catctatggt gcatccacca gggccactgg tatcccagcc   180
aggttcagtg gcattgggtc tgggacagag ttcactctca ttatcagcag cctgcagtct   240
gaagattttg cattttattt ctgtcagcag tataataact ggcctccatt cactttcggc   300
cctgggacca agtgggatat caaa                                          324
```

<210> SEQ ID NO 20
<211> LENGTH: 108

<212> TYPE: PRT
<213> ORGANISM: Artificial Sequence
<220> FEATURE:
<223> OTHER INFORMATION: Synthetic

<400> SEQUENCE: 20

Glu Ile Val Met Thr Gln Ser Pro Ala Thr Leu Ser Val Ser Pro Gly
1               5                   10                  15

Glu Arg Ala Ala Leu Ser Cys Arg Ala Ser Gln Ser Val Ser Ser Asn
            20                  25                  30

Leu Ala Trp Tyr His Gln Lys Pro Gly Gln Ala Pro Arg Leu Leu Ile
        35                  40                  45

Tyr Gly Ala Ser Thr Arg Ala Thr Gly Ile Pro Ala Arg Phe Ser Gly
50                  55                  60

Ile Gly Ser Gly Thr Glu Phe Thr Leu Ile Ile Ser Ser Leu Gln Ser
65                  70                  75                  80

Glu Asp Phe Ala Phe Tyr Phe Cys Gln Gln Tyr Asn Asn Trp Pro Pro
                85                  90                  95

Phe Thr Phe Gly Pro Gly Thr Lys Val Asp Ile Lys
            100                 105

<210> SEQ ID NO 21
<211> LENGTH: 351
<212> TYPE: DNA
<213> ORGANISM: Artificial Sequence
<220> FEATURE:
<223> OTHER INFORMATION: Synthetic

<400> SEQUENCE: 21
gaggtgcagc tggtggagtc tgggggaggc ttggtacagc ctggggggtc cctgagactc      60
tcctgtgcag cctctggatt tactctaagt agttacgaca tgcactgggt ccgccaagct     120
acaggaaaag gtctggagtg gtctcagct attggttcta ccggtgacac atactatcca     180
ggctccgtga aggccgatt caccatctcc agagaaaatg ccaagaactc cttgtatctt     240
caaatgaaca gcctgagagc cggggacacg gctgtgtatt actgtgtaag agaggggtgg     300
gaggtaccct ttgactactg gggccaggga accctggtca ccgtctcctc a              351

<210> SEQ ID NO 22
<211> LENGTH: 117
<212> TYPE: PRT
<213> ORGANISM: Artificial Sequence
<220> FEATURE:
<223> OTHER INFORMATION: Synthetic

<400> SEQUENCE: 22

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Leu Ser Ser Tyr
            20                  25                  30

Asp Met His Trp Val Arg Gln Ala Thr Gly Lys Gly Leu Glu Trp Val
        35                  40                  45

Ser Ala Ile Gly Ser Thr Gly Asp Thr Tyr Tyr Pro Gly Ser Val Lys
50                  55                  60

Gly Arg Phe Thr Ile Ser Arg Glu Asn Ala Lys Asn Ser Leu Tyr Leu
65                  70                  75                  80

Gln Met Asn Ser Leu Arg Ala Gly Asp Thr Ala Val Tyr Tyr Cys Val
                85                  90                  95

Arg Glu Gly Trp Glu Val Pro Phe Asp Tyr Trp Gly Gln Gly Thr Leu

```
                    100                 105                 110
Val Thr Val Ser Ser
            115

<210> SEQ ID NO 23
<211> LENGTH: 324
<212> TYPE: DNA
<213> ORGANISM: Artificial Sequence
<220> FEATURE:
<223> OTHER INFORMATION: Synthetic

<400> SEQUENCE: 23
gaaatagtga tgacgcagtc tccagccacc ctgtctgtgt ctccagggga aagagccacc      60
ctctcctgca gggccagtca gagtgttagc agcaacttag cctggtacca gcagaaacct     120
ggccaggctc ccaggctcct catctatggt gcatccacca gggccactgg tatcccagcc     180
aggttcagtg gcagtgggtc tgggacagag ttcactctca ccatcagcag cctgcagtct     240
gaagattttg cagtttatta ctgtcagcag tataataact ggcctccatt cactttcggc     300
cctgggacca agtggatat caaa                                             324

<210> SEQ ID NO 24
<211> LENGTH: 108
<212> TYPE: PRT
<213> ORGANISM: Artificial Sequence
<220> FEATURE:
<223> OTHER INFORMATION: Synthetic

<400> SEQUENCE: 24

Glu Ile Val Met Thr Gln Ser Pro Ala Thr Leu Ser Val Ser Pro Gly
  1               5                  10                  15

Glu Arg Ala Thr Leu Ser Cys Arg Ala Ser Gln Ser Val Ser Ser Asn
             20                  25                  30

Leu Ala Trp Tyr Gln Gln Lys Pro Gly Gln Ala Pro Arg Leu Leu Ile
         35                  40                  45

Tyr Gly Ala Ser Thr Arg Ala Thr Gly Ile Pro Ala Arg Phe Ser Gly
     50                  55                  60

Ser Gly Ser Gly Thr Glu Phe Thr Leu Thr Ile Ser Ser Leu Gln Ser
 65                  70                  75                  80

Glu Asp Phe Ala Val Tyr Tyr Cys Gln Gln Tyr Asn Asn Trp Pro Pro
                 85                  90                  95

Phe Thr Phe Gly Pro Gly Thr Lys Val Asp Ile Lys
            100                 105

<210> SEQ ID NO 25
<211> LENGTH: 342
<212> TYPE: DNA
<213> ORGANISM: Artificial Sequence
<220> FEATURE:
<223> OTHER INFORMATION: Synthetic

<400> SEQUENCE: 25
caggtgcagc tggtgcagtc tggggaggc gtggtccagc ctggagggtc cctgagactc        60
tcctgtgcag cgtctggatt caccttcagt agctatggca tgcactgggt ccgccaggct     120
ccaggcaagg ggctggagtg ggtggcgttt ataggatttg atggaagtaa tatacattat     180
ggagactccg tgaggggccg aatcatcata tccagagaca attccgagaa cacgttgtat     240
ctggaaatga acagcctgag agccgaggac acggcaatgt actattgtgc gagagagaag     300
ggtttagact ggggccaggg aaccacggtc accgtctcct ca                        342
```

<210> SEQ ID NO 26
<211> LENGTH: 114
<212> TYPE: PRT
<213> ORGANISM: Artificial Sequence
<220> FEATURE:
<223> OTHER INFORMATION: Synthetic

<400> SEQUENCE: 26

```
Gln Val Gln Leu Val Gln Ser Gly Gly Gly Val Val Gln Pro Gly Arg
 1               5                  10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Phe Ile Gly Phe Asp Gly Ser Asn Ile His Tyr Gly Asp Ser Val
    50                  55                  60

Arg Gly Arg Ile Ile Ile Ser Arg Asp Asn Ser Glu Asn Thr Leu Tyr
65                  70                  75                  80

Leu Glu Met Asn Ser Leu Arg Ala Glu Asp Thr Ala Met Tyr Tyr Cys
                85                  90                  95

Ala Arg Glu Lys Gly Leu Asp Trp Gly Gln Gly Thr Thr Val Thr Val
            100                 105                 110

Ser Ser
```

<210> SEQ ID NO 27
<211> LENGTH: 24
<212> TYPE: DNA
<213> ORGANISM: Artificial Sequence
<220> FEATURE:
<223> OTHER INFORMATION: Synthetic

<400> SEQUENCE: 27
ggattcacct tcagtagcta tggc                                    24

<210> SEQ ID NO 28
<211> LENGTH: 8
<212> TYPE: PRT
<213> ORGANISM: Artificial Sequence
<220> FEATURE:
<223> OTHER INFORMATION: Synthetic

<400> SEQUENCE: 28

```
Gly Phe Thr Phe Ser Ser Tyr Gly
 1               5
```

<210> SEQ ID NO 29
<211> LENGTH: 24
<212> TYPE: DNA
<213> ORGANISM: Artificial Sequence
<220> FEATURE:
<223> OTHER INFORMATION: Synthetic

<400> SEQUENCE: 29
ataggatttg atggaagtaa tata                                    24

<210> SEQ ID NO 30
<211> LENGTH: 8
<212> TYPE: PRT
<213> ORGANISM: Artificial Sequence
<220> FEATURE:
<223> OTHER INFORMATION: Synthetic

<400> SEQUENCE: 30

Ile Gly Phe Asp Gly Ser Asn Ile
1               5

<210> SEQ ID NO 31
<211> LENGTH: 21
<212> TYPE: DNA
<213> ORGANISM: Artificial Sequence
<220> FEATURE:
<223> OTHER INFORMATION: Synthetic

<400> SEQUENCE: 31
gcgagagaga agggtttaga c                                          21

<210> SEQ ID NO 32
<211> LENGTH: 7
<212> TYPE: PRT
<213> ORGANISM: Artificial Sequence
<220> FEATURE:
<223> OTHER INFORMATION: Synthetic

<400> SEQUENCE: 32

Ala Arg Glu Lys Gly Leu Asp
1               5

<210> SEQ ID NO 33
<211> LENGTH: 321
<212> TYPE: DNA
<213> ORGANISM: Artificial Sequence
<220> FEATURE:
<223> OTHER INFORMATION: Synthetic

<400> SEQUENCE: 33
gccatccaga tgacccagtc tccttccacc ctgtctgcat ctgtaggaga cagagtcacc    60
atcacttgcc gggccagtca gagtattagt agctggttgg cctggtatca gcagaaacca   120
gggaaagccc ctaagctcct gatctataag gcgtctagtt tagaaagtgg ggtcccatca   180
aggttcagcg gcagtggatc tgggacagaa ttcactctca ccatcagcag cctgcagcct   240
gatgattttg caacttatta ctgccaacag tataatagtt attacacttt tggccagggg   300
accaaggtgg aaatcaaacg a                                            321

<210> SEQ ID NO 34
<211> LENGTH: 107
<212> TYPE: PRT
<213> ORGANISM: Artificial Sequence
<220> FEATURE:
<223> OTHER INFORMATION: Synthetic

<400> SEQUENCE: 34

Ala Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Tyr Lys Ala Ser Ser Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Asn Ser Tyr Tyr Thr
                85                  90                  95

Phe Gly Gln Gly Thr Lys Val Glu Ile Lys Arg
            100                 105

<210> SEQ ID NO 35
<211> LENGTH: 18
<212> TYPE: DNA
<213> ORGANISM: Artificial Sequence
<220> FEATURE:
<223> OTHER INFORMATION: Synthetic

<400> SEQUENCE: 35
cagagtatta gtagctgg                                                 18

<210> SEQ ID NO 36
<211> LENGTH: 6
<212> TYPE: PRT
<213> ORGANISM: Artificial Sequence
<220> FEATURE:
<223> OTHER INFORMATION: Synthetic

<400> SEQUENCE: 36

Gln Ser Ile Ser Ser Trp
 1               5

<210> SEQ ID NO 37
<211> LENGTH: 9
<212> TYPE: DNA
<213> ORGANISM: Artificial Sequence
<220> FEATURE:
<223> OTHER INFORMATION: Synthetic

<400> SEQUENCE: 37 aaggcgtct                                                            9

<210> SEQ ID NO 38
<211> LENGTH: 3
<212> TYPE: PRT
<213> ORGANISM: Artificial Sequence
<220> FEATURE:
<223> OTHER INFORMATION: Synthetic

<400> SEQUENCE: 38

Lys Ala Ser
 1

<210> SEQ ID NO 39
<211> LENGTH: 24
<212> TYPE: DNA
<213> ORGANISM: Artificial Sequence
<220> FEATURE:
<223> OTHER INFORMATION: Synthetic

<400> SEQUENCE: 39
caacagtata atagttatta cact                                          24

<210> SEQ ID NO 40
<211> LENGTH: 8
<212> TYPE: PRT
<213> ORGANISM: Artificial Sequence
<220> FEATURE:
<223> OTHER INFORMATION: Synthetic

<400> SEQUENCE: 40

Gln Gln Tyr Asn Ser Tyr Tyr Thr
 1               5

<210> SEQ ID NO 41
<211> LENGTH: 342
<212> TYPE: DNA
<213> ORGANISM: Artificial Sequence
<220> FEATURE:
<223> OTHER INFORMATION: Synthetic

<400> SEQUENCE: 41

```
caggtgcagc tggtggagtc tgggggaggc gtggtccagc ctgggaggtc cctgagactc      60
tcctgtgcag cgtctggatt caccttcagt agctatggca tgcactgggt ccgccaggct     120
ccaggcaagg gctggagtg gtggcgtttt ataggatttg atggaagtaa tatacattat      180
ggagactccg tgaggggccg aatcatcata tccagagaca attccgagaa cacgttgtat     240
ctggaaatga acagcctgag agccgaggac acggcaatgt actattgtgc gagagagaag     300
ggtttagact ggggccaggg aaccctggtc accgtctcct ca                        342
```

<210> SEQ ID NO 42
<211> LENGTH: 114
<212> TYPE: PRT
<213> ORGANISM: Artificial Sequence
<220> FEATURE:
<223> OTHER INFORMATION: Synthetic

<400> SEQUENCE: 42

```
Gln Val Gln Leu Val Glu Ser Gly Gly Gly Val Val Gln Pro Gly Arg
 1               5                  10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Phe Ile Gly Phe Asp Gly Ser Asn Ile His Tyr Gly Asp Ser Val
    50                  55                  60

Arg Gly Arg Ile Ile Ile Ser Arg Asp Asn Ser Glu Asn Thr Leu Tyr
65                  70                  75                  80

Leu Glu Met Asn Ser Leu Arg Ala Glu Asp Thr Ala Met Tyr Tyr Cys
                85                  90                  95

Ala Arg Glu Lys Gly Leu Asp Trp Gly Gln Gly Thr Leu Val Thr Val
            100                 105                 110

Ser Ser
```

<210> SEQ ID NO 43
<211> LENGTH: 318
<212> TYPE: DNA
<213> ORGANISM: Artificial Sequence
<220> FEATURE:
<223> OTHER INFORMATION: Synthetic

<400> SEQUENCE: 43

```
gacatccaga tgacccagtc tccttccacc ctgtctgcat ctgtaggaga cagagtcacc      60
atcacttgcc gggccagtca gagtattagt agctggttgg cctggtatca gcagaaacca     120
gggaaagccc ctaagctcct gatctataag gcgtctagtt tagaaagtgg ggtcccatca     180
aggttcagcg gcagtggatc tgggacagaa ttcactctca ccatcagcag cctgcagcct     240
gatgattttg caacttatta ctgccaacag tataatagtt attacacttt tggccagggg     300
accaagctgg agatcaaa                                                   318
```

<210> SEQ ID NO 44

```
<211> LENGTH: 106
<212> TYPE: PRT
<213> ORGANISM: Artificial Sequence
<220> FEATURE:
<223> OTHER INFORMATION: Synthetic

<400> SEQUENCE: 44

Asp Ile Gln Met Thr Gln Ser Pro Ser Thr Leu Ser Ala Ser Val Gly
 1               5                  10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Tyr Lys Ala Ser Ser Leu Glu Ser Gly Val Pro Ser Arg Phe Ser Gly
 50                  55                  60

Ser Gly Ser Gly Thr Glu Phe Thr Leu Thr Ile Ser Ser Leu Gln Pro
 65                  70                  75                  80

Asp Asp Phe Ala Thr Tyr Tyr Cys Gln Gln Tyr Asn Ser Tyr Tyr Thr
                85                  90                  95

Phe Gly Gln Gly Thr Lys Leu Glu Ile Lys
            100                 105

<210> SEQ ID NO 45
<211> LENGTH: 342
<212> TYPE: DNA
<213> ORGANISM: Artificial Sequence
<220> FEATURE:
<223> OTHER INFORMATION: Synthetic

<400> SEQUENCE: 45
caggtgcagc tggtggagtc tgggggaggc gtggtccagc ctggggaggtc cctgagactc      60 tcctgtgcag cctctggatt caccttcagt agctatggca tgcactgggt ccgccaggct     120
ccaggcaagg ggctggagtg ggtggcagtt ataggatttg atggaagtaa tatatactat     180
gcagactccg tgaagggccg attcaccatc tccagagaca attccaagaa cacgctgtat     240
ctgcaaatga acagcctgag agctgaggac acggctgtgt attactgtgc gagagagaag     300
ggtttagact ggggccaggg aaccctggtc accgtctcct ca                        342

<210> SEQ ID NO 46
<211> LENGTH: 114
<212> TYPE: PRT
<213> ORGANISM: Artificial Sequence
<220> FEATURE:
<223> OTHER INFORMATION: Synthetic

<400> SEQUENCE: 46

Gln Val Gln Leu Val Glu Ser Gly Gly Gly Val Val Gln Pro Gly Arg
 1               5                  10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Gly Phe Asp Gly Ser Asn Ile Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                85                  90                  95
```

Ala Arg Glu Lys Gly Leu Asp Trp Gly Gln Gly Thr Leu Val Thr Val
            100                 105                 110

Ser Ser

<210> SEQ ID NO 47
<211> LENGTH: 319
<212> TYPE: DNA
<213> ORGANISM: Artificial Sequence
<220> FEATURE:
<223> OTHER INFORMATION: Synthetic

<400> SEQUENCE: 47
gacatccaga tgacccagtc tccttccacc ctgtctgcat ctgtaggaga cagagtcacc    60
atcacttgcc gggccagtca gagtattagt agctggttgg cctggtatca gcagaaacca   120
gggaaagccc ctaagctcct gatctataag gcgtctagtt tagaaagtgg ggtcccatca   180
aggttcagcg gcagtggatc tgggacagaa ttcactctca ccatcagcag cctgcagcct   240
gatgattttg caacttatta ctgccaacag tataatagtt attcacttt tggccagggg    300 accaagctgg agatcaaac                                                319

<210> SEQ ID NO 48
<211> LENGTH: 106
<212> TYPE: PRT
<213> ORGANISM: Artificial Sequence
<220> FEATURE:
<223> OTHER INFORMATION: Synthetic

<400> SEQUENCE: 48

Asp Ile Gln Met Thr Gln Ser Pro Ser Thr Leu Ser Ala Ser Val Gly
 1               5                  10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Tyr Lys Ala Ser Ser Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Asn Ser Tyr Tyr Thr
                85                  90                  95

Phe Gly Gln Gly Thr Lys Leu Glu Ile Lys
            100                 105

<210> SEQ ID NO 49
<211> LENGTH: 342
<212> TYPE: DNA
<213> ORGANISM: Artificial Sequence
<220> FEATURE:
<223> OTHER INFORMATION: Synthetic

<400> SEQUENCE: 49
caggtgcagc tgcaggagtc tgggggaggc gtggtccagc ctgggaggtc cctgagactc    60
tcctgtgcag cgtctggatt caccttcagt agctatggca tgcactgggt ccgccaggct   120
ccaggcaagg ggctggagtg ggtggcgttt ataggatttg atggaagtaa tatatattat   180
ggagactccg tgaggggccg aatcatcata tccagagaca attccgagaa cacgttgtat   240
ctggaaatga acagcctgag agccgaggac acggcagtgt attattgtgc gagagagaag   300
ggtttagact ggggccaggg aaccctggtc actgtctcct ca                      342

<210> SEQ ID NO 50
<211> LENGTH: 114
<212> TYPE: PRT
<213> ORGANISM: Artificial Sequence
<220> FEATURE:
<223> OTHER INFORMATION: Synthetic

<400> SEQUENCE: 50

```
Gln Val Gln Leu Gln Glu Ser Gly Gly Val Val Gln Pro Gly Arg
 1               5                  10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Phe Ile Gly Phe Asp Gly Ser Asn Ile Tyr Tyr Gly Asp Ser Val
    50                  55                  60

Arg Gly Arg Ile Ile Ile Ser Arg Asp Asn Ser Glu Asn Thr Leu Tyr
65                  70                  75                  80

Leu Glu Met Asn Ser Leu Arg Ala Glu Asp Thr Ala Val Tyr Tyr Cys
                85                  90                  95

Ala Arg Glu Lys Gly Leu Asp Trp Gly Gln Gly Thr Leu Val Thr Val
            100                 105                 110

Ser Ser
```

<210> SEQ ID NO 51
<211> LENGTH: 24
<212> TYPE: DNA
<213> ORGANISM: Artificial Sequence
<220> FEATURE:
<223> OTHER INFORMATION: Synthetic

<400> SEQUENCE: 51
ggattcacct tcagtagcta tggc         24

<210> SEQ ID NO 52
<211> LENGTH: 8
<212> TYPE: PRT
<213> ORGANISM: Artificial Sequence
<220> FEATURE:
<223> OTHER INFORMATION: Synthetic

<400> SEQUENCE: 52

```
Gly Phe Thr Phe Ser Ser Tyr Gly
 1               5
```

<210> SEQ ID NO 53
<211> LENGTH: 24
<212> TYPE: DNA
<213> ORGANISM: Artificial Sequence
<220> FEATURE:
<223> OTHER INFORMATION: Synthetic

<400> SEQUENCE: 53
ataggatttg atggaagtaa tata         24

<210> SEQ ID NO 54
<211> LENGTH: 8
<212> TYPE: PRT
<213> ORGANISM: Artificial Sequence
<220> FEATURE:
<223> OTHER INFORMATION: Synthetic

<400> SEQUENCE: 54

Ile Gly Phe Asp Gly Ser Asn Ile
1               5

<210> SEQ ID NO 55
<211> LENGTH: 21
<212> TYPE: DNA
<213> ORGANISM: Artificial Sequence
<220> FEATURE:
<223> OTHER INFORMATION: Synthetic

<400> SEQUENCE: 55
gcgagagaga agggtttaga c                                            21

<210> SEQ ID NO 56
<211> LENGTH: 7
<212> TYPE: PRT
<213> ORGANISM: Artificial Sequence
<220> FEATURE:
<223> OTHER INFORMATION: Synthetic

<400> SEQUENCE: 56

Ala Arg Glu Lys Gly Leu Asp
1               5

<210> SEQ ID NO 57
<211> LENGTH: 342
<212> TYPE: DNA
<213> ORGANISM: Artificial Sequence
<220> FEATURE:
<223> OTHER INFORMATION: Synthetic

<400> SEQUENCE: 57
gccatccaga tgacccagtc tccagactcc ctggctgtgt ctctgggcga gagggccacc    60
atcaactgca agtccagcca gagtgttttt cacacctcca acaataagaa ctacttagtt   120
tggtatcagc agaaaccagg acagcctcct aagttgctcc tttactgggc ctctacccgg   180
gaatccgggg tccctgaccg attcagtggc agcgggtctg ggacagattt cactctcacc   240
atcagcagcc tgcaggctga agatgtggca aattattact gtcaccaata ttacagtatt   300
ccgtggacgt tcggccaagg gaccaaggtg gagatcaaac ga                      342

<210> SEQ ID NO 58
<211> LENGTH: 114
<212> TYPE: PRT
<213> ORGANISM: Artificial Sequence
<220> FEATURE:
<223> OTHER INFORMATION: Synthetic

<400> SEQUENCE: 58

Ala Ile Gln Met Thr Gln Ser Pro Asp Ser Leu Ala Val Ser Leu Gly
1               5                   10                  15

Glu Arg Ala Thr Ile Asn Cys Lys Ser Ser Gln Ser Val Phe His Thr
            20                  25                  30

Ser Asn Asn Lys Asn Tyr Leu Val Trp Tyr Gln Gln Lys Pro Gly Gln
        35                  40                  45

Pro Pro Lys Leu Leu Leu Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Asn Tyr Tyr Cys His Gln
                85                  90                  95

Tyr Tyr Ser Ile Pro Trp Thr Phe Gly Gln Gly Thr Lys Val Glu Ile
            100                 105                 110

Lys Arg

<210> SEQ ID NO 59
<211> LENGTH: 36
<212> TYPE: DNA
<213> ORGANISM: Artificial Sequence
<220> FEATURE:
<223> OTHER INFORMATION: Synthetic

<400> SEQUENCE: 59
cagagtgttt ttcacacctc caacaataag aactac                                 36

<210> SEQ ID NO 60
<211> LENGTH: 12
<212> TYPE: PRT
<213> ORGANISM: Artificial Sequence
<220> FEATURE:
<223> OTHER INFORMATION: Synthetic

<400> SEQUENCE: 60

Gln Ser Val Phe His Thr Ser Asn Asn Lys Asn Tyr
 1               5                  10

<210> SEQ ID NO 61
<211> LENGTH: 9
<212> TYPE: DNA
<213> ORGANISM: Artificial Sequence
<220> FEATURE:
<223> OTHER INFORMATION: Synthetic

<400> SEQUENCE: 61 tgggcctct                                                                9

<210> SEQ ID NO 62
<211> LENGTH: 3
<212> TYPE: PRT
<213> ORGANISM: Artificial Sequence
<220> FEATURE:
<223> OTHER INFORMATION: Synthetic

<400> SEQUENCE: 62

Trp Ala Ser
 1

<210> SEQ ID NO 63
<211> LENGTH: 27
<212> TYPE: DNA
<213> ORGANISM: Artificial Sequence
<220> FEATURE:
<223> OTHER INFORMATION: Synthetic

<400> SEQUENCE: 63
caccaatatt acagtattcc gtggacg                                           27

<210> SEQ ID NO 64
<211> LENGTH: 9
<212> TYPE: PRT
<213> ORGANISM: Artificial Sequence
<220> FEATURE:
<223> OTHER INFORMATION: Synthetic

<400> SEQUENCE: 64

His Gln Tyr Tyr Ser Ile Pro Trp Thr

<210> SEQ ID NO 65
<211> LENGTH: 342
<212> TYPE: DNA
<213> ORGANISM: Artificial Sequence
<220> FEATURE:
<223> OTHER INFORMATION: Synthetic

<400> SEQUENCE: 65

```
caggtgcagc tggtggagtc tgggggaggc gtggtccagc ctggagggtc cctgagactc    60
tcctgtgcag cgtctggatt caccttcagt agctatggca tgcactgggt ccgccaggct   120
ccaggcaagg ggctggagtg ggtggcgttt ataggatttg atggaagtaa tatatattat   180
ggagactccg tgaggggccg aatcatcata tccagagaca attccgagaa cacgttgtat   240
ctggaaatga acagcctgag agccgaggac acggcagtgt attattgtgc gagagagaag   300
ggtttagact ggggccaggg aaccctggtc accgtctcct ca                      342
```

<210> SEQ ID NO 66
<211> LENGTH: 114
<212> TYPE: PRT
<213> ORGANISM: Artificial Sequence
<220> FEATURE:
<223> OTHER INFORMATION: Synthetic

<400> SEQUENCE: 66

Gln Val Gln Leu Val Glu Ser Gly Gly Gly Val Val Gln Pro Gly Arg
1               5                   10                  15
Ser Leu Arg Leu Ser Cys Ala Ala Ser Gly Phe Thr Phe Ser Ser Tyr
            20                  25                  30
Gly Met His Trp Val Arg Gln Ala Pro Gly Lys Gly Leu Glu Trp Val
        35                  40                  45
Ala Phe Ile Gly Phe Asp Gly Ser Asn Ile Tyr Tyr Gly Asp Ser Val
    50                  55                  60
Arg Gly Arg Ile Ile Ile Ser Arg Asp Asn Ser Glu Asn Thr Leu Tyr
65                  70                  75                  80
Leu Glu Met Asn Ser Leu Arg Ala Glu Asp Thr Ala Val Tyr Tyr Cys
                85                  90                  95
Ala Arg Glu Lys Gly Leu Asp Trp Gly Gln Gly Thr Leu Val Thr Val
            100                 105                 110
Ser Ser

<210> SEQ ID NO 67
<211> LENGTH: 339
<212> TYPE: DNA
<213> ORGANISM: Artificial Sequence
<220> FEATURE:
<223> OTHER INFORMATION: Synthetic

<400> SEQUENCE: 67

```
gacatcgtga tgacccagtc tccagactcc ctggctgtgt ctctgggcga gagggccacc    60
atcaactgca gtccagcca gagtgttttt cacacctcca acaataagaa ctacttagtt   120
tggtatcagc agaaaccagg acagcctcct aagttgctcc tttactgggc ctctacccgg   180
gaatccgggg tccctgaccg attcagtggc agcgggtctg ggacagattt cactctcacc   240
atcagcagcc tgcaggctga agatgtgcaa attattact gtcaccaata ttacagtatt   300
ccgtggacgt tcggccaagg gaccaaggtg gaaatcaaa                          339
```

<210> SEQ ID NO 68
<211> LENGTH: 113
<212> TYPE: PRT
<213> ORGANISM: Artificial Sequence
<220> FEATURE:
<223> OTHER INFORMATION: Synthetic

<400> SEQUENCE: 68

```
Asp Ile Val Met Thr Gln Ser Pro Asp Ser Leu Ala Val Ser Leu Gly
 1               5                  10                  15

Glu Arg Ala Thr Ile Asn Cys Lys Ser Ser Gln Ser Val Phe His Thr
            20                  25                  30

Ser Asn Asn Lys Asn Tyr Leu Val Trp Tyr Gln Gln Lys Pro Gly Gln
        35                  40                  45

Pro Pro Lys Leu Leu Leu Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Asn Tyr Tyr Cys His Gln
                85                  90                  95

Tyr Tyr Ser Ile Pro Trp Thr Phe Gly Gln Gly Thr Lys Val Glu Ile
            100                 105                 110

Lys
```

<210> SEQ ID NO 69
<211> LENGTH: 342
<212> TYPE: DNA
<213> ORGANISM: Artificial Sequence
<220> FEATURE:
<223> OTHER INFORMATION: Synthetic

<400> SEQUENCE: 69

```
caggtgcagc tggtggagtc tgggggaggc gtggtccagc ctggggaggtc cctgagactc      60 tcctgtgcag cctctggatt caccttcagt agctatggca tgcactgggt ccgccaggct     120
ccaggcaagg ggctggagtg ggtggcagtt ataggatttg atggaagtaa tatatactat     180
gcagactccg tgaagggccg attcaccatc tccagagaca attccaagaa cacgctgtat     240
ctgcaaatga acagcctgag agctgaggac acggctgtgt attactgtgc gagagagaag     300
ggtttagact ggggccaggg aaccctggtc accgtctcct ca                        342
```

<210> SEQ ID NO 70
<211> LENGTH: 114
<212> TYPE: PRT
<213> ORGANISM: Artificial Sequence
<220> FEATURE:
<223> OTHER INFORMATION: Synthetic

<400> SEQUENCE: 70

```
Gln Val Gln Leu Val Glu Ser Gly Gly Gly Val Val Gln Pro Gly Arg
 1               5                  10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Gly Phe Asp Gly Ser Asn Ile Tyr Tyr Ala Asp Ser Val
    50                  55                  60

Lys Gly Arg Phe Thr Ile Ser Arg Asp Asn Ser Lys Asn Thr Leu Tyr
65                  70                  75                  80
```

Leu Gln Met Asn Ser Leu Arg Ala Glu Asp Thr Ala Val Tyr Tyr Cys
                85                  90                  95

Ala Arg Glu Lys Gly Leu Asp Trp Gly Gln Gly Thr Leu Val Thr Val
            100                 105                 110

Ser Ser

<210> SEQ ID NO 71
<211> LENGTH: 339
<212> TYPE: DNA
<213> ORGANISM: Artificial Sequence
<220> FEATURE:
<223> OTHER INFORMATION: Synthetic

<400> SEQUENCE: 71

```
gacatcgtga tgacccagtc tccagactcc ctggctgtgt ctctgggcga gagggccacc    60
atcaactgca agtccagcca gagtgttttt cacacctcca acaataagaa ctacttagct   120
tggtaccagc agaaaccagg acagcctcct aagctgctca tttactgggc ctctacccgg   180
gaatccgggg tccctgaccg attcagtggc agcgggtctg ggacagattt cactctcacc   240
atcagcagcc tgcaggctga agatgtggca gtttattact gtcaccaata ttacagtatt   300
ccgtggacgt tcggccaagg gaccaaggtg gaaatcaaa                          339
```

<210> SEQ ID NO 72
<211> LENGTH: 113
<212> TYPE: PRT
<213> ORGANISM: Artificial Sequence
<220> FEATURE:
<223> OTHER INFORMATION: Synthetic

<400> SEQUENCE: 72

Asp Ile Val Met Thr Gln Ser Pro Asp Ser Leu Ala Val Ser Leu Gly
 1               5                  10                  15

Glu Arg Ala Thr Ile Asn Cys Lys Ser Ser Gln Ser Val Phe His Thr
            20                  25                  30

Ser Asn Asn Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys His Gln
                85                  90                  95

Tyr Tyr Ser Ile Pro Trp Thr Phe Gly Gln Gly Thr Lys Val Glu Ile
            100                 105                 110

Lys

<210> SEQ ID NO 73
<211> LENGTH: 354
<212> TYPE: DNA
<213> ORGANISM: Artificial Sequence
<220> FEATURE:
<223> OTHER INFORMATION: Synthetic

<400> SEQUENCE: 73

```
gaagtgcagc tggtgcagtc tgggggaggc ttggtacagc ctgggggtc cctgagactc     60 tcctgtgcag cctctggatt caccttaac aactatgcca tgaactgggt ccgccaggct   120
ccaggaaagg gactggactg ggtctcaact attagtggta gcggtggtac tacaaactac   180
```

```
gcagactccg tgaagggccg tttcattatt tcccgagaca gttccaaaca cacgctgtat    240
ctgcaaatga acagcctgag agccgaggac acggccgtat attactgtgc gaaagattct    300
aactggggaa atttcgatct ctggggccgt ggcaccacgg tcactgtctc ctca          354
```

<210> SEQ ID NO 74
<211> LENGTH: 118
<212> TYPE: PRT
<213> ORGANISM: Artificial Sequence
<220> FEATURE:
<223> OTHER INFORMATION: Synthetic

<400> SEQUENCE: 74

```
Glu Val Gln Leu Val Gln Ser Gly Gly Gly Leu Val Gln Pro Gly Gly
 1               5                  10                  15

Ser Leu Arg Leu Ser Cys Ala Ala Ser Gly Phe Thr Phe Asn Asn Tyr
             20                  25                  30

Ala Met Asn Trp Val Arg Gln Ala Pro Gly Lys Gly Leu Asp Trp Val
         35                  40                  45

Ser Thr Ile Ser Gly Ser Gly Gly Thr Thr Asn Tyr Ala Asp Ser Val
     50                  55                  60

Lys Gly Arg Phe Ile Ile Ser Arg Asp Ser Ser Lys His Thr Leu Tyr
 65                  70                  75                  80

Leu Gln Met Asn Ser Leu Arg Ala Glu Asp Thr Ala Val Tyr Tyr Cys
                 85                  90                  95

Ala Lys Asp Ser Asn Trp Gly Asn Phe Asp Leu Trp Gly Arg Gly Thr
            100                 105                 110

Thr Val Thr Val Ser Ser
        115
```

<210> SEQ ID NO 75
<211> LENGTH: 24
<212> TYPE: DNA
<213> ORGANISM: Artificial Sequence
<220> FEATURE:
<223> OTHER INFORMATION: Synthetic

<400> SEQUENCE: 75

```
ggattcacct ttaacaacta tgcc                                            24
```

<210> SEQ ID NO 76
<211> LENGTH: 8
<212> TYPE: PRT
<213> ORGANISM: Artificial Sequence
<220> FEATURE:
<223> OTHER INFORMATION: Synthetic

<400> SEQUENCE: 76

```
Gly Phe Thr Phe Asn Asn Tyr Ala
 1               5
```

<210> SEQ ID NO 77
<211> LENGTH: 24
<212> TYPE: DNA
<213> ORGANISM: Artificial Sequence
<220> FEATURE:
<223> OTHER INFORMATION: Synthetic

<400> SEQUENCE: 77

```
attagtggta gcggtggtac taca                                            24
```

<210> SEQ ID NO 78
<211> LENGTH: 8
<212> TYPE: PRT
<213> ORGANISM: Artificial Sequence
<220> FEATURE:
<223> OTHER INFORMATION: Synthetic

<400> SEQUENCE: 78

```
Ile Ser Gly Ser Gly Gly Thr Thr
1               5
```

<210> SEQ ID NO 79
<211> LENGTH: 33
<212> TYPE: DNA
<213> ORGANISM: Artificial Sequence
<220> FEATURE:
<223> OTHER INFORMATION: Synthetic

<400> SEQUENCE: 79

```
gcgaaagatt ctaactgggg aaatttcgat ctc                              33
```

<210> SEQ ID NO 80
<211> LENGTH: 11
<212> TYPE: PRT
<213> ORGANISM: Artificial Sequence
<220> FEATURE:
<223> OTHER INFORMATION: Synthetic

<400> SEQUENCE: 80

```
Ala Lys Asp Ser Asn Trp Gly Asn Phe Asp Leu
1               5                   10
```

<210> SEQ ID NO 81
<211> LENGTH: 342
<212> TYPE: DNA
<213> ORGANISM: Artificial Sequence
<220> FEATURE:
<223> OTHER INFORMATION: Synthetic

<400> SEQUENCE: 81

```
gacatccaga tgacccagtc tccagactcc ctggctgtgt ctctgggcga gagggccacc    60
atcaactgca agtccagcca gagtgtttta tacaggtcca acaataggaa cttcttaggt   120
tggtaccagc agaaaccagg gcagcctcct aatctactca tttactgggc atctacccgg   180
gaatccgggg tccctgaccg attcagtggc agcgggtctg ggacagattt cactctcacc   240
atcagcagcc tgcaggctga agatgtggca gtttattact gtcaacaata ttatactact   300
ccgtacactt ttggccaggg gaccaaggtg gaaatcaaac ga                     342
```

<210> SEQ ID NO 82
<211> LENGTH: 114
<212> TYPE: PRT
<213> ORGANISM: Artificial Sequence
<220> FEATURE:
<223> OTHER INFORMATION: Synthetic

<400> SEQUENCE: 82

```
Asp Ile Gln Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Tyr Arg
            20                  25                  30

Ser Asn Asn Arg Asn Phe Leu Gly Trp Tyr Gln Gln Lys Pro Gly Gln
        35                  40                  45

Pro Pro Asn Leu Leu Ile Tyr Trp Ala Ser Thr Arg Glu Ser Gly Val
```

-continued

```
                    50                  55                  60
Pro Asp Arg Phe Ser Gly Ser Gly Ser Gly Thr Asp Phe Thr Leu Thr
 65                  70                  75                  80

Ile Ser Ser Leu Gln Ala Glu Asp Val Ala Val Tyr Tyr Cys Gln Gln
                 85                  90                  95

Tyr Tyr Thr Thr Pro Tyr Thr Phe Gly Gln Gly Thr Lys Val Glu Ile
            100                 105                 110

Lys Arg
```

<210> SEQ ID NO 83
<211> LENGTH: 36
<212> TYPE: DNA
<213> ORGANISM: Artificial Sequence
<220> FEATURE:
<223> OTHER INFORMATION: Synthetic

<400> SEQUENCE: 83
cagagtgttt tatacaggtc caacaatagg aacttc                    36

<210> SEQ ID NO 84
<211> LENGTH: 12
<212> TYPE: PRT
<213> ORGANISM: Artificial Sequence
<220> FEATURE:
<223> OTHER INFORMATION: Synthetic

<400> SEQUENCE: 84

```
Gln Ser Val Leu Tyr Arg Ser Asn Asn Arg Asn Phe
 1               5                  10
```

<210> SEQ ID NO 85
<211> LENGTH: 9
<212> TYPE: DNA
<213> ORGANISM: Artificial Sequence
<220> FEATURE:
<223> OTHER INFORMATION: Synthetic

<400> SEQUENCE: 85 tgggcatct                                                   9

<210> SEQ ID NO 86
<211> LENGTH: 3
<212> TYPE: PRT
<213> ORGANISM: Artificial Sequence
<220> FEATURE:
<223> OTHER INFORMATION: Synthetic

<400> SEQUENCE: 86

```
Trp Ala Ser
 1
```

<210> SEQ ID NO 87
<211> LENGTH: 27
<212> TYPE: DNA
<213> ORGANISM: Artificial Sequence
<220> FEATURE:
<223> OTHER INFORMATION: Synthetic

<400> SEQUENCE: 87
caacaatatt atactactcc gtacact                              27

<210> SEQ ID NO 88
<211> LENGTH: 9
<212> TYPE: PRT

<210> ORGANISM: Artificial Sequence
<220> FEATURE:
<223> OTHER INFORMATION: Synthetic

<400> SEQUENCE: 88

```
Gln Gln Tyr Tyr Thr Thr Pro Tyr Thr
1               5
```

<210> SEQ ID NO 89
<211> LENGTH: 354
<212> TYPE: DNA
<213> ORGANISM: Artificial Sequence
<220> FEATURE:
<223> OTHER INFORMATION: Synthetic

<400> SEQUENCE: 89

```
gaggtgcagc tggtggagtc tgggggaggc ttggtacagc ctgggggtc cctgagactc      60 tcctgtgcag cctctggatt caccttaac aactatgcca tgaactgggt ccgccaggct    120
ccaggaaagg gactggactg gtctcaact attagtggta gcggtggtac tacaaactac    180
gcagactccg tgaagggccg tttcattatt tcccgagaca gttccaaaca cacgctgtat    240
ctgcaaatga acagcctgag agccgaggac acggccgtat attactgtgc gaaagattct    300
aactggggaa atttcgatct ctggggccgt ggcaccctgg tcactgtctc ctca           354
```

<210> SEQ ID NO 90
<211> LENGTH: 118
<212> TYPE: PRT
<213> ORGANISM: Artificial Sequence
<220> FEATURE:
<223> OTHER INFORMATION: Synthetic

<400> SEQUENCE: 90

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Asn Asn Tyr
            20                  25                  30

Ala Met Asn Trp Val Arg Gln Ala Pro Gly Lys Gly Leu Asp Trp Val
        35                  40                  45

Ser Thr Ile Ser Gly Ser Gly Gly Thr Thr Asn Tyr Ala Asp Ser Val
    50                  55                  60

Lys Gly Arg Phe Ile Ile Ser Arg Asp Ser Ser Lys His Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Ser Asn Trp Gly Asn Phe Asp Leu Trp Gly Arg Gly Thr
            100                 105                 110

Leu Val Thr Val Ser Ser
        115
```

<210> SEQ ID NO 91
<211> LENGTH: 339
<212> TYPE: DNA
<213> ORGANISM: Artificial Sequence
<220> FEATURE:
<223> OTHER INFORMATION: Synthetic

<400> SEQUENCE: 91

```
gacatcgtga tgacccagtc tccagactcc ctggctgtgt ctctgggcga gagggccacc      60
atcaactgca agtccagcca gagtgtttta tacaggtcca acaataggaa cttcttaggt    120
```

```
tggtaccagc agaaaccagg gcagcctcct aatctactca tttactgggc atctacccgg    180
gaatccgggg tccctgaccg attcagtggc agcgggtctg ggacagattt cactctcacc    240
atcagcagcc tgcaggctga agatgtggca gtttattact gtcaacaata ttatactact    300
ccgtacactt ttggccaggg gaccaagctg gagatcaaa                           339
```

```

<210> SEQ ID NO 92
<211> LENGTH: 113
<212> TYPE: PRT
<213> ORGANISM: Artificial Sequence
<220> FEATURE:
<223> OTHER INFORMATION: Synthetic

<400> SEQUENCE: 92

Asp Ile Val Met Thr Gln Ser Pro Asp Ser Leu Ala Val Ser Leu Gly
 1               5                  10                  15

Glu Arg Ala Thr Ile Asn Cys Lys Ser Ser Gln Ser Val Leu Tyr Arg
            20                  25                  30

Ser Asn Asn Arg Asn Phe Leu Gly Trp Tyr Gln Gln Lys Pro Gly Gln
        35                  40                  45

Pro Pro Asn Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Tyr Thr Thr Pro Tyr Thr Phe Gly Gln Gly Thr Lys Leu Glu Ile
            100                 105                 110

Lys
```

```

<210> SEQ ID NO 93
<211> LENGTH: 354
<212> TYPE: DNA
<213> ORGANISM: Artificial Sequence
<220> FEATURE:
<223> OTHER INFORMATION: Synthetic

<400> SEQUENCE: 93
gaggtgcagc tggtggagtc tgggggaggc ttggtacagc ctggggggtc cctgagactc     60
tcctgtgcag cctctggatt cacctttaac aactatgcca tgagctgggt ccgccaggct    120

ccagggaagg ggctggagtg ggtctcagct attagtggta gcggtggtac tacatactac    180
gcagactccg tgaagggccg gttcaccatc tccagagaca attccaagaa cacgctgtat    240
ctgcaaatga acagcctgag agccgaggac acggccgtat attactgtgc gaaagattct    300
aactggggaa atttcgatct ctggggccgt ggcaccctgg tcactgtctc ctca          354
```

```

<210> SEQ ID NO 94
<211> LENGTH: 118
<212> TYPE: PRT
<213> ORGANISM: Artificial Sequence
<220> FEATURE:
<223> OTHER INFORMATION: Synthetic

<400> SEQUENCE: 94

Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Asn Asn Tyr
            20                  25                  30
```

Ala Met Ser Trp Val Arg Gln Ala Pro Gly Lys Gly Leu Glu Trp Val
           35                  40                  45

Ser Ala Ile Ser Gly Ser Gly Gly Thr Thr Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Asp Ser Asn Trp Gly Asn Phe Asp Leu Trp Gly Arg Gly Thr
                100                 105                 110

Leu Val Thr Val Ser Ser
        115

<210> SEQ ID NO 95
<211> LENGTH: 339
<212> TYPE: DNA
<213> ORGANISM: Artificial Sequence
<220> FEATURE:
<223> OTHER INFORMATION: Synthetic

<400> SEQUENCE: 95
gacatcgtga tgacccagtc tccagactcc ctggctgtgt ctctgggcga gagggccacc    60
atcaactgca gtccagccag agtgttttta tacaggtcca acaataggaa cttcttagct   120
tggtaccagc agaaaccagg acagcctcct aagctgctca tttactgggc atctacccgg   180
gaatccgggg tccctgaccg attcagtggc agcgggtctg ggacagattt cactctcacc   240
atcagcagcc tgcaggctga agatgtggca gtttattact gtcaacaata ttatactact   300
ccgtacactt ttggccaggg gaccaagctg gagatcaaa                          339

<210> SEQ ID NO 96
<211> LENGTH: 113
<212> TYPE: PRT
<213> ORGANISM: Artificial Sequence
<220> FEATURE:
<223> OTHER INFORMATION: Synthetic

<400> SEQUENCE: 96

Asp Ile Val Met Thr Gln Ser Pro Asp Ser Leu Ala Val Ser Leu Gly
  1               5                  10                  15

Glu Arg Ala Thr Ile Asn Cys Lys Ser Ser Gln Ser Val Leu Tyr Arg
                 20                  25                  30

Ser Asn Asn Arg Asn Phe Leu Ala Trp Tyr Gln Gln Lys Pro Gly Gln
             35                  40                  45

Pro Pro Lys Leu Leu Ile Tyr Trp Ala Ser Thr Arg Glu Ser Gly Val
 50                  55                  60

Pro Asp Arg Phe Ser Gly Ser Gly Ser Gly Thr Asp Phe Thr Leu Thr
 65                  70                  75                  80

Ile Ser Ser Leu Gln Ala Glu Asp Val Ala Val Tyr Tyr Cys Gln Gln
                 85                  90                  95

Tyr Tyr Thr Thr Pro Tyr Thr Phe Gly Gln Gly Thr Lys Leu Glu Ile
                100                 105                 110

Lys

<210> SEQ ID NO 97
<211> LENGTH: 351
<212> TYPE: DNA
<213> ORGANISM: Artificial Sequence
<220> FEATURE:

<223> OTHER INFORMATION: Synthetic

<400> SEQUENCE: 97

```
caggtgcagc tggtgcagtc tgggggaggc ttggtacagc ctggggggtc cctgagactc    60
tcctgtgcag tctctggatt caccctcagt agctacgata tgcactgggt ccgccaacct   120
acaggaaaag gtctggagtg ggtctcagct attggttcta ctggtgacac atactatcca   180
ggctccgtga agggccgatt caccatctcc agagaaaatg ccaagaactc cttgtatctt   240
caaatgaaca gcctgagagc cggggacacg gctgtgtatt actgtgcaag agagggatgg   300
gacgtaccct ttgacttctg gggccaggga accctggtca ccgtctcctc a            351
```

<210> SEQ ID NO 98
<211> LENGTH: 117
<212> TYPE: PRT
<213> ORGANISM: Artificial Sequence
<220> FEATURE:
<223> OTHER INFORMATION: Synthetic

<400> SEQUENCE: 98

Gln Val Gln Leu Val Gln Ser Gly Gly Gly Leu Val Gln Pro Gly Gly
 1               5                  10                  15

Ser Leu Arg Leu Ser Cys Ala Val Ser Gly Phe Thr Leu Ser Ser Tyr
            20                  25                  30

Asp Met His Trp Val Arg Gln Pro Thr Gly Lys Gly Leu Glu Trp Val
        35                  40                  45

Ser Ala Ile Gly Ser Thr Gly Asp Thr Tyr Tyr Pro Gly Ser Val Lys
    50                  55                  60

Gly Arg Phe Thr Ile Ser Arg Glu Asn Ala Lys Asn Ser Leu Tyr Leu
65                  70                  75                  80

Gln Met Asn Ser Leu Arg Ala Gly Asp Thr Ala Val Tyr Tyr Cys Ala
                85                  90                  95

Arg Glu Gly Trp Asp Val Pro Phe Asp Phe Trp Gly Gln Gly Thr Leu
            100                 105                 110

Val Thr Val Ser Ser
        115

<210> SEQ ID NO 99
<211> LENGTH: 24
<212> TYPE: DNA
<213> ORGANISM: Artificial Sequence
<220> FEATURE:
<223> OTHER INFORMATION: Synthetic

<400> SEQUENCE: 99

```
ggattcaccc tcagtagcta cgat                                            24
```

<210> SEQ ID NO 100
<211> LENGTH: 8
<212> TYPE: PRT
<213> ORGANISM: Artificial Sequence
<220> FEATURE:
<223> OTHER INFORMATION: Synthetic

<400> SEQUENCE: 100

Gly Phe Thr Leu Ser Ser Tyr Asp
 1               5

<210> SEQ ID NO 101
<211> LENGTH: 21
<212> TYPE: DNA

<213> ORGANISM: Artificial Sequence
<220> FEATURE:
<223> OTHER INFORMATION: Synthetic

<400> SEQUENCE: 101
attggttcta ctggtgacac a                                           21

<210> SEQ ID NO 102
<211> LENGTH: 7
<212> TYPE: PRT
<213> ORGANISM: Artificial Sequence
<220> FEATURE:
<223> OTHER INFORMATION: Synthetic

<400> SEQUENCE: 102

Ile Gly Ser Thr Gly Asp Thr
1               5

<210> SEQ ID NO 103
<211> LENGTH: 33
<212> TYPE: DNA
<213> ORGANISM: Artificial Sequence
<220> FEATURE:
<223> OTHER INFORMATION: Synthetic

<400> SEQUENCE: 103
gcaagagagg gatgggacgt acctttgac ttc                               33

<210> SEQ ID NO 104
<211> LENGTH: 11
<212> TYPE: PRT
<213> ORGANISM: Artificial Sequence
<220> FEATURE:
<223> OTHER INFORMATION: Synthetic

<400> SEQUENCE: 104

Ala Arg Glu Gly Trp Asp Val Pro Phe Asp Phe
1               5                   10

<210> SEQ ID NO 105
<211> LENGTH: 324
<212> TYPE: DNA
<213> ORGANISM: Artificial Sequence
<220> FEATURE:
<223> OTHER INFORMATION: Synthetic

<400> SEQUENCE: 105
gccatccagt tgacccagtc tccatcctcc ctgtctgcat ctgtaggaga cagagtcacc    60
atcacttgcc gggcaagtca ggacattaga aatgatttag gctggtatca gcagaaacca   120
gggaaagccc ctaagctcct gatctatgct gcatccagtt tacaaagtgg ggtcccatca   180
cggttcagcg gcagtggatc tggcacagat ttcactctca ccatcagcag cctgcagcct   240
gaagattttg caacttatta ctgtctacaa gattacaatt acccgtggac gttcggccaa   300
gggaccaagg tggagatcaa acga                                         324

<210> SEQ ID NO 106
<211> LENGTH: 108
<212> TYPE: PRT
<213> ORGANISM: Artificial Sequence
<220> FEATURE:
<223> OTHER INFORMATION: Synthetic

<400> SEQUENCE: 106

Ala Ile Gln Leu Thr Gln Ser Pro Ser Ser Leu Ser Ala Ser Val Gly

```
                1               5                   10                  15
            Asp Arg Val Thr Ile Thr Cys Arg Ala Ser Gln Asp Ile Arg Asn Asp
                            20                  25                  30

Leu Gly Trp Tyr Gln Gln Lys Pro Gly Lys Ala Pro Lys Leu Leu Ile
                        35                  40                  45

Tyr Ala Ala Ser Ser Leu Gln Ser Gly Val Pro Ser Arg Phe Ser Gly
                    50                  55                  60

Ser Gly Ser Gly Thr Asp Phe Thr Leu Thr Ile Ser Ser Leu Gln Pro
             65                 70                  75                  80

Glu Asp Phe Ala Thr Tyr Tyr Cys Leu Gln Asp Tyr Asn Tyr Pro Trp
                            85                  90                  95

Thr Phe Gly Gln Gly Thr Lys Val Glu Ile Lys Arg
                        100                 105
```

<210> SEQ ID NO 107
<211> LENGTH: 18
<212> TYPE: DNA
<213> ORGANISM: Artificial Sequence
<220> FEATURE:
<223> OTHER INFORMATION: Synthetic

<400> SEQUENCE: 107
caggacatta gaaatgat                                                    18

<210> SEQ ID NO 108
<211> LENGTH: 6
<212> TYPE: PRT
<213> ORGANISM: Artificial Sequence
<220> FEATURE:
<223> OTHER INFORMATION: Synthetic

<400> SEQUENCE: 108

Gln Asp Ile Arg Asn Asp
 1               5

<210> SEQ ID NO 109
<211> LENGTH: 9
<212> TYPE: DNA
<213> ORGANISM: Artificial Sequence
<220> FEATURE:
<223> OTHER INFORMATION: Synthetic

<400> SEQUENCE: 109 gctgcatcc                                                               9

<210> SEQ ID NO 110
<211> LENGTH: 3
<212> TYPE: PRT
<213> ORGANISM: Artificial Sequence
<220> FEATURE:
<223> OTHER INFORMATION: Synthetic

<400> SEQUENCE: 110

Ala Ala Ser
 1

<210> SEQ ID NO 111
<211> LENGTH: 27
<212> TYPE: DNA
<213> ORGANISM: Artificial Sequence
<220> FEATURE:
<223> OTHER INFORMATION: Synthetic

<400> SEQUENCE: 111
ctacaagatt acaattaccc gtggacg　　　　　　　　　　　　　　　　　　　　　27

<210> SEQ ID NO 112
<211> LENGTH: 9
<212> TYPE: PRT
<213> ORGANISM: Artificial Sequence
<220> FEATURE:
<223> OTHER INFORMATION: Synthetic

<400> SEQUENCE: 112

Leu Gln Asp Tyr Asn Tyr Pro Trp Thr
 1               5

<210> SEQ ID NO 113
<211> LENGTH: 351
<212> TYPE: DNA
<213> ORGANISM: Artificial Sequence
<220> FEATURE:
<223> OTHER INFORMATION: Synthetic

<400> SEQUENCE: 113
gaggtgcagc tggtggagtc tgggggaggc ttggtacagc ctgggggtc cctgagactc      60 tcctgtgcag tctctggatt caccctcagt agctacgata tgcactgggt ccgccaacct    120
acaggaaaag gtctggagtg ggtctcagct attggttcta ctggtgacac atactatcca    180
ggctccgtga agggccgatt caccatctcc agagaaaatg ccaagaactc cttgtatctt    240
caaatgaaca gcctgagagc cggggacacg gctgtgtatt actgtgcaag agagggatgg    300
gacgtaccct tgacttctg gggccaggga accctggtca ccgtctcctc a              351

<210> SEQ ID NO 114
<211> LENGTH: 117
<212> TYPE: PRT
<213> ORGANISM: Artificial Sequence
<220> FEATURE:
<223> OTHER INFORMATION: Synthetic

<400> SEQUENCE: 114

Glu Val Gln Leu Val Glu Ser Gly Gly Gly Leu Val Gln Pro Gly Gly
 1               5                  10                  15

Ser Leu Arg Leu Ser Cys Ala Val Ser Gly Phe Thr Leu Ser Ser Tyr
                20                  25                  30

Asp Met His Trp Val Arg Gln Pro Thr Gly Lys Gly Leu Glu Trp Val
            35                  40                  45

Ser Ala Ile Gly Ser Thr Gly Asp Thr Tyr Tyr Pro Gly Ser Val Lys
        50                  55                  60

Gly Arg Phe Thr Ile Ser Arg Glu Asn Ala Lys Asn Ser Leu Tyr Leu
65                  70                  75                  80

Gln Met Asn Ser Leu Arg Ala Gly Asp Thr Ala Val Tyr Tyr Cys Ala
                85                  90                  95

Arg Glu Gly Trp Asp Val Pro Phe Asp Phe Trp Gly Gln Gly Thr Leu
            100                 105                 110

Val Thr Val Ser Ser
        115

<210> SEQ ID NO 115
<211> LENGTH: 321
<212> TYPE: DNA
<213> ORGANISM: Artificial Sequence
<220> FEATURE:
<223> OTHER INFORMATION: Synthetic

<400> SEQUENCE: 115

```
gccatccaga tgacccagtc tccatcctcc ctgtctgcat ctgtaggaga cagagtcacc    60
atcacttgcc gggcaagtca ggacattaga aatgatttag ctggtatca gcagaaacca   120
gggaaagccc ctaagctcct gatctatgct gcatccagtt tacaaagtgg ggtcccatca   180
cggttcagcg gcagtggatc tgggacagat ttcactctca ccatcagcag cctgcagcct   240
gaagattttg caacttatta ctgtctacaa gattacaatt acccgtggac gttcggccaa   300
gggaccaagg tggaaatcaa a                                             321
```

<210> SEQ ID NO 116
<211> LENGTH: 107
<212> TYPE: PRT
<213> ORGANISM: Artificial Sequence
<220> FEATURE:
<223> OTHER INFORMATION: Synthetic

<400> SEQUENCE: 116

```
Ala Ile Gln Met Thr Gln Ser Pro Ser Ser Leu Ser Ala Ser Val Gly
 1               5                  10                  15
Asp Arg Val Thr Ile Thr Cys Arg Ala Ser Gln Asp Ile Arg Asn Asp
            20                  25                  30
Leu Gly Trp Tyr Gln Gln Lys Pro Gly Lys Ala Pro Lys Leu Leu Ile
        35                  40                  45
Tyr Ala Ala Ser Ser Leu Gln Ser Gly Val Pro Ser Arg Phe Ser Gly
    50                  55                  60
Ser Gly Ser Gly Thr Asp Phe Thr Leu Thr Ile Ser Ser Leu Gln Pro
65                  70                  75                  80
Glu Asp Phe Ala Thr Tyr Tyr Cys Leu Gln Asp Tyr Asn Tyr Pro Trp
                85                  90                  95
Thr Phe Gly Gln Gly Thr Lys Val Glu Ile Lys
            100                 105
```

<210> SEQ ID NO 117
<211> LENGTH: 351
<212> TYPE: DNA
<213> ORGANISM: Artificial Sequence
<220> FEATURE:
<223> OTHER INFORMATION: Synthetic

<400> SEQUENCE: 117

```
gaggtgcagc tggtggagtc tgggggaggc ttggtacagc ctgggggtc cctgagactc    60
tcctgtgcag cctctggatt caccctcagt agctacgata tgcactgggt ccgccaagct   120
acaggaaaag gtctggagtg ggtctcagct attggttcta ctggtgacac atactatcca   180
ggctccgtga agggccgatt caccatctcc agagaaaatg ccaagaactc cttgtatctt   240
caaatgaaca gcctgagagc cggggacacg gctgtgtatt actgtgcaag agagggatgg   300
gacgtaccct tgacttctg gggccaggga accctggtca ccgtctcctc a            351
```

<210> SEQ ID NO 118
<211> LENGTH: 117
<212> TYPE: PRT
<213> ORGANISM: Artificial Sequence
<220> FEATURE:
<223> OTHER INFORMATION: Synthetic

<400> SEQUENCE: 118

```
Glu Val Gln Leu Val Glu Ser Gly Gly Gly Leu Val Gln Pro Gly Gly
```

```
                1               5              10              15
           Ser Leu Arg Leu Ser Cys Ala Ala Ser Gly Phe Thr Leu Ser Ser Tyr
                        20                  25                  30

Asp Met His Trp Val Arg Gln Ala Thr Gly Lys Gly Leu Glu Trp Val
                        35                  40                  45

Ser Ala Ile Gly Ser Thr Gly Asp Thr Tyr Tyr Pro Gly Ser Val Lys
            50                  55                  60

Gly Arg Phe Thr Ile Ser Arg Glu Asn Ala Lys Asn Ser Leu Tyr Leu
            65                  70                  75                  80

Gln Met Asn Ser Leu Arg Ala Gly Asp Thr Ala Val Tyr Tyr Cys Ala
                        85                  90                  95

Arg Glu Gly Trp Asp Val Pro Phe Asp Phe Trp Gly Gln Gly Thr Leu
                       100                 105                 110

Val Thr Val Ser Ser
                       115
```

<210> SEQ ID NO 119
<211> LENGTH: 321
<212> TYPE: DNA
<213> ORGANISM: Artificial Sequence
<220> FEATURE:
<223> OTHER INFORMATION: Synthetic

<400> SEQUENCE: 119

```
gccatccaga tgacccagtc tccatcctcc ctgtctgcat ctgtaggaga cagagtcacc    60
atcacttgcc gggcaagtca ggacattaga aatgatttag ctggtatcag cagaaaccca   120
gggaaagccc ctaagctcct gatctatgct gcatccagtt tacaaagtgg ggtcccatca   180
aggttcagcg gcagtggatc tggcacagat ttcactctca ccatcagcag cctgcagcct   240
gaagattttg caacttatta ctgtctacaa gattacaatt acccgtggac gttcggccaa   300
gggaccaagg tggaaatcaa a                                             321
```

<210> SEQ ID NO 120
<211> LENGTH: 107
<212> TYPE: PRT
<213> ORGANISM: Artificial Sequence
<220> FEATURE:
<223> OTHER INFORMATION: Synthetic

<400> SEQUENCE: 120

```
           Ala Ile Gln Met Thr Gln Ser Pro Ser Ser Leu Ser Ala Ser Val Gly
            1               5                  10                  15

Asp Arg Val Thr Ile Thr Cys Arg Ala Ser Gln Asp Ile Arg Asn Asp
                        20                  25                  30

Leu Gly Trp Tyr Gln Gln Lys Pro Gly Lys Ala Pro Lys Leu Leu Ile
                        35                  40                  45

Tyr Ala Ala Ser Ser Leu Gln Ser Gly Val Pro Ser Arg Phe Ser Gly
            50                  55                  60

Ser Gly Ser Gly Thr Asp Phe Thr Leu Thr Ile Ser Ser Leu Gln Pro
            65                  70                  75                  80

Glu Asp Phe Ala Thr Tyr Tyr Cys Leu Gln Asp Tyr Asn Tyr Pro Trp
                        85                  90                  95

Thr Phe Gly Gln Gly Thr Lys Val Glu Ile Lys
                       100                 105
```

<210> SEQ ID NO 121
<211> LENGTH: 384

<212> TYPE: DNA
<213> ORGANISM: Artificial Sequence
<220> FEATURE:
<223> OTHER INFORMATION: Synthetic

<400> SEQUENCE: 121

```
caggtgcagc tgcaggagtc ggggccagga ctggtgaagc cttcggagac cctgtccctc      60
acctgcactg tctctgggga ctccatcaat acttactact ggagctggtt ccggcagccc     120
ccagggaagg gactggagtg gattgggtat atctattata gtggaaccac caactacaac     180
ccctccctca agagtcgagt caccatatca atagacacgc caggaaccag gttctccctg     240
aagctgatct ctgtgaccgc agcggacacg gccgtgtatt actgtgcgag agagaggatt     300
actatgattc ggggagttac cctctactat tactcctacg gtatggacgt ctggggccaa     360
gggaccacgg tcaccgtctc ctca                                            384
```

<210> SEQ ID NO 122
<211> LENGTH: 128
<212> TYPE: PRT
<213> ORGANISM: Artificial Sequence
<220> FEATURE:
<223> OTHER INFORMATION: Synthetic

<400> SEQUENCE: 122

```
Gln Val Gln Leu Gln Glu Ser Gly Pro Gly Leu Val Lys Pro Ser Glu
 1               5                  10                  15

Thr Leu Ser Leu Thr Cys Thr Val Ser Gly Asp Ser Ile Asn Thr Tyr
            20                  25                  30

Tyr Trp Ser Trp Phe Arg Gln Pro Pro Gly Lys Gly Leu Glu Trp Ile
        35                  40                  45

Gly Tyr Ile Tyr Tyr Ser Gly Thr Thr Asn Tyr Asn Pro Ser Leu Lys
    50                  55                  60

Ser Arg Val Thr Ile Ser Ile Asp Thr Pro Arg Asn Gln Phe Ser Leu
65                  70                  75                  80

Lys Leu Ile Ser Val Thr Ala Ala Asp Thr Ala Val Tyr Tyr Cys Ala
                85                  90                  95

Arg Glu Arg Ile Thr Met Ile Arg Gly Val Thr Leu Tyr Tyr Tyr Ser
            100                 105                 110

Tyr Gly Met Asp Val Trp Gly Gln Gly Thr Thr Val Thr Val Ser Ser
        115                 120                 125
```

<210> SEQ ID NO 123
<211> LENGTH: 24
<212> TYPE: DNA
<213> ORGANISM: Artificial Sequence
<220> FEATURE:
<223> OTHER INFORMATION: Synthetic

<400> SEQUENCE: 123

```
ggggactcca tcaatactta ctac                                             24
```

<210> SEQ ID NO 124
<211> LENGTH: 8
<212> TYPE: PRT
<213> ORGANISM: Artificial Sequence
<220> FEATURE:
<223> OTHER INFORMATION: Synthetic

<400> SEQUENCE: 124

```
Gly Asp Ser Ile Asn Thr Tyr Tyr
 1               5
```

<210> SEQ ID NO 125
<211> LENGTH: 21
<212> TYPE: DNA
<213> ORGANISM: Artificial Sequence
<220> FEATURE:
<223> OTHER INFORMATION: Synthetic

<400> SEQUENCE: 125
atctattata gtggaaccac c                                                21

<210> SEQ ID NO 126
<211> LENGTH: 7
<212> TYPE: PRT
<213> ORGANISM: Artificial Sequence
<220> FEATURE:
<223> OTHER INFORMATION: Synthetic

<400> SEQUENCE: 126

Ile Tyr Tyr Ser Gly Thr Thr
 1               5

<210> SEQ ID NO 127
<211> LENGTH: 66
<212> TYPE: DNA
<213> ORGANISM: Artificial Sequence
<220> FEATURE:
<223> OTHER INFORMATION: Synthetic

<400> SEQUENCE: 127
gcgagagaga ggattactat gattcgggga gttaccctct actattactc ctacggtatg      60
gacgtc                                                                 66

<210> SEQ ID NO 128
<211> LENGTH: 22
<212> TYPE: PRT
<213> ORGANISM: Artificial Sequence
<220> FEATURE:
<223> OTHER INFORMATION: Synthetic

<400> SEQUENCE: 128

Ala Arg Glu Arg Ile Thr Met Ile Arg Gly Val Thr Leu Tyr Tyr Tyr
 1               5                  10                  15

Ser Tyr Gly Met Asp Val
            20

<210> SEQ ID NO 129
<211> LENGTH: 324
<212> TYPE: DNA
<213> ORGANISM: Artificial Sequence
<220> FEATURE:
<223> OTHER INFORMATION: Synthetic

<400> SEQUENCE: 129
gacatccaga tgacccagtc tccatccttc ctgtctgcat ctgtaggaga cagagtcacc      60
atcacttgct gggccagtca ggacattagc agttatttag cctggtatca gcaaaaacca     120
gggatagccc ctaagctcct gatctatgct gcatccactt tgcaaagtgg ggtcccatca     180
aggttcggcg gcagtggatc tgggacagaa ttcactctca caatcagcag cctgcagcct     240
gaagattttg caacttatta ctgtcaacag cttaatagtt accctcggac gttcggccaa     300
gggaccaagg tggaaatcaa acga                                            324

<210> SEQ ID NO 130
<211> LENGTH: 108
<212> TYPE: PRT
<213> ORGANISM: Artificial Sequence
<220> FEATURE:
<223> OTHER INFORMATION: Synthetic

<400> SEQUENCE: 130

Asp Ile Gln Met Thr Gln Ser Pro Ser Phe Leu Ser Ala Ser Val Gly
1               5                   10                  15
Asp Arg Val Thr Ile Thr Cys Trp Ala Ser Gln Asp Ile Ser Ser Tyr
            20                  25                  30
Leu Ala Trp Tyr Gln Gln Lys Pro Gly Ile Ala Pro Lys Leu Leu Ile
        35                  40                  45
Tyr Ala Ala Ser Thr Leu Gln Ser Gly Val Pro Ser Arg Phe Gly Gly
    50                  55                  60
Ser Gly Ser Gly Thr Glu Phe Thr Leu Thr Ile Ser Ser Leu Gln Pro
65                  70                  75                  80
Glu Asp Phe Ala Thr Tyr Tyr Cys Gln Gln Leu Asn Ser Tyr Pro Arg
                85                  90                  95
Thr Phe Gly Gln Gly Thr Lys Val Glu Ile Lys Arg
            100                 105

<210> SEQ ID NO 131
<211> LENGTH: 18
<212> TYPE: DNA
<213> ORGANISM: Artificial Sequence
<220> FEATURE:
<223> OTHER INFORMATION: Synthetic

<400> SEQUENCE: 131
caggacatta gcagttat                                                 18

<210> SEQ ID NO 132
<211> LENGTH: 6
<212> TYPE: PRT
<213> ORGANISM: Artificial Sequence
<220> FEATURE:
<223> OTHER INFORMATION: Synthetic

<400> SEQUENCE: 132

Gln Asp Ile Ser Ser Tyr
1               5

<210> SEQ ID NO 133
<211> LENGTH: 9
<212> TYPE: DNA
<213> ORGANISM: Artificial Sequence
<220> FEATURE:
<223> OTHER INFORMATION: Synthetic

<400> SEQUENCE: 133 gctgcatcc                                                            9

<210> SEQ ID NO 134
<211> LENGTH: 3
<212> TYPE: PRT
<213> ORGANISM: Artificial Sequence
<220> FEATURE:
<223> OTHER INFORMATION: Synthetic

<400> SEQUENCE: 134

Ala Ala Ser
1

<210> SEQ ID NO 135
<211> LENGTH: 27
<212> TYPE: DNA
<213> ORGANISM: Artificial Sequence
<220> FEATURE:
<223> OTHER INFORMATION: Synthetic

<400> SEQUENCE: 135
caacagctta atagttaccc tcggacg                                    27

<210> SEQ ID NO 136
<211> LENGTH: 9
<212> TYPE: PRT
<213> ORGANISM: Artificial Sequence
<220> FEATURE:
<223> OTHER INFORMATION: Synthetic

<400> SEQUENCE: 136

Gln Gln Leu Asn Ser Tyr Pro Arg Thr
 1               5

<210> SEQ ID NO 137
<211> LENGTH: 384
<212> TYPE: DNA
<213> ORGANISM: Artificial Sequence
<220> FEATURE:
<223> OTHER INFORMATION: Synthetic

<400> SEQUENCE: 137
caggtgcagc tgcaggagtc ggggccagga ctggtgaagc cttcggagac cctgtccctc      60
acctgcactg tctctgggga ctccatcaat acttactact ggagctggtt ccggcagccc     120
ccagggaagg gactggagtg gattgggtat atctattata gtggaaccac caactacaac     180
ccctccctca agagtcgagt caccatatca atagacacgc caggaaccca gttctccctg     240
aagctgatct ctgtgaccgc agcggacacg gccgtgtatt actgtgcgag agagaggatt     300
actatgattc ggggagttac cctctactat tactcctacg gtatggacgt ctggggccaa     360
gggaccacgg tcaccgtctc ctca                                           384

<210> SEQ ID NO 138
<211> LENGTH: 128
<212> TYPE: PRT
<213> ORGANISM: Artificial Sequence
<220> FEATURE:
<223> OTHER INFORMATION: Synthetic

<400> SEQUENCE: 138

Gln Val Gln Leu Gln Glu Ser Gly Pro Gly Leu Val Lys Pro Ser Glu
 1               5                  10                  15

Thr Leu Ser Leu Thr Cys Thr Val Ser Gly Asp Ser Ile Asn Thr Tyr
             20                  25                  30

Tyr Trp Ser Trp Phe Arg Gln Pro Pro Gly Lys Gly Leu Glu Trp Ile
         35                  40                  45

Gly Tyr Ile Tyr Tyr Ser Gly Thr Thr Asn Tyr Asn Pro Ser Leu Lys
     50                  55                  60

Ser Arg Val Thr Ile Ser Ile Asp Thr Pro Arg Asn Gln Phe Ser Leu
 65                  70                  75                  80

Lys Leu Ile Ser Val Thr Ala Ala Asp Thr Ala Val Tyr Tyr Cys Ala
                 85                  90                  95

Arg Glu Arg Ile Thr Met Ile Arg Gly Val Thr Leu Tyr Tyr Tyr Ser

```
                    100                 105                 110
Tyr Gly Met Asp Val Trp Gly Gln Gly Thr Thr Val Thr Val Ser Ser
        115                 120                 125

<210> SEQ ID NO 139
<211> LENGTH: 321
<212> TYPE: DNA
<213> ORGANISM: Artificial Sequence
<220> FEATURE:
<223> OTHER INFORMATION: Synthetic

<400> SEQUENCE: 139
gacatccaga tgacccagtc tccatccttc ctgtctgcat ctgtaggaga cagagtcacc      60
atcacttgct gggccagtca ggacattagc agttatttag cctggtatca gcaaaaacca    120
gggatagccc ctaagctcct gatctatgct gcatccactt tgcaaagtgg ggtcccatca    180
aggttcggcg gcagtggatc tgggacagaa ttcactctca caatcagcag cctgcagcct    240
gaagattttg caacttatta ctgtcaacag cttaatagtt accctcggac gttcggccaa    300
gggaccaagg tggaaatcaa a                                               321

<210> SEQ ID NO 140
<211> LENGTH: 107
<212> TYPE: PRT
<213> ORGANISM: Artificial Sequence
<220> FEATURE:
<223> OTHER INFORMATION: Synthetic

<400> SEQUENCE: 140

Asp Ile Gln Met Thr Gln Ser Pro Ser Phe Leu Ser Ala Ser Val Gly
 1               5                  10                  15

Asp Arg Val Thr Ile Thr Cys Trp Ala Ser Gln Asp Ile Ser Ser Tyr
            20                  25                  30

Leu Ala Trp Tyr Gln Gln Lys Pro Gly Ile Ala Pro Lys Leu Leu Ile
        35                  40                  45

Tyr Ala Ala Ser Thr Leu Gln Ser Gly Val Pro Ser Arg Phe Gly Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Gln Gln Leu Asn Ser Tyr Pro Arg
                85                  90                  95

Thr Phe Gly Gln Gly Thr Lys Val Glu Ile Lys
            100                 105

<210> SEQ ID NO 141
<211> LENGTH: 384
<212> TYPE: DNA
<213> ORGANISM: Artificial Sequence
<220> FEATURE:
<223> OTHER INFORMATION: Synthetic

<400> SEQUENCE: 141
caggtgcagc tgcaggagtc gggcccagga ctggtgaagc cttcggagac cctgtccctc      60
acctgcactg tctctgggga ctccatcaat acttactact ggagctggat ccggcagccc    120
ccagggaagg gactggagtg gattgggtat atctattata gtggaaccac caactacaac    180
ccctccctca gagtcgagt caccatatca gtagacacgt ccaagaacca gttctccctg    240
aagctgagct ctgtgaccgc tgcggacacg gccgtgtatt actgtgcgag agagaggatt    300
actatgattc ggggagttac cctctactat tactcctacg gtatggacgt ctggggccaa    360
```
gggaccacgg tcaccgtctc ctca                                                384

<210> SEQ ID NO 142
<211> LENGTH: 128
<212> TYPE: PRT
<213> ORGANISM: Artificial Sequence
<220> FEATURE:
<223> OTHER INFORMATION: Synthetic

<400> SEQUENCE: 142

Gln Val Gln Leu Gln Glu Ser Gly Pro Gly Leu Val Lys Pro Ser Glu
1               5                   10                  15

Thr Leu Ser Leu Thr Cys Thr Val Ser Gly Asp Ser Ile Asn Thr Tyr
            20                  25                  30

Tyr Trp Ser Trp Ile Arg Gln Pro Pro Gly Lys Gly Leu Glu Trp Ile
        35                  40                  45

Gly Tyr Ile Tyr Tyr Ser Gly Thr Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Glu Arg Ile Thr Met Ile Arg Gly Val Thr Leu Tyr Tyr Tyr Ser
            100                 105                 110

Tyr Gly Met Asp Val Trp Gly Gln Gly Thr Thr Val Thr Val Ser Ser
        115                 120                 125

<210> SEQ ID NO 143
<211> LENGTH: 321
<212> TYPE: DNA
<213> ORGANISM: Artificial Sequence
<220> FEATURE:
<223> OTHER INFORMATION: Synthetic

<400> SEQUENCE: 143
gacatccaga tgacccagtc tccatcctcc ctgtctgcat ctgtaggaga cagagtcacc      60
atcacttgcc gggcaagtca ggacattagc agttatttag ctggtatca gcagaaacca     120 gggaaagccc ctaagcgcct gatctatgct gcatccagtt tgcaaagtgg ggtcccatca    180
aggttcagcg gcagtggatc tgggacagaa ttcactctca caatcagcag cctgcagcct    240
gaagattttg caacttatta ctgtcaacag cttaatagtt accctcggac gttcggccaa    300
gggaccaagg tggaaatcaa a                                               321

<210> SEQ ID NO 144
<211> LENGTH: 107
<212> TYPE: PRT
<213> ORGANISM: Artificial Sequence
<220> FEATURE:
<223> OTHER INFORMATION: Synthetic

<400> SEQUENCE: 144

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Ser Tyr
            20                  25                  30

Leu Gly Trp Tyr Gln Gln Lys Pro Gly Lys Ala Pro Lys Arg Leu Ile
        35                  40                  45

Tyr Ala Ala Ser Ser Leu Gln Ser Gly Val Pro Ser Arg Phe Ser Gly

```
                     50                  55                  60

Ser Gly Ser Gly Thr Glu Phe Thr Leu Thr Ile Ser Ser Leu Gln Pro
 65                  70                  75                  80

Glu Asp Phe Ala Thr Tyr Tyr Cys Gln Gln Leu Asn Ser Tyr Pro Arg
                 85                  90                  95

Thr Phe Gly Gln Gly Thr Lys Val Glu Ile Lys
            100                 105
```

```
<210> SEQ ID NO 145
<211> LENGTH: 378
<212> TYPE: DNA
<213> ORGANISM: Artificial Sequence
<220> FEATURE:
<223> OTHER INFORMATION: Synthetic

<400> SEQUENCE: 145
caggtgcagc tggtgcagtc tggagctgag gtgaagaagc ctggggcctc agtgaaggtc      60
tcctgcaagg cttctggtta cacctttacc aactatggta tcagctgggt gcgacaggcc     120
cctggacaag gacttgagtt aatgggatgg attagtggtt acaatggtaa cacaaactat     180
gcacaagaac tccaggccag agtcaccatg accacagaca catccacgag cacagcctac     240
atggagctga ggaacctgag atctgacgac acggccgtat attactgtgc gagagataga     300
gtcgttgtag cagctgctaa ttactacttt tattctatgg acgtctgggg ccaagggacc     360
acggtcaccg tctcctca                                                    378
```

```
<210> SEQ ID NO 146
<211> LENGTH: 126
<212> TYPE: PRT
<213> ORGANISM: Artificial Sequence
<220> FEATURE:
<223> OTHER INFORMATION: Synthetic

<400> SEQUENCE: 146

Gln Val Gln Leu Val Gln Ser Gly Ala Glu Val Lys Lys Pro Gly Ala
  1               5                  10                  15

Ser Val Lys Val Ser Cys Lys Ala Ser Gly Tyr Thr Phe Thr Asn Tyr
                 20                  25                  30

Gly Ile Ser Trp Val Arg Gln Ala Pro Gly Gln Gly Leu Glu Leu Met
             35                  40                  45

Gly Trp Ile Ser Gly Tyr Asn Gly Asn Thr Asn Tyr Ala Gln Glu Leu
         50                  55                  60

Gln Ala Arg Val Thr Met Thr Thr Asp Thr Ser Thr Ser Thr Ala Tyr
 65                  70                  75                  80

Met Glu Leu Arg Asn Leu Arg Ser Asp Asp Thr Ala Val Tyr Tyr Cys
                 85                  90                  95

Ala Arg Asp Arg Val Val Val Ala Ala Ala Asn Tyr Tyr Phe Tyr Ser
                100                 105                 110

Met Asp Val Trp Gly Gln Gly Thr Thr Val Thr Val Ser Ser
            115                 120                 125
```

```
<210> SEQ ID NO 147
<211> LENGTH: 24
<212> TYPE: DNA
<213> ORGANISM: Artificial Sequence
<220> FEATURE:
<223> OTHER INFORMATION: Synthetic

<400> SEQUENCE: 147
```
ggttacacct ttaccaacta tggt                                              24

<210> SEQ ID NO 148
<211> LENGTH: 8
<212> TYPE: PRT
<213> ORGANISM: Artificial Sequence
<220> FEATURE:
<223> OTHER INFORMATION: Synthetic

<400> SEQUENCE: 148

Gly Tyr Thr Phe Thr Asn Tyr Gly
 1               5

<210> SEQ ID NO 149
<211> LENGTH: 24
<212> TYPE: DNA
<213> ORGANISM: Artificial Sequence
<220> FEATURE:
<223> OTHER INFORMATION: Synthetic

<400> SEQUENCE: 149
attagtggtt acaatggtaa caca                                              24

<210> SEQ ID NO 150
<211> LENGTH: 8
<212> TYPE: PRT
<213> ORGANISM: Artificial Sequence
<220> FEATURE:
<223> OTHER INFORMATION: Synthetic

<400> SEQUENCE: 150

Ile Ser Gly Tyr Asn Gly Asn Thr
 1               5

<210> SEQ ID NO 151
<211> LENGTH: 57
<212> TYPE: DNA
<213> ORGANISM: Artificial Sequence
<220> FEATURE:
<223> OTHER INFORMATION: Synthetic

<400> SEQUENCE: 151
gcgagagata gagtcgttgt agcagctgct aattactact tttattctat ggacgtc         57

<210> SEQ ID NO 152
<211> LENGTH: 19
<212> TYPE: PRT
<213> ORGANISM: Artificial Sequence
<220> FEATURE:
<223> OTHER INFORMATION: Synthetic

<400> SEQUENCE: 152

Ala Arg Asp Arg Val Val Val Ala Ala Ala Asn Tyr Tyr Phe Tyr Ser
 1               5                  10                  15

Met Asp Val

<210> SEQ ID NO 153
<211> LENGTH: 339
<212> TYPE: DNA
<213> ORGANISM: Artificial Sequence
<220> FEATURE:
<223> OTHER INFORMATION: Synthetic

<400> SEQUENCE: 153
gccatccaga tgacccagtc tccactctcc ctgtccgtca cccttggaca gccggcctcc      60

| | | |
|---|---|---|
| atctcctgca ggtctagtca aagcctcgta tacagtgatg gagacaccta cttgaattgg | 120 | |
| tttcagcaga ggccaggcca atctccaagg cgcctaattt ataaggtttc taaccgggac | 180 | |
| tctggggtcc cagacagatt cagcggcagt gggtcaggca ctgctttcac actgaaaatc | 240 | |
| agcggggtgg aggccgagga tgttggggtt tactactgca tgcaagctac acactggcct | 300 | |
| cggacgttcg gccaagggac caaggtggaa atcaaacga | 339 | |

<210> SEQ ID NO 154
<211> LENGTH: 113
<212> TYPE: PRT
<213> ORGANISM: Artificial Sequence
<220> FEATURE:
<223> OTHER INFORMATION: Synthetic

<400> SEQUENCE: 154

Ala Ile Gln Met Thr Gln Ser Pro Leu Ser Leu Ser Val Thr Leu Gly
1               5                   10                  15
Gln Pro Ala Ser Ile Ser Cys Arg Ser Ser Gln Ser Leu Val Tyr Ser
            20                  25                  30
Asp Gly Asp Thr Tyr Leu Asn Trp Phe Gln Gln Arg Pro Gly Gln Ser
        35                  40                  45
Pro Arg Arg Leu Ile Tyr Lys Val Ser Asn Arg Asp Ser Gly Val Pro
    50                  55                  60
Asp Arg Phe Ser Gly Ser Gly Ser Gly Thr Ala Phe Thr Leu Lys Ile
65                  70                  75                  80
Ser Gly Val Glu Ala Glu Asp Val Gly Val Tyr Tyr Cys Met Gln Ala
                85                  90                  95
Thr His Trp Pro Arg Thr Phe Gly Gln Gly Thr Lys Val Glu Ile Lys
            100                 105                 110
Arg

<210> SEQ ID NO 155
<211> LENGTH: 33
<212> TYPE: DNA
<213> ORGANISM: Artificial Sequence
<220> FEATURE:
<223> OTHER INFORMATION: Synthetic

<400> SEQUENCE: 155
caaagcctcg tatacagtga tggagacacc tac        33

<210> SEQ ID NO 156
<211> LENGTH: 11
<212> TYPE: PRT
<213> ORGANISM: Artificial Sequence
<220> FEATURE:
<223> OTHER INFORMATION: Synthetic

<400> SEQUENCE: 156

Gln Ser Leu Val Tyr Ser Asp Gly Asp Thr Tyr
1               5                   10

<210> SEQ ID NO 157
<211> LENGTH: 9
<212> TYPE: DNA
<213> ORGANISM: Artificial Sequence
<220> FEATURE:
<223> OTHER INFORMATION: Synthetic

<400> SEQUENCE: 157 aaggtttct        9

<210> SEQ ID NO 158
<211> LENGTH: 3
<212> TYPE: PRT
<213> ORGANISM: Artificial Sequence
<220> FEATURE:
<223> OTHER INFORMATION: Synthetic

<400> SEQUENCE: 158

Lys Val Ser
 1

<210> SEQ ID NO 159
<211> LENGTH: 27
<212> TYPE: DNA
<213> ORGANISM: Artificial Sequence
<220> FEATURE:
<223> OTHER INFORMATION: Synthetic

<400> SEQUENCE: 159
atgcaagcta cacactggcc tcggacg                                         27

<210> SEQ ID NO 160
<211> LENGTH: 9
<212> TYPE: PRT
<213> ORGANISM: Artificial Sequence
<220> FEATURE:
<223> OTHER INFORMATION: Synthetic

<400> SEQUENCE: 160

Met Gln Ala Thr His Trp Pro Arg Thr
 1               5

<210> SEQ ID NO 161
<211> LENGTH: 378
<212> TYPE: DNA
<213> ORGANISM: Artificial Sequence
<220> FEATURE:
<223> OTHER INFORMATION: Synthetic

<400> SEQUENCE: 161
caggttcagc tggtgcagtc tggagctgag gtgaagaagc ctggggcctc agtgaaggtc      60
tcctgcaagg cttctggtta ccctttacc aactatggta tcagctgggt gcgacaggcc     120
cctggacaag gacttgagtt aatgggatgg attagtggtt acaatggtaa cacaaactat     180
gcacaagaac tccaggccag agtcaccatg accacagaca catccacgag cacagcctac     240
atggagctga ggaacctgag atctgacgac acggccgtat attactgtgc gagagataga     300
gtcgttgtag cagctgctaa ttactacttt tattctatgg acgtctgggg ccaagggacc     360
acggtcaccg tctcctca                                                  378

<210> SEQ ID NO 162
<211> LENGTH: 126
<212> TYPE: PRT
<213> ORGANISM: Artificial Sequence
<220> FEATURE:
<223> OTHER INFORMATION: Synthetic

<400> SEQUENCE: 162

Gln Val Gln Leu Val Gln Ser Gly Ala Glu Val Lys Lys Pro Gly Ala
 1               5                  10                  15

Ser Val Lys Val Ser Cys Lys Ala Ser Gly Tyr Thr Phe Thr Asn Tyr
            20                  25                  30

Gly Ile Ser Trp Val Arg Gln Ala Pro Gly Gln Gly Leu Glu Leu Met
                35                  40                  45

Gly Trp Ile Ser Gly Tyr Asn Gly Asn Thr Asn Tyr Ala Gln Glu Leu
     50                  55                  60

Gln Ala Arg Val Thr Met Thr Thr Asp Thr Ser Thr Ser Thr Ala Tyr
 65                  70                  75                  80

Met Glu Leu Arg Asn Leu Arg Ser Asp Thr Ala Val Tyr Tyr Cys
                 85                  90                  95

Ala Arg Asp Arg Val Val Val Ala Ala Asn Tyr Tyr Phe Tyr Ser
                100                 105                 110

Met Asp Val Trp Gly Gln Gly Thr Thr Val Thr Val Ser Ser
        115                 120                 125

<210> SEQ ID NO 163
<211> LENGTH: 336
<212> TYPE: DNA
<213> ORGANISM: Artificial Sequence
<220> FEATURE:
<223> OTHER INFORMATION: Synthetic

<400> SEQUENCE: 163
gatgttgtga tgactcagtc tccactctcc ctgtccgtca cccttggaca gccggcctcc      60
atctcctgca ggtctagtca aagcctcgta tacagtgatg agacaccta cttgaattgg     120 tttcagcaga ggccaggcca atctccaagg cgcctaattt ataaggtttc taaccgggac     180
tctggggtcc cagacagatt cagcggcagt gggtcaggca ctgctttcac actgaaaatc     240
agcggggtgg aggccgagga tgttggggtt tactactgca tgcaagctac acactggcct     300
cggacgttcg gccaagggac caaggtggaa atcaaa                              336

<210> SEQ ID NO 164
<211> LENGTH: 112
<212> TYPE: PRT
<213> ORGANISM: Artificial Sequence
<220> FEATURE:
<223> OTHER INFORMATION: Synthetic

<400> SEQUENCE: 164

Asp Val Val Met Thr Gln Ser Pro Leu Ser Leu Ser Val Thr Leu Gly
  1               5                  10                  15

Gln Pro Ala Ser Ile Ser Cys Arg Ser Ser Gln Ser Leu Val Tyr Ser
             20                  25                  30

Asp Gly Asp Thr Tyr Leu Asn Trp Phe Gln Gln Arg Pro Gly Gln Ser
         35                  40                  45

Pro Arg Arg Leu Ile Tyr Lys Val Ser Asn Arg Asp Ser Gly Val Pro
 50                  55                  60

Asp Arg Phe Ser Gly Ser Gly Ser Gly Thr Ala Phe Thr Leu Lys Ile
 65                  70                  75                  80

Ser Gly Val Glu Ala Glu Asp Val Gly Val Tyr Tyr Cys Met Gln Ala
                 85                  90                  95

Thr His Trp Pro Arg Thr Phe Gly Gln Gly Thr Lys Val Glu Ile Lys
            100                 105                 110

<210> SEQ ID NO 165
<211> LENGTH: 378
<212> TYPE: DNA
<213> ORGANISM: Artificial Sequence
<220> FEATURE:
<223> OTHER INFORMATION: Synthetic -continued

<400> SEQUENCE: 165

```
caggttcagc tggtgcagtc tggagctgag gtgaagaagc ctggggcctc agtgaaggtc    60
tcctgcaagg cttctggtta cacctttacc aactatggta tcagctgggt gcgacaggcc   120
cctggacaag gcttgagtg gatgggatgg attagtggtt acaatggtaa cacaaactat   180
gcacagaagc tccagggcag agtcaccatg accacagaca catccacgag cacagcctac   240
atggagctga ggagcctgag atctgacgac acggccgtgt attactgtgc gagagataga   300
gtcgttgtag cagctgctaa ttactacttt tattctatgg acgtctgggg ccaagggacc   360
acggtcaccg tctcctca                                                 378
```

<210> SEQ ID NO 166
<211> LENGTH: 126
<212> TYPE: PRT
<213> ORGANISM: Artificial Sequence
<220> FEATURE:
<223> OTHER INFORMATION: Synthetic

<400> SEQUENCE: 166

```
Gln Val Gln Leu Val Gln Ser Gly Ala Glu Val Lys Lys Pro Gly Ala
 1               5                  10                  15

Ser Val Lys Val Ser Cys Lys Ala Ser Gly Tyr Thr Phe Thr Asn Tyr
             20                  25                  30

Gly Ile Ser Trp Val Arg Gln Ala Pro Gly Gln Gly Leu Glu Trp Met
         35                  40                  45

Gly Trp Ile Ser Gly Tyr Asn Gly Asn Thr Asn Tyr Ala Gln Lys Leu
     50                  55                  60

Gln Gly Arg Val Thr Met Thr Thr Asp Thr Ser Thr Ser Thr Ala Tyr
 65                  70                  75                  80

Met Glu Leu Arg Ser Leu Arg Ser Asp Asp Thr Ala Val Tyr Tyr Cys
                 85                  90                  95

Ala Arg Asp Arg Val Val Val Ala Ala Ala Asn Tyr Tyr Phe Tyr Ser
            100                 105                 110

Met Asp Val Trp Gly Gln Gly Thr Thr Val Thr Val Ser Ser
        115                 120                 125
```

<210> SEQ ID NO 167
<211> LENGTH: 336
<212> TYPE: DNA
<213> ORGANISM: Artificial Sequence
<220> FEATURE:
<223> OTHER INFORMATION: Synthetic

<400> SEQUENCE: 167

```
gatgttgtga tgactcagtc tccactctcc ctgcccgtca cccttggaca gccggcctcc    60
atctcctgca ggtctagtca aagcctcgta tacagtgatg gagacaccta cttgaattgg   120
tttcagcaga ggccaggcca atctccaagg cgcctaattt ataaggtttc taaccgggac   180
tctggggtcc cagacagatt cagcggcagt gggtcaggca ctgatttcac actgaaaatc   240
agcagggtgg aggctgagga tgttggggtt tattactgca tgcaagctac acactggcct   300
cggacgttcg gccaagggac caaggtggaa atcaaa                             336
```

<210> SEQ ID NO 168
<211> LENGTH: 112
<212> TYPE: PRT
<213> ORGANISM: Artificial Sequence
<220> FEATURE:
<223> OTHER INFORMATION: Synthetic

<400> SEQUENCE: 168

Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Leu Val Tyr Ser
            20                  25                  30

Asp Gly Asp Thr Tyr Leu Asn Trp Phe Gln Gln Arg Pro Gly Gln Ser
        35                  40                  45

Pro Arg Arg Leu Ile Tyr Lys Val Ser Asn Arg Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Thr His Trp Pro Arg Thr Phe Gly Gln Gly Thr Lys Val Glu Ile Lys
            100                 105                 110

<210> SEQ ID NO 169
<211> LENGTH: 375
<212> TYPE: DNA
<213> ORGANISM: Artificial Sequence
<220> FEATURE:
<223> OTHER INFORMATION: Synthetic

<400> SEQUENCE: 169
caggtccact tgaaggagtc tggtcctacg ctggtgaaac ccacacagac cctcacgctg      60
acctgcacct tctctggatt ctcactcatc actagtggag tgggtgtggg ctggattcgt     120
cagcccccg gaaaggccct ggagtggctt gcactcattt attggaatgg tgataagcgc      180
tacagcccat ctctgaagag caggctcacc atcaccaagg acacctccaa aaaccaggtg     240
gtccttacaa tgaccaacat ggaccctgtg acacagcca catattactg tgcacacagg      300
ataactgaaa ctagttacta cttctactac ggtatggacg tctggggcca agggaccacg     360
gtcaccgtct cctca                                                      375

<210> SEQ ID NO 170
<211> LENGTH: 125
<212> TYPE: PRT
<213> ORGANISM: Artificial Sequence
<220> FEATURE:
<223> OTHER INFORMATION: Synthetic

<400> SEQUENCE: 170

Gln Val His Leu Lys Glu Ser Gly Pro Thr Leu Val Lys Pro Thr Gln
1               5                   10                  15

Thr Leu Thr Leu Thr Cys Thr Phe Ser Gly Phe Ser Leu Ile Thr Ser
            20                  25                  30

Gly Val Gly Val Gly Trp Ile Arg Gln Pro Pro Gly Lys Ala Leu Glu
        35                  40                  45

Trp Leu Ala Leu Ile Tyr Trp Asn Gly Asp Lys Arg Tyr Ser Pro Ser
    50                  55                  60

Leu Lys Ser Arg Leu Thr Ile Thr Lys Asp Thr Ser Lys Asn Gln Val
65                  70                  75                  80

Val Leu Thr Met Thr Asn Met Asp Pro Val Asp Thr Ala Thr Tyr Tyr
                85                  90                  95

Cys Ala His Arg Ile Thr Glu Thr Ser Tyr Tyr Phe Tyr Tyr Gly Met
            100                 105                 110

Asp Val Trp Gly Gln Gly Thr Thr Val Thr Val Ser Ser
         115                 120                 125

<210> SEQ ID NO 171
<211> LENGTH: 30
<212> TYPE: DNA
<213> ORGANISM: Artificial Sequence
<220> FEATURE:
<223> OTHER INFORMATION: Synthetic

<400> SEQUENCE: 171
ggattctcac tcatcactag tggagtgggt                                      30

<210> SEQ ID NO 172
<211> LENGTH: 10
<212> TYPE: PRT
<213> ORGANISM: Artificial Sequence
<220> FEATURE:
<223> OTHER INFORMATION: Synthetic

<400> SEQUENCE: 172

Gly Phe Ser Leu Ile Thr Ser Gly Val Gly
1               5                   10

<210> SEQ ID NO 173
<211> LENGTH: 21
<212> TYPE: DNA
<213> ORGANISM: Artificial Sequence
<220> FEATURE:
<223> OTHER INFORMATION: Synthetic

<400> SEQUENCE: 173
atttattgga atggtgataa g                                               21

<210> SEQ ID NO 174
<211> LENGTH: 7
<212> TYPE: PRT
<213> ORGANISM: Artificial Sequence
<220> FEATURE:
<223> OTHER INFORMATION: Synthetic

<400> SEQUENCE: 174

Ile Tyr Trp Asn Gly Asp Lys
1               5

<210> SEQ ID NO 175
<211> LENGTH: 51
<212> TYPE: DNA
<213> ORGANISM: Artificial Sequence
<220> FEATURE:
<223> OTHER INFORMATION: Synthetic

<400> SEQUENCE: 175
gcacacagga taactgaaac tagttactac ttctactacg gtatggacgt c              51

<210> SEQ ID NO 176
<211> LENGTH: 17
<212> TYPE: PRT
<213> ORGANISM: Artificial Sequence
<220> FEATURE:
<223> OTHER INFORMATION: Synthetic

<400> SEQUENCE: 176

Ala His Arg Ile Thr Glu Thr Ser Tyr Tyr Phe Tyr Tyr Gly Met Asp
1               5                   10                  15

Val

<210> SEQ ID NO 177
<211> LENGTH: 339
<212> TYPE: DNA
<213> ORGANISM: Artificial Sequence
<220> FEATURE:
<223> OTHER INFORMATION: Synthetic

<400> SEQUENCE: 177

```
gacatccaga tgacccagtc tccactctcc ctgcccgtca cccctggaga gccggcctcc      60
atctcctgca ggtctagtca gagcctcctg catagtcatg gatacgacta tttggattgg     120
tacctgcaga agccagggca gtctccacag ctcctgatct atttgggttc taatcgggcc     180
tccggggtcc ctgacaggtt cagtggcagt ggatcaggca cagatttac actgaaaatc      240 agcagagtgg aggctgagga tgttggggtt tattactgca tgcaagctct acaaactccg     300
ctcactttcg gcggagggac caaggtggaa atcaaacga                            339
```

<210> SEQ ID NO 178
<211> LENGTH: 113
<212> TYPE: PRT
<213> ORGANISM: Artificial Sequence
<220> FEATURE:
<223> OTHER INFORMATION: Synthetic

<400> SEQUENCE: 178

Asp Ile Gln Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

His Gly Tyr Asp Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Thr Pro Leu Thr Phe Gly Gly Gly Thr Lys Val Glu Ile Lys
            100                 105                 110

Arg

<210> SEQ ID NO 179
<211> LENGTH: 33
<212> TYPE: DNA
<213> ORGANISM: Artificial Sequence
<220> FEATURE:
<223> OTHER INFORMATION: Synthetic

<400> SEQUENCE: 179

```
cagagcctcc tgcatagtca tggatacgac tat                                   33
```

<210> SEQ ID NO 180
<211> LENGTH: 11
<212> TYPE: PRT
<213> ORGANISM: Artificial Sequence
<220> FEATURE:
<223> OTHER INFORMATION: Synthetic

<400> SEQUENCE: 180

Gln Ser Leu Leu His Ser His Gly Tyr Asp Tyr

```
                1               5                    10
```

<210> SEQ ID NO 181
<211> LENGTH: 9
<212> TYPE: DNA
<213> ORGANISM: Artificial Sequence
<220> FEATURE:
<223> OTHER INFORMATION: Synthetic

<400> SEQUENCE: 181 ttgggttct                                                                 9

<210> SEQ ID NO 182
<211> LENGTH: 3
<212> TYPE: PRT
<213> ORGANISM: Artificial Sequence
<220> FEATURE:
<223> OTHER INFORMATION: Synthetic

<400> SEQUENCE: 182

Leu Gly Ser
 1

<210> SEQ ID NO 183
<211> LENGTH: 27
<212> TYPE: DNA
<213> ORGANISM: Artificial Sequence
<220> FEATURE:
<223> OTHER INFORMATION: Synthetic

<400> SEQUENCE: 183
atgcaagctc tacaaactcc gctcact                                            27

<210> SEQ ID NO 184
<211> LENGTH: 9
<212> TYPE: PRT
<213> ORGANISM: Artificial Sequence
<220> FEATURE:
<223> OTHER INFORMATION: Synthetic

<400> SEQUENCE: 184

Met Gln Ala Leu Gln Thr Pro Leu Thr
 1               5

<210> SEQ ID NO 185
<211> LENGTH: 375
<212> TYPE: DNA
<213> ORGANISM: Artificial Sequence
<220> FEATURE:
<223> OTHER INFORMATION: Synthetic

<400> SEQUENCE: 185
cagatcacct tgaaggagtc tggtcctacg ctggtgaaac ccacacagac cctcacgctg        60
acctgcacct tctctggatt ctcactcatc actagtggag tgggtgtggg ctggattcgt       120 cagcccccg gaaaggccct ggagtggctt gcactcattt attggaatgg tgataagcgc        180
tacagcccat ctctgaagag caggctcacc atcaccaagg acacctccaa aaaccaggtg       240
gtccttacaa tgaccaacat ggaccctgtg gacagagcca catattactg tgcacacagg       300
ataactgaaa ctagttacta cttctactac ggtatggacg tctggggcca agggaccacg       360
gtcaccgtct cctca                                                        375

<210> SEQ ID NO 186
<211> LENGTH: 125

```
<212> TYPE: PRT
<213> ORGANISM: Artificial Sequence
<220> FEATURE:
<223> OTHER INFORMATION: Synthetic

<400> SEQUENCE: 186

Gln Ile Thr Leu Lys Glu Ser Gly Pro Thr Leu Val Lys Pro Thr Gln
 1               5                  10                  15

Thr Leu Thr Leu Thr Cys Thr Phe Ser Gly Phe Ser Leu Ile Thr Ser
             20                  25                  30

Gly Val Gly Val Gly Trp Ile Arg Gln Pro Pro Gly Lys Ala Leu Glu
         35                  40                  45

Trp Leu Ala Leu Ile Tyr Trp Asn Gly Asp Lys Arg Tyr Ser Pro Ser
 50                  55                  60

Leu Lys Ser Arg Leu Thr Ile Thr Lys Asp Thr Ser Lys Asn Gln Val
65                  70                  75                  80

Val Leu Thr Met Thr Asn Met Asp Pro Val Asp Thr Ala Thr Tyr Tyr
                 85                  90                  95

Cys Ala His Arg Ile Thr Glu Thr Ser Tyr Tyr Phe Tyr Tyr Gly Met
            100                 105                 110

Asp Val Trp Gly Gln Gly Thr Thr Val Thr Val Ser Ser
            115                 120                 125

<210> SEQ ID NO 187
<211> LENGTH: 336
<212> TYPE: DNA
<213> ORGANISM: Artificial Sequence
<220> FEATURE:
<223> OTHER INFORMATION: Synthetic

<400> SEQUENCE: 187
gatattgtga tgactcagtc tccactctcc ctgcccgtca cccctggaga gccggcctcc      60
atctcctgca ggtctagtca gagcctcctg catagtcatg gatacgacta tttggattgg     120
tacctgcaga agccagggca gtctccacag ctcctgatct atttgggttc taatcgggcc     180
tccggggtcc ctgacaggtt cagtggcagt ggatcaggca cagattttac actgaaaatc     240
agcagagtgg aggctgagga tgttggggtt tattactgca tgcaagctct acaaactccg     300
ctcactttcg gcggagggac caaggtggag atcaaa                               336

<210> SEQ ID NO 188
<211> LENGTH: 112
<212> TYPE: PRT
<213> ORGANISM: Artificial Sequence
<220> FEATURE:
<223> OTHER INFORMATION: Synthetic

<400> SEQUENCE: 188

Asp Ile Val Met Thr Gln Ser Pro Leu Ser Leu Pro Val Thr Pro Gly
 1               5                  10                  15

Glu Pro Ala Ser Ile Ser Cys Arg Ser Ser Gln Ser Leu Leu His Ser
             20                  25                  30

His Gly Tyr Asp Tyr Leu Asp Trp Tyr Leu Gln Lys Pro Gly Gln Ser
         35                  40                  45

Pro Gln Leu Leu Ile Tyr Leu Gly Ser Asn Arg Ala Ser Gly Val Pro
 50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
```

85                  90                  95
Leu Gln Thr Pro Leu Thr Phe Gly Gly Gly Thr Lys Val Glu Ile Lys
            100                 105                 110

<210> SEQ ID NO 189
<211> LENGTH: 375
<212> TYPE: DNA
<213> ORGANISM: Artificial Sequence
<220> FEATURE:
<223> OTHER INFORMATION: Synthetic

<400> SEQUENCE: 189
cagatcacct tgaaggagtc tggtcctacg ctggtgaaac ccacacagac cctcacgctg      60
acctgcacct tctctggatt ctcactcatc actagtggag tgggtgtggg ctggatccgt     120
cagcccccag gaaaggccct ggagtggctt gcactcattt attggaatgg tgataagcgc     180
tacagcccat ctctgaagag caggctcacc atcaccaagg acacctccaa aaaccaggtg     240
gtccttacaa tgaccaacat ggaccctgtg acacagcca catattactg tgcacacagg      300
ataactgaaa ctagttacta cttctactac ggtatggacg tctggggcca agggaccacg     360
gtcaccgtct cctca                                                      375

<210> SEQ ID NO 190
<211> LENGTH: 125
<212> TYPE: PRT
<213> ORGANISM: Artificial Sequence
<220> FEATURE:
<223> OTHER INFORMATION: Synthetic

<400> SEQUENCE: 190

Gln Ile Thr Leu Lys Glu Ser Gly Pro Thr Leu Val Lys Pro Thr Gln
 1               5                  10                  15

Thr Leu Thr Leu Thr Cys Thr Phe Ser Gly Phe Ser Leu Ile Thr Ser
            20                  25                  30

Gly Val Gly Val Gly Trp Ile Arg Gln Pro Pro Gly Lys Ala Leu Glu
        35                  40                  45

Trp Leu Ala Leu Ile Tyr Trp Asn Gly Asp Lys Arg Tyr Ser Pro Ser
    50                  55                  60

Leu Lys Ser Arg Leu Thr Ile Thr Lys Asp Thr Ser Lys Asn Gln Val
65                  70                  75                  80

Val Leu Thr Met Thr Asn Met Asp Pro Val Asp Thr Ala Thr Tyr Tyr
                85                  90                  95

Cys Ala His Arg Ile Thr Glu Thr Ser Tyr Tyr Phe Tyr Tyr Gly Met
            100                 105                 110

Asp Val Trp Gly Gln Gly Thr Thr Val Thr Val Ser Ser
        115                 120                 125

<210> SEQ ID NO 191
<211> LENGTH: 336
<212> TYPE: DNA
<213> ORGANISM: Artificial Sequence
<220> FEATURE:
<223> OTHER INFORMATION: Synthetic

<400> SEQUENCE: 191
gatattgtga tgactcagtc tccactctcc ctgcccgtca cccctggaga gccggcctcc      60
atctcctgca ggtctagtca gagcctcctg catagtcatg gatacgacta tttggattgg     120
tacctgcaga agccagggca gtctccacag ctcctgatct atttgggttc taatcgggcc     180

```
tccggggtcc ctgacaggtt cagtggcagt ggatcaggca cagattttac actgaaaatc      240
agcagagtgg aggctgagga tgttggggtt tattactgca tgcaagctct acaaactccg      300
ctcactttcg gcggagggac caaggtggag atcaaa                                336
```

<210> SEQ ID NO 192
<211> LENGTH: 112
<212> TYPE: PRT
<213> ORGANISM: Artificial Sequence
<220> FEATURE:
<223> OTHER INFORMATION: Synthetic

<400> SEQUENCE: 192

```
Asp Ile Val Met Thr Gln Ser Pro Leu Ser Leu Pro Val Thr Pro Gly
 1               5                  10                  15

Glu Pro Ala Ser Ile Ser Cys Arg Ser Ser Gln Ser Leu Leu His Ser
             20                  25                  30

His Gly Tyr Asp Tyr Leu Asp Trp Tyr Leu Gln Lys Pro Gly Gln Ser
         35                  40                  45

Pro Gln Leu Leu Ile Tyr Leu Gly Ser Asn Arg Ala Ser Gly Val Pro
     50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Met Gln Ala
                 85                  90                  95

Leu Gln Thr Pro Leu Thr Phe Gly Gly Gly Thr Lys Val Glu Ile Lys
            100                 105                 110
```

<210> SEQ ID NO 193
<211> LENGTH: 375
<212> TYPE: DNA
<213> ORGANISM: Artificial Sequence
<220> FEATURE:
<223> OTHER INFORMATION: Synthetic

<400> SEQUENCE: 193

```
cagatcaccct tgaaggagtc tggtcctact ctggtgaaac cctcacagac cctcacgctg      60
acctgcacct tctctgggtt ctcactcagc actagtggag tgggtgtggg ctggatccgt      120
cagcccccag gaaaggccct ggagtggctt gcactcattt attggaattc tgataagcgc      180
tacagcccat ctctgaagag caggctcacc atcaccaagg acacctccaa aaaccaggta      240
gtccttacaa tgaccaacat ggaccctgtg gacacagcca catattactg tgcacacaga      300
catgacagct cgtcctacta cttctactac ggtatggacg tctggggcca agggatcacg      360
gtcaccgtct cctca                                                       375
```

<210> SEQ ID NO 194
<211> LENGTH: 125
<212> TYPE: PRT
<213> ORGANISM: Artificial Sequence
<220> FEATURE:
<223> OTHER INFORMATION: Synthetic

<400> SEQUENCE: 194

```
Gln Ile Thr Leu Lys Glu Ser Gly Pro Thr Leu Val Lys Pro Ser Gln
 1               5                  10                  15

Thr Leu Thr Leu Thr Cys Thr Phe Ser Gly Phe Ser Leu Ser Thr Ser
             20                  25                  30

Gly Val Gly Val Gly Trp Ile Arg Gln Pro Pro Gly Lys Ala Leu Glu
         35                  40                  45
```

Trp Leu Ala Leu Ile Tyr Trp Asn Ser Asp Lys Arg Tyr Ser Pro Ser
        50                  55                  60

Leu Lys Ser Arg Leu Thr Ile Thr Lys Asp Thr Ser Lys Asn Gln Val
 65                  70                  75                  80

Val Leu Thr Met Thr Asn Met Asp Pro Val Asp Thr Ala Thr Tyr Tyr
                 85                  90                  95

Cys Ala His Arg His Asp Ser Ser Ser Tyr Tyr Phe Tyr Tyr Gly Met
                100                 105                 110

Asp Val Trp Gly Gln Gly Ile Thr Val Thr Val Ser Ser
            115                 120                 125

<210> SEQ ID NO 195
<211> LENGTH: 30
<212> TYPE: DNA
<213> ORGANISM: Artificial Sequence
<220> FEATURE:
<223> OTHER INFORMATION: Synthetic

<400> SEQUENCE: 195
gggttctcac tcagcactag tggagtgggt                                      30

<210> SEQ ID NO 196
<211> LENGTH: 10
<212> TYPE: PRT
<213> ORGANISM: Artificial Sequence
<220> FEATURE:
<223> OTHER INFORMATION: Synthetic

<400> SEQUENCE: 196

Gly Phe Ser Leu Ser Thr Ser Gly Val Gly
 1               5                  10

<210> SEQ ID NO 197
<211> LENGTH: 21
<212> TYPE: DNA
<213> ORGANISM: Artificial Sequence
<220> FEATURE:
<223> OTHER INFORMATION: Synthetic

<400> SEQUENCE: 197
atttattgga attctgataa g                                               21

<210> SEQ ID NO 198
<211> LENGTH: 7
<212> TYPE: PRT
<213> ORGANISM: Artificial Sequence
<220> FEATURE:
<223> OTHER INFORMATION: Synthetic

<400> SEQUENCE: 198

Ile Tyr Trp Asn Ser Asp Lys
 1               5

<210> SEQ ID NO 199
<211> LENGTH: 51
<212> TYPE: DNA
<213> ORGANISM: Artificial Sequence
<220> FEATURE:
<223> OTHER INFORMATION: Synthetic

<400> SEQUENCE: 199
gcacacagac atgacagctc gtcctactac ttctactacg gtatggacgt c              51

```
<210> SEQ ID NO 200
<211> LENGTH: 17
<212> TYPE: PRT
<213> ORGANISM: Artificial Sequence
<220> FEATURE:
<223> OTHER INFORMATION: Synthetic

<400> SEQUENCE: 200

Ala His Arg His Asp Ser Ser Tyr Tyr Phe Tyr Tyr Gly Met Asp
 1               5                  10                  15

Val

<210> SEQ ID NO 201
<211> LENGTH: 339
<212> TYPE: DNA
<213> ORGANISM: Artificial Sequence
<220> FEATURE:
<223> OTHER INFORMATION: Synthetic

<400> SEQUENCE: 201
gacatccaga tgacccagtc tccgctctcc ctgcccgtca cccctggaga gccggcctcc      60
atctcctgca ggtctagtca gagcctcctc catagtcatg gatacaacta tttggattgg     120
tacctgcaga agccagggca gtctccacaa ctcctgatct atttgggttc taatcgggcc     180
tccggggtcc ctgacaggtt cagtggcggt ggatcaggca cagattttac actgaaaatc     240
agcagagtgg aggctgagga tgttgggatt tattactgca tgcaagctct acagactcct     300
ctcactttcg gcggagggac caaggtggag atcaaacga                            339

<210> SEQ ID NO 202
<211> LENGTH: 113
<212> TYPE: PRT
<213> ORGANISM: Artificial Sequence
<220> FEATURE:
<223> OTHER INFORMATION: Synthetic

<400> SEQUENCE: 202

Asp Ile Gln Met Thr Gln Ser Pro Leu Ser Leu Pro Val Thr Pro Gly
 1               5                  10                  15

Glu Pro Ala Ser Ile Ser Cys Arg Ser Ser Gln Ser Leu Leu His Ser
            20                  25                  30

His Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Gly Gly Ser Gly Thr Asp Phe Thr Leu Lys Ile
65                  70                  75                  80

Ser Arg Val Glu Ala Glu Asp Val Gly Ile Tyr Tyr Cys Met Gln Ala
                85                  90                  95

Leu Gln Thr Pro Leu Thr Phe Gly Gly Gly Thr Lys Val Glu Ile Lys
            100                 105                 110

Arg

<210> SEQ ID NO 203
<211> LENGTH: 33
<212> TYPE: DNA
<213> ORGANISM: Artificial Sequence
<220> FEATURE:
<223> OTHER INFORMATION: Synthetic

<400> SEQUENCE: 203
```
cagagcctcc tccatagtca tggatacaac tat                                    33

<210> SEQ ID NO 204
<211> LENGTH: 11
<212> TYPE: PRT
<213> ORGANISM: Artificial Sequence
<220> FEATURE:
<223> OTHER INFORMATION: Synthetic

<400> SEQUENCE: 204

Gln Ser Leu Leu His Ser His Gly Tyr Asn Tyr
 1               5                  10

<210> SEQ ID NO 205
<211> LENGTH: 9
<212> TYPE: DNA
<213> ORGANISM: Artificial Sequence
<220> FEATURE:
<223> OTHER INFORMATION: Synthetic

<400> SEQUENCE: 205 ttgggttct                                                                9

<210> SEQ ID NO 206
<211> LENGTH: 3
<212> TYPE: PRT
<213> ORGANISM: Artificial Sequence
<220> FEATURE:
<223> OTHER INFORMATION: Synthetic

<400> SEQUENCE: 206

Leu Gly Ser
 1

<210> SEQ ID NO 207
<211> LENGTH: 27
<212> TYPE: DNA
<213> ORGANISM: Artificial Sequence
<220> FEATURE:
<223> OTHER INFORMATION: Synthetic

<400> SEQUENCE: 207
atgcaagctc tacagactcc tctcact                                           27

<210> SEQ ID NO 208
<211> LENGTH: 9
<212> TYPE: PRT
<213> ORGANISM: Artificial Sequence
<220> FEATURE:
<223> OTHER INFORMATION: Synthetic

<400> SEQUENCE: 208

Met Gln Ala Leu Gln Thr Pro Leu Thr
 1               5

<210> SEQ ID NO 209
<211> LENGTH: 375
<212> TYPE: DNA
<213> ORGANISM: Artificial Sequence
<220> FEATURE:
<223> OTHER INFORMATION: Synthetic

<400> SEQUENCE: 209
cagatcacct tgaaggagtc tggtcctact ctggtgaaac cctcacagac cctcacgctg      60
acctgcacct tctctgggtt ctcactcagc actagtggag tgggtgtggg ctggatccgt     120

```
cagcccccag gaaaggccct ggagtggctt gcactcattt attggaattc tgataagcgc    180
tacagcccat ctctgaagag caggctcacc atcaccaagg acacctccaa aaaccaggta    240
gtccttacaa tgaccaacat ggaccctgtg acacagcca catattactg tgcacacaga    300
catgacagct cgtcctacta cttctactac ggtatggacg tctggggcca agggaccacg    360
gtcaccgtct cctca                                                     375
```

<210> SEQ ID NO 210
<211> LENGTH: 125
<212> TYPE: PRT
<213> ORGANISM: Artificial Sequence
<220> FEATURE:
<223> OTHER INFORMATION: Synthetic

<400> SEQUENCE: 210

```
Gln Ile Thr Leu Lys Glu Ser Gly Pro Thr Leu Val Lys Pro Ser Gln
1               5                   10                  15

Thr Leu Thr Leu Thr Cys Thr Phe Ser Gly Phe Ser Leu Ser Thr Ser
            20                  25                  30

Gly Val Gly Val Gly Trp Ile Arg Gln Pro Pro Gly Lys Ala Leu Glu
        35                  40                  45

Trp Leu Ala Leu Ile Tyr Trp Asn Ser Asp Lys Arg Tyr Ser Pro Ser
    50                  55                  60

Leu Lys Ser Arg Leu Thr Ile Thr Lys Asp Thr Ser Lys Asn Gln Val
65                  70                  75                  80

Val Leu Thr Met Thr Asn Met Asp Pro Val Asp Thr Ala Thr Tyr Tyr
                85                  90                  95

Cys Ala His Arg His Asp Ser Ser Ser Tyr Tyr Phe Tyr Tyr Gly Met
            100                 105                 110

Asp Val Trp Gly Gln Gly Thr Thr Val Thr Val Ser Ser
        115                 120                 125
```

<210> SEQ ID NO 211
<211> LENGTH: 336
<212> TYPE: DNA
<213> ORGANISM: Artificial Sequence
<220> FEATURE:
<223> OTHER INFORMATION: Synthetic

<400> SEQUENCE: 211

```
gatattgtga tgactcagtc tccgctctcc ctgcccgtca cccctggaga gccggcctcc     60
atctcctgca ggtctagtca gagcctcctc catagtcatg gatacaacta tttggattgg    120
tacctgcaga agccagggca gtctccacaa ctcctgatct atttgggttc taatcgggcc    180
tccggggtcc ctgacaggtt cagtggcggt ggatcaggca cagattttac actgaaaatc    240
agcagagtgg aggctgagga tgttggggatt tattactgca tgcaagctct acagactcct    300
ctcactttcg gcggagggac caaggtggag atcaaa                              336
```

<210> SEQ ID NO 212
<211> LENGTH: 112
<212> TYPE: PRT
<213> ORGANISM: Artificial Sequence
<220> FEATURE:
<223> OTHER INFORMATION: Synthetic

<400> SEQUENCE: 212

```
Asp Ile Val Met Thr Gln Ser Pro Leu Ser Leu Pro Val Thr Pro Gly
1               5                   10                  15
```

Glu Pro Ala Ser Ile Ser Cys Arg Ser Ser Gln Ser Leu Leu His Ser
            20                  25                  30

His Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Gly Ser Gly Thr Asp Phe Thr Leu Lys Ile
65                  70                  75                  80

Ser Arg Val Glu Ala Glu Asp Val Gly Ile Tyr Tyr Cys Met Gln Ala
                85                  90                  95

Leu Gln Thr Pro Leu Thr Phe Gly Gly Gly Thr Lys Val Glu Ile Lys
            100                 105                 110

<210> SEQ ID NO 213
<211> LENGTH: 375
<212> TYPE: DNA
<213> ORGANISM: Artificial Sequence
<220> FEATURE:
<223> OTHER INFORMATION: Synthetic

<400> SEQUENCE: 213
cagatcacct tgaaggagtc tggtcctacg ctggtgaaac ccacacagac cctcacgctg     60
acctgcacct tctctgggtt ctcactcagc actagtggag tgggtgtggg ctggatccgt    120
cagcccccag gaaaggccct ggagtggctt gcactcattt attggaattc tgataagcgc    180
tacagcccat ctctgaagag caggctcacc atcaccaagg acacctccaa aaaccaggtg    240
gtccttacaa tgaccaacat ggaccctgtg gacacagcca catattactg tgcacacaga    300
catgacagct cgtcctacta cttctactac ggtatggacg tctggggcca agggaccacg    360
gtcaccgtct cctca                                                     375

<210> SEQ ID NO 214
<211> LENGTH: 125
<212> TYPE: PRT
<213> ORGANISM: Artificial Sequence
<220> FEATURE:
<223> OTHER INFORMATION: Synthetic

<400> SEQUENCE: 214

Gln Ile Thr Leu Lys Glu Ser Gly Pro Thr Leu Val Lys Pro Thr Gln
1               5                   10                  15

Thr Leu Thr Leu Thr Cys Thr Phe Ser Gly Phe Ser Leu Ser Thr Ser
            20                  25                  30

Gly Val Gly Val Gly Trp Ile Arg Gln Pro Pro Gly Lys Ala Leu Glu
        35                  40                  45

Trp Leu Ala Leu Ile Tyr Trp Asn Ser Asp Lys Arg Tyr Ser Pro Ser
    50                  55                  60

Leu Lys Ser Arg Leu Thr Ile Thr Lys Asp Thr Ser Lys Asn Gln Val
65                  70                  75                  80

Val Leu Thr Met Thr Asn Met Asp Pro Val Asp Thr Ala Thr Tyr Tyr
                85                  90                  95

Cys Ala His Arg His Asp Ser Ser Tyr Tyr Phe Tyr Tyr Gly Met
            100                 105                 110

Asp Val Trp Gly Gln Gly Thr Thr Val Thr Val Ser Ser
            115                 120                 125

<210> SEQ ID NO 215
<211> LENGTH: 336

<212> TYPE: DNA
<213> ORGANISM: Artificial Sequence
<220> FEATURE:
<223> OTHER INFORMATION: Synthetic

<400> SEQUENCE: 215

```
gatattgtga tgactcagtc tccactctcc ctgcccgtca cccctggaga gccggcctcc    60
atctcctgca ggtctagtca gagcctcctc catagtcatg gatacaacta tttggattgg   120
tacctgcaga agccagggca gtctccacag ctcctgatct atttgggttc aatcgggcc    180
tccggggtcc ctgacaggtt cagtggcagt ggatcaggca cagatttac actgaaaatc    240
agcagagtgg aggctgagga tgttggggtt attactgca tgcaagctct acagactcct    300
ctcactttcg gcggagggac caaggtggag atcaaa                             336
```

<210> SEQ ID NO 216
<211> LENGTH: 112
<212> TYPE: PRT
<213> ORGANISM: Artificial Sequence
<220> FEATURE:
<223> OTHER INFORMATION: Synthetic

<400> SEQUENCE: 216

```
Asp Ile Val Met Thr Gln Ser Pro Leu Ser Leu Pro Val Thr Pro Gly
 1               5                  10                  15
Glu Pro Ala Ser Ile Ser Cys Arg Ser Ser Gln Ser Leu Leu His Ser
            20                  25                  30
His Gly Tyr Asn Tyr Leu Asp Trp Tyr Leu Gln Lys Pro Gly Gln Ser
        35                  40                  45
Pro Gln Leu Leu Ile Tyr Leu Gly Ser Asn Arg Ala Ser Gly Val Pro
    50                  55                  60
Asp Arg Phe Ser Gly Ser Gly Ser Gly Thr Asp Phe Thr Leu Lys Ile
65                  70                  75                  80
Ser Arg Val Glu Ala Glu Asp Val Gly Val Tyr Tyr Cys Met Gln Ala
                85                  90                  95
Leu Gln Thr Pro Leu Thr Phe Gly Gly Gly Thr Lys Val Glu Ile Lys
            100                 105                 110
```

<210> SEQ ID NO 217
<211> LENGTH: 381
<212> TYPE: DNA
<213> ORGANISM: Artificial Sequence
<220> FEATURE:
<223> OTHER INFORMATION: Synthetic

<400> SEQUENCE: 217

```
gagatgcaac tggtggagtc tgggggaggc ttggtccagc ctggggggtc cctgagactc    60
tcctgtgcag cctctggatt cacctttagt agtcactgga tgaagtgggt ccgccaggct   120
ccagggaagg ggctggagtg ggtggccaac ataaaccaag atggaagtga gaaatactat   180
gtggactctg tgaagggccg attcaccatc tccagagaca cgccaagaa ctcactgttt   240
ctgcaaatga acagcctgag agccgaggac acggctgtgt attactgtgc gagagatatt   300
gtactaatgg tctatgatat ggactactac tactacggta tggacgtctg gggccaaggg   360
accacggtca ccgtctcctc a                                             381
```

<210> SEQ ID NO 218
<211> LENGTH: 127
<212> TYPE: PRT
<213> ORGANISM: Artificial Sequence

```
<220> FEATURE:
<223> OTHER INFORMATION: Synthetic

<400> SEQUENCE: 218

Glu Met Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Ser Ser His
            20                  25                  30

Trp Met Lys Trp Val Arg Gln Ala Pro Gly Lys Gly Leu Glu Trp Val
        35                  40                  45

Ala Asn Ile Asn Gln Asp Gly Ser Glu Lys Tyr Tyr Val Asp Ser Val
    50                  55                  60

Lys Gly Arg Phe Thr Ile Ser Arg Asp Asn Ala Lys Asn Ser Leu Phe
65                  70                  75                  80

Leu Gln Met Asn Ser Leu Arg Ala Glu Asp Thr Ala Val Tyr Tyr Cys
                85                  90                  95

Ala Arg Asp Ile Val Leu Met Val Tyr Asp Met Asp Tyr Tyr Tyr Tyr
            100                 105                 110

Gly Met Asp Val Trp Gly Gln Gly Thr Thr Val Thr Val Ser Ser
        115                 120                 125

<210> SEQ ID NO 219
<211> LENGTH: 24
<212> TYPE: DNA
<213> ORGANISM: Artificial Sequence
<220> FEATURE:
<223> OTHER INFORMATION: Synthetic

<400> SEQUENCE: 219
ggattcacct ttagtagtca ctgg                                          24

<210> SEQ ID NO 220
<211> LENGTH: 8
<212> TYPE: PRT
<213> ORGANISM: Artificial Sequence
<220> FEATURE:
<223> OTHER INFORMATION: Synthetic

<400> SEQUENCE: 220

Gly Phe Thr Phe Ser Ser His Trp
 1               5

<210> SEQ ID NO 221
<211> LENGTH: 24
<212> TYPE: DNA
<213> ORGANISM: Artificial Sequence
<220> FEATURE:
<223> OTHER INFORMATION: Synthetic

<400> SEQUENCE: 221
ataaaccaag atggaagtga gaaa                                          24

<210> SEQ ID NO 222
<211> LENGTH: 8
<212> TYPE: PRT
<213> ORGANISM: Artificial Sequence
<220> FEATURE:
<223> OTHER INFORMATION: Synthetic

<400> SEQUENCE: 222

Ile Asn Gln Asp Gly Ser Glu Lys
 1               5
```

<210> SEQ ID NO 223
<211> LENGTH: 60
<212> TYPE: DNA
<213> ORGANISM: Artificial Sequence
<220> FEATURE:
<223> OTHER INFORMATION: Synthetic

<400> SEQUENCE: 223

```
gcgagagata ttgtactaat ggtctatgat atggactact actactacgg tatggacgtc    60
```

<210> SEQ ID NO 224
<211> LENGTH: 20
<212> TYPE: PRT
<213> ORGANISM: Artificial Sequence
<220> FEATURE:
<223> OTHER INFORMATION: Synthetic

<400> SEQUENCE: 224

Ala Arg Asp Ile Val Leu Met Val Tyr Asp Met Asp Tyr Tyr Tyr Tyr
1               5                   10                  15

Gly Met Asp Val
            20

<210> SEQ ID NO 225
<211> LENGTH: 336
<212> TYPE: DNA
<213> ORGANISM: Artificial Sequence
<220> FEATURE:
<223> OTHER INFORMATION: Synthetic

<400> SEQUENCE: 225

```
gatattgtga tgactcagtc tccactctcc ctgcccgtca cccctggaga gccggcctcc    60
atctcctgca ggtctagtca gagcctcctg catagtaatg aaacaactta tttggattgg   120
tacctgcaga agccagggca gtctccacag ctcctgatct atttgggttc taatcgggcc   180
tccggggtcc ctgacaggtt cagtggcagt ggatcaggca cagattttac actgaaaatc   240
agcagagtgg aggctgagga tgttggggtt tattactgca tgcaaactct acaaactccg   300
ctcactttcg gcggagggac caaggtggag atcaaa                             336
```

<210> SEQ ID NO 226
<211> LENGTH: 112
<212> TYPE: PRT
<213> ORGANISM: Artificial Sequence
<220> FEATURE:
<223> OTHER INFORMATION: Synthetic

<400> SEQUENCE: 226

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Asn Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Thr
                85                  90                  95

Leu Gln Thr Pro Leu Thr Phe Gly Gly Gly Thr Lys Val Glu Ile Lys

<210> SEQ ID NO 227
<211> LENGTH: 33
<212> TYPE: DNA
<213> ORGANISM: Artificial Sequence
<220> FEATURE:
<223> OTHER INFORMATION: Synthetic

<400> SEQUENCE: 227
cagagcctcc tgcatagtaa tggaaacaac tat                                    33

<210> SEQ ID NO 228
<211> LENGTH: 11
<212> TYPE: PRT
<213> ORGANISM: Artificial Sequence
<220> FEATURE:
<223> OTHER INFORMATION: Synthetic

<400> SEQUENCE: 228

Ser Ser Gln Ser Leu Leu His Ser Asn Gly Asn
 1               5                  10

<210> SEQ ID NO 229
<211> LENGTH: 9
<212> TYPE: DNA
<213> ORGANISM: Artificial Sequence
<220> FEATURE:
<223> OTHER INFORMATION: Synthetic

<400> SEQUENCE: 229 ttgggttct                                                                9

<210> SEQ ID NO 230
<211> LENGTH: 3
<212> TYPE: PRT
<213> ORGANISM: Artificial Sequence
<220> FEATURE:
<223> OTHER INFORMATION: Synthetic

<400> SEQUENCE: 230

Leu Gly Ser
 1

<210> SEQ ID NO 231
<211> LENGTH: 27
<212> TYPE: DNA
<213> ORGANISM: Artificial Sequence
<220> FEATURE:
<223> OTHER INFORMATION: Synthetic

<400> SEQUENCE: 231
atgcaaactc tacaaactcc gctcact                                           27

<210> SEQ ID NO 232
<211> LENGTH: 9
<212> TYPE: PRT
<213> ORGANISM: Artificial Sequence
<220> FEATURE:
<223> OTHER INFORMATION: Synthetic

<400> SEQUENCE: 232

Met Gln Thr Leu Gln Thr Pro Leu Thr
 1               5

<210> SEQ ID NO 233

<211> LENGTH: 381
<212> TYPE: DNA
<213> ORGANISM: Artificial Sequence
<220> FEATURE:
<223> OTHER INFORMATION: Synthetic

<400> SEQUENCE: 233

| | | | | | |
|---|---|---|---|---|---|
| gaggtgcagc | tggtggagtc | tgggggaggc | ttggtccagc | ctggggggtc | cctgagactc | 60 |
| tcctgtgcag | cctctggatt | cacctttagt | agtcactgga | tgaagtgggt | ccgccaggct | 120 |
| ccagggaagg | gctggagtg | gtggccaac | ataaaccaag | atggaagtga | aaatactat | 180 |
| gtggactctg | tgaagggccg | attcaccatc | tccagagaca | acgccaagaa | ctcactgttt | 240 |
| ctgcaaatga | acagcctgag | agccgaggac | acggctgtgt | attactgtgc | gagagatatt | 300 |
| gtactaatgg | tctatgatat | ggactactac | tactacggta | tggacgtctg | gggccaaggg | 360 |
| accacggtca | ccgtctcctc | a | | | | 381 |

<210> SEQ ID NO 234
<211> LENGTH: 127
<212> TYPE: PRT
<213> ORGANISM: Artificial Sequence
<220> FEATURE:
<223> OTHER INFORMATION: Synthetic

<400> SEQUENCE: 234

Glu Val Gln Leu Val Glu Ser Gly Gly Gly Leu Val Gln Pro Gly Gly
1               5                   10                  15
Ser Leu Arg Leu Ser Cys Ala Ala Ser Gly Phe Thr Phe Ser Ser His
            20                  25                  30
Trp Met Lys Trp Val Arg Gln Ala Pro Gly Lys Gly Leu Glu Trp Val
        35                  40                  45
Ala Asn Ile Asn Gln Asp Gly Ser Glu Lys Tyr Tyr Val Asp Ser Val
    50                  55                  60
Lys Gly Arg Phe Thr Ile Ser Arg Asp Asn Ala Lys Asn Ser Leu Phe
65                  70                  75                  80
Leu Gln Met Asn Ser Leu Arg Ala Glu Asp Thr Ala Val Tyr Tyr Cys
                85                  90                  95
Ala Arg Asp Ile Val Leu Met Val Tyr Asp Met Asp Tyr Tyr Tyr Tyr
            100                 105                 110
Gly Met Asp Val Trp Gly Gln Gly Thr Thr Val Thr Val Ser Ser
        115                 120                 125

<210> SEQ ID NO 235
<211> LENGTH: 336
<212> TYPE: DNA
<213> ORGANISM: Artificial Sequence
<220> FEATURE:
<223> OTHER INFORMATION: Synthetic

<400> SEQUENCE: 235

| | | | | | |
|---|---|---|---|---|---|
| gatattgtga | tgactcagtc | tccactctcc | ctgcccgtca | cccctggaga | gccggcctcc | 60 |
| atctcctgca | ggtctagtca | gagcctcctg | catagtaatg | gaaacaacta | tttggattgg | 120 |
| tacctgcaga | agccagggca | gtctccacag | ctcctgatct | atttgggttc | taatcgggcc | 180 |
| tccggggtcc | ctgacaggtt | cagtggcagt | ggatcaggca | cagattttac | actgaaaatc | 240 |
| agcagagtgg | aggctgagga | tgttggggtt | tattactgca | tgcaaactct | acaaactccg | 300 |
| ctcactttcg | gcggagggac | caaggtggag | atcaaa | | | 336 |

<210> SEQ ID NO 236
<211> LENGTH: 112
<212> TYPE: PRT
<213> ORGANISM: Artificial Sequence
<220> FEATURE:
<223> OTHER INFORMATION: Synthetic

<400> SEQUENCE: 236

```
Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Asn Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Thr
                85                  90                  95

Leu Gln Thr Pro Leu Thr Phe Gly Gly Gly Thr Lys Val Glu Ile Lys
            100                 105                 110
```

<210> SEQ ID NO 237
<211> LENGTH: 381
<212> TYPE: DNA
<213> ORGANISM: Artificial Sequence
<220> FEATURE:
<223> OTHER INFORMATION: Synthetic

<400> SEQUENCE: 237

```
gaggtgcagc tggtggagtc tgggggaggc ttggtccagc ctggggggtc cctgagactc      60
tcctgtgcag cctctggatt cacctttagt agtcactgga tgagctgggt ccgccaggct     120
ccagggaagg ggctggagtg ggtggccaac ataaaccaag atggaagtga aaatactat      180 gtggactctg tgaagggccg attcaccatc tccagagaca acgccaagaa ctcactgtat     240
ctgcaaatga acagcctgag agccgaggac acggctgtgt attactgtgc gagagatatt     300
gtactaatgg tctatgatat ggactactac tactacggta tggacgtctg ggggcaaggg     360
accacggtca ccgtctcctc a                                                381
```

<210> SEQ ID NO 238
<211> LENGTH: 127
<212> TYPE: PRT
<213> ORGANISM: Artificial Sequence
<220> FEATURE:
<223> OTHER INFORMATION: Synthetic

<400> SEQUENCE: 238

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser His
            20                  25                  30

Trp Met Ser Trp Val Arg Gln Ala Pro Gly Lys Gly Leu Glu Trp Val
        35                  40                  45

Ala Asn Ile Asn Gln Asp Gly Ser Glu Lys Tyr Tyr Val Asp Ser Val
    50                  55                  60

Lys Gly Arg Phe Thr Ile Ser Arg Asp Asn Ala Lys Asn Ser Leu Tyr
65                  70                  75                  80
```

```
Leu Gln Met Asn Ser Leu Arg Ala Glu Asp Thr Ala Val Tyr Tyr Cys
             85                  90                  95

Ala Arg Asp Ile Val Leu Met Val Tyr Asp Met Asp Tyr Tyr Tyr Tyr
        100                 105                 110

Gly Met Asp Val Trp Gly Gln Gly Thr Thr Val Thr Val Ser Ser
    115                 120                 125
```

<210> SEQ ID NO 239
<211> LENGTH: 336
<212> TYPE: DNA
<213> ORGANISM: Artificial Sequence
<220> FEATURE:
<223> OTHER INFORMATION: Synthetic

<400> SEQUENCE: 239

```
gatattgtga tgactcagtc tccactctcc ctgcccgtca cccctggaga gccggcctcc    60
atctcctgca ggtctagtca gagcctcctg catagtaatg gaaacaacta tttggattgg   120
tacctgcaga agccagggca gtctccacag ctcctgatct atttgggttc taatcgggcc   180
tccggggtcc ctgacaggtt cagtggcagt ggatcaggca cagatttttac actgaaaatc   240 agcagagtgg aggctgagga tgttggggtt tattactgca tgcaaactct acaaactccg   300
ctcactttcg gcggagggac caaggtggag atcaaa                              336
```

<210> SEQ ID NO 240
<211> LENGTH: 112
<212> TYPE: PRT
<213> ORGANISM: Artificial Sequence
<220> FEATURE:
<223> OTHER INFORMATION: Synthetic

<400> SEQUENCE: 240

```
Asp Ile Val Met Thr Gln Ser Pro Leu Ser Leu Pro Val Thr Pro Gly
1               5                  10                  15

Glu Pro Ala Ser Ile Ser Cys Arg Ser Ser Gln Ser Leu Leu His Ser
             20                  25                  30

Asn Gly Asn Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Thr
                85                  90                  95

Leu Gln Thr Pro Leu Thr Phe Gly Gly Gly Thr Lys Val Glu Ile Lys
            100                 105                 110
```

<210> SEQ ID NO 241
<211> LENGTH: 381
<212> TYPE: DNA
<213> ORGANISM: Artificial Sequence
<220> FEATURE:
<223> OTHER INFORMATION: Synthetic

<400> SEQUENCE: 241

```
caggtgcagc tggtggagtc tgggggaggc gtggtccagc ctggggaggtc cctgagactc    60 tcctgtgcag tctctggatt caccttcagt agctatggca tgcactgggt ccgccaggct   120
ccaggcaagg ggctggagtg ggtggcagct atatcatatg atggaagtaa taatactat   180 gtagactccg tgaagggccg attcaccatc tccagagaca attccaagaa aacgctgtat   240
```

```
ctgcaaatga acagcctgag agctgaggac acggctgtgt ataattgtgc gaaaaatatt    300
gtactagtga tgtatgatat agactatcac tactatggga tggacgtctg gggccaaggg    360
accacggtca ccgtctcctc a                                              381
```

<210> SEQ ID NO 242
<211> LENGTH: 127
<212> TYPE: PRT
<213> ORGANISM: Artificial Sequence
<220> FEATURE:
<223> OTHER INFORMATION: Synthetic

<400> SEQUENCE: 242

```
Gln Val Gln Leu Val Glu Ser Gly Gly Gly Val Val Gln Pro Gly Arg
  1               5                  10                  15

Ser Leu Arg Leu Ser Cys Ala Val Ser Gly Phe Thr Phe Ser Ser Tyr
             20                  25                  30

Gly Met His Trp Val Arg Gln Ala Pro Gly Lys Gly Leu Glu Trp Val
         35                  40                  45

Ala Ala Ile Ser Tyr Asp Gly Ser Asn Lys Tyr Tyr Val Asp Ser Val
     50                  55                  60

Lys Gly Arg Phe Thr Ile Ser Arg Asp Asn Ser Lys Lys Thr Leu Tyr
 65                  70                  75                  80

Leu Gln Met Asn Ser Leu Arg Ala Glu Asp Thr Ala Val Tyr Asn Cys
                 85                  90                  95

Ala Lys Asn Ile Val Leu Val Met Tyr Asp Ile Asp Tyr His Tyr Tyr
            100                 105                 110

Gly Met Asp Val Trp Gly Gln Gly Thr Thr Val Thr Val Ser Ser
        115                 120                 125
```

<210> SEQ ID NO 243
<211> LENGTH: 24
<212> TYPE: DNA
<213> ORGANISM: Artificial Sequence
<220> FEATURE:
<223> OTHER INFORMATION: Synthetic

<400> SEQUENCE: 243

```
ggattcacct tcagtagcta tggc                                            24
```

<210> SEQ ID NO 244
<211> LENGTH: 8
<212> TYPE: PRT
<213> ORGANISM: Artificial Sequence
<220> FEATURE:
<223> OTHER INFORMATION: Synthetic

<400> SEQUENCE: 244

```
Gly Phe Thr Phe Ser Ser Tyr Gly
  1               5
```

<210> SEQ ID NO 245
<211> LENGTH: 24
<212> TYPE: DNA
<213> ORGANISM: Artificial Sequence
<220> FEATURE:
<223> OTHER INFORMATION: Synthetic

<400> SEQUENCE: 245

```
atatcatatg atggaagtaa taaa                                            24
```

<210> SEQ ID NO 246
<211> LENGTH: 8
<212> TYPE: PRT
<213> ORGANISM: Artificial Sequence
<220> FEATURE:
<223> OTHER INFORMATION: Synthetic

<400> SEQUENCE: 246

Ile Ser Tyr Asp Gly Ser Asn Lys
1               5

<210> SEQ ID NO 247
<211> LENGTH: 60
<212> TYPE: DNA
<213> ORGANISM: Artificial Sequence
<220> FEATURE:
<223> OTHER INFORMATION: Synthetic

<400> SEQUENCE: 247
gcgaaaaata ttgtactagt gatgtatgat atagactatc actactatgg gatggacgtc    60

<210> SEQ ID NO 248
<211> LENGTH: 20
<212> TYPE: PRT
<213> ORGANISM: Artificial Sequence
<220> FEATURE:
<223> OTHER INFORMATION: Synthetic

<400> SEQUENCE: 248

Ala Lys Asn Ile Val Leu Val Met Tyr Asp Ile Asp Tyr His Tyr Tyr
1               5                   10                  15

Gly Met Asp Val
            20

<210> SEQ ID NO 249
<211> LENGTH: 336
<212> TYPE: DNA
<213> ORGANISM: Artificial Sequence
<220> FEATURE:
<223> OTHER INFORMATION: Synthetic

<400> SEQUENCE: 249
gatattgtga tgactcagtc tccactctcc ctgcccgtca cccctggaga gccggcctcc    60
atctcctgca ggtctagtca gagcctcctg catagtaatg gatacaacta tttggattgg   120
tacctgcaga agccagggca gtctccacaa ctcctgatct atttgggttt taatcgggcc   180
tccggggtcc ctgacaggtt cagtggcagt ggatcaggca cagattttac actgaaaatc   240
agcagagtgg aggctgagga tgttggggtt tattactgca tgcaagctct acaaactcct   300
ctcactttcg gcggagggac caaggtggag atcaga                             336

<210> SEQ ID NO 250
<211> LENGTH: 112
<212> TYPE: PRT
<213> ORGANISM: Artificial Sequence
<220> FEATURE:
<223> OTHER INFORMATION: Synthetic

<400> SEQUENCE: 250

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Pro Gly Gln Ser

```
                35                  40                  45
Pro Gln Leu Leu Ile Tyr Leu Gly Phe Asn Arg Ala Ser Gly Val Pro
         50                  55                  60
Asp Arg Phe Ser Gly Ser Gly Ser Gly Thr Asp Phe Thr Leu Lys Ile
 65                  70                  75                  80
Ser Arg Val Glu Ala Glu Asp Val Gly Val Tyr Tyr Cys Met Gln Ala
                 85                  90                  95
Leu Gln Thr Pro Leu Thr Phe Gly Gly Gly Thr Lys Val Glu Ile Arg
            100                 105                 110
```

<210> SEQ ID NO 251
<211> LENGTH: 33
<212> TYPE: DNA
<213> ORGANISM: Artificial Sequence
<220> FEATURE:
<223> OTHER INFORMATION: Synthetic

<400> SEQUENCE: 251
cagagcctcc tgcatagtaa tggatacaac tat             33

<210> SEQ ID NO 252
<211> LENGTH: 11
<212> TYPE: PRT
<213> ORGANISM: Artificial Sequence
<220> FEATURE:
<223> OTHER INFORMATION: Synthetic

<400> SEQUENCE: 252

```
Gln Ser Leu Leu His Ser Asn Gly Tyr Asn Tyr
 1               5                  10
```

<210> SEQ ID NO 253
<211> LENGTH: 9
<212> TYPE: DNA
<213> ORGANISM: Artificial Sequence
<220> FEATURE:
<223> OTHER INFORMATION: Synthetic

<400> SEQUENCE: 253 ttgggtttt             9

<210> SEQ ID NO 254
<211> LENGTH: 3
<212> TYPE: PRT
<213> ORGANISM: Artificial Sequence
<220> FEATURE:
<223> OTHER INFORMATION: Synthetic

<400> SEQUENCE: 254

```
Leu Gly Phe
 1
```

<210> SEQ ID NO 255
<211> LENGTH: 27
<212> TYPE: DNA
<213> ORGANISM: Artificial Sequence
<220> FEATURE:
<223> OTHER INFORMATION: Synthetic

<400> SEQUENCE: 255
atgcaagctc tacaaactcc tctcact             27

<210> SEQ ID NO 256
<211> LENGTH: 9

```
<212> TYPE: PRT
<213> ORGANISM: Artificial Sequence
<220> FEATURE:
<223> OTHER INFORMATION: Synthetic

<400> SEQUENCE: 256

Met Gln Ala Leu Gln Thr Pro Leu Thr
 1               5

<210> SEQ ID NO 257
<211> LENGTH: 381
<212> TYPE: DNA
<213> ORGANISM: Artificial Sequence
<220> FEATURE:
<223> OTHER INFORMATION: Synthetic

<400> SEQUENCE: 257
caggtgcagc tggtggagtc tgggggaggc gtggtccagc ctggggaggtc cctgagactc     60 tcctgtgcag tctctggatt caccttcagt agctatggca tgcactgggt ccgccaggct    120
ccaggcaagg ggctggagtg ggtggcagct atatcatatg atggaagtaa taaatactat    180
gtagactccg tgaagggccg attcaccatc tccagagaca attccaagaa aacgctgtat    240
ctgcaaatga acagcctgag agctgaggac acggctgtgt ataattgtgc gaaaaatatt    300
gtactagtga tgtatgatat agactatcac tactatggga tggacgtctg gggccaaggg    360
accacggtca ccgtctcctc a                                              381

<210> SEQ ID NO 258
<211> LENGTH: 127
<212> TYPE: PRT
<213> ORGANISM: Artificial Sequence
<220> FEATURE:
<223> OTHER INFORMATION: Synthetic

<400> SEQUENCE: 258

Gln Val Gln Leu Val Glu Ser Gly Gly Gly Val Val Gln Pro Gly Arg
 1               5                  10                  15

Ser Leu Arg Leu Ser Cys Ala Val Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Ala Ile Ser Tyr Asp Gly Ser Asn Lys Tyr Tyr Val Asp Ser Val
    50                  55                  60

Lys Gly Arg Phe Thr Ile Ser Arg Asp Asn Ser Lys Lys Thr Leu Tyr
65                  70                  75                  80

Leu Gln Met Asn Ser Leu Arg Ala Glu Asp Thr Ala Val Tyr Asn Cys
                85                  90                  95

Ala Lys Asn Ile Val Leu Val Met Tyr Asp Ile Asp Tyr His Tyr Tyr
            100                 105                 110

Gly Met Asp Val Trp Gly Gln Gly Thr Thr Val Thr Val Ser Ser
        115                 120                 125

<210> SEQ ID NO 259
<211> LENGTH: 336
<212> TYPE: DNA
<213> ORGANISM: Artificial Sequence
<220> FEATURE:
<223> OTHER INFORMATION: Synthetic

<400> SEQUENCE: 259
gatattgtga tgactcagtc tccactctcc ctgcccgtca cccctggaga gccggcctcc     60
```

```
atctcctgca ggtctagtca gagcctcctg catagtaatg gatacaacta tttggattgg    120
tacctgcaga agccagggca gtctccacaa ctcctgatct atttgggttt taatcgggcc    180
tccggggtcc ctgacaggtt cagtggcagt ggatcaggca cagattttac actgaaaatc    240
agcagagtgg aggctgagga tgttggggtt tattactgca tgcaagctct acaaactcct    300
ctcactttcg gcggagggac caaggtggag atcaaa                              336
```

<210> SEQ ID NO 260
<211> LENGTH: 112
<212> TYPE: PRT
<213> ORGANISM: Artificial Sequence
<220> FEATURE:
<223> OTHER INFORMATION: Synthetic

<400> SEQUENCE: 260

```
Asp Ile Val Met Thr Gln Ser Pro Leu Ser Leu Pro Val Thr Pro Gly
  1               5                  10                  15

Glu Pro Ala Ser Ile Ser Cys Arg Ser Ser Gln Ser Leu Leu His Ser
             20                  25                  30

Asn Gly Tyr Asn Tyr Leu Asp Trp Tyr Leu Gln Lys Pro Gly Gln Ser
         35                  40                  45

Pro Gln Leu Leu Ile Tyr Leu Gly Phe Asn Arg Ala Ser Gly Val Pro
     50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Met Gln Ala
                 85                  90                  95

Leu Gln Thr Pro Leu Thr Phe Gly Gly Gly Thr Lys Val Glu Ile Lys
            100                 105                 110
```

<210> SEQ ID NO 261
<211> LENGTH: 381
<212> TYPE: DNA
<213> ORGANISM: Artificial Sequence
<220> FEATURE:
<223> OTHER INFORMATION: Synthetic

<400> SEQUENCE: 261

```
caggtgcagc tggtggagtc tgggggaggc gtggtccagc ctggggaggtc cctgagactc     60 tcctgtgcag cctctggatt caccttcagt agctatggca tgcactgggt ccgccaggct    120
ccaggcaagg ggctggagtg gtggcagtt atatcatatg atggaagtaa taaatactat    180
gcagactccg tgaagggccg attcaccatc tccagagaca attccaagaa cacgctgtat    240
ctgcaaatga acagcctgag agctgaggac acggctgtgt attactgtgc gaaaaatatt    300
gtactagtga tgtatgatat agactatcac tactatggga tggacgtctg ggggcaaggg    360
accacggtca ccgtctcctc a                                              381
```

<210> SEQ ID NO 262
<211> LENGTH: 127
<212> TYPE: PRT
<213> ORGANISM: Artificial Sequence
<220> FEATURE:
<223> OTHER INFORMATION: Synthetic

<400> SEQUENCE: 262

```
Gln Val Gln Leu Val Glu Ser Gly Gly Gly Val Val Gln Pro Gly Arg
  1               5                  10                  15
```

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asn Ile Val Leu Val Met Tyr Asp Ile Asp Tyr His Tyr Tyr
            100                 105                 110

Gly Met Asp Val Trp Gly Gln Gly Thr Thr Val Thr Val Ser Ser
        115                 120                 125

<210> SEQ ID NO 263
<211> LENGTH: 336
<212> TYPE: DNA
<213> ORGANISM: Artificial Sequence
<220> FEATURE:
<223> OTHER INFORMATION: Synthetic

<400> SEQUENCE: 263
gatattgtga tgactcagtc tccactctcc ctgcccgtca cccctggaga gccggcctcc     60
atctcctgca ggtctagtca gagcctcctg catagtaatg gatacaacta tttggattgg    120
tacctgcaga agccagggca gtctccacag ctcctgatct atttgggttt taatcgggcc    180
tccggggtcc ctgacaggtt cagtggcagt ggatcaggca cagatttac actgaaaatc     240 agcagagtgg aggctgagga tgttggggtt tattactgca tgcaagctct acaaactcct    300
ctcactttcg gcggagggac caaggtggag atcaaa                              336

<210> SEQ ID NO 264
<211> LENGTH: 112
<212> TYPE: PRT
<213> ORGANISM: Artificial Sequence
<220> FEATURE:
<223> OTHER INFORMATION: Synthetic

<400> SEQUENCE: 264

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Gly Phe Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Thr Pro Leu Thr Phe Gly Gly Gly Thr Lys Val Glu Ile Lys
            100                 105                 110

<210> SEQ ID NO 265
<211> LENGTH: 381
<212> TYPE: DNA
<213> ORGANISM: Artificial Sequence
<220> FEATURE:
<223> OTHER INFORMATION: Synthetic

<400> SEQUENCE: 265

```
caggtgcagc tggtggagtc tgggggaggc gtggtccagc ctgggaggtc cctgagactc    60
tcctgtgcag tctctggatt caccttcagt agctatggca tgcactgggt ccgccaggct   120
ccaggcaagg ggctggagtg ggtggcagct atatcatatg atggaagtaa taaatactat   180
gtagactccg tgaagggccg attcaccatc tccagagaca attccaagaa aacgctgtat   240
ctgcaaatga acagcctgag agctgaggac acggctgtgt ataattgtgc gaaaaatatt   300
gtactagtga tgtatgatat agactatcac tactatggga tggacgtctg gggccaaggg   360
accacggtca ccgtctcctc a                                             381
```

<210> SEQ ID NO 266
<211> LENGTH: 127
<212> TYPE: PRT
<213> ORGANISM: Artificial Sequence
<220> FEATURE:
<223> OTHER INFORMATION: Synthetic

<400> SEQUENCE: 266

```
Gln Val Gln Leu Val Glu Ser Gly Gly Gly Val Val Gln Pro Gly Arg
 1               5                  10                  15

Ser Leu Arg Leu Ser Cys Ala Val Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Ala Ile Ser Tyr Asp Gly Ser Asn Lys Tyr Tyr Val Asp Ser Val
    50                  55                  60

Lys Gly Arg Phe Thr Ile Ser Arg Asp Asn Ser Lys Lys Thr Leu Tyr
65                  70                  75                  80

Leu Gln Met Asn Ser Leu Arg Ala Glu Asp Thr Ala Val Tyr Asn Cys
                85                  90                  95

Ala Lys Asn Ile Val Leu Val Met Tyr Asp Ile Asp Tyr His Tyr Tyr
            100                 105                 110

Gly Met Asp Val Trp Gly Gln Gly Thr Thr Val Thr Val Ser Ser
        115                 120                 125
```

<210> SEQ ID NO 267
<211> LENGTH: 24
<212> TYPE: DNA
<213> ORGANISM: Artificial Sequence
<220> FEATURE:
<223> OTHER INFORMATION: Synthetic

<400> SEQUENCE: 267

```
ggattcacct tcagtagcta tggc                                           24
```

<210> SEQ ID NO 268
<211> LENGTH: 8
<212> TYPE: PRT
<213> ORGANISM: Artificial Sequence
<220> FEATURE:
<223> OTHER INFORMATION: Synthetic

<400> SEQUENCE: 268

```
Gly Phe Thr Phe Ser Ser Tyr Gly
 1               5
```

<210> SEQ ID NO 269
<211> LENGTH: 24
<212> TYPE: DNA
<213> ORGANISM: Artificial Sequence
<220> FEATURE:
<223> OTHER INFORMATION: Synthetic

<400> SEQUENCE: 269
atatcatatg atggaagtaa taaa                                           24

<210> SEQ ID NO 270
<211> LENGTH: 8
<212> TYPE: PRT
<213> ORGANISM: Artificial Sequence
<220> FEATURE:
<223> OTHER INFORMATION: Synthetic

<400> SEQUENCE: 270

Ile Ser Tyr Asp Gly Ser Asn Lys
 1               5

<210> SEQ ID NO 271
<211> LENGTH: 60
<212> TYPE: DNA
<213> ORGANISM: Artificial Sequence
<220> FEATURE:
<223> OTHER INFORMATION: Synthetic

<400> SEQUENCE: 271
gcgaaaaata ttgtactagt gatgtatgat atagactatc actactatgg gatggacgtc    60

<210> SEQ ID NO 272
<211> LENGTH: 20
<212> TYPE: PRT
<213> ORGANISM: Artificial Sequence
<220> FEATURE:
<223> OTHER INFORMATION: Synthetic

<400> SEQUENCE: 272

Ala Lys Asn Ile Val Leu Val Met Tyr Asp Ile Asp Tyr His Tyr Tyr
 1               5                  10                  15

Gly Met Asp Val
         20

<210> SEQ ID NO 273
<211> LENGTH: 336
<212> TYPE: DNA
<213> ORGANISM: Artificial Sequence
<220> FEATURE:
<223> OTHER INFORMATION: Synthetic

<400> SEQUENCE: 273
gatattgtga tgactcagtc tccactctcc ctgcccgtca cccctggaga gccggcctcc    60
atctcctgca ggtctagtca gagcctcctg catagtaatg gatacaacta tttggattgg   120
tacctgcaga agccagggca gtctccacaa ctcctgatct atttgggttt taatcgggcc   180
tccggggtcc ctgacaggtt cagtggcagt ggatcaggca cagatttac actgaaaatc   240 agcagagtgg aggctgagga tgttggggtt tattactgca tgcaagctct acaaactcct   300
ctcactttcg gcggagggac caaggtggag atcaga                             336

<210> SEQ ID NO 274
<211> LENGTH: 112
<212> TYPE: PRT
<213> ORGANISM: Artificial Sequence

```
<220> FEATURE:
<223> OTHER INFORMATION: Synthetic

<400> SEQUENCE: 274

Asp Ile Val Met Thr Gln Ser Pro Leu Ser Leu Pro Val Thr Pro Gly
 1               5                  10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Gly Phe Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Thr Pro Leu Thr Phe Gly Gly Gly Thr Lys Val Glu Ile Arg
            100                 105                 110

<210> SEQ ID NO 275
<211> LENGTH: 33
<212> TYPE: DNA
<213> ORGANISM: Artificial Sequence
<220> FEATURE:
<223> OTHER INFORMATION: Synthetic

<400> SEQUENCE: 275
cagagcctcc tgcatagtaa tggatacaac tat                                    33

<210> SEQ ID NO 276
<211> LENGTH: 11
<212> TYPE: PRT
<213> ORGANISM: Artificial Sequence
<220> FEATURE:
<223> OTHER INFORMATION: Synthetic

<400> SEQUENCE: 276

Gln Ser Leu Leu His Ser Asn Gly Tyr Asn Tyr
 1               5                  10

<210> SEQ ID NO 277
<211> LENGTH: 9
<212> TYPE: DNA
<213> ORGANISM: Artificial Sequence
<220> FEATURE:
<223> OTHER INFORMATION: Synthetic

<400> SEQUENCE: 277 ttgggtttt                                                                9

<210> SEQ ID NO 278
<211> LENGTH: 3
<212> TYPE: PRT
<213> ORGANISM: Artificial Sequence
<220> FEATURE:
<223> OTHER INFORMATION: Synthetic

<400> SEQUENCE: 278

Leu Gly Phe
 1

<210> SEQ ID NO 279
<211> LENGTH: 27
```

```
<212> TYPE: DNA
<213> ORGANISM: Artificial Sequence
<220> FEATURE:
<223> OTHER INFORMATION: Synthetic

<400> SEQUENCE: 279
atgcaagctc tacaaactcc tctcact                                              27

<210> SEQ ID NO 280
<211> LENGTH: 9
<212> TYPE: PRT
<213> ORGANISM: Artificial Sequence
<220> FEATURE:
<223> OTHER INFORMATION: Synthetic

<400> SEQUENCE: 280

Met Gln Ala Leu Gln Thr Pro Leu Thr
 1               5

<210> SEQ ID NO 281
<211> LENGTH: 381
<212> TYPE: DNA
<213> ORGANISM: Artificial Sequence
<220> FEATURE:
<223> OTHER INFORMATION: Synthetic

<400> SEQUENCE: 281
caggtgcagc tggtggagtc tgggggaggc gtggtccagc ctggggaggtc cctgagactc         60 tcctgtgcag tctctggatt caccttcagt agctatggca tgcactgggt ccgccaggct        120
ccaggcaagg ggctggagtg ggtggcagct atatcatatg atggaagtaa taaatactat        180
gtagactccg tgaagggccg attcaccatc tccagagaca attccaagaa aacgctgtat        240
ctgcaaatga acagcctgag agctgaggac acggctgtgt ataattgtgc gaaaaatatt        300
gtactagtga tgtatgatat agactatcac tactatggga tggacgtctg gggccaaggg        360
accacggtca ccgtctcctc a                                                  381

<210> SEQ ID NO 282
<211> LENGTH: 127
<212> TYPE: PRT
<213> ORGANISM: Artificial Sequence
<220> FEATURE:
<223> OTHER INFORMATION: Synthetic

<400> SEQUENCE: 282

Gln Val Gln Leu Val Glu Ser Gly Gly Gly Val Val Gln Pro Gly Arg
 1               5                  10                  15

Ser Leu Arg Leu Ser Cys Ala Val Ser Gly Phe Thr Phe Ser Ser Tyr
             20                  25                  30

Gly Met His Trp Val Arg Gln Ala Pro Gly Lys Gly Leu Glu Trp Val
         35                  40                  45

Ala Ala Ile Ser Tyr Asp Gly Ser Asn Lys Tyr Tyr Val Asp Ser Val
     50                  55                  60

Lys Gly Arg Phe Thr Ile Ser Arg Asp Asn Ser Lys Lys Thr Leu Tyr
 65                  70                  75                  80

Leu Gln Met Asn Ser Leu Arg Ala Glu Asp Thr Ala Val Tyr Asn Cys
                 85                  90                  95

Ala Lys Asn Ile Val Leu Val Met Tyr Asp Ile Asp Tyr His Tyr Tyr
            100                 105                 110

Gly Met Asp Val Trp Gly Gln Gly Thr Thr Val Thr Val Ser Ser
        115                 120                 125
```

<210> SEQ ID NO 283
<211> LENGTH: 336
<212> TYPE: DNA
<213> ORGANISM: Artificial Sequence
<220> FEATURE:
<223> OTHER INFORMATION: Synthetic

<400> SEQUENCE: 283

```
gatattgtga tgactcagtc tccactctcc ctgcccgtca cccctggaga gccggcctcc      60
atctcctgca ggtctagtca gagcctcctg catagtaatg gatacaacta tttggattgg    120
tacctgcaga agccagggca gtctccacaa ctcctgatct atttgggttt taatcgggcc    180
tccggggtcc ctgacaggtt cagtggcagt ggatcaggca cagatttttac actgaaaatc    240 agcagagtgg aggctgagga tgttggggtt tattactgca tgcaagctct acaaactcct    300
ctcactttcg gcggagggac caaggtggag atcaaa                              336
```

<210> SEQ ID NO 284
<211> LENGTH: 112
<212> TYPE: PRT
<213> ORGANISM: Artificial Sequence
<220> FEATURE:
<223> OTHER INFORMATION: Synthetic

<400> SEQUENCE: 284

```
Asp Ile Val Met Thr Gln Ser Pro Leu Ser Leu Pro Val Thr Pro Gly
  1               5                  10                  15

Glu Pro Ala Ser Ile Ser Cys Arg Ser Ser Gln Ser Leu Leu His Ser
             20                  25                  30

Asn Gly Tyr Asn Tyr Leu Asp Trp Tyr Leu Gln Lys Pro Gly Gln Ser
         35                  40                  45

Pro Gln Leu Leu Ile Tyr Leu Gly Phe Asn Arg Ala Ser Gly Val Pro
     50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Met Gln Ala
                 85                  90                  95

Leu Gln Thr Pro Leu Thr Phe Gly Gly Gly Thr Lys Val Glu Ile Lys
            100                 105                 110
```

<210> SEQ ID NO 285
<211> LENGTH: 381
<212> TYPE: DNA
<213> ORGANISM: Artificial Sequence
<220> FEATURE:
<223> OTHER INFORMATION: Synthetic

<400> SEQUENCE: 285

```
caggtgcagc tggtggagtc tggggggaggc gtggtccagc ctggggaggtc cctgagactc     60 tcctgtgcag cctctggatt caccttcagt agctatggca tgcactgggt ccgccaggct    120
ccaggcaagg ggctggagtg ggtggcagtt atatcatatg atggaagtaa taaatactat    180
gcagactccg tgaagggccg attcaccatc tccagagaca attccaagaa cacgctgtat    240
ctgcaaatga acagcctgag agctgaggac acggctgtgt attactgtgc gaaaaatatt    300
gtactagtga tgtatgatat agactatcac tactatggga tggacgtctg ggggcaaggg    360
accacggtca ccgtctcctc a                                              381
```

<210> SEQ ID NO 286
<211> LENGTH: 127
<212> TYPE: PRT
<213> ORGANISM: Artificial Sequence
<220> FEATURE:
<223> OTHER INFORMATION: Synthetic

<400> SEQUENCE: 286

```
Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asn Ile Val Leu Val Met Tyr Asp Ile Asp Tyr His Tyr Tyr
            100                 105                 110

Gly Met Asp Val Trp Gly Gln Gly Thr Thr Val Thr Val Ser Ser
        115                 120                 125
```

<210> SEQ ID NO 287
<211> LENGTH: 336
<212> TYPE: DNA
<213> ORGANISM: Artificial Sequence
<220> FEATURE:
<223> OTHER INFORMATION: Synthetic

<400> SEQUENCE: 287

```
gatattgtga tgactcagtc tccactctcc ctgcccgtca cccctggaga gccggcctcc      60
atctcctgca ggtctagtca gagcctcctg catagtaatg gatacaacta tttggattgg     120
tacctgcaga agccagggca gtctccacag ctcctgatct atttgggttt taatcgggcc     180
tccggggtcc ctgacaggtt cagtggcagt ggatcaggca cagattttac actgaaaatc     240
agcagagtgg aggctgagga tgttggggtt tattactgca tgcaagctct acaaactcct     300
ctcactttcg gcggagggac caaggtggag atcaaa                               336
```

<210> SEQ ID NO 288
<211> LENGTH: 112
<212> TYPE: PRT
<213> ORGANISM: Artificial Sequence
<220> FEATURE:
<223> OTHER INFORMATION: Synthetic

<400> SEQUENCE: 288

```
Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Gly Phe Asn Arg Ala Ser Gly Val Pro
    50                  55                  60

Asp Arg Phe Ser Gly Ser Gly Ser Gly Thr Asp Phe Thr Leu Lys Ile
65                  70                  75                  80
```

Ser Arg Val Glu Ala Glu Asp Val Gly Val Tyr Tyr Cys Met Gln Ala
                85                  90                  95

Leu Gln Thr Pro Leu Thr Phe Gly Gly Thr Lys Val Glu Ile Lys
            100                 105                 110

<210> SEQ ID NO 289
<211> LENGTH: 372
<212> TYPE: DNA
<213> ORGANISM: Artificial Sequence
<220> FEATURE:
<223> OTHER INFORMATION: Synthetic

<400> SEQUENCE: 289
cagatcacct tgaaggagtc tggtcctacg ctggtaaaac ccacacagac cctcacgctg      60
acctgcacct tctctgggtt ctcactcagc gctagtggag tgggtgtggg ctggttccgt     120
cagcccccag gaaaggccct ggagtggctt gcactcattt attggaatga tgataagcgt     180
tacagcccat ctctaaagaa cagcctcacc atcaccaagg acacctccaa aaaccaggtg     240
gtccttacaa tgaccaacat ggaccctgtg gacacagcca catattactg tgcacacaga     300
atacatctat ggtcctactt ctactacggt atggacgtct ggggccaagg gaccacggtc     360
accgtctcct ca                                                        372

<210> SEQ ID NO 290
<211> LENGTH: 124
<212> TYPE: PRT
<213> ORGANISM: Artificial Sequence
<220> FEATURE:
<223> OTHER INFORMATION: Synthetic

<400> SEQUENCE: 290

Gln Ile Thr Leu Lys Glu Ser Gly Pro Thr Leu Val Lys Pro Thr Gln
  1               5                  10                  15

Thr Leu Thr Leu Thr Cys Thr Phe Ser Gly Phe Ser Leu Ser Ala Ser
             20                  25                  30

Gly Val Gly Val Gly Trp Phe Arg Gln Pro Pro Gly Lys Ala Leu Glu
         35                  40                  45

Trp Leu Ala Leu Ile Tyr Trp Asn Asp Asp Lys Arg Tyr Ser Pro Ser
     50                  55                  60

Leu Lys Asn Ser Leu Thr Ile Thr Lys Asp Thr Ser Lys Asn Gln Val
 65                  70                  75                  80

Val Leu Thr Met Thr Asn Met Asp Pro Val Asp Thr Ala Thr Tyr Tyr
                85                  90                  95

Cys Ala His Arg Ile His Leu Trp Ser Tyr Phe Tyr Tyr Gly Met Asp
            100                 105                 110

Val Trp Gly Gln Gly Thr Thr Val Thr Val Ser Ser
        115                 120

<210> SEQ ID NO 291
<211> LENGTH: 30
<212> TYPE: DNA
<213> ORGANISM: Artificial Sequence
<220> FEATURE:
<223> OTHER INFORMATION: Synthetic

<400> SEQUENCE: 291
gggttctcac tcagcgctag tggagtgggt                                      30

<210> SEQ ID NO 292

```
<211> LENGTH: 10
<212> TYPE: PRT
<213> ORGANISM: Artificial Sequence
<220> FEATURE:
<223> OTHER INFORMATION: Synthetic

<400> SEQUENCE: 292

Gly Phe Ser Leu Ser Ala Ser Gly Val Gly
 1               5                  10

<210> SEQ ID NO 293
<211> LENGTH: 21
<212> TYPE: DNA
<213> ORGANISM: Artificial Sequence
<220> FEATURE:
<223> OTHER INFORMATION: Synthetic

<400> SEQUENCE: 293
atttattgga atgatgataa g                                        21

<210> SEQ ID NO 294
<211> LENGTH: 7
<212> TYPE: PRT
<213> ORGANISM: Artificial Sequence
<220> FEATURE:
<223> OTHER INFORMATION: Synthetic

<400> SEQUENCE: 294

Ile Tyr Trp Asn Asp Asp Lys
 1               5

<210> SEQ ID NO 295
<211> LENGTH: 48
<212> TYPE: DNA
<213> ORGANISM: Artificial Sequence
<220> FEATURE:
<223> OTHER INFORMATION: Synthetic

<400> SEQUENCE: 295
gcacacagaa tacatctatg gtcctacttc tactacggta tggacgtc           48

<210> SEQ ID NO 296
<211> LENGTH: 16
<212> TYPE: PRT
<213> ORGANISM: Artificial Sequence
<220> FEATURE:
<223> OTHER INFORMATION: Synthetic

<400> SEQUENCE: 296

Ala His Arg Ile His Leu Trp Ser Tyr Phe Tyr Tyr Gly Met Asp Val
 1               5                  10                  15

<210> SEQ ID NO 297
<211> LENGTH: 336
<212> TYPE: DNA
<213> ORGANISM: Artificial Sequence
<220> FEATURE:
<223> OTHER INFORMATION: Synthetic

<400> SEQUENCE: 297
gatattgtga tgactcagtc tccactctcc ctgcccgtca cccctggaga gccggcctcc    60
atctcctgca ggtctagtca gactctcctg catagtaatg gatacaacta tttcgattgg   120
tacctgcaga agccagggca gtctccacag ctcctgatct atttgggttc taatcgggcc   180
tccggggtcc ctgacagatt cagtggcagt ggatcaggca cagattttac actgaaaatc   240
```

```
agcagagtgg aggctgagga tgttggaatt tattactgca tgcaagctct acaaactcct      300
ctcactttcg gcggagggac caaggtggag atcaga                                336
```

<210> SEQ ID NO 298
<211> LENGTH: 112
<212> TYPE: PRT
<213> ORGANISM: Artificial Sequence
<220> FEATURE:
<223> OTHER INFORMATION: Synthetic

<400> SEQUENCE: 298

```
Asp Ile Val Met Thr Gln Ser Pro Leu Ser Leu Pro Val Thr Pro Gly
 1               5                  10                  15

Glu Pro Ala Ser Ile Ser Cys Arg Ser Ser Gln Thr Leu Leu His Ser
            20                  25                  30

Asn Gly Tyr Asn Tyr Phe Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Ile Tyr Tyr Cys Met Gln Ala
                85                  90                  95

Leu Gln Thr Pro Leu Thr Phe Gly Gly Gly Thr Lys Val Glu Ile Arg
            100                 105                 110
```

<210> SEQ ID NO 299
<211> LENGTH: 33
<212> TYPE: DNA
<213> ORGANISM: Artificial Sequence
<220> FEATURE:
<223> OTHER INFORMATION: Synthetic

<400> SEQUENCE: 299

```
cagactctcc tgcatagtaa tggatacaac tat                                    33
```

<210> SEQ ID NO 300
<211> LENGTH: 11
<212> TYPE: PRT
<213> ORGANISM: Artificial Sequence
<220> FEATURE:
<223> OTHER INFORMATION: Synthetic

<400> SEQUENCE: 300

```
Gln Thr Leu Leu His Ser Asn Gly Tyr Asn Tyr
 1               5                  10
```

<210> SEQ ID NO 301
<211> LENGTH: 9
<212> TYPE: DNA
<213> ORGANISM: Artificial Sequence
<220> FEATURE:
<223> OTHER INFORMATION: Synthetic

<400> SEQUENCE: 301

```
ttgggttct                                                                9
```

<210> SEQ ID NO 302
<211> LENGTH: 3
<212> TYPE: PRT
<213> ORGANISM: Artificial Sequence
<220> FEATURE:
<223> OTHER INFORMATION: Synthetic

<400> SEQUENCE: 302

Leu Gly Ser
 1

<210> SEQ ID NO 303
<211> LENGTH: 27
<212> TYPE: DNA
<213> ORGANISM: Artificial Sequence
<220> FEATURE:
<223> OTHER INFORMATION: Synthetic

<400> SEQUENCE: 303
atgcaagctc tacaaactcc tctcact                                          27

<210> SEQ ID NO 304
<211> LENGTH: 9
<212> TYPE: PRT
<213> ORGANISM: Artificial Sequence
<220> FEATURE:
<223> OTHER INFORMATION: Synthetic

<400> SEQUENCE: 304

Met Gln Ala Leu Gln Thr Pro Leu Thr
 1               5

<210> SEQ ID NO 305
<211> LENGTH: 372
<212> TYPE: DNA
<213> ORGANISM: Artificial Sequence
<220> FEATURE:
<223> OTHER INFORMATION: Synthetic

<400> SEQUENCE: 305
cagatcacct tgaaggagtc tggtcctacg ctggtaaaac ccacacagac cctcacgctg      60
acctgcacct tctctgggtt ctcactcagc gctagtggag tgggtgtggg ctggttccgt     120
cagcccccag gaaaggccct ggagtggctt gcactcattt attggaatga tgataagcgt     180
tacagcccat ctctaaagaa cagcctcacc atcaccaagg acacctccaa aaaccaggtg     240
gtccttacaa tgaccaacat ggaccctgtg acacagccca tattactgtg tgcacacaga     300
atacatctat ggtcctactt ctactacggt atggacgtct ggggccaagg gaccacggtc     360
accgtctcct ca                                                         372

<210> SEQ ID NO 306
<211> LENGTH: 124
<212> TYPE: PRT
<213> ORGANISM: Artificial Sequence
<220> FEATURE:
<223> OTHER INFORMATION: Synthetic

<400> SEQUENCE: 306

Gln Ile Thr Leu Lys Glu Ser Gly Pro Thr Leu Val Lys Pro Thr Gln
 1               5                  10                  15

Thr Leu Thr Leu Thr Cys Thr Phe Ser Gly Phe Ser Leu Ser Ala Ser
                20                  25                  30

Gly Val Gly Val Gly Trp Phe Arg Gln Pro Pro Gly Lys Ala Leu Glu
            35                  40                  45

Trp Leu Ala Leu Ile Tyr Trp Asn Asp Asp Lys Arg Tyr Ser Pro Ser
        50                  55                  60

Leu Lys Asn Ser Leu Thr Ile Thr Lys Asp Thr Ser Lys Asn Gln Val
65                  70                  75                  80

```
Val Leu Thr Met Thr Asn Met Asp Pro Val Asp Thr Ala Thr Tyr Tyr
                85                  90                  95

Cys Ala His Arg Ile His Leu Trp Ser Tyr Phe Tyr Tyr Gly Met Asp
            100                 105                 110

Val Trp Gly Gln Gly Thr Thr Val Thr Val Ser Ser
        115                 120
```

<210> SEQ ID NO 307
<211> LENGTH: 336
<212> TYPE: DNA
<213> ORGANISM: Artificial Sequence
<220> FEATURE:
<223> OTHER INFORMATION: Synthetic

<400> SEQUENCE: 307

| | | |
|---|---|---|
| gatattgtga tgactcagtc tccactctcc ctgcccgtca cccctggaga gccggcctcc | 60 |
| atctcctgca ggtctagtca gactctcctg catagtaatg gatacaacta tttcgattgg | 120 |
| tacctgcaga agccagggca gtctccacag ctcctgatct atttgggttc taatcggggcc | 180 |
| tccggggtcc ctgacagatt cagtggcagt ggatcaggca cagattttac actgaaaatc | 240 |
| agcagagtgg aggctgagga tgttggaatt tattactgca tgcaagctct acaaactcct | 300 |
| ctcactttcg gcggagggac caaggtggag atcaaa | 336 |

<210> SEQ ID NO 308
<211> LENGTH: 112
<212> TYPE: PRT
<213> ORGANISM: Artificial Sequence
<220> FEATURE:
<223> OTHER INFORMATION: Synthetic

<400> SEQUENCE: 308

```
Asp Ile Val Met Thr Gln Ser Pro Leu Ser Leu Pro Val Thr Pro Gly
  1               5                  10                  15

Glu Pro Ala Ser Ile Ser Cys Arg Ser Ser Gln Thr Leu Leu His Ser
             20                  25                  30

Asn Gly Tyr Asn Tyr Phe Asp Trp Tyr Leu Gln Lys Pro Gly Gln Ser
         35                  40                  45

Pro Gln Leu Leu Ile Tyr Leu Gly Ser Asn Arg Ala Ser Gly Val Pro
     50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Ile Tyr Tyr Cys Met Gln Ala
                 85                  90                  95

Leu Gln Thr Pro Leu Thr Phe Gly Gly Gly Thr Lys Val Glu Ile Lys
            100                 105                 110
```

<210> SEQ ID NO 309
<211> LENGTH: 372
<212> TYPE: DNA
<213> ORGANISM: Artificial Sequence
<220> FEATURE:
<223> OTHER INFORMATION: Synthetic

<400> SEQUENCE: 309

| | | |
|---|---|---|
| cagatcacct tgaaggagtc tggtcctacg ctggtgaaac ccacacagac cctcacgctg | 60 |
| acctgcacct tctctgggtt ctcactcagc gctagtggag tgggtgtggg ctggatccgt | 120 |
| cagcccccag gaaaggccct ggagtggctt gcactcattt attggaatga tgataagcgc | 180 |

```
tacagcccat ctctgaagag caggctcacc atcaccaagg acacctccaa aaaccaggtg    240
gtccttacaa tgaccaacat ggaccctgtg gacacagcca catattactg tgcacacaga    300
atacatctat ggtcctactt ctactacggt atggacgtct gggggcaagg gaccacggtc    360
accgtctcct ca                                                        372
```

<210> SEQ ID NO 310
<211> LENGTH: 124
<212> TYPE: PRT
<213> ORGANISM: Artificial Sequence
<220> FEATURE:
<223> OTHER INFORMATION: Synthetic

<400> SEQUENCE: 310

```
Gln Ile Thr Leu Lys Glu Ser Gly Pro Thr Leu Val Lys Pro Thr Gln
  1               5                  10                  15

Thr Leu Thr Leu Thr Cys Thr Phe Ser Gly Phe Ser Leu Ser Ala Ser
             20                  25                  30

Gly Val Gly Val Gly Trp Ile Arg Gln Pro Pro Gly Lys Ala Leu Glu
         35                  40                  45

Trp Leu Ala Leu Ile Tyr Trp Asn Asp Asp Lys Arg Tyr Ser Pro Ser
 50                  55                  60

Leu Lys Ser Arg Leu Thr Ile Thr Lys Asp Thr Ser Lys Asn Gln Val
 65                  70                  75                  80

Val Leu Thr Met Thr Asn Met Asp Pro Val Asp Thr Ala Thr Tyr Tyr
                 85                  90                  95

Cys Ala His Arg Ile His Leu Trp Ser Tyr Phe Tyr Tyr Gly Met Asp
            100                 105                 110

Val Trp Gly Gln Gly Thr Thr Val Thr Val Ser Ser
        115                 120
```

<210> SEQ ID NO 311
<211> LENGTH: 336
<212> TYPE: DNA
<213> ORGANISM: Artificial Sequence
<220> FEATURE:
<223> OTHER INFORMATION: Synthetic

<400> SEQUENCE: 311

```
gatattgtga tgactcagtc tccactctcc ctgcccgtca cccctggaga gccggcctcc     60
atctcctgca ggtctagtca gactctcctg catagtaatg gatacaacta tttggattgg    120
tacctgcaga agccagggca gtctccacag ctcctgatct atttgggttc taatcgggcc    180
tccggggtcc ctgacaggtt cagtggcagt ggatcaggca cagattttac actgaaaatc    240
agcagagtgg aggctgagga tgttggggtt tattactgca tgcaagctct acaaactcct    300
ctcactttcg gcggagggac caaggtggag atcaaa                              336
```

<210> SEQ ID NO 312
<211> LENGTH: 112
<212> TYPE: PRT
<213> ORGANISM: Artificial Sequence
<220> FEATURE:
<223> OTHER INFORMATION: Synthetic

<400> SEQUENCE: 312

```
Asp Ile Val Met Thr Gln Ser Pro Leu Ser Leu Pro Val Thr Pro Gly
  1               5                  10                  15

Glu Pro Ala Ser Ile Ser Cys Arg Ser Ser Gln Thr Leu Leu His Ser
             20                  25                  30
```

Asn Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Thr Pro Leu Thr Phe Gly Gly Gly Thr Lys Val Glu Ile Lys
            100                 105                 110

<210> SEQ ID NO 313
<211> LENGTH: 381
<212> TYPE: DNA
<213> ORGANISM: Artificial Sequence
<220> FEATURE:
<223> OTHER INFORMATION: Synthetic

<400> SEQUENCE: 313
caggttcagc tggtgcagtc tggacctgag gtgaagaacc ctggggcctc agtgaaggtc      60
tcctgcaagg cttctggtta cacctttacc acctatggta tcagttgggt acgacaggcc    120
cctggacaag ggcttgagtg gatgggatgg atcagcggtt acaatggtaa acaaacgat    180 gcacagaagt tccaggacag agtcgccatg accacagaca catccacgag cacagcctac    240
atggagctga ggagcctgag atctgacgac acggccattt attactgttc gagagatcgt    300
ttagtagtac cacctgccct taattattcc tactacgtta tggacgtctg gggccaaggg    360
accacggtca ccgtctcctc a                                              381

<210> SEQ ID NO 314
<211> LENGTH: 127
<212> TYPE: PRT
<213> ORGANISM: Artificial Sequence
<220> FEATURE:
<223> OTHER INFORMATION: Synthetic

<400> SEQUENCE: 314

Gln Val Gln Leu Val Gln Ser Gly Pro Glu Val Lys Asn Pro Gly Ala
1               5                   10                  15

Ser Val Lys Val Ser Cys Lys Ala Ser Gly Tyr Thr Phe Thr Thr Tyr
            20                  25                  30

Gly Ile Ser Trp Val Arg Gln Ala Pro Gly Gln Gly Leu Glu Trp Met
        35                  40                  45

Gly Trp Ile Ser Gly Tyr Asn Gly Lys Thr Asn Asp Ala Gln Lys Phe
    50                  55                  60

Gln Asp Arg Val Ala Met Thr Thr Asp Thr Ser Thr Ser Thr Ala Tyr
65                  70                  75                  80

Met Glu Leu Arg Ser Leu Arg Ser Asp Asp Thr Ala Ile Tyr Tyr Cys
                85                  90                  95

Ser Arg Asp Arg Leu Val Val Pro Pro Ala Leu Asn Tyr Ser Tyr Tyr
            100                 105                 110

Val Met Asp Val Trp Gly Gln Gly Thr Thr Val Thr Val Ser Ser
        115                 120                 125

<210> SEQ ID NO 315
<211> LENGTH: 24
<212> TYPE: DNA
<213> ORGANISM: Artificial Sequence
<220> FEATURE:
<223> OTHER INFORMATION: Synthetic

<400> SEQUENCE: 315
ggttacacct ttaccaccta tggt                                             24

<210> SEQ ID NO 316
<211> LENGTH: 8
<212> TYPE: PRT
<213> ORGANISM: Artificial Sequence
<220> FEATURE:
<223> OTHER INFORMATION: Synthetic

<400> SEQUENCE: 316

Gly Tyr Thr Phe Thr Thr Tyr Gly
1               5

<210> SEQ ID NO 317
<211> LENGTH: 24
<212> TYPE: DNA
<213> ORGANISM: Artificial Sequence
<220> FEATURE:
<223> OTHER INFORMATION: Synthetic

<400> SEQUENCE: 317
atcagcggtt acaatggtaa aaca                                             24

<210> SEQ ID NO 318
<211> LENGTH: 8
<212> TYPE: PRT
<213> ORGANISM: Artificial Sequence
<220> FEATURE:
<223> OTHER INFORMATION: Synthetic

<400> SEQUENCE: 318

Ile Ser Gly Tyr Asn Gly Lys Thr
1               5

<210> SEQ ID NO 319
<211> LENGTH: 60
<212> TYPE: DNA
<213> ORGANISM: Artificial Sequence
<220> FEATURE:
<223> OTHER INFORMATION: Synthetic

<400> SEQUENCE: 319
tcgagagatc gtttagtagt accacctgcc cttaattatt cctactacgt tatggacgtc      60

<210> SEQ ID NO 320
<211> LENGTH: 20
<212> TYPE: PRT
<213> ORGANISM: Artificial Sequence
<220> FEATURE:
<223> OTHER INFORMATION: Synthetic

<400> SEQUENCE: 320

Ser Arg Asp Arg Leu Val Val Pro Pro Ala Leu Asn Tyr Ser Tyr Tyr
1               5                   10                  15
Val Met Asp Val
            20

<210> SEQ ID NO 321
<211> LENGTH: 336
<212> TYPE: DNA
<213> ORGANISM: Artificial Sequence
<220> FEATURE:

<223> OTHER INFORMATION: Synthetic

<400> SEQUENCE: 321

```
gatgttgtga tgactcagtc tccactctcc ctgcccgtca cccttggaca gccggcctcc      60
atctcctgca ggtctagtca aagcctcgta tacagtgatg aaacaccta cttgaattgg     120
tctcagcaga ggccaggtca atctccaagg cgcctaattt ataaggtttc taaccgggac    180
tctggggtcc cagacagatt cagcggcagt gggtcaggca ctgatttcac actgaaaatc    240
agcagggtgg aggctgagga tgttggggtt tattactgca tgcaaggtac acactggccg    300
tacacttttg gccaggggac caagctggag atcaaa                              336
```

<210> SEQ ID NO 322
<211> LENGTH: 112
<212> TYPE: PRT
<213> ORGANISM: Artificial Sequence
<220> FEATURE:
<223> OTHER INFORMATION: Synthetic

<400> SEQUENCE: 322

```
Asp Val Val Met Thr Gln Ser Pro Leu Ser Leu Pro Val Thr Leu Gly
 1               5                  10                  15

Gln Pro Ala Ser Ile Ser Cys Arg Ser Ser Gln Ser Leu Val Tyr Ser
            20                  25                  30

Asp Gly Asn Thr Tyr Leu Asn Trp Ser Gln Gln Arg Pro Gly Gln Ser
        35                  40                  45

Pro Arg Arg Leu Ile Tyr Lys Val Ser Asn Arg Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Gly
                85                  90                  95

Thr His Trp Pro Tyr Thr Phe Gly Gln Gly Thr Lys Leu Glu Ile Lys
            100                 105                 110
```

<210> SEQ ID NO 323
<211> LENGTH: 33
<212> TYPE: DNA
<213> ORGANISM: Artificial Sequence
<220> FEATURE:
<223> OTHER INFORMATION: Synthetic

<400> SEQUENCE: 323

```
caaagcctcg tatacagtga tggaaacacc tac                                  33
```

<210> SEQ ID NO 324
<211> LENGTH: 11
<212> TYPE: PRT
<213> ORGANISM: Artificial Sequence
<220> FEATURE:
<223> OTHER INFORMATION: Synthetic

<400> SEQUENCE: 324

```
Gln Ser Leu Val Tyr Ser Asp Gly Asn Thr Tyr
 1               5                  10
```

<210> SEQ ID NO 325
<211> LENGTH: 9
<212> TYPE: DNA
<213> ORGANISM: Artificial Sequence
<220> FEATURE:
<223> OTHER INFORMATION: Synthetic

<400> SEQUENCE: 325 aaggtttct                                                                                      9

<210> SEQ ID NO 326
<211> LENGTH: 3
<212> TYPE: PRT
<213> ORGANISM: Artificial Sequence
<220> FEATURE:
<223> OTHER INFORMATION: Synthetic

<400> SEQUENCE: 326

Lys Val Ser
 1

<210> SEQ ID NO 327
<211> LENGTH: 27
<212> TYPE: DNA
<213> ORGANISM: Artificial Sequence
<220> FEATURE:
<223> OTHER INFORMATION: Synthetic

<400> SEQUENCE: 327
atgcaaggta cacactggcc gtacact                                                                 27

<210> SEQ ID NO 328
<211> LENGTH: 9
<212> TYPE: PRT
<213> ORGANISM: Artificial Sequence
<220> FEATURE:
<223> OTHER INFORMATION: Synthetic

<400> SEQUENCE: 328

Met Gln Gly Thr His Trp Pro Tyr Thr
 1               5

<210> SEQ ID NO 329
<211> LENGTH: 381
<212> TYPE: DNA
<213> ORGANISM: Artificial Sequence
<220> FEATURE:
<223> OTHER INFORMATION: Synthetic

<400> SEQUENCE: 329
caggttcagc tggtgcagtc tggacctgag gtgaagaacc ctggggcctc agtgaaggtc    60
tcctgcaagg cttctggtta ccctttacc acctatggta tcagttgggt acgacaggcc   120
cctggacaag ggcttgagtg gatgggatgg atcagcggtt acaatggtaa aacaaacgat   180
gcacagaagt tccaggacag agtcgccatg accacagaca catccacgag cacagcctac   240
atggagctga ggagcctgag atctgacgac acggccattt attactgttc gagagatcgt   300
ttagtagtac cacctgccct taattattcc tactacgtta tggacgtctg gggccaaggg   360
accacggtca ccgtctcctc a                                            381

<210> SEQ ID NO 330
<211> LENGTH: 127
<212> TYPE: PRT
<213> ORGANISM: Artificial Sequence
<220> FEATURE:
<223> OTHER INFORMATION: Synthetic

<400> SEQUENCE: 330

Gln Val Gln Leu Val Gln Ser Gly Pro Glu Val Lys Asn Pro Gly Ala
 1               5                  10                  15

Ser Val Lys Val Ser Cys Lys Ala Ser Gly Tyr Thr Phe Thr Thr Tyr
            20                  25                  30

Gly Ile Ser Trp Val Arg Gln Ala Pro Gly Gln Gly Leu Glu Trp Met
        35                  40                  45

Gly Trp Ile Ser Gly Tyr Asn Gly Lys Thr Asn Asp Ala Gln Lys Phe
    50                  55                  60

Gln Asp Arg Val Ala Met Thr Thr Asp Thr Ser Thr Ser Thr Ala Tyr
65                  70                  75                  80

Met Glu Leu Arg Ser Leu Arg Ser Asp Asp Thr Ala Ile Tyr Tyr Cys
                85                  90                  95

Ser Arg Asp Arg Leu Val Val Pro Pro Ala Leu Asn Tyr Ser Tyr Tyr
            100                 105                 110

Val Met Asp Val Trp Gly Gln Gly Thr Thr Val Thr Val Ser Ser
        115                 120                 125

<210> SEQ ID NO 331
<211> LENGTH: 336
<212> TYPE: DNA
<213> ORGANISM: Artificial Sequence
<220> FEATURE:
<223> OTHER INFORMATION: Synthetic

<400> SEQUENCE: 331
gatgttgtga tgactcagtc tccactctcc ctgcccgtca cccttggaca gccggcctcc      60
atctcctgca ggtctagtca aagcctcgta tacagtgatg gaaacaccta cttgaattgg    120
tctcagcaga ggccaggtca atctccaagg cgcctaattt ataaggtttc taaccgggac    180
tctggggtcc cagacagatt cagcggcagt gggtcaggca ctgatttcac actgaaaatc    240
agcagggtgg aggctgagga tgttgggggtt tattactgca tgcaaggtac acactggccg    300 tacactttg gccaggggac caagctggag atcaaa                                336

<210> SEQ ID NO 332
<211> LENGTH: 112
<212> TYPE: PRT
<213> ORGANISM: Artificial Sequence
<220> FEATURE:
<223> OTHER INFORMATION: Synthetic

<400> SEQUENCE: 332

Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Leu Val Tyr Ser
            20                  25                  30

Asp Gly Asn Thr Tyr Leu Asn Trp Ser Gln Gln Arg Pro Gly Gln Ser
        35                  40                  45

Pro Arg Arg Leu Ile Tyr Lys Val Ser Asn Arg Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Gly
                85                  90                  95

Thr His Trp Pro Tyr Thr Phe Gly Gln Gly Thr Lys Leu Glu Ile Lys
            100                 105                 110

<210> SEQ ID NO 333
<211> LENGTH: 381
<212> TYPE: DNA

<213> ORGANISM: Artificial Sequence
<220> FEATURE:
<223> OTHER INFORMATION: Synthetic

<400> SEQUENCE: 333

```
caggttcagc tggtgcagtc tggagctgag gtgaagaagc ctggggcctc agtgaaggtc    60
tcctgcaagg cttctggtta cacctttacc acctatggta tcagctgggt gcgacaggcc   120
cctggacaag gcttgagtg gatgggatgg atcagcggtt acaatggtaa acaaactat    180
gcacagaagc tccagggcag agtcaccatg accacagaca catccacgag cacagcctac   240
atggagctga ggagcctgag atctgacgac acggccgtgt attactgttc gagagatcgt   300
ttagtagtac cacctgccct taattattcc tactacgtta tggacgtctg ggggcaaggg   360
accacggtca ccgtctcctc a                                             381
```

<210> SEQ ID NO 334
<211> LENGTH: 127
<212> TYPE: PRT
<213> ORGANISM: Artificial Sequence
<220> FEATURE:
<223> OTHER INFORMATION: Synthetic

<400> SEQUENCE: 334

```
Gln Val Gln Leu Val Gln Ser Gly Ala Glu Val Lys Lys Pro Gly Ala
  1               5                  10                  15
Ser Val Lys Val Ser Cys Lys Ala Ser Gly Tyr Thr Phe Thr Thr Tyr
             20                  25                  30
Gly Ile Ser Trp Val Arg Gln Ala Pro Gly Gln Gly Leu Glu Trp Met
         35                  40                  45
Gly Trp Ile Ser Gly Tyr Asn Gly Lys Thr Asn Tyr Ala Gln Lys Leu
     50                  55                  60
Gln Gly Arg Val Thr Met Thr Thr Asp Thr Ser Thr Ser Thr Ala Tyr
 65                  70                  75                  80
Met Glu Leu Arg Ser Leu Arg Ser Asp Asp Thr Ala Val Tyr Tyr Cys
                 85                  90                  95
Ser Arg Asp Arg Leu Val Val Pro Pro Ala Leu Asn Tyr Ser Tyr Tyr
            100                 105                 110
Val Met Asp Val Trp Gly Gln Gly Thr Thr Val Thr Val Ser Ser
        115                 120                 125
```

<210> SEQ ID NO 335
<211> LENGTH: 336
<212> TYPE: DNA
<213> ORGANISM: Artificial Sequence
<220> FEATURE:
<223> OTHER INFORMATION: Synthetic

<400> SEQUENCE: 335

```
gatgttgtga tgactcagtc tccactctcc ctgcccgtca cccttggaca gccggcctcc    60
atctcctgca ggtctagtca aagcctcgta tacagtgatg gaaacaccta cttgaattgg   120
tttcagcaga ggccaggcca atctccaagg cgcctaattt ataaggtttc taaccgggac   180
tctggggtcc cagacagatt cagcggcagt gggtcaggca ctgatttcac actgaaaatc   240
agcagggtgg aggctgagga tgttggggtt tattactgca tgcaaggtac acactggccg   300
tacactttg ccaggggac caagctggag atcaaa                                336
```

<210> SEQ ID NO 336
<211> LENGTH: 112

```
<212> TYPE: PRT
<213> ORGANISM: Artificial Sequence
<220> FEATURE:
<223> OTHER INFORMATION: Synthetic

<400> SEQUENCE: 336
```

| | | | | | | | | | | | | | | |
|---|---|---|---|---|---|---|---|---|---|---|---|---|---|---|
|Asp|Val|Val|Met|Thr|Gln|Ser|Pro|Leu|Ser|Leu|Pro|Val|Thr|Leu|Gly|
|1| | | |5| | | | |10| | | | |15| |

Gln Pro Ala Ser Ile Ser Cys Arg Ser Ser Gln Ser Leu Val Tyr Ser
              20                  25                  30

Asp Gly Asn Thr Tyr Leu Asn Trp Phe Gln Gln Arg Pro Gly Gln Ser
          35                  40                  45

Pro Arg Arg Leu Ile Tyr Lys Val Ser Asn Arg Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Gly
                85                  90                  95

Thr His Trp Pro Tyr Thr Phe Gly Gln Gly Thr Lys Leu Glu Ile Lys
            100                 105                 110

```
<210> SEQ ID NO 337
<211> LENGTH: 354
<212> TYPE: DNA
<213> ORGANISM: Artificial Sequence
<220> FEATURE:
<223> OTHER INFORMATION: Synthetic

<400> SEQUENCE: 337
gaggtgcagc tggtggagtc tgggggaggc ctggtcaagc ctggggggtc cctgagactc      60
tcctgtgcag cctctggatt caccttcagt agctatagca tggactgggt ccgccaggct     120
ccagggaagg ggctggagtg ggtctcatcc attagtagta gtagtagtta catatactac     180
gcagactctg tgaagggccg attcaccatc tccagagaca ccgccaagaa ctcactgtat     240
ctgcaaatga acagcctgag agacgaggac acggctgttt attactgtgc gagagagggc     300
agtagcagac ttttgacta ctggggccag ggaaccctgg tcaccgtctc ctca            354

<210> SEQ ID NO 338
<211> LENGTH: 118
<212> TYPE: PRT
<213> ORGANISM: Artificial Sequence
<220> FEATURE:
<223> OTHER INFORMATION: Synthetic

<400> SEQUENCE: 338
```

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Ser Met Asp Trp Val Arg Gln Ala Pro Gly Lys Gly Leu Glu Trp Val
        35                  40                  45

Ser Ser Ile Ser Ser Ser Ser Ser Tyr Ile Tyr Tyr Ala Asp Ser Val
    50                  55                  60

Lys Gly Arg Phe Thr Ile Ser Arg Asp Thr Ala Lys Asn Ser Leu Tyr
65                  70                  75                  80

Leu Gln Met Asn Ser Leu Arg Asp Glu Asp Thr Ala Val Tyr Tyr Cys
                85                  90                  95

Ala Arg Glu Gly Ser Ser Arg Leu Phe Asp Tyr Trp Gly Gln Gly Thr

Leu Val Thr Val Ser Ser
        115

<210> SEQ ID NO 339
<211> LENGTH: 24
<212> TYPE: DNA
<213> ORGANISM: Artificial Sequence
<220> FEATURE:
<223> OTHER INFORMATION: Synthetic

<400> SEQUENCE: 339
ggattcacct tcagtagcta tagc                                    24

<210> SEQ ID NO 340
<211> LENGTH: 8
<212> TYPE: PRT
<213> ORGANISM: Artificial Sequence
<220> FEATURE:
<223> OTHER INFORMATION: Synthetic

<400> SEQUENCE: 340

Gly Phe Thr Phe Ser Ser Tyr Ser
1               5

<210> SEQ ID NO 341
<211> LENGTH: 24
<212> TYPE: DNA
<213> ORGANISM: Artificial Sequence
<220> FEATURE:
<223> OTHER INFORMATION: Synthetic

<400> SEQUENCE: 341
attagtagta gtagtagtta cata                                    24

<210> SEQ ID NO 342
<211> LENGTH: 8
<212> TYPE: PRT
<213> ORGANISM: Artificial Sequence
<220> FEATURE:
<223> OTHER INFORMATION: Synthetic

<400> SEQUENCE: 342

Ile Ser Ser Ser Ser Ser Tyr Ile
1               5

<210> SEQ ID NO 343
<211> LENGTH: 33
<212> TYPE: DNA
<213> ORGANISM: Artificial Sequence
<220> FEATURE:
<223> OTHER INFORMATION: Synthetic

<400> SEQUENCE: 343
gcgagagagg gcagtagcag acttttgac tac                           33

<210> SEQ ID NO 344
<211> LENGTH: 11
<212> TYPE: PRT
<213> ORGANISM: Artificial Sequence
<220> FEATURE:
<223> OTHER INFORMATION: Synthetic

<400> SEQUENCE: 344

Ala Arg Glu Gly Ser Ser Arg Leu Phe Asp Tyr
1               5                   10

-continued

<210> SEQ ID NO 345
<211> LENGTH: 321
<212> TYPE: DNA
<213> ORGANISM: Artificial Sequence
<220> FEATURE:
<223> OTHER INFORMATION: Synthetic

<400> SEQUENCE: 345

```
gacatccaga tgacccagtc tccttccacc ctgtctgcat ctgtaggaga cagagtcacc    60
atcacttgcc gggccagtca gagtattagt agctggttgg cctggtatca gcagagacca   120
gggaaagccc ctaagctcct gatctataag gcgtctagtt tagaaggtgg agtcccatca   180
aggttcagcg gcagtggatc tgggacagaa ttcactctca ccatcagcag cctgcagcct   240
gaggattttg caacttatta ctgccaacag tataatagtt attggtacac ttttggccag   300
gggaccaagc tggagatcaa a                                             321
```

<210> SEQ ID NO 346
<211> LENGTH: 107
<212> TYPE: PRT
<213> ORGANISM: Artificial Sequence
<220> FEATURE:
<223> OTHER INFORMATION: Synthetic

<400> SEQUENCE: 346

```
Asp Ile Gln Met Thr Gln Ser Pro Ser Thr Leu Ser Ala Ser Val Gly
 1               5                  10                  15

Asp Arg Val Thr Ile Thr Cys Arg Ala Ser Gln Ser Ile Ser Ser Trp
            20                  25                  30

Leu Ala Trp Tyr Gln Gln Arg Pro Gly Lys Ala Pro Lys Leu Leu Ile
        35                  40                  45

Tyr Lys Ala Ser Ser Leu Glu Gly Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Gln Gln Tyr Asn Ser Tyr Trp Tyr
                85                  90                  95

Thr Phe Gly Gln Gly Thr Lys Leu Glu Ile Lys
            100                 105
```

<210> SEQ ID NO 347
<211> LENGTH: 18
<212> TYPE: DNA
<213> ORGANISM: Artificial Sequence
<220> FEATURE:
<223> OTHER INFORMATION: Synthetic

<400> SEQUENCE: 347

```
cagagtatta gtagctgg                                                  18
```

<210> SEQ ID NO 348
<211> LENGTH: 6
<212> TYPE: PRT
<213> ORGANISM: Artificial Sequence
<220> FEATURE:
<223> OTHER INFORMATION: Synthetic

<400> SEQUENCE: 348

```
Gln Ser Ile Ser Ser Trp
 1               5
```

<210> SEQ ID NO 349
<211> LENGTH: 9
<212> TYPE: DNA
<213> ORGANISM: Artificial Sequence
<220> FEATURE:
<223> OTHER INFORMATION: Synthetic

<400> SEQUENCE: 349 aaggcgtct                                                                         9

<210> SEQ ID NO 350
<211> LENGTH: 3
<212> TYPE: PRT
<213> ORGANISM: Artificial Sequence
<220> FEATURE:
<223> OTHER INFORMATION: Synthetic

<400> SEQUENCE: 350

Lys Ala Ser
 1

<210> SEQ ID NO 351
<211> LENGTH: 27
<212> TYPE: DNA
<213> ORGANISM: Artificial Sequence
<220> FEATURE:
<223> OTHER INFORMATION: Synthetic

<400> SEQUENCE: 351
caacagtata atagttattg gtacact                                                    27

<210> SEQ ID NO 352
<211> LENGTH: 9
<212> TYPE: PRT
<213> ORGANISM: Artificial Sequence
<220> FEATURE:
<223> OTHER INFORMATION: Synthetic

<400> SEQUENCE: 352

Gln Gln Tyr Asn Ser Tyr Trp Tyr Thr
 1               5

<210> SEQ ID NO 353
<211> LENGTH: 354
<212> TYPE: DNA
<213> ORGANISM: Artificial Sequence
<220> FEATURE:
<223> OTHER INFORMATION: Synthetic

<400> SEQUENCE: 353
gaggtgcagc tggtggagtc tgggggaggc ctggtcaagc ctgggggtc cctgagactc           60 tcctgtgcag cctctggatt caccttcagt agctatagca tggactgggt ccgccaggct        120
ccagggaagg ggctggagtg gtctctcatcc attagtagta gtagtagtta catatactac       180
gcagactctg tgaagggccg attcaccatc tccagagaca ccgccaagaa ctcactgtat        240
ctgcaaatga acagcctgag agacgaggac acggctgttt attactgtgc gagagagggc       300
agtagcagac tttttgacta ctggggccag ggaaccctgg tcaccgtctc ctca              354

<210> SEQ ID NO 354
<211> LENGTH: 118
<212> TYPE: PRT
<213> ORGANISM: Artificial Sequence
<220> FEATURE:
<223> OTHER INFORMATION: Synthetic

<400> SEQUENCE: 354

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Ser Met Asp Trp Val Arg Gln Ala Pro Gly Lys Gly Leu Glu Trp Val
        35                  40                  45

Ser Ser Ile Ser Ser Ser Ser Tyr Ile Tyr Tyr Ala Asp Ser Val
    50                  55                  60

Lys Gly Arg Phe Thr Ile Ser Arg Asp Thr Ala Lys Asn Ser Leu Tyr
65                  70                  75                  80

Leu Gln Met Asn Ser Leu Arg Asp Glu Asp Thr Ala Val Tyr Tyr Cys
                85                  90                  95

Ala Arg Glu Gly Ser Ser Arg Leu Phe Asp Tyr Trp Gly Gln Gly Thr
            100                 105                 110

Leu Val Thr Val Ser Ser
            115

<210> SEQ ID NO 355
<211> LENGTH: 321
<212> TYPE: DNA
<213> ORGANISM: Artificial Sequence
<220> FEATURE:
<223> OTHER INFORMATION: Synthetic

<400> SEQUENCE: 355
gacatccaga tgacccagtc tccttccacc ctgtctgcat ctgtaggaga cagagtcacc      60
atcacttgcc gggccagtca gagtattagt agctggttgg cctggtatca gcagagacca    120
gggaaagccc ctaagctcct gatctataag gcgtctagtt tagaaggtgg agtcccatca    180
aggttcagcg gcagtggatc tgggacagaa ttcactctca ccatcagcag cctgcagcct    240
gaggattttg caacttatta ctgccaacag tataatagtt attggtacac ttttggccag    300
gggaccaagc tggagatcaa a                                              321

<210> SEQ ID NO 356
<211> LENGTH: 107
<212> TYPE: PRT
<213> ORGANISM: Artificial Sequence
<220> FEATURE:
<223> OTHER INFORMATION: Synthetic

<400> SEQUENCE: 356

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Arg Pro Gly Lys Ala Pro Lys Leu Leu Ile
        35                  40                  45

Tyr Lys Ala Ser Ser Leu Glu Gly Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Gln Gln Tyr Asn Ser Tyr Trp Tyr
                85                  90                  95

Thr Phe Gly Gln Gly Thr Lys Leu Glu Ile Lys
            100                 105

<210> SEQ ID NO 357
<211> LENGTH: 354
<212> TYPE: DNA
<213> ORGANISM: Artificial Sequence
<220> FEATURE:
<223> OTHER INFORMATION: Synthetic

<400> SEQUENCE: 357

```
gaggtgcagc tggtggagtc tgggggaggc ctggtcaagc ctgggggtc cctgagactc      60
tcctgtgcag cctctggatt caccttcagt agctatagca tgaactgggt ccgccaggct    120
ccagggaagg gctggagtg gtctcatcc attagtagta gtagtagtta catatactac      180
gcagactcag tgaagggccg attcaccatc tccagagaca acgccaagaa ctcactgtat    240
ctgcaaatga acagcctgag agccgaggac acggctgtgt attactgtgc gagagagggc    300
agtagcagac ttttgacta ctggggccaa ggaaccctgg tcaccgtctc ctca           354
```

<210> SEQ ID NO 358
<211> LENGTH: 118
<212> TYPE: PRT
<213> ORGANISM: Artificial Sequence
<220> FEATURE:
<223> OTHER INFORMATION: Synthetic

<400> SEQUENCE: 358

```
Glu Val Gln Leu Val Glu Ser Gly Gly Gly Leu Val Lys Pro Gly Gly
  1               5                  10                  15
Ser Leu Arg Leu Ser Cys Ala Ala Ser Gly Phe Thr Phe Ser Ser Tyr
             20                  25                  30
Ser Met Asn Trp Val Arg Gln Ala Pro Gly Lys Gly Leu Glu Trp Val
         35                  40                  45
Ser Ser Ile Ser Ser Ser Ser Tyr Ile Tyr Tyr Ala Asp Ser Val
     50                  55                  60
Lys Gly Arg Phe Thr Ile Ser Arg Asp Asn Ala Lys Asn Ser Leu Tyr
 65                  70                  75                  80
Leu Gln Met Asn Ser Leu Arg Ala Glu Asp Thr Ala Val Tyr Tyr Cys
                 85                  90                  95
Ala Arg Glu Gly Ser Ser Arg Leu Phe Asp Tyr Trp Gly Gln Gly Thr
            100                 105                 110
Leu Val Thr Val Ser Ser
        115
```

<210> SEQ ID NO 359
<211> LENGTH: 321
<212> TYPE: DNA
<213> ORGANISM: Artificial Sequence
<220> FEATURE:
<223> OTHER INFORMATION: Synthetic

<400> SEQUENCE: 359

```
gacatccaga tgacccagtc tccttccacc ctgtctgcat ctgtaggaga cagagtcacc     60
atcacttgcc gggccagtca gagtattagt agctggttgg cctggtatca gcagaaacca   120
gggaaagccc ctaagctcct gatctataag gcgtctagtt tagaaagtgg ggtcccatca   180
aggttcagcg gcagtggatc tgggacagaa ttcactctca ccatcagcag cctgcagcct   240
gatgattttg caacttatta ctgccaacag tataatagtt attggtacac ttttggccag   300
gggaccaagc tggagatcaa a                                              321
```

<210> SEQ ID NO 360
<211> LENGTH: 107
<212> TYPE: PRT
<213> ORGANISM: Artificial Sequence
<220> FEATURE:
<223> OTHER INFORMATION: Synthetic

<400> SEQUENCE: 360

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Tyr Lys Ala Ser Ser Leu Glu Ser Gly Val Pro Ser Arg Phe Ser Gly
50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Asn Ser Tyr Trp Tyr
                85                  90                  95

Thr Phe Gly Gln Gly Thr Lys Leu Glu Ile Lys
            100                 105

<210> SEQ ID NO 361
<211> LENGTH: 384
<212> TYPE: DNA
<213> ORGANISM: Artificial Sequence
<220> FEATURE:
<223> OTHER INFORMATION: Synthetic

<400> SEQUENCE: 361
caggtgcacc tggtggagtc tgggggaggc ttggtcaagc ctggagggtc cctgagactc      60
tcctgtgcag cctctggatt caccttcagt gaccactaca tgagctggat ccgccaggct     120
ccagggaagg ggctggagtg gatttcatac attagtaatg atggtggtac caaatactat     180
gtggactctg tggagggccg attcatcatt tccaggaca acgccaagaa ctcattgtat      240
ctacatatga acagcctcag agccgacgac acggccgtgt attactgtgc gagagatcag     300
ggatatattg ctacgactc gtattattac tattcctacg gtatggacgt ctggggccaa      360
gggaccacgg tcaccgtcgc ctca                                            384

<210> SEQ ID NO 362
<211> LENGTH: 128
<212> TYPE: PRT
<213> ORGANISM: Artificial Sequence
<220> FEATURE:
<223> OTHER INFORMATION: Synthetic

<400> SEQUENCE: 362

Gln Val His Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp His
            20                  25                  30

Tyr Met Ser Trp Ile Arg Gln Ala Pro Gly Lys Gly Leu Glu Trp Ile
        35                  40                  45

Ser Tyr Ile Ser Asn Asp Gly Gly Thr Lys Tyr Tyr Val Asp Ser Val
    50                  55                  60

Glu Gly Arg Phe Ile Ile Ser Arg Asp Asn Ala Lys Asn Ser Leu Tyr
65                  70                  75                  80

Leu His Met Asn Ser Leu Arg Ala Asp Asp Thr Ala Val Tyr Tyr Cys
            85                  90                  95

Ala Arg Asp Gln Gly Tyr Ile Gly Tyr Asp Ser Tyr Tyr Tyr Tyr Ser
        100                 105                 110

Tyr Gly Met Asp Val Trp Gly Gln Gly Thr Thr Val Thr Val Ala Ser
    115                 120                 125

<210> SEQ ID NO 363
<211> LENGTH: 24
<212> TYPE: DNA
<213> ORGANISM: Artificial Sequence
<220> FEATURE:
<223> OTHER INFORMATION: Synthetic

<400> SEQUENCE: 363
ggattcacct tcagtgacca ctac                                          24

<210> SEQ ID NO 364
<211> LENGTH: 8
<212> TYPE: PRT
<213> ORGANISM: Artificial Sequence
<220> FEATURE:
<223> OTHER INFORMATION: Synthetic

<400> SEQUENCE: 364

Gly Phe Thr Phe Ser Asp His Tyr
1               5

<210> SEQ ID NO 365
<211> LENGTH: 24
<212> TYPE: DNA
<213> ORGANISM: Artificial Sequence
<220> FEATURE:
<223> OTHER INFORMATION: Synthetic

<400> SEQUENCE: 365
attagtaatg atggtggtac caaa                                          24

<210> SEQ ID NO 366
<211> LENGTH: 8
<212> TYPE: PRT
<213> ORGANISM: Artificial Sequence
<220> FEATURE:
<223> OTHER INFORMATION: Synthetic

<400> SEQUENCE: 366

Ile Ser Asn Asp Gly Gly Thr Lys
1               5

<210> SEQ ID NO 367
<211> LENGTH: 63
<212> TYPE: DNA
<213> ORGANISM: Artificial Sequence
<220> FEATURE:
<223> OTHER INFORMATION: Synthetic

<400> SEQUENCE: 367
gcgagagatc aggatatat tggctacgac tcgtattatt actattccta cggtatggac     60
gtc                                                                 63

<210> SEQ ID NO 368
<211> LENGTH: 21
<212> TYPE: PRT
<213> ORGANISM: Artificial Sequence
<220> FEATURE:
<223> OTHER INFORMATION: Synthetic

<400> SEQUENCE: 368

Ala Arg Asp Gln Gly Tyr Ile Gly Tyr Asp Ser Tyr Tyr Tyr Ser
1               5                   10                  15

Tyr Gly Met Asp Val
            20

<210> SEQ ID NO 369
<211> LENGTH: 321
<212> TYPE: DNA
<213> ORGANISM: Artificial Sequence
<220> FEATURE:
<223> OTHER INFORMATION: Synthetic

<400> SEQUENCE: 369
aaaattgtgt tgacgcagtc tccaggcacc ctgcctttgt tccagggga aagagccacc        60
ctctcctgta gggccagtca gagtgttaac aacaaattct tagcctggta ccagcagaaa      120
tctggccagg ctcccaggct cctcatctat ggtgcatcca gcagggccac tggcatccca      180
gacaggttca gtggcagtgg gtctgggacc gacttcactc tcaccatcag cggactggag      240
cctgaagatt ttgaagtgta ttattgtcaa gtatatggta actcactcac tctcggcgga      300
gggaccaagg tggagatcaa g                                                321

<210> SEQ ID NO 370
<211> LENGTH: 107
<212> TYPE: PRT
<213> ORGANISM: Artificial Sequence
<220> FEATURE:
<223> OTHER INFORMATION: Synthetic

<400> SEQUENCE: 370

Lys Ile Val Leu Thr Gln Ser Pro Gly Thr Leu Pro Leu Phe Pro Gly
1               5                   10                  15

Glu Arg Ala Thr Leu Ser Cys Arg Ala Ser Gln Ser Val Asn Asn Lys
                20                  25                  30

Phe Leu Ala Trp Tyr Gln Lys Ser Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Gly Leu Glu
65                  70                  75                  80

Pro Glu Asp Phe Glu Val Tyr Tyr Cys Gln Val Tyr Gly Asn Ser Leu
                85                  90                  95

Thr Leu Gly Gly Gly Thr Lys Val Glu Ile Lys
            100                 105

<210> SEQ ID NO 371
<211> LENGTH: 21
<212> TYPE: DNA
<213> ORGANISM: Artificial Sequence
<220> FEATURE:
<223> OTHER INFORMATION: Synthetic

<400> SEQUENCE: 371
cagagtgtta acaacaaatt c                                                 21

<210> SEQ ID NO 372
<211> LENGTH: 7

```
<212> TYPE: PRT
<213> ORGANISM: Artificial Sequence
<220> FEATURE:
<223> OTHER INFORMATION: Synthetic

<400> SEQUENCE: 372

Gln Ser Val Asn Asn Lys Phe
 1               5

<210> SEQ ID NO 373
<211> LENGTH: 9
<212> TYPE: DNA
<213> ORGANISM: Artificial Sequence
<220> FEATURE:
<223> OTHER INFORMATION: Synthetic

<400> SEQUENCE: 373 ggtgcatcc                                                                 9

<210> SEQ ID NO 374
<211> LENGTH: 3
<212> TYPE: PRT
<213> ORGANISM: Artificial Sequence
<220> FEATURE:
<223> OTHER INFORMATION: Synthetic

<400> SEQUENCE: 374

Gly Ala Ser
 1

<210> SEQ ID NO 375
<211> LENGTH: 24
<212> TYPE: DNA
<213> ORGANISM: Artificial Sequence
<220> FEATURE:
<223> OTHER INFORMATION: Synthetic

<400> SEQUENCE: 375
caagtatatg gtaactcact cact                                               24

<210> SEQ ID NO 376
<211> LENGTH: 8
<212> TYPE: PRT
<213> ORGANISM: Artificial Sequence
<220> FEATURE:
<223> OTHER INFORMATION: Synthetic

<400> SEQUENCE: 376

Gln Val Tyr Gly Asn Ser Leu Thr
 1               5

<210> SEQ ID NO 377
<211> LENGTH: 384
<212> TYPE: DNA
<213> ORGANISM: Artificial Sequence
<220> FEATURE:
<223> OTHER INFORMATION: Synthetic

<400> SEQUENCE: 377
caggtgcagc tggtggagtc tgggggaggc ttggtcaagc ctggagggtc cctgagactc        60
tcctgtgcag cctctggatt caccttcagt gaccactaca tgagctggat ccgccaggct       120
ccagggaagg ggctggagtg gatttcatac attagtaatg atggtggtac caaatactat       180
gtggactctg tgaagggccg attcatcatt tccagggaca cgccaagaa ctcattgtat        240 ctacatatga acagcctcag agccgacgac acggccgtgt attactgtgc gagagatcag       300
```

```
ggatatattg gctacgactc gtattattac tattcctacg gtatggacgt ctggggccaa    360
gggaccacgg tcaccgtctc ctca                                          384
```

<210> SEQ ID NO 378
<211> LENGTH: 128
<212> TYPE: PRT
<213> ORGANISM: Artificial Sequence
<220> FEATURE:
<223> OTHER INFORMATION: Synthetic

<400> SEQUENCE: 378

```
Gln Val Gln Leu Val Glu Ser Gly Gly Gly Leu Val Lys Pro Gly Gly
 1               5                  10                  15

Ser Leu Arg Leu Ser Cys Ala Ala Ser Gly Phe Thr Phe Ser Asp His
            20                  25                  30

Tyr Met Ser Trp Ile Arg Gln Ala Pro Gly Lys Gly Leu Glu Trp Ile
        35                  40                  45

Ser Tyr Ile Ser Asn Asp Gly Thr Lys Tyr Tyr Val Asp Ser Val
    50                  55                  60

Glu Gly Arg Phe Ile Ile Ser Arg Asp Asn Ala Lys Asn Ser Leu Tyr
65                  70                  75                  80

Leu His Met Asn Ser Leu Arg Ala Asp Asp Thr Ala Val Tyr Tyr Cys
                85                  90                  95

Ala Arg Asp Gln Gly Tyr Ile Gly Tyr Asp Ser Tyr Tyr Tyr Tyr Ser
            100                 105                 110

Tyr Gly Met Asp Val Trp Gly Gln Gly Thr Thr Val Thr Val Ser Ser
        115                 120                 125
```

<210> SEQ ID NO 379
<211> LENGTH: 321
<212> TYPE: DNA
<213> ORGANISM: Artificial Sequence
<220> FEATURE:
<223> OTHER INFORMATION: Synthetic

<400> SEQUENCE: 379

```
gaaattgtgt tgacgcagtc tccaggcacc ctgcctttgt tcccagggga aagagccacc    60
ctctcctgta gggccagtca gagtgttaac aacaaattct tagcctggta ccagcagaaa   120
tctggccagg ctcccaggct cctcatctat ggtgcatcca gcagggccac tggcatccca   180
gacaggttca gtggcagtgg gtctgggacc gacttcactc tcaccatcag cggactggag   240
cctgaagatt ttgaagtgta ttattgtcaa gtatatggta actcactcac tctcggcgga   300
gggaccaagg tggagatcaa a                                             321
```

<210> SEQ ID NO 380
<211> LENGTH: 107
<212> TYPE: PRT
<213> ORGANISM: Artificial Sequence
<220> FEATURE:
<223> OTHER INFORMATION: Synthetic

<400> SEQUENCE: 380

```
Glu Ile Val Leu Thr Gln Ser Pro Gly Thr Leu Pro Leu Phe Pro Gly
 1               5                  10                  15

Glu Arg Ala Thr Leu Ser Cys Arg Ala Ser Gln Ser Val Asn Asn Lys
            20                  25                  30

Phe Leu Ala Trp Tyr Gln Gln Lys Ser Gly Gln Ala Pro Arg Leu Leu
        35                  40                  45
```

Ile Tyr Gly Ala Ser Ser Arg Ala Thr Gly Ile Pro Asp Arg Phe Ser
            50                  55                  60

Gly Ser Gly Ser Gly Thr Asp Phe Thr Leu Thr Ile Ser Gly Leu Glu
 65                  70                  75                  80

Pro Glu Asp Phe Glu Val Tyr Tyr Cys Gln Val Tyr Gly Asn Ser Leu
                 85                  90                  95

Thr Leu Gly Gly Gly Thr Lys Val Glu Ile Lys
            100                 105

<210> SEQ ID NO 381
<211> LENGTH: 384
<212> TYPE: DNA
<213> ORGANISM: Artificial Sequence
<220> FEATURE:
<223> OTHER INFORMATION: Synthetic

<400> SEQUENCE: 381
caggtgcagc tggtggagtc tgggggaggc ttggtcaagc ctggagggtc cctgagactc      60
tcctgtgcag cctctggatt caccttcagt gaccactaca tgagctggat ccgccaggct     120
ccagggaagg gactggagtg ggtttcatac attagtaatg atggtggtac caaatactac     180
gcagactctg tgaagggccg attcaccatc tccagggaca acgccaagaa ctcactgtat     240
ctgcaaatga acagcctgag agccgaggac acggccgtgt attactgtgc gagagatcag     300
ggatatattg gctacgactc gtattattac tattcctacg gtatggacgt ctggggggcaa    360 gggaccacgg tcaccgtctc ctca                                            384

<210> SEQ ID NO 382
<211> LENGTH: 128
<212> TYPE: PRT
<213> ORGANISM: Artificial Sequence
<220> FEATURE:
<223> OTHER INFORMATION: Synthetic

<400> SEQUENCE: 382

Gln Val Gln Leu Val Glu Ser Gly Gly Gly Leu Val Lys Pro Gly Gly
 1               5                  10                  15

Ser Leu Arg Leu Ser Cys Ala Ala Ser Gly Phe Thr Phe Ser Asp His
            20                  25                  30

Tyr Met Ser Trp Ile Arg Gln Ala Pro Gly Lys Gly Leu Glu Trp Val
        35                  40                  45

Ser Tyr Ile Ser Asn Asp Gly Gly Thr Lys Tyr Tyr Ala Asp Ser Val
    50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                 85                  90                  95

Ala Arg Asp Gln Gly Tyr Ile Gly Tyr Asp Ser Tyr Tyr Tyr Tyr Ser
            100                 105                 110

Tyr Gly Met Asp Val Trp Gly Gln Gly Thr Thr Val Thr Val Ser Ser
        115                 120                 125

<210> SEQ ID NO 383
<211> LENGTH: 321
<212> TYPE: DNA
<213> ORGANISM: Artificial Sequence
<220> FEATURE:
<223> OTHER INFORMATION: Synthetic -continued

```
<400> SEQUENCE: 383
gaaattgtgt tgacgcagtc tccaggcacc ctgtctttgt ctccagggga aagagccacc    60
ctctcctgca gggccagtca gagtgttaac aacaaattct tagcctggta ccagcagaaa   120
cctggccagg ctcccaggct cctcatctat ggtgcatcca gcagggccac tggcatccca   180
gacaggttca gtggcagtgg gtctgggaca gacttcactc tcaccatcag cagactggag   240
cctgaagatt ttgcagtgta ttactgtcaa gtatatggta actcactcac tttcggcgga   300
gggaccaagg tggagatcaa a                                             321

<210> SEQ ID NO 384
<211> LENGTH: 107
<212> TYPE: PRT
<213> ORGANISM: Artificial Sequence
<220> FEATURE:
<223> OTHER INFORMATION: Synthetic

<400> SEQUENCE: 384

Glu Ile Val Leu Thr Gln Ser Pro Gly Thr Leu Ser Leu Ser Pro Gly
 1               5                  10                  15

Glu Arg Ala Thr Leu Ser Cys Arg Ala Ser Gln Ser Val Asn Asn Lys
             20                  25                  30

Phe Leu Ala Trp Tyr Gln Gln Lys Pro Gly Gln Ala Pro Arg Leu Leu
         35                  40                  45

Ile Tyr Gly Ala Ser Ser Arg Ala Thr Gly Ile Pro Asp Arg Phe Ser
     50                  55                  60

Gly Ser Gly Ser Gly Thr Asp Phe Thr Leu Thr Ile Ser Arg Leu Glu
 65                  70                  75                  80

Pro Glu Asp Phe Ala Val Tyr Tyr Cys Gln Val Tyr Gly Asn Ser Leu
                 85                  90                  95

Thr Phe Gly Gly Gly Thr Lys Val Glu Ile Lys
            100                 105

<210> SEQ ID NO 385
<211> LENGTH: 360
<212> TYPE: DNA
<213> ORGANISM: Artificial Sequence
<220> FEATURE:
<223> OTHER INFORMATION: Synthetic

<400> SEQUENCE: 385
gaggtgcaga aggtggagtc tgggggaggc ctggtcaagc cggggggtc cctgagactc    60 tcctgtacag cctctggatt caccttcagt acttataaca tgaattgggt ccgccaggct   120
ccagggaagg gactggagtg gtctcatcc attaggagta gtagtaatta catatactac   180
gcagactcag tgaagggccg attcaccatc tccagagaca cgccaagaa ttcactgtat   240 ctgcaaatga acagcctgag agccgatgac acggctgtgt attactgtgc gagagatggc   300
agcagttggt acgactactc tgactactgg ggccaggaa ccctggtcac cgtctcctca   360

<210> SEQ ID NO 386
<211> LENGTH: 120
<212> TYPE: PRT
<213> ORGANISM: Artificial Sequence
<220> FEATURE:
<223> OTHER INFORMATION: Synthetic

<400> SEQUENCE: 386

Glu Val Gln Lys Val Glu Ser Gly Gly Gly Leu Val Lys Pro Gly Gly
 1               5                  10                  15
```

Ser Leu Arg Leu Ser Cys Thr Ala Ser Gly Phe Thr Phe Ser Thr Tyr
         20                  25                  30

Asn Met Asn Trp Val Arg Gln Ala Pro Gly Lys Gly Leu Glu Trp Val
             35                  40                  45

Ser Ser Ile Arg Ser Ser Asn Tyr Ile Tyr Tyr Ala Asp Ser Val
 50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Asp Asp Thr Ala Val Tyr Tyr Cys
                 85                  90                  95

Ala Arg Asp Gly Ser Ser Trp Tyr Asp Tyr Ser Asp Tyr Trp Gly Gln
             100                 105                 110

Gly Thr Leu Val Thr Val Ser Ser
         115                 120

<210> SEQ ID NO 387
<211> LENGTH: 24
<212> TYPE: DNA
<213> ORGANISM: Artificial Sequence
<220> FEATURE:
<223> OTHER INFORMATION: Synthetic

<400> SEQUENCE: 387
ggattcacct tcagtactta taac                                           24

<210> SEQ ID NO 388
<211> LENGTH: 8
<212> TYPE: PRT
<213> ORGANISM: Artificial Sequence
<220> FEATURE:
<223> OTHER INFORMATION: Synthetic

<400> SEQUENCE: 388

Gly Phe Thr Phe Ser Thr Tyr Asn
 1               5

<210> SEQ ID NO 389
<211> LENGTH: 24
<212> TYPE: DNA
<213> ORGANISM: Artificial Sequence
<220> FEATURE:
<223> OTHER INFORMATION: Synthetic

<400> SEQUENCE: 389
attaggagta gtagtaatta cata                                           24

<210> SEQ ID NO 390
<211> LENGTH: 8
<212> TYPE: PRT
<213> ORGANISM: Artificial Sequence
<220> FEATURE:
<223> OTHER INFORMATION: Synthetic

<400> SEQUENCE: 390

Ile Arg Ser Ser Ser Asn Tyr Ile
 1               5

<210> SEQ ID NO 391
<211> LENGTH: 39
<212> TYPE: DNA
<213> ORGANISM: Artificial Sequence
<220> FEATURE:
<223> OTHER INFORMATION: Synthetic

<400> SEQUENCE: 391
gcgagagatg gcagcagttg gtacgactac tctgactac            39

<210> SEQ ID NO 392
<211> LENGTH: 13
<212> TYPE: PRT
<213> ORGANISM: Artificial Sequence
<220> FEATURE:
<223> OTHER INFORMATION: Synthetic

<400> SEQUENCE: 392

Ala Arg Asp Gly Ser Ser Trp Tyr Asp Tyr Ser Asp Tyr
 1               5                  10

<210> SEQ ID NO 393
<211> LENGTH: 321
<212> TYPE: DNA
<213> ORGANISM: Artificial Sequence
<220> FEATURE:
<223> OTHER INFORMATION: Synthetic

<400> SEQUENCE: 393
gacatccaga tgacccagtc tccttccacc ctgtctgcat ctgtaggaga cagagtcacc    60
atcacttgcc gggccagtca gagtattagt agctggttgg cctggtatca acagatacca   120
gggaaagccc ctaaactcct gatctataag gcgtctagtt tagaaaatgg ggtcccatca   180
aggttcagcg gcagtggatc tgggacagaa ttcactctca tcatcagcag cctgcagcct   240
gatgattttg caacttatta ctgccaacag tatattagtt attctcggac gttcggccaa   300
gggaccaagg tggaaatcaa a                                              321

<210> SEQ ID NO 394
<211> LENGTH: 107
<212> TYPE: PRT
<213> ORGANISM: Artificial Sequence
<220> FEATURE:
<223> OTHER INFORMATION: Synthetic

<400> SEQUENCE: 394

Asp Ile Gln Met Thr Gln Ser Pro Ser Thr Leu Ser Ala Ser Val Gly
 1               5                  10                  15

Asp Arg Val Thr Ile Thr Cys Arg Ala Ser Gln Ser Ile Ser Ser Trp
             20                  25                  30

Leu Ala Trp Tyr Gln Gln Ile Pro Gly Lys Ala Pro Lys Leu Leu Ile
         35                  40                  45

Tyr Lys Ala Ser Ser Leu Glu Asn Gly Val Pro Ser Arg Phe Ser Gly
     50                  55                  60

Ser Gly Ser Gly Thr Glu Phe Thr Leu Ile Ile Ser Ser Leu Gln Pro
 65                  70                  75                  80

Asp Asp Phe Ala Thr Tyr Tyr Cys Gln Gln Tyr Ile Ser Tyr Ser Arg
                 85                  90                  95

Thr Phe Gly Gln Gly Thr Lys Val Glu Ile Lys
            100                 105

<210> SEQ ID NO 395
<211> LENGTH: 18
<212> TYPE: DNA
<213> ORGANISM: Artificial Sequence
<220> FEATURE:
<223> OTHER INFORMATION: Synthetic

```
<400> SEQUENCE: 395
cagagtatta gtagctgg                                                   18

<210> SEQ ID NO 396
<211> LENGTH: 6
<212> TYPE: PRT
<213> ORGANISM: Artificial Sequence
<220> FEATURE:
<223> OTHER INFORMATION: Synthetic

<400> SEQUENCE: 396

Gln Ser Ile Ser Ser Trp
 1               5

<210> SEQ ID NO 397
<211> LENGTH: 9
<212> TYPE: DNA
<213> ORGANISM: Artificial Sequence
<220> FEATURE:
<223> OTHER INFORMATION: Synthetic

<400> SEQUENCE: 397 aaggcgtct                                                              9

<210> SEQ ID NO 398
<211> LENGTH: 3
<212> TYPE: PRT
<213> ORGANISM: Artificial Sequence
<220> FEATURE:
<223> OTHER INFORMATION: Synthetic

<400> SEQUENCE: 398

Lys Ala Ser
 1

<210> SEQ ID NO 399
<211> LENGTH: 27
<212> TYPE: DNA
<213> ORGANISM: Artificial Sequence
<220> FEATURE:
<223> OTHER INFORMATION: Synthetic

<400> SEQUENCE: 399
caacagtata ttagttattc tcggacg                                         27

<210> SEQ ID NO 400
<211> LENGTH: 9
<212> TYPE: PRT
<213> ORGANISM: Artificial Sequence
<220> FEATURE:
<223> OTHER INFORMATION: Synthetic

<400> SEQUENCE: 400

Gln Gln Tyr Ile Ser Tyr Ser Arg Thr
 1               5

<210> SEQ ID NO 401
<211> LENGTH: 360
<212> TYPE: DNA
<213> ORGANISM: Artificial Sequence
<220> FEATURE:
<223> OTHER INFORMATION: Synthetic

<400> SEQUENCE: 401
gaggtgcagc tggtggagtc tgggggaggc ctggtcaagc cggggggtc cctgagactc      60
```

```
tcctgtacag cctctggatt caccttcagt acttataaca tgaattgggt ccgccaggct    120
ccagggaagg gactggagtg ggtctcatcc attaggagta gtagtaatta catatactac    180
gcagactcag tgaagggccg attcaccatc tccagagaca acgccaagaa ttcactgtat    240
ctgcaaatga acagcctgag agccgatgac acggctgtgt attactgtgc gagagatggc    300
agcagttggt acgactactc tgactactgg ggccagggaa ccctggtcac cgtctcctca    360
```

<210> SEQ ID NO 402
<211> LENGTH: 120
<212> TYPE: PRT
<213> ORGANISM: Artificial Sequence
<220> FEATURE:
<223> OTHER INFORMATION: Synthetic

<400> SEQUENCE: 402

Glu Val Gln Leu Val Glu Ser Gly Gly Gly Leu Val Lys Pro Gly Gly
1               5                   10                  15

Ser Leu Arg Leu Ser Cys Thr Ala Ser Gly Phe Thr Phe Ser Thr Tyr
            20                  25                  30

Asn Met Asn Trp Val Arg Gln Ala Pro Gly Lys Gly Leu Glu Trp Val
        35                  40                  45

Ser Ser Ile Arg Ser Ser Asn Tyr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Asp Asp Thr Ala Val Tyr Tyr Cys
                85                  90                  95

Ala Arg Asp Gly Ser Ser Trp Tyr Asp Tyr Ser Asp Tyr Trp Gly Gln
            100                 105                 110

Gly Thr Leu Val Thr Val Ser Ser
        115                 120

<210> SEQ ID NO 403
<211> LENGTH: 321
<212> TYPE: DNA
<213> ORGANISM: Artificial Sequence
<220> FEATURE:
<223> OTHER INFORMATION: Synthetic

<400> SEQUENCE: 403

```
gacatccaga tgacccagtc tccttccacc ctgtctgcat ctgtaggaga cagagtcacc     60
atcacttgcc gggccagtca gagtattagt agctggttgg cctggtatca acagatacca    120
gggaaagccc ctaaactcct gatctataag gcgtctagtt tagaaaatgg ggtcccatca    180
aggttcagcg gcagtggatc tgggacagaa ttcactctca tcatcagcag cctgcagcct    240
gatgattttg caacttatta ctgccaacag tatattagtt attctcggac gttcggccaa    300
gggaccaagg tggaaatcaa a                                              321
```

<210> SEQ ID NO 404
<211> LENGTH: 107
<212> TYPE: PRT
<213> ORGANISM: Artificial Sequence
<220> FEATURE:
<223> OTHER INFORMATION: Synthetic

<400> SEQUENCE: 404

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Ile Pro Gly Lys Ala Pro Lys Leu Leu Ile
        35                  40                  45

Tyr Lys Ala Ser Ser Leu Glu Asn Gly Val Pro Ser Arg Phe Ser Gly
50                  55                  60

Ser Gly Ser Gly Thr Glu Phe Thr Leu Ile Ile Ser Ser Leu Gln Pro
65                  70                  75                  80

Asp Asp Phe Ala Thr Tyr Tyr Cys Gln Gln Tyr Ile Ser Tyr Ser Arg
                85                  90                  95

Thr Phe Gly Gln Gly Thr Lys Val Glu Ile Lys
            100                 105

<210> SEQ ID NO 405
<211> LENGTH: 360
<212> TYPE: DNA
<213> ORGANISM: Artificial Sequence
<220> FEATURE:
<223> OTHER INFORMATION: Synthetic

<400> SEQUENCE: 405
gaggtgcagc tggtggagtc tgggggaggc ctggtcaagc ctgggggtc cctgagactc      60 tcctgtgcag cctctggatt caccttcagt acttataaca tgaactgggt ccgccaggct    120
ccagggaagg ggctggagtg ggtctcatcc attaggagta gtagtaatta catatactac    180
gcagactcag tgaagggccg attcaccatc tccagagaca acgccaagaa ctcactgtat    240
ctgcaaatga acagcctgag agccgaggac acggctgtgt attactgtgc gagagatggc    300
agcagttggt acgactactc tgactactgg ggccaaggaa ccctggtcac cgtctcctca    360

<210> SEQ ID NO 406
<211> LENGTH: 120
<212> TYPE: PRT
<213> ORGANISM: Artificial Sequence
<220> FEATURE:
<223> OTHER INFORMATION: Synthetic

<400> SEQUENCE: 406

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Thr Tyr
            20                  25                  30

Asn Met Asn Trp Val Arg Gln Ala Pro Gly Lys Gly Leu Glu Trp Val
        35                  40                  45

Ser Ser Ile Arg Ser Ser Ser Asn Tyr Ile Tyr Tyr Ala Asp Ser Val
50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Gly Ser Ser Trp Tyr Asp Tyr Ser Asp Tyr Trp Gly Gln
            100                 105                 110

Gly Thr Leu Val Thr Val Ser Ser
        115                 120

<210> SEQ ID NO 407
<211> LENGTH: 321
<212> TYPE: DNA
<213> ORGANISM: Artificial Sequence
<220> FEATURE:
<223> OTHER INFORMATION: Synthetic

<400> SEQUENCE: 407

```
gacatccaga tgacccagtc tccttccacc ctgtctgcat ctgtaggaga cagagtcacc    60
atcacttgcc gggccagtca gagtattagt agctggttgg cctggtatca gcagaaacca   120
gggaaagccc ctaagctcct gatctataag gcgtctagtt tagaaagtgg ggtcccatca   180
aggttcagcg gcagtggatc tgggacagaa ttcactctca ccatcagcag cctgcagcct   240
gatgattttg caacttatta ctgccaacag tatattagtt attctcggac gttcggccaa   300
gggaccaagg tggaaatcaa a                                             321
```

<210> SEQ ID NO 408
<211> LENGTH: 107
<212> TYPE: PRT
<213> ORGANISM: Artificial Sequence
<220> FEATURE:
<223> OTHER INFORMATION: Synthetic

<400> SEQUENCE: 408

```
Asp Ile Gln Met Thr Gln Ser Pro Ser Thr Leu Ser Ala Ser Val Gly
 1               5                  10                  15
Asp Arg Val Thr Ile Thr Cys Arg Ala Ser Gln Ser Ile Ser Ser Trp
            20                  25                  30
Leu Ala Trp Tyr Gln Gln Lys Pro Gly Lys Ala Pro Lys Leu Leu Ile
        35                  40                  45
Tyr Lys Ala Ser Ser Leu Glu Ser Gly Val Pro Ser Arg Phe Ser Gly
    50                  55                  60
Ser Gly Ser Gly Thr Glu Phe Thr Leu Thr Ile Ser Ser Leu Gln Pro
65                  70                  75                  80
Asp Asp Phe Ala Thr Tyr Tyr Cys Gln Gln Tyr Ile Ser Tyr Ser Arg
                85                  90                  95
Thr Phe Gly Gln Gly Thr Lys Val Glu Ile Lys
            100                 105
```

<210> SEQ ID NO 409
<211> LENGTH: 360
<212> TYPE: DNA
<213> ORGANISM: Artificial Sequence
<220> FEATURE:
<223> OTHER INFORMATION: Synthetic

<400> SEQUENCE: 409

```
gaggtgcagc tggtggagtc tgggggaggc ctggtcaagc cggggggtc cctgagactc     60
tcctgtacag cctctggatt caccttcagt acttataaca tgaattgggt ccgccaggct   120
ccagggaagg gactggagtg gtctcatcc attaggagta gtagtaatta catatactac    180
gcagactcag tgaagggccg attcaccatc tccagagaca cgccaagaa ttcactgtat    240
ctgcaaatga acagcctgag agccgatgac acggctgtgt attactgtgc gagagatggc   300
agcagttggt acgactactc tgactactgg ggccagggaa ccctggtcac cgtctcctca   360
```

<210> SEQ ID NO 410
<211> LENGTH: 120
<212> TYPE: PRT
<213> ORGANISM: Artificial Sequence
<220> FEATURE:
<223> OTHER INFORMATION: Synthetic

<400> SEQUENCE: 410

Glu Val Gln Leu Val Glu Ser Gly Gly Gly Leu Val Lys Pro Gly Gly
1               5                   10                  15

Ser Leu Arg Leu Ser Cys Thr Ala Ser Gly Phe Thr Phe Ser Thr Tyr
            20                  25                  30

Asn Met Asn Trp Val Arg Gln Ala Pro Gly Lys Gly Leu Glu Trp Val
        35                  40                  45

Ser Ser Ile Arg Ser Ser Ser Asn Tyr Ile Tyr Tyr Ala Asp Ser Val
50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Asp Asp Thr Ala Val Tyr Tyr Cys
                85                  90                  95

Ala Arg Asp Gly Ser Ser Trp Tyr Asp Tyr Ser Asp Tyr Trp Gly Gln
            100                 105                 110

Gly Thr Leu Val Thr Val Ser Ser
        115                 120

<210> SEQ ID NO 411
<211> LENGTH: 24
<212> TYPE: DNA
<213> ORGANISM: Artificial Sequence
<220> FEATURE:
<223> OTHER INFORMATION: Synthetic

<400> SEQUENCE: 411
ggattcacct tcagtactta taac                                          24

<210> SEQ ID NO 412
<211> LENGTH: 8
<212> TYPE: PRT
<213> ORGANISM: Artificial Sequence
<220> FEATURE:
<223> OTHER INFORMATION: Synthetic

<400> SEQUENCE: 412

Gly Phe Thr Phe Ser Thr Tyr Asn
1               5

<210> SEQ ID NO 413
<211> LENGTH: 24
<212> TYPE: DNA
<213> ORGANISM: Artificial Sequence
<220> FEATURE:
<223> OTHER INFORMATION: Synthetic

<400> SEQUENCE: 413
attaggagta gtagtaatta cata                                          24

<210> SEQ ID NO 414
<211> LENGTH: 8
<212> TYPE: PRT
<213> ORGANISM: Artificial Sequence
<220> FEATURE:
<223> OTHER INFORMATION: Synthetic

<400> SEQUENCE: 414

Ile Arg Ser Ser Ser Asn Tyr Ile
1               5

<210> SEQ ID NO 415
<211> LENGTH: 39
<212> TYPE: DNA

<213> ORGANISM: Artificial Sequence
<220> FEATURE:
<223> OTHER INFORMATION: Synthetic

<400> SEQUENCE: 415

```
gcgagagatg gcagcagttg gtacgactac tctgactac                    39
```

<210> SEQ ID NO 416
<211> LENGTH: 13
<212> TYPE: PRT
<213> ORGANISM: Artificial Sequence
<220> FEATURE:
<223> OTHER INFORMATION: Synthetic

<400> SEQUENCE: 416

```
Ala Arg Asp Gly Ser Ser Trp Tyr Asp Tyr Ser Asp Tyr
 1               5                  10
```

<210> SEQ ID NO 417
<211> LENGTH: 321
<212> TYPE: DNA
<213> ORGANISM: Artificial Sequence
<220> FEATURE:
<223> OTHER INFORMATION: Synthetic

<400> SEQUENCE: 417

```
gacatccaga tgacccagtc tccttccacc ctgtctgcat ctgtaggaga cagagtcacc   60
atcacttgcc gggccagtca gagtattagt agctggttgg cctggtatca acagatacca  120
gggaaagccc ctaaactcct gatctataag gcgtctagtt tagaaaatgg ggtcccatca  180
aggttcagcg gcagtggatc tgggacagaa ttcactctca tcatcagcag cctgcagcct  240
gatgattttg caacttatta ctgccaacag tatattagtt attctcggac gttcggccaa  300
gggaccaagg tggaaatcaa a                                            321
```

<210> SEQ ID NO 418
<211> LENGTH: 107
<212> TYPE: PRT
<213> ORGANISM: Artificial Sequence
<220> FEATURE:
<223> OTHER INFORMATION: Synthetic

<400> SEQUENCE: 418

```
Asp Ile Gln Met Thr Gln Ser Pro Ser Thr Leu Ser Ala Ser Val Gly
 1               5                  10                  15

Asp Arg Val Thr Ile Thr Cys Arg Ala Ser Gln Ser Ile Ser Ser Trp
            20                  25                  30

Leu Ala Trp Tyr Gln Gln Ile Pro Gly Lys Ala Pro Lys Leu Leu Ile
        35                  40                  45

Tyr Lys Ala Ser Ser Leu Glu Asn Gly Val Pro Ser Arg Phe Ser Gly
    50                  55                  60

Ser Gly Ser Gly Thr Glu Phe Thr Leu Ile Ile Ser Ser Leu Gln Pro
65                  70                  75                  80

Asp Asp Phe Ala Thr Tyr Tyr Cys Gln Gln Tyr Ile Ser Tyr Ser Arg
                85                  90                  95

Thr Phe Gly Gln Gly Thr Lys Val Glu Ile Lys
            100                 105
```

<210> SEQ ID NO 419
<211> LENGTH: 18
<212> TYPE: DNA
<213> ORGANISM: Artificial Sequence
<220> FEATURE:
<223> OTHER INFORMATION: Synthetic

<400> SEQUENCE: 419
cagagtatta gtagctgg                                                    18

<210> SEQ ID NO 420
<211> LENGTH: 6
<212> TYPE: PRT
<213> ORGANISM: Artificial Sequence
<220> FEATURE:
<223> OTHER INFORMATION: Synthetic

<400> SEQUENCE: 420

Gln Ser Ile Ser Ser Trp
 1               5

<210> SEQ ID NO 421
<211> LENGTH: 9
<212> TYPE: DNA
<213> ORGANISM: Artificial Sequence
<220> FEATURE:
<223> OTHER INFORMATION: Synthetic

<400> SEQUENCE: 421 aaggcgtct                                                               9

<210> SEQ ID NO 422
<211> LENGTH: 3
<212> TYPE: PRT
<213> ORGANISM: Artificial Sequence
<220> FEATURE:
<223> OTHER INFORMATION: Synthetic

<400> SEQUENCE: 422

Lys Ala Ser
 1

<210> SEQ ID NO 423
<211> LENGTH: 27
<212> TYPE: DNA
<213> ORGANISM: Artificial Sequence
<220> FEATURE:
<223> OTHER INFORMATION: Synthetic

<400> SEQUENCE: 423
caacagtata ttagttattc tcggacg                                          27

<210> SEQ ID NO 424
<211> LENGTH: 9
<212> TYPE: PRT
<213> ORGANISM: Artificial Sequence
<220> FEATURE:
<223> OTHER INFORMATION: Synthetic

<400> SEQUENCE: 424

Gln Gln Tyr Ile Ser Tyr Ser Arg Thr
 1               5

<210> SEQ ID NO 425
<211> LENGTH: 360
<212> TYPE: DNA
<213> ORGANISM: Artificial Sequence
<220> FEATURE:
<223> OTHER INFORMATION: Synthetic

<400> SEQUENCE: 425

```
gaggtgcagc tggtggagtc tgggggaggc ctggtcaagc cggggggggtc cctgagactc    60 tcctgtacag cctctggatt caccttcagt acttataaca tgaattgggt ccgccaggct   120
ccagggaagg gactggagtg ggtctcatcc attaggagta gtagtaatta catatactac   180
gcagactcag tgaagggccg attcaccatc tccagagaca cgccaagaa ttcactgtat    240 ctgcaaatga acagcctgag agccgatgac acggctgtgt attactgtgc gagagatggc   300
agcagttggt acgactactc tgactactgg ggccagggaa ccctggtcac cgtctcctca   360
```

<210> SEQ ID NO 426
<211> LENGTH: 120
<212> TYPE: PRT
<213> ORGANISM: Artificial Sequence
<220> FEATURE:
<223> OTHER INFORMATION: Synthetic

<400> SEQUENCE: 426

```
Glu Val Gln Leu Val Glu Ser Gly Gly Gly Leu Val Lys Pro Gly Gly
 1               5                  10                  15

Ser Leu Arg Leu Ser Cys Thr Ala Ser Gly Phe Thr Phe Ser Thr Tyr
            20                  25                  30

Asn Met Asn Trp Val Arg Gln Ala Pro Gly Lys Gly Leu Glu Trp Val
        35                  40                  45

Ser Ser Ile Arg Ser Ser Ser Asn Tyr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Asp Asp Thr Ala Val Tyr Tyr Cys
                85                  90                  95

Ala Arg Asp Gly Ser Ser Trp Tyr Asp Tyr Ser Asp Tyr Trp Gly Gln
            100                 105                 110

Gly Thr Leu Val Thr Val Ser Ser
        115                 120
```

<210> SEQ ID NO 427
<211> LENGTH: 321
<212> TYPE: DNA
<213> ORGANISM: Artificial Sequence
<220> FEATURE:
<223> OTHER INFORMATION: Synthetic

<400> SEQUENCE: 427

```
gacatccaga tgacccagtc tccttccacc ctgtctgcat ctgtaggaga cagagtcacc    60
atcacttgcc gggccagtca gagtattagt agctggttgg cctggtatca acagatacca   120
gggaaagccc ctaaactcct gatctataag gcgtctagtt tagaaaatgg ggtcccatca   180
aggttcagcg gcagtggatc tgggacagaa ttcactctca tcatcagcag cctgcagcct   240
gatgattttg caacttatta ctgccaacag tatattagtt attctcggac gttcggccaa   300
gggaccaagg tggaaatcaa a                                             321
```

<210> SEQ ID NO 428
<211> LENGTH: 107
<212> TYPE: PRT
<213> ORGANISM: Artificial Sequence
<220> FEATURE:
<223> OTHER INFORMATION: Synthetic

<400> SEQUENCE: 428

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Ile Pro Gly Lys Ala Pro Lys Leu Leu Ile
        35                  40                  45

Tyr Lys Ala Ser Ser Leu Glu Asn Gly Val Pro Ser Arg Phe Ser Gly
50                  55                  60

Ser Gly Ser Gly Thr Glu Phe Thr Leu Ile Ile Ser Ser Leu Gln Pro
65                  70                  75                  80

Asp Asp Phe Ala Thr Tyr Tyr Cys Gln Gln Tyr Ile Ser Tyr Ser Arg
                85                  90                  95

Thr Phe Gly Gln Gly Thr Lys Val Glu Ile Lys
            100                 105

<210> SEQ ID NO 429
<211> LENGTH: 360
<212> TYPE: DNA
<213> ORGANISM: Artificial Sequence
<220> FEATURE:
<223> OTHER INFORMATION: Synthetic

<400> SEQUENCE: 429
gaggtgcagc tggtggagtc tgggggaggc ctggtcaagc ctggggggtc cctgagactc      60
tcctgtgcag cctctggatt caccttcagt acttataaca tgaactgggt ccgccaggct     120
ccagggaagg gctggagtg gtctcatcc attaggagta gtagtaatta catatactac       180
gcagactcag tgaagggccg attcaccatc tccagagaca cgccaagaa ctcactgtat      240 ctgcaaatga acagcctgag agccgaggac acggctgtgt attactgtgc gagagatggc    300
agcagttggt acgactactc tgactactgg ggccaaggaa ccctggtcac cgtctcctca    360

<210> SEQ ID NO 430
<211> LENGTH: 120
<212> TYPE: PRT
<213> ORGANISM: Artificial Sequence
<220> FEATURE:
<223> OTHER INFORMATION: Synthetic

<400> SEQUENCE: 430

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Thr Tyr
            20                  25                  30

Asn Met Asn Trp Val Arg Gln Ala Pro Gly Lys Gly Leu Glu Trp Val
        35                  40                  45

Ser Ser Ile Arg Ser Ser Ser Asn Tyr Ile Tyr Tyr Ala Asp Ser Val
50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Gly Ser Ser Trp Tyr Asp Tyr Ser Asp Tyr Trp Gly Gln
            100                 105                 110

Gly Thr Leu Val Thr Val Ser Ser
        115                 120

<210> SEQ ID NO 431

<211> LENGTH: 321
<212> TYPE: DNA
<213> ORGANISM: Artificial Sequence
<220> FEATURE:
<223> OTHER INFORMATION: Synthetic

<400> SEQUENCE: 431

```
gacatccaga tgacccagtc tccttccacc ctgtctgcat ctgtaggaga cagagtcacc    60
atcacttgcc gggccagtca gagtattagt agctggttgg cctggtatca gcagaaacca   120
gggaaagccc ctaagctcct gatctataag gcgtctagtt tagaaagtgg ggtcccatca   180
aggttcagcg gcagtggatc tgggacagaa ttcactctca ccatcagcag cctgcagcct   240
gatgattttg caacttatta ctgccaacag tatattagtt attctcggac gttcggccaa   300
gggaccaagg tggaaatcaa a                                             321
```

<210> SEQ ID NO 432
<211> LENGTH: 107
<212> TYPE: PRT
<213> ORGANISM: Artificial Sequence
<220> FEATURE:
<223> OTHER INFORMATION: Synthetic

<400> SEQUENCE: 432

```
Asp Ile Gln Met Thr Gln Ser Pro Ser Thr Leu Ser Ala Ser Val Gly
 1               5                  10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Tyr Lys Ala Ser Ser Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Ile Ser Tyr Ser Arg
                85                  90                  95

Thr Phe Gly Gln Gly Thr Lys Val Glu Ile Lys
            100                 105
```

<210> SEQ ID NO 433
<211> LENGTH: 360
<212> TYPE: DNA
<213> ORGANISM: Artificial Sequence
<220> FEATURE:
<223> OTHER INFORMATION: Synthetic

<400> SEQUENCE: 433

```
gaggtgcagc tggtggagtc tgggggaggc ctggtcaagc cggggggtc cctgagactc     60
tcctgtacag cctctggatt caccttcagt acttataaca tgaattgggt ccgccaggct   120
ccagggaagg gactggagtg gtctcatcc attaggagta gtagtaatta catatactac   180
gcagactcag tgaagggccg attcaccatc tccagagaca acgccaagag ttcactgtat   240
ctgcaaatga acagcctgag agccgaggac acggctgtgt attactgtgc gagagatggc   300
agcagttggt acgactactc tgactactgg ggccaggaa ccctggtcac cgtctcctca   360
```

<210> SEQ ID NO 434
<211> LENGTH: 120
<212> TYPE: PRT
<213> ORGANISM: Artificial Sequence
<220> FEATURE:

<223> OTHER INFORMATION: Synthetic

<400> SEQUENCE: 434

Glu Val Gln Leu Val Glu Ser Gly Gly Gly Leu Val Lys Pro Gly Gly
1               5                   10                  15

Ser Leu Arg Leu Ser Cys Thr Ala Ser Gly Phe Thr Phe Ser Thr Tyr
            20                  25                  30

Asn Met Asn Trp Val Arg Gln Ala Pro Gly Lys Gly Leu Glu Trp Val
        35                  40                  45

Ser Ser Ile Arg Ser Ser Ser Asn Tyr Ile Tyr Tyr Ala Asp Ser Val
    50                  55                  60

Lys Gly Arg Phe Thr Ile Ser Arg Asp Asn Ala Lys Ser Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Gly Ser Ser Trp Tyr Asp Tyr Ser Asp Tyr Trp Gly Gln
            100                 105                 110

Gly Thr Leu Val Thr Val Ser Ser
        115                 120

<210> SEQ ID NO 435
<211> LENGTH: 24
<212> TYPE: DNA
<213> ORGANISM: Artificial Sequence
<220> FEATURE:
<223> OTHER INFORMATION: Synthetic

<400> SEQUENCE: 435
ggattcacct tcagtactta taac                                          24

<210> SEQ ID NO 436
<211> LENGTH: 8
<212> TYPE: PRT
<213> ORGANISM: Artificial Sequence
<220> FEATURE:
<223> OTHER INFORMATION: Synthetic

<400> SEQUENCE: 436

Gly Phe Thr Phe Ser Thr Tyr Asn
1               5

<210> SEQ ID NO 437
<211> LENGTH: 24
<212> TYPE: DNA
<213> ORGANISM: Artificial Sequence
<220> FEATURE:
<223> OTHER INFORMATION: Synthetic

<400> SEQUENCE: 437
attaggagta gtagtaatta cata                                          24

<210> SEQ ID NO 438
<211> LENGTH: 8
<212> TYPE: PRT
<213> ORGANISM: Artificial Sequence
<220> FEATURE:
<223> OTHER INFORMATION: Synthetic

<400> SEQUENCE: 438

Ile Arg Ser Ser Ser Asn Tyr Ile
1               5

```
<210> SEQ ID NO 439
<211> LENGTH: 39
<212> TYPE: DNA
<213> ORGANISM: Artificial Sequence
<220> FEATURE:
<223> OTHER INFORMATION: Synthetic

<400> SEQUENCE: 439
gcgagagatg gcagcagttg gtacgactac tctgactac                              39

<210> SEQ ID NO 440
<211> LENGTH: 13
<212> TYPE: PRT
<213> ORGANISM: Artificial Sequence
<220> FEATURE:
<223> OTHER INFORMATION: Synthetic

<400> SEQUENCE: 440

Ala Arg Asp Gly Ser Ser Trp Tyr Asp Tyr Ser Asp Tyr
 1               5                  10

<210> SEQ ID NO 441
<211> LENGTH: 321
<212> TYPE: DNA
<213> ORGANISM: Artificial Sequence
<220> FEATURE:
<223> OTHER INFORMATION: Synthetic

<400> SEQUENCE: 441
gacatccaga tgacccagtc tccttccacc ctgtctgcat ctgtaggaga cagagtcacc       60
atcacttgcc gggccagtca gagtattagt agctggttgg cctggtatca acaggtacca      120
gggaaagccc ctaaactcct gatctataag gcgtctagtt tagaaaatgg ggtcccatca      180
aggttcagcg gcagtggatc tgggacagaa ttcactctca tcatcagcag cctgcagcct      240
gatgattttg caacttatta ctgccaacag tatattagtt attctcggac gttcggccaa      300
gggaccaagg tggaaatcaa a                                                321

<210> SEQ ID NO 442
<211> LENGTH: 107
<212> TYPE: PRT
<213> ORGANISM: Artificial Sequence
<220> FEATURE:
<223> OTHER INFORMATION: Synthetic

<400> SEQUENCE: 442

Asp Ile Gln Met Thr Gln Ser Pro Ser Thr Leu Ser Ala Ser Val Gly
 1               5                  10                  15

Asp Arg Val Thr Ile Thr Cys Arg Ala Ser Gln Ser Ile Ser Ser Trp
            20                  25                  30

Leu Ala Trp Tyr Gln Gln Val Pro Gly Lys Ala Pro Lys Leu Leu Ile
        35                  40                  45

Tyr Lys Ala Ser Ser Leu Glu Asn Gly Val Pro Ser Arg Phe Ser Gly
    50                  55                  60

Ser Gly Ser Gly Thr Glu Phe Thr Leu Ile Ile Ser Ser Leu Gln Pro
65                  70                  75                  80

Asp Asp Phe Ala Thr Tyr Tyr Cys Gln Gln Tyr Ile Ser Tyr Ser Arg
                85                  90                  95

Thr Phe Gly Gln Gly Thr Lys Val Glu Ile Lys
            100                 105

<210> SEQ ID NO 443
```

```
<211> LENGTH: 18
<212> TYPE: DNA
<213> ORGANISM: Artificial Sequence
<220> FEATURE:
<223> OTHER INFORMATION: Synthetic

<400> SEQUENCE: 443
cagagtatta gtagctgg                                                  18

<210> SEQ ID NO 444
<211> LENGTH: 6
<212> TYPE: PRT
<213> ORGANISM: Artificial Sequence
<220> FEATURE:
<223> OTHER INFORMATION: Synthetic

<400> SEQUENCE: 444

Gln Ser Ile Ser Ser Trp
 1               5

<210> SEQ ID NO 445
<211> LENGTH: 9
<212> TYPE: DNA
<213> ORGANISM: Artificial Sequence
<220> FEATURE:
<223> OTHER INFORMATION: Synthetic

<400> SEQUENCE: 445 aaggcgtct                                                             9

<210> SEQ ID NO 446
<211> LENGTH: 3
<212> TYPE: PRT
<213> ORGANISM: Artificial Sequence
<220> FEATURE:
<223> OTHER INFORMATION: Synthetic

<400> SEQUENCE: 446

Lys Ala Ser
 1

<210> SEQ ID NO 447
<211> LENGTH: 27
<212> TYPE: DNA
<213> ORGANISM: Artificial Sequence
<220> FEATURE:
<223> OTHER INFORMATION: Synthetic

<400> SEQUENCE: 447
caacagtata ttagttattc tcggacg                                        27

<210> SEQ ID NO 448
<211> LENGTH: 9
<212> TYPE: PRT
<213> ORGANISM: Artificial Sequence
<220> FEATURE:
<223> OTHER INFORMATION: Synthetic

<400> SEQUENCE: 448

Gln Gln Tyr Ile Ser Tyr Ser Arg Thr
 1               5

<210> SEQ ID NO 449
<211> LENGTH: 360
<212> TYPE: DNA
<213> ORGANISM: Artificial Sequence
<220> FEATURE:
```

<223> OTHER INFORMATION: Synthetic

<400> SEQUENCE: 449

```
gaggtgcagc tggtggagtc tgggggaggc ctggtcaagc cggggggggtc cctgagactc    60
tcctgtacag cctctggatt caccttcagt acttataaca tgaattgggt ccgccaggct   120
ccagggaagg gactggagtg ggtctcatcc attaggagta gtagtaatta catatactac   180
gcagactcag tgaagggccg attcaccatc tccagagaca acgccaagag ttcactgtat   240
ctgcaaatga acagcctgag agccgaggac acggctgtgt attactgtgc gagagatggc   300
agcagttggt acgactactc tgactactgg ggccagggaa ccctggtcac cgtctcctca   360
```

<210> SEQ ID NO 450
<211> LENGTH: 120
<212> TYPE: PRT
<213> ORGANISM: Artificial Sequence
<220> FEATURE:
<223> OTHER INFORMATION: Synthetic

<400> SEQUENCE: 450

```
Glu Val Gln Leu Val Glu Ser Gly Gly Gly Leu Val Lys Pro Gly Gly
 1               5                  10                  15

Ser Leu Arg Leu Ser Cys Thr Ala Ser Gly Phe Thr Phe Ser Thr Tyr
             20                  25                  30

Asn Met Asn Trp Val Arg Gln Ala Pro Gly Lys Gly Leu Glu Trp Val
         35                  40                  45

Ser Ser Ile Arg Ser Ser Ser Asn Tyr Ile Tyr Tyr Ala Asp Ser Val
     50                  55                  60

Lys Gly Arg Phe Thr Ile Ser Arg Asp Asn Ala Lys Ser Ser Leu Tyr
 65                  70                  75                  80

Leu Gln Met Asn Ser Leu Arg Ala Glu Asp Thr Ala Val Tyr Tyr Cys
                 85                  90                  95

Ala Arg Asp Gly Ser Ser Trp Tyr Asp Tyr Ser Asp Tyr Trp Gly Gln
            100                 105                 110

Gly Thr Leu Val Thr Val Ser Ser
        115                 120
```

<210> SEQ ID NO 451
<211> LENGTH: 321
<212> TYPE: DNA
<213> ORGANISM: Artificial Sequence
<220> FEATURE:
<223> OTHER INFORMATION: Synthetic

<400> SEQUENCE: 451

```
gacatccaga tgacccagtc tccttccacc ctgtctgcat ctgtaggaga cagagtcacc    60
atcacttgcc gggccagtca gagtattagt agctggttgg cctggtatca acaggtacca   120
gggaaagccc ctaaactcct gatctataag gcgtctagtt tagaaaatgg ggtcccatca   180
aggttcagcg gcagtggatc tgggacagaa ttcactctca tcatcagcag cctgcagcct   240
gatgattttg caacttatta ctgccaacag tatattagtt attctcggac gttcggccaa   300
gggaccaagg tggaaatcaa a                                             321
```

<210> SEQ ID NO 452
<211> LENGTH: 107
<212> TYPE: PRT
<213> ORGANISM: Artificial Sequence
<220> FEATURE:
<223> OTHER INFORMATION: Synthetic

<400> SEQUENCE: 452

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Val Pro Gly Lys Ala Pro Lys Leu Leu Ile
        35                  40                  45

Tyr Lys Ala Ser Ser Leu Glu Asn Gly Val Pro Ser Arg Phe Ser Gly
50                  55                  60

Ser Gly Ser Gly Thr Glu Phe Thr Leu Ile Ile Ser Ser Leu Gln Pro
65                  70                  75                  80

Asp Asp Phe Ala Thr Tyr Tyr Cys Gln Gln Tyr Ile Ser Tyr Ser Arg
                85                  90                  95

Thr Phe Gly Gln Gly Thr Lys Val Glu Ile Lys
            100                 105

<210> SEQ ID NO 453
<211> LENGTH: 360
<212> TYPE: DNA
<213> ORGANISM: Artificial Sequence
<220> FEATURE:
<223> OTHER INFORMATION: Synthetic

<400> SEQUENCE: 453

```
gaggtgcagc tggtggagtc tgggggaggc ttggtcaagc ctggggggtc cctgagactc    60
tcctgtgcag cctctggatt caccttcagt acttataaca tgaactgggt ccgccaggct   120
ccagggaagg ggctggagtg ggtctcatcc attaggagta gtagtaatta catatactac   180
gcagactcag tgaagggccg attcaccatc tccagagaca cgccaagaa ctcactgtat    240
ctgcaaatga acagcctgag agccgaggac acggctgtgt attactgtgc gagagatggc   300
agcagttggt acgactactc tgactactgg ggccaggaa ccctggtcac cgtctcctca    360
```

<210> SEQ ID NO 454
<211> LENGTH: 120
<212> TYPE: PRT
<213> ORGANISM: Artificial Sequence
<220> FEATURE:
<223> OTHER INFORMATION: Synthetic

<400> SEQUENCE: 454

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Thr Tyr
            20                  25                  30

Asn Met Asn Trp Val Arg Gln Ala Pro Gly Lys Gly Leu Glu Trp Val
        35                  40                  45

Ser Ser Ile Arg Ser Ser Ser Asn Tyr Ile Tyr Tyr Ala Asp Ser Val
50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Gly Ser Ser Trp Tyr Asp Tyr Ser Asp Tyr Trp Gly Gln
            100                 105                 110

Gly Thr Leu Val Thr Val Ser Ser
        115                 120

<210> SEQ ID NO 455
<211> LENGTH: 321
<212> TYPE: DNA
<213> ORGANISM: Artificial Sequence
<220> FEATURE:
<223> OTHER INFORMATION: Synthetic

<400> SEQUENCE: 455

```
gacatccaga tgacccagtc tccttccacc ctgtctgcat ctgtaggaga cagagtcacc    60
atcacttgcc gggccagtca gagtattagt agctggttgg cctggtatca gcagaaacca   120
gggaaagccc ctaagctcct gatctataag gcgtctagtt tagaaagtgg ggtcccatca   180
aggttcagcg gcagtggatc tgggacagaa ttcactctca ccatcagcag cctgcagcct   240
gatgattttg caacttatta ctgccaacag tatattagtt attctcggac gttcggccaa   300
gggaccaagg tggaaatcaa a                                             321
```

<210> SEQ ID NO 456
<211> LENGTH: 107
<212> TYPE: PRT
<213> ORGANISM: Artificial Sequence
<220> FEATURE:
<223> OTHER INFORMATION: Synthetic

<400> SEQUENCE: 456

```
Asp Ile Gln Met Thr Gln Ser Pro Ser Thr Leu Ser Ala Ser Val Gly
 1               5                  10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Tyr Lys Ala Ser Ser Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Ile Ser Tyr Ser Arg
                85                  90                  95

Thr Phe Gly Gln Gly Thr Lys Val Glu Ile Lys
            100                 105
```

<210> SEQ ID NO 457
<211> LENGTH: 360
<212> TYPE: DNA
<213> ORGANISM: Artificial Sequence
<220> FEATURE:
<223> OTHER INFORMATION: Synthetic

<400> SEQUENCE: 457

```
gaggtgcagc tggtggagtc tgggggaggc ctggtcaagc cggggggggtc cctgagactc    60
tcctgtacag cctctggatt caccttcagt acttataaca tgaattgggt ccgccaggct   120
ccagggaagg gactggagtg ggtctcatcc attaggagta gtagtaatta catatactac   180
gcagactcag tgaagggccg attcaccatc tccagagaca cgccaagaa ttcactgtat   240
ctgcaaatga acagcctgag agccgatgac acggctgtgt attactgtgc gagagatggc   300
agcagttggt acgactactc tgactactgg ggccagggaa ccctggtcac cgtctcctca   360
```

<210> SEQ ID NO 458
<211> LENGTH: 120

```
<212> TYPE: PRT
<213> ORGANISM: Artificial Sequence
<220> FEATURE:
<223> OTHER INFORMATION: Synthetic

<400> SEQUENCE: 458

Glu Val Gln Leu Val Glu Ser Gly Gly Gly Leu Val Lys Pro Gly Gly
 1               5                  10                  15

Ser Leu Arg Leu Ser Cys Thr Ala Ser Gly Phe Thr Phe Ser Thr Tyr
            20                  25                  30

Asn Met Asn Trp Val Arg Gln Ala Pro Gly Lys Gly Leu Glu Trp Val
        35                  40                  45

Ser Ser Ile Arg Ser Ser Ser Asn Tyr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Asp Asp Thr Ala Val Tyr Tyr Cys
                85                  90                  95

Ala Arg Asp Gly Ser Ser Trp Tyr Asp Tyr Ser Asp Tyr Trp Gly Gln
            100                 105                 110

Gly Thr Leu Val Thr Val Ser Ser
        115                 120

<210> SEQ ID NO 459
<211> LENGTH: 24
<212> TYPE: DNA
<213> ORGANISM: Artificial Sequence
<220> FEATURE:
<223> OTHER INFORMATION: Synthetic

<400> SEQUENCE: 459
ggattcacct tcagtactta taac                                           24

<210> SEQ ID NO 460
<211> LENGTH: 8
<212> TYPE: PRT
<213> ORGANISM: Artificial Sequence
<220> FEATURE:
<223> OTHER INFORMATION: Synthetic

<400> SEQUENCE: 460

Gly Phe Thr Phe Ser Thr Tyr Asn
 1               5

<210> SEQ ID NO 461
<211> LENGTH: 24
<212> TYPE: DNA
<213> ORGANISM: Artificial Sequence
<220> FEATURE:
<223> OTHER INFORMATION: Synthetic

<400> SEQUENCE: 461
attaggagta gtagtaatta cata                                           24

<210> SEQ ID NO 462
<211> LENGTH: 8
<212> TYPE: PRT
<213> ORGANISM: Artificial Sequence
<220> FEATURE:
<223> OTHER INFORMATION: Synthetic

<400> SEQUENCE: 462

Ile Arg Ser Ser Ser Asn Tyr Ile
```

<210> SEQ ID NO 463
<211> LENGTH: 39
<212> TYPE: DNA
<213> ORGANISM: Artificial Sequence
<220> FEATURE:
<223> OTHER INFORMATION: Synthetic

<400> SEQUENCE: 463
gcgagagatg gcagcagttg gtacgactac tctgactac                    39

<210> SEQ ID NO 464
<211> LENGTH: 13
<212> TYPE: PRT
<213> ORGANISM: Artificial Sequence
<220> FEATURE:
<223> OTHER INFORMATION: Synthetic

<400> SEQUENCE: 464

Ala Arg Asp Gly Ser Ser Trp Tyr Asp Tyr Ser Asp Tyr
 1               5                  10

<210> SEQ ID NO 465
<211> LENGTH: 321
<212> TYPE: DNA
<213> ORGANISM: Artificial Sequence
<220> FEATURE:
<223> OTHER INFORMATION: Synthetic

<400> SEQUENCE: 465
gacatccaga tgacccagtc tccttccacc ctgtctgcat ctgtaggaga cagagtcacc    60
atcacttgcc gggccagtca gagtattagt agctggttgg cctggtatca acagatacca   120
gggaaagccc ctaaactcct gatctataag gcgtctagtt tagaaaatgg ggtcccatca   180
aggttcagcg gcagtggatc tgggacagaa ttcactctca tcatcagcag cctgcagcct   240
gatgattttg caacttatta ctgccaacag tatattagtt attctcggac gttcggccaa   300
gggaccaagg tggaaatcaa a                                            321

<210> SEQ ID NO 466
<211> LENGTH: 107
<212> TYPE: PRT
<213> ORGANISM: Artificial Sequence
<220> FEATURE:
<223> OTHER INFORMATION: Synthetic

<400> SEQUENCE: 466

Asp Ile Gln Met Thr Gln Ser Pro Ser Thr Leu Ser Ala Ser Val Gly
 1               5                  10                  15

Asp Arg Val Thr Ile Thr Cys Arg Ala Ser Gln Ser Ile Ser Ser Trp
             20                  25                  30

Leu Ala Trp Tyr Gln Gln Ile Pro Gly Lys Ala Pro Lys Leu Leu Ile
         35                  40                  45

Tyr Lys Ala Ser Ser Leu Glu Asn Gly Val Pro Ser Arg Phe Ser Gly
     50                  55                  60

Ser Gly Ser Gly Thr Glu Phe Thr Leu Ile Ile Ser Ser Leu Gln Pro
 65                  70                  75                  80

Asp Asp Phe Ala Thr Tyr Tyr Cys Gln Gln Tyr Ile Ser Tyr Ser Arg
                 85                  90                  95

Thr Phe Gly Gln Gly Thr Lys Val Glu Ile Lys
            100                 105

<210> SEQ ID NO 467
<211> LENGTH: 18
<212> TYPE: DNA
<213> ORGANISM: Artificial Sequence
<220> FEATURE:
<223> OTHER INFORMATION: Synthetic

<400> SEQUENCE: 467
cagagtatta gtagctgg                                             18

<210> SEQ ID NO 468
<211> LENGTH: 6
<212> TYPE: PRT
<213> ORGANISM: Artificial Sequence
<220> FEATURE:
<223> OTHER INFORMATION: Synthetic

<400> SEQUENCE: 468

Gln Ser Ile Ser Ser Trp
 1               5

<210> SEQ ID NO 469
<211> LENGTH: 9
<212> TYPE: DNA
<213> ORGANISM: Artificial Sequence
<220> FEATURE:
<223> OTHER INFORMATION: Synthetic

<400> SEQUENCE: 469 aaggcgtct                                                        9

<210> SEQ ID NO 470
<211> LENGTH: 3
<212> TYPE: PRT
<213> ORGANISM: Artificial Sequence
<220> FEATURE:
<223> OTHER INFORMATION: Synthetic

<400> SEQUENCE: 470

Lys Ala Ser
 1

<210> SEQ ID NO 471
<211> LENGTH: 27
<212> TYPE: DNA
<213> ORGANISM: Artificial Sequence
<220> FEATURE:
<223> OTHER INFORMATION: Synthetic

<400> SEQUENCE: 471
caacagtata ttagttattc tcggacg                                   27

<210> SEQ ID NO 472
<211> LENGTH: 9
<212> TYPE: PRT
<213> ORGANISM: Artificial Sequence
<220> FEATURE:
<223> OTHER INFORMATION: Synthetic

<400> SEQUENCE: 472

Gln Gln Tyr Ile Ser Tyr Ser Arg Thr
 1               5

<210> SEQ ID NO 473
<211> LENGTH: 360

```
<212> TYPE: DNA
<213> ORGANISM: Artificial Sequence
<220> FEATURE:
<223> OTHER INFORMATION: Synthetic

<400> SEQUENCE: 473
gaggtgcagc tggtggagtc tgggggaggc ctggtcaagc cggggggggtc cctgagactc      60 tcctgtacag cctctggatt caccttcagt acttataaca tgaattgggt ccgccaggct     120
ccagggaagg gactggagtg gtctcatcc attaggagta gtagtaatta catatactac     180
gcagactcag tgaagggccg attcaccatc tccagagaca acgccaagaa ttcactgtat     240
ctgcaaatga acagcctgag agccgatgac acggctgtgt attactgtgc gagagatggc     300
agcagttggt acgactactc tgactactgg ggccagggaa ccctggtcac cgtctcctca     360

<210> SEQ ID NO 474
<211> LENGTH: 120
<212> TYPE: PRT
<213> ORGANISM: Artificial Sequence
<220> FEATURE:
<223> OTHER INFORMATION: Synthetic

<400> SEQUENCE: 474

Glu Val Gln Leu Val Glu Ser Gly Gly Gly Leu Val Lys Pro Gly Gly
 1               5                  10                  15

Ser Leu Arg Leu Ser Cys Thr Ala Ser Gly Phe Thr Phe Ser Thr Tyr
            20                  25                  30

Asn Met Asn Trp Val Arg Gln Ala Pro Gly Lys Gly Leu Glu Trp Val
        35                  40                  45

Ser Ser Ile Arg Ser Ser Ser Asn Tyr Ile Tyr Tyr Ala Asp Ser Val
    50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Asp Asp Thr Ala Val Tyr Tyr Cys
                85                  90                  95

Ala Arg Asp Gly Ser Ser Trp Tyr Asp Tyr Ser Asp Tyr Trp Gly Gln
            100                 105                 110

Gly Thr Leu Val Thr Val Ser Ser
        115                 120

<210> SEQ ID NO 475
<211> LENGTH: 321
<212> TYPE: DNA
<213> ORGANISM: Artificial Sequence
<220> FEATURE:
<223> OTHER INFORMATION: Synthetic

<400> SEQUENCE: 475
gacatccaga tgacccagtc tccttccacc ctgtctgcat ctgtaggaga cagagtcacc      60
atcacttgcc gggccagtca gagtattagt agctggttgg cctggtatca acagatacca     120
gggaaagccc ctaaactcct gatctataag gcgtctagtt tagaaaatgg ggtcccatca     180
aggttcagcg gcagtggatc tgggacagaa ttcactctca tcatcagcag cctgcagcct     240
gatgattttg caacttatta ctgccaacag tatattagtt attctcggac gttcggccaa     300
gggaccaagg tggaaatcaa a                                                321

<210> SEQ ID NO 476
<211> LENGTH: 107
<212> TYPE: PRT
```

<213> ORGANISM: Artificial Sequence
<220> FEATURE:
<223> OTHER INFORMATION: Synthetic

<400> SEQUENCE: 476

```
Asp Ile Gln Met Thr Gln Ser Pro Ser Thr Leu Ser Ala Ser Val Gly
  1               5                  10                  15

Asp Arg Val Thr Ile Thr Cys Arg Ala Ser Gln Ser Ile Ser Ser Trp
             20                  25                  30

Leu Ala Trp Tyr Gln Gln Ile Pro Gly Lys Ala Pro Lys Leu Leu Ile
         35                  40                  45

Tyr Lys Ala Ser Ser Leu Glu Asn Gly Val Pro Ser Arg Phe Ser Gly
 50                  55                  60

Ser Gly Ser Gly Thr Glu Phe Thr Leu Ile Ile Ser Ser Leu Gln Pro
 65                  70                  75                  80

Asp Asp Phe Ala Thr Tyr Tyr Cys Gln Gln Tyr Ile Ser Tyr Ser Arg
             85                  90                  95

Thr Phe Gly Gln Gly Thr Lys Val Glu Ile Lys
            100                 105
```

<210> SEQ ID NO 477
<211> LENGTH: 360
<212> TYPE: DNA
<213> ORGANISM: Artificial Sequence
<220> FEATURE:
<223> OTHER INFORMATION: Synthetic

<400> SEQUENCE: 477

```
gaggtgcagc tggtggagtc tgggggaggc ctggtcaagc ctgggggtc cctgagactc      60 tcctgtgcag cctctggatt caccttcagt acttataaca tgaactgggt ccgccaggct     120
ccagggaagg ggctggagtg ggtctcatcc attaggagta gtagtaatta catatactac    180
gcagactcag tgaagggccg attcaccatc tccagagaca cgccaagaa ctcactgtat    240 ctgcaaatga acagcctgag agccgaggac acggctgtgt attactgtgc gagagatggc   300
agcagttggt acgactactc tgactactgg ggccaaggaa ccctggtcac cgtctcctca    360
```

<210> SEQ ID NO 478
<211> LENGTH: 120
<212> TYPE: PRT
<213> ORGANISM: Artificial Sequence
<220> FEATURE:
<223> OTHER INFORMATION: Synthetic

<400> SEQUENCE: 478

```
Glu Val Gln Leu Val Glu Ser Gly Gly Gly Leu Val Lys Pro Gly Gly
  1               5                  10                  15

Ser Leu Arg Leu Ser Cys Ala Ala Ser Gly Phe Thr Phe Ser Thr Tyr
             20                  25                  30

Asn Met Asn Trp Val Arg Gln Ala Pro Gly Lys Gly Leu Glu Trp Val
         35                  40                  45

Ser Ser Ile Arg Ser Ser Ser Asn Tyr Ile Tyr Tyr Ala Asp Ser Val
 50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
             85                  90                  95

Ala Arg Asp Gly Ser Ser Trp Tyr Asp Tyr Ser Asp Tyr Trp Gly Gln
            100                 105                 110
```

```
Gly Thr Leu Val Thr Val Ser Ser
        115                 120
```

<210> SEQ ID NO 479
<211> LENGTH: 321
<212> TYPE: DNA
<213> ORGANISM: Artificial Sequence
<220> FEATURE:
<223> OTHER INFORMATION: Synthetic

<400> SEQUENCE: 479

```
gacatccaga tgacccagtc tccttccacc ctgtctgcat ctgtaggaga cagagtcacc    60
atcacttgcc gggccagtca gagtattagt agctggttgg cctggtatca gcagaaacca   120
gggaaagccc ctaagctcct gatctataag gcgtctagtt tagaaagtgg ggtcccatca   180
aggttcagcg gcagtggatc tgggacagaa ttcactctca ccatcagcag cctgcagcct   240
gatgattttg caacttatta ctgccaacag tatattagtt attctcggac gttcggccaa   300
gggaccaagg tggaaatcaa a                                             321
```

<210> SEQ ID NO 480
<211> LENGTH: 107
<212> TYPE: PRT
<213> ORGANISM: Artificial Sequence
<220> FEATURE:
<223> OTHER INFORMATION: Synthetic

<400> SEQUENCE: 480

```
Asp Ile Gln Met Thr Gln Ser Pro Ser Thr Leu Ser Ala Ser Val Gly
  1               5                  10                  15

Asp Arg Val Thr Ile Thr Cys Arg Ala Ser Gln Ser Ile Ser Ser Trp
             20                  25                  30

Leu Ala Trp Tyr Gln Gln Lys Pro Gly Lys Ala Pro Lys Leu Leu Ile
         35                  40                  45

Tyr Lys Ala Ser Ser Leu Glu Ser Gly Val Pro Ser Arg Phe Ser Gly
 50                  55                  60

Ser Gly Ser Gly Thr Glu Phe Thr Leu Thr Ile Ser Ser Leu Gln Pro
 65                  70                  75                  80

Asp Asp Phe Ala Thr Tyr Tyr Cys Gln Gln Tyr Ile Ser Tyr Ser Arg
                 85                  90                  95

Thr Phe Gly Gln Gly Thr Lys Val Glu Ile Lys
            100                 105
```

<210> SEQ ID NO 481
<211> LENGTH: 354
<212> TYPE: DNA
<213> ORGANISM: Artificial Sequence
<220> FEATURE:
<223> OTHER INFORMATION: Synthetic

<400> SEQUENCE: 481

```
gaggtgcaac tagtggagtc tgggggaggc ttggtacagc ctggggggtc cctgagactc    60
tcctgtgtag tctctggatt caccttcggt gactacgaca tgcactgggt ccgtcaagct   120
acaggaagag gtctggagtg gtctcaggt attgctcctg ctggtgacac atcctataca   180
ggctccgtga agggccgatt caccatctcc agagagaatg ccaagaactc cttgcatctt   240
caaatgaaca gcctgacaac cggggacacg gctatatatt attgtgctag agaggatata   300
gcagtgcctg gttttgatta ctggggccag ggaaccctgg tcaccgtctc ctca        354
```

<210> SEQ ID NO 482
<211> LENGTH: 118
<212> TYPE: PRT
<213> ORGANISM: Artificial Sequence
<220> FEATURE:
<223> OTHER INFORMATION: Synthetic

<400> SEQUENCE: 482

```
Glu Val Gln Leu Val Glu Ser Gly Gly Gly Leu Val Gln Pro Gly Gly
  1               5                  10                  15

Ser Leu Arg Leu Ser Cys Val Val Ser Gly Phe Thr Phe Gly Asp Tyr
             20                  25                  30

Asp Met His Trp Val Arg Gln Ala Thr Gly Arg Gly Leu Glu Trp Val
         35                  40                  45

Ser Gly Ile Ala Pro Ala Gly Asp Thr Ser Tyr Thr Gly Ser Val Lys
     50                  55                  60

Gly Arg Phe Thr Ile Ser Arg Glu Asn Ala Lys Asn Ser Leu His Leu
 65                  70                  75                  80

Gln Met Asn Ser Leu Thr Thr Gly Asp Thr Ala Ile Tyr Tyr Cys Ala
                 85                  90                  95

Arg Glu Asp Ile Ala Val Pro Gly Phe Asp Tyr Trp Gly Gln Gly Thr
            100                 105                 110

Leu Val Thr Val Ser Ser
        115
```

<210> SEQ ID NO 483
<211> LENGTH: 24
<212> TYPE: DNA
<213> ORGANISM: Artificial Sequence
<220> FEATURE:
<223> OTHER INFORMATION: Synthetic

<400> SEQUENCE: 483
ggattcacct tcggtgacta cgac                24

<210> SEQ ID NO 484
<211> LENGTH: 8
<212> TYPE: PRT
<213> ORGANISM: Artificial Sequence
<220> FEATURE:
<223> OTHER INFORMATION: Synthetic

<400> SEQUENCE: 484

```
Gly Phe Thr Phe Gly Asp Tyr Asp
  1               5
```

<210> SEQ ID NO 485
<211> LENGTH: 21
<212> TYPE: DNA
<213> ORGANISM: Artificial Sequence
<220> FEATURE:
<223> OTHER INFORMATION: Synthetic

<400> SEQUENCE: 485
attgctcctg ctggtgacac a                21

<210> SEQ ID NO 486
<211> LENGTH: 7
<212> TYPE: PRT
<213> ORGANISM: Artificial Sequence
<220> FEATURE:
<223> OTHER INFORMATION: Synthetic

<400> SEQUENCE: 486

Ile Ala Pro Ala Gly Asp Thr
1               5

<210> SEQ ID NO 487
<211> LENGTH: 36
<212> TYPE: DNA
<213> ORGANISM: Artificial Sequence
<220> FEATURE:
<223> OTHER INFORMATION: Synthetic

<400> SEQUENCE: 487
gctagagagg atatagcagt gcctggtttt gattac                                  36

<210> SEQ ID NO 488
<211> LENGTH: 12
<212> TYPE: PRT
<213> ORGANISM: Artificial Sequence
<220> FEATURE:
<223> OTHER INFORMATION: Synthetic

<400> SEQUENCE: 488

Ala Arg Glu Asp Ile Ala Val Pro Gly Phe Asp Tyr
1               5                   10

<210> SEQ ID NO 489
<211> LENGTH: 324
<212> TYPE: DNA
<213> ORGANISM: Artificial Sequence
<220> FEATURE:
<223> OTHER INFORMATION: Synthetic

<400> SEQUENCE: 489
gaaatagtga tgacgcagtc tccagccacc ctgtctgtgt ctccagggga acgaggcacc         60
ctctcctgca gggccagtca gagtgttagc agcaacttag cctggtacca gcagaaacct        120
ggccaggctc ccagactcct catctatggt gcatccacga gggccactgg cttcccagcc        180
aggttcagtg gcagtgggtc tgggacagag ttcactctca ccatcagcag cctgcagtct        240
gaagattttg cagtttatta ctgtcagcag tataataagt ggcctccgtt cactttcggc        300
cctgggacca aagtggattt caaa                                              324

<210> SEQ ID NO 490
<211> LENGTH: 108
<212> TYPE: PRT
<213> ORGANISM: Artificial Sequence
<220> FEATURE:
<223> OTHER INFORMATION: Synthetic

<400> SEQUENCE: 490

Glu Ile Val Met Thr Gln Ser Pro Ala Thr Leu Ser Val Ser Pro Gly
1               5                   10                  15

Glu Arg Gly Thr Leu Ser Cys Arg Ala Ser Gln Ser Val Ser Ser Asn
            20                  25                  30

Leu Ala Trp Tyr Gln Gln Lys Pro Gly Gln Ala Pro Arg Leu Leu Ile
        35                  40                  45

Tyr Gly Ala Ser Thr Arg Ala Thr Gly Phe Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Asn Lys Trp Pro Pro
                85                  90                  95

Phe Thr Phe Gly Pro Gly Thr Lys Val Asp Phe Lys
            100                 105

<210> SEQ ID NO 491
<211> LENGTH: 18
<212> TYPE: DNA
<213> ORGANISM: Artificial Sequence
<220> FEATURE:
<223> OTHER INFORMATION: Synthetic

<400> SEQUENCE: 491
cagagtgtta gcagcaac                                                 18

<210> SEQ ID NO 492
<211> LENGTH: 6
<212> TYPE: PRT
<213> ORGANISM: Artificial Sequence
<220> FEATURE:
<223> OTHER INFORMATION: Synthetic

<400> SEQUENCE: 492

Gln Ser Val Ser Ser Asn
 1               5

<210> SEQ ID NO 493
<211> LENGTH: 9
<212> TYPE: DNA
<213> ORGANISM: Artificial Sequence
<220> FEATURE:
<223> OTHER INFORMATION: Synthetic

<400> SEQUENCE: 493 ggtgcatcc                                                            9

<210> SEQ ID NO 494
<211> LENGTH: 3
<212> TYPE: PRT
<213> ORGANISM: Artificial Sequence
<220> FEATURE:
<223> OTHER INFORMATION: Synthetic

<400> SEQUENCE: 494

Gly Ala Ser
 1

<210> SEQ ID NO 495
<211> LENGTH: 30
<212> TYPE: DNA
<213> ORGANISM: Artificial Sequence
<220> FEATURE:
<223> OTHER INFORMATION: Synthetic

<400> SEQUENCE: 495
cagcagtata ataagtggcc tccgttcact                                    30

<210> SEQ ID NO 496
<211> LENGTH: 10
<212> TYPE: PRT
<213> ORGANISM: Artificial Sequence
<220> FEATURE:
<223> OTHER INFORMATION: Synthetic

<400> SEQUENCE: 496

Gln Gln Tyr Asn Lys Trp Pro Pro Phe Thr
 1               5                  10

<210> SEQ ID NO 497
<211> LENGTH: 354
<212> TYPE: DNA
<213> ORGANISM: Artificial Sequence
<220> FEATURE:
<223> OTHER INFORMATION: Synthetic

<400> SEQUENCE: 497

```
gaggtgcaac tagtggagtc tgggggaggc ttggtacagc ctgggggtc cctgagactc      60
tcctgtgtag tctctggatt caccttcggt gactacgaca tgcactgggt ccgtcaagct     120
acaggaagag gtctggagtg gtctcaggt attgctcctg ctggtgacac atcctataca     180
ggctccgtga agggccgatt caccatctcc agagagaatg ccaagaactc cttgcatctt    240
caaatgaaca gcctgacaac cggggacacg gctatatatt attgtgctag agaggatata    300
gcagtgcctg gttttgatta ctggggccag ggaaccctgg tcaccgtctc ctca           354
```

<210> SEQ ID NO 498
<211> LENGTH: 118
<212> TYPE: PRT
<213> ORGANISM: Artificial Sequence
<220> FEATURE:
<223> OTHER INFORMATION: Synthetic

<400> SEQUENCE: 498

Glu Val Gln Leu Val Glu Ser Gly Gly Gly Leu Val Gln Pro Gly Gly
1               5                   10                  15

Ser Leu Arg Leu Ser Cys Val Val Ser Gly Phe Thr Phe Gly Asp Tyr
            20                  25                  30

Asp Met His Trp Val Arg Gln Ala Thr Gly Arg Gly Leu Glu Trp Val
        35                  40                  45

Ser Gly Ile Ala Pro Ala Gly Asp Thr Ser Tyr Thr Gly Ser Val Lys
    50                  55                  60

Gly Arg Phe Thr Ile Ser Arg Glu Asn Ala Lys Asn Ser Leu His Leu
65                  70                  75                  80

Gln Met Asn Ser Leu Thr Thr Gly Asp Thr Ala Ile Tyr Tyr Cys Ala
                85                  90                  95

Arg Glu Asp Ile Ala Val Pro Gly Phe Asp Tyr Trp Gly Gln Gly Thr
            100                 105                 110

Leu Val Thr Val Ser Ser
        115

<210> SEQ ID NO 499
<211> LENGTH: 324
<212> TYPE: DNA
<213> ORGANISM: Artificial Sequence
<220> FEATURE:
<223> OTHER INFORMATION: Synthetic

<400> SEQUENCE: 499

```
gaaatagtga tgacgcagtc tccagccacc ctgtctgtgt ctccagggga acgaggcacc      60
ctctcctgca gggccagtca gagtgttagc agcaacttag cctggtacca gcagaaacct    120
ggccaggctc ccagactcct catctatggt gcatccacga gggccactgg cttcccagcc    180
aggttcagtg gcagtgggtc tgggacagag ttcactctca ccatcagcag cctgcagtct    240
gaagattttg cagtttatta ctgtcagcag tataataagt ggcctccgtt cactttcggc    300
cctgggacca aagtggatat caaa                                           324
```

<210> SEQ ID NO 500
<211> LENGTH: 108
<212> TYPE: PRT
<213> ORGANISM: Artificial Sequence
<220> FEATURE:
<223> OTHER INFORMATION: Synthetic

<400> SEQUENCE: 500

```
Glu Ile Val Met Thr Gln Ser Pro Ala Thr Leu Ser Val Ser Pro Gly
1               5                   10                  15
Glu Arg Gly Thr Leu Ser Cys Arg Ala Ser Gln Ser Val Ser Ser Asn
            20                  25                  30
Leu Ala Trp Tyr Gln Gln Lys Pro Gly Gln Ala Pro Arg Leu Leu Ile
        35                  40                  45
Tyr Gly Ala Ser Thr Arg Ala Thr Gly Phe Pro Ala Arg Phe Ser Gly
50                  55                  60
Ser Gly Ser Gly Thr Glu Phe Thr Leu Thr Ile Ser Ser Leu Gln Ser
65                  70                  75                  80
Glu Asp Phe Ala Val Tyr Tyr Cys Gln Gln Tyr Asn Lys Trp Pro Pro
                85                  90                  95
Phe Thr Phe Gly Pro Gly Thr Lys Val Asp Ile Lys
            100                 105
```

<210> SEQ ID NO 501
<211> LENGTH: 354
<212> TYPE: DNA
<213> ORGANISM: Artificial Sequence
<220> FEATURE:
<223> OTHER INFORMATION: Synthetic

<400> SEQUENCE: 501

```
gaggtgcagc tggtggagtc tgggggaggc ttggtacagc ctgggggggtc cctgagactc      60
tcctgtgcag cctctggatt caccttcggt gactacgaca tgcactgggt ccgccaagct     120
acaggaaaag gtctggagtg ggtctcagct attgctcctg ctggtgacac atactatcca     180
ggctccgtga agggccgatt caccatctcc agagaaaatg ccaagaactc cttgtatctt     240
caaatgaaca gcctgagagc cggggacacg gctgtgtatt actgtgctag agaggatata     300
gcagtgcctg gttttgatta ctggggccaa ggaaccctgg tcaccgtctc ctca           354
```

<210> SEQ ID NO 502
<211> LENGTH: 118
<212> TYPE: PRT
<213> ORGANISM: Artificial Sequence
<220> FEATURE:
<223> OTHER INFORMATION: Synthetic

<400> SEQUENCE: 502

```
Glu Val Gln Leu Val Glu Ser Gly Gly Gly Leu Val Gln Pro Gly Gly
1               5                   10                  15
Ser Leu Arg Leu Ser Cys Ala Ala Ser Gly Phe Thr Phe Gly Asp Tyr
            20                  25                  30
Asp Met His Trp Val Arg Gln Ala Thr Gly Lys Gly Leu Glu Trp Val
        35                  40                  45
Ser Ala Ile Ala Pro Ala Gly Asp Thr Tyr Tyr Pro Gly Ser Val Lys
50                  55                  60
Gly Arg Phe Thr Ile Ser Arg Glu Asn Ala Lys Asn Ser Leu Tyr Leu
65                  70                  75                  80
Gln Met Asn Ser Leu Arg Ala Gly Asp Thr Ala Val Tyr Tyr Cys Ala
                85                  90                  95
```

Arg Glu Asp Ile Ala Val Pro Gly Phe Asp Tyr Trp Gly Gln Gly Thr
            100                 105                 110

Leu Val Thr Val Ser Ser
        115

<210> SEQ ID NO 503
<211> LENGTH: 324
<212> TYPE: DNA
<213> ORGANISM: Artificial Sequence
<220> FEATURE:
<223> OTHER INFORMATION: Synthetic

<400> SEQUENCE: 503
gaaatagtga tgacgcagtc tccagccacc ctgtctgtgt ctccagggga aagagccacc    60
ctctcctgca gggccagtca gagtgttagc agcaacttag cctggtacca gcagaaacct   120
ggccaggctc ccaggctcct catctatggt gcatccacca gggccactgg tatcccagcc   180
aggttcagtg gcagtgggtc tgggacagag ttcactctca ccatcagcag cctgcagtct   240
gaagattttg cagtttatta ctgtcagcag tataataagt ggcctccgtt cactttcggc   300
cctgggacca agtggatat caaa                                           324

<210> SEQ ID NO 504
<211> LENGTH: 108
<212> TYPE: PRT
<213> ORGANISM: Artificial Sequence
<220> FEATURE:
<223> OTHER INFORMATION: Synthetic

<400> SEQUENCE: 504

Glu Ile Val Met Thr Gln Ser Pro Ala Thr Leu Ser Val Ser Pro Gly
 1               5                  10                  15

Glu Arg Ala Thr Leu Ser Cys Arg Ala Ser Gln Ser Val Ser Ser Asn
             20                  25                  30

Leu Ala Trp Tyr Gln Gln Lys Pro Gly Gln Ala Pro Arg Leu Leu Ile
         35                  40                  45

Tyr Gly Ala Ser Thr Arg Ala Thr Gly Ile Pro Ala Arg Phe Ser Gly
 50                  55                  60

Ser Gly Ser Gly Thr Glu Phe Thr Leu Thr Ile Ser Ser Leu Gln Ser
65                   70                  75                  80

Glu Asp Phe Ala Val Tyr Tyr Cys Gln Gln Tyr Asn Lys Trp Pro Pro
                 85                  90                  95

Phe Thr Phe Gly Pro Gly Thr Lys Val Asp Ile Lys
            100                 105

<210> SEQ ID NO 505
<211> LENGTH: 378
<212> TYPE: DNA
<213> ORGANISM: Artificial Sequence
<220> FEATURE:
<223> OTHER INFORMATION: Synthetic

<400> SEQUENCE: 505
caaattctgc tggtgcaatc tggacctgag gtgaaggagc tggggcctc agtgaaggtc     60 tcctgcaagg cttctggtta caccttacc aactacgcta tcagctgggt gcgacaggtc   120
cctggacaag gcttgagtg gatgggatgg gtcagcgctt acaatggtca cacaaactat   180
gcacatgaag tccagggcag agtcaccatg accacagaca catccacgac acagcctac   240 atggagctga ggagcctgag atctgacgac acggccatgt attactgtgc gagaggggt   300

```
gtagtcgtgc cagttgctcc ccacttctac aacggtatgg acgtctgggg ccaagggacc    360
acggtcaccg tctcctca                                                  378
```

<210> SEQ ID NO 506
<211> LENGTH: 126
<212> TYPE: PRT
<213> ORGANISM: Artificial Sequence
<220> FEATURE:
<223> OTHER INFORMATION: Synthetic

<400> SEQUENCE: 506

```
Gln Ile Leu Leu Val Gln Ser Gly Pro Glu Val Lys Glu Pro Gly Ala
  1               5                  10                  15

Ser Val Lys Val Ser Cys Lys Ala Ser Gly Tyr Thr Phe Thr Asn Tyr
             20                  25                  30

Ala Ile Ser Trp Val Arg Gln Val Pro Gly Gln Gly Leu Glu Trp Met
         35                  40                  45

Gly Trp Val Ser Ala Tyr Asn Gly His Thr Asn Tyr Ala His Glu Val
     50                  55                  60

Gln Gly Arg Val Thr Met Thr Thr Asp Thr Ser Thr Thr Thr Ala Tyr
 65                  70                  75                  80

Met Glu Leu Arg Ser Leu Arg Ser Asp Asp Thr Ala Met Tyr Tyr Cys
                 85                  90                  95

Ala Arg Gly Gly Val Val Val Pro Val Ala Pro His Phe Tyr Asn Gly
                100                 105                 110

Met Asp Val Trp Gly Gln Gly Thr Thr Val Thr Val Ser Ser
            115                 120                 125
```

<210> SEQ ID NO 507
<211> LENGTH: 24
<212> TYPE: DNA
<213> ORGANISM: Artificial Sequence
<220> FEATURE:
<223> OTHER INFORMATION: Synthetic

<400> SEQUENCE: 507

```
ggttacacct ttaccaacta cgct                                            24
```

<210> SEQ ID NO 508
<211> LENGTH: 8
<212> TYPE: PRT
<213> ORGANISM: Artificial Sequence
<220> FEATURE:
<223> OTHER INFORMATION: Synthetic

<400> SEQUENCE: 508

```
Gly Tyr Thr Phe Thr Asn Tyr Ala
  1               5
```

<210> SEQ ID NO 509
<211> LENGTH: 24
<212> TYPE: DNA
<213> ORGANISM: Artificial Sequence
<220> FEATURE:
<223> OTHER INFORMATION: Synthetic

<400> SEQUENCE: 509

```
gtcagcgctt acaatggtca caca                                            24
```

<210> SEQ ID NO 510
<211> LENGTH: 8

```
<212> TYPE: PRT
<213> ORGANISM: Artificial Sequence
<220> FEATURE:
<223> OTHER INFORMATION: Synthetic

<400> SEQUENCE: 510

Val Ser Ala Tyr Asn Gly His Thr
 1               5

<210> SEQ ID NO 511
<211> LENGTH: 57
<212> TYPE: DNA
<213> ORGANISM: Artificial Sequence
<220> FEATURE:
<223> OTHER INFORMATION: Synthetic

<400> SEQUENCE: 511
gcgagagggg gtgtagtcgt gccagttgct ccccacttct acaacggtat ggacgtc      57

<210> SEQ ID NO 512
<211> LENGTH: 19
<212> TYPE: PRT
<213> ORGANISM: Artificial Sequence
<220> FEATURE:
<223> OTHER INFORMATION: Synthetic

<400> SEQUENCE: 512

Ala Arg Gly Gly Val Val Val Pro Val Ala Pro His Phe Tyr Asn Gly
 1               5                  10                  15

Met Asp Val

<210> SEQ ID NO 513
<211> LENGTH: 336
<212> TYPE: DNA
<213> ORGANISM: Artificial Sequence
<220> FEATURE:
<223> OTHER INFORMATION: Synthetic

<400> SEQUENCE: 513
gatattgtga tgactcagtt tccactctcc ctgcccgtca cccctggaga gccggcctcc     60
atctcctgca ggtctagtca gagcctcctg catattaatg aatacaacta tttggattgg   120
tacctaaaga agccagggca gtctccacag ctcctgatct atttgggttt taatcgggcc   180
tccggggtcc ctgacaggtt cagtggcagt ggatcaggca cagattttac actgaaaatc   240
agcagagtgg aggctgagga tgttggggtc tattactgca tgcaagctct tcaaactccg   300
tggacgttag gccaagggac caaggtggaa atcaaa                              336

<210> SEQ ID NO 514
<211> LENGTH: 112
<212> TYPE: PRT
<213> ORGANISM: Artificial Sequence
<220> FEATURE:
<223> OTHER INFORMATION: Synthetic

<400> SEQUENCE: 514

Asp Ile Val Met Thr Gln Phe Pro Leu Ser Leu Pro Val Thr Pro Gly
 1               5                  10                  15

Glu Pro Ala Ser Ile Ser Cys Arg Ser Ser Gln Ser Leu Leu His Ile
                20                  25                  30

Asn Glu Tyr Asn Tyr Leu Asp Trp Tyr Leu Lys Lys Pro Gly Gln Ser
            35                  40                  45

Pro Gln Leu Leu Ile Tyr Leu Gly Phe Asn Arg Ala Ser Gly Val Pro
```

```
                50                  55                  60
Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Met Gln Ala
                 85                  90                  95

Leu Gln Thr Pro Trp Thr Leu Gly Gln Gly Thr Lys Val Glu Ile Lys
            100                 105                 110

<210> SEQ ID NO 515
<211> LENGTH: 33
<212> TYPE: DNA
<213> ORGANISM: Artificial Sequence
<220> FEATURE:
<223> OTHER INFORMATION: Synthetic

<400> SEQUENCE: 515
cagagcctcc tgcatattaa tgaatacaac tat                            33

<210> SEQ ID NO 516
<211> LENGTH: 11
<212> TYPE: PRT
<213> ORGANISM: Artificial Sequence
<220> FEATURE:
<223> OTHER INFORMATION: Synthetic

<400> SEQUENCE: 516

Gln Ser Leu Leu His Ile Asn Glu Tyr Asn Tyr
 1               5                  10

<210> SEQ ID NO 517
<211> LENGTH: 9
<212> TYPE: DNA
<213> ORGANISM: Artificial Sequence
<220> FEATURE:
<223> OTHER INFORMATION: Synthetic

<400> SEQUENCE: 517 ttgggtttt                                                        9

<210> SEQ ID NO 518
<211> LENGTH: 3
<212> TYPE: PRT
<213> ORGANISM: Artificial Sequence
<220> FEATURE:
<223> OTHER INFORMATION: Synthetic

<400> SEQUENCE: 518

Leu Gly Phe
 1

<210> SEQ ID NO 519
<211> LENGTH: 27
<212> TYPE: DNA
<213> ORGANISM: Artificial Sequence
<220> FEATURE:
<223> OTHER INFORMATION: Synthetic

<400> SEQUENCE: 519
atgcaagctc ttcaaactcc gtggacg                                   27

<210> SEQ ID NO 520
<211> LENGTH: 9
<212> TYPE: PRT
<213> ORGANISM: Artificial Sequence
<220> FEATURE:
```

<223> OTHER INFORMATION: Synthetic

<400> SEQUENCE: 520

Met Gln Ala Leu Gln Thr Pro Trp Thr
 1               5

<210> SEQ ID NO 521
<211> LENGTH: 378
<212> TYPE: DNA
<213> ORGANISM: Artificial Sequence
<220> FEATURE:
<223> OTHER INFORMATION: Synthetic

<400> SEQUENCE: 521
caggttcagc tggtgcagtc tggacctgag gtgaaggagc ctggggcctc agtgaaggtc      60
tcctgcaagg cttctggtta cacctttacc aactacgcta tcagctgggt gcgacaggtc     120
cctggacaag gcttgagtg atgggatgg gtcagcgctt acaatggtca cacaaactat      180
gcacatgaag tccagggcag agtcaccatg accacagaca catccacgac cacagcctac    240
atggagctga ggagcctgag atctgacgac acggccatgt attactgtgc gagagggggt    300
gtagtcgtgc cagttgctcc ccacttctac aacggtatgg acgtctgggg ccaagggacc    360
acggtcaccg tctcctca                                                  378

<210> SEQ ID NO 522
<211> LENGTH: 126
<212> TYPE: PRT
<213> ORGANISM: Artificial Sequence
<220> FEATURE:
<223> OTHER INFORMATION: Synthetic

<400> SEQUENCE: 522

Gln Val Gln Leu Val Gln Ser Gly Pro Glu Val Lys Glu Pro Gly Ala
 1               5                  10                  15

Ser Val Lys Val Ser Cys Lys Ala Ser Gly Tyr Thr Phe Thr Asn Tyr
                20                  25                  30

Ala Ile Ser Trp Val Arg Gln Val Pro Gly Gln Gly Leu Glu Trp Met
            35                  40                  45

Gly Trp Val Ser Ala Tyr Asn Gly His Thr Asn Tyr Ala His Glu Val
        50                  55                  60

Gln Gly Arg Val Thr Met Thr Thr Asp Thr Ser Thr Thr Thr Ala Tyr
65                  70                  75                  80

Met Glu Leu Arg Ser Leu Arg Ser Asp Asp Thr Ala Met Tyr Tyr Cys
                85                  90                  95

Ala Arg Gly Gly Val Val Val Pro Val Ala Pro His Phe Tyr Asn Gly
            100                 105                 110

Met Asp Val Trp Gly Gln Gly Thr Thr Val Thr Val Ser Ser
        115                 120                 125

<210> SEQ ID NO 523
<211> LENGTH: 336
<212> TYPE: DNA
<213> ORGANISM: Artificial Sequence
<220> FEATURE:
<223> OTHER INFORMATION: Synthetic

<400> SEQUENCE: 523
gatattgtga tgactcagtc tccactctcc ctgcccgtca cccctggaga gccggcctcc      60
atctcctgca ggtctagtca gagcctcctg catattaatg aatacaacta tttggattgg    120

```
tacctaaaga agccagggca gtctccacag ctcctgatct atttgggttt taatcgggcc    180
tccggggtcc ctgacaggtt cagtggcagt ggatcaggca cagattttac actgaaaatc    240
agcagagtgg aggctgagga tgttggggtc tattactgca tgcaagctct tcaaactccg    300
tggacgttag gccaagggac caaggtggaa atcaaa                              336
```

<210> SEQ ID NO 524
<211> LENGTH: 112
<212> TYPE: PRT
<213> ORGANISM: Artificial Sequence
<220> FEATURE:
<223> OTHER INFORMATION: Synthetic

<400> SEQUENCE: 524

```
Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ile
            20                  25                  30

Asn Glu Tyr Asn Tyr Leu Asp Trp Tyr Leu Lys Lys Pro Gly Gln Ser
        35                  40                  45

Pro Gln Leu Leu Ile Tyr Leu Gly Phe Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Thr Pro Trp Thr Leu Gly Gln Gly Thr Lys Val Glu Ile Lys
            100                 105                 110
```

<210> SEQ ID NO 525
<211> LENGTH: 378
<212> TYPE: DNA
<213> ORGANISM: Artificial Sequence
<220> FEATURE:
<223> OTHER INFORMATION: Synthetic

<400> SEQUENCE: 525

```
caggttcagc tggtgcagtc tggagctgag gtgaagaagc ctggggcctc agtgaaggtc     60
tcctgcaagg cttctggtta cacctttacc aactacgcta tcagctgggt gcgacaggcc    120
cctggacaag gcttgagtg gatgggatgg gtcagcgctt acaatggtca cacaaactat     180
gcacagaagc tccagggcag agtcaccatg accacagaca tccacgag cacagcctac      240 atggagctga ggagcctgag atctgacgac acggccgtgt attactgtgc gagggggt      300 gtagtcgtgc cagttgctcc ccacttctac aacggtatgg acgtctgggg gcaagggacc    360
acggtcaccg tctcctca                                                  378
```

<210> SEQ ID NO 526
<211> LENGTH: 126
<212> TYPE: PRT
<213> ORGANISM: Artificial Sequence
<220> FEATURE:
<223> OTHER INFORMATION: Synthetic

<400> SEQUENCE: 526

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30
```

Ala Ile Ser Trp Val Arg Gln Ala Pro Gly Gln Gly Leu Glu Trp Met
            35                  40                  45

Gly Trp Val Ser Ala Tyr Asn Gly His Thr Asn Tyr Ala Gln Lys Leu
 50                  55                  60

Gln Gly Arg Val Thr Met Thr Thr Asp Thr Ser Thr Ser Thr Ala Tyr
 65                  70                  75                  80

Met Glu Leu Arg Ser Leu Arg Ser Asp Asp Thr Ala Val Tyr Tyr Cys
                 85                  90                  95

Ala Arg Gly Gly Val Val Pro Val Ala Pro His Phe Tyr Asn Gly
            100                 105                 110

Met Asp Val Trp Gly Gln Gly Thr Thr Val Thr Val Ser Ser
            115                 120                 125

<210> SEQ ID NO 527
<211> LENGTH: 336
<212> TYPE: DNA
<213> ORGANISM: Artificial Sequence
<220> FEATURE:
<223> OTHER INFORMATION: Synthetic

<400> SEQUENCE: 527
gatattgtga tgactcagtc tccactctcc ctgcccgtca cccctggaga gccggcctcc    60
atctcctgca ggtctagtca gagcctcctg catattaatg aatacaacta tttggattgg   120
tacctgcaga agccagggca gtctccacag ctcctgatct atttgggttc taatcgggcc   180
tccggggtcc ctgacaggtt cagtggcagt ggatcaggca cagattttac actgaaaatc   240
agcagagtgg aggctgagga tgttggggtt tattactgca tgcaagctct tcaaactccg   300
tggacgttcg gccaagggac caaggtggaa atcaaa                              336

<210> SEQ ID NO 528
<211> LENGTH: 112
<212> TYPE: PRT
<213> ORGANISM: Artificial Sequence
<220> FEATURE:
<223> OTHER INFORMATION: Synthetic

<400> SEQUENCE: 528

Asp Ile Val Met Thr Gln Ser Pro Leu Ser Leu Pro Val Thr Pro Gly
 1               5                  10                  15

Glu Pro Ala Ser Ile Ser Cys Arg Ser Ser Gln Ser Leu Leu His Ile
            20                  25                  30

Asn Glu Tyr Asn Tyr Leu Asp Trp Tyr Leu Gln Lys Pro Gly Gln Ser
            35                  40                  45

Pro Gln Leu Leu Ile Tyr Leu Gly Ser Asn Arg Ala Ser Gly Val Pro
 50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Met Gln Ala
                 85                  90                  95

Leu Gln Thr Pro Trp Thr Phe Gly Gln Gly Thr Lys Val Glu Ile Lys
            100                 105                 110

<210> SEQ ID NO 529
<211> LENGTH: 351
<212> TYPE: DNA
<213> ORGANISM: Artificial Sequence
<220> FEATURE:
<223> OTHER INFORMATION: Synthetic -continued

<400> SEQUENCE: 529

```
gaggtgcagc tggtggagtc tgggggaggc ttggtacagc ctggggggtc cctgagactc    60
tcctgtgcag cctctggatt caccctaagt agctacgaca tgcactgggt ccgccaagca   120
acaggaaaag gtctggagtg gtctcagct attggcagta ctggtgacac atactataca   180
ggctccgtga tgggccgatt caccatctcc agagacgctg ccaaaaactc cttctatctt   240
gaaatgaaca gcctgagagt cggggacacg gctgtatatt actgtgcaag agagggaata   300
agaacaccct atgattattg gggccaggga gcccgggtca ccgtctcctc a            351
```

<210> SEQ ID NO 530
<211> LENGTH: 117
<212> TYPE: PRT
<213> ORGANISM: Artificial Sequence
<220> FEATURE:
<223> OTHER INFORMATION: Synthetic

<400> SEQUENCE: 530

```
Glu Val Gln Leu Val Glu Ser Gly Gly Gly Leu Val Gln Pro Gly Gly
  1               5                  10                  15
Ser Leu Arg Leu Ser Cys Ala Ala Ser Gly Phe Thr Leu Ser Ser Tyr
             20                  25                  30
Asp Met His Trp Val Arg Gln Ala Thr Gly Lys Gly Leu Glu Trp Val
         35                  40                  45
Ser Ala Ile Gly Ser Thr Gly Asp Thr Tyr Tyr Thr Gly Ser Val Met
     50                  55                  60
Gly Arg Phe Thr Ile Ser Arg Asp Ala Ala Lys Asn Ser Phe Tyr Leu
 65                  70                  75                  80
Glu Met Asn Ser Leu Arg Val Gly Asp Thr Ala Val Tyr Tyr Cys Ala
                 85                  90                  95
Arg Glu Gly Ile Arg Thr Pro Tyr Asp Tyr Trp Gly Gln Gly Ala Arg
            100                 105                 110
Val Thr Val Ser Ser
        115
```

<210> SEQ ID NO 531
<211> LENGTH: 24
<212> TYPE: DNA
<213> ORGANISM: Artificial Sequence
<220> FEATURE:
<223> OTHER INFORMATION: Synthetic

<400> SEQUENCE: 531

```
ggattcaccc taagtagcta cgac                                          24
```

<210> SEQ ID NO 532
<211> LENGTH: 8
<212> TYPE: PRT
<213> ORGANISM: Artificial Sequence
<220> FEATURE:
<223> OTHER INFORMATION: Synthetic

<400> SEQUENCE: 532

```
Gly Phe Thr Leu Ser Ser Tyr Asp
  1               5
```

<210> SEQ ID NO 533
<211> LENGTH: 21
<212> TYPE: DNA
<213> ORGANISM: Artificial Sequence
<220> FEATURE:

<223> OTHER INFORMATION: Synthetic

<400> SEQUENCE: 533
attggcagta ctggtgacac a                                              21

<210> SEQ ID NO 534
<211> LENGTH: 7
<212> TYPE: PRT
<213> ORGANISM: Artificial Sequence
<220> FEATURE:
<223> OTHER INFORMATION: Synthetic

<400> SEQUENCE: 534

Ile Gly Ser Thr Gly Asp Thr
1               5

<210> SEQ ID NO 535
<211> LENGTH: 33
<212> TYPE: DNA
<213> ORGANISM: Artificial Sequence
<220> FEATURE:
<223> OTHER INFORMATION: Synthetic

<400> SEQUENCE: 535
gcaagagagg gaataagaac accctatgat tat                                 33

<210> SEQ ID NO 536
<211> LENGTH: 11
<212> TYPE: PRT
<213> ORGANISM: Artificial Sequence
<220> FEATURE:
<223> OTHER INFORMATION: Synthetic

<400> SEQUENCE: 536

Ala Arg Glu Gly Ile Arg Thr Pro Tyr Asp Tyr
1               5                   10

<210> SEQ ID NO 537
<211> LENGTH: 324
<212> TYPE: DNA
<213> ORGANISM: Artificial Sequence
<220> FEATURE:
<223> OTHER INFORMATION: Synthetic

<400> SEQUENCE: 537
gaaatagtga tgacgcagtc tccagccacc ctgtctgtgt ctccagggga aagagccacc     60
ctctcctgca gggccagtca gagtgttagc agcaatgtag cctggtacca gcagaaacct    120
ggccaggctc ccaggctcct catctatggt gcatccacca gggccactgg tatcccagcc    180
aggttcagtg gcagtgggtc tgggacagaa ttcactctca ccatcagcag cctgcagtct    240
gaagattttg cagtttatta ctgtcagcag tataataatt ggcctccatt cactttcggc    300
cctgggacca agtggatat caaa                                            324

<210> SEQ ID NO 538
<211> LENGTH: 108
<212> TYPE: PRT
<213> ORGANISM: Artificial Sequence
<220> FEATURE:
<223> OTHER INFORMATION: Synthetic

<400> SEQUENCE: 538

Glu Ile Val Met Thr Gln Ser Pro Ala Thr Leu Ser Val Ser Pro Gly
1               5                   10                  15

```
Glu Arg Ala Thr Leu Ser Cys Arg Ala Ser Gln Ser Val Ser Ser Asn
             20                  25                  30

Val Ala Trp Tyr Gln Gln Lys Pro Gly Gln Ala Pro Arg Leu Leu Ile
         35                  40                  45

Tyr Gly Ala Ser Thr Arg Ala Thr Gly Ile Pro Ala Arg Phe Ser Gly
     50                  55                  60

Ser Gly Ser Gly Thr Glu Phe Thr Leu Thr Ile Ser Ser Leu Gln Ser
 65                  70                  75                  80

Glu Asp Phe Ala Val Tyr Tyr Cys Gln Gln Tyr Asn Asn Trp Pro Pro
                 85                  90                  95

Phe Thr Phe Gly Pro Gly Thr Lys Val Asp Ile Lys
            100                 105
```

<210> SEQ ID NO 539
<211> LENGTH: 18
<212> TYPE: DNA
<213> ORGANISM: Artificial Sequence
<220> FEATURE:
<223> OTHER INFORMATION: Synthetic

<400> SEQUENCE: 539
cagagtgtta gcagcaat                                                18

<210> SEQ ID NO 540
<211> LENGTH: 6
<212> TYPE: PRT
<213> ORGANISM: Artificial Sequence
<220> FEATURE:
<223> OTHER INFORMATION: Synthetic

<400> SEQUENCE: 540

```
Gln Ser Val Ser Ser Asn
 1               5
```

<210> SEQ ID NO 541
<211> LENGTH: 9
<212> TYPE: DNA
<213> ORGANISM: Artificial Sequence
<220> FEATURE:
<223> OTHER INFORMATION: Synthetic

<400> SEQUENCE: 541 ggtgcatcc                                                           9

<210> SEQ ID NO 542
<211> LENGTH: 3
<212> TYPE: PRT
<213> ORGANISM: Artificial Sequence
<220> FEATURE:
<223> OTHER INFORMATION: Synthetic

<400> SEQUENCE: 542

```
Gly Ala Ser
 1
```

<210> SEQ ID NO 543
<211> LENGTH: 30
<212> TYPE: DNA
<213> ORGANISM: Artificial Sequence
<220> FEATURE:
<223> OTHER INFORMATION: Synthetic

<400> SEQUENCE: 543
cagcagtata ataattggcc tccattcact                                    30

<210> SEQ ID NO 544
<211> LENGTH: 10
<212> TYPE: PRT
<213> ORGANISM: Artificial Sequence
<220> FEATURE:
<223> OTHER INFORMATION: Synthetic

<400> SEQUENCE: 544

Gln Gln Tyr Asn Asn Trp Pro Pro Phe Thr
1               5                   10

<210> SEQ ID NO 545
<211> LENGTH: 351
<212> TYPE: DNA
<213> ORGANISM: Artificial Sequence
<220> FEATURE:
<223> OTHER INFORMATION: Synthetic

<400> SEQUENCE: 545
gaggtgcagc tggtggagtc tgggggaggc ttggtacagc ctggggggtc cctgagactc      60
tcctgtgcag cctctggatt caccctaagt agctacgaca tgcactgggt ccgccaagca     120
acaggaaaag gtctggagtg ggtctcagct attggcagta ctggtgacac atactataca     180
ggctccgtga tgggccgatt caccatctcc agagacgctg ccaaaaactc cttctatctt     240
gaaatgaaca gcctgagagt cggggacacg gctgtatatt actgtgcaag agagggaata     300
agaacaccct atgattattg gggccaggga accctggtca ccgtctcctc a              351

<210> SEQ ID NO 546
<211> LENGTH: 117
<212> TYPE: PRT
<213> ORGANISM: Artificial Sequence
<220> FEATURE:
<223> OTHER INFORMATION: Synthetic

<400> SEQUENCE: 546

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Leu Ser Ser Tyr
            20                  25                  30

Asp Met His Trp Val Arg Gln Ala Thr Gly Lys Gly Leu Glu Trp Val
        35                  40                  45

Ser Ala Ile Gly Ser Thr Gly Asp Thr Tyr Tyr Thr Gly Ser Val Met
    50                  55                  60

Gly Arg Phe Thr Ile Ser Arg Asp Ala Ala Lys Asn Ser Phe Tyr Leu
65                  70                  75                  80

Glu Met Asn Ser Leu Arg Val Gly Asp Thr Ala Val Tyr Tyr Cys Ala
                85                  90                  95

Arg Glu Gly Ile Arg Thr Pro Tyr Asp Tyr Trp Gly Gln Gly Thr Leu
            100                 105                 110

Val Thr Val Ser Ser
        115

<210> SEQ ID NO 547
<211> LENGTH: 324
<212> TYPE: DNA
<213> ORGANISM: Artificial Sequence
<220> FEATURE:
<223> OTHER INFORMATION: Synthetic

<400> SEQUENCE: 547

```
gaaatagtga tgacgcagtc tccagccacc ctgtctgtgt ctccagggga aagagccacc    60
ctctcctgca gggccagtca gagtgttagc agcaatgtag cctggtacca gcagaaacct   120
ggccaggctc ccaggctcct catctatggt gcatccacca gggccactgg tatcccagcc   180
aggttcagtg gcagtgggtc tgggacagaa ttcactctca ccatcagcag cctgcagtct   240
gaagattttg cagtttatta ctgtcagcag tataataatt ggcctccatt cactttcggc   300
cctgggacca aagtggatat caaa                                          324
```

<210> SEQ ID NO 548
<211> LENGTH: 108
<212> TYPE: PRT
<213> ORGANISM: Artificial Sequence
<220> FEATURE:
<223> OTHER INFORMATION: Synthetic

<400> SEQUENCE: 548

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Val Ser Ser Asn
            20                  25                  30

Val Ala Trp Tyr Gln Gln Lys Pro Gly Gln Ala Pro Arg Leu Leu Ile
        35                  40                  45

Tyr Gly Ala Ser Thr Arg Ala Thr Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Asn Asn Trp Pro Pro
                85                  90                  95

Phe Thr Phe Gly Pro Gly Thr Lys Val Asp Ile Lys
            100                 105

<210> SEQ ID NO 549
<211> LENGTH: 351
<212> TYPE: DNA
<213> ORGANISM: Artificial Sequence
<220> FEATURE:
<223> OTHER INFORMATION: Synthetic

<400> SEQUENCE: 549

```
gaggtgcagc tggtggagtc tgggggaggc ttggtacagc ctggggggtc cctgagactc    60
tcctgtgcag cctctggatt caccctaagt agctacgaca tgcactgggt ccgccaagct   120
acaggaaaag gtctggagtg ggtctcagct attggcagta ctggtgacac atactatcca   180
ggctccgtga agggccgatt caccatctcc agagaaaatg ccaagaactc cttgtatctt   240
caaatgaaca gcctgagagc cggggacacg gctgtgtatt actgtgcaag agagggaata   300
agaacaccct atgattattg gggccaagga accctggtca ccgtctcctc a            351
```

<210> SEQ ID NO 550
<211> LENGTH: 117
<212> TYPE: PRT
<213> ORGANISM: Artificial Sequence
<220> FEATURE:
<223> OTHER INFORMATION: Synthetic

<400> SEQUENCE: 550

Glu Val Gln Leu Val Glu Ser Gly Gly Gly Leu Val Gln Pro Gly Gly
1               5                   10                  15

```
Ser Leu Arg Leu Ser Cys Ala Ala Ser Gly Phe Thr Leu Ser Ser Tyr
            20                  25                  30

Asp Met His Trp Val Arg Gln Ala Thr Gly Lys Gly Leu Glu Trp Val
        35                  40                  45

Ser Ala Ile Gly Ser Thr Gly Asp Thr Tyr Tyr Pro Gly Ser Val Lys
    50                  55                  60

Gly Arg Phe Thr Ile Ser Arg Glu Asn Ala Lys Asn Ser Leu Tyr Leu
65                  70                  75                  80

Gln Met Asn Ser Leu Arg Ala Gly Asp Thr Ala Val Tyr Tyr Cys Ala
                85                  90                  95

Arg Glu Gly Ile Arg Thr Pro Tyr Asp Tyr Trp Gly Gln Gly Thr Leu
            100                 105                 110

Val Thr Val Ser Ser
        115

<210> SEQ ID NO 551
<211> LENGTH: 324
<212> TYPE: DNA
<213> ORGANISM: Artificial Sequence
<220> FEATURE:
<223> OTHER INFORMATION: Synthetic

<400> SEQUENCE: 551
gaaatagtga tgacgcagtc tccagccacc ctgtctgtgt ctccagggga aagagccacc      60
ctctcctgca gggccagtca gagtgttagc agcaatttag cctggtacca gcagaaacct     120
ggccaggctc ccaggctcct catctatggt gcatccacca gggccactgg tatcccagcc     180
aggttcagtg gcagtgggtc tgggacagag ttcactctca ccatcagcag cctgcagtct     240
gaagattttg cagtttatta ctgtcagcag tataataatt ggcctccatt cactttcggc     300
cctgggacca aagtggatat caaa                                             324

<210> SEQ ID NO 552
<211> LENGTH: 108
<212> TYPE: PRT
<213> ORGANISM: Artificial Sequence
<220> FEATURE:
<223> OTHER INFORMATION: Synthetic

<400> SEQUENCE: 552

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Val Ser Ser Asn
            20                  25                  30

Leu Ala Trp Tyr Gln Gln Lys Pro Gly Gln Ala Pro Arg Leu Leu Ile
        35                  40                  45

Tyr Gly Ala Ser Thr Arg Ala Thr Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Asn Asn Trp Pro Pro
                85                  90                  95

Phe Thr Phe Gly Pro Gly Thr Lys Val Asp Ile Lys
            100                 105

<210> SEQ ID NO 553
<211> LENGTH: 351
<212> TYPE: DNA
<213> ORGANISM: Artificial Sequence
```

<220> FEATURE:
<223> OTHER INFORMATION: Synthetic

<400> SEQUENCE: 553

```
gaggtgcagc tggtggagtc tgggggaggc ttggtacagc ctggggggtc cctgagactc    60
tcctgtgcag cctctggatt caccctaagt agctacgaca tgcactgggt ccgccaagca   120
acaggaaaag gtctggagtg ggtctcagct attggcagta ctggtgacac atactataca   180
ggctccgtga tgggccgatt caccatctcc agagacgctg ccaaaaactc cttctatctt   240
gaaatgaaca gcctgagagt cggggacacg gctgtatatt actgtgcaag agagggaata   300
agaacaccct atgattattg gggccaggga gcccgggtca ccgtctcctc a            351
```

<210> SEQ ID NO 554
<211> LENGTH: 117
<212> TYPE: PRT
<213> ORGANISM: Artificial Sequence
<220> FEATURE:
<223> OTHER INFORMATION: Synthetic

<400> SEQUENCE: 554

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Leu Ser Ser Tyr
            20                  25                  30

Asp Met His Trp Val Arg Gln Ala Thr Gly Lys Gly Leu Glu Trp Val
        35                  40                  45

Ser Ala Ile Gly Ser Thr Gly Asp Thr Tyr Tyr Thr Gly Ser Val Met
    50                  55                  60

Gly Arg Phe Thr Ile Ser Arg Asp Ala Ala Lys Asn Ser Phe Tyr Leu
65                  70                  75                  80

Glu Met Asn Ser Leu Arg Val Gly Asp Thr Ala Val Tyr Tyr Cys Ala
                85                  90                  95

Arg Glu Gly Ile Arg Thr Pro Tyr Asp Tyr Trp Gly Gln Gly Ala Arg
            100                 105                 110

Val Thr Val Ser Ser
        115

<210> SEQ ID NO 555
<211> LENGTH: 24
<212> TYPE: DNA
<213> ORGANISM: Artificial Sequence
<220> FEATURE:
<223> OTHER INFORMATION: Synthetic

<400> SEQUENCE: 555

```
ggattcaccc taagtagcta cgac                                            24
```

<210> SEQ ID NO 556
<211> LENGTH: 8
<212> TYPE: PRT
<213> ORGANISM: Artificial Sequence
<220> FEATURE:
<223> OTHER INFORMATION: Synthetic

<400> SEQUENCE: 556

Gly Phe Thr Leu Ser Ser Tyr Asp
1               5

<210> SEQ ID NO 557
<211> LENGTH: 21

```
<212> TYPE: DNA
<213> ORGANISM: Artificial Sequence
<220> FEATURE:
<223> OTHER INFORMATION: Synthetic

<400> SEQUENCE: 557
attggcagta ctggtgacac a                                          21

<210> SEQ ID NO 558
<211> LENGTH: 7
<212> TYPE: PRT
<213> ORGANISM: Artificial Sequence
<220> FEATURE:
<223> OTHER INFORMATION: Synthetic

<400> SEQUENCE: 558

Ile Gly Ser Thr Gly Asp Thr
 1               5

<210> SEQ ID NO 559
<211> LENGTH: 33
<212> TYPE: DNA
<213> ORGANISM: Artificial Sequence
<220> FEATURE:
<223> OTHER INFORMATION: Synthetic

<400> SEQUENCE: 559
gcaagagagg gaataagaac accctatgat tat                             33

<210> SEQ ID NO 560
<211> LENGTH: 11
<212> TYPE: PRT
<213> ORGANISM: Artificial Sequence
<220> FEATURE:
<223> OTHER INFORMATION: Synthetic

<400> SEQUENCE: 560

Ala Arg Glu Gly Ile Arg Thr Pro Tyr Asp Tyr
 1               5                  10

<210> SEQ ID NO 561
<211> LENGTH: 324
<212> TYPE: DNA
<213> ORGANISM: Artificial Sequence
<220> FEATURE:
<223> OTHER INFORMATION: Synthetic

<400> SEQUENCE: 561
gaaatagtga tgacgcagtc tccagccacc ctgtctgtgt ctccagggga aagagccacc    60
ctctcctgca gggccagtca gagtgttagc agcaatgtag cctggtacca gcagaaacct   120
ggccaggctc ccaggctcct catctatggt gcatccacca gggccactgg tatcccagcc   180
aggttcagtg gcagtgggtc tgggacagaa ttcactctca ccatcagcag cctgcagtct   240
gaagattttg cagtttatta ctgtcagcag tataataatt ggcctccatt cactttcggc   300
cctgggacca aagtggatat caaa                                         324

<210> SEQ ID NO 562
<211> LENGTH: 108
<212> TYPE: PRT
<213> ORGANISM: Artificial Sequence
<220> FEATURE:
<223> OTHER INFORMATION: Synthetic

<400> SEQUENCE: 562
```

```
Glu Ile Val Met Thr Gln Ser Pro Ala Thr Leu Ser Val Ser Pro Gly
 1               5                  10                  15

Glu Arg Ala Thr Leu Ser Cys Arg Ala Ser Gln Ser Val Ser Ser Asn
                20                  25                  30

Val Ala Trp Tyr Gln Gln Lys Pro Gly Gln Ala Pro Arg Leu Leu Ile
            35                  40                  45

Tyr Gly Ala Ser Thr Arg Ala Thr Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Asn Asn Trp Pro Pro
                85                  90                  95

Phe Thr Phe Gly Pro Gly Thr Lys Val Asp Ile Lys
                100                 105
```

<210> SEQ ID NO 563
<211> LENGTH: 18
<212> TYPE: DNA
<213> ORGANISM: Artificial Sequence
<220> FEATURE:
<223> OTHER INFORMATION: Synthetic

<400> SEQUENCE: 563
cagagtgtta gcagcaat                                                18

<210> SEQ ID NO 564
<211> LENGTH: 6
<212> TYPE: PRT
<213> ORGANISM: Artificial Sequence
<220> FEATURE:
<223> OTHER INFORMATION: Synthetic

<400> SEQUENCE: 564

```
Gln Ser Val Ser Ser Asn
 1               5
```

<210> SEQ ID NO 565
<211> LENGTH: 9
<212> TYPE: DNA
<213> ORGANISM: Artificial Sequence
<220> FEATURE:
<223> OTHER INFORMATION: Synthetic

<400> SEQUENCE: 565 ggtgcatcc                                                           9

<210> SEQ ID NO 566
<211> LENGTH: 3
<212> TYPE: PRT
<213> ORGANISM: Artificial Sequence
<220> FEATURE:
<223> OTHER INFORMATION: Synthetic

<400> SEQUENCE: 566

```
Gly Ala Ser
 1
```

<210> SEQ ID NO 567
<211> LENGTH: 30
<212> TYPE: DNA
<213> ORGANISM: Artificial Sequence
<220> FEATURE:
<223> OTHER INFORMATION: Synthetic

<400> SEQUENCE: 567
cagcagtata ataattggcc tccattcact                                          30

<210> SEQ ID NO 568
<211> LENGTH: 10
<212> TYPE: PRT
<213> ORGANISM: Artificial Sequence
<220> FEATURE:
<223> OTHER INFORMATION: Synthetic

<400> SEQUENCE: 568

Gln Gln Tyr Asn Asn Trp Pro Pro Phe Thr
1               5                   10

<210> SEQ ID NO 569
<211> LENGTH: 351
<212> TYPE: DNA
<213> ORGANISM: Artificial Sequence
<220> FEATURE:
<223> OTHER INFORMATION: Synthetic

<400> SEQUENCE: 569
gaggtgcagc tggtggagtc tgggggaggc ttggtacagc ctggggggtc cctgagactc         60
tcctgtgcag cctctggatt caccctaagt agctacgaca tgcactgggt ccgccaagca        120
acaggaaaag gtctggagtg ggtctcagct attggcagta ctggtgacac atactataca        180
ggctccgtga tgggccgatt caccatctcc agagacgctg ccaaaaactc cttctatctt        240
gaaatgaaca gcctgagagt cggggacacg gctgtatatt actgtgcaag agagggaata        300
agaacaccct atgattattg gggccaggga accctggtca ccgtctcctc a                 351

<210> SEQ ID NO 570
<211> LENGTH: 117
<212> TYPE: PRT
<213> ORGANISM: Artificial Sequence
<220> FEATURE:
<223> OTHER INFORMATION: Synthetic

<400> SEQUENCE: 570

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Leu Ser Ser Tyr
            20                  25                  30

Asp Met His Trp Val Arg Gln Ala Thr Gly Lys Gly Leu Glu Trp Val
        35                  40                  45

Ser Ala Ile Gly Ser Thr Gly Asp Thr Tyr Tyr Thr Gly Ser Val Met
    50                  55                  60

Gly Arg Phe Thr Ile Ser Arg Asp Ala Ala Lys Asn Ser Phe Tyr Leu
65                  70                  75                  80

Glu Met Asn Ser Leu Arg Val Gly Asp Thr Ala Val Tyr Tyr Cys Ala
                85                  90                  95

Arg Glu Gly Ile Arg Thr Pro Tyr Asp Tyr Trp Gly Gln Gly Thr Leu
            100                 105                 110

Val Thr Val Ser Ser
        115

<210> SEQ ID NO 571
<211> LENGTH: 324
<212> TYPE: DNA
<213> ORGANISM: Artificial Sequence
<220> FEATURE:

<223> OTHER INFORMATION: Synthetic

<400> SEQUENCE: 571

```
gaaatagtga tgacgcagtc tccagccacc ctgtctgtgt ctccagggga aagagccacc      60
ctctcctgca gggccagtca gagtgttagc agcaatgtag cctggtacca gcagaaacct     120
ggccaggctc ccaggctcct catctatggt gcatccacca gggccactgg tatcccagcc     180
aggttcagtg gcagtgggtc tgggacagaa ttcactctca ccatcagcag cctgcagtct     240
gaagattttg cagtttatta ctgtcagcag tataataatt ggcctccatt cactttcggc     300
cctgggacca aagtggatat caaa                                            324
```

<210> SEQ ID NO 572
<211> LENGTH: 108
<212> TYPE: PRT
<213> ORGANISM: Artificial Sequence
<220> FEATURE:
<223> OTHER INFORMATION: Synthetic

<400> SEQUENCE: 572

```
Glu Ile Val Met Thr Gln Ser Pro Ala Thr Leu Ser Val Ser Pro Gly
 1               5                  10                  15

Glu Arg Ala Thr Leu Ser Cys Arg Ala Ser Gln Ser Val Ser Ser Asn
            20                  25                  30

Val Ala Trp Tyr Gln Gln Lys Pro Gly Gln Ala Pro Arg Leu Leu Ile
        35                  40                  45

Tyr Gly Ala Ser Thr Arg Ala Thr Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Asn Asn Trp Pro Pro
                85                  90                  95

Phe Thr Phe Gly Pro Gly Thr Lys Val Asp Ile Lys
            100                 105
```

<210> SEQ ID NO 573
<211> LENGTH: 351
<212> TYPE: DNA
<213> ORGANISM: Artificial Sequence
<220> FEATURE:
<223> OTHER INFORMATION: Synthetic

<400> SEQUENCE: 573

```
gaggtgcagc tggtggagtc tgggggaggc ttggtacagc ctggggggtc cctgagactc      60
tcctgtgcag cctctggatt caccctaagt agctacgaca tgcactgggt ccgccaagct     120
acaggaaaag gtctggagtg gtctcagct attggcagta ctggtgacac atactatcca     180
ggctccgtga agggccgatt caccatctcc agagaaaatg ccaagaactc cttgtatctt     240
caaatgaaca gcctgagagc cggggacacg gctgtgtatt actgtgcaag agagggaata     300
agaacaccct atgattattg gggccaagga acccctggtca ccgtctcctc a             351
```

<210> SEQ ID NO 574
<211> LENGTH: 117
<212> TYPE: PRT
<213> ORGANISM: Artificial Sequence
<220> FEATURE:
<223> OTHER INFORMATION: Synthetic

<400> SEQUENCE: 574

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Leu Ser Ser Tyr
            20                  25                  30

Asp Met His Trp Val Arg Gln Ala Thr Gly Lys Gly Leu Glu Trp Val
        35                  40                  45

Ser Ala Ile Gly Ser Thr Gly Asp Thr Tyr Tyr Pro Gly Ser Val Lys
50                  55                  60

Gly Arg Phe Thr Ile Ser Arg Glu Asn Ala Lys Asn Ser Leu Tyr Leu
65                  70                  75                  80

Gln Met Asn Ser Leu Arg Ala Gly Asp Thr Ala Val Tyr Tyr Cys Ala
                85                  90                  95

Arg Glu Gly Ile Arg Thr Pro Tyr Asp Tyr Trp Gly Gln Gly Thr Leu
            100                 105                 110

Val Thr Val Ser Ser
            115

<210> SEQ ID NO 575
<211> LENGTH: 324
<212> TYPE: DNA
<213> ORGANISM: Artificial Sequence
<220> FEATURE:
<223> OTHER INFORMATION: Synthetic

<400> SEQUENCE: 575
gaaatagtga tgacgcagtc tccagccacc ctgtctgtgt ctccagggga aagagccacc      60
ctctcctgca gggccagtca gagtgttagc agcaatttag cctggtacca gcagaaacct     120
ggccaggctc ccaggctcct catctatggt gcatccacca gggccactgg tatcccagcc     180
aggttcagtg gcagtgggtc tgggacagag ttcactctca ccatcagcag cctgcagtct     240
gaagattttg cagtttatta ctgtcagcag tataataatt ggcctccatt cactttcggc     300
cctgggacca agtggatat caaa                                              324

<210> SEQ ID NO 576
<211> LENGTH: 108
<212> TYPE: PRT
<213> ORGANISM: Artificial Sequence
<220> FEATURE:
<223> OTHER INFORMATION: Synthetic

<400> SEQUENCE: 576

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Val Ser Ser Asn
            20                  25                  30

Leu Ala Trp Tyr Gln Gln Lys Pro Gly Gln Ala Pro Arg Leu Leu Ile
        35                  40                  45

Tyr Gly Ala Ser Thr Arg Ala Thr Gly Ile Pro Ala Arg Phe Ser Gly
50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Asn Asn Trp Pro Pro
                85                  90                  95

Phe Thr Phe Gly Pro Gly Thr Lys Val Asp Ile Lys
            100                 105

<210> SEQ ID NO 577

```
<211> LENGTH: 363
<212> TYPE: DNA
<213> ORGANISM: Artificial Sequence
<220> FEATURE:
<223> OTHER INFORMATION: Synthetic

<400> SEQUENCE: 577
gaagtgcagc tggtggagtc tgggggaggc ttggtacagc ctggcaggtc cctgagactc      60
tcctgtgcag cctctggatt cacctttgat gattatgcca tgcactgggt ccggcaagct     120
ccagggaagg gcctggagtg ggtctcaggt attaattgga acagtggtag cataggctat     180
gcggactctg tgaagggccg attcaccatc tccagagaca cgccaagca ctccctgtat      240
ctgcaaatga acagtctgag acctgaggac acggccttgt attactgtgt aaaagaggtg     300
actacgggat actactacgg tatggacgtc tggggccaag gaccacggt caccgtctcc      360
tca                                                                   363

<210> SEQ ID NO 578
<211> LENGTH: 121
<212> TYPE: PRT
<213> ORGANISM: Artificial Sequence
<220> FEATURE:
<223> OTHER INFORMATION: Synthetic

<400> SEQUENCE: 578

Glu Val Gln Leu Val Glu Ser Gly Gly Gly Leu Val Gln Pro Gly Arg
 1               5                  10                  15

Ser Leu Arg Leu Ser Cys Ala Ala Ser Gly Phe Thr Phe Asp Asp Tyr
             20                  25                  30

Ala Met His Trp Val Arg Gln Ala Pro Gly Lys Gly Leu Glu Trp Val
         35                  40                  45

Ser Gly Ile Asn Trp Asn Ser Gly Ser Ile Gly Tyr Ala Asp Ser Val
     50                  55                  60

Lys Gly Arg Phe Thr Ile Ser Arg Asp Asn Ala Lys His Ser Leu Tyr
 65                  70                  75                  80

Leu Gln Met Asn Ser Leu Arg Pro Glu Asp Thr Ala Leu Tyr Tyr Cys
                 85                  90                  95

Val Lys Glu Val Thr Thr Gly Tyr Tyr Tyr Gly Met Asp Val Trp Gly
            100                 105                 110

Gln Gly Thr Thr Val Thr Val Ser Ser
        115                 120

<210> SEQ ID NO 579
<211> LENGTH: 24
<212> TYPE: DNA
<213> ORGANISM: Artificial Sequence
<220> FEATURE:
<223> OTHER INFORMATION: Synthetic

<400> SEQUENCE: 579
ggattcacct ttgatgatta tgcc                                             24

<210> SEQ ID NO 580
<211> LENGTH: 8
<212> TYPE: PRT
<213> ORGANISM: Artificial Sequence
<220> FEATURE:
<223> OTHER INFORMATION: Synthetic

<400> SEQUENCE: 580

Gly Phe Thr Phe Asp Asp Tyr Ala
```

<210> SEQ ID NO 581
<211> LENGTH: 24
<212> TYPE: DNA
<213> ORGANISM: Artificial Sequence
<220> FEATURE:
<223> OTHER INFORMATION: Synthetic

<400> SEQUENCE: 581
attaattgga acagtggtag cata                                            24

<210> SEQ ID NO 582
<211> LENGTH: 8
<212> TYPE: PRT
<213> ORGANISM: Artificial Sequence
<220> FEATURE:
<223> OTHER INFORMATION: Synthetic

<400> SEQUENCE: 582

Ile Asn Trp Asn Ser Gly Ser Ile
 1               5

<210> SEQ ID NO 583
<211> LENGTH: 42
<212> TYPE: DNA
<213> ORGANISM: Artificial Sequence
<220> FEATURE:
<223> OTHER INFORMATION: Synthetic

<400> SEQUENCE: 583
gtaaaagagg tgactacggg atactactac ggtatggacg tc                        42

<210> SEQ ID NO 584
<211> LENGTH: 14
<212> TYPE: PRT
<213> ORGANISM: Artificial Sequence
<220> FEATURE:
<223> OTHER INFORMATION: Synthetic

<400> SEQUENCE: 584

Val Lys Glu Val Thr Thr Gly Tyr Tyr Tyr Gly Met Asp Val
 1               5                  10

<210> SEQ ID NO 585
<211> LENGTH: 321
<212> TYPE: DNA
<213> ORGANISM: Artificial Sequence
<220> FEATURE:
<223> OTHER INFORMATION: Synthetic

<400> SEQUENCE: 585
gacatccagt tgacccagtc tccatccttc ctgtctgcat ctgtaggaga cagagtcacc      60
atcacttgct gggccagtca gggcattagc agttatttag cctggtatca gaaaaaacca     120
gggaaagccc ctaacctcct gatctatgat gcatccactt tgcaaagtgg ggtcccatca     180
aggttcagcg gcagtggatc tgggacagaa ttcactctca cactcagcag cctgcagcct     240
gaagattttg caacttatta ctgtcaacag cttaatattt acccattcac tttcggccct     300
gggaccaaag tggatatcaa a                                              321

<210> SEQ ID NO 586
<211> LENGTH: 107
<212> TYPE: PRT
<213> ORGANISM: Artificial Sequence
<220> FEATURE:
<223> OTHER INFORMATION: Synthetic

<400> SEQUENCE: 586

Asp Ile Gln Leu Thr Gln Ser Pro Ser Phe Leu Ser Ala Ser Val Gly
1               5                   10                  15

Asp Arg Val Thr Ile Thr Cys Trp Ala Ser Gln Gly Ile Ser Ser Tyr
            20                  25                  30

Leu Ala Trp Tyr Gln Lys Lys Pro Gly Lys Ala Pro Asn Leu Leu Ile
        35                  40                  45

Tyr Asp Ala Ser Thr Leu Gln Ser Gly Val Pro Ser Arg Phe Ser Gly
50                  55                  60

Ser Gly Ser Gly Thr Glu Phe Thr Leu Thr Leu Ser Ser Leu Gln Pro
65                  70                  75                  80

Glu Asp Phe Ala Thr Tyr Tyr Cys Gln Gln Leu Asn Ile Tyr Pro Phe
                85                  90                  95

Thr Phe Gly Pro Gly Thr Lys Val Asp Ile Lys
            100                 105

<210> SEQ ID NO 587
<211> LENGTH: 18
<212> TYPE: DNA
<213> ORGANISM: Artificial Sequence
<220> FEATURE:
<223> OTHER INFORMATION: Synthetic

<400> SEQUENCE: 587
cagggcatta gcagttat                                              18

<210> SEQ ID NO 588
<211> LENGTH: 6
<212> TYPE: PRT
<213> ORGANISM: Artificial Sequence
<220> FEATURE:
<223> OTHER INFORMATION: Synthetic

<400> SEQUENCE: 588

Gln Gly Ile Ser Ser Tyr
1               5

<210> SEQ ID NO 589
<211> LENGTH: 9
<212> TYPE: DNA
<213> ORGANISM: Artificial Sequence
<220> FEATURE:
<223> OTHER INFORMATION: Synthetic

<400> SEQUENCE: 589 gatgcatcc                                                         9

<210> SEQ ID NO 590
<211> LENGTH: 3
<212> TYPE: PRT
<213> ORGANISM: Artificial Sequence
<220> FEATURE:
<223> OTHER INFORMATION: Synthetic

<400> SEQUENCE: 590

Asp Ala Ser
1

<210> SEQ ID NO 591
<211> LENGTH: 27

```
<212> TYPE: DNA
<213> ORGANISM: Artificial Sequence
<220> FEATURE:
<223> OTHER INFORMATION: Synthetic

<400> SEQUENCE: 591
caacagctta atatttaccc attcact                                            27

<210> SEQ ID NO 592
<211> LENGTH: 9
<212> TYPE: PRT
<213> ORGANISM: Artificial Sequence
<220> FEATURE:
<223> OTHER INFORMATION: Synthetic

<400> SEQUENCE: 592

Gln Gln Leu Asn Ile Tyr Pro Phe Thr
 1               5

<210> SEQ ID NO 593
<211> LENGTH: 363
<212> TYPE: DNA
<213> ORGANISM: Artificial Sequence
<220> FEATURE:
<223> OTHER INFORMATION: Synthetic

<400> SEQUENCE: 593
gaagtgcagc tggtggagtc tgggggaggc ttggtacagc ctggcaggtc cctgagactc         60
tcctgtgcag cctctggatt cacctttgat gattatgcca tgcactgggt ccggcaagct        120
ccagggaagg gcctggagtg ggtctcaggt attaattgga acagtggtag cataggctat        180
gcggactctg tgaagggccg attcaccatc tccagagaca acgccaagca ctccctgtat        240
ctgcaaatga acagtctgag acctgaggac acggccttgt attactgtgt aaaagaggtg        300
actacgggat actactacgg tatggacgtc tggggccaag ggaccacggt caccgtctcc        360
tca                                                                     363

<210> SEQ ID NO 594
<211> LENGTH: 121
<212> TYPE: PRT
<213> ORGANISM: Artificial Sequence
<220> FEATURE:
<223> OTHER INFORMATION: Synthetic

<400> SEQUENCE: 594

Glu Val Gln Leu Val Glu Ser Gly Gly Gly Leu Val Gln Pro Gly Arg
 1               5                  10                  15

Ser Leu Arg Leu Ser Cys Ala Ala Ser Gly Phe Thr Phe Asp Asp Tyr
             20                  25                  30

Ala Met His Trp Val Arg Gln Ala Pro Gly Lys Gly Leu Glu Trp Val
         35                  40                  45

Ser Gly Ile Asn Trp Asn Ser Gly Ser Ile Gly Tyr Ala Asp Ser Val
     50                  55                  60

Lys Gly Arg Phe Thr Ile Ser Arg Asp Asn Ala Lys His Ser Leu Tyr
 65                  70                  75                  80

Leu Gln Met Asn Ser Leu Arg Pro Glu Asp Thr Ala Leu Tyr Tyr Cys
                 85                  90                  95

Val Lys Glu Val Thr Thr Gly Tyr Tyr Tyr Gly Met Asp Val Trp Gly
            100                 105                 110

Gln Gly Thr Thr Val Thr Val Ser Ser
        115                 120
```

<210> SEQ ID NO 595
<211> LENGTH: 321
<212> TYPE: DNA
<213> ORGANISM: Artificial Sequence
<220> FEATURE:
<223> OTHER INFORMATION: Synthetic

<400> SEQUENCE: 595

```
gacatccagt tgacccagtc tccatccttc ctgtctgcat ctgtaggaga cagagtcacc      60
atcacttgct gggccagtca gggcattagc agttatttag cctggtatca gaaaaaacca     120
gggaaagccc ctaacctcct gatctatgat gcatccactt tgcaaagtgg ggtcccatca     180
aggttcagcg gcagtggatc tgggacagaa ttcactctca cactcagcag cctgcagcct     240
gaagattttg caacttatta ctgtcaacag cttaatattt acccattcac tttcggccct     300
gggaccaaag tggatatcaa a                                               321
```

<210> SEQ ID NO 596
<211> LENGTH: 107
<212> TYPE: PRT
<213> ORGANISM: Artificial Sequence
<220> FEATURE:
<223> OTHER INFORMATION: Synthetic

<400> SEQUENCE: 596

Asp Ile Gln Leu Thr Gln Ser Pro Ser Phe Leu Ser Ala Ser Val Gly
 1               5                  10                  15

Asp Arg Val Thr Ile Thr Cys Trp Ala Ser Gln Gly Ile Ser Ser Tyr
            20                  25                  30

Leu Ala Trp Tyr Gln Lys Lys Pro Gly Lys Ala Pro Asn Leu Leu Ile
        35                  40                  45

Tyr Asp Ala Ser Thr Leu Gln Ser Gly Val Pro Ser Arg Phe Ser Gly
    50                  55                  60

Ser Gly Ser Gly Thr Glu Phe Thr Leu Thr Leu Ser Ser Leu Gln Pro
65                  70                  75                  80

Glu Asp Phe Ala Thr Tyr Tyr Cys Gln Gln Leu Asn Ile Tyr Pro Phe
                85                  90                  95

Thr Phe Gly Pro Gly Thr Lys Val Asp Ile Lys
            100                 105

<210> SEQ ID NO 597
<211> LENGTH: 363
<212> TYPE: DNA
<213> ORGANISM: Artificial Sequence
<220> FEATURE:
<223> OTHER INFORMATION: Synthetic

<400> SEQUENCE: 597

```
gaagtgcagc tggtggagtc tgggggaggc ttggtacagc ctggcaggtc cctgagactc      60
tcctgtgcag cctctggatt cacctttgat gattatgcca tgcactgggt ccggcaagct     120
ccagggaagg gcctggagtg ggtctcaggt attaattgga acagtggtag cataggctat     180
gcggactctg tgaagggccg attcaccatc tccagagaca acgccaagaa ctccctgtat     240
ctgcaaatga acagtctgag agctgaggac acggccttgt attactgtgt aaaagaggtg     300
actacgggat actactacgg tatggacgtc tggggcaag ggaccacggt caccgtctcc     360
tca                                                                  363
```

<210> SEQ ID NO 598
<211> LENGTH: 121
<212> TYPE: PRT
<213> ORGANISM: Artificial Sequence
<220> FEATURE:
<223> OTHER INFORMATION: Synthetic

<400> SEQUENCE: 598

```
Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ser Gly Ile Asn Trp Asn Ser Gly Ser Ile Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Val Lys Glu Val Thr Thr Gly Tyr Tyr Tyr Gly Met Asp Val Trp Gly
            100                 105                 110

Gln Gly Thr Thr Val Thr Val Ser Ser
        115                 120
```

<210> SEQ ID NO 599
<211> LENGTH: 321
<212> TYPE: DNA
<213> ORGANISM: Artificial Sequence
<220> FEATURE:
<223> OTHER INFORMATION: Synthetic

<400> SEQUENCE: 599

```
gacatccagt tgacccagtc tccatccttc ctgtctgcat ctgtaggaga cagagtcacc    60
atcacttgcc gggccagtca gggcattagc agttatttag cctggtatca gcaaaaacca   120
gggaaagccc ctaagctcct gatctatgat gcatccactt tgcaaagtgg ggtcccatca   180
aggttcagcg gcagtggatc tgggacagaa ttcactctca caatcagcag cctgcagcct   240
gaagattttg caacttatta ctgtcaacag cttaatattt acccattcac tttcggccct   300
gggaccaaag tggatatcaa a                                             321
```

<210> SEQ ID NO 600
<211> LENGTH: 107
<212> TYPE: PRT
<213> ORGANISM: Artificial Sequence
<220> FEATURE:
<223> OTHER INFORMATION: Synthetic

<400> SEQUENCE: 600

```
Asp Ile Gln Leu Thr Gln Ser Pro Ser Phe Leu Ser Ala Ser Val Gly
1               5                   10                  15

Asp Arg Val Thr Ile Thr Cys Arg Ala Ser Gln Gly Ile Ser Ser Tyr
            20                  25                  30

Leu Ala Trp Tyr Gln Gln Lys Pro Gly Lys Ala Pro Lys Leu Leu Ile
        35                  40                  45

Tyr Asp Ala Ser Thr Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80
```

```
Glu Asp Phe Ala Thr Tyr Tyr Cys Gln Gln Leu Asn Ile Tyr Pro Phe
                85                  90                  95

Thr Phe Gly Pro Gly Thr Lys Val Asp Ile Lys
            100                 105

<210> SEQ ID NO 601
<211> LENGTH: 366
<212> TYPE: DNA
<213> ORGANISM: Artificial Sequence
<220> FEATURE:
<223> OTHER INFORMATION: Synthetic

<400> SEQUENCE: 601
gaggtgcagt tgttggagtc tgggggaggc ttggtacagc ctgggggggtc cctgagactc      60 tcctgtgcag cctctggatt cacgtttagt agctatgcca tgaactgggt ccgccaggct     120
ccagggaagg ggctggattg ggtctcaggt atcagtggta atggtggtag cacctactac     180
gcagactccg tgaagggccg gttcaccatc tccagagaca tttccaagaa cacgctgtat     240
gtgcaaatgc acagcctgag agtcgaggac acggccgttt actactgtgc gaaagcccgt     300
tattacgatt tttggggggg gaatttcgat ctctggggcc gtggcaccca ggtcactgtc     360
tcctca                                                                366

<210> SEQ ID NO 602
<211> LENGTH: 122
<212> TYPE: PRT
<213> ORGANISM: Artificial Sequence
<220> FEATURE:
<223> OTHER INFORMATION: Synthetic

<400> SEQUENCE: 602

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser Ser Tyr
            20                  25                  30

Ala Met Asn Trp Val Arg Gln Ala Pro Gly Lys Gly Leu Asp Trp Val
        35                  40                  45

Ser Gly Ile Ser Gly Asn Gly Gly Ser Thr Tyr Tyr Ala Asp Ser Val
    50                  55                  60

Lys Gly Arg Phe Thr Ile Ser Arg Asp Ile Ser Lys Asn Thr Leu Tyr
65                  70                  75                  80

Val Gln Met His Ser Leu Arg Val Glu Asp Thr Ala Val Tyr Tyr Cys
                85                  90                  95

Ala Lys Ala Arg Tyr Tyr Asp Phe Trp Gly Gly Asn Phe Asp Leu Trp
            100                 105                 110

Gly Arg Gly Thr Gln Val Thr Val Ser Ser
        115                 120

<210> SEQ ID NO 603
<211> LENGTH: 24
<212> TYPE: DNA
<213> ORGANISM: Artificial Sequence
<220> FEATURE:
<223> OTHER INFORMATION: Synthetic

<400> SEQUENCE: 603
ggattcacgt ttagtagcta tgcc                                              24

<210> SEQ ID NO 604
```

```
<211> LENGTH: 8
<212> TYPE: PRT
<213> ORGANISM: Artificial Sequence
<220> FEATURE:
<223> OTHER INFORMATION: Synthetic

<400> SEQUENCE: 604

Gly Phe Thr Phe Ser Ser Tyr Ala
1               5

<210> SEQ ID NO 605
<211> LENGTH: 24
<212> TYPE: DNA
<213> ORGANISM: Artificial Sequence
<220> FEATURE:
<223> OTHER INFORMATION: Synthetic

<400> SEQUENCE: 605
atcagtggta atggtggtag cacc                                           24

<210> SEQ ID NO 606
<211> LENGTH: 8
<212> TYPE: PRT
<213> ORGANISM: Artificial Sequence
<220> FEATURE:
<223> OTHER INFORMATION: Synthetic

<400> SEQUENCE: 606

Ile Ser Gly Asn Gly Gly Ser Thr
1               5

<210> SEQ ID NO 607
<211> LENGTH: 45
<212> TYPE: DNA
<213> ORGANISM: Artificial Sequence
<220> FEATURE:
<223> OTHER INFORMATION: Synthetic

<400> SEQUENCE: 607
gcgaaagccc gttattacga tttttggggg gggaatttcg atctc                    45

<210> SEQ ID NO 608
<211> LENGTH: 15
<212> TYPE: PRT
<213> ORGANISM: Artificial Sequence
<220> FEATURE:
<223> OTHER INFORMATION: Synthetic

<400> SEQUENCE: 608

Ala Lys Ala Arg Tyr Tyr Asp Phe Trp Gly Gly Asn Phe Asp Leu
1               5                   10                  15

<210> SEQ ID NO 609
<211> LENGTH: 324
<212> TYPE: DNA
<213> ORGANISM: Artificial Sequence
<220> FEATURE:
<223> OTHER INFORMATION: Synthetic

<400> SEQUENCE: 609
gaaattgtgt tgacgcagtc tccaggcacc ctgtctttgt ctccagggga aagagccacc    60
ctctcctgca gggccagtca gagtgttagc atcaggtact tagcctggta tcagcagaaa   120
cctggccagg ctcccaggct cctcatctat ggtgcatcca gcagggccac tggcatccca   180
gacaggttca gtgtcagtgt gtctgggaca gacttcactc tcaccatcac tagactggag   240
```
cctgaagatt ttgcagtcta ttactgtcag caatatggta gttcaccgct cactttcggc    300
ggagggacca aggtggagat caaa    324

<210> SEQ ID NO 610
<211> LENGTH: 108
<212> TYPE: PRT
<213> ORGANISM: Artificial Sequence
<220> FEATURE:
<223> OTHER INFORMATION: Synthetic

<400> SEQUENCE: 610

Glu Ile Val Leu Thr Gln Ser Pro Gly Thr Leu Ser Leu Ser Pro Gly
 1               5                  10                  15

Glu Arg Ala Thr Leu Ser Cys Arg Ala Ser Gln Ser Val Ser Ile Arg
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Val Ser Val Ser Gly Thr Asp Phe Thr Leu Thr Ile Thr Arg Leu Glu
65                  70                  75                  80

Pro Glu Asp Phe Ala Val Tyr Tyr Cys Gln Gln Tyr Gly Ser Ser Pro
                85                  90                  95

Leu Thr Phe Gly Gly Gly Thr Lys Val Glu Ile Lys
            100                 105

<210> SEQ ID NO 611
<211> LENGTH: 21
<212> TYPE: DNA
<213> ORGANISM: Artificial Sequence
<220> FEATURE:
<223> OTHER INFORMATION: Synthetic

<400> SEQUENCE: 611
cagagtgtta gcatcaggta c    21

<210> SEQ ID NO 612
<211> LENGTH: 7
<212> TYPE: PRT
<213> ORGANISM: Artificial Sequence
<220> FEATURE:
<223> OTHER INFORMATION: Synthetic

<400> SEQUENCE: 612

Gln Ser Val Ser Ile Arg Tyr
 1               5

<210> SEQ ID NO 613
<211> LENGTH: 9
<212> TYPE: DNA
<213> ORGANISM: Artificial Sequence
<220> FEATURE:
<223> OTHER INFORMATION: Synthetic

<400> SEQUENCE: 613 ggtgcatcc    9

<210> SEQ ID NO 614
<211> LENGTH: 3
<212> TYPE: PRT
<213> ORGANISM: Artificial Sequence
<220> FEATURE:
<223> OTHER INFORMATION: Synthetic

<400> SEQUENCE: 614

Gly Ala Ser
 1

<210> SEQ ID NO 615
<211> LENGTH: 27
<212> TYPE: DNA
<213> ORGANISM: Artificial Sequence
<220> FEATURE:
<223> OTHER INFORMATION: Synthetic

<400> SEQUENCE: 615
cagcaatatg gtagttcacc gctcact                                         27

<210> SEQ ID NO 616
<211> LENGTH: 9
<212> TYPE: PRT
<213> ORGANISM: Artificial Sequence
<220> FEATURE:
<223> OTHER INFORMATION: Synthetic

<400> SEQUENCE: 616

Gln Gln Tyr Gly Ser Ser Pro Leu Thr
 1               5

<210> SEQ ID NO 617
<211> LENGTH: 366
<212> TYPE: DNA
<213> ORGANISM: Artificial Sequence
<220> FEATURE:
<223> OTHER INFORMATION: Synthetic

<400> SEQUENCE: 617
gaggtgcagt tgttggagtc tgggggaggc ttggtacagc ctgggggtc cctgagactc      60 tcctgtgcag cctctggatt cacgtttagt agctatgcca tgaactgggt ccgccaggct    120
ccagggaagg ggctggattg ggtctcaggt atcagtggta atggtggtag cacctactac    180
gcagactccg tgaagggccg gttcaccatc tccagagaca tttccaagaa cacgctgtat    240
gtgcaaatgc acagcctgag agtcgaggac acggccgttt actactgtgc gaaagcccgt    300
tattacgatt tttgggggggg gaatttcgat ctctggggcc gtggcaccct ggtcactgtc    360
tcctca                                                              366

<210> SEQ ID NO 618
<211> LENGTH: 122
<212> TYPE: PRT
<213> ORGANISM: Artificial Sequence
<220> FEATURE:
<223> OTHER INFORMATION: Synthetic

<400> SEQUENCE: 618

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser Ser Tyr
             20                  25                  30

Ala Met Asn Trp Val Arg Gln Ala Pro Gly Lys Gly Leu Asp Trp Val
         35                  40                  45

Ser Gly Ile Ser Gly Asn Gly Gly Ser Thr Tyr Tyr Ala Asp Ser Val
     50                  55                  60

Lys Gly Arg Phe Thr Ile Ser Arg Asp Ile Ser Lys Asn Thr Leu Tyr
 65                  70                  75                  80

Val Gln Met His Ser Leu Arg Val Glu Asp Thr Ala Val Tyr Tyr Cys
                85                  90                  95

Ala Lys Ala Arg Tyr Tyr Asp Phe Trp Gly Gly Asn Phe Asp Leu Trp
            100                 105                 110

Gly Arg Gly Thr Leu Val Thr Val Ser Ser
        115                 120

<210> SEQ ID NO 619
<211> LENGTH: 324
<212> TYPE: DNA
<213> ORGANISM: Artificial Sequence
<220> FEATURE:
<223> OTHER INFORMATION: Synthetic

<400> SEQUENCE: 619
gaaattgtgt tgacgcagtc tccaggcacc ctgtctttgt ctccagggga aagagccacc      60
ctctcctgca gggccagtca gagtgttagc atcaggtact tagcctggta tcagcagaaa     120
cctggccagg ctcccaggct cctcatctat ggtgcatccc gcagggccac tggcatccca     180
gacaggttca gtgtcagtgt gtctgggaca gacttcactc tcaccatcac tagactggag     240
cctgaagatt ttgcagtcta ttactgtcag caatatggta gttcaccgct cactttcggc     300
ggagggacca aggtggagat caaa                                             324

<210> SEQ ID NO 620
<211> LENGTH: 108
<212> TYPE: PRT
<213> ORGANISM: Artificial Sequence
<220> FEATURE:
<223> OTHER INFORMATION: Synthetic

<400> SEQUENCE: 620

Glu Ile Val Leu Thr Gln Ser Pro Gly Thr Leu Ser Leu Ser Pro Gly
 1               5                  10                  15

Glu Arg Ala Thr Leu Ser Cys Arg Ala Ser Gln Ser Val Ser Ile Arg
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Val Ser Val Ser Gly Thr Asp Phe Thr Leu Thr Ile Thr Arg Leu Glu
65                  70                  75                  80

Pro Glu Asp Phe Ala Val Tyr Tyr Cys Gln Gln Tyr Gly Ser Ser Pro
                85                  90                  95

Leu Thr Phe Gly Gly Gly Thr Lys Val Glu Ile Lys
            100                 105

<210> SEQ ID NO 621
<211> LENGTH: 366
<212> TYPE: DNA
<213> ORGANISM: Artificial Sequence
<220> FEATURE:
<223> OTHER INFORMATION: Synthetic

<400> SEQUENCE: 621
gaggtgcagc tgttggagtc tgggggaggc ttggtacagc ctggggggtc cctgagactc      60
tcctgtgcag cctctggatt cacgtttagt agctatgcca tgagctgggt ccgccaggct     120
ccagggaagg ggctggagtg ggtctcagct atcagtggta atggtggtag cacctactac     180

```
gcagactccg tgaagggccg gttcaccatc tccagagaca attccaagaa cacgctgtat    240
ctgcaaatga acagcctgag agccgaggac acggccgtat attactgtgc gaaagcccgt    300
tattacgatt tttgggggggg gaatttcgat ctctggggcc gtggcaccct ggtcactgtc    360
tcctca                                                               366
```

```
<210> SEQ ID NO 622
<211> LENGTH: 122
<212> TYPE: PRT
<213> ORGANISM: Artificial Sequence
<220> FEATURE:
<223> OTHER INFORMATION: Synthetic

<400> SEQUENCE: 622
```

```
Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Asn Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ala Arg Tyr Tyr Asp Phe Trp Gly Asn Phe Asp Leu Trp
            100                 105                 110

Gly Arg Gly Thr Leu Val Thr Val Ser Ser
        115                 120
```

```
<210> SEQ ID NO 623
<211> LENGTH: 324
<212> TYPE: DNA
<213> ORGANISM: Artificial Sequence
<220> FEATURE:
<223> OTHER INFORMATION: Synthetic

<400> SEQUENCE: 623
```

```
gaaattgtgt tgacgcagtc tccaggcacc ctgtctttgt ctccagggga aagagccacc    60
ctctcctgca gggccagtca gagtgttagc atcaggtact tagcctggta ccagcagaaa    120
cctggccagg ctcccaggct cctcatctat ggtgcatcca gcagggccac tggcatccca    180
gacaggttca gtggcagtgg gtctgggaca gacttcactc tcaccatcag cagactggag    240
cctgaagatt ttgcagtgta ttactgtcag caatatggta gttcaccgct cactttcggc    300
ggagggacca aggtggagat caaa                                           324
```

```
<210> SEQ ID NO 624
<211> LENGTH: 108
<212> TYPE: PRT
<213> ORGANISM: Artificial Sequence
<220> FEATURE:
<223> OTHER INFORMATION: Synthetic

<400> SEQUENCE: 624
```

```
Glu Ile Val Leu Thr Gln Ser Pro Gly Thr Leu Ser Leu Ser Pro Gly
 1               5                  10                  15

Glu Arg Ala Thr Leu Ser Cys Arg Ala Ser Gln Ser Val Ser Ile Arg
            20                  25                  30
```

Tyr Leu Ala Trp Tyr Gln Gln Lys Pro Gly Gln Ala Pro Arg Leu Leu
                35                  40                  45

Ile Tyr Gly Ala Ser Ser Arg Ala Thr Gly Ile Pro Asp Arg Phe Ser
 50                  55                  60

Gly Ser Gly Ser Gly Thr Asp Phe Thr Leu Thr Ile Ser Arg Leu Glu
 65                  70                  75                  80

Pro Glu Asp Phe Ala Val Tyr Tyr Cys Gln Gln Tyr Gly Ser Ser Pro
                 85                  90                  95

Leu Thr Phe Gly Gly Gly Thr Lys Val Glu Ile Lys
                100                 105

<210> SEQ ID NO 625
<211> LENGTH: 381
<212> TYPE: DNA
<213> ORGANISM: Artificial Sequence
<220> FEATURE:
<223> OTHER INFORMATION: Synthetic

<400> SEQUENCE: 625
caggttcagc tggtgcagtc tggacctgag gtgaagaacc ctggggcctc agtgaaggtc     60
tcctgcaagg cttctggtta cacctttacc acctatggta tcagttgggt acgacaggcc    120
cctggacaag ggcttgagtg gatgggatgg atcagcggtt acaatggtaa acaaacgat    180 gcacagaagt tccaggacag agtcgccatg accacagaca catccacgag cacagcctac    240
atggagctga ggagcctgag atctgacgac acggccattt attactgttc gagagatcgt    300
ttagtagtac cacctgccct ttattattcc tactacgtta tggacgtctg gggccaaggg    360
accacggtca ccgtctcctc a                                              381

<210> SEQ ID NO 626
<211> LENGTH: 127
<212> TYPE: PRT
<213> ORGANISM: Artificial Sequence
<220> FEATURE:
<223> OTHER INFORMATION: Synthetic

<400> SEQUENCE: 626

Gln Val Gln Leu Val Gln Ser Gly Pro Glu Val Lys Asn Pro Gly Ala
 1               5                  10                  15

Ser Val Lys Val Ser Cys Lys Ala Ser Gly Tyr Thr Phe Thr Thr Tyr
                20                  25                  30

Gly Ile Ser Trp Val Arg Gln Ala Pro Gly Gln Gly Leu Glu Trp Met
                35                  40                  45

Gly Trp Ile Ser Gly Tyr Asn Gly Lys Thr Asn Asp Ala Gln Lys Phe
 50                  55                  60

Gln Asp Arg Val Ala Met Thr Thr Asp Thr Ser Thr Ser Thr Ala Tyr
 65                  70                  75                  80

Met Glu Leu Arg Ser Leu Arg Ser Asp Asp Thr Ala Ile Tyr Tyr Cys
                 85                  90                  95

Ser Arg Asp Arg Leu Val Val Pro Pro Ala Leu Tyr Tyr Ser Tyr Tyr
                100                 105                 110

Val Met Asp Val Trp Gly Gln Gly Thr Thr Val Thr Val Ser Ser
            115                 120                 125

<210> SEQ ID NO 627
<211> LENGTH: 24
<212> TYPE: DNA
<213> ORGANISM: Artificial Sequence

```
<220> FEATURE:
<223> OTHER INFORMATION: Synthetic

<400> SEQUENCE: 627
ggttacacct ttaccaccta tggt                                              24

<210> SEQ ID NO 628
<211> LENGTH: 8
<212> TYPE: PRT
<213> ORGANISM: Artificial Sequence
<220> FEATURE:
<223> OTHER INFORMATION: Synthetic

<400> SEQUENCE: 628

Gly Tyr Thr Phe Thr Thr Tyr Gly
1               5

<210> SEQ ID NO 629
<211> LENGTH: 24
<212> TYPE: DNA
<213> ORGANISM: Artificial Sequence
<220> FEATURE:
<223> OTHER INFORMATION: Synthetic

<400> SEQUENCE: 629
atcagcggtt acaatggtaa aaca                                              24

<210> SEQ ID NO 630
<211> LENGTH: 8
<212> TYPE: PRT
<213> ORGANISM: Artificial Sequence
<220> FEATURE:
<223> OTHER INFORMATION: Synthetic

<400> SEQUENCE: 630

Ile Ser Gly Tyr Asn Gly Lys Thr
1               5

<210> SEQ ID NO 631
<211> LENGTH: 60
<212> TYPE: DNA
<213> ORGANISM: Artificial Sequence
<220> FEATURE:
<223> OTHER INFORMATION: Synthetic

<400> SEQUENCE: 631
tcgagagatc gtttagtagt accacctgcc ctttattatt cctactacgt tatggacgtc       60

<210> SEQ ID NO 632
<211> LENGTH: 20
<212> TYPE: PRT
<213> ORGANISM: Artificial Sequence
<220> FEATURE:
<223> OTHER INFORMATION: Synthetic

<400> SEQUENCE: 632

Ser Arg Asp Arg Leu Val Val Pro Pro Ala Leu Tyr Tyr Ser Tyr Tyr
1               5                   10                  15

Val Met Asp Val
            20

<210> SEQ ID NO 633
<211> LENGTH: 336
<212> TYPE: DNA
<213> ORGANISM: Artificial Sequence
<220> FEATURE:
```

<223> OTHER INFORMATION: Synthetic

<400> SEQUENCE: 633

```
gatgttgtga tgactcagtc tccactctcc ctgcccgtca cccttggaca gccggcctcc    60
atctcctgca ggtctagtca aagcctcgta tacagtgatg aaacaccta cttgaattgg   120
tttcagcaga ggccaggtca atctccaagg cgcctaattt ataaggtttc taaccgggac   180
tctggggtcc cagacagatt cagcggcagt gggtcaggca ctgatttcac actgaaaatc   240
agcagggtgg aggctgagga tgttggggtt tattactgca tgcaaggtac acactggccg   300
tacactttg gccaggggac caagctggag atcaaa                             336
```

<210> SEQ ID NO 634
<211> LENGTH: 112
<212> TYPE: PRT
<213> ORGANISM: Artificial Sequence
<220> FEATURE:
<223> OTHER INFORMATION: Synthetic

<400> SEQUENCE: 634

Asp Val Val Met Thr Gln Ser Pro Leu Ser Leu Pro Val Thr Leu Gly
1               5                   10                  15
Gln Pro Ala Ser Ile Ser Cys Arg Ser Ser Gln Ser Leu Val Tyr Ser
            20                  25                  30
Asp Gly Asn Thr Tyr Leu Asn Trp Phe Gln Gln Arg Pro Gly Gln Ser
        35                  40                  45
Pro Arg Arg Leu Ile Tyr Lys Val Ser Asn Arg Asp Ser Gly Val Pro
    50                  55                  60
Asp Arg Phe Ser Gly Ser Gly Ser Gly Thr Asp Phe Thr Leu Lys Ile
65                  70                  75                  80
Ser Arg Val Glu Ala Glu Asp Val Gly Val Tyr Tyr Cys Met Gln Gly
                85                  90                  95
Thr His Trp Pro Tyr Thr Phe Gly Gln Gly Thr Lys Leu Glu Ile Lys
            100                 105                 110

<210> SEQ ID NO 635
<211> LENGTH: 33
<212> TYPE: DNA
<213> ORGANISM: Artificial Sequence
<220> FEATURE:
<223> OTHER INFORMATION: Synthetic

<400> SEQUENCE: 635
caaagcctcg tatacagtga tggaaacacc tac                                33

<210> SEQ ID NO 636
<211> LENGTH: 11
<212> TYPE: PRT
<213> ORGANISM: Artificial Sequence
<220> FEATURE:
<223> OTHER INFORMATION: Synthetic

<400> SEQUENCE: 636

Gln Ser Leu Val Tyr Ser Asp Gly Asn Thr Tyr
1               5                   10

<210> SEQ ID NO 637
<211> LENGTH: 9
<212> TYPE: DNA
<213> ORGANISM: Artificial Sequence
<220> FEATURE:
<223> OTHER INFORMATION: Synthetic -continued

<400> SEQUENCE: 637 aaggtttct                                                                9

<210> SEQ ID NO 638
<211> LENGTH: 3
<212> TYPE: PRT
<213> ORGANISM: Artificial Sequence
<220> FEATURE:
<223> OTHER INFORMATION: Synthetic

<400> SEQUENCE: 638

Lys Val Ser
 1

<210> SEQ ID NO 639
<211> LENGTH: 27
<212> TYPE: DNA
<213> ORGANISM: Artificial Sequence
<220> FEATURE:
<223> OTHER INFORMATION: Synthetic

<400> SEQUENCE: 639
atgcaaggta cacactggcc gtacact                                           27

<210> SEQ ID NO 640
<211> LENGTH: 9
<212> TYPE: PRT
<213> ORGANISM: Artificial Sequence
<220> FEATURE:
<223> OTHER INFORMATION: Synthetic

<400> SEQUENCE: 640

Met Gln Gly Thr His Trp Pro Tyr Thr
 1               5

<210> SEQ ID NO 641
<211> LENGTH: 381
<212> TYPE: DNA
<213> ORGANISM: Artificial Sequence
<220> FEATURE:
<223> OTHER INFORMATION: Synthetic

<400> SEQUENCE: 641
caggttcagc tggtgcagtc tggacctgag gtgaagaacc ctggggcctc agtgaaggtc        60
tcctgcaagg cttctggtta ccctttacc acctatggta tcagttgggt acgacaggcc       120
cctggacaag gcttgagtg gatgggatgg atcagcggtt acaatggtaa aacaaacgat       180
gcacagaagt tccaggacag agtcgccatg accacagaca catccacgag cacagcctac      240
atggagctga ggagcctgag atctgacgac acggccattt attactgttc gagagatcgt      300
ttagtagtac cacctgccct ttattattcc tactacgtta tggacgtctg gggccaaggg      360
accacggtca ccgtctcctc a                                               381

<210> SEQ ID NO 642
<211> LENGTH: 127
<212> TYPE: PRT
<213> ORGANISM: Artificial Sequence
<220> FEATURE:
<223> OTHER INFORMATION: Synthetic

<400> SEQUENCE: 642

Gln Val Gln Leu Val Gln Ser Gly Pro Glu Val Lys Asn Pro Gly Ala
 1               5                  10                  15

-continued

Ser Val Lys Val Ser Cys Lys Ala Ser Gly Tyr Thr Phe Thr Thr Tyr
            20                  25                  30

Gly Ile Ser Trp Val Arg Gln Ala Pro Gly Gln Gly Leu Glu Trp Met
        35                  40                  45

Gly Trp Ile Ser Gly Tyr Asn Gly Lys Thr Asn Asp Ala Gln Lys Phe
    50                  55                  60

Gln Asp Arg Val Ala Met Thr Thr Asp Thr Ser Thr Ser Thr Ala Tyr
65                  70                  75                  80

Met Glu Leu Arg Ser Leu Arg Ser Asp Asp Thr Ala Ile Tyr Tyr Cys
                85                  90                  95

Ser Arg Asp Arg Leu Val Val Pro Pro Ala Leu Tyr Tyr Ser Tyr Tyr
            100                 105                 110

Val Met Asp Val Trp Gly Gln Gly Thr Thr Val Thr Val Ser Ser
        115                 120                 125

<210> SEQ ID NO 643
<211> LENGTH: 336
<212> TYPE: DNA
<213> ORGANISM: Artificial Sequence
<220> FEATURE:
<223> OTHER INFORMATION: Synthetic

<400> SEQUENCE: 643
gatgttgtga tgactcagtc tccactctcc ctgcccgtca cccttggaca gccggcctcc    60
atctcctgca ggtctagtca aagcctcgta tacagtgatg aaacaccta cttgaattgg   120 tttcagcaga ggccaggtca atctccaagg cgcctaattt ataaggtttc taaccgggac   180
tctggggtcc cagacagatt cagcggcagt gggtcaggca ctgatttcac actgaaaatc   240
agcagggtgg aggctgagga tgttggggtt tattactgca tgcaaggtac acactggccg   300
tacacttttg gccaggggac caagctggag atcaaa                             336

<210> SEQ ID NO 644
<211> LENGTH: 112
<212> TYPE: PRT
<213> ORGANISM: Artificial Sequence
<220> FEATURE:
<223> OTHER INFORMATION: Synthetic

<400> SEQUENCE: 644

Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Leu Val Tyr Ser
            20                  25                  30

Asp Gly Asn Thr Tyr Leu Asn Trp Phe Gln Gln Arg Pro Gly Gln Ser
        35                  40                  45

Pro Arg Arg Leu Ile Tyr Lys Val Ser Asn Arg Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Gly
                85                  90                  95

Thr His Trp Pro Tyr Thr Phe Gly Gln Gly Thr Lys Leu Glu Ile Lys
            100                 105                 110

<210> SEQ ID NO 645
<211> LENGTH: 381
<212> TYPE: DNA

<213> ORGANISM: Artificial Sequence
<220> FEATURE:
<223> OTHER INFORMATION: Synthetic

<400> SEQUENCE: 645

```
caggttcagc tggtgcagtc tggagctgag gtgaagaagc ctggggcctc agtgaaggtc      60
tcctgcaagg cttctggtta cacctttacc acctatggta tcagctgggt gcgacaggcc     120
cctggacaag gcttgagtg gatgggatgg atcagcggtt acaatggtaa aacaaactat      180
gcacagaagc tccagggcag agtcaccatg accacagaca catccacgag cacagcctac     240
atggagctga ggagcctgag atctgacgac acggccgtgt attactgttc gagagatcgt     300
ttagtagtac cacctgccct ttattattcc tactacgtta tggacgtctg ggggcaaggg     360
accacggtca ccgtctcctc a                                                381
```

<210> SEQ ID NO 646
<211> LENGTH: 127
<212> TYPE: PRT
<213> ORGANISM: Artificial Sequence
<220> FEATURE:
<223> OTHER INFORMATION: Synthetic

<400> SEQUENCE: 646

```
Gln Val Gln Leu Val Gln Ser Gly Ala Glu Val Lys Lys Pro Gly Ala
  1               5                  10                  15
Ser Val Lys Val Ser Cys Lys Ala Ser Gly Tyr Thr Phe Thr Thr Tyr
                 20                  25                  30
Gly Ile Ser Trp Val Arg Gln Ala Pro Gly Gln Gly Leu Glu Trp Met
             35                  40                  45
Gly Trp Ile Ser Gly Tyr Asn Gly Lys Thr Asn Tyr Ala Gln Lys Leu
         50                  55                  60
Gln Gly Arg Val Thr Met Thr Thr Asp Thr Ser Thr Ser Thr Ala Tyr
 65                  70                  75                  80
Met Glu Leu Arg Ser Leu Arg Ser Asp Asp Thr Ala Val Tyr Tyr Cys
                 85                  90                  95
Ser Arg Asp Arg Leu Val Val Pro Pro Ala Leu Tyr Tyr Ser Tyr Tyr
                100                 105                 110
Val Met Asp Val Trp Gly Gln Gly Thr Thr Val Thr Val Ser Ser
            115                 120                 125
```

<210> SEQ ID NO 647
<211> LENGTH: 336
<212> TYPE: DNA
<213> ORGANISM: Artificial Sequence
<220> FEATURE:
<223> OTHER INFORMATION: Synthetic

<400> SEQUENCE: 647

```
gatgttgtga tgactcagtc tccactctcc ctgcccgtca cccttggaca gccggcctcc      60
atctcctgca ggtctagtca aagcctcgta tacagtgatg gaaacaccta cttgaattgg     120
tttcagcaga ggccaggcca atctccaagg cgcctaattt ataaggtttc taaccgggac     180
tctggggtcc cagacagatt cagcggcagt gggtcaggca ctgatttcac actgaaaatc     240
agcagggtgg aggctgagga tgttggggtt tattactgca tgcaaggtac acactggccg     300
tacactttg gccaggggac caagctggag atcaaa                                 336
```

<210> SEQ ID NO 648
<211> LENGTH: 112

```
<212> TYPE: PRT
<213> ORGANISM: Artificial Sequence
<220> FEATURE:
<223> OTHER INFORMATION: Synthetic

<400> SEQUENCE: 648

Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Leu Val Tyr Ser
            20                  25                  30

Asp Gly Asn Thr Tyr Leu Asn Trp Phe Gln Gln Arg Pro Gly Gln Ser
        35                  40                  45

Pro Arg Arg Leu Ile Tyr Lys Val Ser Asn Arg Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Gly
                85                  90                  95

Thr His Trp Pro Tyr Thr Phe Gly Gln Gly Thr Lys Leu Glu Ile Lys
            100                 105                 110

<210> SEQ ID NO 649
<211> LENGTH: 381
<212> TYPE: DNA
<213> ORGANISM: Artificial Sequence
<220> FEATURE:
<223> OTHER INFORMATION: Synthetic

<400> SEQUENCE: 649
caggttcagc tggtgcagtc tggacctgag gtgaagaacc ctggggcctc agtgaaggtc     60
tcctgcaagg cttctggtta caccttacc acctatggta tcagttgggt acgacaggcc    120
cctggacaag ggcttgagtg gatgggatgg atcagcggtt acaatggtaa acaaacgat    180
gcacagaagt tccaggacag agtcgccatg accacagaca catccacgag cacagcctac    240
atggagctga ggagcctgag atctgacgac acggccattt attactgttc gagagatcgt    300
ttagtagtac cacctgccct taattattac tactacgtta tggacgtctg gggccaaggg    360
accacggtca ccgtctcctc a                                              381

<210> SEQ ID NO 650
<211> LENGTH: 127
<212> TYPE: PRT
<213> ORGANISM: Artificial Sequence
<220> FEATURE:
<223> OTHER INFORMATION: Synthetic

<400> SEQUENCE: 650

Gln Val Gln Leu Val Gln Ser Gly Pro Glu Val Lys Asn Pro Gly Ala
1               5                   10                  15

Ser Val Lys Val Ser Cys Lys Ala Ser Gly Tyr Thr Phe Thr Thr Tyr
            20                  25                  30

Gly Ile Ser Trp Val Arg Gln Ala Pro Gly Gln Gly Leu Glu Trp Met
        35                  40                  45

Gly Trp Ile Ser Gly Tyr Asn Gly Lys Thr Asn Asp Ala Gln Lys Phe
    50                  55                  60

Gln Asp Arg Val Ala Met Thr Thr Asp Thr Ser Thr Ser Thr Ala Tyr
65                  70                  75                  80

Met Glu Leu Arg Ser Leu Arg Ser Asp Asp Thr Ala Ile Tyr Tyr Cys
                85                  90                  95
```

```
Ser Arg Asp Arg Leu Val Val Pro Pro Ala Leu Asn Tyr Tyr Tyr Tyr
            100                 105                 110

Val Met Asp Val Trp Gly Gln Gly Thr Thr Val Thr Val Ser Ser
            115                 120                 125
```

<210> SEQ ID NO 651
<211> LENGTH: 24
<212> TYPE: DNA
<213> ORGANISM: Artificial Sequence
<220> FEATURE:
<223> OTHER INFORMATION: Synthetic

<400> SEQUENCE: 651
ggttacacct ttaccaccta tggt                                            24

<210> SEQ ID NO 652
<211> LENGTH: 8
<212> TYPE: PRT
<213> ORGANISM: Artificial Sequence
<220> FEATURE:
<223> OTHER INFORMATION: Synthetic

<400> SEQUENCE: 652

Gly Tyr Thr Phe Thr Thr Tyr Gly
 1               5

<210> SEQ ID NO 653
<211> LENGTH: 24
<212> TYPE: DNA
<213> ORGANISM: Artificial Sequence
<220> FEATURE:
<223> OTHER INFORMATION: Synthetic

<400> SEQUENCE: 653
atcagcggtt acaatggtaa aaca                                            24

<210> SEQ ID NO 654
<211> LENGTH: 8
<212> TYPE: PRT
<213> ORGANISM: Artificial Sequence
<220> FEATURE:
<223> OTHER INFORMATION: Synthetic

<400> SEQUENCE: 654

Ile Ser Gly Tyr Asn Gly Lys Thr
 1               5

<210> SEQ ID NO 655
<211> LENGTH: 60
<212> TYPE: DNA
<213> ORGANISM: Artificial Sequence
<220> FEATURE:
<223> OTHER INFORMATION: Synthetic

<400> SEQUENCE: 655
tcgagagatc gtttagtagt accacctgcc cttaattatt actactacgt tatggacgtc     60

<210> SEQ ID NO 656
<211> LENGTH: 20
<212> TYPE: PRT
<213> ORGANISM: Artificial Sequence
<220> FEATURE:
<223> OTHER INFORMATION: Synthetic

<400> SEQUENCE: 656

Ser Arg Asp Arg Leu Val Val Pro Pro Ala Leu Asn Tyr Tyr Tyr Tyr
1               5                   10                  15

Val Met Asp Val
            20

<210> SEQ ID NO 657
<211> LENGTH: 336
<212> TYPE: DNA
<213> ORGANISM: Artificial Sequence
<220> FEATURE:
<223> OTHER INFORMATION: Synthetic

<400> SEQUENCE: 657
gatgttgtga tgactcagtc tccactctcc ctgcccgtca cccttggaca gccggcctcc    60
atctcctgca ggtctagtca aagcctcgta tacagtgatg aaacaccta cttgaattgg   120 tttcagcaga ggccaggtca atctccaagg cgcctaattt ataaggtttc taaccgggac   180
tctggggtcc cagacagatt cagcggcagt gggtcaggca ctgatttcac actgaaaatc   240
agcagggtgg aggctgagga tgttggggtt tattactgca tgcaaggtac acactggccg   300
tacacttttg gccaggggac caagctggag atcaaa                            336

<210> SEQ ID NO 658
<211> LENGTH: 112
<212> TYPE: PRT
<213> ORGANISM: Artificial Sequence
<220> FEATURE:
<223> OTHER INFORMATION: Synthetic

<400> SEQUENCE: 658

Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Leu Val Tyr Ser
            20                  25                  30

Asp Gly Asn Thr Tyr Leu Asn Trp Phe Gln Gln Arg Pro Gly Gln Ser
        35                  40                  45

Pro Arg Arg Leu Ile Tyr Lys Val Ser Asn Arg Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Gly
                85                  90                  95

Thr His Trp Pro Tyr Thr Phe Gly Gln Gly Thr Lys Leu Glu Ile Lys
            100                 105                 110

<210> SEQ ID NO 659
<211> LENGTH: 33
<212> TYPE: DNA
<213> ORGANISM: Artificial Sequence
<220> FEATURE:
<223> OTHER INFORMATION: Synthetic

<400> SEQUENCE: 659
caaagcctcg tatacagtga tggaaacacc tac                                33

<210> SEQ ID NO 660
<211> LENGTH: 11
<212> TYPE: PRT
<213> ORGANISM: Artificial Sequence
<220> FEATURE:
<223> OTHER INFORMATION: Synthetic -continued

<400> SEQUENCE: 660

Gln Ser Leu Val Tyr Ser Asp Gly Asn Thr Tyr
1               5                   10

<210> SEQ ID NO 661
<211> LENGTH: 9
<212> TYPE: DNA
<213> ORGANISM: Artificial Sequence
<220> FEATURE:
<223> OTHER INFORMATION: Synthetic

<400> SEQUENCE: 661 aaggtttct                                                                  9

<210> SEQ ID NO 662
<211> LENGTH: 3
<212> TYPE: PRT
<213> ORGANISM: Artificial Sequence
<220> FEATURE:
<223> OTHER INFORMATION: Synthetic

<400> SEQUENCE: 662

Lys Val Ser
1

<210> SEQ ID NO 663
<211> LENGTH: 27
<212> TYPE: DNA
<213> ORGANISM: Artificial Sequence
<220> FEATURE:
<223> OTHER INFORMATION: Synthetic

<400> SEQUENCE: 663
atgcaaggta cacactggcc gtacact                                             27

<210> SEQ ID NO 664
<211> LENGTH: 9
<212> TYPE: PRT
<213> ORGANISM: Artificial Sequence
<220> FEATURE:
<223> OTHER INFORMATION: Synthetic

<400> SEQUENCE: 664

Met Gln Gly Thr His Trp Pro Tyr Thr
1               5

<210> SEQ ID NO 665
<211> LENGTH: 381
<212> TYPE: DNA
<213> ORGANISM: Artificial Sequence
<220> FEATURE:
<223> OTHER INFORMATION: Synthetic

<400> SEQUENCE: 665
caggttcagc tggtgcagtc tggacctgag gtgaagaacc ctggggcctc agtgaaggtc         60
tcctgcaagg cttctggtta cacctttacc acctatggta tcagttgggt acgacaggcc        120
cctggacaag gcttgagtg gatgggatgg atcagcggtt acaatggtaa aacaaacgat         180
gcacagaagt tccaggacag agtcgccatg accacagaca catccacgag cacagcctac        240
atggagctga ggagcctgag atctgacgac acggccattt attactgttc gagagatcgt        300
ttagtagtac cacctgccct aattattac tactacgtta tggacgtctg ggccaaggg         360 accacggtca ccgtctcctc a                                                  381

```
<210> SEQ ID NO 666
<211> LENGTH: 127
<212> TYPE: PRT
<213> ORGANISM: Artificial Sequence
<220> FEATURE:
<223> OTHER INFORMATION: Synthetic

<400> SEQUENCE: 666
```

Gln Val Gln Leu Val Gln Ser Gly Pro Glu Val Lys Asn Pro Gly Ala
 1               5                  10                  15

Ser Val Lys Val Ser Cys Lys Ala Ser Gly Tyr Thr Phe Thr Thr Tyr
             20                  25                  30

Gly Ile Ser Trp Val Arg Gln Ala Pro Gly Gln Gly Leu Glu Trp Met
         35                  40                  45

Gly Trp Ile Ser Gly Tyr Asn Gly Lys Thr Asn Asp Ala Gln Lys Phe
     50                  55                  60

Gln Asp Arg Val Ala Met Thr Thr Asp Thr Ser Thr Ser Thr Ala Tyr
 65                  70                  75                  80

Met Glu Leu Arg Ser Leu Arg Ser Asp Asp Thr Ala Ile Tyr Tyr Cys
                 85                  90                  95

Ser Arg Asp Arg Leu Val Val Pro Pro Ala Leu Asn Tyr Tyr Tyr Tyr
            100                 105                 110

Val Met Asp Val Trp Gly Gln Gly Thr Thr Val Thr Val Ser Ser
        115                 120                 125

```
<210> SEQ ID NO 667
<211> LENGTH: 336
<212> TYPE: DNA
<213> ORGANISM: Artificial Sequence
<220> FEATURE:
<223> OTHER INFORMATION: Synthetic

<400> SEQUENCE: 667
```
gatgttgtga tgactcagtc tccactctcc ctgcccgtca cccttggaca gccggcctcc     60
atctcctgca ggtctagtca aagcctcgta tacagtgatg aaacacccta cttgaattgg    120
tttcagcaga ggccaggtca atctccaagg cgcctaattt ataaggtttc taaccgggac    180
tctggggtcc cagacagatt cagcggcagt gggtcaggca ctgatttcac actgaaaatc    240
agcagggtgg aggctgagga tgttggggtt tattactgca tgcaaggtac acactggccg    300
tacacttttg gccaggggac caagctggag atcaaa                              336

```
<210> SEQ ID NO 668
<211> LENGTH: 112
<212> TYPE: PRT
<213> ORGANISM: Artificial Sequence
<220> FEATURE:
<223> OTHER INFORMATION: Synthetic

<400> SEQUENCE: 668
```

Asp Val Val Met Thr Gln Ser Pro Leu Ser Leu Pro Val Thr Leu Gly
 1               5                  10                  15

Gln Pro Ala Ser Ile Ser Cys Arg Ser Ser Gln Ser Leu Val Tyr Ser
             20                  25                  30

Asp Gly Asn Thr Tyr Leu Asn Trp Phe Gln Gln Arg Pro Gly Gln Ser
         35                  40                  45

Pro Arg Arg Leu Ile Tyr Lys Val Ser Asn Arg Asp Ser Gly Val Pro
     50                  55                  60

Asp Arg Phe Ser Gly Ser Gly Ser Gly Thr Asp Phe Thr Leu Lys Ile

```
                65                  70                  75                  80
Ser Arg Val Glu Ala Glu Asp Val Gly Val Tyr Tyr Cys Met Gln Gly
                    85                  90                  95

Thr His Trp Pro Tyr Thr Phe Gly Gln Gly Thr Lys Leu Glu Ile Lys
                100                 105                 110
```

<210> SEQ ID NO 669
<211> LENGTH: 381
<212> TYPE: DNA
<213> ORGANISM: Artificial Sequence
<220> FEATURE:
<223> OTHER INFORMATION: Synthetic

<400> SEQUENCE: 669

```
caggttcagc tggtgcagtc tggagctgag gtgaagaagc ctggggcctc agtgaaggtc      60
tcctgcaagg cttctggtta caccttt acc acctatggta tcagctgggt gcgacaggcc    120
cctggacaag gcttgagtg gatgggatgg atcagcggtt acaatggtaa aacaaactat     180
gcacagaagc tccagggcag agtcaccatg accacagaca catccacgag cacagcctac    240
atggagctga ggagcctgag atctgacgac acggccgtgt attactgttc gagagatcgt    300
ttagtagtac cacctgccct aattattac tactacgtta tggacgtctg ggggcaaggg    360
accacggtca ccgtctcctc a                                              381
```

<210> SEQ ID NO 670
<211> LENGTH: 127
<212> TYPE: PRT
<213> ORGANISM: Artificial Sequence
<220> FEATURE:
<223> OTHER INFORMATION: Synthetic

<400> SEQUENCE: 670

```
Gln Val Gln Leu Val Gln Ser Gly Ala Glu Val Lys Lys Pro Gly Ala
 1               5                  10                  15

Ser Val Lys Val Ser Cys Lys Ala Ser Gly Tyr Thr Phe Thr Thr Tyr
                20                  25                  30

Gly Ile Ser Trp Val Arg Gln Ala Pro Gly Gln Gly Leu Glu Trp Met
            35                  40                  45

Gly Trp Ile Ser Gly Tyr Asn Gly Lys Thr Asn Tyr Ala Gln Lys Leu
        50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ser Arg Asp Arg Leu Val Val Pro Pro Ala Leu Asn Tyr Tyr Tyr Tyr
                100                 105                 110

Val Met Asp Val Trp Gly Gln Gly Thr Thr Val Thr Val Ser Ser
            115                 120                 125
```

<210> SEQ ID NO 671
<211> LENGTH: 336
<212> TYPE: DNA
<213> ORGANISM: Artificial Sequence
<220> FEATURE:
<223> OTHER INFORMATION: Synthetic

<400> SEQUENCE: 671

```
gatgttgtga tgactcagtc tccactctcc ctgcccgtca cccttggaca gccggcctcc      60
atctcctgca ggtctagtca aagcctcgta tacagtgatg gaaacaccta cttgaattgg    120
```

```
tttcagcaga ggccaggcca atctccaagg cgcctaattt ataaggtttc taaccgggac    180 tctgggtcc cagacagatt cagcggcagt gggtcaggca ctgatttcac actgaaaatc    240
agcagggtgg aggctgagga tgttggggtt tattactgca tgcaaggtac acactggccg    300 tacactttg gccaggggac caagctggag atcaaa                              336
```

<210> SEQ ID NO 672
<211> LENGTH: 112
<212> TYPE: PRT
<213> ORGANISM: Artificial Sequence
<220> FEATURE:
<223> OTHER INFORMATION: Synthetic

<400> SEQUENCE: 672

```
Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Leu Val Tyr Ser
            20                  25                  30

Asp Gly Asn Thr Tyr Leu Asn Trp Phe Gln Gln Arg Pro Gly Gln Ser
        35                  40                  45

Pro Arg Arg Leu Ile Tyr Lys Val Ser Asn Arg Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Gly
                85                  90                  95

Thr His Trp Pro Tyr Thr Phe Gly Gln Gly Thr Lys Leu Glu Ile Lys
            100                 105                 110
```

<210> SEQ ID NO 673
<211> LENGTH: 381
<212> TYPE: DNA
<213> ORGANISM: Artificial Sequence
<220> FEATURE:
<223> OTHER INFORMATION: Synthetic

<400> SEQUENCE: 673

```
caggttcagc tggtgcagtc tggacctgag gtgaagaacc ctggggcctc agtgaaggtc    60
tcctgcaagg cttctggtta caccttacc acctatggta tcagttgggt acgacaggcc   120
cctggacaag ggcttgagtg gatgggatgg atcagcggtt acaatggtaa acaaacgat   180 gcacagaagt tccaggacag agtcgccatg accacagaca catccacgag cacagcctac   240
atggagctga ggagcctgag atctgacgac acggccattt attactgttc gagagatcgt   300
ttagtagtac cacctgccct ttattattac tactacgtta tggacgtctg ggccaaggg   360 accacggtca ccgtctcctc a                                              381
```

<210> SEQ ID NO 674
<211> LENGTH: 127
<212> TYPE: PRT
<213> ORGANISM: Artificial Sequence
<220> FEATURE:
<223> OTHER INFORMATION: Synthetic

<400> SEQUENCE: 674

```
Gln Val Gln Leu Val Gln Ser Gly Pro Glu Val Lys Asn Pro Gly Ala
1               5                   10                  15

Ser Val Lys Val Ser Cys Lys Ala Ser Gly Tyr Thr Phe Thr Thr Tyr
            20                  25                  30
```

Gly Ile Ser Trp Val Arg Gln Ala Pro Gly Gln Gly Leu Glu Trp Met
            35                  40                  45

Gly Trp Ile Ser Gly Tyr Asn Gly Lys Thr Asn Asp Ala Gln Lys Phe
        50                  55                  60

Gln Asp Arg Val Ala Met Thr Thr Asp Thr Ser Thr Ser Thr Ala Tyr
65                  70                  75                  80

Met Glu Leu Arg Ser Leu Arg Ser Asp Asp Thr Ala Ile Tyr Tyr Cys
                85                  90                  95

Ser Arg Asp Arg Leu Val Val Pro Pro Ala Leu Tyr Tyr Tyr Tyr Tyr
            100                 105                 110

Val Met Asp Val Trp Gly Gln Gly Thr Thr Val Thr Val Ser Ser
            115                 120                 125

<210> SEQ ID NO 675
<211> LENGTH: 24
<212> TYPE: DNA
<213> ORGANISM: Artificial Sequence
<220> FEATURE:
<223> OTHER INFORMATION: Synthetic

<400> SEQUENCE: 675
ggttacacct ttaccaccta tggt                                              24

<210> SEQ ID NO 676
<211> LENGTH: 8
<212> TYPE: PRT
<213> ORGANISM: Artificial Sequence
<220> FEATURE:
<223> OTHER INFORMATION: Synthetic

<400> SEQUENCE: 676

Gly Tyr Thr Phe Thr Thr Tyr Gly
1               5

<210> SEQ ID NO 677
<211> LENGTH: 24
<212> TYPE: DNA
<213> ORGANISM: Artificial Sequence
<220> FEATURE:
<223> OTHER INFORMATION: Synthetic

<400> SEQUENCE: 677
atcagcggtt acaatggtaa aaca                                              24

<210> SEQ ID NO 678
<211> LENGTH: 8
<212> TYPE: PRT
<213> ORGANISM: Artificial Sequence
<220> FEATURE:
<223> OTHER INFORMATION: Synthetic

<400> SEQUENCE: 678

Ile Ser Gly Tyr Asn Gly Lys Thr
1               5

<210> SEQ ID NO 679
<211> LENGTH: 60
<212> TYPE: DNA
<213> ORGANISM: Artificial Sequence
<220> FEATURE:
<223> OTHER INFORMATION: Synthetic

<400> SEQUENCE: 679
tcgagagatc gtttagtagt accacctgcc ctttattatt actactacgt tatggacgtc    60

<210> SEQ ID NO 680
<211> LENGTH: 20
<212> TYPE: PRT
<213> ORGANISM: Artificial Sequence
<220> FEATURE:
<223> OTHER INFORMATION: Synthetic

<400> SEQUENCE: 680

Ser Arg Asp Arg Leu Val Val Pro Pro Ala Leu Tyr Tyr Tyr Tyr Tyr
 1               5                  10                  15

Val Met Asp Val
            20

<210> SEQ ID NO 681
<211> LENGTH: 336
<212> TYPE: DNA
<213> ORGANISM: Artificial Sequence
<220> FEATURE:
<223> OTHER INFORMATION: Synthetic

<400> SEQUENCE: 681
gatgttgtga tgactcagtc tccactctcc ctgcccgtca cccttggaca gccggcctcc    60
atctcctgca ggtctagtca aagcctcgta tacagtgatg gaaacaccta cttgaattgg   120
tttcagcaga ggccaggtca atctccaagg cgcctaattt ataaggtttc taaccgggac   180
tctggggtcc cagacagatt cagcggcagt gggtcaggca ctgatttcac actgaaaatc   240
agcagggtgg aggctgagga tgttggggtt tattactgca tgcaaggtac acactggccg   300 tacactttg gccaggggac caagctggag atcaaa                              336

<210> SEQ ID NO 682
<211> LENGTH: 112
<212> TYPE: PRT
<213> ORGANISM: Artificial Sequence
<220> FEATURE:
<223> OTHER INFORMATION: Synthetic

<400> SEQUENCE: 682

Asp Val Val Met Thr Gln Ser Pro Leu Ser Leu Pro Val Thr Leu Gly
 1               5                  10                  15

Gln Pro Ala Ser Ile Ser Cys Arg Ser Ser Gln Ser Leu Val Tyr Ser
            20                  25                  30

Asp Gly Asn Thr Tyr Leu Asn Trp Phe Gln Gln Arg Pro Gly Gln Ser
        35                  40                  45

Pro Arg Arg Leu Ile Tyr Lys Val Ser Asn Arg Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Gly
                85                  90                  95

Thr His Trp Pro Tyr Thr Phe Gly Gln Gly Thr Lys Leu Glu Ile Lys
            100                 105                 110

<210> SEQ ID NO 683
<211> LENGTH: 33
<212> TYPE: DNA
<213> ORGANISM: Artificial Sequence
<220> FEATURE:
<223> OTHER INFORMATION: Synthetic

```
<400> SEQUENCE: 683
caaagcctcg tatacagtga tggaaacacc tac                           33

<210> SEQ ID NO 684
<211> LENGTH: 11
<212> TYPE: PRT
<213> ORGANISM: Artificial Sequence
<220> FEATURE:
<223> OTHER INFORMATION: Synthetic

<400> SEQUENCE: 684

Gln Ser Leu Val Tyr Ser Asp Gly Asn Thr Tyr
 1               5                  10

<210> SEQ ID NO 685
<211> LENGTH: 9
<212> TYPE: DNA
<213> ORGANISM: Artificial Sequence
<220> FEATURE:
<223> OTHER INFORMATION: Synthetic

<400> SEQUENCE: 685 aaggtttct                                                      9

<210> SEQ ID NO 686
<211> LENGTH: 3
<212> TYPE: PRT
<213> ORGANISM: Artificial Sequence
<220> FEATURE:
<223> OTHER INFORMATION: Synthetic

<400> SEQUENCE: 686

Lys Val Ser
 1

<210> SEQ ID NO 687
<211> LENGTH: 27
<212> TYPE: DNA
<213> ORGANISM: Artificial Sequence
<220> FEATURE:
<223> OTHER INFORMATION: Synthetic

<400> SEQUENCE: 687
atgcaaggta cacactggcc gtacact                                  27

<210> SEQ ID NO 688
<211> LENGTH: 9
<212> TYPE: PRT
<213> ORGANISM: Artificial Sequence
<220> FEATURE:
<223> OTHER INFORMATION: Synthetic

<400> SEQUENCE: 688

Met Gln Gly Thr His Trp Pro Tyr Thr
 1               5

<210> SEQ ID NO 689
<211> LENGTH: 381
<212> TYPE: DNA
<213> ORGANISM: Artificial Sequence
<220> FEATURE:
<223> OTHER INFORMATION: Synthetic

<400> SEQUENCE: 689
caggttcagc tggtgcagtc tggacctgag gtgaagaacc ctggggcctc agtgaaggtc    60
```

```
tcctgcaagg cttctggtta cacctttacc acctatggta tcagttgggt acgacaggcc    120
cctggacaag ggcttgagtg gatgggatgg atcagcggtt acaatggtaa aacaaacgat    180
gcacagaagt tccaggacag agtcgccatg accacagaca catccacgag cacagcctac    240
atggagctga ggagcctgag atctgacgac acggccattt attactgttc gagagatcgt    300
ttagtagtac cacctgccct ttattattac tactacgtta tggacgtctg gggccaaggg    360
accacggtca ccgtctcctc a                                              381
```

```
<210> SEQ ID NO 690
<211> LENGTH: 127
<212> TYPE: PRT
<213> ORGANISM: Artificial Sequence
<220> FEATURE:
<223> OTHER INFORMATION: Synthetic

<400> SEQUENCE: 690
```

Gln Val Gln Leu Val Gln Ser Gly Pro Glu Val Lys Asn Pro Gly Ala
1               5                   10                  15

Ser Val Lys Val Ser Cys Lys Ala Ser Gly Tyr Thr Phe Thr Thr Tyr
            20                  25                  30

Gly Ile Ser Trp Val Arg Gln Ala Pro Gly Gln Gly Leu Glu Trp Met
        35                  40                  45

Gly Trp Ile Ser Gly Tyr Asn Gly Lys Thr Asn Asp Ala Gln Lys Phe
    50                  55                  60

Gln Asp Arg Val Ala Met Thr Thr Asp Thr Ser Thr Ser Thr Ala Tyr
65                  70                  75                  80

Met Glu Leu Arg Ser Leu Arg Ser Asp Asp Thr Ala Ile Tyr Tyr Cys
                85                  90                  95

Ser Arg Asp Arg Leu Val Val Pro Pro Ala Leu Tyr Tyr Tyr Tyr Tyr
            100                 105                 110

Val Met Asp Val Trp Gly Gln Gly Thr Thr Val Thr Val Ser Ser
        115                 120                 125

```
<210> SEQ ID NO 691
<211> LENGTH: 336
<212> TYPE: DNA
<213> ORGANISM: Artificial Sequence
<220> FEATURE:
<223> OTHER INFORMATION: Synthetic

<400> SEQUENCE: 691
gatgttgtga tgactcagtc tccactctcc ctgcccgtca cccttggaca gccggcctcc     60
atctcctgca ggtctagtca aagcctcgta tacagtgatg gaaacaccta cttgaattgg    120
tttcagcaga ggccaggtca atctccaagg cgcctaattt ataaggtttc taaccgggac    180
tctggggtcc cagacagatt cagcggcagt gggtcaggca ctgatttcac actgaaaatc    240
agcagggtgg aggctgagga tgttggggtt tattactgca tgcaaggtac acactggccg    300
tacacttttg gccaggggac caagctggag atcaaa                              336
```

```
<210> SEQ ID NO 692
<211> LENGTH: 112
<212> TYPE: PRT
<213> ORGANISM: Artificial Sequence
<220> FEATURE:
<223> OTHER INFORMATION: Synthetic

<400> SEQUENCE: 692
```

Asp Val Val Met Thr Gln Ser Pro Leu Ser Leu Pro Val Thr Leu Gly

```
            1               5                  10                 15
          Gln Pro Ala Ser Ile Ser Cys Arg Ser Ser Gln Ser Leu Val Tyr Ser
                       20                  25                  30

Asp Gly Asn Thr Tyr Leu Asn Trp Phe Gln Gln Arg Pro Gly Gln Ser
                       35                  40                  45

Pro Arg Leu Ile Tyr Lys Val Ser Asn Arg Asp Ser Gly Val Pro
                       50                  55                  60

Asp Arg Phe Ser Gly Ser Gly Ser Gly Thr Asp Phe Thr Leu Lys Ile
          65                   70                  75                  80

Ser Arg Val Glu Ala Glu Asp Val Gly Val Tyr Tyr Cys Met Gln Gly
                               85                  90                  95

Thr His Trp Pro Tyr Thr Phe Gly Gln Gly Thr Lys Leu Glu Ile Lys
                          100                 105                 110
```

<210> SEQ ID NO 693
<211> LENGTH: 381
<212> TYPE: DNA
<213> ORGANISM: Artificial Sequence
<220> FEATURE:
<223> OTHER INFORMATION: Synthetic

<400> SEQUENCE: 693

```
caggttcagc tggtgcagtc tggagctgag gtgaagaagc ctggggcctc agtgaaggtc      60
tcctgcaagg cttctggtta cacctttacc acctatggta tcagctgggt gcgacaggcc     120
cctggacaag gcttgagtg gatgggatgg atcagcggtt acaatggtaa aacaaactat      180
gcacagaagc tccagggcag agtcaccatg accacagaca catccacgag cacagcctac     240
atggagctga ggagcctgag atctgacgac acggccgtgt attactgttc gagagatcgt     300
ttagtagtac cacctgccct ttattattac tactacgtta tggacgtctg ggggcaaggg     360
accacggtca ccgtctcctc a                                                381
```

<210> SEQ ID NO 694
<211> LENGTH: 127
<212> TYPE: PRT
<213> ORGANISM: Artificial Sequence
<220> FEATURE:
<223> OTHER INFORMATION: Synthetic

<400> SEQUENCE: 694

```
          Gln Val Gln Leu Val Gln Ser Gly Ala Glu Val Lys Lys Pro Gly Ala
          1               5                  10                  15

Ser Val Lys Val Ser Cys Lys Ala Ser Gly Tyr Thr Phe Thr Thr Tyr
                       20                  25                  30

Gly Ile Ser Trp Val Arg Gln Ala Pro Gly Gln Gly Leu Glu Trp Met
                       35                  40                  45

Gly Trp Ile Ser Gly Tyr Asn Gly Lys Thr Asn Tyr Ala Gln Lys Leu
                       50                  55                  60

Gln Gly Arg Val Thr Met Thr Thr Asp Thr Ser Thr Ser Thr Ala Tyr
          65                   70                  75                  80

Met Glu Leu Arg Ser Leu Arg Ser Asp Asp Thr Ala Val Tyr Tyr Cys
                               85                  90                  95

Ser Arg Asp Arg Leu Val Val Pro Pro Ala Leu Tyr Tyr Tyr Tyr Tyr
                          100                 105                 110

Val Met Asp Val Trp Gly Gln Gly Thr Thr Val Thr Val Ser Ser
                          115                 120                 125
```

<210> SEQ ID NO 695
<211> LENGTH: 336
<212> TYPE: DNA
<213> ORGANISM: Artificial Sequence
<220> FEATURE:
<223> OTHER INFORMATION: Synthetic

<400> SEQUENCE: 695

```
gatgttgtga tgactcagtc tccactctcc ctgcccgtca cccttggaca gccggcctcc      60
atctcctgca ggtctagtca aagcctcgta tacagtgatg aaacaccta cttgaattgg     120
tttcagcaga ggccaggcca atctccaagg cgcctaattt ataaggtttc taaccgggac     180
tctggggtcc cagacagatt cagcggcagt gggtcaggca ctgatttcac actgaaaatc     240
agcagggtgg aggctgagga tgttggggtt tattactgca tgcaaggtac acactggccg     300
tacacttttg gccaggggac caagctggag atcaaa                              336
```

<210> SEQ ID NO 696
<211> LENGTH: 112
<212> TYPE: PRT
<213> ORGANISM: Artificial Sequence
<220> FEATURE:
<223> OTHER INFORMATION: Synthetic

<400> SEQUENCE: 696

Asp Val Val Met Thr Gln Ser Pro Leu Ser Leu Pro Val Thr Leu Gly
1               5                   10                  15
Gln Pro Ala Ser Ile Ser Cys Arg Ser Ser Gln Ser Leu Val Tyr Ser
            20                  25                  30
Asp Gly Asn Thr Tyr Leu Asn Trp Phe Gln Gln Arg Pro Gly Gln Ser
        35                  40                  45
Pro Arg Arg Leu Ile Tyr Lys Val Ser Asn Arg Asp Ser Gly Val Pro
    50                  55                  60
Asp Arg Phe Ser Gly Ser Gly Ser Gly Thr Asp Phe Thr Leu Lys Ile
65                  70                  75                  80
Ser Arg Val Glu Ala Glu Asp Val Gly Val Tyr Tyr Cys Met Gln Gly
                85                  90                  95
Thr His Trp Pro Tyr Thr Phe Gly Gln Gly Thr Lys Leu Glu Ile Lys
            100                 105                 110

<210> SEQ ID NO 697
<211> LENGTH: 384
<212> TYPE: DNA
<213> ORGANISM: Artificial Sequence
<220> FEATURE:
<223> OTHER INFORMATION: Synthetic

<400> SEQUENCE: 697

```
caggtgcacc tggtggagtc tgggggaggc ttggtcaagc ctggagggtc cctgagactc      60
tcctgtgcag cctctggatt caccttcagt gaccactaca tgagctggat ccgccaggct     120
ccagggaagg ggctggagtg gatttcatac attagtaatg atggtggtac caaatactat     180
gtggactctg tggagggccg attcatcatt tccagggaca acgccaagaa ctcattgtat     240
ctacatatga acagcctcag agccgacgac acggccgtgt attactgtgc gagagatcag     300
ggatatattg ctacgactcg tattattac tattcctacg gtatggacgt ctggggccaa     360
gggaccacgg tcaccgtcgc ctca                                          384
```

<210> SEQ ID NO 698
<211> LENGTH: 128

<212> TYPE: PRT
<213> ORGANISM: Artificial Sequence
<220> FEATURE:
<223> OTHER INFORMATION: Synthetic

<400> SEQUENCE: 698

Gln Val His Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp His
            20                  25                  30

Tyr Met Ser Trp Ile Arg Gln Ala Pro Gly Lys Gly Leu Glu Trp Ile
        35                  40                  45

Ser Tyr Ile Ser Asn Asp Gly Gly Thr Lys Tyr Tyr Val Asp Ser Val
    50                  55                  60

Glu Gly Arg Phe Ile Ile Ser Arg Asp Asn Ala Lys Asn Ser Leu Tyr
65                  70                  75                  80

Leu His Met Asn Ser Leu Arg Ala Asp Thr Ala Val Tyr Tyr Cys
            85                  90                  95

Ala Arg Asp Gln Gly Tyr Ile Gly Tyr Asp Ser Tyr Tyr Tyr Tyr Ser
            100                 105                 110

Tyr Gly Met Asp Val Trp Gly Gln Gly Thr Thr Val Thr Val Ala Ser
            115                 120                 125

<210> SEQ ID NO 699
<211> LENGTH: 24
<212> TYPE: DNA
<213> ORGANISM: Artificial Sequence
<220> FEATURE:
<223> OTHER INFORMATION: Synthetic

<400> SEQUENCE: 699
ggattcacct tcagtgacca ctac                                         24

<210> SEQ ID NO 700
<211> LENGTH: 8
<212> TYPE: PRT
<213> ORGANISM: Artificial Sequence
<220> FEATURE:
<223> OTHER INFORMATION: Synthetic

<400> SEQUENCE: 700

Gly Phe Thr Phe Ser Asp His Tyr
1               5

<210> SEQ ID NO 701
<211> LENGTH: 24
<212> TYPE: DNA
<213> ORGANISM: Artificial Sequence
<220> FEATURE:
<223> OTHER INFORMATION: Synthetic

<400> SEQUENCE: 701
attagtaatg atggtggtac caaa                                         24

<210> SEQ ID NO 702
<211> LENGTH: 8
<212> TYPE: PRT
<213> ORGANISM: Artificial Sequence
<220> FEATURE:
<223> OTHER INFORMATION: Synthetic

<400> SEQUENCE: 702

Ile Ser Asn Asp Gly Gly Thr Lys

<210> SEQ ID NO 703
<211> LENGTH: 63
<212> TYPE: DNA
<213> ORGANISM: Artificial Sequence
<220> FEATURE:
<223> OTHER INFORMATION: Synthetic

<400> SEQUENCE: 703
gcgagagatc agggatatat tggctacgac tcgtattatt actattccta cggtatggac    60
gtc                                                                  63

<210> SEQ ID NO 704
<211> LENGTH: 21
<212> TYPE: PRT
<213> ORGANISM: Artificial Sequence
<220> FEATURE:
<223> OTHER INFORMATION: Synthetic

<400> SEQUENCE: 704

Ala Arg Asp Gln Gly Tyr Ile Gly Tyr Asp Ser Tyr Tyr Tyr Ser
1               5                   10                  15

Tyr Gly Met Asp Val
            20

<210> SEQ ID NO 705
<211> LENGTH: 321
<212> TYPE: DNA
<213> ORGANISM: Artificial Sequence
<220> FEATURE:
<223> OTHER INFORMATION: Synthetic

<400> SEQUENCE: 705
aaaattgtgt tgacgcagtc tccaggcacc ctgcctttgt ttccagggga aagagccacc    60
ctctcctgta gggccagtca gagtgttaac aacaaattct tagcctggta ccagcagaaa   120
tctggccagg ctcccaggct cctcatctat ggtgcatcca gcagggccac tggcatccca   180
gacaggttca gtggcagtgg gtctgggacc gacttcactc tcaccatcag cggactggag   240
cctgaagatt ttgaagtgta ttattgtcaa gtatatggta actcactcac tttcggcgga   300
gggaccaagg tggagatcaa g                                             321

<210> SEQ ID NO 706
<211> LENGTH: 107
<212> TYPE: PRT
<213> ORGANISM: Artificial Sequence
<220> FEATURE:
<223> OTHER INFORMATION: Synthetic

<400> SEQUENCE: 706

Lys Ile Val Leu Thr Gln Ser Pro Gly Thr Leu Pro Leu Phe Pro Gly
1               5                   10                  15

Glu Arg Ala Thr Leu Ser Cys Arg Ala Ser Gln Ser Val Asn Asn Lys
            20                  25                  30

Phe Leu Ala Trp Tyr Gln Gln Lys Ser Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Gly Leu Glu
65                  70                  75                  80

Pro Glu Asp Phe Glu Val Tyr Tyr Cys Gln Val Tyr Gly Asn Ser Leu
            85                  90                  95

Thr Phe Gly Gly Gly Thr Lys Val Glu Ile Lys
            100                 105

<210> SEQ ID NO 707
<211> LENGTH: 21
<212> TYPE: DNA
<213> ORGANISM: Artificial Sequence
<220> FEATURE:
<223> OTHER INFORMATION: Synthetic

<400> SEQUENCE: 707
cagagtgtta acaacaaatt c                                               21

<210> SEQ ID NO 708
<211> LENGTH: 7
<212> TYPE: PRT
<213> ORGANISM: Artificial Sequence
<220> FEATURE:
<223> OTHER INFORMATION: Synthetic

<400> SEQUENCE: 708

Gln Ser Val Asn Asn Lys Phe
 1               5

<210> SEQ ID NO 709
<211> LENGTH: 9
<212> TYPE: DNA
<213> ORGANISM: Artificial Sequence
<220> FEATURE:
<223> OTHER INFORMATION: Synthetic

<400> SEQUENCE: 709 ggtgcatcc                                                              9

<210> SEQ ID NO 710
<211> LENGTH: 3
<212> TYPE: PRT
<213> ORGANISM: Artificial Sequence
<220> FEATURE:
<223> OTHER INFORMATION: Synthetic

<400> SEQUENCE: 710

Gly Ala Ser
 1

<210> SEQ ID NO 711
<211> LENGTH: 24
<212> TYPE: DNA
<213> ORGANISM: Artificial Sequence
<220> FEATURE:
<223> OTHER INFORMATION: Synthetic

<400> SEQUENCE: 711
caagtatatg gtaactcact cact                                            24

<210> SEQ ID NO 712
<211> LENGTH: 8
<212> TYPE: PRT
<213> ORGANISM: Artificial Sequence
<220> FEATURE:
<223> OTHER INFORMATION: Synthetic

<400> SEQUENCE: 712

Gln Val Tyr Gly Asn Ser Leu Thr

<210> SEQ ID NO 713
<211> LENGTH: 384
<212> TYPE: DNA
<213> ORGANISM: Artificial Sequence
<220> FEATURE:
<223> OTHER INFORMATION: Synthetic

<400> SEQUENCE: 713

```
caggtgcagc tggtggagtc tgggggaggc ttggtcaagc ctggagggtc cctgagactc      60
tcctgtgcag cctctggatt caccttcagt gaccactaca tgagctggat ccgccaggct     120
ccagggaagg ggctggagtg gatttcatac attagtaatg atggtggtac caaatactat     180
gtggactctg tggagggccg attcatcatt tccaggaca acgccaagaa ctcattgtat      240
ctacatatga acagcctcag agccgacgac acggccgtgt attactgtgc gagagatcag     300
ggatatattg ctacgactc gtattattac tattcctacg gtatggacgt ctggggccaa      360
gggaccacgg tcaccgtctc ctca                                            384
```

<210> SEQ ID NO 714
<211> LENGTH: 128
<212> TYPE: PRT
<213> ORGANISM: Artificial Sequence
<220> FEATURE:
<223> OTHER INFORMATION: Synthetic

<400> SEQUENCE: 714

```
Gln Val Gln Leu Val Glu Ser Gly Gly Gly Leu Val Lys Pro Gly Gly
  1               5                  10                  15

Ser Leu Arg Leu Ser Cys Ala Ala Ser Gly Phe Thr Phe Ser Asp His
             20                  25                  30

Tyr Met Ser Trp Ile Arg Gln Ala Pro Gly Lys Gly Leu Glu Trp Ile
         35                  40                  45

Ser Tyr Ile Ser Asn Asp Gly Gly Thr Lys Tyr Tyr Val Asp Ser Val
     50                  55                  60

Glu Gly Arg Phe Ile Ile Ser Arg Asp Asn Ala Lys Asn Ser Leu Tyr
 65                  70                  75                  80

Leu His Met Asn Ser Leu Arg Ala Asp Asp Thr Ala Val Tyr Tyr Cys
                 85                  90                  95

Ala Arg Asp Gln Gly Tyr Ile Gly Tyr Asp Ser Tyr Tyr Tyr Tyr Ser
            100                 105                 110

Tyr Gly Met Asp Val Trp Gly Gln Gly Thr Thr Val Thr Val Ser Ser
        115                 120                 125
```

<210> SEQ ID NO 715
<211> LENGTH: 321
<212> TYPE: DNA
<213> ORGANISM: Artificial Sequence
<220> FEATURE:
<223> OTHER INFORMATION: Synthetic

<400> SEQUENCE: 715

```
gaaattgtgt tgacgcagtc tccaggcacc ctgcctttgt tccaggggga aagagccacc      60
ctctcctgta gggccagtca gagtgttaac aacaaattct tagcctggta ccagcagaaa     120
tctggccagg ctcccaggct cctcatctat ggtgcatcca gcagggccac tggcatccca     180
gacaggttca gtgcagtgg gtctgggacc gacttcactc tcaccatcag cggactggag      240
cctgaagatt ttgaagtgta ttattgtcaa gtatatggta actcactcac tttcggcgga     300
```
gggaccaagg tggagatcaa a                                              321

<210> SEQ ID NO 716
<211> LENGTH: 107
<212> TYPE: PRT
<213> ORGANISM: Artificial Sequence
<220> FEATURE:
<223> OTHER INFORMATION: Synthetic

<400> SEQUENCE: 716

Glu Ile Val Leu Thr Gln Ser Pro Gly Thr Leu Pro Leu Phe Pro Gly
1               5                   10                  15

Glu Arg Ala Thr Leu Ser Cys Arg Ala Ser Gln Ser Val Asn Asn Lys
            20                  25                  30

Phe Leu Ala Trp Tyr Gln Gln Lys Ser Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Gly Leu Glu
65                  70                  75                  80

Pro Glu Asp Phe Glu Val Tyr Tyr Cys Gln Val Tyr Gly Asn Ser Leu
                85                  90                  95

Thr Phe Gly Gly Gly Thr Lys Val Glu Ile Lys
            100                 105

<210> SEQ ID NO 717
<211> LENGTH: 384
<212> TYPE: DNA
<213> ORGANISM: Artificial Sequence
<220> FEATURE:
<223> OTHER INFORMATION: Synthetic

<400> SEQUENCE: 717
caggtgcagc tggtggagtc tgggggaggc ttggtcaagc ctggagggtc cctgagactc      60
tcctgtgcag cctctggatt caccttcagt gaccactaca tgagctggat ccgccaggct     120
ccagggaagg gctggagtg gtttcatac attagtaatg atggtggtac caaatactac       180
gcagactctg tgaagggccg attcaccatc tccagggaca acgccaagaa ctcactgtat     240
ctgcaaatga acagcctgag agccgaggac acggccgtgt attactgtgc gagagatcag     300
ggatatattg gctacgactc gtattattac tattcctacg gtatggacgt ctggggggcaa    360 gggaccacgg tcaccgtctc ctca                                            384

<210> SEQ ID NO 718
<211> LENGTH: 128
<212> TYPE: PRT
<213> ORGANISM: Artificial Sequence
<220> FEATURE:
<223> OTHER INFORMATION: Synthetic

<400> SEQUENCE: 718

Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp His
            20                  25                  30

Tyr Met Ser Trp Ile Arg Gln Ala Pro Gly Lys Gly Leu Glu Trp Val
        35                  40                  45

Ser Tyr Ile Ser Asn Asp Gly Gly Thr Lys Tyr Tyr Ala Asp Ser Val
    50                  55                  60

```
Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                 85                  90                  95

Ala Arg Asp Gln Gly Tyr Ile Gly Tyr Asp Ser Tyr Tyr Tyr Tyr Ser
            100                 105                 110

Tyr Gly Met Asp Val Trp Gly Gln Gly Thr Thr Val Thr Val Ser Ser
        115                 120                 125

<210> SEQ ID NO 719
<211> LENGTH: 321
<212> TYPE: DNA
<213> ORGANISM: Artificial Sequence
<220> FEATURE:
<223> OTHER INFORMATION: Synthetic

<400> SEQUENCE: 719
gaaattgtgt tgacgcagtc tccaggcacc ctgtctttgt ctccagggga aagagccacc      60
ctctcctgca gggccagtca gagtgttaac aacaaattct tagcctggta ccagcagaaa     120
cctggccagg ctcccaggct cctcatctat ggtgcatcca gcagggccac tggcatccca     180
gacaggttca gtggcagtgg gtctgggaca gacttcactc tcaccatcag cagactggag     240
cctgaagatt ttgcagtgta ttactgtcaa gtatatggta actcactcac tttcggcgga     300
gggaccaagg tggagatcaa a                                               321

<210> SEQ ID NO 720
<211> LENGTH: 107
<212> TYPE: PRT
<213> ORGANISM: Artificial Sequence
<220> FEATURE:
<223> OTHER INFORMATION: Synthetic

<400> SEQUENCE: 720

Glu Ile Val Leu Thr Gln Ser Pro Gly Thr Leu Ser Leu Ser Pro Gly
  1               5                  10                  15

Glu Arg Ala Thr Leu Ser Cys Arg Ala Ser Gln Ser Val Asn Asn Lys
             20                  25                  30

Phe Leu Ala Trp Tyr Gln Gln Lys Pro Gly Gln Ala Pro Arg Leu Leu
         35                  40                  45

Ile Tyr Gly Ala Ser Ser Arg Ala Thr Gly Ile Pro Asp Arg Phe Ser
     50                  55                  60

Gly Ser Gly Ser Gly Thr Asp Phe Thr Leu Thr Ile Ser Arg Leu Glu
 65                  70                  75                  80

Pro Glu Asp Phe Ala Val Tyr Tyr Cys Gln Val Tyr Gly Asn Ser Leu
                 85                  90                  95

Thr Phe Gly Gly Gly Thr Lys Val Glu Ile Lys
            100                 105

<210> SEQ ID NO 721
<211> LENGTH: 378
<212> TYPE: DNA
<213> ORGANISM: Artificial Sequence
<220> FEATURE:
<223> OTHER INFORMATION: Synthetic

<400> SEQUENCE: 721
caaattctgc tggtgcaatc tggacctgag gtgaaggagc tggggcctc agtgaaggtc       60 tcctgcaagg cttctggtta caccttttacc aactacgcta tcagctgggt gcgacaggtc   120
```

```
cctggacaag ggcttgagtg gatgggatgg gtcagcgctt acaatggtca cacaaactat      180
gcacatgaag tccagggcag agtcaccatg accacagaca catccacgac acagcctac      240 atggagctga ggagcctgag atctgacgac acggccatgt attactgtgc gagaggggt      300 gtagtcgtgc cagttgctcc ccacttctac aacggtatgg acgtctgggg ccaagggacc     360
acggtcaccg tctcctca                                                    378
```

<210> SEQ ID NO 722
<211> LENGTH: 126
<212> TYPE: PRT
<213> ORGANISM: Artificial Sequence
<220> FEATURE:
<223> OTHER INFORMATION: Synthetic

<400> SEQUENCE: 722

```
Gln Ile Leu Leu Val Gln Ser Gly Pro Glu Val Lys Glu Pro Gly Ala
 1               5                  10                  15

Ser Val Lys Val Ser Cys Lys Ala Ser Gly Tyr Thr Phe Thr Asn Tyr
            20                  25                  30

Ala Ile Ser Trp Val Arg Gln Val Pro Gly Gln Gly Leu Glu Trp Met
        35                  40                  45

Gly Trp Val Ser Ala Tyr Asn Gly His Thr Asn Tyr Ala His Glu Val
    50                  55                  60

Gln Gly Arg Val Thr Met Thr Thr Asp Thr Ser Thr Thr Thr Ala Tyr
65                  70                  75                  80

Met Glu Leu Arg Ser Leu Arg Ser Asp Asp Thr Ala Met Tyr Tyr Cys
                85                  90                  95

Ala Arg Gly Gly Val Val Val Pro Val Ala Pro His Phe Tyr Asn Gly
            100                 105                 110

Met Asp Val Trp Gly Gln Gly Thr Thr Val Thr Val Ser Ser
        115                 120                 125
```

<210> SEQ ID NO 723
<211> LENGTH: 24
<212> TYPE: DNA
<213> ORGANISM: Artificial Sequence
<220> FEATURE:
<223> OTHER INFORMATION: Synthetic

<400> SEQUENCE: 723

```
ggttacacct ttaccaacta cgct                                              24
```

<210> SEQ ID NO 724
<211> LENGTH: 8
<212> TYPE: PRT
<213> ORGANISM: Artificial Sequence
<220> FEATURE:
<223> OTHER INFORMATION: Synthetic

<400> SEQUENCE: 724

```
Gly Tyr Thr Phe Thr Asn Tyr Ala
 1               5
```

<210> SEQ ID NO 725
<211> LENGTH: 24
<212> TYPE: DNA
<213> ORGANISM: Artificial Sequence
<220> FEATURE:
<223> OTHER INFORMATION: Synthetic

<400> SEQUENCE: 725

```
gtcagcgctt acaatggtca caca                                           24
```

<210> SEQ ID NO 726
<211> LENGTH: 8
<212> TYPE: PRT
<213> ORGANISM: Artificial Sequence
<220> FEATURE:
<223> OTHER INFORMATION: Synthetic

<400> SEQUENCE: 726

Val Ser Ala Tyr Asn Gly His Thr
 1               5

<210> SEQ ID NO 727
<211> LENGTH: 57
<212> TYPE: DNA
<213> ORGANISM: Artificial Sequence
<220> FEATURE:
<223> OTHER INFORMATION: Synthetic

<400> SEQUENCE: 727

```
gcgagagggg gtgtagtcgt gccagttgct ccccacttct acaacggtat ggacgtc      57
```

<210> SEQ ID NO 728
<211> LENGTH: 19
<212> TYPE: PRT
<213> ORGANISM: Artificial Sequence
<220> FEATURE:
<223> OTHER INFORMATION: Synthetic

<400> SEQUENCE: 728

Ala Arg Gly Gly Val Val Pro Val Ala Pro His Phe Tyr Asn Gly
 1               5                  10                  15

Met Asp Val

<210> SEQ ID NO 729
<211> LENGTH: 336
<212> TYPE: DNA
<213> ORGANISM: Artificial Sequence
<220> FEATURE:
<223> OTHER INFORMATION: Synthetic

<400> SEQUENCE: 729

```
gatattgtga tgactcagtt tccactctcc ctgcccgtca cccctggaga gccggcctcc    60
atctcctgca ggtctagtca gagcctcctg catattaatg aatacaacta tttggattgg   120
tacctaaaga agccagggca gtctccacag ctcctgatct atttgggttt taatcgggcc   180
tccggggtcc ctgacaggtt cagtggcagt ggatcaggca cagattttac actgaaaatc   240
agcagagtgg aggctgagga tgttggggtc tattactgca tgcaagctct tcaaactccg   300
tggacgttcg gccaagggac caaggtggaa atcaaa                             336
```

<210> SEQ ID NO 730
<211> LENGTH: 112
<212> TYPE: PRT
<213> ORGANISM: Artificial Sequence
<220> FEATURE:
<223> OTHER INFORMATION: Synthetic

<400> SEQUENCE: 730

Asp Ile Val Met Thr Gln Phe Pro Leu Ser Leu Pro Val Thr Pro Gly
 1               5                  10                  15

Glu Pro Ala Ser Ile Ser Cys Arg Ser Ser Gln Ser Leu Leu His Ile

```
            20                  25                  30
Asn Glu Tyr Asn Tyr Leu Asp Trp Tyr Leu Lys Lys Pro Gly Gln Ser
        35                  40                  45

Pro Gln Leu Leu Ile Tyr Leu Gly Phe Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Thr Pro Trp Thr Phe Gly Gln Gly Thr Lys Val Glu Ile Lys
            100                 105                 110
```

<210> SEQ ID NO 731
<211> LENGTH: 33
<212> TYPE: DNA
<213> ORGANISM: Artificial Sequence
<220> FEATURE:
<223> OTHER INFORMATION: Synthetic

<400> SEQUENCE: 731
cagagcctcc tgcatattaa tgaatacaac tat                               33

<210> SEQ ID NO 732
<211> LENGTH: 11
<212> TYPE: PRT
<213> ORGANISM: Artificial Sequence
<220> FEATURE:
<223> OTHER INFORMATION: Synthetic

<400> SEQUENCE: 732

```
Gln Ser Leu Leu His Ile Asn Glu Tyr Asn Tyr
1               5                   10
```

<210> SEQ ID NO 733
<211> LENGTH: 9
<212> TYPE: DNA
<213> ORGANISM: Artificial Sequence
<220> FEATURE:
<223> OTHER INFORMATION: Synthetic

<400> SEQUENCE: 733 ttgggtttt                                                          9

<210> SEQ ID NO 734
<211> LENGTH: 3
<212> TYPE: PRT
<213> ORGANISM: Artificial Sequence
<220> FEATURE:
<223> OTHER INFORMATION: Synthetic

<400> SEQUENCE: 734

```
Leu Gly Phe
 1
```

<210> SEQ ID NO 735
<211> LENGTH: 27
<212> TYPE: DNA
<213> ORGANISM: Artificial Sequence
<220> FEATURE:
<223> OTHER INFORMATION: Synthetic

<400> SEQUENCE: 735
atgcaagctc ttcaaactcc gtggacg                                      27

<210> SEQ ID NO 736
<211> LENGTH: 9
<212> TYPE: PRT
<213> ORGANISM: Artificial Sequence
<220> FEATURE:
<223> OTHER INFORMATION: Synthetic

<400> SEQUENCE: 736

Met Gln Ala Leu Gln Thr Pro Trp Thr
1               5

<210> SEQ ID NO 737
<211> LENGTH: 378
<212> TYPE: DNA
<213> ORGANISM: Artificial Sequence
<220> FEATURE:
<223> OTHER INFORMATION: Synthetic

<400> SEQUENCE: 737
caggttcagc tggtgcagtc tggacctgag gtgaaggagc ctggggcctc agtgaaggtc      60
tcctgcaagg cttctggtta cacctttacc aactacgcta tcagctgggt gcgacaggtc    120
cctggacaag gcttgagtg gatgggatgg gtcagcgctt acaatggtca cacaaactat     180
gcacatgaag tccagggcag agtcaccatg accacagaca catccacgac cacagcctac    240
atggagctga ggagcctgag atctgacgac acggccatgt attactgtgc gagagggggt    300
gtagtcgtgc cagttgctcc ccacttctac aacggtatgg acgtctgggg ccaagggacc    360
acggtcaccg tctcctca                                                  378

<210> SEQ ID NO 738
<211> LENGTH: 126
<212> TYPE: PRT
<213> ORGANISM: Artificial Sequence
<220> FEATURE:
<223> OTHER INFORMATION: Synthetic

<400> SEQUENCE: 738

Gln Val Gln Leu Val Gln Ser Gly Pro Glu Val Lys Glu Pro Gly Ala
1               5                   10                  15

Ser Val Lys Val Ser Cys Lys Ala Ser Gly Tyr Thr Phe Thr Asn Tyr
                20                  25                  30

Ala Ile Ser Trp Val Arg Gln Val Pro Gly Gln Gly Leu Glu Trp Met
            35                  40                  45

Gly Trp Val Ser Ala Tyr Asn Gly His Thr Asn Tyr Ala His Glu Val
        50                  55                  60

Gln Gly Arg Val Thr Met Thr Thr Asp Thr Ser Thr Thr Thr Ala Tyr
65                  70                  75                  80

Met Glu Leu Arg Ser Leu Arg Ser Asp Asp Thr Ala Met Tyr Tyr Cys
                85                  90                  95

Ala Arg Gly Gly Val Val Val Pro Val Ala Pro His Phe Tyr Asn Gly
            100                 105                 110

Met Asp Val Trp Gly Gln Gly Thr Thr Val Thr Val Ser Ser
        115                 120                 125

<210> SEQ ID NO 739
<211> LENGTH: 336
<212> TYPE: DNA
<213> ORGANISM: Artificial Sequence
<220> FEATURE:
<223> OTHER INFORMATION: Synthetic -continued

<400> SEQUENCE: 739

```
gatattgtga tgactcagtc tccactctcc ctgcccgtca ccctggaga gccggcctcc    60 atctcctgca ggtctagtca gagcctcctg catattaatg aatacaacta tttggattgg   120
tacctaaaga agccagggca gtctccacag ctcctgatct atttgggttt taatcgggcc   180
tccggggtcc ctgacaggtt cagtggcagt ggatcaggca cagattttac actgaaaatc   240
agcagagtgg aggctgagga tgttggggtc tattactgca tgcaagctct tcaaactccg   300
tggacgttcg gccaagggac caaggtggaa atcaaa                             336
```

<210> SEQ ID NO 740
<211> LENGTH: 112
<212> TYPE: PRT
<213> ORGANISM: Artificial Sequence
<220> FEATURE:
<223> OTHER INFORMATION: Synthetic

<400> SEQUENCE: 740

```
Asp Ile Val Met Thr Gln Ser Pro Leu Ser Leu Pro Val Thr Pro Gly
 1               5                  10                  15

Glu Pro Ala Ser Ile Ser Cys Arg Ser Ser Gln Ser Leu Leu His Ile
            20                  25                  30

Asn Glu Tyr Asn Tyr Leu Asp Trp Tyr Leu Lys Lys Pro Gly Gln Ser
        35                  40                  45

Pro Gln Leu Leu Ile Tyr Leu Gly Phe Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Thr Pro Trp Thr Phe Gly Gln Gly Thr Lys Val Glu Ile Lys
            100                 105                 110
```

<210> SEQ ID NO 741
<211> LENGTH: 378
<212> TYPE: DNA
<213> ORGANISM: Artificial Sequence
<220> FEATURE:
<223> OTHER INFORMATION: Synthetic

<400> SEQUENCE: 741

```
caggttcagc tggtgcagtc tggagctgag gtgaagaagc ctggggcctc agtgaaggtc    60
tcctgcaagg cttctggtta ccctttacc aactacgctg tcagctgggt gcgacaggcc   120
cctggacaag gcttgagtg gatgggatgg gtcagcgctt acaatggtca cacaaactat   180
gcacagaagc tccagggcag agtcaccatg accacagaca catccacgag cacagcctac   240
atggagctga ggagcctgag atctgacgac acggccgtgt attactgtgc gagggggggt   300
gtagtcgtgc cagttgctcc ccacttctac aacggtatgg acgtctgggg gcaagggacc   360
acggtcaccg tctcctca                                                 378
```

<210> SEQ ID NO 742
<211> LENGTH: 126
<212> TYPE: PRT
<213> ORGANISM: Artificial Sequence
<220> FEATURE:
<223> OTHER INFORMATION: Synthetic

<400> SEQUENCE: 742

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
                20                  25                  30

Ala Ile Ser Trp Val Arg Gln Ala Pro Gly Gln Gly Leu Glu Trp Met
            35                  40                  45

Gly Trp Val Ser Ala Tyr Asn Gly His Thr Asn Tyr Ala Gln Lys Leu
50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Gly Gly Val Val Pro Val Ala Pro His Phe Tyr Asn Gly
            100                 105                 110

Met Asp Val Trp Gly Gln Gly Thr Thr Val Thr Val Ser Ser
            115                 120                 125

<210> SEQ ID NO 743
<211> LENGTH: 336
<212> TYPE: DNA
<213> ORGANISM: Artificial Sequence
<220> FEATURE:
<223> OTHER INFORMATION: Synthetic

<400> SEQUENCE: 743
gatattgtga tgactcagtc tccactctcc ctgcccgtca cccctggaga gccggcctcc      60
atctcctgca ggtctagtca gagcctcctg catattaatg aatacaacta tttggattgg    120
tacctgcaga agccagggca gtctccacag ctcctgatct atttgggttc taatcgggcc    180
tccggggtcc ctgacaggtt cagtggcagt ggatcaggca cagattttac actgaaaatc    240
agcagagtgg aggctgagga tgttggggtt tattactgca tgcaagctct tcaaactccg    300
tggacgttcg gccaagggac caaggtggaa atcaaa                              336

<210> SEQ ID NO 744
<211> LENGTH: 112
<212> TYPE: PRT
<213> ORGANISM: Artificial Sequence
<220> FEATURE:
<223> OTHER INFORMATION: Synthetic

<400> SEQUENCE: 744

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ile
                20                  25                  30

Asn Glu Tyr Asn Tyr Leu Asp Trp Tyr Leu Gln Lys Pro Gly Gln Ser
            35                  40                  45

Pro Gln Leu Leu Ile Tyr Leu Gly Ser Asn Arg Ala Ser Gly Val Pro
50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Thr Pro Trp Thr Phe Gly Gln Gly Thr Lys Val Glu Ile Lys
            100                 105                 110

<210> SEQ ID NO 745

```
<211> LENGTH: 8
<212> TYPE: PRT
<213> ORGANISM: Artificial Sequence
<220> FEATURE:
<223> OTHER INFORMATION: Synthetic
<221> NAME/KEY: VARIANT
<222> LOCATION: (1)...(8)
<223> OTHER INFORMATION: Xaa = Any amino acid

<400> SEQUENCE: 745

Xaa Xaa Xaa Xaa Xaa Xaa Xaa Xaa
 1               5

<210> SEQ ID NO 746
<211> LENGTH: 8
<212> TYPE: PRT
<213> ORGANISM: Artificial Sequence
<220> FEATURE:
<223> OTHER INFORMATION: Synthetic
<221> NAME/KEY: VARIANT
<222> LOCATION: (1)...(8)
<223> OTHER INFORMATION: Xaa - Any amino acid

<400> SEQUENCE: 746

Xaa Xaa Xaa Xaa Xaa Xaa Xaa Xaa
 1               5

<210> SEQ ID NO 747
<211> LENGTH: 16
<212> TYPE: PRT
<213> ORGANISM: Artificial Sequence
<220> FEATURE:
<223> OTHER INFORMATION: Synthetic
<221> NAME/KEY: VARIANT
<222> LOCATION: (1)...(16)
<223> OTHER INFORMATION: Xaa = Any amino acid

<400> SEQUENCE: 747

Xaa Xaa Xaa Xaa Xaa Xaa Xaa Xaa Xaa Xaa Xaa Xaa Xaa Xaa Xaa Xaa
 1               5                  10                  15

<210> SEQ ID NO 748
<211> LENGTH: 12
<212> TYPE: PRT
<213> ORGANISM: Artificial Sequence
<220> FEATURE:
<223> OTHER INFORMATION: Synthetic
<221> NAME/KEY: VARIANT
<222> LOCATION: (1)...(12)
<223> OTHER INFORMATION: Xaa = Any amino acid

<400> SEQUENCE: 748

Xaa Xaa Xaa Xaa Xaa Xaa Xaa Xaa Xaa Xaa Xaa Xaa
 1               5                  10

<210> SEQ ID NO 749
<211> LENGTH: 3
<212> TYPE: PRT
<213> ORGANISM: Artificial Sequence
<220> FEATURE:
<223> OTHER INFORMATION: Synthetic
<221> NAME/KEY: VARIANT
<222> LOCATION: (1)...(3)
<223> OTHER INFORMATION: Xaa = Any amino acid

<400> SEQUENCE: 749

Xaa Xaa Xaa
 1
```

```
<210> SEQ ID NO 750
<211> LENGTH: 9
<212> TYPE: PRT
<213> ORGANISM: Artificial Sequence
<220> FEATURE:
<223> OTHER INFORMATION: Synthetic
<221> NAME/KEY: VARIANT
<222> LOCATION: (1)...(9)
<223> OTHER INFORMATION: Xaa = Any amino acid

<400> SEQUENCE: 750

Xaa Xaa Xaa Xaa Xaa Xaa Xaa Xaa Xaa
 1               5

<210> SEQ ID NO 751
<211> LENGTH: 330
<212> TYPE: PRT
<213> ORGANISM: Artificial Sequence
<220> FEATURE:
<223> OTHER INFORMATION: Synthetic

<400> SEQUENCE: 751

Ala Ser Thr Lys Gly Pro Ser Val Phe Pro Leu Ala Pro Ser Ser Lys
 1               5                  10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285
```

Leu Tyr Ser Lys Leu Thr Val Asp Lys Ser Arg Trp Gln Gln Gly Asn
            290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
            325                 330

<210> SEQ ID NO 752
<211> LENGTH: 327
<212> TYPE: PRT
<213> ORGANISM: Artificial Sequence
<220> FEATURE:
<223> OTHER INFORMATION: Synthetic

<400> SEQUENCE: 752

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Ser Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
290                 295                 300

Cys Ser Val Met His Glu Ala Leu His Asn His Tyr Thr Gln Lys Ser
305                 310                 315                 320

```
Leu Ser Leu Ser Leu Gly Lys
            325

<210> SEQ ID NO 753
<211> LENGTH: 327
<212> TYPE: PRT
<213> ORGANISM: Artificial Sequence
<220> FEATURE:
<223> OTHER INFORMATION: Synthetic

<400> SEQUENCE: 753

Ala Ser Thr Lys Gly Pro Ser Val Phe Pro Leu Ala Pro Cys Ser Arg
 1               5                  10                  15

Ser Thr Ser Glu Ser Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Leu Gly Lys
            325

<210> SEQ ID NO 754
<211> LENGTH: 2076
```

<212> TYPE: DNA
<213> ORGANISM: Homo sapiens

<400> SEQUENCE: 754

```
atgggcaccg tcagctccag gcggtcctgg tggccgctgc cactgctgct gctgctgctg    60
ctgctcctgg gtcccgcggg cgcccgtgcg caggaggacg aggacggcga ctacgaggag   120
ctggtgctag ccttgcgttc gcggaggac ggcctggccg aagcacccga gcacggaacc    180
acagccacct ccaccgctg cgccaaggat ccgtggaggt tgcctggcac ctacgtggtg    240
gtgctgaagg aggagaccca cctctcgcag tcagagcgca ctgcccgccg cctgcaggcc   300
caggctgccc gccggggata cctcaccaag atcctgcatg tcttccatgg ccttcttcct   360
ggcttcctgg tgaagatgag tggcgacctg ctggagctgg ccttgaagtt gccccatgtc   420
gactacatcg aggaggactc ctctgtcttt gcccagagca tcccgtggaa cctggagcgg   480
attccccctc cacggtaccg ggcggatgaa taccagcccc ccgacggagg cagcctggtg   540
gaggtgtatc tcctagacac cagcatacag agtgaccacc gggaaatcga gggcagggtc   600
atggtcaccg acttcgagaa tgtgcccgag gaggacggga cccgcttcca cagacaggcc   660
agcaagtgtg acagtcatgg cacccacctg gcagggtgg tcagcggccg ggatgccggc    720
gtggccaagg gtgccagcat gcgcagcctg cgcgtgctca actgccaagg gaagggcacg   780
gttagcggca ccctcatagg cctggagttt attcggaaaa gccagctggt ccagcctgtg   840
gggccactgg tggtgctgct gccctggcg ggtgggtaca gccgcgtcct caacgccgcc    900
tgccagcgcc tggcgagggc tggggtcgtg ctggtcaccg ctgccggcaa cttccgggac   960
gatgcctgcc tctactcccc agcctcagct cccgaggtca tcacagttgg ggccaccaat   1020
gcccaagacc agccggtgac cctggggact tggggaccaa actttggccg ctgtgtggac   1080
ctctttgccc caggggagga catcattggt gcctccagcg actgcagcac ctgctttgtg   1140
tcacagagtg gacatcaca ggctgctgcc cacgtggctg gcattgcagc catgatgctg    1200
tctgccgagc cggagctcac cctggccgag ttgaggcaga gactgatcca cttctctgcc   1260
aaagatgtca tcaatgaggc ctggttccct gaggaccagc gggtactgac ccccaacctg   1320
gtggccgccc tgccccccag cacccatggg gcaggttggc agctgttttg caggactgta   1380
tggtcagcac actcggggcc tacacggatg ccacagccg tcgcccgctg cgccccagat   1440
gaggagctgc tgagctgctc cagtttctcc aggagtggga gcggcgggg cgagcgcatg   1500
gaggcccaag ggggcaagct ggtctgccgg gcccacaacg cttttggggg tgagggtgtc   1560
tacgccattg ccaggtgctg cctgctaccc caggccaact gcagcgtcca cagctcca    1620
ccagctgagg ccagcatggg gacccgtgtc cactgccacc aacagggcca cgtcctcaca   1680
ggctgcagct cccactggga ggtggaggac cttggcaccc acaagccgcc tgtgctgagg   1740
ccacgaggtc agcccaacca gtgcgtgggc cacagggagg ccagcatcca cgcttcctgc   1800
tgccatgccc caggtctgga atgcaaagtc aaggagcatg gaatcccggc ccctcaggag   1860
caggtgaccg tggcctgcga ggagggctgg accctgactg gctgcagtgc cctccctggg   1920
acctcccacg tcctggggc ctacgccgta gacaacacgt gtgtagtcag gagccgggac   1980
gtcagcacta caggcagcac cagcgaaggg ccgtgacac ccgttgccat ctgctgccgg    2040
agccggcacc tggcgcaggc ctcccaggag ctccag                              2076
```

<210> SEQ ID NO 755
<211> LENGTH: 692
<212> TYPE: PRT

<213> ORGANISM: Homo sapiens

<400> SEQUENCE: 755

```
Met Gly Thr Val Ser Ser Arg Arg Ser Trp Trp Pro Leu Pro Leu Leu
1               5                   10                  15
Leu Leu Leu Leu Leu Leu Leu Gly Pro Ala Gly Ala Arg Ala Gln Glu
            20                  25                  30
Asp Glu Asp Gly Asp Tyr Glu Glu Leu Val Leu Ala Leu Arg Ser Glu
        35                  40                  45
Glu Asp Gly Leu Ala Glu Ala Pro Glu His Gly Thr Thr Ala Thr Phe
    50                  55                  60
His Arg Cys Ala Lys Asp Pro Trp Arg Leu Pro Gly Thr Tyr Val Val
65                  70                  75                  80
Val Leu Lys Glu Glu Thr His Leu Ser Gln Ser Glu Arg Thr Ala Arg
                85                  90                  95
Arg Leu Gln Ala Gln Ala Ala Arg Arg Gly Tyr Leu Thr Lys Ile Leu
            100                 105                 110
His Val Phe His Gly Leu Leu Pro Gly Phe Leu Val Lys Met Ser Gly
        115                 120                 125
Asp Leu Leu Glu Leu Ala Leu Lys Leu Pro His Val Asp Tyr Ile Glu
    130                 135                 140
Glu Asp Ser Ser Val Phe Ala Gln Ser Ile Pro Trp Asn Leu Glu Arg
145                 150                 155                 160
Ile Thr Pro Pro Arg Tyr Arg Ala Asp Glu Tyr Gln Pro Pro Asp Gly
                165                 170                 175
Gly Ser Leu Val Glu Val Tyr Leu Leu Asp Thr Ser Ile Gln Ser Asp
            180                 185                 190
His Arg Glu Ile Glu Gly Arg Val Met Val Thr Asp Phe Glu Asn Val
        195                 200                 205
Pro Glu Glu Asp Gly Thr Arg Phe His Arg Gln Ala Ser Lys Cys Asp
    210                 215                 220
Ser His Gly Thr His Leu Ala Gly Val Val Ser Gly Arg Asp Ala Gly
225                 230                 235                 240
Val Ala Lys Gly Ala Ser Met Arg Ser Leu Arg Val Leu Asn Cys Gln
                245                 250                 255
Gly Lys Gly Thr Val Ser Gly Thr Leu Ile Gly Leu Glu Phe Ile Arg
            260                 265                 270
Lys Ser Gln Leu Val Gln Pro Val Gly Pro Leu Val Val Leu Leu Pro
        275                 280                 285
Leu Ala Gly Gly Tyr Ser Arg Val Leu Asn Ala Ala Cys Gln Arg Leu
    290                 295                 300
Ala Arg Ala Gly Val Val Leu Val Thr Ala Ala Gly Asn Phe Arg Asp
305                 310                 315                 320
Asp Ala Cys Leu Tyr Ser Pro Ala Ser Ala Pro Glu Val Ile Thr Val
                325                 330                 335
Gly Ala Thr Asn Ala Gln Asp Gln Pro Val Thr Leu Gly Thr Leu Gly
            340                 345                 350
Thr Asn Phe Gly Arg Cys Val Asp Leu Phe Ala Pro Gly Glu Asp Ile
        355                 360                 365
Ile Gly Ala Ser Ser Asp Cys Ser Thr Cys Phe Val Ser Gln Ser Gly
    370                 375                 380
Thr Ser Gln Ala Ala Ala His Val Ala Gly Ile Ala Ala Met Met Leu
385                 390                 395                 400
```

```
Ser Ala Glu Pro Glu Leu Thr Leu Ala Glu Leu Arg Gln Arg Leu Ile
            405                 410                 415

His Phe Ser Ala Lys Asp Val Ile Asn Glu Ala Trp Phe Pro Glu Asp
        420                 425                 430

Gln Arg Val Leu Thr Pro Asn Leu Val Ala Ala Leu Pro Pro Ser Thr
    435                 440                 445

His Gly Ala Gly Trp Gln Leu Phe Cys Arg Thr Val Trp Ser Ala His
450                 455                 460

Ser Gly Pro Thr Arg Met Ala Thr Ala Val Ala Arg Cys Ala Pro Asp
465                 470                 475                 480

Glu Glu Leu Leu Ser Cys Ser Ser Phe Ser Arg Ser Gly Lys Arg Arg
                485                 490                 495

Gly Glu Arg Met Glu Ala Gln Gly Gly Lys Leu Val Cys Arg Ala His
            500                 505                 510

Asn Ala Phe Gly Gly Glu Gly Val Tyr Ala Ile Ala Arg Cys Cys Leu
        515                 520                 525

Leu Pro Gln Ala Asn Cys Ser Val His Thr Ala Pro Pro Ala Glu Ala
    530                 535                 540

Ser Met Gly Thr Arg Val His Cys His Gln Gln Gly His Val Leu Thr
545                 550                 555                 560

Gly Cys Ser Ser His Trp Glu Val Glu Asp Leu Gly Thr His Lys Pro
                565                 570                 575

Pro Val Leu Arg Pro Arg Gly Gln Pro Asn Gln Cys Val Gly His Arg
            580                 585                 590

Glu Ala Ser Ile His Ala Ser Cys Cys His Ala Pro Gly Leu Glu Cys
        595                 600                 605

Lys Val Lys Glu His Gly Ile Pro Ala Pro Gln Glu Gln Val Thr Val
    610                 615                 620

Ala Cys Glu Glu Gly Trp Thr Leu Thr Gly Cys Ser Ala Leu Pro Gly
625                 630                 635                 640

Thr Ser His Val Leu Gly Ala Tyr Ala Val Asp Asn Thr Cys Val Val
                645                 650                 655

Arg Ser Arg Asp Val Ser Thr Thr Gly Ser Thr Ser Glu Gly Ala Val
            660                 665                 670

Thr Ala Val Ala Ile Cys Cys Arg Ser Arg His Leu Ala Gln Ala Ser
        675                 680                 685

Gln Glu Leu Gln
    690

<210> SEQ ID NO 756
<211> LENGTH: 692
<212> TYPE: PRT
<213> ORGANISM: Macaca mulata

<400> SEQUENCE: 756

Met Gly Thr Val Ser Ser Arg Arg Ser Trp Trp Pro Leu Pro Leu Pro
1               5                   10                  15

Leu Leu Leu Leu Leu Leu Leu Gly Pro Ala Gly Ala Arg Ala Gln Glu
            20                  25                  30

Asp Glu Asp Gly Asp Tyr Glu Glu Leu Val Leu Ala Leu Arg Ser Glu
        35                  40                  45

Glu Asp Gly Leu Ala Asp Ala Pro Glu His Gly Ala Thr Ala Thr Phe
    50                  55                  60

His Arg Cys Ala Lys Asp Pro Trp Arg Leu Pro Gly Thr Tyr Val Val
65                  70                  75                  80
```

```
Val Leu Lys Glu Glu Thr His Arg Ser Gln Ser Glu Arg Thr Ala Arg
                85                  90                  95

Arg Leu Gln Ala Gln Ala Ala Arg Arg Gly Tyr Leu Thr Lys Ile Leu
                100                 105                 110

His Val Phe His His Leu Leu Pro Gly Phe Leu Val Lys Met Ser Gly
            115                 120                 125

Asp Leu Leu Glu Leu Ala Leu Lys Leu Pro His Val Asp Tyr Ile Glu
        130                 135                 140

Glu Asp Ser Ser Val Phe Ala Gln Ser Ile Pro Trp Asn Leu Glu Arg
145                 150                 155                 160

Ile Thr Pro Ala Arg Tyr Arg Ala Asp Glu Tyr Gln Pro Pro Lys Gly
                165                 170                 175

Gly Ser Leu Val Glu Val Tyr Leu Leu Asp Thr Ser Ile Gln Ser Asp
                180                 185                 190

His Arg Glu Ile Glu Gly Arg Val Met Val Thr Asp Phe Glu Ser Val
                195                 200                 205

Pro Glu Glu Asp Gly Thr Arg Phe His Arg Gln Ala Ser Lys Cys Asp
        210                 215                 220

Ser His Gly Thr His Leu Ala Gly Val Val Ser Gly Arg Asp Ala Gly
225                 230                 235                 240

Val Ala Lys Gly Ala Gly Leu Arg Ser Leu Arg Val Leu Asn Cys Gln
                245                 250                 255

Gly Lys Gly Thr Val Ser Gly Thr Leu Ile Gly Leu Glu Phe Ile Arg
                260                 265                 270

Lys Ser Gln Leu Val Gln Pro Val Gly Pro Leu Val Val Leu Leu Pro
            275                 280                 285

Leu Ala Gly Gly Tyr Ser Arg Val Phe Asn Ala Ala Cys Gln Arg Leu
        290                 295                 300

Ala Arg Ala Gly Val Val Leu Val Thr Ala Ala Gly Asn Phe Arg Asp
305                 310                 315                 320

Asp Ala Cys Leu Tyr Ser Pro Ala Ser Ala Pro Glu Val Ile Thr Val
                325                 330                 335

Gly Ala Thr Asn Ala Gln Asp Gln Pro Val Thr Leu Gly Thr Leu Gly
                340                 345                 350

Thr Asn Phe Gly Arg Cys Val Asp Leu Phe Ala Pro Gly Glu Asp Ile
            355                 360                 365

Ile Gly Ala Ser Ser Asp Cys Ser Thr Cys Phe Val Ser Arg Ser Gly
        370                 375                 380

Thr Ser Gln Ala Ala Ala His Val Ala Gly Ile Ala Ala Met Met Leu
385                 390                 395                 400

Ser Ala Glu Pro Glu Leu Thr Leu Ala Glu Leu Arg Gln Arg Leu Ile
                405                 410                 415

His Phe Ser Ala Lys Asp Val Ile Asn Glu Ala Trp Phe Pro Glu Asp
                420                 425                 430

Gln Arg Val Leu Thr Pro Asn Leu Val Ala Ala Leu Pro Pro Ser Thr
            435                 440                 445

His Arg Ala Gly Trp Gln Leu Phe Cys Arg Thr Val Trp Ser Ala His
        450                 455                 460

Ser Gly Pro Thr Arg Met Ala Thr Ala Val Ala Arg Cys Ala Gln Asp
465                 470                 475                 480

Glu Glu Leu Leu Ser Cys Ser Ser Phe Ser Arg Ser Gly Lys Arg Arg
                485                 490                 495
```

```
Gly Glu Arg Ile Glu Ala Gln Gly Gly Lys Arg Val Cys Arg Ala His
                500                 505                 510

Asn Ala Phe Gly Gly Glu Gly Val Tyr Ala Ile Ala Arg Cys Cys Leu
            515                 520                 525

Leu Pro Gln Val Asn Cys Ser Val His Thr Ala Pro Pro Ala Gly Ala
        530                 535                 540

Ser Met Gly Thr Arg Val His Cys His Gln Gln Gly His Val Leu Thr
545                 550                 555                 560

Gly Cys Ser Ser His Trp Glu Val Glu Asp Leu Gly Thr His Lys Pro
                565                 570                 575

Pro Val Leu Arg Pro Arg Gly Gln Pro Asn Gln Cys Val Gly His Arg
            580                 585                 590

Glu Ala Ser Ile His Ala Ser Cys Cys His Ala Pro Gly Leu Glu Cys
        595                 600                 605

Lys Val Lys Glu His Gly Ile Pro Ala Pro Gln Glu Gln Val Ile Val
        610                 615                 620

Ala Cys Glu Asp Gly Trp Thr Leu Thr Gly Cys Ser Pro Leu Pro Gly
625                 630                 635                 640

Thr Ser His Val Leu Gly Ala Tyr Ala Val Asp Asn Thr Cys Val Val
                645                 650                 655

Arg Ser Arg Asp Val Ser Thr Thr Gly Ser Thr Ser Lys Glu Ala Val
            660                 665                 670

Ala Ala Val Ala Ile Cys Cys Arg Ser Arg His Leu Val Gln Ala Ser
        675                 680                 685

Gln Glu Leu Gln
    690

<210> SEQ ID NO 757
<211> LENGTH: 694
<212> TYPE: PRT
<213> ORGANISM: Mus muscular

<400> SEQUENCE: 757

Met Gly Thr His Cys Ser Ala Trp Leu Arg Trp Pro Leu Leu Pro Leu
1               5                   10                  15

Leu Pro Pro Leu Leu Leu Leu Leu Leu Cys Pro Thr Gly Ala
            20                  25                  30

Gly Ala Gln Asp Glu Asp Gly Asp Tyr Glu Glu Leu Met Leu Ala Leu
            35                  40                  45

Pro Ser Gln Glu Asp Gly Leu Ala Asp Glu Ala His Val Ala Thr
        50                  55                  60

Ala Thr Phe Arg Arg Cys Ser Lys Glu Ala Trp Arg Leu Pro Gly Thr
65                  70                  75                  80

Tyr Ile Val Val Leu Met Glu Glu Thr Gln Arg Leu Gln Ile Glu Gln
                85                  90                  95

Thr Ala His Arg Leu Gln Thr Arg Ala Ala Arg Gly Tyr Val Ile
            100                 105                 110

Lys Val Leu His Ile Phe Tyr Asp Leu Phe Pro Gly Phe Leu Val Lys
        115                 120                 125

Met Ser Ser Asp Leu Leu Gly Leu Ala Leu Lys Leu Pro His Val Glu
    130                 135                 140

Tyr Ile Glu Glu Asp Ser Phe Val Phe Ala Gln Ser Ile Pro Trp Asn
145                 150                 155                 160

Leu Glu Arg Ile Ile Pro Ala Trp His Gln Thr Glu Glu Asp Arg Ser
                165                 170                 175
```

```
Pro Asp Gly Ser Ser Gln Val Glu Val Tyr Leu Leu Asp Thr Ser Ile
            180                 185                 190

Gln Gly Ala His Arg Glu Ile Glu Gly Arg Val Thr Ile Thr Asp Phe
        195                 200                 205

Asn Ser Val Pro Glu Glu Asp Gly Thr Arg Phe His Arg Gln Ala Ser
    210                 215                 220

Lys Cys Asp Ser His Gly Thr His Leu Ala Gly Val Val Ser Gly Arg
225                 230                 235                 240

Asp Ala Gly Val Ala Lys Gly Thr Ser Leu His Ser Leu Arg Val Leu
                245                 250                 255

Asn Cys Gln Gly Lys Gly Thr Val Ser Gly Thr Leu Ile Gly Leu Glu
            260                 265                 270

Phe Ile Arg Lys Ser Gln Leu Ile Gln Pro Ser Gly Pro Leu Val Val
        275                 280                 285

Leu Leu Pro Leu Ala Gly Gly Tyr Ser Arg Ile Leu Asn Ala Ala Cys
    290                 295                 300

Arg His Leu Ala Arg Thr Gly Val Val Leu Val Ala Ala Ala Gly Asn
305                 310                 315                 320

Phe Arg Asp Asp Ala Cys Leu Tyr Ser Pro Ala Ser Ala Pro Glu Val
                325                 330                 335

Ile Thr Val Gly Ala Thr Asn Ala Gln Asp Gln Pro Val Thr Leu Gly
            340                 345                 350

Thr Leu Gly Thr Asn Phe Gly Arg Cys Val Asp Leu Phe Ala Pro Gly
        355                 360                 365

Lys Asp Ile Ile Gly Ala Ser Ser Asp Cys Ser Thr Cys Phe Met Ser
    370                 375                 380

Gln Ser Gly Thr Ser Gln Ala Ala Ala His Val Ala Gly Ile Val Ala
385                 390                 395                 400

Arg Met Leu Ser Arg Glu Pro Thr Leu Thr Leu Ala Glu Leu Arg Gln
                405                 410                 415

Arg Leu Ile His Phe Ser Thr Lys Asp Val Ile Asn Met Ala Trp Phe
            420                 425                 430

Pro Glu Asp Gln Gln Val Leu Thr Pro Asn Leu Val Ala Thr Leu Pro
        435                 440                 445

Pro Ser Thr His Glu Thr Gly Gly Gln Leu Leu Cys Arg Thr Val Trp
    450                 455                 460

Ser Ala His Ser Gly Pro Thr Arg Thr Ala Thr Ala Thr Ala Arg Cys
465                 470                 475                 480

Ala Pro Glu Glu Glu Leu Leu Ser Cys Ser Phe Ser Arg Ser Gly
                485                 490                 495

Arg Arg Arg Gly Asp Trp Ile Glu Ala Ile Gly Gly Gln Gln Val Cys
            500                 505                 510

Lys Ala Leu Asn Ala Phe Gly Gly Glu Gly Val Tyr Ala Val Ala Arg
        515                 520                 525

Cys Cys Leu Val Pro Arg Ala Asn Cys Ser Ile His Asn Thr Pro Ala
    530                 535                 540

Ala Arg Ala Gly Leu Glu Thr His Val His Cys His Gln Lys Asp His
545                 550                 555                 560

Val Leu Thr Gly Cys Ser Phe His Trp Glu Val Glu Asp Leu Ser Val
                565                 570                 575

Arg Arg Gln Pro Ala Leu Arg Ser Arg Arg Gln Pro Gly Gln Cys Val
            580                 585                 590
```

```
Gly His Gln Ala Ala Ser Val Tyr Ala Ser Cys Cys His Ala Pro Gly
            595                 600                 605

Leu Glu Cys Lys Ile Lys Glu His Gly Ile Ser Gly Pro Ser Glu Gln
610                 615                 620

Val Thr Val Ala Cys Glu Ala Gly Trp Thr Leu Thr Gly Cys Asn Val
625                 630                 635                 640

Leu Pro Gly Ala Ser Leu Thr Leu Gly Ala Tyr Ser Val Asp Asn Leu
            645                 650                 655

Cys Val Ala Arg Val His Asp Thr Ala Arg Ala Asp Arg Thr Ser Gly
            660                 665                 670

Glu Ala Thr Val Ala Ala Ile Cys Cys Arg Ser Arg Pro Ser Ala
            675                 680                 685

Lys Ala Ser Trp Val Gln
            690

<210> SEQ ID NO 758
<211> LENGTH: 653
<212> TYPE: PRT
<213> ORGANISM: Homo sapiens

<400> SEQUENCE: 758

Glu Phe Arg Cys His Asp Gly Lys Cys Ile Ser Arg Gln Phe Val Cys
 1               5                  10                  15

Asp Ser Asp Arg Asp Cys Leu Asp Gly Ser Asp Glu Ala Ser Cys Pro
             20                  25                  30

Val Leu Thr Cys Gly Pro Ala Ser Phe Gln Cys Asn Ser Ser Thr Cys
         35                  40                  45

Ile Pro Gln Leu Trp Ala Cys Asp Asn Asp Pro Asp Cys Glu Asp Gly
     50                  55                  60

Ser Asp Glu Trp Pro Gln Arg Cys Arg Gly Leu Tyr Val Phe Gln Gly
65                  70                  75                  80

Asp Ser Ser Pro Cys Ser Ala Phe Glu Phe His Cys Leu Ser Gly Glu
                 85                  90                  95

Cys Ile His Ser Ser Trp Arg Cys Asp Gly Gly Pro Asp Cys Lys Asp
            100                 105                 110

Lys Ser Asp Glu Glu Asn Cys Ala Val Ala Thr Cys Arg Pro Asp Glu
        115                 120                 125

Phe Gln Cys Ser Asp Gly Asn Cys Ile His Gly Ser Arg Gln Cys Asp
    130                 135                 140

Arg Glu Tyr Asp Cys Lys Asp Met Ser Asp Glu Val Gly Cys Val Asn
145                 150                 155                 160

Val Thr Leu Cys Glu Gly Pro Asn Lys Phe Lys Cys His Ser Gly Glu
                165                 170                 175

Cys Ile Thr Leu Asp Lys Val Cys Asn Met Ala Arg Asp Cys Arg Asp
            180                 185                 190

Trp Ser Asp Glu Pro Ile Lys Glu Cys Gly Thr Asn Glu Cys Leu Asp
        195                 200                 205

Asn Asn Gly Gly Cys Ser His Val Cys Asn Asp Leu Lys Ile Gly Tyr
    210                 215                 220

Glu Cys Leu Cys Pro Asp Gly Phe Gln Leu Val Ala Gln Arg Arg Cys
225                 230                 235                 240

Glu Asp Ile Asp Glu Cys Gln Asp Pro Asp Thr Cys Ser Gln Leu Cys
                245                 250                 255

Val Asn Leu Glu Gly Gly Tyr Lys Cys Gln Cys Glu Glu Gly Phe Gln
            260                 265                 270
```

-continued

```
Leu Asp Pro His Thr Lys Ala Cys Lys Ala Val Gly Ser Ile Ala Tyr
        275                 280                 285

Leu Phe Phe Thr Asn Arg His Glu Val Arg Lys Met Thr Leu Asp Arg
        290                 295                 300

Ser Glu Tyr Thr Ser Leu Ile Pro Asn Leu Arg Asn Val Val Ala Leu
305                 310                 315                 320

Asp Thr Glu Val Ala Ser Asn Arg Ile Tyr Trp Ser Asp Leu Ser Gln
                325                 330                 335

Arg Met Ile Cys Ser Thr Gln Leu Asp Arg Ala His Gly Val Ser Ser
                340                 345                 350

Tyr Asp Thr Val Ile Ser Arg Asp Ile Gln Ala Pro Asp Gly Leu Ala
        355                 360                 365

Val Asp Trp Ile His Ser Asn Ile Tyr Trp Thr Asp Ser Val Leu Gly
        370                 375                 380

Thr Val Ser Val Ala Asp Thr Lys Gly Val Lys Arg Lys Thr Leu Phe
385                 390                 395                 400

Arg Glu Asn Gly Ser Lys Pro Arg Ala Ile Val Val Asp Pro Val His
                405                 410                 415

Gly Phe Met Tyr Trp Thr Asp Trp Gly Thr Pro Ala Lys Ile Lys Lys
                420                 425                 430

Gly Gly Leu Asn Gly Val Asp Ile Tyr Ser Leu Val Thr Glu Asn Ile
            435                 440                 445

Gln Trp Pro Asn Gly Ile Thr Leu Asp Leu Leu Ser Gly Arg Leu Tyr
    450                 455                 460

Trp Val Asp Ser Lys Leu His Ser Ile Ser Ser Ile Asp Val Asn Gly
465                 470                 475                 480

Gly Asn Arg Lys Thr Ile Leu Glu Asp Glu Lys Arg Leu Ala His Pro
                485                 490                 495

Phe Ser Leu Ala Val Phe Glu Asp Lys Val Phe Trp Thr Asp Ile Ile
                500                 505                 510

Asn Glu Ala Ile Phe Ser Ala Asn Arg Leu Thr Gly Ser Asp Val Asn
        515                 520                 525

Leu Leu Ala Glu Asn Leu Leu Ser Pro Glu Asp Met Val Leu Phe His
        530                 535                 540

Asn Leu Thr Gln Pro Arg Gly Val Asn Trp Cys Glu Arg Thr Thr Leu
545                 550                 555                 560

Ser Asn Gly Gly Cys Gln Tyr Leu Cys Leu Pro Ala Pro Gln Ile Asn
                565                 570                 575

Pro His Ser Pro Lys Phe Thr Cys Ala Cys Pro Asp Gly Met Leu Leu
                580                 585                 590

Ala Arg Asp Met Arg Ser Cys Leu Thr Glu Ala Glu Ala Ala Val Ala
                595                 600                 605

Thr Gln Glu Thr Ser Thr Val Arg Leu Lys Val Ser Ser Thr Ala Val
        610                 615                 620

Arg Thr Gln His Thr Thr Thr Arg Pro Val Pro Asp Thr Ser Arg Leu
625                 630                 635                 640

Pro Gly Ala Thr Pro Gly Leu Thr Thr Val Glu Ile Val
                645                 650
```